US011161916B2

(12) United States Patent
Gschwind et al.

(10) Patent No.: US 11,161,916 B2
(45) Date of Patent: Nov. 2, 2021

(54) BISPECIFIC BINDING MOLECULES BINDING TO VEGF AND ANG2

(71) Applicant: Boehringer Ingelheim International GmbH, Ingelheim am Rhein (DE)

(72) Inventors: Andreas Gschwind, Ingelheim am Rhein (DE); Rene Georg Ott, Perchtoldsdorf (AT); Joachim Boucneau, De Pinte (BE); Marie-Ange Buyse, Merelbeke (BE); Erik Depla, Destelbergen (BE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/515,231

(22) Filed: Jul. 18, 2019

(65) Prior Publication Data

US 2020/0010569 A1 Jan. 9, 2020

Related U.S. Application Data

(60) Continuation of application No. 15/350,364, filed on Nov. 14, 2016, now Pat. No. 10,414,828, which is a division of application No. 13/433,359, filed on Mar. 29, 2012, now Pat. No. 9,527,925.

(30) Foreign Application Priority Data

Apr. 1, 2011 (EP) .................................... 11160921

(51) Int. Cl.
*C07K 16/46* (2006.01)
*C07K 16/18* (2006.01)
*C07K 16/22* (2006.01)

(52) U.S. Cl.
CPC ............ *C07K 16/468* (2013.01); *C07K 16/18* (2013.01); *C07K 16/22* (2013.01); *C07K 2317/22* (2013.01); *C07K 2317/31* (2013.01); *C07K 2317/33* (2013.01); *C07K 2317/565* (2013.01); *C07K 2317/567* (2013.01); *C07K 2317/569* (2013.01); *C07K 2317/62* (2013.01); *C07K 2317/73* (2013.01); *C07K 2317/76* (2013.01); *C07K 2317/92* (2013.01); *C07K 2317/94* (2013.01)

(58) Field of Classification Search
CPC ...... C07K 16/468; C07K 16/18; C07K 16/22; C07K 2317/22; C07K 2317/31; C07K 2317/33; C07K 2317/565; C07K 2317/567; C07K 2317/569; C07K 2317/62; C07K 2317/73; C07K 2317/76; C07K 2317/92; C07K 2317/94; C07K 16/26; A61P 9/00; A61P 5/00; A61P 35/00; A61P 27/02
See application file for complete search history.

(56) References Cited

U.S. PATENT DOCUMENTS

| | | | |
|---|---|---|---|
| 5,408,535 | A | 4/1995 | Howard, III et al. |
| 6,884,879 | B1 | 4/2005 | Baca et al. |
| 7,070,959 | B1 | 7/2006 | Papadopoulos et al. |
| 8,945,552 | B2 | 2/2015 | Baehner et al. |
| 2005/0261477 | A1 | 11/2005 | Champion et al. |
| 2006/0134121 | A1 | 6/2006 | Thurston et al. |
| 2007/0027102 | A1 | 2/2007 | Guyer et al. |
| 2007/0071675 | A1 | 3/2007 | Wu et al. |
| 2007/0196095 | A1 | 8/2007 | Perala et al. |
| 2007/0269422 | A1 | 11/2007 | Beimaert et al. |
| 2008/0175847 | A1 | 7/2008 | Yan et al. |
| 2008/0242587 | A1 | 10/2008 | Kim et al. |
| 2009/0002880 | A1 | 1/2009 | Ueda et al. |
| 2009/0246199 | A1 | 10/2009 | Noguera-Troise et al. |
| 2010/0129368 | A9 | 5/2010 | Lasters et al. |
| 2010/0260668 | A1 | 10/2010 | Ghayur et al. |
| 2011/0027268 | A1 | 2/2011 | Kahnert et al. |
| 2011/0105733 | A1 | 5/2011 | Saunders et al. |
| 2011/0172398 | A1 | 7/2011 | Borges et al. |
| 2011/0195494 | A1 | 8/2011 | Borges et al. |
| 2011/0236388 | A1 | 9/2011 | Baehner et al. |
| 2012/0123686 | A1 | 5/2012 | Xiang et al. |
| 2012/0225081 | A1 | 9/2012 | Gschwind et al. |
| 2013/0078247 | A1 | 3/2013 | Gschwind et al. |
| 2013/0078248 | A1 | 3/2013 | Gschwind et al. |
| 2013/0259859 | A1 | 10/2013 | Ott et al. |
| 2014/0120095 | A1 | 5/2014 | Borges et al. |

FOREIGN PATENT DOCUMENTS

| | | | |
|---|---|---|---|
| GB | 2449354 | A | 11/2008 |
| WO | 199630046 | A1 | 10/1996 |
| WO | 1998045331 | A2 | 10/1998 |

(Continued)

OTHER PUBLICATIONS

Yu et al., Investigative Ophthalmology & Visual Science 49(2): 522-527 (Year: 2008).*

(Continued)

*Primary Examiner* — Phuong Huynh
(74) *Attorney, Agent, or Firm* — Wendy M. Gombert

(57) ABSTRACT

Bispecifc binding molecules binding to both VEGF and Ang2, preferably in the form of immunoglobulin single variable domains like VHHs and domain antibodies, pharmaceutical compositions containing the same and their use in the treatment of diseases that are associated with VEGF- and/or Ang2-mediated effects on angiogenesis are disclosed. Further, nucleic acids encoding bispecific binding molecules, host cells and methods for preparing same are also described.

5 Claims, 135 Drawing Sheets

Specification includes a Sequence Listing.

(56) References Cited

FOREIGN PATENT DOCUMENTS

| | | | |
|---|---|---|---|
| WO | 03074670 | A2 | 9/2003 |
| WO | 2004041865 | A2 | 5/2004 |
| WO | 2004062551 | A2 | 7/2004 |
| WO | 2004081026 | A2 | 9/2004 |
| WO | 2005020972 | A2 | 3/2005 |
| WO | 2005040219 | A1 | 5/2005 |
| WO | 2006066086 | A1 | 6/2006 |
| WO | 2006068953 | A2 | 6/2006 |
| WO | 2006122786 | A2 | 11/2006 |
| WO | 2006122825 | A2 | 11/2006 |
| WO | 2007028110 | A2 | 3/2007 |
| WO | 2007053186 | A2 | 5/2007 |
| WO | 2007068895 | A1 | 6/2007 |
| WO | 2007070671 | A2 | 6/2007 |
| WO | 2007085815 | A2 | 8/2007 |
| WO | 2007089445 | A2 | 8/2007 |
| WO | 2007143689 | A2 | 12/2007 |
| WO | 2008019144 | A2 | 2/2008 |
| WO | 2008028977 | A2 | 3/2008 |
| WO | 2008060705 | A2 | 5/2008 |
| WO | 2008076379 | A2 | 6/2008 |
| WO | 2008101985 | A2 | 8/2008 |
| WO | 2008119353 | A1 | 10/2008 |
| WO | 2008133706 | A2 | 11/2008 |
| WO | 2008149147 | A2 | 12/2008 |
| WO | 2008149149 | A2 | 12/2008 |
| WO | 2009007124 | A1 | 1/2009 |
| WO | 2009055343 | A2 | 4/2009 |
| WO | 2009105269 | A1 | 8/2009 |
| WO | 2009117277 | A2 | 9/2009 |
| WO | 2009124931 | A2 | 10/2009 |
| WO | 2009134776 | A2 | 11/2009 |
| WO | 2009147248 | A2 | 12/2009 |
| WO | 2009155724 | A2 | 12/2009 |
| WO | 2010027981 | A1 | 3/2010 |
| WO | 2010032060 | A1 | 3/2010 |
| WO | 2010040508 | A1 | 4/2010 |
| WO | 2010066836 | A2 | 6/2010 |
| WO | 2010069532 | A1 | 6/2010 |
| WO | 2010124009 | A2 | 10/2010 |
| WO | 2010129304 | A2 | 11/2010 |
| WO | 2010148223 | A2 | 12/2010 |
| WO | 2011014469 | A1 | 2/2011 |
| WO | 2011039368 | A2 | 4/2011 |
| WO | 2011039370 | A1 | 4/2011 |
| WO | 2011106300 | A2 | 9/2011 |
| WO | 2011117329 | A1 | 9/2011 |
| WO | 2012012499 | A1 | 1/2012 |
| WO | 2012061374 | A2 | 5/2012 |
| WO | 2012131078 | A1 | 10/2012 |
| WO | 2012166287 | A1 | 12/2012 |
| WO | 2013044215 | A1 | 3/2013 |

OTHER PUBLICATIONS

Stancovski et al., PNAS, 88: 8691-8695 (Year: 1991).*

Sullivan, D.C. et al. "New molecular pathways in angiogenesis" British Journal of Cancer (2003) vol. 89, pp. 228-231.

Vajdos, Felix F. et al. "Comprehensive Functional Maps of the Antigen-Binding Site of an Anti-ErbB2 Antibody Obtained with Shotgun Scanning Mutagenesis"; Journal Molecular Biology (2002) vol. 320, pp. 415-428.

Vincke, Cecile et al. "General Strategy to Humanize a Camelid Single-domain Antibody and Identification of a Universal Humanized Nanobody Scaffold" Journal of Biological Chemistry, (2009) vol. 284, No. 5, pp. 3273-3284.

Wark, Kim L et al. "Latest technologies for the enhancement of anitbody affinity" Advanced Drug Delivery Reviews (2006) vol. 58, pp. 657-670.

Williams, Cassin Kimmel et al. "Up-regulation of the Notch ligand Delta-like 4 inhibits VEGF-induced endothelial cell function" Blood (2006) vol. 107, No. 3, pp. 931-939.

WO2009134776 (Part 1 of 2) International Publication Date: Nov. 5, 2009. Patentee: Abbott Laboratories. Inventor Larig Ghayur Title: Dual Variable Domain Immunoglobulins and Uses Thereof. Total pp. 481. This foreign patent is too large for EFS submission via the foreign patent section. Therefore filing in two parts in the NPL section. pp. 1-220.

WO2009134776 (Part 2 of 2) International Publication Date: Nov. 5, 2009. Patentee: Abbott Laboratories. Inventor Larig Ghayur Title: Dual Variable Domain Immunoglobulins and Uses Thereof Total pp. 481. This foreign patent is too large for EFS submission via the foreign patent section. Therefore filing in two parts in the NPL section. pp. 221-481.

Wu, Herren et al. "Humanization of a Murine Monoclonal Antibody by Simultaneous Optimization of Framework and CDR Residues" Journal Molecular Biology (1999) vol. 294, pp. 151-162.

Yan, Xiao-Qiang et al. "A novel Notch ligand, Dll4, induces T-cell leukemia/lymphoma when overexpressed in mice by retroviral-mediated gene transfer" Blood, (2001) vol. 98, No. 13, pp. 3793-3799.

Zhang, Jianghui et al. "Angiopoietin-1/Tie2 Signal Augments Basal Notch Signal Controlling Vascular Quiescence by Inducing Delta-Like 4 Expression through AKT-mediated Activation of b-Catenin*" Journal of Biological Chemistry, (2011) vol. 286, No. 10, pp. 8055-8065.

Lund, Multiple Interactions of IgG with its core oligosaccharide can modulate recognition complement and human Fc gamma recept and influence the synthesis of its oligosaccharide chains, J. immuno 1996, vol. 157.

Rudikoff, Single amino acid substitution Altering antigen binding specificity, Proc. Natl, Acad, Sci, vol. 79, 1982.

Tijink, Improved tumor targeting of anti-epidermal growth factor receptor Nanobodies through albumin binding: taking advantage of modular Nanobody technology, Molecular Cancer Therapeutics, 2008, vol. 7.

Ahmadvand, Davoud et al. "Production and Characterization of a High-Affinity Nanobody Against Human Endoglin" Hybridoma, (2008) vol. 27, pp. 353-360.

Berkower, Ira "The promise and pitfalls of monoclonal antibody therapeutics" Current Opinion in Biotechnology (1996) vol. 7, pp. 622-628.

Brown et al., "Tolerance of single, but not multiple, amino acid replacements in antibody VH CDR 2: a means of minimizing B cell wastage from somatic hypermutation?", The Journal of Immunology, May 1, 1996, vol. 156, No. 9, pp. 3285-3291.

Brown, Jeffrey L. et al. "A Human Monoclonal Anti-ANG2 Antibody Leads to Broad Antitumor Activity in Combination with VEGF Inhibitors and Chemotherapy Agents in Preclinical Models" Molecular Cancer Therapeutics (2010) pp. 145-156.

Carter, Paul J. "Potent Anitbody Therapeutics by Design" Nature Reviews (2006) vol. 6, pp. 343-357.

Casset, Florence et al. "A peptide mimetic of an anti-CD4 monoclonal antibody by rational design" Biochemical and Biophysical Research Communications (2003) vol. 307, pp. 198-205.

Colman, P.M. "Effects of amino acid sequence changes on antibody-antigen interactions" Research in Immunology (1994) vol. 145, pp. 33-35.

Conrath, Katja Els et al. "Camel Single-domain Antibodies as Modular Building Units in Bispecific and Bivalent Antibody Constructs" The Journal of Biological Chemistry (2001) vol. 276, No. 10, pp. 7346-7350.

Conrath, Katja et al. "Antigen Binding and Solubility Effects upon the Veneering of a Camel VHH in Framework-2 to Mimic a VH" Journal Molecular Biology (2005) vol. 350, pp. 112-125.

De Pascalis, Roberto et al. "Grafting of 'Abbreviated' Complementarity-Determining Regions Containing Specificity-Determining Residues Essential for Ligand Contact to Engineer a Less Immunogenic Humanized Monoclonal Antibody" The Journal of Immunology (2002) pp. 3076-3084.

Doppalapudi, Venkata R. et al. "Chemical generation of bispecific antibodies" Proceedings of the National Academy of Sciences, (2010) vol. 107, No. 52, pp. 22611-22616.

(56) References Cited

OTHER PUBLICATIONS

Dufner, Patrick et al. "Harnessing phage and ribosome display for antibody optimisation" Trends Biotechnology (2006) vol. 24 No. 11, pp. 523-529.
Ewert et al., "Biophysical Properties of Camelid VHH Domains Compared to Those of Human VH3 Domains", Biochemistry, American Chemical Society, US, Feb. 19, 2002, vol. 41, No. 11, pp. 3628-3636.
Gundry, Rebekah L. et al. "Investigation o fan albumin-enriched fraction of human serum and its albuminome" Proteomics Clin. Appl. (2007), 1 (1), pp. 73-88.
Gussow, Detlef et al. "[5] Humanization of Monoclonal Antibodies" Methods of Enzymology (1991) vol. 203, pp. 99-121.
Harmsen, M.M. et al. "Properties, production, and applications of camelid single-domain antibody fragments" Applied Microbiology and Biotechnology (2007) vol. 77, pp. 13-22.
Hashizume, Hiroya et al. "Complementary Actions of Inhibitors of Angiopoientin-2 and VEGF on Tumor Angiogenesis and Growth" Cancer Research, (2010) vol. 70, pp. 2213-2223.
Hellstrom, Mats "DII4 signalling through Notch1 regulates formation of tip cells during angiogenesis" (2007) Nature, vol. 445, pp. 776-780.
Hicks, Carol et al. "A Secreted Delta1-Fc Fusion Protein Functions both as an Activator and Inhibitor of Notch1 Signaling" Journal of Neuroscience Reasearch (2002) vol. 68, pp. 655-667.
Hoeben, Ann et al. "Vascular Endothelial Growth Factor and Angiogenesis" Pharmacological Reviews (2004) vol. 56, No. 4, pp. 549-580.
Holt, Lucy J. et al. "Domain antibodies: proteins for therapy" (2003) Trends in Biotechnology vol. 21, No. 11, pp. 484-490.
International Search Report and Written Opinion for PCT/EP2010/064695 dated Mar. 15, 2011.
International Search Report for PCT/EP2010/064693 dated May 6, 2011.
International Search Report for PCT/EP2012/055897 dated Sep. 5, 2012.
International Search Report for PCT/EP2012/055901 dated Jun. 5, 2012.
International Search Report for PCT/EP2013/056635 filed Mar. 27, 2013.
Kienast, Yvonne et al. "Ang-2-VEGF-A CrossMab, a novel bispecific human IgG1 antibody blocking VEGF-A and Ang-2 functions simultaneously, mediates potent anti-tumor, anti-angiogenic, and anti-metastatic efficacy" Clinical Cancer Research, published Oct. 4, 2013, 36 pgs clincancerres.aacrjournals.org.
Kotia et al., "Analysis of monoclonal 1 antibody product heterogeneity resulting from alternate cleavage sites of signal peptide", Analytical Biochemistry, Elsevier, Amsterdam, NL, vol. 399. No. 2., Apr. 15, 2010, pp. 190-195
Li, Ji-Liang, et al. "Notch signaling from tumor cells: A new mechanism of angiogenesis" Cancer Cell (2005) vol. 8, pp. 1-3.
Liang, Wei-Ching et al. "Cross-species Vascular Endothelial Growth Factor (VEGF)-blocking Antibodies Completely Inhibit the Growth of Human Tumor Xenografts and Measure the Contribution of Stromal VEGF*" The Journal of Biological Chemistry (2006) vol. 281 No. 2, pp. 951-961.
Liu, Zhao-Jun et al. "Regulation of Notch1 and DII4 by Vascular Endothelial Growth Factor in Arterial Endothelial Cells: Implications for Modulating Arteriogenesis and Angiogenesis" Molecular and Cellular Biology, (2003) vol. 23, No. 1, pp. 14-25.

MacCallum, Robert M. et al. "Antibody-antigen Interactions: Contact Analysis and Binding Site Topography" Journal of Molecular Biology (1996) vol. 262, pp. 732-745.
Makinen, Taija et al. "Inhibition of lymphangiogenesis with resulting lymphedema in transgenic mice expressing soluble VEGF receptor-3" Nature Medicine (2001) vol. 7, No. 2, pp. 199-205.
Mariuzza, R.A. et al. "The Structural Basis of Antigen-Antibody Recognition" Ann. Rev. Biophys. Biophys. Chem. (1987) vol. 16, pp. 139-159.
Marriott, Ian et al. "CD40-CD40 LIgand Interactions Augment Survival of Normal Mice, but not CD40 LIgand Knockout Mice, Challenged Orally with Salmonella dublin" Infection and Immunity (1999) vol. 67, No. 10, pp. 5253-5257.
Marvin, Jonathan S. et al. "Bispecific antibodies for dual-modality cancer therapy: Killing two signaling cascades with one stone" Current Opinion in Drug Discovery and Development, (2006) vol. 9, No. 2, pp. 184-193.
Muyldermans, S. "Nanobodies: Natural Single-Domain Antibodies" Ann. Rev. Biochem. (2013) pp. 17.1-17.23.
Muyldermans, S. et al. "Camelid immunoglobulins and nanobody technology" Veterinary Immunology and Immunopathology (2009) vol. 128, pp. 178-183.
Muyldermans, Serge et al. "Unique single-domain antigen binding fragments derived from naturally occurring carnel heavy-chain antibodies" Journal of Molecular Recognition (1999) vol. 12, pp. 131-140.
Nam, Yunsun et al. "Notch signaling as a therapeutic target" Current Opinion in Chemical Biology (2002) vol. 6, pp. 501-509.
Paul, William E. "Fundamental Immunology, Third Edition" (1993) pp. 292-295.
Revets, Hilde et al. "Nanobodies as Novel Agents for Cancer Therapy" Expert Opinion on Biological Therapy (2005) vol. 5, No. 1, pp. 111-124.
Ridgeway, J. et al. "Chronic DLL4 blockade induces vascular neoplasms" Nature (2006) 444, pp. 1083-1087.
Roovers, Rob C. et al. "Nanobodies in therapeutic applications" Current Opinion in Molecular Therapeutics (2007) 9(4) pp. 327-335.
Rudikoff, Stuart et al. "Single amino acid substitution altering antigen-binding spoecificity" Proceedings of the National Academy Sciences, (1982) vol. 79, pp. 1979-1983.
Schaefer, Wolfgang et al. "Immunoglobulin domain crossover as a generic approach for the production of bispecific IgG antibodies" (2011) Proceedings of the National Academy of Sciences, vol. 108, No. 27 pp. 11187-11192.
Scheuer, W. et al. "Anti-tumoral and anti-metastatic activity of a tetravalent bispecific antibody (TAvi6) targeting VEGF and Angiopoletin-2" European Journal of Cancer, (2010) Poster 468, pp. 150-151.
Sequence search result from EPO provided on Feb. 26, 2015. SA1115660 filing date Mar. 30, 2012. XP055172462; 1 pg; http://ibis.internal.epo.org/exam/jobResult?id=308647.
Shaw et al. "A spontaneous variant of an antidigoxin hybridoma antibody with increased affinity arises from a heavy chain signal peptide mutation", Molecular Immunology, Pergamon, GB, vol. 29, No. 4, Apr. 1, 1992, pp. 525-529.
Shen, Juqun "Single variable domain antibody as a versatile building block for the construction of IgG-like bispecific antibodies" Journal of Immunological Methods (2007) vol. 318, pp. 65-74.

* cited by examiner

Figure 16:
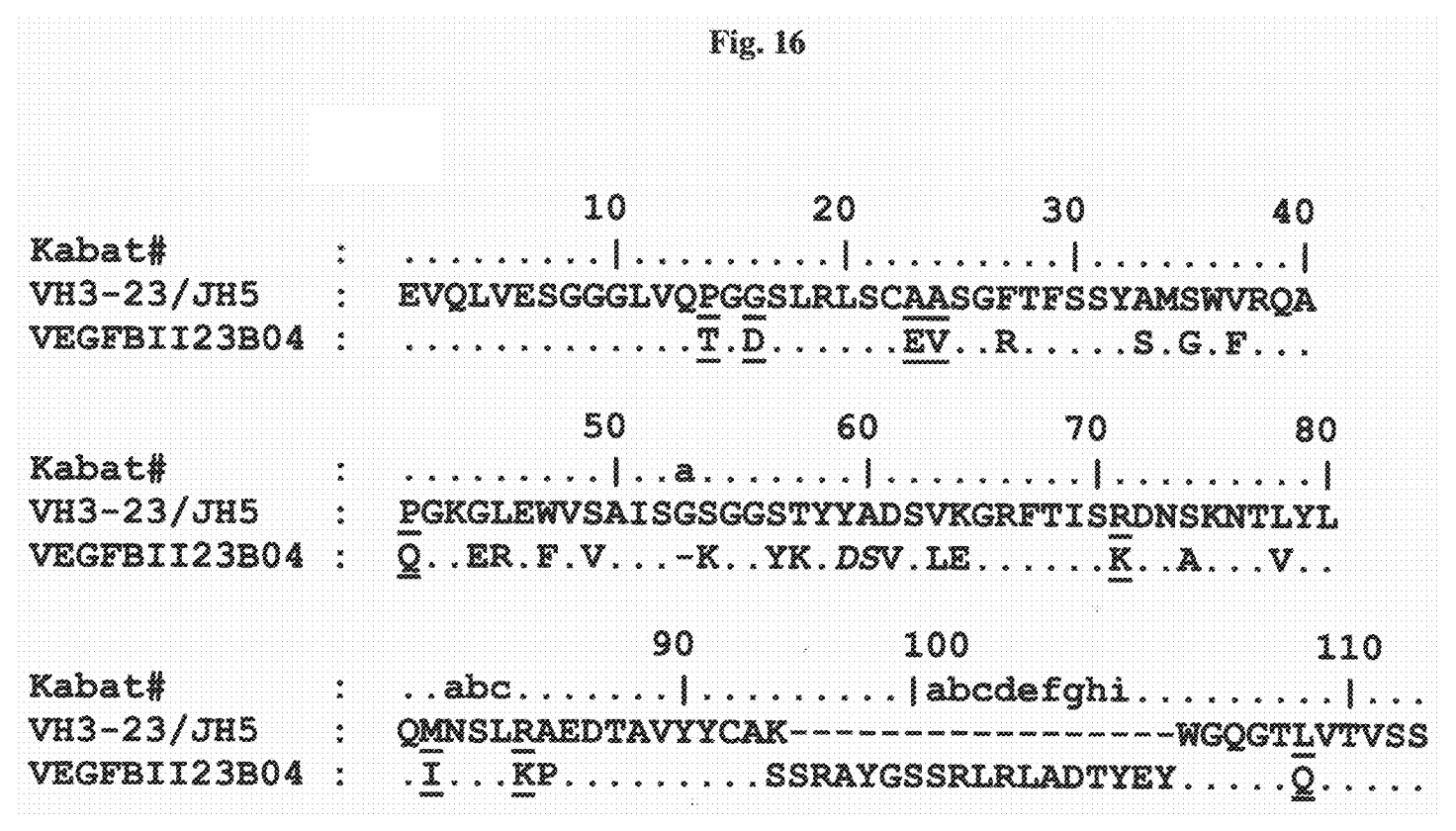

```
                        10        20        30        40
Kabat#         :  .........|.........|.........|.........|
VH3-23/JH5     :  EVQLVESGGGLVQPGGSLRLSCAASGFTFSSYAMSWVRQA
VEGFBII23B04   :  .............T.D......EV..R.....S.G.F...

                        50         60        70        80
Kabat#         :  .........|..a.......|.........|.........|
VH3-23/JH5     :  PGKGLEWVSAISGSGGSTYYADSVKGRFTISRDNSKNTLYL
VEGFBII23B04   :  Q..ER.F.V...-K..YK.DSV.LE......K..A...V..

                           90        100                110
Kabat#         :  ..abc.......|.........|abcdefghi.........|...
VH3-23/JH5     :  QMNSLRAEDTAVYYCAK----------------WGQGTLVTVSS
VEGFBII23B04   :  .I...KP.........SSRAYGSSRLRLADTYEY.....Q.....
```

Fig. 19

```
                           10        20        30        40
Kabat#           : .........|.........|.........|.........|
VH3-23/JH5       : EVQLVESGGGLVQPGGSLRLSCAASGFTFSSYAMSWVRQA
PVEGFBIIPMP5B5   : ......................V...IR.MSM.--.Y...

                           50        60        70        80
Kabat#           : .........|..a......|.........|.........|
VH3-23/JH5       : PGKGLEWVSAISGSGGSTYYADSVKGRFTISRDNSKNTLYL
PVEGFBIIPMP5B5   : ...HR.L.AR..-...T.A.V.................V..

                              90       101      110
Kabat#           : ..abc.......|.........|........|...
VH3-23/JH5       : QMNSLRAEDTAVYYCAK-------WGQGTLVTVSS
PVEGFBIIPMP5B5   : .....KA........NTFSSRPNP..A..Q.....
```

| VHH ID | Format | Description |
|---|---|---|
| ANGBII00001 |  | 1D01-9gs-1D01 |
| ANGBII00002 |  | 1D01-40gs-1D01 |
| ANGBII00003 |  | 11B07-9gs-11B07 |
| ANGBII00004 |  | 00027-9gs-00027 |
| ANGBII00005 |  | 00027-40gs-00027 |
| ANGBII00006 |  | 00908-9gs-00908 |

Legend:

| | Description |
|---|---|
|  | 1D01 |
|  | 11B07 |
|  | 00027 |
|  | 00908 |
|  | *9 GlySer* linker |
|  | *40 GlySer* linker |

| VHH ID | Format | Expression (mg/L) |
|---|---|---|
| ANGBII00001 |  | 31 |
| ANGBII00002 |  | 37 |
| ANGBII00003 |  | 28 |
| ANGBII00004 |  | 651 |
| ANGBII00005 |  | 203 |
| ANGBII00006 |  | 3 |

| | | hAng2 | mAng2 | cAng2 | hAng1/hAng2 ratio |
|---|---|---|---|---|---|
| VHH ID | Format | $IC_{50}$ (pM) | $IC_{50}$ (pM) | $IC_{50}$ (pM) | |
| 1D01 |  | 6,973 | 10,455 | 9,484 | >10,800 |
| ANGBII00001 |  | 11 | 18 | 27 | n.d. |
| ANGBII00002 |  | 20 | 32 | n.d. | n.d. |
| 11B07 |  | 15,205 | 10,000 | 16,400 | > 8,570 |
| ANGBII00003 |  | 24 | 47 | 35 | n.d. |
| 00027 |  | 541 | 1,785 | 568 | >14,878 |
| ANGBII00004 |  | 17 | 33 | 34 | n.d. |
| ANGBII00005 |  | 13 | 32 | n.d. | n.d. |
| 00908 |  | 52 | 85 | 79 | >192,014 |
| ANGBII00006 |  | 19 | 28 | 25 | 6,052,631 |
| AMG386 | | 4 | 3 | 10 | 5,600 | n.d., not determined

| VHH ID | Format | Description |
|---|---|---|
| VEGFANGBII00001 |  | VEGFBII00038-9gs-ALB11-9gs-00027 |
| VEGFANGBII00002 |  | 00027-9gs-ALB11-9gs-VEGFBII00038 |
| VEGFANGBII00003 |  | 00027-9gs-VEGFBII00038-9gs-ALB11 |
| VEGFANGBII00004 |  | VEGFBII00038-*AAA*-ALB11-*AAA*-00027 |

Legend:

| | Description |
|---|---|
|  | VEGFBII00038 |
|  | 00027 |
|  | ALB11 |
| AAA | *triple Ala* linker |
|  | *9 GlySer* linker |

Fig. 23 B
Fig. 23 C
00038 ALB11
ALB11 00038
00038 ALB11
00038 AAA ALB11 AAA
00038 ALB11
ALB11 00038
00038 ALB11
00038 AAA ALB11 AAA

| VHH ID | Format | Expression (mg/L) |
|---|---|---|
| VEGFANGBII00001 |  | 13.3 |
| VEGFANGBII00002 |  | 11.3 |
| VEGFANGBII00003 |  | 15.4 |
| VEGFANGBII00004 |  | 19.2 |

| VHH ID | Format | HSA | $IC_{50}$ (nM) | % inh |
|---|---|---|---|---|
| VEGFBII00038 |  | - | 0.5 | 100 |
| | | + | 0.5 | 100 |
| VEGFANGBII00001 |  | - | 0.4 | 100 |
| | | + | 0.6 | 100 |
| VEGFANGBII00002 |  | - | 0.7 | 100 |
| | | + | 1.2 | 100 |
| VEGFANGBII00003 |  | - | 0.6 | 100 |
| | | + | 1.3 | 100 |
| VEGFANGBII00004 |  | - | 0.5 | 100 |
| | | + | 0.7 | 100 |
| Ranibizumab | | - | 0.8 | 100 |
| | | + | 1.1 | 100 |

| VHH ID | Format | HSA | $IC_{50}$ (pM) |
|---|---|---|---|
| 00027 |  | - | 516 |
| | | + | n.d. |
| VEGFANGBII00001 |  | - | 240 |
| | | + | 179 |
| VEGFANGBII00002 |  | - | 463 |
| | | + | 330 |
| VEGFANGBII00003 |  | - | 273 |
| | | + | 154 |
| VEGFANGBII00004 |  | - | 111 |
| | | + | 92 |
| AMG386 | | - | 2 |
| | | + | n.d. | n.d., not determined

Figure 26 A

| VHH ID | Format | Description |
|---|---|---|
| VEGFANGBII00005 | 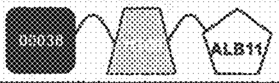 | VEGFBII00038-9gs-7G08-9gs-ALB11 |
| VEGFANGBII00006 | 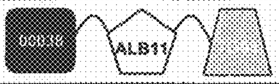 | VEGFBII00038-9gs-ALB11-9gs-7G08 |
| VEGFANGBII00007 | 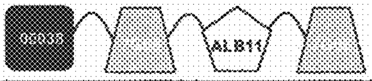 | VEGFBII00038-9gs-7G08-9gs-ALB11-9gs-7G08 |
| VEGFANGBII00008 | 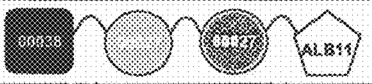 | VEGFBII00038-9gs-00027-9gs-00027-9gs-ALB11 |
| VEGFANGBII00009 | 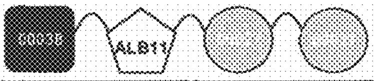 | VEGFBII00038-9gs-ALB11-9gs-00027-9gs-00027 |
| VEGFANGBII00010 | 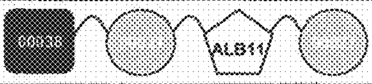 | VEGFBII00038-9gs-00027-9gs-ALB11-9gs-00027 |
| VEGFANGBII00011 | 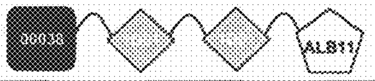 | VEGFBII00038-9gs-1D01-9gs-1D01-9gs-ALB11 |
| VEGFANGBII00012 | 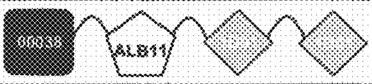 | VEGFBII00038-9gs-ALB11-9gs-1D01-9gs-1D01 |
| VEGFANGBII00013 |  | VEGFBII00038-9gs-1D01-9gs-ALB11-9gs-1D01 |
| VEGFANGBII00014 | 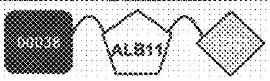 | VEGFBII00038-9gs-ALB11-9gs-1D01 |

Legend:

| | Description | | Description |
|---|---|---|---|
|  | VEGFBII00038 |  | ALB11 |
|  | 00027 | AAA | *triple Ala* linker |
|  | 1D01 |  | *9 GlySer* linker |
|  | 7G08 | | |

| VHH ID | Format | Expression (mg/L) |
|---|---|---|
| VEGFANGBII00005 |  | 1.3 |
| VEGFANGBII00006 |  | 1.3 |
| VEGFANGBII00007 |  | 0.3 |
| VEGFANGBII00008 |  | 30.0 |
| VEGFANGBII00009 |  | 71.4 |
| VEGFANGBII00010 |  | 25.0 |
| VEGFANGBII00011 |  | 4.0 |
| VEGFANGBII00012 |  | 6.6 |
| VEGFANGBII00013 |  | 2.9 |
| VEGFANGBII00014 |  | 45.6 |

| | | | VEGFR1 | | VEGFR2 | |
|---|---|---|---|---|---|---|
| VHH ID | Format | HSA | $IC_{50}$ (nM) | % inh | $IC_{50}$ (nM) | % inh |
| VEGFBII00038 |  | - | 0.6 | 67 | 0.5 | 100 |
| | | + | 0.6 | 64 | 0.5 | 100 |
| VEGFANGBII00005 |  | - | n.d. | n.d. | n.d. | n.d. |
| | | + | n.d. | n.d. | n.d. | n.d. |
| VEGFANGBII00006 |  | - | 0.8 | 64 | 1.0 | 100 |
| | | + | 1.0 | 71 | 1.4 | 100 |
| VEGFANGBII00007 |  | - | n.d. | n.d. | n.d. | n.d. |
| | | + | n.d. | n.d. | n.d. | n.d. |
| VEGFANGBII00008 |  | - | 0.6 | 77 | 0.3 | 100 |
| | | + | 0.7 | 73 | 0.4 | 100 |
| VEGFANGBII00009 |  | - | 0.8 | 71 | 0.4 | 100 |
| | | + | 1.5 | 72 | 0.7 | 100 |
| VEGFANGBII00010 |  | - | 0.5 | 72 | 0.3 | 100 |
| | | + | 1.1 | 78 | 0.7 | 100 |
| VEGFANGBII00001 |  | - | 0.6 | 68 | 0.4 | 100 |
| | | + | 0.8 | 76 | 0.6 | 100 |
| VEGFANGBII00011 |  | - | 0.8 | 74 | 0.9 | 100 |
| | | + | 2.5 | 81 | 0.8 | 100 |
| VEGFANGBII00012 |  | - | 1.0 | 74 | 0.4 | 100 |
| | | + | 1.5 | 80 | 0.7 | 100 |
| VEGFANGBII00013 |  | - | n.d. | n.d. | n.d. | n.d. |
| | | + | n.d. | n.d. | n.d. | n.d. |
| VEGFANGBII00014 |  | - | 0.8 | 69 | 0.4 | 100 |
| | | + | 1.0 | 80 | 0.7 | 100 |
| Ranibizumab | | - | 2.5 | 92 | 1.2 | 100 |
| | | + | 5.3 | 86 | 1.1 | 100 | n.d., not determine

| | | | hAng2 | | mAng2 | | cAng2 | | HUVEC survival | |
|---|---|---|---|---|---|---|---|---|---|---|
| VHH ID | Format | HSA | $IC_{50}$ (pM) | % inh | $IC_{50}$ (pM) | % inh | $IC_{50}$ (pM) | % inh | $IC_{50}$ (nM) | % inh |
| 7G08 |  | + | 110 | 100 | n.d. | n.d. | n.d. | n.d. | 1.5 | 100 |
| | | - | n.d. | n.d. | n.d. | n.d. | n.d. | n.d. | n.d. | n.d. |
| VEGFANGBII00 005 |   | - | n.d. | n.d. | n.d. | n.d. | n.d. | n.d. | n.d. | n.d. |
| | | + | n.d. | n.d. | n.d. | n.d. | n.d. | n.d. | n.d. | n.d. |
| VEGFANGBII00 006 |   | - | 560 | 100 | n.d. | n.d. | n.d. | n.d. | 4.9 | 100 |
| | | + | 400 | 100 | n.d. | n.d. | n.d. | n.d. | n.d. | n.d. |
| VEGFANGBII00 007 |   | - | n.d. | n.d. | n.d. | n.d. | n.d. | n.d. | n.d. | n.d. |
| | | + | n.d. | n.d. | n.d. | n.d. | n.d. | n.d. | n.d. | n.d. |
| AMG386 | | - | 5 | 100 | n.d. | n.d. | n.d. | n.d. | 1.2 | 100 |
| | | + | 4 | 100 | n.d. | n.d. | n.d. | n.d. | n.d. | n.d. |
| | | | | | | | | | | |
| 00027 |  | - | 540 | 100 | 1,800 | 100 | 570 | 100 | 2.0 | 100 |
| | | + | n.d. | n.d. | n.d. | n.d. | n.d. | n.d. | n.d. | n.d. |
| VEGFANGBII00 001 |   | - | 360 | 100 | 1,300 | 100 | 390 | 100 | 5.7 | 100 |
| | | + | 290 | 100 | n.d. | n.d. | n.d. | n.d. | n.d. | n.d. |

| | | | | | | | | | | |
|---|---|---|---|---|---|---|---|---|---|---|
| VEGFANGBII00 008 |  | - | 47 | 100 | 71 | 100 | 79 | 100 | 5.6. | 100 |
| | | + | 52 | 100 | n.d. | n.d. | n.d. | n.d. | n.d. | n.d. |
| VEGFANGBII00 009 |  | - | 33 | 100 | 36 | 100 | 46 | 100 | 3.6. | 100 |
| | | + | 39 | 100 | n.d. | n.d. | n.d. | n.d. | n.d. | n.d. |
| VEGFANGBII00 010 |  | - | 32 | 100 | 78 | 100 | 59 | 100 | n.d. | n.d. |
| | | + | 49 | 100 | n.d. | n.d. | n.d. | n.d. | n.d. | n.d. |
| AMG386 | | - | 5 | 100 | 4 | 100 | 3 | 100 | 1.3 | 100 |
| | | + | 4 | 100 | n.d. | n.d. | n.d. | n.d. | n.d. | n.d. |
| | | | | | | | | | | |
| 1D01 |  | - | 7,000 | 100 | 10,000 | 100 | 9,500 | 100 | 7.8 | 100 |
| | | + | n.d. | n.d. | n.d. | n.d. | n.d. | n.d. | n.d. | n.d. |
| VEGFANGBII00 011 |  | - | 31 | 100 | 56 | 100 | 95 | 100 | 3.7 | 100 |
| | | + | 34 | 100 | n.d. | n.d. | n.d. | n.d. | n.d. | n.d. |
| VEGFANGBII00 012 |  | - | 40 | 100 | 68 | 100 | 100 | 100 | 3.6 | 100 |
| | | + | 65 | 100 | n.d. | n.d. | n.d. | n.d. | n.d. | n.d. |
| VEGFANGBII00 013 |  | - | n.d. | n.d. | n.d. | n.d. | n.d. | n.d. | n.d. | n.d. |
| | | + | n.d. | n.d. | n.d. | n.d. | n.d. | n.d. | n.d. | n.d. |
| VEGFANGBII00 014 |  | - | 710 | 100 | 1,000 | 100 | 1,100 | 100 | n.d. | n.d. |
| | | + | 1,200 | 100 | n.d. | n.d. | n.d. | n.d. | n.d. | n.d. |
| AMG386 | | - | 4 | 100 | 4 | 100 | 10 | 100 | 1.3 | |
| | | + | 4 | 100 | n.d. | n.d. | n.d. | n.d. | n.d. | n.d. | n.d., not determined

Figure 30 A

| VHH ID | Format | Description |
|---|---|---|
| VEGFANGBII00015 |   | VEGFBII00038-9gs-ALB11-9gs-00908 |
| VEGFANGBII00016 |   | VEGFBII00038-9gs-ALB11-9gs-00932 |
| VEGFANGBII00017 |   | VEGFBII00038-9gs-ALB11-9gs-00933 |
| VEGFANGBII00018 |   | VEGFBII00038-9gs-ALB11-9gs-00934 |
| VEGFANGBII00019 |   | VEGFBII00038-9gs-ALB11-9gs-00935 |
| VEGFANGBII00020 |   | VEGFBII00038-9gs-ALB11-9gs-00936 |
| VEGFANGBII00021 |   | VEGFBII00038-9gs-ALB11-9gs-00937 |
| VEGFANGBII00022 |   | VEGFBII00038-9gs-ALB11-9gs-00938 |
| VEGFANGBII00023 |   | VEGFBII00038-9gs-ALB11-9gs-00919-9gs-00919 |
| VEGFANGBII00024 | 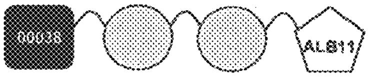  | VEGFBII00038-9gs-00919-9gs-00919-9gs-ALB11 |
| VEGFANGBII00025 |   | VEGFBII00038-9gs-ALB11-9gs-00921-9gs-00921 |
| VEGFANGBII00026 | 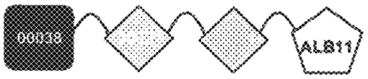  | VEGFBII00038-9gs-00921-9gs-00921-9gs-ALB11 |
| VEGFANGBII00027 |   | VEGFBII00038-9gs-ALB11-9gs-00928 |
| VEGFANGBII00028 |   | VEGFBII00038-9gs-ALB11-9gs-00956-9gs-00956 |

Legend:

| | Description | | Description |
|---|---|---|---|
|  | VEGFBII00038 |  | 00937 |
|  | 00908 |  | 00938 |
|  | 00919 |  | 00956 |
|  | 00932 |  | 00921 |
|  | 00933 |  | 00928 |
|  | 00934 |  | ALB11 |
|  | 00935 |  | *9 GlySer* linker |
|  | 00936 | | |

| VHH ID | Format | Expression (mg/L) |
|---|---|---|
| VEGFANGBII00022 |  | |
| VEGFANGBII00025 |  | |
| VEGFANGBII00028 |  | |

| | | | VEGFR1 | | VEGFR2 | |
|---|---|---|---|---|---|---|
| VHH ID | Format | HSA | $IC_{50}$ (nM) | % inh | $IC_{50}$ (nM) | % inh |
| VEGFBII00038 |  | - | 0.4 | 57 | 0.2 | 100 |
| | | + | n.d. | n.d. | n.d. | n.d. |
| VEGFANGBII00022 |  | - | 0.4 | 64 | 0.2 | 100 |
| | | + | 0.6 | 75 | 0.3 | 100 |
| VEGFANGBII00025 |  | - | 0.6 | 68 | 0.2 | 100 |
| | | + | 0.9 | 75 | 0.3 | 100 |
| VEGFANGBII00028 |  | - | 0.5 | 64 | 0.2 | 100 |
| | | + | 0.5 | 64 | 0.2 | 100 |
| Ranibizumab | | - | 3.2 | 97 | 0.7 | 100 |
| | | + | n.d. | n.d. | 0.9 | 100 | n.d., not determined

Fig. 30D

| | ka1 (1/Ms) | kd1 (1/s) | ka2 (1/s) | kd2 (1/s) | KD1 (M) |
|---|---|---|---|---|---|
| VEGFBII00038 | 2.6E+05 | 1.3E-02 | 1.3E-02 | 1.9E-04 | 7.5E-10 |
| VEGFANGBII00022 | 1.6E+05 | 1.4E-02 | 1.4E-02 | 2.2E-04 | 1.4E-09 |
| VEGFANGBII00025 | 1.1E+05 | 1.4E-02 | 1.4E-02 | 2.1E-04 | 1.9E-09 |
| VEGFANGBII00028 | 1.7E+05 | 1.3E-02 | 1.3E-02 | 2.1E-04 | 1.1E-09 |

| | | | ELISA | | | | | | | HUVEC survival | |
|---|---|---|---|---|---|---|---|---|---|---|---|
| | | | Ang2 | | mAng2 | | cAng2 | | hAng1 | | |
| VHH ID | Format | HSA | $IC_{50}$ (pM) | % inh | $IC_{50}$ (pM) | % inh | $IC_{50}$ (pM) | % inh | $IC_{50}$ ratio hAng1/hAng2 | IC50 (nM) | % inh |
| 00938 |  | - | 33 | 100 | 58 | 100 | 86 | 100 | > 60,395 | 4.3 | 100 |
| VEGFANGBII00022 |  | - | 50 | 100 | 56 | 100 | 101 | 100 | > 39,902 | 1.9 | 100 |
| | | + | 45 | 100 | 68 | 100 | 115 | 100 | > 44,771 | n.d. | n.d. |
| AMG386 | | - | 5 | 100 | 2 | 100 | 13 | 100 | 5,656 | 1.4 | 100 |
| | | | | | | | | | | | |
| 00921 |  | - | 15,940 | 100 | 27,990 | 100 | 43,500 | 100 | > 125 | 18.8 | 100 |
| VEGFANGBII00025 |  | - | 12 | 100 | 15 | 100 | 38 | 100 | > 160,694 | 2.2 | 100 |
| | | + | 15 | 100 | 17 | 100 | 37 | 100 | > 133,660 | n.d. | n.d. |
| AMG386 | | - | 5 | 100 | 2 | 100 | 15 | 100 | 5,632 | 1.2 | 100 |
| | | | | | | | | | | | |
| 00956 |  | - | 1,010 | 100 | 1,816 | 100 | 1,294 | 100 | > 1,979 | 6.8 | 100 |
| VEGFANGBII00028 |  | - | 30 | 100 | 72 | 100 | 65 | 100 | > 66,222 | 3.7 | 100 |
| | | + | 39 | 100 | 69 | 100 | 78 | 100 | > 50,816 | n.d. | n.d. |
| AMG386 | | - | 4 | 100 | 3 | 100 | 14 | 100 | 5,194 | 1.0 | 100 | n.d., not determined

BISPECIFIC BINDING MOLECULES BINDING TO VEGF AND ANG2

CROSS-REFERENCES TO RELATED APPLICATIONS

This application is a continuation of U.S. Ser. No. 15/350,364, filed Nov. 14, 2016 which issued as U.S. Pat. No. 10,414,828, on Sep. 17, 2019, which is a division of U.S. patent application Ser. No. 13/433,359, filed Mar. 29, 2012, which issued as U.S. Pat. No. 9,527,925, on Dec. 27, 2016, all of which is incorporated by reference herein.

SEQUENCE LISTING

The instant application contains a Sequence Listing which has been submitted electronically in ASCII format and is hereby incorporated by reference in its entirety. Said ASCII copy, created on Apr. 10, 2019, named 12-0332-US-2_SL.txt and is 503,868 bytes in size.

FIELD OF THE INVENTION

The invention relates to the field of human therapy, in particular cancer therapy and agents and compositions useful in such therapy.

BACKGROUND OF THE INVENTION

When tumors reach a critical size of approximately 1 $mm^3$ they become dependent on angiogenesis for maintaining blood supply with oxygen and nutrients to allow for further growth. Anti-angiogenesis therapies have become an important treatment option for several types of tumors. These therapies have focused on blocking the VEGF pathway (Ferrara et al., Nat Rev Drug Discov. 2004 May; 3(5):391-400.) by neutralizing VEGF (Avastin) or its receptors (Sutent and Sorafinib). Recent studies in mice have shown, that Angiopoietin2 (Ang2), a ligand of the Tie2 receptor, controls vascular remodeling by enabling the functions of other angiogenic factors, such as VEGF. Ang2 is primarily expressed by endothelial cells, strongly induced by hypoxia and other angiogenic factors and has been demonstrated to regulate tumor vessel plasticity, allowing vessels to respond to VEGF and FGF2 (Augustin et al., Nat Rev Mol Cell Biol. 2009 March; 10(3):165-77.). Consistent with this role, the deletion or inhibition of Ang2 results in reduced angiogenesis (Gale et al., Dev Cell. 2002 September; 3(3):302-4.) (Falcon et al., Am J Pathol. 2009 November; 175(5):2159-70.). Elevated Ang2 serum concentrations have been reported for patients with colorectal cancer, NSCLC and melanoma (Goede et al., Br J Cancer. 2010 Oct. 26; 103(9):1407-14), (Park et al., Chest. 2007 July; 132(1): 200-6.), (Helfrich et al., Clin Cancer Res. 2009 Feb. 15; 15(4):1384-92.). In CRC cancer Ang2 serum levels correlate with therapeutic response to anti-VEGF therapy.

The Ang-Tie system consists of 2 receptors (Tie1 and Tie2) and 3 ligands (Ang1, Ang2 and Ang4) (Augustin et al., Nat Rev Mol Cell Biol. 2009 March; 10(3):165-77.). Tie2, Ang1 and Ang2 are the best studied members of this family, Tie1 is an orphan receptor and the role of Ang4 for vascular remodelling still needs to be defined. Ang2 and Ang1 mediate opposing functions upon Tie2 binding and activation. Ang2-mediated Tie2 activation results in endothelial cell activation, pericyte dissociation, vessel leakage and induction of vessel sprouting. In contrast to Ang2, Ang1 signaling maintains vessel integrity by recruitment of pericytes, thereby maintaining endothelial cell quiescence.

Angiopoietin 2 (Ang2) is a secreted, 66 kDa ligand for the Tie2 receptor tyrosine kinase (Augustin et al., Nat Rev Mol Cell Biol. 2009 March; 10(3):165-77.). Ang2 consists of an N-terminal coiled-coil domain and a C-terminal fibrinogen-like domain, the latter is required for Tie2 interaction. Ang2 is primarily expressed by endothelial cells and strongly induced by hypoxia and other angiogenic factors, including VEGF. Tie2 is found on endothelial cells, haematopoietic stem cells and tumor cells. Ang2-Tie2 has been demonstrated to regulate tumor vessel plasticity, allowing vessels to respond to VEGF and FGF2.

In vitro Ang2 has been shown to act as a modest mitogen, chemoattractant and inducer of tube formation in human umbilical vein endothelial cells (HUVEC). Ang2 induces tyrosine phosphorylation of ectopically expressed Tie2 in fibroblasts and promotes downstream signaling events, such as phosphorylation of ERK-MAPK, AKT and FAK in HUVEC. An antagonistic role of Ang2 in Ang1-induced endothelial cell responses has been described.

Ang2-deficiency has been shown to result in a profound lymphatic patterning defect in mice. Although the loss of Ang2 is dispensable for embryonic vascular development, Ang2-deficient mice have persistent vascular defects in the retina and kidney. Together with the dynamic pattern of Ang2 expression at sites of angiogenesis (for example ovary), these findings indicate that Ang2 controls vascular remodeling by enabling the functions of other angiogenic factors, such as VEGF.

The Ang2-Tie2 system exerts crucial roles during the angiogenic switch and later stages of tumor angiogenesis. Ang2 expression is strongly up-regulated in the tumor-associated endothelium. Reduced growth of tumors has been observed when implanted into Ang2-deficient mice, especially during early stages of tumor growth. Therapeutic blocking of Ang2 with Ang2 mAbs has shown broad efficacy in a variety of tumor xenograft models. Additive effects of Ang2 mAbs with inhibitors of VEGFR2 (mAbs and small molecular weight inhibitors) have been described.

As described in e.g. US2008/0014196 and WO2008/101985, angiogenesis is implicated in the pathogenesis of a number of disorders, including solid tumors and metastasis as well as eye diseases. One of the most important pro-angiogenic factors is vascular endothelial growth factor (VEGF), also termed VEGF-A or vascular permeability factor (VPF). VEGF belongs to a gene family that includes placenta growth factor (PIGF), VEGF-B, VEGF-C, VEGF-D, VEGF-E and VEGF-F. Alternative splicing of mRNA of a single gene of human VEGF results in at least six isoforms (VEGF121, VEGF145, VEGF165, VEGF183, VEGF189, and VEGF206), VEGF165 being the most abundant isoform.

Two VEGF tyrosine kinase receptors (VEGFR) have been identified that interact with VEGF, i.e. VEGFR-1 (also known as Flt-1) and VEGFR-2 (also known as KDR or FIK-1). VEGFR-1 has the highest affinity for VEGF, while VEGFR-2 has a somewhat lower affinity for VEGF. Ferrara (Endocrine Rev. 2004, 25: 581-611) provide a detailed description of VEGF, the interaction with its receptors and its function in normal and pathological processes can be found in Hoeben et al. Pharmacol. Rev. 2004, 56: 549-580.

VEGF has been reported to be a pivotal regulator of both normal and abnormal angiogenesis (Ferrara and Davis-Smyth, Endocrine Rev. 1997, 18: 4-25; Ferrara J. MoL Med. 1999, 77: 527-543). Compared to other growth factors that contribute to the processes of vascular formation, VEGF is unique in its high specificity for endothelial cells within the vascular system.

VEGF mRNA is overexpressed by the majority of human tumors. In the case of tumor growth, angiogenesis appears to be crucial for the transition from hyperplasia to neoplasia, and for providing nourishment for the growth and metastasis of the tumor (Folkman et al., 1989, Nature 339-58), which allows the tumor cells to acquire a growth advantage compared to the normal cells. Therefore, anti-angiogenesis therapies have become an important treatment option for several types of tumors. These therapies have focused on blocking the VEGF pathway (Ferrara et al., Nat Rev Drug Discov. 2004 May; 3(5): 391-400.

VEGF is also involved in eye diseases. The concentration of VEGF in eye fluids is highly correlated with the presence of active proliferation of blood vessels in patients with diabetic and other ischemia-related retinopathies. Furthermore, recent studies have demonstrated the localization of VEGF in choroidal neovascular membranes in patients affected by age-related macular degeneration (AMD). Up-regulation of VEGF has also been observed in various inflammatory disorders. VEGF has been implicated in the pathogenesis of rheutatoid arthritis, an inflammatory disease in which angiogenesis plays a significant role.

The elucidation of VEGF and its role in angiogenesis and different processes has provided a potential new target of therapeutic intervention. The function of VEGF has been inhibited by small molecules that block or prevent activation of VEGF receptor tyrosine kinases (Schlaeppi and Wood, 1999, Cancer Metastasis Rev., 18: 473-481) and consequently interfere with the VEGF receptor signal transduction pathway. Cytotoxic conjugates containing bacterial or plant toxins can inhibit the stimulating effect of VEGF on tumor angiogenesis. VEGF-DT385 toxin conjugates (diphtheria toxin domains fused or chemically conjugated to VEGF165), for example, efficiently inhibit tumor growth in vivo. Tumor growth inhibition could also be achieved by delivering a Flk-1 mutant or soluble VEGF receptors by a retrovirus.

VEGF-neutralizing antibodies, such as A4.6.I and MV833, have been developed to block VEGF from binding to its receptors and have shown preclinical antitumor activity (Kim et al. Nature 1993, 362: 841-844; Folkman Nat. Med. 1995, 1: 27-31; Presta et al. Cancer Res. 1997, 57: 4593-4599; Kanai et al. Int. J. Cancer 1998, 77: 933-936; Ferrara and Alitalo Nat. Med. 1999, 5: 1359-1364; 320, 340. For a review of therapeutic anti-VEGF approaches trials, see Campochiaro and Hackett (Oncogene 2003, 22: 6537-6548).

Most clinical experience has been obtained with A4.6.1, also called bevacizumab (Avastin®; Genentech, San Francisco, Calif.).

WO2008/101985 describes immunoglobulin single variable domains from camelides (VHHs or "Nanobodies®, as defined herein) that bind to VEGF, and their use in the treatment of conditions and diseases characterized by excessive and/or pathological angiogenesis or neovascularization.

It has been an object of the present invention to provide novel anti-angiogenic binding molecules for human therapy.

It has been a further object of the invention to provide methods for the prevention, treatment, alleviation and/or diagnosis of such diseases, disorders or conditions, involving the use and/or administration of such binding molecules and compositions comprising them. In particular, it is has been an object of the invention to provide such pharmacologically active binding molecules, compositions and/or methods that provide advantages compared to the agents, compositions and/or methods currently used and/or known in the art. These advantages include improved therapeutic and/or pharmacological properties and/or other advantageous properties, e.g. for manufacturing purposes, especially as compared to conventional antibodies as those described above, or fragments thereof.

BRIEF SUMMARY OF THE INVENTION

According to a first aspect, there are provided bispecific binding molecules, preferably bispecific immunoglobulins, preferably immunoglobulin single variable domains like VHHs and domain antibodies, which comprise at least one VEGF-binding component and at least one Ang2-binding component in a single molecule. Preferably, said bispecific binding molecules further comprise a serum albumin binding component.

More specifically, a bispecific binding molecule of the invention essentially comprises (i) a Ang2-binding component specifically binding to at least one epitope of Ang2 and (ii) a VEGF-binding component specifically binding to at least an epitope of VEGF, wherein the components are linked to each other in such a way that they simultaneously bind to Ang2 and VEGF or that they bind to either Ang2 or VEGF at a time.

According to preferred aspects of the invention, the two components comprise one or more immunoglobulin single variable domains that may be, independently of each other, VHHs or domain antibodies, and/or any other sort of immunoglobulin single variable domains, such as VL domains, as defined herein, provided that each of these immunoglobulin single variable domains will bind the antigen, i.e. Ang2 or VEGF, respectively.

According to a preferred embodiment, the immunoglobulin single variable domains are of the same type, in particular, all immunoglobulin single variable domains are VHHs or domain antibodies.

According to a particularly preferred embodiment, all immunoglobulin single variable domains are VHHs, preferably humanized (or "sequence-optimized", as defined herein) VHHs. Accordingly, the invention relates to bispecific binding molecules comprising an (optionally humanized or sequence-optimized) anti-Ang2 VHH and an (optionally humanized or sequence-optimized) anti-VEGF VHH.

However, it will be clear to the skilled person that the teaching herein may be applied analogously to bispecific binding molecules including other anti-Ang2 or anti-VEGF immunoglobulin single variable domains, such as domain antibodies.

In another aspect, the invention relates to nucleic acids encoding the bispecific binding molecules of the invention as well as host cells containing same.

The invention further relates to a product or composition containing or comprising at least one bispecific binding molecule of the invention and optionally one or more further components of such compositions.

The invention further relates to methods for preparing or generating the bispecific binding molecules, nucleic acids, host cells, products and compositions described herein.

The invention further relates to applications and uses of the bispecific binding molecules, nucleic acids, host cells, products and compositions described herein, as well as to methods for the prevention and/or treatment for diseases and disorders that can be modulated by inhibition of Ang2.

It has been found that the Ang2-binding component of the bispecific binding molecules according to the present invention binds to and antagonizes Ang2 with a potency at least 5,000 times higher, preferably 10,000 times higher than to Ang1 or Ang4. This will largely avoid blocking activation of Ang1-mediated signalling, which would counter the intended anti-angiogenetic effect.

It has further been found that the VEGF-binding component of the bi-specific binding molecules according to the present invention binds to VEGF-A with an affinity of at least 1,000 times higher, preferably at least 5,000 times higher, more preferably at least 10,000 times higher than to VEGF-B, VEGF-C, VEGF-D or PLGF. Due to the highly preferential binding to VEGF-A the signaling of VEGFR3, which modulates of lymph angiogenesis, is not interfered with.

In a preferred embodiment the bispecific binding molecules of the present invention are provided as linked VHH domains. Such molecules are significantly smaller than conventional antibodies and have thus the potential for penetrating into a tumor deeper than such conventional antibodies. This benefit is further accentuated by the specific sequences disclosed herein after being free of glycosylation sites.

Further, due to the bispecific nature (VEGF- and Ang2-binding components in one molecule) the tumor penetration of both functionalities will be necessarily equal, which will ensure that the beneficial effects of the combined antagonism of VEGF and Ang2 will be provided within the whole depth of penetration of the tumor. This is an advantage over the combination of individual antagonists against these targets, since the depth of penetration of individual antagonists will always vary to some degree.

Another advantage of a preferred bispecific binding molecules of the present invention is their increased serum half-like due to a serum albumin binding component such as a serum albumin binding molecule as described herein.

These and other aspects, embodiments, advantages and applications of the invention will become clear from the further description hereinbelow.

DEFINITIONS

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" ($2^{nd}$ Ed.), Gower Medical Publishing, London, New York (1989), as well as to the general background art cited herein; Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

The term "bispecific binding molecule" refers to a molecule comprising at least one Ang2-binding molecule (or "Ang2-binding component") and at least one VEGF-binding molecule (or "VEGF-binding component"). A bispecific binding molecule may contain more than one Ang2-binding molecule and/or more than one VEGF-binding molecule, i.e. in the case that the bispecific binding molecule contains a biparatopic (as defined below) Ang2-binding molecule and/or a biparatopic VEGF-binding molecule, in the part of the molecule that binds to Ang2 or to VEGF, i.e. in its "Ang2-binding component" (or anti-Ang2 component) or "VEGF-binding component" (or anti-VEGF component), respectively. The word "bispecific" in this context is however not to be construed as to exclude further binding components with binding specificity to molecules other than VEGF and Ang2 from the bispecific binding molecule. Non-limiting examples of such further binding components are binding components binding to serum albumin.

Unless indicated otherwise, the terms "immunoglobulin" and "immunoglobulin sequence"—whether used herein to refer to a heavy chain antibody or to a conventional 4-chain antibody—are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "(single) variable domain sequence", "VHH sequence" or "protein sequence"), should generally be understood to include both the relevant amino acid sequence as well as nucleic acid sequences or nucleotide sequences encoding the same, unless the context requires a more limited interpretation.

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a 2-layer sandwich of about 7 antiparallel beta-strands arranged in two beta-sheets, optionally stabilized by a conserved disulphide bond. An immunoglobulin domain comprises (a) variable domain(s), i.e., one or more immunoglobulin variable domains.

The term "immunoglobulin variable domain" as used herein means an immunoglobulin domain essentially consisting of four "framework regions" which are referred to in the art and hereinbelow as "framework region 1" or "FR1"; as "framework region 2" or"FR2"; as "framework region 3" or "FR3"; and as "framework region 4" or "FR4", respectively; which framework regions are interrupted by three "complementarity determining regions" or "CDRs", which are referred to in the art and hereinbelow as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site. In the context of the present invention immunoglobulin single variable domains like VHHs and domain antibodies are preferred.

The term "immunoglobulin single variable domain" as used herein means an immunoglobulin variable domain which is capable of specifically binding to an epitope of the antigen without pairing with an additional variable immunoglobulin domain. One example of immunoglobulin single variable domains in the meaning of the present invention are "domain antibodies", such as the immunoglobulin single variable domains VH and VL (VH domains and VL domains). Another example of immunoglobulin single variable domains are "VHH domains" (or simply "VHHs") from camelids, as defined hereinafter.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e. by a VH-VL pair of immunoglobulin domains, which jointly bind to an epitope of the respective antigen.

"VHH domains", also known as VHHs, VHH domains, VHH antibody fragments, and VHH antibodies, have originally been described as the antigen binding immunoglobulin (variable) domain of "heavy chain antibodies" (i.e. of "antibodies devoid of light chains"; Hamers-Casterman C, Atarhouch T, Muyldermans S, Robinson G, Hamers C, Songa E B, Bendahman N, Hamers R.: "Naturally occurring antibodies devoid of light chains"; Nature 363, 446-448 (1993)). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the present invention, the terms VHH domain, VHH, $V_H$H domain, VHH antibody fragment, VHH antibody, as well as "Nanobody®" and "Nanobody® domain" ("Nanobody" being a trademark of the company Ablynx N.V.; Ghent; Belgium) are used interchangeably and are representatives of immunoglobulin single variable domains (having the structure FR1-CDR1-FR2-CDR2-FR3-CDR3-FR4 and specifically binding to an epitope without requiring the presence of a second immunoglobulin variable domain), and which are distinguished from VH domains by the so-called "hallmark residues", as defined in e.g. WO2009/109635, FIG. 1.

The amino acid residues of a immunoglobulin single variable domain, e.g. a VHH, are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g. in FIG. 2 of Riechmann and Muyldermans, J. Immunol. Methods 231, 25-38 (1999). According to this numbering FR1 comprises the amino acid residues at positions 1-30,
CDR1 comprises the amino acid residues at positions 31-35,
FR2 comprises the amino acids at positions 36-49,
CDR2 comprises the amino acid residues at positions 50-65,
FR3 comprises the amino acid residues at positions 66-94,
CDR3 comprises the amino acid residues at positions 95-102, and
FR4 comprises the amino acid residues at positions 103-113.

However, it should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of $V_H$ domains, which methods can also be applied in an analogous manner to VHH domains, are known in the art. However, in the present description, claims and figures, the numbering according to Kabat and applied to VHH domains as described above will be followed, unless indicated otherwise.

The total number of amino acid residues in a VHH domain will usually be in the range of from 110 to 120, often between 112 and 115. It should however be noted that smaller and longer sequences may also be suitable for the purposes described herein.

Immunoglobulin single variable domains, e.g. VHHs and domain antibodies, according to the preferred embodiments of the invention, have a number of unique structural characteristics and functional properties which makes them highly advantageous for use in therapy as functional antigen-binding molecules. In particular, and without being limited thereto, VHH domains (which have been "designed" by nature to functionally bind to an antigen without pairing with a light chain variable domain) can function as single, relatively small, functional antigen-binding structural units.

Due to their unique properties, immunoglobulin single variable domains, as defined herein, like VHHs or VHs (or VLs)—either alone or as part of a larger polypeptide, e.g. a biparatopic molecule—offer a number of significant advantages:

- only a single domain is required to bind an antigen with high affinity and with high selectivity, so that there is no need to have two separate domains present, nor to assure that these two domains are present in the right spacial conformation and configuration (i.e. through the use of especially designed linkers, as with scFv's);
- immunoglobulin single variable domains can be expressed from a single nucleic acid molecule and do not require any post-translational modification (like glycosylation;
- immunoglobulin single variable domains can easily be engineered into multivalent and multispecific formats (as further discussed herein);
- immunoglobulin single variable domains have high specificity and affinity for their target, low inherent toxicity and can be administered via alternative routes than infusion or injection;
- immunoglobulin single variable domains are highly stable to heat, pH, proteases and other denaturing agents or conditions and, thus, may be prepared, stored or transported without the use of refrigeration equipments;

immunoglobulin single variable domains are easy and relatively inexpensive to prepare, both on small scale and on a manufacturing scale. For example, immunoglobulin single variable domains can be produced using microbial fermentation (e.g. as further described below) and do not require the use of mammalian expression systems, as with for example conventional antibodies;

immunoglobulin single variable domains are relatively small (approximately 15 kDa, or 10 times smaller than a conventional IgG) compared to conventional 4-chain antibodies and antigen-binding fragments thereof, and therefore show high(er) penetration into tissues (including but not limited to solid tumors and other dense tissues) and can be administered in higher doses than such conventional 4-chain antibodies and antigen-binding fragments thereof;

VHHs have specific so-called "cavity-binding properties" (inter alia due to their extended CDR3 loop, compared to VH domains from 4-chain antibodies) and can therefore also access targets and epitopes not accessible to conventional 4-chain antibodies and antigen-binding fragments thereof;

VHHs have the particular advantage that they are highly soluble and very stable and do not have a tendency to aggregate (as with the mouse-derived antigen-binding domains described by Ward et al., Nature 341: 544-546 (1989)).

The immunoglobulin single variable domains of the invention are not limited with respect to a specific biological source from which they have been obtained or to a specific method of preparation. For example, obtaining VHHs may include the following steps:

(1) isolating the VHH domain of a naturally occurring heavy chain antibody; or screening a library comprising heavy chain antibodies or VHHs and isolating VHHs therefrom;

(2) expressing a nucleic acid molecule encoding a VHH with the naturally occurring sequence;

(3) "humanizing" (as described herein) a VHH, optionally after affinity maturation, with a naturally occurring sequence or expressing a nucleic acid encoding such humanized VHH;

(4) "camelizing" (as described below) a immunoglobulin single variable heavy domain from a naturally occurring antibody from an animal species, in particular a species of mammal, such as from a human being, or expressing a nucleic acid molecule encoding such camelized domain;

(5) "camelizing" a VH, or expressing a nucleic acid molecule encoding such a camelized VH;

(6) using techniques for preparing synthetically or semi-synthetically proteins, polypeptides or other amino acid sequences;

(7) preparing a nucleic acid molecule encoding a VHH domain using techniques for nucleic acid synthesis, followed by expression of the nucleic acid thus obtained;

(8) subjecting heavy chain antibodies or VHHs to affinity maturation, to mutagenesis (e.g. random mutagenesis or site-directed mutagenesis) and/or any other technique(s) in order to increase the affinity and/or specificity of the VHH; and/or (9) combinations or selections of the foregoing steps.

Suitable methods and techniques for performing the above-described steps are known in the art and will be clear to the skilled person. By way of example, methods of obtaining VHH domains binding to a specific antigen or epitope have been described in WO2006/040153 and WO2006/122786.

According to specific embodiments, the immunoglobulin single variable domains of the invention or present in the polypeptides of the invention are VHH domains with an amino acid sequence that essentially corresponds to the amino acid sequence of a naturally occurring VHH domain, but that has been "humanized" or "sequence-optimized" (optionally after affinity-maturation), i.e. by replacing one or more amino acid residues in the amino acid sequence of said naturally occurring VHH sequence by one or more of the amino acid residues that occur at the corresponding position(s) in a variable heavy domain of a conventional 4-chain antibody from a human being. This can be performed using methods known in the art, which can by routinely used by the skilled person.

A humanized VHH domain may contain one or more fully human framework region sequences, and, in an even more specific embodiment, may contain human framework region sequences derived from the human germline Vh3 sequences DP-29, DP-47, DP-51, or parts thereof, or be highly homologous thereto, optionally combined with JH sequences, such as JH5. Thus, a humanization protocol may comprise the replacement of any of the VHH residues with the corresponding framework 1, 2 and 3 (FRI, FR2 and FR3) residues of germline VH genes such as DP 47, DP 29 and DP 51) either alone or in combination. Suitable framework regions (FR) of the immunoglobulin single variable domains of the invention can be selected from those as set out e.g. in WO2006/004678 and specifically, include the so-called "KERE" (SEQ ID NO: 276) and "GLEW" (SEQ ID NO: 277) classes. Examples are immunoglobulin single variable domains having the amino acid sequence G-L-E-W (SEQ ID NO: 277) at about positions 44 to 47, and their respective humanized counterparts. A humanized VHH domain may contain one or more fully human framework region sequences.

By way of example, a humanizing substitution for VHHs belonging to the 103 P,R,S-group and/or the GLEW-group (SEQ ID NO: 277) (as defined below) is 108Q to 108L. Methods for humanizing immunoglobulin single variable domains are known in the art.

Binding immunoglobulin single variable domains with improved properties in view of therapeutic application, e.g. enhanced affinity or decreased immunogenicity, may be obtained from individual binding molecules by techniques known in the art, such as affinity maturation (for example, starting from synthetic, random or naturally occurring immunoglobulin sequences), CDR grafting, humanizing, combining fragments derived from different immunoglobulin sequences, PCR assembly using overlapping primers, and similar techniques for engineering immunoglobulin sequences well known to the skilled person; or any suitable combination of any of the foregoing, also termed "sequence optimization", as described herein. Reference is, for example, made to standard handbooks, as well as to the further description and Examples.

If appropriate, a binding molecule with increased affinity may be obtained by affinity-maturation of another binding molecule, the latter representing, with respect to the affinity-matured molecule, the "parent" binding molecule.

Methods of obtaining VHHs that bind to a specific antigen or epitope have been described earlier, e.g. in WO2006/040153 and WO2006/122786. As also described therein in detail, VHH domains derived from camelids can be "humanized" (also termed "sequence-optimized" herein, "sequence-optimizing" may, in addition to humanization, encompass an additional modification of the sequence by one or more mutations that furnish the VHH with improved properties, such as the removal of potential post translational modification sites) by replacing one or more amino acid residues in the amino acid sequence of the original VHH sequence by one or more of the amino acid residues that occur at the corresponding position(s) in a VH domain from a conventional 4-chain antibody from a human being. A humanized VHH domain can contain one or more fully human framework region sequences, and, in an even more specific embodiment, can contain human framework region sequences derived from DP-29, DP-47, DP-51, or parts thereof, optionally combined with JH sequences, such as JH5.

Domain antibodies, also known as "Dab"s and "dAbs" (the terms "Domain Antibodies" and "dAbs" being used as trademarks by the GlaxoSmithKline group of companies) have been described in e.g. Ward, E. S., et al.: "Binding activities of a repertoire of single immunoglobulin variable domains secreted from *Escherichia coli*"; Nature 341: 544-546 (1989); Holt, L. J. et al.: "Domain antibodies: proteins for therapy"; TRENDS in Biotechnology 21(11): 484-490 (2003); and WO2003/002609.

Domain antibodies essentially correspond to the VH or VL domains of antibodies from non-camelid mammals, in particular human 4-chain antibodies. In order to bind an epitope as a single antigen binding domain, i.e. without being paired with a VL or VH domain, respectively, specific selection for such antigen binding properties is required, e.g. by using libraries of human single VH or VL domain sequences.

Domain antibodies have, like VHHs, a molecular weight of approximately 13 to approximately 16 kDa and, if derived from fully human sequences, do not require humanization for e.g. therapeutical use in humans. As in the case of VHH domains, they are well expressed also in prokaryotic expression systems, providing a significant reduction in overall manufacturing cost.

Furthermore, it will also be clear to the skilled person that it is possible to "graft" one or more of the CDR's mentioned above onto other "scaffolds", including but not limited to human scaffolds or non-immunoglobulin scaffolds. Suitable scaffolds and techniques for such CDR grafting are known in the art.

The terms "epitope" and "antigenic determinant", which can be used interchangeably, refer to the part of a macromolecule, such as a polypeptide, that is recognized by antigen-binding molecules, such as conventional antibodies or the polypeptides of the invention, and more particularly by the antigen-binding site of said molecules. Epitopes define the minimum binding site for an immunoglobulin, and thus represent the target of specificity of an immunoglobulin.

A polypeptide (such as an immunoglobulin, an antibody, an immunoglobulin single variable domain of the invention, or generally an antigen-binding molecule or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein. In this context, a VEGF-binding component may also be referred to as "VEGF-neutralizing".

Generally, the term "specificity" refers to the number of different types of antigens or epitopes to which a particular antigen-binding molecule or antigen-binding protein (such as an immunoglobulin single variable domain of the invention) molecule can bind. The specificity of an antigen-binding molecule can be determined based on its affinity and/or avidity. The affinity, represented by the equilibrium constant for the dissociation of an antigen with an antigen-binding protein (KD), is a measure for the binding strength between an epitope and an antigen-binding site on the antigen-binding protein: the lesser the value of the KD, the stronger the binding strength between an epitope and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as an immunoglobulin, an antibody, an immunoglobulin single variable domain or a polypeptides containing it and the pertinent antigen. Avidity is related to both the affinity between an epitope and its antigen binding site on the antigen-binding molecule and the number of pertinent binding sites present on the antigen-binding molecule.

The part of an antigen-binding molecule that recognizes the epitope is called a paratope.

Unless indicated otherwise, the term "VEGF-binding molecule" or "Ang2-binding molecule" includes anti-VEGF or anti-Ang2 antibodies, anti-VEGF antibody or anti-Ang2 antibody fragments, "anti-VEGF antibody-like molecules" or "anti-Ang2 antibody-like molecules", as defined herein, and conjugates with any of these. Antibodies include, but are not limited to, monoclonal and chimerized monoclonal antibodies. The term "antibody" encompasses complete immunoglobulins, like monoclonal antibodies produced by recombinant expression in host cells, as well as antibody fragments or "antibody-like molecules", including single-chain antibodies and linear antibodies, so-called "SMIPs" ("Small Modular Immunopharmaceuticals"), as e.g described in WO2002/056910; Antibody-like molecules include immunoglobulin single variable domains, as defined herein. Other examples for antibody-like molecules are immunoglobulin super family antibodies (IgSF), or CDR-grafted molecules.

"Ang2-binding molecule" or "VEGF-binding molecule" respectively, refers to both monovalent target-binding molecules (i.e. molecules that bind to one epitope of the respective target) as well as to bi- or multivalent binding molecules (i.e. binding molecules that bind to more than one epitope, e.g. "biparatopic" molecules as defined hereinbelow). Ang2 (or VEGF)-binding molecules containing more than one Ang2 (or VEGF)-binding immunoglobulin single variable domain are also termed "formatted" binding molecules, they may, within the target-binding component, in addition to the immunoglobulin single variable domains, comprise linkers and/or moieties with effector functions, e.g. half-life-extending moieties like albumin-binding immunoglobulin single variable domains, and/or a fusion partner like serum albumin and/or an attached polymer like PEG.

The term "biparatopic Ang2(or VEGF)-binding molecule" or "biparatopic immunoglobulin single variable domain" as used herein shall mean a binding molecule comprising a first immunoglobulin single variable domain and a second immunoglobulin single variable domain as herein defined, wherein the two molecules bind to two non-overlapping epitopes of the respective antigen. The biparatopic binding molecules are composed of immunoglobulin single variable domains which have different specificities with respect to the epitope. The part of an antigen-binding molecule (such as an antibody or an immunoglobulin single variable domain of the invention) that recognizes the epitope is called a paratope.

A formatted binding molecule may, albeit less preferred, also comprise two identical immunoglobulin single variable domains or two different immunoglobulin single variable domains that recognize the same or overlapping epitopes or their respective antigen. In this case, with respect to VEGF, the two immunoglobulin single variable domains may bind to the same or an overlapping epitope in each of the two monomers that form the VEGF dimer.

Typically, the binding molecules of the invention will bind with a dissociation constant ($K_D$) of 10E-5 to 10E-14 moles/liter (M) or less, and preferably 10E-7 to 10E-14 moles/liter (M) or less, more preferably 10E-8 to 10E-14 moles/liter, and even more preferably 10E-11 to 10E-13, as measured e.g. in a Biacore or in a Kinexa assay), and/or with an association constant ($K_A$) of at least 10E7 ME-1, preferably at least 10E8 ME-1, more preferably at least 10E9 ME-1, such as at least 10E11 ME-1. Any $K_D$ value greater than 10E-4 M is generally considered to indicate non-specific binding. Preferably, a polypeptide of the invention will bind to the desired antigen, i.e. VEGF or Ang2, respectively, with a $K_D$ less than 500 nM, preferably less than 200 nM, more preferably less than 10 nM, such as less than 500 pM. Specific binding of an antigen-binding protein to an antigen or epitope can be determined in any suitable manner known per se, including, for example, the assays described herein, Scatchard analysis and/or competitive binding assays, such as radioimmunoassays (RIA), enzyme immunoassays (EIA) and sandwich competition assays, and the different variants thereof known per se in the art.

Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, for example from WO1998/49185, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gln; (iii) polar, positively charged residues: His, Arg and Lys; (iv) large aliphatic, nonpolar residues: Met, Leu, Ile, Val and Cys; and (v) aromatic residues: Phe, Tyr and Trp. Particularly preferred conservative amino acid substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp or into Phe; Val into Ile or into Leu.

A polypeptide or nucleic acid molecule is considered to be "(in) essentially isolated (form)"—for example, when compared to its native biological source and/or the reaction medium or cultivation medium from which it has been obtained—when it has been separated from at least one other component with which it is usually associated in said source or medium, such as another protein/polypeptide, another nucleic acid, another biological component or macromolecule or at least one contaminant, impurity or minor component. In particular, a polypeptide or nucleic acid molecule is considered "essentially isolated" when it has been purified at least 2-fold, in particular at least 10-fold, more in particular at least 100-fold, and up to 1000-fold or more. A polypeptide or nucleic acid molecule that is "in essentially isolated form" is preferably essentially homogeneous, as determined using a suitable technique, such as a suitable chromatographical technique, such as polyacrylamide gel electrophoresis.

"Sequence identity" between two VEGF-binding molecule sequences or between two Ang2-binding molecule sequences indicates the percentage of amino acids that are identical between the sequences. It may be calculated or determined as described in paragraph f) on pages 49 and 50 of WO2008/020079. "Sequence similarity" indicates the percentage of amino acids that either are identical or that represent conservative amino acid substitutions.

Alternative methods for numbering the amino acid residues of VH domains, which methods can also be applied in an analogous manner to VHH domains, are known in the art. However, in the present description, claims and figures, the numbering according to Kabat and applied to VHH domains as described above will be followed, unless indicated otherwise.

An "affinity-matured" VEGF-binding molecule or Ang2-binding molecule, in particular a VHH or a domain antibody, has one or more alterations in one or more CDRs which result in an improved affinity for VEGF or Ang2, as compared to the respective parent VEGF-binding molecule or Ang2-binding molecule. Affinity-matured VEGF-binding molecules or Ang2-binding molecules of the invention may be prepared by methods known in the art, for example, as described by Marks et al., 1992, Biotechnology 10: 779-783, or Barbas, et al., 1994, Proc. Nat. Acad. Sci, USA 91: 3809-3813.; Shier et al., 1995, Gene 169:147-155; Yelton et al., 1995, Immunol. 155: 1994-2004; Jackson et al., 1995, J. Immunol. 154(7):3310-9; and Hawkins et al., 1992, J. Mol. Biol. 226(3): 889 896; KS Johnson and RE Hawkins, "Affinity maturation of antibodies using phage display", Oxford University Press 1996.

For the present invention, an "amino acid sequences of SEQ ID NO: x": includes, if not otherwise stated, an amino acid sequence that is 100% identical with the sequence shown in the respective SEQ ID NO: x;

a) amino acid sequences that have at least 80% amino acid identity with the sequence shown in the respective SEQ ID NO: x;

b) amino acid sequences that have 3, 2, or 1 amino acid differences with the sequence shown in the respective SEQ ID NO: x.

The terms "cancer" and "cancerous" refer to or describe the physiological condition in mammals that is typically characterized by unregulated cell growth/proliferation. Examples of cancer to be treated with a bispecific binding molecule of the invention, include but are not limited to carcinoma, lymphoma, blastoma, sarcoma, and leukemia. More particular examples of such cancers, as suggested for treatment with VEGF antagonists in US 2008/0014196, include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, gastric cancer, melanoma, and various types of head and neck cancer. Dysregulation of angiogenesis can lead to many disorders that can be treated by compositions and methods of the invention. These disorders include both non-neoplastic and neoplastic conditions. Neoplasties include but are not limited those described above.

Non-neoplastic disorders include, but are not limited to, as suggested for treatment with VEGF antagonists in US2008/0014196, undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osier-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

DETAILED DESCRIPTION OF THE INVENTION

In a first aspect, the present invention relates to a bispecific binding molecule comprising at least one Ang2-binding component and at least one VEGF-binding component.

In a preferred embodiment, the present invention relates to a bispecific binding molecule comprising at least one VEGF-binding component and at least one Ang2-binding component which further comprises at least a further binding component, preferably a serum albumin binding component (serum albumin binding molecule).

In a preferred embodiment, the serum albumin binding component of the binding molecule of the present invention is an isolated immunoglobulin single variable domain or a polypeptide containing one or more of said immunoglobulin single variable domains, wherein said immunoglobulin single variable domain consists of four framework regions and three complementarity determining regions CDR1, CDR2 and CDR3, respectively, and wherein said CDR3 has an amino acid sequence selected from amino acid sequences shown in SEQ ID NOs: 257, 260, 263, 266, 269, 272, or 275.

More preferably, said one or more immunoglobulin single variable domain of the serum albumin binding component contain a. a CDR3 with an amino acid sequence selected from a first group of amino acid sequences shown in SEQ ID NOs: SEQ IDs NOs: 257, 260, 263, 266, 269, 272, or 275;
b. a CDR1 with an amino acid sequences selected from a second group of amino acid sequences shown SEQ ID NOs:255, 258, 261, 264, 267, 270, or 273;
c. a CDR2 with an amino acid sequences selected from a second group of amino acid sequences shown SEQ ID NOs:256, 259, 262, 265, 268, 271, or 274.

In a more preferred embodiment, said one or more immunoglobulin single variable domains of the serum albumin binding component are VHHs, preferably having an amino acid sequence shown in SEQ ID NOs: 98 or 254.

According to preferred embodiments, said Ang2-binding component and said VEGF-binding component comprise at least one Ang2-binding immunoglobulin single variable domain and at least one VEGF-binding immunoglobulin single variable domain, respectively.

In a preferred aspect, said Ang2-binding component and said VEGF-binding component each comprise at least one VEGF-binding immunoglobulin single variable domain and at least one Ang2-binding immunoglobulin single variable domain, respectively, wherein each of said immunoglobulin single variable domains has four framework regions and three complementarity determining regions CDR1, CDR2 and CDR3, respectively.

Thus, the anti-Ang2 and/or the anti-VEGF component contained in the bispecific binding molecules of the invention may include two (or more) anti-Ang2 (or anti-VEGF, respectively) immunoglobulin single variable domains, wherein the immunoglobulin single variable domains are directed against different epitopes within the Ang2 (or VEGF) target. Thus, the two immunoglobulin single variable domains in a bispecific binding molecule will have different antigen specificity and therefore different CDR sequences.

Such bivalent binding molecules are also named "biparatopic single domain antibody constructs" (if the immunoglobulin single variable domains consist or essentially consist of single domain antibodies), or "biparatopic VHH constructs" (if the immunoglobulin single variable domains consist or essentially consist of VHHs), respectively, as the two immunoglobulin single variable domains will include two different paratopes.

In the bispecific binding molecule of the invention, one or both of the binding molecules may be bivalent; e.g. the VEGF-binding component may be biparatopic and the Ang2-binding component may be one immunoglobulin single variable domain, or the VEGF-binding component may be one immunoglobulin single variable domain and the Ang2-binding component may be biparatopic.

In bispecific binding molecules of the invention, it is preferably the VEGF-binding component that contains a bivalent VEGF-binding immunoglobulin single variable domain, e.g. a biparatopic VHH.

Such VEGF-binding immunoglobulin single variable domain may be two or more VEGF-binding VHHs, which are a. identical VHHs that are capable of blocking the interaction between recombinant human VEGF and the recombinant human VEGFR-2 with an inhibition rate of 60% or b. different VHHs that bind to non-overlapping epitopes of VEGF, wherein at least one VHH is capable of blocking the interaction between recombinant human VEGF and the recombinant human VEGFR-2 with an inhibition rate of ≥60% and wherein at least one VHH is capable of blocking said interaction with an inhibition rate of 60%.

The VEGF-binding component comprising at least a variable domain with four framework regions and three complementarity determining regions CDR1, CDR2 and CDR3, respectively, wherein said CDR3 has the amino acid sequence Ser Arg Ala Tyr Xaa Ser Xaa Arg Leu Arg Leu Xaa Xaa Thr Tyr Xaa Tyr as shown in SEQ ID NO: 1, wherein Xaa at position 5 is Gly or Ala;
Xaa at position 7 is Ser or Gly;
Xaa at position 12 is Gly, Ala or Pro;
Xaa at position 13 is Asp or Gly;
Xaa at position 16 is Asp or Glu; and wherein said VEGF-binding component is capable of blocking the interaction of human recombinant VEGF165 with the human recombinant VEGFR-2 with an inhibition rate of ≥60%.

According to preferred embodiments, Xaa at position 5 is Gly, Xaa at position 7 is Ser, Xaa at position 12 is Ala, and Xaa at position 13 is Asp.

In particular, said CDR3 has a sequence selected from

```
                                  SEQ ID NO: 2
SRAYGSSRLRLGDTYDY,

                                  SEQ ID NO: 3
SRAYGSSRLRLADTYDY;

                                  SEQ ID NO: 4
SRAYGSSRLRLADTYEY;

                                  SEQ ID NO: 5
SRAYGSGRLRLADTYDY;

                                  SEQ ID NO: 6
SRAYASSRLRLADTYDY;

                                  SEQ ID NO: 7
SRAYGSSRLRLPDTYDY;

                                  SEQ ID NO: 8
SRAYGSSRLRLPGTYDY.
```

According to certain embodiments, a VEGF-binding component comprises one or more immunoglobulin single variable domains each containing a. a CDR3 with an amino acid sequence selected from a first group of sequences shown in SEQ ID NO: 2 to 8;
b. a CDR1 and a CDR2 with an amino acid sequences that is contained, as indicated in Table 3, in a sequence selected from a second group of amino acid sequences shown in SEQ ID NOs: 9 to 46, wherein said second sequence contains the respective CDR3 selected according to a).

According to preferred embodiments, the immunoglobulin single variable domains are VHHs.

According to specific embodiments, the VHHs have amino acid sequences selected from sequences shown in SEQ ID NOs: 9-46.

According to another specific embodiment, the VHHs have amino acid sequences selected from SEQ ID NOs: 15, SEQ ID NO: 18 and SEQ ID NO: 25.

The invention also relates to VEGF-binding component that have been obtained by affinity maturation and/or sequence optimization of an above-defined VHH, e.g. to a VHH that has been obtained by sequence optimization of a VHH having an amino acid sequence shown in SEQ ID NO: 18. Examples are VHHs having amino acid sequences selected from sequences shown in SEQ ID NOs: 47-57.

According to certain embodiments, a VEGF-binding domain of the invention may be formatted, as herein defined, e.g. it may be biparatopic or comprise two identical immunoglobulin single variable domains. Such VEGF-binding components may comprise two or more VHHs, which are a) identical VHHs that are capable of blocking the interaction between recombinant human VEGF and the recombinant human VEGFR-2 with an inhibition rate of ≥60% or
b) different VHHs that bind to non-overlapping epitopes of VEGF, wherein at least one VHH is capable of blocking the interaction between recombinant human VEGF and the recombinant human VEGFR-2 with an inhibition rate of ≥60% and wherein at least one VHH binds is capable of blocking said interaction with an inhibition rate of ≤60%.

The percentage of blocking said interaction at an inhibition rate of ≥60% or ≤60%, respectively, refers to an inhibition rate as determined by an Amplified Luminescent Proximity Homogeneous Assay (AlphaScreen®), a competition ELISA, a plasmon resonance (SPR) based assay (Biacore®) as used in the Examples.

In the following, the ability of VHHs according to a) is also termed “receptor-blocking”, while the ability of VHHs according to b) is also termed “non-receptor-blocking”.

Preferably, the receptor-blocking VHHs have an inhibition rate of ≥80%, more preferably ≥90%; the most preferred VHHs being complete receptor blockers, i.e. have an inhibition rate of 100%.

A VEGF-binding component may contain two or more identical VHHs a) selected from VHHs having amino acid sequences shown in SEQ ID NOs: 9-46 or VHHs that have been obtained by affinity maturation and/or sequence optimization of such VHH. The VHH may be selected from VHHs having the amino acid shown in SEQ ID NO: 18 or SEQ ID NO: 47-57.

According to preferred embodiments, a formatted VEGF-binding component comprises two VHHs each having the amino acid sequence shown in SEQ ID NO: 57.

In formatted VEGF-binding components comprising two different VHHs a) said one or more VHHs with an inhibition rate of 60% are selected from
   i. VHHs having an amino acid sequence selected from amino acid sequences shown in SEQ ID NOs: 9-46 or
   ii. VHHs that have been obtained by affinity maturation and/or sequence optimization of such VHHs, and wherein
b) said one or more VHHs with an inhibition rate of ≤60% are selected from
   i. SEQ ID NOs: 58-124 or
   ii. VHHs that have been obtained by affinity maturation and/or sequence optimization of such VHH.

According to preferred embodiments, two VHHs are contained in polypeptides with amino acid sequences shown in SEQ ID NOs: 128-168, separated by linker sequences as indicated in Table 15.

In a preferred VEGF-binding component VHH a) i. has an amino acid sequence shown in SEQ ID NO: 18 and VHH b) i. has an amino acid sequence shown in SEQ ID NO: 64.

In other preferred VEGF-binding components VHHs according to a) ii. are selected from VHHs having an amino acid sequence shown in SEQ ID NOs: 47-57 and VHHs according to b) ii. are selected from VHHs having an amino acid sequence shown in SEQ ID NOs: 125-127.

Particularly preferred is a biparatopic VEGF-binding component comprising two VHHs, one of them having the amino acid shown in SEQ ID NO: 57 and one of them having the amino acid shown in SEQ ID NO: 127.

The Ang2-binding component comprises at least a variable domain with four framework regions and three complementarity determining regions CDR1, CDR2 and CDR3, respectively, wherein said CDR3 has an amino acid sequence selected from amino acid sequences shown in SEQ ID NOs: 226, 229, 232, 235, 238, 241, 244, 247, 250, or 253.

In a second aspect, said Ang2-binding component is an isolated immunoglobulin single variable domain or a polypeptide containing one or more of said immunoglobulin single variable domains, wherein said immunoglobulin single variable domain consists of four framework regions and three complementarity determining regions CDR1, CDR2 and CDR3, respectively, and wherein said CDR3 has an amino acid sequence selected from amino acid sequences shown in SEQ ID NOs: 226, 229, 232, 235, 238, 241, 244, 247, 250, or 253.

In a further aspect, said immunoglobulin single variable domain of the Ang2-binding component contains a. a CDR3 with an amino acid sequence selected from a first group of amino acid sequences shown in SEQ ID NOs: SEQ IDs NOs: 226, 229, 232, 235, 238, 241, 244, 247, 250, or 253 (see also Table 49);

b. a CDR1 with an amino acid sequences that is contained, as indicated in Table 36-A, 38-A, 41-A, or 45-A, as partial sequence in a sequence selected from a second group of amino acid sequences shown SEQ ID NOs: 224, 227, 230, 233, 236, 239, 242, 245, 248, or 251 (see also Table 49);

c. a CDR2 with an amino acid sequences that is contained, as indicated in Table 36-A, 38-A, 41-A, or 45-A, as partial sequence in a sequence selected from a second group of amino acid sequences shown SEQ ID NOs: 225, 228, 231, 234, 237, 240, 243, 246, 249, or 252 (see also Table 49).

Preferably, the immunoglobulin single variable domain of the Ang2-binding component is a VHH, preferably having amino acid sequence selected from amino acid sequences shown in SEQ ID NOs: 214, 215, 216, 217, 218, 219, 220, 221, 222, or 223.

In another preferred embodiment, the immunoglobulin single variable domain of the Ang2-binding component has been obtained by affinity maturation or humanization of an immunoglobulin single variable domain as described herein.

Similarly, the present invention also relates to a VHH which has been obtained by affinity maturation or humanization of a VHH of the Ang2-binding component as described herein.

The present invention thus also relates to an Ang2-binding VHH with an amino acid sequence selected from acid sequences shown in SEQ ID NOs: 214, 215, 216, 217, 218, 219, 220, 221, 222, or 223.

Suitable parent Ang2-binding components for affinity maturation are, by way of example, the above-described VHHs with amino acid sequences shown in SEQ ID NOs: 214, 215, 216, 217, 21 i8, or 219.

Accordingly, the invention also relates to Ang2-binding molecules that have been obtained by affinity maturation and/or sequence optimization of an above-defined VHH, e.g. to a VHH that has been obtained by sequence optimization of a VHH having an amino acid sequence shown as SEQ ID NOs: 217, 218, 219, 220, 221, 222, or 223. The "source" amino acid sequences that were used to generate the latter VHHs are shown in SEQ ID NOs: 214, 215, or 216. Also these amino acid sequences are suitable Ang2-binding components that can be applied in the binding molecules of the present invention.

As described herein, the binding molecule of the present invention preferably comprises at least one serum albumin binding component. Particularly preferred binding molecules thus have at least one VEGF-binding component, at least one Ang2-binding component and at least one serum albumin binding component. The order of these three binding components could be any possible order such as the order set out in FIG. 20B, 23B, 23D, 26B, 26C, 29G, 30B, 30C, or 38; or in FIG. 20A, 23A, 26A, or 30A, e.g. the VEGF-, Ang2-or serum albumin binding component can be N-terminal or C-terminal. Notably, "1 D01" (SEQ ID No: 214), "11B07", "00027" (SEQ ID No:216), "00908", "7G08" (SEQ ID No:215), "00919", "00921" (SEQ ID No: 220), "00928" (SEQ ID No:221), "00932", "00933", "00934", "00935", "00936", "00937", "00938" (SEQ ID No:222), or "00956" (SEQ ID No:223) as referred to in the legend of the aforementioned Tables and Figures stand for Ang2-binding components, while "00038" stands for a VEGF-binding component and "ALB11" stands for a serum albumin binding component. None of them is to be construed to a specific sequence, but stands for a Ang2-, VEGF- and serum albumin binding component in general when used in the context of possible set-ups of binding molecules of the present invention.

However, it is preferred that the serum albumin binding component is in between the VEGF- and Ang2-binding component (or vice versa), while it is particularly preferred that at least one VEGF-binding component is N-terminal, followed by at least one serum albumin binding component, followed by at least one Ang2-binding component at the C-Terminus. This set-up is shown to be specifically useful.

The present invention relates thus in a preferred aspect to binding molecules comprising at least one VEGF-binding component, at least one Ang2-binding component and at least one serum albumin binding component having an amino acid sequence selected from the amino acid sequences shown in SEQ ID NOs: 180-213, "At least one" binding component (VEGF, Ang2 or serum albumin) when used herein includes that a binding molecule of the present invention may contain one, two, three, four or five VEGF-, Ang2-, and/or serum albumin binding components (i.e., entities/units) which are preferably represented by an immunoglobulin singly variable domain as described herein.

The VEGF- and/or Ang2-binding components with improved properties in view of therapeutic application, e.g. enhanced affinity or decreased immunogenicity, may be obtained from individual VEGF-or Ang2-binding components of the invention by techniques known in the art, such as affinity maturation (for example, starting from synthetic, random or naturally occurring immunoglobulin sequences), CDR grafting, humanizing, combining fragments derived from different immunoglobulin sequences, PCR assembly using overlapping primers, and similar techniques for engineering immunoglobulin sequences well known to the skilled person; or any suitable combination of any of the foregoing, also termed "sequence optimization", as described herein. Reference is, for example, made to standard handbooks, as well as to the further description and Examples.

If appropriate, a VEGF-or Ang2-binding component of the invention with increased affinity may be obtained by affinity-maturation of another VEGF-or Ang2-binding component, the latter representing, with respect to the affinity-matured molecule, the "parent" VEGF-binding component.

In VEGF or Ang2 VHHs of the invention that start with EVQ, the N-terminal E may be replaced by a D (which is often a result of sequence-optimization) or it may be missing (as for expression of the VHH in *E. coli*). For formatted VEGF-binding components, this usually applies only to the VHH that is situated N-terminally.

A preferred, but non-limiting humanizing substitution for VEGF VHH domains belonging to the 103 P,R,S-group and/or the GLEW-group (SEQ ID NO: 277) (as defined below) is 108Q to 108L. Methods for humanizing immunoglobulin single variable domains are known in the art.

According to another embodiment, the immunoglobulin single variable domain is a domain antibody, as defined herein.

In yet another embodiment, the representatives of the class of VEGF- and/or Ang2-binding immunoglobulin single variable domains of the invention have amino acid sequences that correspond to the amino acid sequence of a naturally occurring VH domain that has been "camelized", i.e. by replacing one or more amino acid residues in the amino acid sequence of a naturally occurring variable heavy chain from a conventional 4-chain antibody by one or more amino acid residues that occur at the corresponding position(s) in a VHH domain of a heavy chain antibody. This can be performed in a manner known per se, which will be clear to the skilled person, and reference is additionally be made to WO1994/04678. Such camelization may preferentially occur at amino acid positions which are present at the VH-VL interface and at the so-called Camelidae Hallmark residues (see for example also WO1994/04678). A detailed description of such "humanization" and "camelization" techniques and preferred framework region sequences consistent therewith can additionally be taken from e.g. pp. 46 and pp. 98 of WO2006/040153 and pp. 107 of WO2006/122786.

The VEGF-binding components of the invention, e.g. immunoglobulin single variable domains, have specificity for VEGF in that they comprise one or more immunoglobulin single variable domains specifically binding to one or more epitopes within the VEGF molecule. The same is true for Ang2-binding components of the invention.

Specific binding of an VEGF-binding component to its antigen VEGF can be determined in any suitable manner known per se, including, for example, the assays described herein, Scatchard analysis and/or competitive binding assays, such as radioimmunoassays (RIA), enzyme immunoassays (EIA and ELISA) and sandwich competition assays, and the different variants thereof known per se in the art. The same is true for an Ang2-binding component when binding to its antigen.

With regard to the antigen VEGF, a VEGF-binding component of the invention, e.g. an immunoglobulin single variable domain, is not limited with regard to the species. Thus, the immunoglobulin single variable domains of the invention preferably bind to human VEGF, if intended for therapeutic purposes in humans. However, immunoglobulin single variable domains that bind to VEGF from another mammalian species are also within the scope of the invention. An immunoglobulin single variable domain of the invention binding to one species form of VEGF may cross-react with VEGF, which has a different sequence than the human one, from one or more other species. For example, immunoglobulin single variable domains of the invention binding to human VEGF may exhibit cross reactivity with VEGF from one or more other species of primates and/or with VEGF from one or more species of animals that are used in animal models for diseases, for example monkey, mouse, rat, rabbit, pig, dog, and in particular in animal models for diseases and disorders associated with VEGF-mediated effects on angiogenesis (such as the species and animal models mentioned herein). Immunoglobulin single variable domains of the invention that show such cross-reactivity are advantageous in a research and/or drug development, since it allows the immunoglobulin single variable domains of the invention to be tested in acknowledged disease models such as monkeys, in particular Cynomolgus or Rhesus, or mice and rats.

Preferably, in view of cross-reactivity with one or more VEGF molecules from species other than human that is/are intended for use as an animal model during development of a therapeutic VEGF antagonist, a VEGF-binding component recognizes an epitope in a region of the VEGF of interest that has a high degree of identity with human VEGF.

An immunoglobulin single variable domain of the invention recognizes an epitope which is, totally or in part, located in a region of VEGF that is relevant for binding to its receptor, in particular to VEGFR-2, which has been shown to be the receptor whose activation is causally involved in the neovascularisation of tumors. According to preferred aspects, immunoglobulin single variable domains of the invention block VEGF receptor activation, in particular VEGFR-2 activation, at least partially, preferably substantially and most preferably totally.

As described above, the ability of a VEGF-binding component to block the interaction between VEGF and its receptors, in particular the VEGFR-2, can be determined by an Amplified Luminescent Proximity Homogeneous Assay (AlphaScreen®), a competition ELISA, or a plasmon resonance (SPR) based assay (Biacore®), as described in the Examples.

Preferably, an immunoglobulin single variable domain of the invention binds to VEGF with an affinity less than 500 nM, preferably less than 200 nM, more preferably less than 10 nM, such as less than 500 pM (as determined by Surface Plasmon Resonance analysis, as described in Example 5.7). The same is true for an immunoglobulin single variable domain of the invention binds to angiopoietin.

Preferably, the immunoglobulin single variable domains of the invention have $IC_{50}$ values, as measured in a competition ELISA assay as described in Example 5.1. in the range of $10^{-6}$ to $10^{-10}$ moles/litre or less, more preferably in the range of $10^{-8}$ to $10^{-10}$ moles/litre or less and even more preferably in the range of $10^{-9}$ to $10^{-10}$ moles/litre or less.

According to a non-limiting but preferred embodiment of the invention, VEGF-binding immunoglobulin single variable domains of the invention bind to VEGF with an dissociation constant ($K_D$) of $10^{-5}$ to $10^{-12}$ moles/liter (M) or less, and preferably $10^{-7}$ to $10^{-12}$ moles/liter (M) or less and more preferably $10^{-8}$ to $10^{-12}$ moles/liter (M), and/or with an association constant ($K_A$) of at least $10^{7}$ $M^{-1}$, preferably at least $10^{8}$ $M^{-1}$, more preferably at least $10^{9}$ $M^{-1}$, such as at least $10^{12}$ $M^{-1}$; and in particular with a $K_D$ less than 500 nM, preferably less than 200 nM, more preferably less than 10 nM, such as less than 500 pM. The $K_D$ and $K_A$ values of the immunoglobulin single variable domain of the invention against VEGF can be determined. The same is true for an Ang2-binding immunoglobulin single variable domain of the invention.

Biparatopic VEGF-binding components comprising two or more immunoglobulin single variable domains essentially consist of or comprise (i) a first immunoglobulin single variable domain specifically binding to a first epitope of VEGF and (ii) a second immunoglobulin single variable domain specifically binding to a second epitope of VEGF, wherein the first epitope of VEGF and the second epitope of VEGF are not identical epitopes. In other words, such polypeptide of the invention comprises or essentially consist of two or more immunoglobulin single variable domains that are directed against at least two non-overlapping epitopes present in VEGF, wherein said immunoglobulin single variable domains are linked to each other in such a way that they are capable of simultaneously binding VEGF. In this sense, the polypeptide of the invention can also be regarded as a "bivalent" or "multivalent" immunoglobulin construct, and especially as a "multivalent immunoglobulin single variable domain construct", in that the polypeptide contains at least two binding sites for VEGF. (Such constructs are also termed "formatted" VEGF binding molecules, e.g. "formatted" VHHs). The same is true for biparatopic Ang2-binding components, mutatis mutandis.

Such VEGF-or Ang2-binding component of the invention includes (at least) two anti-VEGF or Ang2 immunoglobulin single variable domains, respectively, wherein (the) two immunoglobulin single variable domains are preferably directed against non-overlapping epitopes within the VEGF molecule or angiopoietin molecule, respectively. Thus, these two immunoglobulin single variable domains will have a different antigen specificity and therefore different CDR sequences. For this reason, such polypeptides of the invention will herein also be named "biparatopic polypeptides", or "biparatopic domain antibody constructs" (if the immunoglobulin single variable domains consist or essentially consist of domain antibodies), or "biparatopic VHH constructs" (if the immunoglobulin single variable domains consist or essentially consist of VHHs), respectively, as the two immunoglobulin single variable domains will include two different paratopes.

If a polypeptide of the invention is a biparatopic molecule as defined herein, at least one of the immunoglobulin single variable domain components binds to an epitope such that the interaction between recombinant human VEGF and recombinant humen VEGFR-2 is blocked at an inhibition rate of ≥80%. As has been shown in experiments of the invention, certain formatted molecules contain two VHHs that both block the VEGFR2 receptor at an inhibition rate of ≥80%. Certain VHHs of the invention block the VEGFR-2 at an inhibition rate of 100%, i.e. they are complete blockers.

In both cases, additional sequences and moieties may be present within the VEGF-binding components of the invention, e.g. N-terminally, C-terminally, or located between the two immunoglobulin single variable domains, e.g. linker sequences and sequences providing for effector functions, as set out in more detail herein.

According to another, albeit less preferred embodiment, a VEGF-binding component of the invention may include more than two anti-VEGF immunoglobulin single variable domains, i.e. three, four or even more anti-VEGF VHHs. In this case, at least two of the anti-VEGF immunoglobulin single variable domains are directed against non-overlapping epitopes within the VEGF molecule, wherein any further immunoglobulin single variable domain may bind to any of the two non-overlapping epitopes and/or a further epitope present in the VEGF molecule.

According to the invention, the two or more immunoglobulin single variable domains can be, independently of each other, VHHs or domain antibodies, and/or any other sort of immunoglobulin single variable domains, such as VL domains, as defined herein, provided that these immunoglobulin single variable domains will bind the antigen, i.e. VEGF or angiopoietin, respectively.

The detailed description of the binding components is primarily provided for the VEGF-binding component. However, all features and options outlined herein for the VEGF-binding component also apply equivalently for the Ang2-binding component, mutatis mutandis.

According to preferred embodiments, the binding molecules present in the bispecific binding molecules (the Ang2-binding molecules within the Ang2-binding component or the VEGF-binding molecules within the VEGF-binding component or the two adjacent Ang2- and VEGF-binding components) may be connected with each other directly (i.e. without use of a linker) or via a linker. The linker is preferably a linker peptide and will be selected so as to allow binding of the two different binding molecules to each of non-overlapping epitopes of the targets, either within one and the same target molecule, or within two different molecules.

In the case of biparatopic binding molecules, selection of linkers within the Ang2- or the VEGF-binding component will inter alia depend on the epitopes and, specifically, the distance between the epitopes on the target to which the immunoglobulin single variable domains bind, and will be clear to the skilled person based on the disclosure herein, optionally after some limited degree of routine experimentation.

Two binding molecules (two VHHs or domain antibodies or VHH and a domain antibody), or two binding components, may be linked to each other via an additional VHH or domain antibody, respectively (in such binding molecules, the two or more immunoglobulin single variable domains may be linked directly to said additional immunoglobulin single variable domain or via suitable linkers). Such an additional VHH or domain antibody may for example be a VHH or domain antibody that provides for an increased half-life. For example, the latter VHH or domain antibody may be one that is capable of binding to a (human) serum protein such as (human) serum albumin or (human) transferrin.

Alternatively, the two or more immunoglobulin single variable domains that bind to the respective target may be linked in series (either directly or via a suitable linker) and the additional VHH or domain antibody (which may provide for increased half-life) may be connected directly or via a linker to one of these two or more aforementioned immunoglobulin sequences.

Suitable linkers are described herein in connection with specific polypeptides of the invention and may—for example and without limitation—comprise an amino acid sequence, which amino acid sequence preferably has a length of 9 or more amino acids, more preferably at least 17 amino acids, such as about 20 to 40 amino acids. However, the upper limit is not critical but is chosen for reasons of convenience regarding e.g. biopharmaceutical production of such polypeptides.

The linker sequence may be a naturally occurring sequence or a non-naturally occurring sequence. If used for therapeutic purposes, the linker is preferably non-immunogenic in the subject to which the bispecific binding molecule of the invention is administered.

One useful group of linker sequences are linkers derived from the hinge region of heavy chain antibodies as described in WO1996/34103 and WO1994/04678.

Other examples are poly-alanine linker sequences such as Ala-Ala-Ala.

Further preferred examples of linker sequences are Gly/Ser linkers of different length such as $(gly_x ser_y)_z$ linkers, including $(gly_4 ser)_3$ (SEQ ID NO:278), $(gly_4 ser)_4$ (SEQ ID NO: 279), $(gly_4 ser)$ (SEQ ID NO: 280), $(gly_3 ser)$ (SEQ ID NO: 281), $gly_3$, and $(gly_3 ser_2)_3$ (SEQ ID NO: 282).

Some non-limiting examples of linkers are contained in bispecific binding molecules of the invention shown in Table 15 (SEQ ID NOs 128-168), e.g. the linkers

```
                                (35GS; SEQ ID NO: 169)
GGGGSGGGGSGGGGSGGGGSGGGGSGGGGSGGGGS;

                                 (9GS; SEQ ID NO: 170)
GGGGSGGGS;

                                (40GS; SEQ ID NO: 171)
GGGGSGGGGSGGGGSGGGGSGGGGSGGGGSGGGGSGGGGS.
```

If a formatted bispecific binding molecule of the invention is modified by the attachment of a polymer, for example of a polyethylene glycol PEG (polyethylene glycol) moiety, the linker sequence preferably includes an amino acid residue, such as a cysteine or a lysine, allowing such modification, e.g. PEGylation, in the linker region.

Examples of linkers useful for for PEGylation are:

```
                           ("GS9,C5", SEQ ID NO: 172)
GGGGCGGGS;

                           ("GS25,C5, SEQ ID NO: 173)
GGGGCGGGGSGGGGSGGGGSGGGGS

                          ("GS27,C14", SEQ ID NO: 174)
GGGSGGGGSGGGGCGGGGSGGGGSGGG,

                          ("GS35,C15", SEQ ID NO: 175)
GGGGSGGGGSGGGGCGGGGSGGGGSGGGGSGGGGS,
and

                           ("GS35,C5", SEQ ID NO: 176)
GGGGCGGGGSGGGGSGGGGSGGGGSGGGGSGGGGS.
```

Furthermore, the linker may also be a poly(ethylene glycol) moiety, as shown in e.g. WO2004/081026.

In another embodiment, the immunoglobulin single variable domains are linked to each other via another moiety (optionally via one or two linkers), such as another polypeptide which, in a preferred but non-limiting embodiment, may be a further immunoglobulin single variable domain as described above. Such moiety may either be essentially inactive or may have a biological effect such as improving the desired properties of the polypeptide or may confer one or more additional desired properties to the polypeptide. For example, and without limitation, the moiety may improve the half-life of the protein or polypeptide, and/or may reduce its immunogenicity or improve any other desired property.

According to a preferred embodiment, a bispecific binding molecule of the invention includes, especially when intended for use or used as a therapeutic agent, a moiety which extends the half-life of the polypeptide of the invention in serum or other body fluids of a patient. The term "half-life" is defined as the time it takes for the serum concentration of the (modified) polypeptide to reduce by 50%, in vivo, for example due to degradation of the polypeptide and/or clearance and/or sequestration by natural mechanisms.

More specifically, such half-life extending moiety can be covalently linked to or fused to an immunoglobulin single variable domain and may be, without limitation, an Fc portion, an albumin moiety, a fragment of an albumin moiety, an albumin binding moiety, such as an anti-albumin immunoglobulin single variable domain, a transferrin binding moiety, such as an anti-transferrin immunoglobulin single variable domain, a polyoxyalkylene molecule, such as a polyethylene glycol molecule, an albumin binding peptide or a hydroxyethyl starch (HES) derivative.

In another embodiment, the bispecific binding molecule of the invention comprises a moiety which binds to an antigen found in blood, such as serum albumin, serum immunoglobulins, thyroxine-binding protein, fibrinogen or transferrin, thereby conferring an increased half-life in vivo to the resulting polypeptide of the invention. According to a specifically preferred embodiment, such moiety is an albumin-binding immunoglobulin and, especially preferred, an albumin-binding immunoglobulin single variable domain such as an albumin-binding VHH domain.

If intended for use in humans, such albumin-binding immunoglobulin single variable domain preferably binds to human serum albumin and preferably is a humanized albumin-binding VHH domain.

Immunoglobulin single variable domains binding to human serum albumin are known in the art and are described in further detail in e.g. WO2006/122786. Specifically, useful albumin binding VHHs are ALB 1 and its humanized counterpart, ALB 8 (WO2009/095489). Other albumin binding VHH domains mentioned in the above patent publication may, however, be used as well.

A specifically useful albumin binding VHH domain is ALB8 which consists of or contains the amino acid sequence shown in SEQ ID NO: 98 or 254.

According to a further embodiment of the invention, the two immunoglobulin single variable domains, in preferably VHHs, may be fused to a serum albumin molecule, such as described e.g. in WO2001/79271 and WO2003/59934. As e.g. described in WO2001/79271, the fusion protein may be obtained by conventional recombinant technology: a DNA molecule coding for serum albumin, or a fragment thereof, is joined to the DNA coding for the bispecific binding molecule, the obtained construct is inserted into a plasmid suitable for expression in the selected host cell, e.g. a yeast cell like *Pichia pastoris* or a bacterial cell, and the host cell is then transfected with the fused nucleotide sequence and grown under suitable conditions. The sequence of a useful HSA is shown in SEQ ID NO: 99.

According to another embodiment, a half-life extending modification of a polypeptide of the invention (such modification also reducing immunogenicity of the polypeptide) comprises attachment of a suitable pharmacologically acceptable polymer, such as straight or branched chain poly(ethylene glycol) (PEG) or derivatives thereof (such as methoxypoly(ethylene glycol) or mPEG). Generally, any suitable form of PEGylation can be used, such as the PEGylation used in the art for antibodies and antibody fragments (including but not limited to domain antibodies and scFv's); reference is made, for example, to: Chapman, Nat. Biotechnol., 54, 531-545 (2002); Veronese and Harris, Adv. Drug Deliv. Rev. 54, 453-456 (2003); Harris and Chess, Nat. Rev. Drug. Discov. 2 (2003); and WO2004/060965.

Various reagents for PEGylation of polypeptides are also commercially available, for example from Nektar Therapeutics, USA, or NOF Corporation, Japan, such as the Sunbright® EA Series, SH Series, MA Series, CA Series, and ME Series, such as Sunbright® ME-100MA, Sunbright® ME-200MA, and Sunbright® ME-400MA.

Preferably, site-directed PEGylation is used, in particular via a cysteine-residue (see for example Yang et al., Protein Engineering 16, 761-770 (2003)). For example, for this purpose, PEG may be attached to a cysteine residue that naturally occurs in a polypeptide of the invention, a polypeptide of the invention may be modified so as to suitably introduce one or more cysteine residues for attachment of PEG, or an amino acid sequence comprising one or more cysteine residues for attachment of PEG may be fused to the N- and/or C-terminus of a polypeptide of the invention, all using techniques of protein engineering known per se to the skilled person.

Preferably, for the polypeptides of the invention, a PEG is used with a molecular weight of more than 5 kDa, such as more than 10 kDa and less than 200 kDa, such as less than 100 kDa; for example in the range of 20 kDa to 80 kDa.

With regard to PEGylation, its should be noted that generally, the invention also encompasses any bispecific binding molecule that has been PEGylated at one or more amino acid positions, preferably in such a way that said PEGylation either (1) increases the half-life in vivo; (2) reduces immunogenicity; (3) provides one or more further beneficial properties known per se for PEGylation; (4) does not essentially affect the affinity of the polypeptide for its target (e.g. does not reduce said affinity by more than 50%, and more preferably not by more than 10%, as determined by a suitable assay described in the art); and/or (4) does not affect any of the other desired properties of the bispecific binding molecules of the invention. Suitable PEG-groups and methods for attaching them, either specifically or non-specifically, will be clear to the skilled person. Various reagents for PEGylation of polypeptides are also commercially available, for example from Nektar Therapeutics, USA, or NOF Corporation, Japan, such as the Sunbright® EA Series, SH Series, MA Series, CA Series, and ME Series, such as Sunbright® ME-100MA, Sunbright® ME-200MA, and Sunbright® ME-400MA.

According to an especially preferred embodiment of the invention, a PEGylated polypeptide of the invention includes one PEG moiety of linear PEG having a molecular weight of 40 kDa or 60 kDa, wherein the PEG moiety is attached to the polypeptide in a linker region and, specifially, at a Cys residue at position 5 of a GS9-linker peptide as shown in SEQ ID NO:93, at position 14 of a GS27-linker peptide as shown in SEQ ID NO:95, or at position 15 of a GS35-linker peptide as shown in SEQ ID NO:96, or at position 5 of a 35GS-linker peptide as shown in SEQ ID NO:97.

A bispecific binding molecule of the invention may be PEGylated with one of the PEG reagents as mentioned above, such as "Sunbright® ME-400MA", as shown in the following chemical formula:

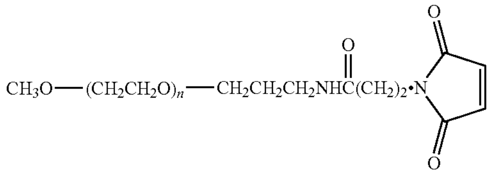

Bispecific binding molecules that contain linkers and/or half-life extending functional groups are shown in SEQ ID NO: 81 and in FIG. 48.

According to another embodiment, the immunoglobulin single variable domains are domain antibodies, as defined herein.

Immunoglobulin single variable domains present in the bispecific binding molecules of the invention may also have sequences that correspond to the amino acid sequence of a naturally occurring VH domain that has been "camelized", i.e. by replacing one or more amino acid residues in the amino acid sequence of a naturally occurring variable heavy chain from a conventional 4-chain antibody by one or more amino acid residues that occur at the corresponding position(s) in a VHH domain of a heavy chain antibody. This can be performed in a manner known per se, which will be clear to the skilled person, and reference is additionally be made to WO1994/04678. Such camelization may preferentially occur at amino acid positions which are present at the VH-VL interface and at the so-called Camelidae Hallmark residues (see for example also WO1994/04678). A detailed description of such "humanization" and "camelization" techniques and preferred framework region sequences consistent therewith can additionally be taken from e.g. pp. 46 and pp. 98 of WO2006/040153 and pp. 107 of WO2006/122786.

The binding components have specificity for Ang2 or VEGF, respectively, in that they comprise in a preferred embodiment one or more immunoglobulin single variable domains specifically binding to one or more epitopes within the Ang2 molecule or within the VEGF molecule, respectively.

Specific binding of a binding component to its antigen Ang2 or VEGF can be determined in any suitable manner known per se, including, for example, the assays described herein, Scatchard analysis and/or competitive binding assays, such as radioimmunoassays (RIA), enzyme immunoassays (EIA and ELISA) and sandwich competition assays, and the different variants thereof known per se in the art.

With regard to the antigen Ang2 or VEGF, respectively, an immunoglobulin single variable domain is not limited with regard to the species. Thus, the immunoglobulin single variable domains preferably bind to human Ang2 or to human VEGF, respectively, if intended for therapeutic purposes in humans. However, immunoglobulin single variable domains that bind to Ang2 or VEGF, respectively, from another mammalian species, or polypeptides containing them, are also within the scope of the invention. An immunoglobulin single variable domain binding to one species form of Ang2 or VEGF may cross-react with the respective antigen from one or more other species. For example, immunoglobulin single variable domains binding to the human antigen may exhibit cross reactivity with the respective antigen from one or more other species of primates and/or with the antigen from one or more species of animals that are used in animal models for diseases, for example monkey (in particular Cynomolgus or Rhesus), mouse, rat, rabbit, pig, dog or) and in particular in animal models for diseases and disorders that can be modulated by inhibition of Ang2 (such as the species and animal models mentioned herein). Immunoglobulin single variable domains of the invention that show such cross-reactivity are advantageous in a research and/or drug development, since it allows the immunoglobulin single variable domains of the invention to be tested in acknowledged disease models such as monkeys, in particular Cynomolgus or Rhesus, or mice and rats.

Also, the binding components are not limited to or defined by a specific domain or an antigenic determinant of the antigen against which they are directed. Preferably, in view of cross-reactivity with one or more antigen molecules from species other than human that is/are intended for use as an animal model during development of a therapeutic Ang2/VEGF antagonist, a binding component recognizes an epitope in a region of the the respective antigen that has a high degree of identity with the human antigen. By way of example, in view of using a mouse model, an anti-Ang2 immunoglobulin single variable domain contained in the bispecific binding molecules of the invention recognizes an epitope which is, totally or in part, located within the FLD domain of Ang2, which shows a high identity between human and mouse.

Preferably, the VEGF-binding component binds to the VEGF isoforms VEGF165 and/or VEGF121.

In another aspect, the invention relates to nucleic acid molecules that encode bispecific binding molecules of the invention. Such nucleic acid molecules will also be referred to herein as "nucleic acids of the invention" and may also be in the form of a genetic construct, as defined herein. A nucleic acid of the invention may be genomic DNA, cDNA or synthetic DNA (such as DNA with a codon usage that has been specifically adapted for expression in the intended host cell or host organism). According to one embodiment of the invention, the nucleic acid of the invention is in essentially isolated form, as defined hereabove.

The nucleic acid of the invention may also be in the form of, may be present in and/or may be part of a vector, such as for example a plasmid, cosmid or YAC. The vector may especially be an expression vector, i.e. a vector that can provide for expression of the bispecific binding molecule in vitro and/or in vivo (i.e. in a suitable host cell, host organism and/or expression system). Such expression vector generally comprises at least one nucleic acid of the invention that is operably linked to one or more suitable regulatory elements, such as promoter(s), enhancer(s), terminator(s), and the like. Such elements and their selection in view of expression of a specific sequence in a specific host are common knowledge of the skilled person. Specific examples of regulatory elements and other elements useful or necessary for expressing bispecific binding molecules of the invention, such as promoters, enhancers, terminators, integration factors, selection markers, leader sequences, reporter genes, and the like, are disclosed e.g. on pp. 131 to 133 of WO2006/040153.

The nucleic acids of the invention may be prepared or obtained in a manner known per se (e.g. by automated DNA synthesis and/or recombinant DNA technology), based on the information on the amino acid sequences for the polypeptides of the invention given herein, and/or can be isolated from a suitable natural source.

In another aspect, the invention relates to host cells that express or that are capable of expressing one or more bispecific binding molecules of the invention; and/or that contain a nucleic acid of the invention. According to a particularly preferred embodiment, said host cells are bacterial cells; other useful cells are yeast cells, fungal cells or mammalian cells.

Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (for example *Saccharomyces cerevisiae*), *Schizosaccharomyces* (for example *Schizosaccharomyces pombe*), *Pichia* (for example *Pichia pastoris* and *Pichia methanolica*), and *Hansenula*.

Suitable mammalian cells include for example CHO cells, BHK cells, HeLa cells, COS cells, and the like. However, amphibian cells, insect cells, plant cells, and any other cells used in the art for the expression of heterologous proteins can be used as well.

The invention further provides methods of manufacturing a bispecific binding molecule of the invention, such methods generally comprising the steps of:

culturing host cells comprising a nucleic acid capable of encoding a bispecific binding molecule under conditions that allow expression of the bispecific binding molecule of the invention; and recovering or isolating the polypeptide expressed by the host cells from the culture; and optionally further purifying and/or modifying and/or formulating the bispecific binding molecule of the invention.

For production on an industrial scale, preferred host organisms include strains of *E. coli, Pichia pastoris*, and *S. cerevisiae* that are suitable for large scale expression, production and fermentation, and in particular for large scale pharmaceutical expression, production and fermentation.

The choice of the specific expression system depends in part on the requirement for certain post-translational modifications, more specifically glycosylation. The production of a bispecific binding molecule of the invention for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression.

Bispecific binding molecules of the invention may be produced either in a cell as set out above intracellullarly (e.g. in the cytosol, in the periplasma or in inclusion bodies) and then isolated from the host cells and optionally further purified; or they can be produced extracellularly (e.g. in the medium in which the host cells are cultured) and then isolated from the culture medium and optionally further purified.

Methods and reagents used for the recombinant production of polypeptides, such as specific suitable expression vectors, transformation or transfection methods, selection markers, methods of induction of protein expression, culture conditions, and the like, are known in the art. Similarly, protein isolation and purification techniques useful in a method of manufacture of a polypeptide of the invention are well known to the skilled person.

In a further aspect, the invention relates to a peptide having an amino acid sequence of a CDR3 contained in an anti-VEGF-VHH having an amino acid sequence selected from sequences shown in SEQ ID NOs: 9 to 57 or SEQ ID NOs: 58-127, respectively, and a nucleic acid molecule encoding same.

These peptides correspond to CDR3s derived from the VHHs of the invention. They, in particular the nucleic acid molecules encoding them, are useful for CDR grafting in order to replace a CDR3 in an immunoglobulin chain, or for insertion into a non-immunoglobulin scaffold, e.g. a protease inhibitor, DNA-binding protein, cytochrome b562, a helix-bundle protein, a disulfide-bridged peptide, a lipocalin or an anticalin, thus conferring target-binding properties to such scaffold. The method of CDR-grafting is well known in the art and has been widely used, e.g. for humanizing antibodies (which usually comprises grafting the CDRs from a rodent antibody onto the Fv frameworks of a human antibody).

In order to obtain an immunoglobulin or a non-immunoglobulin scaffold containing a CDR3 of the invention, the DNA encoding such molecule may be obtained according to standard methods of molecular biology, e.g. by gene synthesis, by oligonucleotide annealing or by means of overlapping PCR fragments, as e.g. described by Daugherty et al., 1991, Nucleic Acids Research, Vol. 19, 9, 2471-2476. A method for inserting a VHH CDR3 into a non-immunoglobulin scaffold has been described by Nicaise et al., 2004, Protein Science, 13, 1882-1891.

The invention further relates to a product or composition containing or comprising at least one bispecific binding molecule of the invention and optionally one or more further components of such compositions known per se, i.e. depending on the intended use of the composition.

For pharmaceutical use, a bispecific binding molecule of the invention may be formulated as a pharmaceutical preparation or composition comprising at least one bispecific binding molecule of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one bispecific binding molecule, in particular one immunoglobulin single variable domain, of the invention and at least one suitable carrier, diluent or excipient (i.e. suitable for pharmaceutical use), and optionally one or more further active substances.

The bispecific binding molecules of the invention may be formulated and administered in any suitable manner known per se: Reference, in particular for the immunoglobulin single variable domains, is for example made to WO2004/041862, WO2004/041863, WO2004/041865, WO2004/041867 and WO2008/020079, as well as to the standard handbooks, such as Remington's Pharmaceutical Sciences, 18th Ed., Mack Publishing Company, USA (1990), Remington, the Science and Practice of Pharmacy, 21th Edition, Lippincott Williams and Wilkins (2005); or the Handbook of Therapeutic Antibodies (S. Dubel, Ed.), Wiley, Weinheim, 2007 (see for example pages 252-255).

For example, an immunoglobulin single variable domain of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, sterile water and pharmaceutically acceptable aqueous buffers and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

Thus, the bispecific binding molecule of the invention may be systemically administered, e.g., orally, in combination with a pharmaceutically acceptable vehicle such as an inert diluent or an assimilable edible carrier. For oral therapeutic administration, the bispecific binding molecule of the invention may be combined with one or more excipients and used in the form of ingestible tablets, buccal tablets, troches, capsules, elixirs, suspensions, syrups, wafers, and the like. Such compositions and preparations should contain at least 0.1% of the binding molecule of the invention. Their percentage in the compositions and preparations may, of course, be varied and may conveniently be between about 2 to about 60% of the weight of a given unit dosage form. The amount of the bispecific binding molecule of the invention in such therapeutically useful compositions is such that an effective dosage level will be obtained.

The tablets, pills, capsules, and the like may also contain binders, excipients, disintegrating agents, lubricants and sweetening or flavouring agents, for example those mentioned on pages 143-144 of WO2008/020079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the binding molecules of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the bispecific binding molecules of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The bispecific binding molecules of the invention may also be administered intravenously or intraperitoneally by infusion or injection, as further described on pages 144 and 145 of WO2008/020079.

For topical administration of the bispecific binding molecules of the invention, it will generally be desirable to administer them to the skin as compositions or formulations, in combination with a dermatologically acceptable carrier, which may be a solid or a liquid, as further described on page 145 of WO2008/020079.

Generally, the concentration of the bispecific binding molecules of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the bispecific binding molecules of the invention required for use in treatment will vary not only with the particular binding molecule selected, but also with the route of administration, the nature of the condition being treated and the age and condition of the patient and will be ultimately at the discretion of the attendant physician or clinician. Also, the dosage of the binding molecules of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen may include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

According to a further embodiment, the invention relates to the use of bispecific binding molecules, e.g. immunoglobulin single variable domains, for therapeutic purposes, such as

- for the prevention, treatment and/or alleviation of a disorder, disease or condition, especially in a human being, that is associated with VEGF- and/or Ang2-mediated effects on angiogenesis or that can be prevented, treated or alleviated by modulating the Notch signaling pathway and/or the Tie2 signalling pathway with a bispecific binding molecule according to the invention,
- in a method of treatment of a patient in need of such therapy, such method comprising administering, to a subject in need thereof, a pharmaceutically active amount of at least one bispecific binding molecule of the invention, e.g. an immunoglobulin single variable domain, or a pharmaceutical composition containing same;
- for the preparation of a medicament for the prevention, treatment or alleviation of disorders, diseases or conditions associated with VEGF- and/or Ang2-mediated effects on angiogenesis;
- as an active ingredient in a pharmaceutical composition or medicament used for the above purposes.

According to a specific aspect, said disorder disorder, disease or condition is a cancer or cancerous disease, as defined herein.

According to another aspect, the disease is an eye disease associated with VEGF- and/or Ang2-mediated effects on angiogenesis or which can be treated or alleviated by modulating the Notch signaling pathway with a bispecific binding molecule.

Depending on the cancerous disease to be treated, a bispecific binding molecule of the invention may be used on its own or in combination with one or more additional therapeutic agents, in particular selected from chemotherapeutic agents like DNA damaging agents or therapeutically active compounds that inhibit angiogenesis, signal transduction pathways or mitotic checkpoints in cancer cells.

The additional therapeutic agent may be administered simultaneously with, optionally as a component of the same pharmaceutical preparation, or before or after administration of the binding molecule.

In certain embodiments, the additional therapeutic agent may be, without limitation (and in the case of the receptors, including the respective ligands), one or more inhibitors selected from the group of inhibitors of EGFR, VEGFR, HER2-neu, Her3, AuroraA, AuroraB, PLK and PI3 kinase, FGFR, PDGFR, Raf, Ras, KSP, PDK1, PTK2, IGF-R or IR.

Further examples of additional therapeutic agents are inhibitors of CDK, Akt, src/bcr abl, cKit, cMet/HGF, c-Myc, Flt3, HSP90, hedgehog antagonists, inhibitors of JAK/STAT, MEK, mTor, NFkappaB, the proteasome, Rho, an inhibitor of wnt signaling or an inhibitor of the ubiquitination pathway or another inhibitor of the Notch signaling pathway.

Examples for Aurora inhibitors are, without limitation, PHA-739358, AZD-1152, AT 9283, CYC-116, R-763, VX-680, VX-667, MLN-8045, PF-3814735.

An example for a PLK inhibitor is GSK-461364.

Examples for raf inhibitors are BAY-73-4506 (also a VEGFR inhibitor), PLX 4032, RAF-265 (also in addition a VEGFR inhibitor), sorafenib (also in addition a VEGFR inhibitor), and XL 281.

Examples for KSP inhibitors are ispinesib, ARRY-520, AZD-4877, CK-1122697, GSK 246053A, GSK-923295, MK-0731, and SB-743921.

Examples for a src and/or bcr-abl inhibitors are dasatinib, AZD-0530, bosutinib, XL 228 (also an IGF-1R inhibitor), nilotinib (also a PDGFR and cKit inhibitor), imatinib (also a cKit inhibitor), and NS-187.

An example for a PDK1 inhibitor is BX-517.

An example for a Rho inhibitor is BA-210.

Examples for PI3 kinase inhibitors are PX-866, BEZ-235 (also an mTor inhibitor), XL 418 (also an Akt inhibitor), XL-147, and XL 765 (also an mTor inhibitor).

Examples for inhibitors of cMet or HGF are XL-184 (also an inhibitor of VEGFR, cKit, Flt3), PF-2341066, MK-2461, XL-880 (also an inhibitor of VEGFR), MGCD-265 (also an inhibitor of VEGFR, Ron, Tie2), SU-11274, PHA-665752, AMG-102, and AV-299.

An example for a c-Myc inhibitor is CX-3543.

Examples for Flt3 inhibitors are AC-220 (also an inhibitor of cKit and PDGFR), KW 2449, lestaurtinib (also an inhibitor of VEGFR, PDGFR, PKC), TG-101348 (also an inhibitor of JAK2), XL-999 (also an inhibitor of cKit, FGFR, PDGFR and VEGFR), sunitinib (also an inhibitor of PDGFR, VEGFR and cKit), and tandutinib (also an inhibitor of PDGFR, and cKit).

Examples for HSP90 inhibitors are tanespimycin, alvespimycin, IPI-504 and CNF 2024.

Examples for JAK/STAT inhibitors are CYT-997 (also interacting with tubulin), TG 101348 (also an inhibitor of Flt3), and XL-019.

Examples for MEK inhibitors are ARRY-142886, PD-325901, AZD-8330, and XL 518.

Examples for mTor inhibitors are temsirolimus, AP-23573 (which also acts as a VEGF inhibitor), everolimus (a VEGF inhibitor in addition). XL-765 (also a PI3 kinase inhibitor), and BEZ-235 (also a PI3 kinase inhibitor).

Examples for Akt inhibitors are perifosine, GSK-690693, RX-0201, and triciribine.

Examples for cKit inhibitors are AB-1010, OSI-930 (also acts as a VEGFR inhibitor), AC-220 (also an inhibitor of Flt3 and PDGFR), tandutinib (also an inhibitor of Flt3 and PDGFR), axitinib (also an inhibitor of VEGFR and PDGFR), XL-999 (also an inhibitor of Flt3, PDGFR, VEGFR, FGFR), sunitinib (also an inhibitor of Flt3, PDGFR, VEGFR), and XL-820 (also acts as a VEGFR- and PDGFR inhibitor), imatinib (also a bcr-abl inhibitor), nilotinib (also an inhibitor of bcr-abl and PDGFR).

Examples for hedgehog antagonists are IPI-609 and CUR-61414.

Examples for CDK inhibitors are seliciclib, AT-7519, P-276, ZK-CDK (also inhibiting VEGFR2 and PDGFR), PD-332991, R-547, SNS-032, PHA-690509, and AG 024322.

Examples for proteasome inhibitors are bortezomib, carfilzomib, and NPI-0052 (also an inhibitor of NFkappaB).

An example for an NFkappaB pathway inhibitor is NPI-0052.

An example for an ubiquitination pathway inhibitor is HBX-41108.

In preferred embodiments, the additional therapeutic agent is an anti-angiogenic agent.

Examples for anti-angiogenic agents are inhibitors of the FGFR, PDGFR and VEGFR or the respective ligands (e.g VEGF inhibitors like pegaptanib or the anti-VEGF antibody bevacizumab), EGFL7 inhibitors, such as anti-EGFL7 MAb, angiopoietinl/2 inhibitors such as AMG386, and thalidomides, such agents being selected from, without limitation, bevacizumab, motesanib, CDP-791, SU-14813, telatinib, KRN-951, ZK-CDK (also an inhibitor of CDK), ABT-869, BMS-690514, RAF-265, IMC-KDR, IMC-18F1, IMiDs (immunomodulatory drugs), thalidomide derivative CC-4047, lenalidomide, ENMD 0995, IMC-D11, Ki 23057, brivanib, cediranib, XL-999 (also an inhibitor of cKit and Flt3), 1B3, CP 868596, IMC 3G3, R-1530 (also an inhibitor of Flt3), sunitinib (also an inhibitor of cKit and Flt3), axitinib (also an inhibitor of cKit), lestaurtinib (also an inhibitor of Flt3 and PKC), vatalanib, tandutinib (also an inhibitor of Flt3 and cKit), pazopanib, GW 786034, PF-337210, IMC-1121B, AVE-0005, AG-13736, E-7080, CHIR 258, sorafenib tosylate (also an inhibitor of Raf), RAF-265 (also an inhibitor of Raf), vandetanib, CP-547632, OSI-930, AEE-788 (also an inhibitor of EGFR and Her2), BAY-57-9352 (also an inhibitor of Raf), BAY-73-4506 (also an inhibitor of Raf), XL 880 (also an inhibitor of cMet), XL-647 (also an inhibitor of EGFR and EphB4), XL 820 (also an inhibitor of cKit), and nilotinib (also an inhibitor of cKit and brc-abl).

The additional therapeutic agent may also be selected from EGFR inhibitors, it may be a small molecule EGFR inhibitor or an anti-EGFR antibody. Examples for anti-EGFR antibodies, without limitation, are cetuximab, panitumumab, matuzumab; an example for a small molecule EGFR inhibitor is gefitinib. Another example for an EGFR modulator is the EGF fusion toxin.

Among the EGFR and Her2 inhibitors useful for combination with the bispecific binding molecule of the invention are lapatinib, gefitinib, erlotinib, cetuximab, trastuzumab, nimotuzumab, zalutumumab, vandetanib (also an inhibitor of VEGFR), pertuzumab, XL-647, HKI-272, BMS-599626 ARRY-334543, AV 412, mAB-806, BMS-690514, JNJ-26483327, AEE-788 (also an inhibitor of VEGFR), ARRY-333786, IMC-11F8, Zemab.

Other agents that may be advantageously combined in a therapy with the bispecific binding molecule of the invention are tositumumab and ibritumomab tiuxetan (two radiolabelled anti-CD20 antibodies), alemtuzumab (an anti-CD52 antibody), denosumab, (an osteoclast differentiation factor ligand inhibitor), galiximab (a CD80 antagonist), ofatumumab (a CD20 inhibitor), zanolimumab (a CD4 antagonist), SGN40 (a CD40 ligand receptor modulator), rituximab (a CD20 inhibitor), mapatumumab (a TRAIL-1 receptor agonist), REGN421 (SAR153192) or OMP-21M18 (DII4 inhibitors).

Other chemotherapeutic drugs that may be used in combination with the bispecific binding molecule of the present invention are selected from, but not limited to hormones, hormonal analogues and antihormonals (e.g. tamoxifen, toremifene, raloxifene, fulvestrant, megestrol acetate, flutamide, nilutamide, bicalutamide, cyproterone acetate, finasteride, buserelin acetate, fludrocortisone, fluoxymesterone, medroxyprogesterone, octreotide, arzoxifene, pasireotide, vapreotide), aromatase inhibitors (e.g. anastrozole, letrozole, liarozole, exemestane, atamestane, formestane), LHRH agonists and antagonists (e.g. goserelin acetate, leuprolide, abarelix, cetrorelix, deslorelin, histrelin, triptorelin), antimetabolites (e.g. antifolates like methotrexate, pemetrexed, pyrimidine analogues like 5 fluorouracil, capecitabine, decitabine, nelarabine, and gemcitabine, purine and adenosine analogues such as mercaptopurine thioguanine, cladribine and pentostatin, cytarabine, fludarabine); antitumor antibiotics (e.g. anthracyclines like doxorubicin, daunorubicin, epirubicin and idarubicin, mitomycin-C, bleomycin dactinomycin, plicamycin, mitoxantrone, pixantrone, streptozocin); platinum derivatives (e.g. cisplatin, oxaliplatin, carboplatin, lobaplatin, satraplatin); alkylating agents (e.g. estramustine, meclorethamine, melphalan, chlorambucil, busulphan, dacarbazine, cyclophosphamide, ifosfamide, hydroxyurea, temozolomide, nitrosoureas such as carmustine and lomustine, thiotepa); antimitotic agents (e.g. *vinca* alkaloids like vinblastine, vindesine, vinorelbine, vinflunine and vincristine; and taxanes like paclitaxel, docetaxel and their formulations, larotaxel; simotaxel, and epothilones like ixabepilone, patupilone, ZK-EPO); topoisomerase inhibitors (e.g. epipodophyllotoxins like etoposide and etopophos, teniposide, amsacrine, topotecan, irinotecan) and miscellaneous chemotherapeutics such as amifostine, anagrelide, interferone alpha, procarbazine, mitotane, and porfimer, bexarotene, celecoxib.

The efficacy of bispecific binding molecule of the invention or polypeptides, and of compositions comprising the same, can be tested using any suitable in vitro assay, cell-based assay, in vivo assay and/or animal model known per se, or any combination thereof, depending on the specific disease or disorder of interest. Suitable assays and animal models will be clear to the skilled person, and for example include the assays described herein and used in the Examples below, e.g. a proliferation assay.

The data obtained in the experiments of the invention confirm that bispecific binding molecules of the invention have properties that are superior to those of binding molecules of the prior art. Among such properties are complete inhibition of the VEGF165-VEGFR2 interaction and a low IC50, as can e.g. be taken from the ELISA data of FIG. 1 and Table 5 as well as the $IC_{50}$ (nM) values for VHHs in the AlphaScreen assay as shown in FIGS. 3, 17, 18 and Table 7; and the affinity $K_D$ (nM) of purified VHHs on recombinant human VEGF and mouse VEGF in Table 9, 10 and FIG. 5. Also, as shown in Table 13, VEGF binders of the invention have high potency, i.e. in the subnanomolar range, in the HUVEC proliferation assay. This indicates that bispecific binding molecules of the invention are promising candidates to have therapeutic efficacy in diseases and disorders associated with VEGF-mediated effects on angiogenesis, such as cancer.

According to another embodiment of the invention, there is provided a method of diagnosing a disease by a) contacting a sample with a binding molecule of the invention as defined above, and b) detecting binding of said binding molecule to said sample, and c) comparing the binding detected in step (b) with a standard, wherein a difference in binding relative to said sample is diagnostic of a disease or disorder associated with VEGF- and/or Ang2-mediated effects on angiogenesis.

For this and other uses, it may be useful to further modify a bispecific binding molecule of the invention, such as by introduction of a functional group that is one part of a specific binding pair, such as the biotin-(strept)avidin binding pair. Such a functional group may be used to link the binding molecule of the invention to another protein, polypeptide or chemical compound that is bound to the other half of the binding pair, i.e. through formation of the binding pair. For example, a bispecific binding molecule of the invention may be conjugated to biotin, and linked to another protein, polypeptide, compound or carrier conjugated to avidin or streptavidin. For example, such a conjugated bispecific binding molecule of the invention may be used as a reporter, for example in a diagnostic system where a detectable signal-producing agent is conjugated to avidin or streptavidin.

BRIEF DESCRIPTION OF THE FIGURES

FIG. 16: Sequence alignment of VHH VEGFBII23B04 (SEQ ID NO:18) with human VH3/JH (SEQ ID NO:179) germline consensus sequence

FIG. 19: Sequence alignment of VHH VEGFBII5B05 (SEQ ID NO: 64) with human VH3/JH (SEQ ID NO: 179) germline consensus sequence FIG. 20 A-20C: Description bivalent Ang2 VHHs: A. discloses "9GS" and "9 GlySer" as SEQ ID NO: 170 and "40GS" and "40 GlySer" as SEQ ID NO: 171; B. Expression levels of all bivalent VHHs is depicted in FIG. 20 A; C. $IC_{50}$ values (pM) in human Ang2/human Tie2, mouse Ang2/mouse Tie2, cyno Ang2/cyno Tie2 and hAng1/hTie2 competition ELISA.

FIG. 28-1A to 28-1H; 28-2A to 28-2G; 28-3A to 28-3G: Purified trivalent and tetravalent VEGFxAng2 VHHs blocking hAng2-hTie2 (32-1), mAng2-mTie2 (32-2) and cAng2-cTie2 (32-3) interaction (ELISA)

FIG. 31-1A to 31-1C; 31-2A to 31-2C: Purified VEGFANGBII00022-25-28 VEGFxAng2 VHHs blocking hVEGF-hVEGFR2 (35-1) and hVEGF-hVEGFR1 (35-2) interaction (AlphaScreen)

FIG. 35-1A to 35-1C; 35-2A to 35-2C; 35-3A to 35-3C: Purified VEGFANGBII00022-25-28 VEGFxAng2 VHHs blocking hAng2-hTie2 (39-1), mAng2-mTie2 (39-2) and cAng2-cTie2 (39-3) interaction (ELISA)

Figure 1:
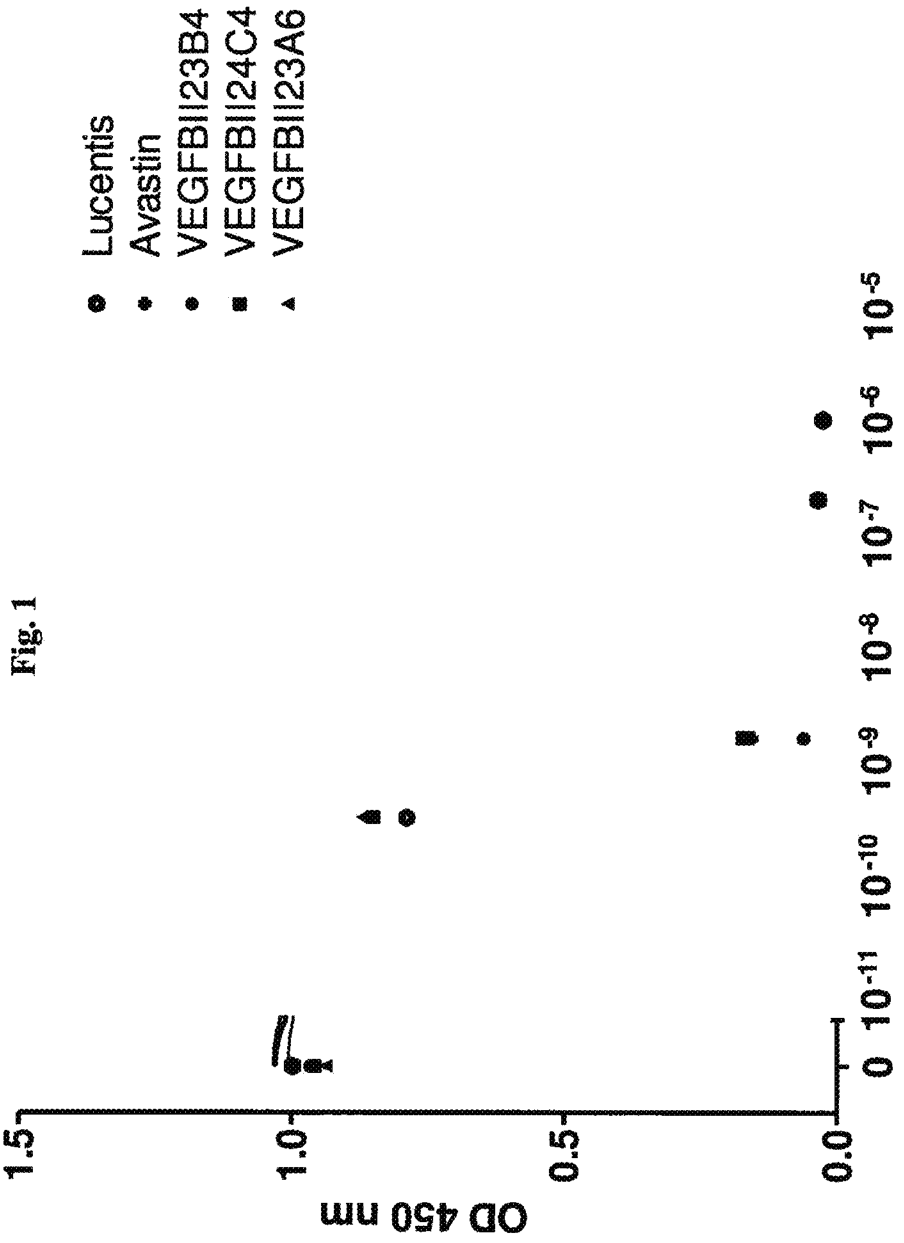
FIG. 1: Purified monovalent VHHs block the hVEGF165/hVEGFR2-Fc interaction (ELISA)

MATERIALS AND METHODS a) Production and Functionality Testing of VEGF109

A cDNA encoding the receptor binding domain of human vascular endothelial growth factor isoform VEGF165 (GenBank: AAM03108.1; AA residues 27-135) is cloned into pET28a vector (Novagen, Madison, Wis.) and overexpressed in *E. coli* (BL21 Star DE3) as a His-tagged insoluble protein. Expression is induced by addition of 1 mM IPTG and allowed to continue for 4 hours at 3TC. Cells are harvested by centrifugation and lysed by sonication of the cell pellet. Inclusion bodies are isolated by centrifugation. After a washing step with 1% Triton X 100 (Sigma-Aldrich), proteins are solubilized using 7.5M guanidine hydrochloride and refolded by consecutive rounds of overnight dialysis using buffers with decreasing urea concentrations from 6M till 0M. The refolded protein is purified by ion exchange chromatography using a MonoQ5/50GL (Amersham BioSciences) column followed by gel filtration with a Superdex75 10/300 GL column (Amersheim BioSciences). The purity and homogeneity of the protein is confirmed by SDS-PAGE and Western blot. In addition, binding activity to VEGFR1, VEGFR2 and Bevacizumab is monitored by ELISA. To this end, 1 μg/mL of recombinant human VEGF109 is immobilized overnight at 4° C. in a 96-well MaxiSorp plate (Nunc, Wiesbaden, Germany). Wells are blocked with a casein solution (1%). Serial dilutions of VEGFR1, VEGFR2 or Bevacizumab are added to the VEGF109 coated plate and binding is detected using alkaline phosphatase (AP) conjugated goat anti-human IgG, Fc specific (Jackson Immuno Research Laboratories Inc., West Grove, Pa., USA) and a subsequent enzymatic reaction in the presence of the substrate PNPP (p-nitrophenylphosphate) (Sigma-Aldrich). VEGF109 could bind to VEGFR1, VEGFR2 and Bevacizumab, indicating that the produced VEGF109 is active.

b) KLH Conjugation of VEGF165 and Functionality Testing of KLH-Conjugated VEGF165

Recombinant human VEGF165 (R&D Systems, Minneapolis, Minn., USA) is conjugated to mariculture keyhole limpet hemocyanin (mcKLH) using the Imject Immunogen EDC kit with mcKLH (Pierce, Rockford, Ill., USA) according to the manufacturer's instructions. Efficient conjugation of the polypeptide to mcKLH is confirmed by SDS-PAGE. Functionality of the conjugated protein is checked by ELISA: 2 μg/mL of KLH conjugated VEGF165 is immobilized overnight at 4° C. in a 96-well MaxiSorp plate (Nunc, Wiesbaden, Germany). Wells are blocked with a casein solution (1%). Serial dilutions of VEGFR1 or VEGFR2 are added and binding is detected using a horseradish peroxidase (HRP)-conjugated goat anti-human IgG, Fc specific (Jackson Immuno Research Laboratories Inc., West Grove, Pa., USA) and a subsequent enzymatic reaction in the presence of the substrate TMB (3,3',5,5'-tetramentylbenzidine) (Pierce, Rockford, Ill., USA). The KLH conjugated protein could still interact with VEGFR1, VEGFR2 and Bevacizumab, confirming that the relevant epitopes onVEGF165 are still accessible.

Example 1

Immunization with Different VEGF Formats Induces a Humoral Immune Response in Llama 1.1 Immunizations After approval of the Ethical Committee of the faculty of Veterinary Medicine (University Ghent, Belgium), 4 llamas (designated No. 264, 265, 266, 267) are immunized according to standard protocols with 6 intramuscular injections (100 or 50 μg/dose at weekly intervals) of recombinant human VEGF109. The first injection at day 0 is formulated in Complete Freund's Adjuvant (Difco, Detroit, Mich., USA), while the subsequent injections are formulated in Incomplete Freund's Adjuvant (Difco, Detroit, Mich., USA). In addition, four llamas (designated No. 234, 235, 280 and 281) are immunized according to the following protocol: 5 intramuscular injections with KLH-conjugated human VEGH165 (100 or 50 μg/dose at biweekly intervals) followed by 4 intramuscular injections of human VEGF109 (first dose of 100 μg followed 2 weeks later with three 50 μg/dose at weekly interval).

1.2 Evaluation of VEGF-Induced Immune Responses in Llama

To monitor VEGF specific serum titers, an ELISA assay is set up in which 2 μg/mL of recombinant human VEGF165 or VEGF109 is immobilized overnight at 4° C. in a 96-well MaxiSorp plate (Nunc, Wiesbaden, Germany). Wells are blocked with a casein solution (1%). After addition of serum dilutions, bound total IgG is detected using horseradish peroxidase (HRP)-conjugated goat anti-llama immunoglobulin (Bethyl Laboratories Inc., Montgomery, Tex., USA) and a subsequent enzymatic reaction in the presence of the substrate TMB (3,3',5,5'-tetramentylbenzidine) (Pierce, Rockford, Ill., USA). For llamas 264, 265, 266 and 267, an additional ELISA is performed in which the isotype-specific responses against VEGF165 and VEGF109 are evaluated. Isotype specific responses are detected using mouse mAbs specifically recognizing conventional llama IgG1 and the heavy-chain only llama IgG2 and IgG3 [Daley et al. (2005). Clin. Diagn. Lab. Imm. 12:380-386] followed by a rabbit anti-mouse-HRP conjugate (DAKO). ELISAs are developed using TMB as chromogenic substrate and absorbance is measured at 450 nm. The serum titers for each llama are depicted in Table 1.

TABLE 1

Antibody-mediated specific serum response against VEGF165 and VEGF109 ELISA (recombinant protein solid phase coated)

| | | Recombinant human EGF165 | | | | Recombinant human VEGF109 | | | |
|---|---|---|---|---|---|---|---|---|---|
| Llama | Immunogen | Total IgG | IgG1 | IgG2 | IgG3 | Total IgG | IgG1 | IgG2 | IgG3 |
| 234 | VEGF165-KLH + VEGF109 | ++ | n/d | n/d | n/d | ++ | n/d | n/d | n/d |
| 235 | VEGF165-KLH + VEGF109 | ++ | n/d | n/d | n/d | ++ | n/d | n/d | n/d |
| 280 | VEGF165-KLH + VEGF109 | + | n/d | n/d | n/d | + | n/d | n/d | n/d |
| 281 | VEGF165-KLH + VEGF109 | + | n/d | n/d | n/d | + | n/d | n/d | n/d |
| 264 | VEGF109 | n/d | ++ | + | + | ++ | ++ | + | + |
| 265 | VEGF109 | n/d | ++ | + | + | + | ++ | + | + |
| 266 | VEGF109 | n/d | ++ | + | +/− | ++ | ++ | + | +/− |
| 267 | VEGF109 | n/d | +/− | — | — | +/− | +/− | — | — |

n/d, not determined

Example 2

Cloning of the Heavy-Chain Only Antibody Fragment Repertoires and Preparation of Phage Following the final immunogen injection, immune tissues as the source of B-cells that produce the heavy-chain antibodies are collected from the immunized llamas. Typically, two 150-ml blood samples, collected 4 and 8 days after the last antigen injection, and one lymph node biopsy, collected 4 days after the last antigen injection are collected per animal. From the blood samples, peripheral blood mononuclear cells (PBMCs) are prepared using Ficoll-Hypaque according to the manufacturer's instructions (Amersham Biosciences, Piscataway, N.J., USA). From the PBMCs and the lymph node biopsy, total RNA is extracted, which is used as starting material for RT-PCR to amplify the VHH encoding DNA segments, as described in WO2005/044858. For each immunized llama, a library is constructed by pooling the total RNA isolated from all collected immune tissues of that animal. In short, the PCR-amplified VHH repertoire is cloned via specific restriction sites into a vector designed to facilitate phage display of the VHH library. The vector is derived from pUC119 and contains the LacZ promoter, a M13 phage gIII protein coding sequence, a resistance gene for ampicillin or carbenicillin, a multiple cloning site and a hybrid gIII-peIB leader sequence (pAX050). In frame with the VHH coding sequence, the vector encodes a C-terminal c-myc tag and a His6 tag (SEQ ID NO: 283). Phage are prepared according to standard protocols and stored after filter sterilization at 4° C. for further use.

Example 3

Selection of VEGF-Specific VHHs Via Phage Display

VHH phage libraries are used in different selection strategies applying a multiplicity of selection conditions. Variables include i) the VEGF protein format (rhVEGF165, rhVEGF109 or rmVEGF164), ii) the antigen presentation method (solid phase: directly coated or via a biotin-tag onto Neutravidin-coated plates; solution phase: incubation in solution followed by capturing on Neutravidin-coated plates), iii) the antigen concentration and iv) the elution method (trypsin or competitive elution using VEGFR2). All selections are carried out in Maxisorp 96-well plates (Nunc, Wiesbaden, Germany).

Selections are performed as follows: Phage libraries are incubated at RT with variable concentrations of VEGF antigen, either in solution or immobilized on a solid support. After 2 hrs of incubation and extensive washing, bound phage are eluted. In case trypsin is used for phage elution, the protease activity is immediately neutralized by addition of 0.8 mM protease inhibitor AEBSF. Phage outputs that show enrichment over background are used to infect *E. coli*. Infected *E. coli* cells are either used to prepare phage for the next selection round (phage rescue) or plated on agar plates (LB+amp+glucose$^{2\%}$) for analysis of individual VHH clones. In order to screen a selection output for specific binders, single colonies are picked from the agar plates and grown in 1 mL 96-deep-well plates. The lacZ-controlled VHH expression is induced by adding IPTG (0.1-1 mM final). Periplasmic extracts (in a volume of ~80 μL) are prepared according to standard methods.

Example 4

Identification of VEGF-Binding and VEGF Receptor-Blocking VHHs

Periplasmic extracts are tested for binding to human VEGF165 by ELISA. In brief, 2 μg/mL of recombinant human VEGF165 is immobilized overnight at 4° C. in a 96-well MaxiSorp plate (Nunc, Wiesbaden, Germany). Wells are blocked with a casein solution (1%). After addition of typically a 10-fold dilution of the periplasmic extracts, VHH binding is detected using a mouse anti-myc (Roche) and an anti-mouse-HRP conjugate (DAKO). Clones showing ELISA signals of >3-fold above background are considered as VEGF binding VHHs.

In addition, periplasmic extracts are screened in a human VEGF165/human VEGFR2 AlphaScreen assay (Amplified Luminescent Proximity Homogeneous Assay) to assess the blocking capacity of the VHHs. Human VEGF165 is biotinylated using Sulfo-NHS-LC-Biotin (Pierce, Rockford, Ill., USA). Human VEGFR2/Fc chimera (R&D Systems, Minneapolis, Minn., USA) is captured using an anti-humanFc VHH which is coupled to acceptor beads according to the manufacturer's instructions (Perkin Elmer, Waltham, Mass., US). To evaluate the neutralizing capacity of the VHHs, periplasmic extracts are diluted 1/25 in PBS buffer containing 0.03% Tween 20 (Sigma-Aldrich) and preincubated with 0.4 nM biotinylated human VEGF165 for 15 minutes at room temperature (RT). To this mixture the acceptor beads (10 μg/ml) and 0.4 nM VEGFR2-huFc are added and further incubated for 1 hour at RT in the dark. Subsequently donor beads (10 μg/ml) are added followed by incubation of 1 hour at RT in the dark. Fluorescence is measured by reading plates on the Envision Multi label Plate reader (Perkin Elmer, Waltham, Mass., USA) using an excitation wavelength of 680 nm and an emission wavelength between 520 nm and 620 nm. Periplasmic extract containing irrelevant VHH is used as negative control. Periplasmic extracts containing anti-VEGF165 VHHs which are able to decrease the fluorescence signal with more than 60% relative to the signal of the negative control are identified as a hit. All hits identified in the AlphaScreen are confirmed in a competition ELISA. To this end, 1 μg/mL of human VEGFR2 chimera (R&D Systems, Minneapolis, Minn., USA) is coated in a 96-well MaxiSorp plate (Nunc, Wiesbaden, Germany). Five-fold dilutions of the periplasmic extracts are incubated in the presence of a fixed concentration (4 nM) of biotinylated human VEGF165 in PBS buffer containing 0.1% casein and 0.05% Tween 20 (Sigma-Aldrich). Binding of these VHH/bio-VEGF165 complexes to the human VEGFR2 chimera coated plate is detected using horseradish peroxidase (HRP) conjugated extravidin (Sigma, St Louis, Mo., USA). VHH sequence IDs and the corresponding AA sequences of VEGF-binding (non-receptor-blocking) VHHs and inhibitory (receptor-blocking) VHHs are listed in Table 2 and Table 3, respectively.

TABLE 2

Sequence IDs and AA sequences of monovalent "non-receptor-blocking" anti-VEGF VHHs (FR, framework; CDR, complementary determining region)

| VHH ID/ SEQ ID NO: | FR1/SEQ ID NO: | CDR1/ SEQ ID NO: | FR2/SEQ ID NO: | CDR2/SEQ ID NO: | FR3/SEQ ID NO: | CDR3/SEQ ID NO: | FR4/SEQ ID NO: |
|---|---|---|---|---|---|---|---|
| VEGFBII01C02/ 58 | EVQLVESGGG LVQAGGSLRL SCTASGGSFS/ 466 | SYGMG/ 284 | WFRQSPG KEREFVS/ 517 | AISEYSNTYC SDSVRG/330 | RFTISRDNTKN TVYLQMNSLTP DDTAIYYCAA/ 548 | SPTILLTTEQW YKY/389 | WGQGTQVT VSS/603 |
| VEGFBII01E07/ 59 | EVQLVESGGG LVQAGDSLRL SCVATGRTFR/ 467 | ASDMG/ 285 | WFRQAPG KEREFVA/ 518 | AINWSGLSTF YTDSVKG/331 | RFTISRDNDNG ALYLQMNTLKP EDTAVYSCAA/ 549 | GRIPSSSRFSS PAAYAS/390 | WGQGTQVT VSS/603 |
| VEGFBII03D12/ 60 | EVQLVESGGG LVQAGGSLRL SCTASTSIYT/ 468 | ITVMA/ 286 | WFRQAPG KEREFVA/ 518 | AITWSAPTTY YADSVKG/332 | RFTISRDNAKN TVYLRMNSLKP EDSAIYYCAA/ 550 | DRFKGRSIVTP SDYRY/391 | WGQGTQVT VSS/603 |
| VEGFBII04B08/ 61 | EVQLVESGGG LVQPGGSLRL SCAASGSAVG/ 469 | DITVA/ 287 | WYRQAPG IQRQLVA/ 519 | TITPSGYTYY WDFVKG/333 | RFTISRDNSKN IVYLQMNSLKP EDTAAYYCNT/ 551 | QFY/392 | WGQGTQVT VSS/603 |
| VEGFBII05B02/ 62 | EVQLVESGGG LVQAGGSLRL SCAASGRTFS/ 470 | TDDVG/ 288 | WFRQAPG KEREFVA/ 518 | VIRWSTGGTY TSDSVKG/334 | RFTLSRDNAKN TMYLQMNSLKP EDTAVYYCAA/ 552 | RSRPLGAGAWY SGEKHYN Y/393 | WGQGTQVT VSS/603 |
| VEGFBII05B03/ 63 | EVQLVESGGG LAQAGDSLRL SCAASGRSFS/ 471 | HYNMG/ 289 | WFRQAPG KEREFVA/ 518 | SIRGGGGSTT YANSVKD/335 | RFTISRENAKN TVYLQMNSLKP EDTAVYYCAA/ 553 | TAFYRGPYDYD Y/394 | WGQGTQVT VSS/603 |
| VEGFBII05B05/ 64 | EVQLVESGGG LVQPGGSLRL SCVASGIRFM/ 472 | SMA/ 290 | WYRQAPG KHRELVA/ 520 | RISSGGTTAY VDSVKG/336 | RFTISRDNSKN TVYLQMNSLKA EDTAVYYCNT/ 554 | FSSRPNP/395 | WGAGTQVT VSS/604 |
| VEGFBII06G02/ 65 | EVQLVESGGG LVQPGGSLRL SCAASGNIFS/ 473 | NNAMA/ 291 | WYRQAPG KQRELVA/ 521 | RISSGGGFTY YLDSVKG/337 | RFTVSRDNAKN TVYLQMNSLKP EDTAVYYCNA/ 555 | AYRTYNY/396 | WGQGTQVT VSS/603 |
| VEGFBII07A03/ 66 | EVQLVESGGG LVQAGGSLRL SCAASTSIYS/ 474 | ITVMA/ 286 | WFRQAPG KESEFVA/ 522 | AITWSAPSSY YADSVKG/338 | RFTISRDNAKN TVYLQMNSLKP EDSAIYYCAA/ 556 | DRFKGRSIVTR SDYKY/397 | WGQGTQVT VSS/603 |
| VEGFBII07A06/ 67 | EVQLVESGGG LVQAGGSLRL SCAVSTSIYS/ 475 | ISVMA/ 292 | WFRQAPG KERAFVA/ 523 | AITWSAPTTY YADSVKG/332 | RFTISRDNAKN TVYLQTNSLKP EDSAIYYCAA/ 557 | DRFKGRSIVTR SDYRY/398 | WGQGTQVT VSS/603 |
| VEGFBII07D08/ 68 | EVQLVESGGG LVQTGGSLRL SCAASGRTFS/ 476 | NYAMA/ 293 | WFRQAPG KEREFVS/ 524 | AINQRGSNTN YADSVKG/339 | RFTISRDSAKN SVFLQMNSLKP EDTAVYYCAA/ 558 | STWYGYSTYAR REEYRY/399 | WGQGTQVT VSS/603 |

TABLE 2-continued

Sequence IDs and AA sequences of monovalent "non-receptor-blocking" anti-VEGF VHHs (FR, framework; CDR, complementary determining region)

| VHH ID/ SEQ ID NO: | FR1/SEQ ID NO: | CDR1/ SEQ ID NO: | FR2/SEQ ID NO: | CDR2/SEQ ID NO: | FR3/SEQ ID NO: | CDR3/SEQ ID NO: | FR4/SEQ ID NO: |
|---|---|---|---|---|---|---|---|
| VEGFBII08D09/ 69 | EVQLVESGGG LVQAGGSLRL SCAASGRSFS/ 477 | DNVMG/ 294 | WFRQAAG KEREFVA/ 525 | HISRGGSRTE YAESVKG/340 | RFTISRDNTKK TMYLQMNSLKP EDTAVYYCAA/ 559 | SRSVALATARP YDY/400 | WGQGTQVT VSS/603 |
| VEGFBII08E07/ 70 | EVQLVESGGG LAQAGGSLRL SCTTSGLTFS/ 478 | SYYMG/ 295 | WFRQAPG KEREFVA/ 518 | TISWNKISTI YTDSVKG/341 | RFTVSRDNNKN TVYLQMNSLKP EDTAVYYCAA/ 560 | DASRPTLRIPQ Y/401 | WGQGTQVT VSS/603 |
| VEGFBII08F06/ 71 | EVQLVESGGG LVQPGGSLRL SCAASGSIVR 479 | SDVMG/ 296 | WYRQAPG KQRELVA/ 521 | FIRSLGSTYY AGSVKG/342 | RFTISRDDAAN TVYLQMNNLKP EDTAVYYCNA/ 561 | RFSGESY/402 | WGQGTPVT VSS/605 |
| VEGFBII08F07/ 72 | EVQLVESGGG LVQAGGSLRL SCAVSGSTFG/ 480 | LYAMG/ 297 | WFRQAPG REREFLS/ 526 | AITWSAGDTQ YADSVKG/343 | RFTISRDNARN TVNLQMNGLKP EDTAVYYCAG/ 562 | RQWGGTYYYHG SYAY/403 | WGQGTQVT VSS/603 |
| VEGFBII09A09/ 73 | EVQLVESGGG LVQPGGSLRL SCVASGIRFM/ 472 | SMA/ 290 | WYRQAPG KHRELVA/ 520 | RISSEGTTAY VDSVKG/344 | RFTISRDNSKN TVYLQMNSLKA EDTAVYYCNT/ 554 | FSSRPNP/395 | WGAGTTVT VSS/606 |
| VEGFBII09A12/ 74 | EVQLVESGGG LVQAGGSLRL SCAASGRTFS/ 470 | TDDVG/ 288 | WFRQAPG KEREFVA/ 518 | VIRWSTGGTY TSDSVAG/345 | RFTLSRDNAKN TMYLQMNSLKP EDTAVYYCAA/ 552 | RSRPLGAGAWY TGETRYDS/405 | WGQGTQVT VSS/603 |
| VEGFBII09D05/ 75 | EVQLVESGGG LVQPGDSLRL SCAASGLSFS/ 481 | RYGMG/ 298 | WFRQAPG KEREFVI/ 527 | AISEYDNVYT ADSVRG/346 | RFTISRDNSKS TVYLQMNSLKS EDTAVYYCAA/ 563 | SPTILLSTDEW YKY/406 | WGRGTQVT VSS/607 |
| VEGFBII09F05/ 76 | EVQLVESGGG LVQAGGSLRL SCAASGRTFS/ 470 | TDDVG/ 288 | WFRQAPG KEREFVA/ 518 | VIRWSTGGTY TSDSVKG/334 | RFTLSRDNAKN TMYLQMNSLKP EDTAVYYCAA/ 552 | RSRPLGAGAWY TGETRYNY/407 | WGQGTQVT VSS/603 |
| VEGFBII10007/ 77 | EVQLVESGGG LVQAGGSLSL SCAASARAFS/ 482 | NYAMG/ 299 | WFRQVPG REREFVA/ 528 | VITRSPSNTY YTDSVKG/347 | RFTISRDNAKN IVYLQMNSLKP EDTAVYYCAA/ 564 | HYWNSDSYTYT DSRWYNY/408 | WGQGTQVT VSS/603 |
| VEGFBII10E07/ 78 | EVQLVESGGG LVQAGGSLRL SCAASGRTFS/ 470 | NYAMG/ 299 | WFRQAPG KERVLVA/ 529 | DISSSGINTY VADAVKG/348 | RFTISRDNAKN TVYLQMNSLKP EDTAVYYCAA/ 565 | SAWWYSQMARD NYRY/409 | WGQGTQVT VSS/603 |
| VEGFBII10G04/ 79 | EVQLVESGGG LVQAGGSLRL SCAASGDTLS/ 483 | RYAMG/ 300 | WFRQAPG KEREFVA/ 518 | SINTSGKRTS YADSMKG/ 349 | RFAVSRDNAKN TGYLQMNSLKL EDTATYYCAA/ 566 | DRFFGSDSNEP RAYRY/410 | WGQGTQVT VSS/603 |
| VEGFBII10G05/ 80 | EVQLVESGGG LVQAGESLRL SCVASGITFS/ 484 | NYNMG/ 301 | WFRQAPG KEREFVA/ 518 | TIRHHGYDTY YAESVKG/350 | RFTISRDNAKN TVYLQMNSLKP EDTALYSCAK/ 567 | KLFWDMDPKTG FSS/411 | WGQGTQVT VSS/603 |
| VEGFBII11C08/ 81 | EVQLVESGGG LVQAGGSLRL SCAASGRTLS/ 485 | SYGLG/ 302 | WFRQAPG KEREFVA/ 518 | AIGWSGSSTY YADSVKG/351 | RFTVSVDNAKN TVYLKMNSLEP EDTAVYYCAA/ 568 | KVRNFNSDWDL LTSYNY/412 | WGQGTQVT VSS/603 |
| VEGFBII11C11/ 82 | EVQLVESGGG LVQAGGSLML SCAASGRALS/ 486 | SYAIG/ 303 | WFRQAPG REREFVA/ 530 | RISWSGANTY YADSVKG/ 352 | RFTISRGNAKN TVYLQMNSLKP EDTAAYYCAA/ 569 | QTTSKYDNYDA RAYGY/413 | WGQGTQVT VSS/603 |

TABLE 2-continued

Sequence IDs and AA sequences of monovalent "non-receptor-blocking" anti-VEGF VHHs (FR, framework; CDR, complementary determining region)

| VHH ID/ SEQ ID NO: | FR1/SEQ ID NO: | CDR1/ SEQ ID NO: | FR2/SEQ ID NO: | CDR2/SEQ ID NO: | FR3/SEQ ID NO: | CDR3/SEQ ID NO: | FR4/SEQ ID NO: |
|---|---|---|---|---|---|---|---|
| VEGFBII11D09/ 83 | EEQLVESGGGLVQAGGSLMLSCAASGRALS/ 487 | SYAIG/ 303 | WFRQAPGREREFVA/ 530 | RISWSGANTYYADSVKG/352 | RFTISRGNAKNTVYLQMNSLKPEDTAAYYCAA/ 569 | QTTSKYDNYDARAYGY/413 | WGQGTQVTVSS/603 |
| VEGFBII11E04/ 84 | EVQLVESGGGLVQAGGSLRLSCAASGRTFS/ 470 | SYAMG/ 304 | WFRQAPGKEREFVA/ 518 | TISQSGYSTYYADSVKG/353 | RFTISRDNAKNTVNLQMNSLKPEDTAVYYCAA/ 570 | DPFYSYGSPSPYRY/414 | WGQGTQVTVSS/603 |
| VEGFBII11E05/ 85 | EVQLVESGGGLVQPGGSLRLSCASSGRLFS/ 488 | FSAMG/ 305 | WFRQAPGKEREFVA/ 518 | AFKWSGSTTYYADYVKG/354 | RFTISTDNAKNILFLQMNSLKPEDTAIYYCAV/ 571 | DRFYTGRYYSSDEYDY/415 | WGQGTQVTVSS/603 |
| VEGFBII11F10/ 86 | EVQLVESGGGLVQAGGSLRLSCAASTSIYS/ 474 | ITVMA/ 286 | WFRQAPGKEREFVA/ 518 | AITWSAPSSYYADSVKG/ 355 | RFTISRDNAKNTVYLQVNSLKPEDSAIYYCAA/ 572 | DRFKGRSIVTRSDYRY/416 | WGQGTQVTVSS/603 |
| VEGFBII11F12/ 87 | EVQLVESGGGLVQSGGSLRLSCAASGRSFS/ 489 | SLAMG/ 306 | WFRQVPGKDREFVA/ 531 | SISQSGITTSYADSVKS/356 | RFTISRDSAKNTVYLQMNLLKPEDTAVYYCAT/ 573 | SVFYSTALTRPVDYRY/417 | WGQGTQVTVSS/603 |
| VEGFBII11G09/ 88 | EVQLVESGGGLVQAGGSLRLSCAASTSIYS/ 474 | ITVMA/ 286 | WFRQAPGKEREFVA/ 518 | AITWSAPTTYSADSVKG/ 357 | RFTISRDNAKNTVYLQMNSLKPEDSAIYYCAA/ 556 | DRFKGRSIVTRSDYRY/416 | WGQGTQVTVSS/603 |
| VEGFBII12A07/ 89 | EVQLVESGGGLVQAGGSLRLSCSVTGRTFN/ 490 | KYVMG/ 307 | WFRQAPGNDREFVA/ 532 | AITSRDGPTYYADSVKG/358 | RFTISGDNTKNKIFLQMNSLMPEDTAVYYCAI/ 574 | DEDLYHYSSYHFTRVDLYHY/418 | WGQGTQVTVSS/603 |
| VEGFBII12B01/ 90 | EVQLVESGGGLVQPGGSLRLACAASGFTLS/ 491 | SSWMY/ 308 | WVRQAPGKGLEWVS/ 533 | RISPGGLFTYYVDSVKG/359 | RFSVSTDNANNTLYLQMNSLKPEDTALYSCAK/ 575 | GGAPNYTP/419 | RGRGTQVTVSS/608 |
| VEGFBII12C04/ 91 | EVQLVESGGGLVQPGGSLRLSCAASGSIVR/ 479 | SDVMG/ 296 | WYRQAPGKQRELVA/ 521 | FIRSLGSTYYAGSVKG/342 | RFTISRDNAANTVYLQMNNLKPEDTAVYYCNA/ 576 | RFSGESY/402 | WGQGTPVTVSS/605 |
| VEGFBII12E10/ 92 | EVQLVESGGGLAQAGGSLRLSCTASGRTFN/ 492 | NYVMG/ 309 | WFRQAPGNEREFVA/ 534 | AITSTNGPTYYADSVKG/360 | RFTISGDNTKNKVFLQMDSLRPEDTAVYYCAI/ 577 | DEDLYHYSSYHYTRVALYHY/420 | WGQGTQVTVSS/603 |
| VEGFBII12G04/ 93 | EVQLVESGGGLVQSGDSLRLSCAVSGNTFG/ 493 | LYAMG/ 297 | WFRQAPGREREFVS/ 535 | AITWSAGDTQYADSVKG/343 | RFTISRDNARNTVNLQMNGLKPEDTAVYYCAG/ 562 | RQWGGTYYYHGSYAW/421 | WGQGTQVTVSS/603 |
| VEGFBII16C03/ 94 | EVQLVESEGGLVQAGGSLRLSCAASGRTFS/ 494 | TDDVG/ 288 | WFRQAPGKEREFVA/ 518 | VIRWSTGGTYTSDSVKG/ 334 | RFTLSRDNAKNTMYLQMNSLKPEDTAVYYCAA/ 552 | RSRPLGAGAWYTGENYYNY/ 422 | WGQGTQVTVSS/603 |
| VEGFBII16F11/ 95 | EVQLVESGGGLVQAGGSLRLSCAASGRTSS/ 495 | GYDMG/ 310 | WFRQAPGKEREFVT/ 536 | AITWSGGSTYSPDSVKG/361 | RFTISRDNAKNTVYLQMNNLTPEDTAVYYCAS/ 578 | GRIWRSRDYDSEKYYDI/423 | WGHGTQVTVSS/609 |
| VEGFBII36C08/ 96 | EVQLVESGGGLVQAGGSLRLSCAASGRTFS/ 470 | AYDMG/ 311 | WFRQAPGKEREFVA/ 518 | VISWTNSMTYYADSVKG/362 | RFTISRDNAKNTVYLQMNSLKPEDTAVYYCAV/ 579 | DRRRTYSRWRFYTGVNDYDY/424 | WGQGTQVTVSS/603 |

TABLE 2-continued

Sequence IDs and AA sequences of monovalent "non-receptor-blocking" anti-VEGF VHHs (FR, framework; CDR, complementary determining region)

| VHH ID/ SEQ ID NO: | FR1/SEQ ID NO: | CDR1/ SEQ ID NO: | FR2/SEQ ID NO: | CDR2/SEQ ID NO: | FR3/SEQ ID NO: | CDR3/SEQ ID NO: | FR4/SEQ ID NO: |
|---|---|---|---|---|---|---|---|
| VEGFBII37F09/ 97 | EVQLVESGGG LVQTGGSLRL SCAASGRTFS/ 476 | AYDMG/ 311 | WFRQAPG KEREFVA/ 518 | VISWSGGMTY YADSVQG/363 | RFTISRDNAKS TVYLQMNSPKP EDTAVYYCAV/ 580 | DRRRAYSRWRY YTGVNDYEF/ 425 | WGQGTQVT VSS/603 |
| VEGFBII38A06/ 98 | EVQLVESGGG LVQAGGSLRL SCAASGRTFS/ 470 | AYDMG/ 311 | WFRQAPG KEREFVA/ 518 | VISWSGGMTY YADSVKG/364 | RFTISRDNAKN TVYLQMNSLKP EDTAVYYCAV/ 579 | DRRRLYSRWRY YTGVNDYDY/ 426 | WGQGTQVT VSS/603 |
| VEGFBII39H11/ 99 | EVQLVESGGG LVQAGGSLRL SCAASGRTFS/ 470 | AYDMG/ 311 | WFRQAPG KEREFVA/ 518 | VISWTGGMTY YADSVKG/365 | RFTISRDKAKN TVSLQMNSLKP EDTAVYYCAV/ 581 | DRRRTYSRWRY YTGVNEYEY/ 427 | WGQGTQVT VSS/603 |
| VEGFBII41B06/ 100 | EVQLVESGGG LVQAGGSLRL SCAASGRTFS/ 470 | AYDMG/ 311 | WFRQAPG KEREFVA/ 518 | VISWTGDMTY YADSVKG/ 366 | RFTISRDKAKN TVSLQMNSLKP EDTAVYYCAA/ 582 | DRRRTYSRWRY YTGVNEYEY/ 427 | WGQGTQVT VSS/603 |
| VEGFBII41C05/ 101 | EVQLVESGGG LVQAGGSLRL SCAASGRTFS/ 470 | VYTMG/ 312 | WFRQAPG KEREFVA/ 518 | TISRTGDRTS YANSVKG/367 | RFTISRENAKN TVYLQMNSLKP EDTAVYSCAA/ 583 | GPIAPSPRPRE YYY/428 | WGQGTQVT VSS/603 |
| VEGFBII41D11/ 102 | EVQLMESGGG LVQAGGSLRL SCAASGRTFS/ 496 | AYDMG/ 311 | WFRQAPG KEREFVA/ 518 | VISWTGGMTY YADSVKG/ 365 | RFTISRDKAKN TVSLQMNSLKP EDTAVYYCAV/ 581 | DRRRTYSRWRY YTGVNEYEY/427 | WGQGTQVT VSS/603 |
| VEGFBII42F10/ 103 | EVQLVESGGG LVQAGGSLRL SCAASGRTFS/ 470 | AYDMG/ 311 | WFRQAPG KEREFVA/ 518 | VISWSGGMTD YADSVKG/368 | RFTISRENAKN TQFLQMNSLKP EDTAVYYCAV/ 584 | GRRRAYSRWRY YTGVNEYDY/ 429 | WGQGTQVT VSS/603 |
| VEGFBII86C11/ 104 | EVQLVESGGG LVQAGDSLRL SCTASGRTFN/ 497 | SYAMG/ 304 | WFRQAPG KERESVA/ 537 | HINRSGSSTY YADSVKG/ 369 | RFTISRDNAKN TVYLQLNSLKP EDTAVYYCAA/ 585 | GRYYSSDGVPS ASFNY/430 | WGQGTQVT VSS/603 |
| VEGFBII86E11/ 105 | EVQLVESGGG LVQAGDSLRL SCFTSARTFD/ 498 | TWAMA/ 313 | WFRQAPG KEREFIS/ 538 | AISWSGSMTY YTDSVKG/ 370 | RFIISRDNAQN TLFLQMNNTAP EDTAVYYCAA/ 586 | KTVDYCSAYEC YARLEYDY/ 431 | WGRGAQVT VSS/610 |
| VEGFBII86G08/ 106 | EVQLVESGGG LMQTGDSLRL SCAASGLRFT/ 499 | STNMG/ 314 | WFRQGPG KEREFVA/ 539 | AITLSGTTYY AEAVKG/ 371 | RFTISRDNDKN TVALQMNSLKP EDTAVYYCGA/ 587 | DPSYYSTSRYT KATEYDY/ 432 | WGQGTQVT VSS/603 |
| VEGFBII86G10/ 107 | EVQLVESGGG LVQAGGSLRL SCAASGRTFN/ 500 | TYTMG/ 315 | WFRQTPG TEREFVA/ 540 | AIRWTVNITY YADSVKG/ 372 | RFTISRDIVKN TVYLQMNSLKP EDTAVYYCAA/ 588 | QTSAPRSLIRM SNEYPY/433 | WGQGTQVT VSS/603 |
| VEGFBII86G11/ 108 | EVQLVESGGG LVQAGGSLRL SCAASGLTFS/ 501 | LYTVG/ 316 | WFRQAPG KEREFVA/ 518 | YISRSGSNRY YVDSVKG/ 373 | RFTLSRDNAKN TVDLQMNSLKT EDTAVYYCAA/ 589 | TSRGLSSLAGE YNY/434 | WGRGTQVT VSS/607 |
| VEGFBII86H09/ 109 | EVQLVESGGG LVQAGGSLRL SCTASGSAFK/ 502 | SYRMG/ 317 | WFRRTPG KEDEFVA/ 541 | SISWTYGSTF YADSVKG/ 374 | RFTMSRDKAKN AGYLQMNSLKP EDTALYYCAA/ 590 | GAQSDRYNIRS YDY/435 | WGQGTQVT VSS/603 |
| VEGFBII87B07/ 110 | EVQLVESGGG LVQPGGSLKL SCTASGFTFS/ 503 | TSWMH/ 318 | WVRQAPG KGLEWVS/ 533 | SIPPVGHFAN YAPSVKG/ 375 | RFTISRDNAKN TLFLQMNSLKS EDTAVYYCAK/ 591 | DSAGRT/436 | KGQGTQVT VSS/611 |
| VEGFBII88A01/ 111 | KVQLVESGGG LVQAGGSLRL | NYAMD/ 319 | WFRQAPG KEREFVA/ | AITRSGGGTY YADSVKG/ | RFTISRDNAKN TVYLQMNSLKP | TRSSTIVVGVG GMEY/437 | WGKGTLVT VSS/612 |

TABLE 2-continued

Sequence IDs and AA sequences of monovalent "non-receptor-blocking" anti-VEGF VHHs (FR, framework; CDR, complementary determining region)

| VHH ID/ SEQ ID NO: | FR1/SEQ ID NO: | CDR1/ SEQ ID NO: | FR2/SEQ ID NO: | CDR2/SEQ ID NO: | FR3/SEQ ID NO: | CDR3/SEQ ID NO: | FR4/SEQ ID NO: |
|---|---|---|---|---|---|---|---|
| | SCAASERTFS/504 | | 518 | 376 | EDTAVYYCAA/565 | | |
| VEGFBII88A02/112 | EVQLVESGGGLVQAGGSLRLSCAASGFTFG/505 | DYDIG/320 | WFRQAPGNEREGVS/542 | CITTDVGTTYYADSVKG/377 | RFTISSDNAKNTVYLQINDLKPEDTAIYYCAV/592 | DTQDLGLDIFCRGNGPFDG/438 | WGQGTQVTVSS/603 |
| VEGFBII88B02/113 | EVQLVESGGGLVQPGGSLRLSCTASGLNLD/506 | DYAIG/230 | WFRQAPGKEREGVS/543 | CISSYDSVTYYADHVKG/378 | RFTISRDSAKNTLYLQMNSLSIEDTGVYYCAA/593 | EREQLRRRESPHDELLRLCFYGMRY/439 | SGKGTLVTVSS/613 |
| VEGFBII88E02/114 | EVQLVESGGGLVQPGGSLRLSCVASGFRLD/507 | DYAIG/230 | WFRQAPGKEREAVS/544 | CISSSDTSIDYTNSVKG/379 | RFTFSRDNAKNTVYLQMNSLKPEDTAVYYCAA/594 | AFRCSGYELRGFPT/440 | WGQGTQVTVSS/603 |
| VEGFBII88G03/115 | EVQLVESGGGLVQAGGSLRLSCAASGGTFS/508 | SLAVG/321 | WFRQAPGKEREFVA/518 | RITWSGATTYYADAVKD/380 | RFTISRDNAKNTMYLQMNSLKPEDTAVYYCAA/595 | DRSPNIINVVTAYEYDY/441 | WGQGTQVTVSS/603 |
| VEGFBII88G05/116 | EVQLVESGGGLVQPGASLRLSCAASGDGFT/509 | LYNMG/322 | WFRQAPGKEREFVA/518 | AITSSPMSTYYADSVKG/381 | RFSISINNDKTTGFLQMNVLKPEDTGVYFCAA/596 | PEGSFRRQYADRAMYDY/442 | WGQGTQVTVSS/603 |
| VEGFBII88G11/117 | EVQLVESGGGLAQAGGSLRLSCAASGRTFS/510 | GSDMG/323 | WFRQSPGKEREIVA/545 | AIRLSGSITYYPDSVKG/382 | RFTISRDNAKNTVYLQMNSLKPEDTAVYYCAA/565 | RSTYSYYLALADRGGYDY/443 | WGQGTQVTVSS/603 |
| VEGFBII88H01/118 | EVQLVESGGGLVQAGGSLRLSCVASGFTLG/511 | TYAIG/324 | WFRQAPGKEREAVS/544 | CMSAGDSIPWYTASVKG/383 | RFTTSTDNARNTVYLQMNSLKPEDTAHYYCAA/597 | ARYHGDYCYYEGYYPF/444 | WGQGTQVTVSS/603 |
| VEGFBII89B04/119 | EVQLVESGGGLVQAGGSLRLSCAASTSISS/512 | TNFMG/325 | WYRQAPGKQRELVA/521 | TITSSSITNYVDSVKG/384 | RFTISRDNAKNTVYLQMTSLKPEDTAVYYCHA/598 | RWRWSDVEY/445 | WGKGTLVTVSS/612 |
| VEGFBII89B08/120 | EVQLVESGGGLVQPGGSLRLSCAASGTTSS/513 | IFAMR/326 | WYRQAPGKQRELVA/521 | SITRSSITTYADSVKG/385 | RFTPSRDNAKNTVSLQMNSLKPEDTAVYYCNA/599 | AIRPELYSVVNDY/446 | WGQGTQVTVSS/603 |
| VEGFBII89D04/121 | EVQLVESGGGLVQPGGSLRLSCATSGLTFS/514 | DYNLG/327 | WFRQAPGKERQFVA/546 | VISWRDSFAYYAEPVKG/386 | RFTISRDNAKNTVYLQMNSLKPEDTAVYYCAA/565 | DRVSSRLVLPNTSPDFGS/447 | WGQGTQVTVSS/603 |
| VEGFBII89F09/122 | EVQLVESGGGLVQAGDSLRLSCAASGRTFN/515 | NAIMG/328 | WFRQAPGQEREFVA/547 | AMNWRGGPTYYADSVKG/387 | RFTISGDNTKNTVFLQMNFLKPEDTAVYYCAA/600 | DEDLYHYSSYHYSRVDLYHY/448 | WGQGTQVTVSS/603 |
| VEGFBII89G09/123 | EVQLVESGGGLVQPGGSLRLSCAASGTTSS/513 | IFAMR/326 | WYRQAPGKQRELVA/521 | SITRSSITTYADSVKG/385 | RFTLSRDNAKNTVSLQMNSLKPEDTAVYYCNA/601 | AIRPELYSVVNDY/446 | WGQGTQVTVSS/603 |
| VEGFBII89H08/124 | EVQLVESGGGLVQAGGSLRLSCAASGGSFS/516 | SYAPG/329 | WFRQAPGKEREFVA/518 | AFTRSSNIPYYKDSVKG/388 | RFTISRDNAHTVYLQMNSLKPEDTAIYYCAV/602 | NLGSTWSRDQRTYDY/449 | WGQGTQVTVSS/603 |

TABLE 3

Sequence IDs and AA sequences of monovalent receptor-blocking anti-VEGF VHHs (FR, framework; CDR, complementary determining region) SEQ ID NO: 9-46

| VHH ID/ SEQ ID NO: | FR1/SEQ ID NO: | CDR1/SEQ ID NO: | FR2/SEQ ID NO: | CDR2/SEQ ID NO: | FR3/SEQ ID NO: | CDR3/SEQ ID NO: | FR4/SEQ ID NO: |
|---|---|---|---|---|---|---|---|
| VEGFBII22A10/9 | EVQLVESGGGLVQPGDSLKLSCAFSGRTFS/614 | SYSMG/450 | WFRQAQGKEREFVV/636 | AISSSGGYIYDSVSLEG/453 | RFTISRDNTKNTVYLQTPSLKPEDTADYYCAA/638 | SRAYGSSRLRLADTYDY/3 | WGQGTQVTVSS/603 |
| VEGFBII22A11/10 | EVQLVESGGGLVQPGDSLKLSCAFSGRTFS/614 | SYSMA/451 | WFRQAQGKEREFVV/636 | AISSGGFIYDAVSLEG/454 | RFTISRDNTKNTVYLQTPSLKPEDTAVYYCAA/639 | SRAYGSSRLRLADTYDY/3 | WGQGTQVTVSS/603 |
| VEGFBII22B06/11 | EVQLVESGGGLVQPGDSLKLSCAASGRTFS/615 | SYSMG/450 | WFRQAQGKEREFVV/636 | AISSSGGYIYDSVSLEG/453 | RFTISRDNTKNTVYLQTPSLKPEDTAVYYCAA/639 | SRAYGSSRLRLADTYDY/3 | WGQGTQVTVSS/603 |
| VEGFBII22B07/12 | EVQLVESGGGLVQAGDSLRLSCAASGRTFS/616 | SYSMG/450 | WFRQAQGKEREFVV/636 | AISSSGNYKYDSVSLEG/455 | RFTISRDNTKNTVYLQINSLKPEDTAVYYCAA/640 | SRAYGSSRLRLGDTYDY/2 | WGQGTQVTVSS/603 |
| VEGFBII22E04/13 | EVQLVESGGGLVQPGDSLKLSCVASGRTSS/617 | SYSMG/450 | WFRQAQGKEREFVV/636 | AISSGGSIYDSVSLQG/456 | RFTISRDNTKNTVYLQTPSLKPEDTAVYYCAA/639 | SRAYASSRLRLADTYDY/6 | WGQGTQVTVSS/603 |
| VEGFBII23A03/14 | EVQLVESGGGLVQPGDSLKLSCVASGRTFS/618 | SYSMG/450 | WFRQAQGKEREFVV/636 | AISSGGYIYDSVSLQG/457 | RFTISRDNTKNTVYLQTPSLKPEDTAVYYCAA/639 | SRAYGSSRLRLADTYDY/3 | WGQGTQVTVSS/603 |
| VEGFBII23A06/15 | EVQLVESGGGLVQPGDSLKLSCAFSGRTFS/619 | SYSMG/450 | WFRQAQGKEREFVV/636 | AISSGGFIYDAVSLEG/454 | RFTISRDNTKNTVYLQTPSLKPEDTAVYYCAA/639 | SRAYGSSRLRLADTYDY/3 | WGQGTQVTVSS/603 |
| VEGFBII23A08/16 | EVQLVESGGGLVQTGDSLRLSCVASGRTFS/620 | SYSMG/450 | WFRQAQGKEREFVV/636 | AISNGGYKYDSVSLEG/458 | RFTISRDNTKNTVYLQINSLKPEDTAVYYCAA/640 | SRAYGSSRLRLADTYDY/3 | WGQGTQVTVSS/603 |
| VEGFBII23A09/17 | EVQLVESGGGLVQPGDSLKLSCAFSGRTFG/621 | SYSMG/450 | WFRQAQGKEREFVV/636 | AISSSGGYIYDSVSLEG/453 | RFTISRDNSKNTVYLQTPSLKPEDTAVYYCAA/641 | SRAYGSSRLRLPDTYDY/7 | WGQGTQVTVSS/603 |
| VEGFBII23B04/18 | EVQLVESGGGLVQTGDSLRLSCEVSGRTFS/622 | SYSMG/450 | WFRQAQGKEREFVV/636 | AISKGGYKYDSVSLEG/459 | RFTISKDNAKNTVYLQINSLKPEDTAVYYCAS/642 | SRAYGSSRLRLADTYEY/4 | WGQGTQVTVSS/603 |
| VEGFBII23D11/19 | EVQLVESGGGLVQPGDSLRLSCAFSGRTFS/623 | SYSMA/451 | WFRQAQGKEREFVV/636 | AISSGGFIYDAVSLEG/454 | RFTISRDNTKNTVYLQTPSLKPEDTAVYYCAA/639 | SRAYGSSRLRLADTYDY/3 | WGQGTQVTVSS/603 |
| VEGFBII23E05/20 | EVQLVESEGGLVQPGDSLKLSCVASGRTSS/624 | SYSMG/450 | WFRQAQGKEREFVV/636 | AISSGGYIYDSVSLQG/457 | RFTISRDNTKNTVYLQTPSLKPEDTAVYYCAA/639 | SRAYGSSRLRLADTYDY/3 | WGQGTQVTVSS/603 |
| VEGFBII23E02/21 | EMQLVESGGGLVQPGDSLKLSCAFSGRTFS/625 | SYSMG/450 | WFRQAQGKEREFVV/636 | AISSSGGYIYDSVSLEG/453 | RFTISRDNTKNTVYLQTPSLKPEDTADYYCAA/638 | SRAYGSSRLRLADTYDY/3 | WGQGTQVTVSS/603 |
| VEGFBII23E05/22 | EVQLVESGGGLVQAGDSLRLSCAASGRTFS/616 | SYSMG/450 | WFRQAQGKEREFVV/636 | AISSSGNYKYDSVSLEG/455 | RFTISRDNTKNTVYLQINSLKPKDTAVYYCAA/643 | SRAYGSSRLRLGDTYDY/2 | WGQGTQVTVSS/603 |
| VEGFBII23E11/23 | EVQLVESGGGLVQPGDSLKLSCAFSGRTFS/614 | SYSMG/450 | WFRQAQGKEREFVV/636 | AISSGGGYIYDSVSLEG/460 | RFTISRDNTKNTVYLQTPSLKPEDTADYYCAA/638 | SRAYGSSRLRLADTYDY/3 | WGQGTQVTVSS/603 |

TABLE 3-continued

Sequence IDs and AA sequences of monovalent receptor-blocking anti-VEGF VHHs (FR, framework; CDR, complementary determining region) SEQ ID NO: 9-46

| VHH ID/ SEQ ID NO: | FR1/SEQ ID NO: | CDR1/SEQ ID NO: | FR2/SEQ ID NO: | CDR2/SEQ ID NO: | FR3/SEQ ID NO: | CDR3/SEQ ID NO: | FR4/SEQ ID NO: |
|---|---|---|---|---|---|---|---|
| VEGFBII23G03/ 24 | EVQLVESGGGLVQPGDSLKLSCAFSGRTFG/621 | SYSMG/ 450 | WFRQAQGKEREFVV/636 | AISSSGGYIYDSVSLEG/ 453 | RFTISRDNSKNTVYLQTPSLKPEDTAVYYCAA/641 | SRAYGSSRLRLPGTYDY/8 | WGQGTQVTVSS/603 |
| VEGFBII24C04/ 25 | EVQLVESGGGLVQPGDSLKLSCVASGRTSS/617 | SYSMG/450 | WFRQAQGKEREFVV/636 | AISSGGYIYDSVSLQG/ 457 | RFTISRDNTKNTVYLQTPSLKPEDTAVYYCAA/639 | SRAYGSSRLRLADTYDY/3 | WGQGTQVTVSS/603 |
| VEGFBII27D08/ 26 | EVQLVESGGGLVQTGDSLRLSCAASGRTFS/626 | SYSMG/450 | WFRQAQGKEREFVV/636 | AISSGGYKYDSVSLEG/ 461 | RFTISRDNTQNTVYLQINSLKPEDTAVYYCAA/644 | SRAYGSGRLRLADTYDY/5 | WGQGTQVTVSS/603 |
| VEGFBII27G07/ 27 | EVQLVESGGGLVQPGDSLKLSCVASGRTSS/617 | SYSMG/450 | WFRQAQGQEREFVV/637 | AISSGGYIYDSVSLQG/ 457 | RFTISRDNTKNTVYLQTPSLKPEDTAVYYCAA/639 | SRAYGSSRLRLADTYDY/3 | WGQGTQVTVSS/603 |
| VEGFBII30C09/ 28 | EVQLVESGGGLVQPGDSLKLSCIASGRTSS/627 | SYSMG/450 | WFRQAQGQEREFVV/637 | AISSGGYIYDSVSLQG/457 | RFTISRDNTKNTVYLQTPSLKPEDTAVYYCAA/639 | SRAYGSSRLRLADTYDY/3 | WGQGTQVTVSS/603 |
| VEGFBII30E07/ 29 | EVQLVESGGGLVQAGDSLRLSCAASGRTFS/616 | SYSMG/450 | WFRQAQGKEREFVV/636 | AISSSGNYKYDSVSLEG/ 455 | RFTISRDNTKNTVYLQINSLKPEDTAVYYCAA/640 | SRAYGSSRLRLGDTYDY/2 | WGQGTRVTVSS/652 |
| VEGFBII31C07/ 30 | EVQLVESGGGLVQTGDSLRLSCAASGGTFS/628 | SYSMG/450 | WFRQAQGKEREFVV/636 | AISSSGGYIYDSVSLEG/ 453 | RFTISRDNTKNTVYLQTPSLKPEDTADYYCAA/638 | SRAYGSSRLRLADTYDY/3 | WGQGTQVTVSS/603 |
| VEGFBII39E02/ 31 | EVQLVESGGGLVQPGDPLKLSCAFSGRTFS/629 | SYSMG/450 | WFRQAQGKEREFVV/636 | AISSSGGYIYDSVSLEG/ 453 | RFTISRDNTKNTVYLQTPSLKPEDTADYYCAA/638 | SRAYGSSRLRLADTYDY/3 | WGQGTQVTVSS/603 |
| VEGFBII39G04/ 32 | EVPLVESGGGLVQAGDSLRLSCAASGRTFS/630 | SYSMG/450 | WFRQAQGKEREFVV/636 | AISSSGNYKYDSASLEG/ 462 | RFTISRDNTKNTVYLQINSLKPEDTAVYYCAA/640 | SRAYGSSRLRLGDTYDY/2 | WGQGTQVTVSS/603 |
| VEGFBII40E02/ 33 | EVQLVESGGGLVQPGDSLKLSCAFSGRTFS/614 | SYSMA/ 451 | WFRQAQGKEREFVV/636 | AISSGGFIYDAVSLEG/454 | RFTISRDNTKNTVYLQTPSLKPEGTAVYYCAA/645 | SRAYGSSRLRLADTYDY/3 | WGQGTQVTVSS/603 |
| VEGFBII40G07/ 34 | EVQLVESGGGLVQPGDSLKLSCAFSGRTFS/614 | SYSMG/450 | WFRQAQGKEREFVV/636 | AISSSGGYIYDSVSLEG/ 453 | RFTISRDNTKNAVYLQTPSLKPEDTADYYCAA/646 | SRAYGSSRLRLADTYDY/3 | WGQGTQVTVSS/603 |
| VEGFBII40H10/ 35 | EVQLMESGGGLVQPGDSLKLSCAFSGRTFS/631 | SYSMG/450 | WFRQAQGKEREFVV/636 | AISSSGGYIYDSVSLEG/ 453 | RFTISRDNTKNTVYLQTPSLKPEDTADYYCAA/638 | SRAYGSSRLRLADTYDY/3 | WGQGTQVTVSS/603 |
| VEGFBII41B05/ 36 | EVQLVESGGGLVQPGGSLRLSCAFSGRTFS/632 | SYSMG/450 | WFRQAQGKEREFVV/636 | AISSGGFIYDAVSLEG/ 454 | RFTISRDNTKNTVYLQTPSLKPEDTAVYYCAA/639 | SRAYGSSRLRLADTYDY/3 | WGQGTQVTVSS/603 |
| VEGFBII41G03/ 37 | EVQLVESGGGLVQPGDSLKLSCAFSGRTFS/614 | SYSMA/451 | WFRQAQGKEREFVV/636 | AISSGGFIYDAVSLEG/454 | RFTISRENTKNTVYLQTPSLKPEDTAVYYCAA/647 | SRAYGSSRLRLADTYDY/3 | WGQGTQVTVSS/603 |

TABLE 3-continued

Sequence IDs and AA sequences of monovalent receptor-blocking anti-VEGF VHHs (FR, framework; CDR, complementary determining region) SEQ ID NO: 9-46

| VHH ID/ SEQ ID NO: | FR1/SEQ ID NO: | CDR1/SEQ ID NO: | FR2/SEQ ID NO: | CDR2/SEQ ID NO: | FR3/SEQ ID NO: | CDR3/SEQ ID NO: | FR4/SEQ ID NO: |
|---|---|---|---|---|---|---|---|
| VEGFBII42A05/ 38 | EVQLVESGG GLVQPGDSL KLSCAFSGR TFS/614 | SYSM G/450 | WFRQAQGKE REFVV/636 | AISSSGGYI YDSVSLEG/ 453 | RFTISRDNTKNT VYLQMPSLKPED TADYYCAA/648 | SRAYGSSRLRL ADTYDY/3 | WGQGTQV TVSS/603 |
| VEGFBII42D05/ 39 | EVQLVESGG GLVQPGDSL KLSCAFSGR TFS/614 | SYSM G/ 450 | WFRQAQGKE REFVV/636 | AISSSGGYI YDSVSLEG/ 453 | RFTISRDNTKNT VYLQTPSLKPED TAVYYCAA/639 | SRAYGSSRLRL ADTYDY/3 | WGQGTQV TVSS/603 |
| VEGFBII42E11/ 40 | EVQLVESGG GLVQPGDSL KLSCVASGR TSS/617 | SYSV G/ 452 | WFRQAQGKE REFVV/636 | AISSGGYIY DSVSLQG/ 457 | RFTISRDNTKNT VYLQTPSLKPED TAVYYCAA/639 | SRAYGSSRLRL ADTYDY/3 | WGQGTQV TVSS/603 |
| VEGFBII56E11/ 41 | EVQLVESGG GLVQPGDSL KLSCAFSGR TFS/614 | SYSM G/ 450 | WFRQAQGKE REFVV/636 | AISSSGGYI YDSVSLEG/ 453 | RFTISRDNTKNT VYLQTPSLKPED AADYYCAA/649 | SRAYGSSRLRL ADTYDY/3 | WGQGTQV TVSS/603 |
| VEGFBII60A09/ 42 | EVQLVESGG GLVQPGDSL KLSCAFSGR TFS/614 | SYSM G/ 450 | WFRQAQGKE REFVV/636 | AISSSGGYI YDSVSLEG/ 453 | RFTISRDNTRNT VYLQTPSLKPED TADYYCAA/650 | SRAYGSSRLRL ADTYDY/3 | WGQGTQV TVSS/603 |
| VEGFBII61A01/ 43 | EVQLVESGG GLVQAGGSL RLSCAFSGR TFS/633 | SYSM G/450 | WFRQAQGKE REFVV/636 | AISSGGYKY DAVSLEG/ 463 | RFTISRDNTKNT VYLQTPSLKPED TAVYYCAA/639 | SRAYASSRLRL ADTYDY/6 | WGQGTQV TVSS/603 |
| VEGFBII62A09/ 44 | EVQLVESGG DLVQPGDSL KLSCAASGR TFS/634 | SYSM G/ 450 | WFRQAQGKE REFVV/636 | AISSSGGYI YDSVSLEG/ 453 | RFTISRDNTKNT VYLQTPSLKPED TAVYYCAA/639 | SRAYGSSRLRL ADTYDY/3 | WGQGTQV TVSS/603 |
| VEGFBII62D10/ 45 | EVQLVESEG GLVQAGDSL RLSCAASGR TFS/635 | SYSM G/450 | WFRQAQGKE REFVV/636 | AISSSGNYK YDSVSLEG/ 455 | RFTISRDNTKNT VYLQINSLKPED TAVYYCAA/640 | SRAYGSSRLRL GDTYDY/2 | WGQGTQV TVSS/603 |
| VEGFBII62E02/ 46 | EVQLVESGG GLVQPGDSL KLSCAFSGR TFS/614 | SYSM G/ 450 | WFRQAQGKE REFVV/636 | AIASGGYIY DAVSLEG/ 464 | RFTISRDNTKDT VYLQTPSLKPED TAVYYCAA/651 | SRAYGSSRLRL ADTYDY/3 | WGQGTQV TVSS/603 |

Dissociation rates of inhibitory VHHs are analyzed on Biacore (Biacore T100 instrument, GE Healthcare). HBS-EP+buffer is used as running buffer and experiments are performed at 25° C. Recombinant human VEGF165 is irreversibly captured on a CM5 sensor chip via amine coupling (using EDC and NHS) up to a target level of +/−1500RU. After immobilization, surfaces are deactivated with 10 min injection of 1M ethanolamine pH8.5. A reference surface is activated and deactivated with respectively EDC/NHS and ethanolamine. Periplasmic extracts of VHHs are injected at a 10-fold dilution in running buffer for 2 min at 45 μl/min and allowed to dissociate for 10 or 15 min. Between different samples, the surfaces are regenerated with regeneration buffer. Data are double referenced by subtraction of the curves on the reference channel and of a blank running buffer injection. The of the processed curves is evaluated by fitting a two phase decay model in the Biacore T100 Evaluation software v2.0.1. Values for $k_d$-fast, $k_d$-slow and % fast are listed in Table 4.

TABLE 4

Off-rate determination of anti-VEGF receptor-blocking VHHs with Biacore

| B-cell lineage | Unique sequence variant | Representative VHH ID | $k_d$(fast) | $k_d$(slow) | % fast | Binding level (RU) |
|---|---|---|---|---|---|---|
| 1 | 1 | VEGFBII22B07 | 1.50E−02 | 7.80E−05 | 31 | 328 |
| 1 | 2 | VEGFBII23A08 | 1.30E−02 | 5.00E−05 | 19 | 502 |
| 1 | 3 | VEGFBII23B04 | 8.80E−03 | 4.00E−05 | 12 | 768 |
| 1 | 4 | VEGFBII27D08 | 2.40E−02 | 8.10E−05 | 13 | 225 |
| 1 | 5 | VEGFBII24C04 | 1.30E−02 | 3.40E−05 | 17 | 456 |
| 1 | 6 | VEGFBII27G07 | 1.30E−02 | 3.80E−05 | 18 | 471 |

TABLE 4-continued

Off-rate determination of anti-VEGF receptor-blocking VHHs with Biacore

| B-cell lineage | Unique sequence variant | Representative VHH ID | $k_d$(fast) | $k_d$(slow) | % fast | Binding level (RU) |
|---|---|---|---|---|---|---|
| 1 | 7 | VEGFBII22E04 | 1.80E−02 | 1.10E−04 | 14 | 520 |
| 1 | 8 | VEGFBII23A03 | 1.50E−02 | 3.20E−05 | 15 | 487 |
| 1 | 9 | VEGFBII22B06 | 3.80E−02 | 9.00E−05 | 23 | 168 |
| 1 | 10 | VEGFBII23A09 | 2.70E−02 | 4.60E−05 | 20 | 247 |
| 1 | 11 | VEGFBII23G03 | 2.80E−02 | 8.60E−05 | 28 | 141 |
| 1 | 12 | VEGFBII22A11 | 2.20E−02 | 4.70E−05 | 12 | 461 |
| 1 | 13 | VEGFBII23A06 | 1.70E−02 | 3.70E−05 | 13 | 547 |
| 1 | 14 | VEGFBII23F11 | 2.70E−02 | 1.30E−04 | 22 | 134 |
| 1 | 15 | VEGFBII22A10 | 3.70E−02 | 4.00E−05 | 19 | 229 |
| 1 | 16 | VEGFBII23F05 | 1.60E−02 | 1.30E−04 | 29 | 198 |
| 1 | 17 | VEGFBII23D11 | 1.90E−02 | 5.80E−05 | 13 | 510 |
| 1 | 18 | VEGFBII23F02 | n/d | n/d | n/d | n/d |
| 1 | 19 | VEGFBII23E05 | 1.50E−02 | 6.90E−05 | 18 | 275 |
| 1 | 20 | VEGFBII31C07 | 3.70E−02 | 1.50E−04 | 25 | 77 |
| 1 | 21 | VEGFBII30C09 | 1.50E−02 | 7.60E−05 | 19 | 264 |
| 1 | 22 | VEGFBII30E07 | 1.70E−02 | 1.30E−04 | 29 | 226 |
| 1 | 23 | VEGFBII39G04 | 1.40E−02 | 7.40E−04 | 40 | 210 |
| 1 | 24 | VEGFBII41G03 | 1.20E−02 | 2.70E−04 | 20 | 332 |
| 1 | 25 | VEGFBII41B05 | 1.90E−02 | 1.20E−04 | 16 | 324 |
| 1 | 26 | VEGFBII40F02 | 1.20E−02 | 9.80E−05 | 20 | 258 |
| 1 | 27 | VEGFBII39E02 | 1.90E−02 | 2.40E−04 | 13 | 181 |
| 1 | 28 | VEGFBII42D05 | 3.30E−02 | 1.50E−04 | 26 | 77 |
| 1 | 29 | VEGFBII40G07 | 1.80E−02 | 3.20E−04 | 19 | 139 |
| 1 | 30 | VEGFBII42A05 | 1.60E−02 | 3.40E−04 | 25 | 118 |
| 1 | 31 | VEGFBII42F11 | 9.10E−03 | 5.00E−04 | 46 | 100 |
| 1 | 32 | VEGFBII40H10 | 1.40E−02 | 2.90E−04 | 17 | 200 |
| 1 | 33 | VEGFBII62A09 | 4.10E−02 | 1.10E−04 | 23 | 84 |
| 1 | 34 | VEGFBII60A09 | 3.70E−02 | 9.30E−05 | 20 | 106 |
| 1 | 35 | VEGFBII62F02 | 1.40E−02 | 8.50E−05 | 21 | 205 |
| 1 | 36 | VEGFBII62D10 | 1.90E−02 | 1.60E−04 | 40 | 94 |
| 1 | 37 | VEGFBII61A01 | 7.40E−03 | 1.70E−04 | 21 | 275 |
| 1 | 38 | VEGFBII56E11 | 3.30E−02 | 1.40E−04 | 24 | 76 |

n/d, not determined

Example 5

Characterization of Purified Anti-VEGF VHHs

Three inhibitory anti-VEGF VHHs are selected for further characterization as purified protein: VEGFBII23B04, VEGFBII24C4 and VEGFBII23A6. These VHHs are expressed in *E. coli* TG1 as c-myc, His6-tagged proteins ("His6" disclosed as SEQ ID NO: 283). Expression is induced by addition of 1 mM IPTG and allowed to continue for 4 hours at 3TC. After spinning the cell cultures, periplasmic extracts are prepared by freeze-thawing the pellets. These extracts are used as starting material for VHH purification via IMAC and size exclusion chromatography (SEC). Final VHH preparations show 95% purity as assessed via SDS-PAGE.

5.1 Evaluation of Human VEGF165/VEGFR2 Blocking VHHs in Human VEGF165/Human VEGFR2-Fc Blocking ELISA The blocking capacity of the VHHs is evaluated in a human VEGF165/human VEGFR2-Fc blocking ELISA. In brief, 1 μg/mL of VEGFR2-Fc chimera (R&D Systems, Minneapolis, Minn., USA) is coated in a 96-well MaxiSorp plate (Nunc, Wiesbaden, Germany). Dilution series (concentration range 1 mM-64 pM) of the purified VHHs in PBS buffer containing 0.1% casein and 0.05% Tween 20 (Sigma) are incubated in the presence of 4 nM biotinlyated VEGF165. Residual binding of bio-VEGF165 to VEGFR2 is detected using horseradish peroxidase (HRP) conjugated extravidin (Sigma, St Louis, Mo., USA) and TMB as substrate. As controls Bevacizumab (Avastin®) and Ranibizumab (Lucentis®) are taken along. Dose inhibition curves are shown in FIG. 1; the corresponding $IC_{50}$ values and % inhibition are summarized in Table 5.

TABLE 5

$IC_{50}$ (nM) values and % inhibition for monovalent VHHs in hVEGF165/hVEGFR2-Fc competition ELISA

| VHH ID | $IC_{50}$ (nM) | % inhibition |
|---|---|---|
| VEGFBII23B04 | 2.1 | 100 |
| VEGFBII23A06 | 3.0 | 100 |
| VEGFBII24C04 | 2.5 | 100 |
| Ranibizumab | 1.6 | 100 |
| Bevacizumab | 1.7 | 100 |

Figure 2:
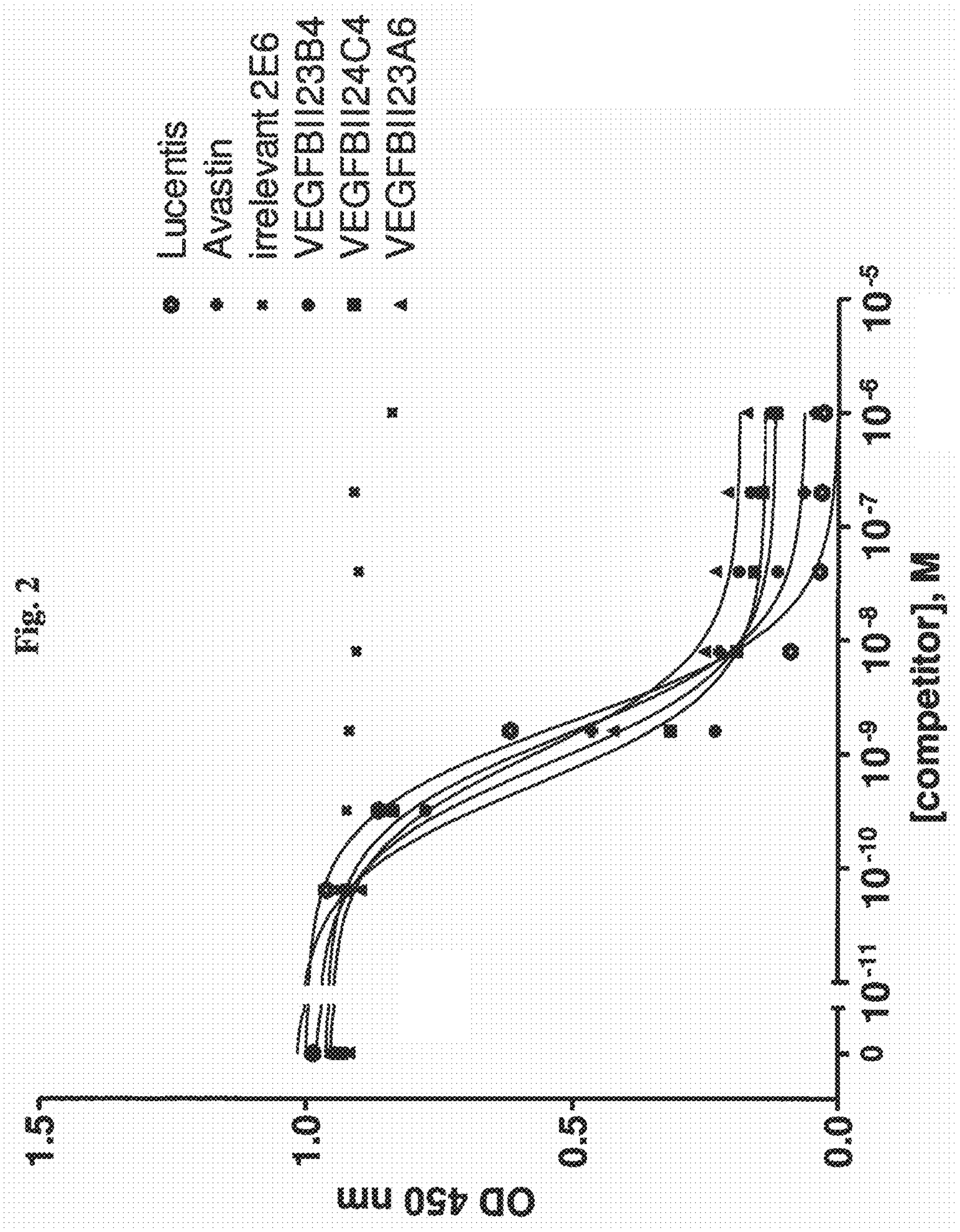
FIG. 2: Purified monovalent VHHs block the hVEGF165/hVEGFR1-Fc interaction (ELISA)

5.2 Evaluation of Human VEGF165/VEGFR2 Blocking VHHs in Human VEGF165/Human VEGFR1-Fc Blocking ELISA VHHs are also evaluated in a human VEGF165/human VEGFR1-Fc blocking ELISA. In brief, 2 μg/mL of VEGFR1-Fc chimera (R&D Systems, Minneapolis, Minn., USA) is coated in a 96-well MaxiSorp plate (Nunc, Wiesbaden, Germany). Dilution series (concentration range 1 mM-64 pM) of the purified VHHs in PBS buffer containing 0.1% casein and 0.05% Tween 20 (Sigma) are incubated in the presence of 0.5 nM biotinlyated VEGF165. Residual binding of bio-VEGF165 to VEGFR1 is detected using horseradish peroxidase (HRP) conjugated extravidin (Sigma, St Louis, Mo., USA) and TMB as substrate. As controls Bevacizumab, Ranibizumab and an irrelevant VHH (2E6) are taken along. Dose inhibition curves are shown in FIG. 2; the corresponding $IC_{50}$ values and % inhibition are summarized in Table 6.

TABLE 6

| $IC_{50}$ (nM) values and % inhibition of monovalent VHHs in hVEGF165/hVEGFR1-Fc competition ELISA | | |
|---|---|---|
| VHH ID | $IC_{50}$ (nM) | % inhibition |
| VEGFBII23B04 | 0.5 | 64 |
| VEGFBII23A06 | 0.9 | 55 |
| VEGFBII24C04 | 0.8 | 71 |
| Ranibizumab | 1.2 | 91 |
| Bevacizumab | 1.5 | 96 |

5.3 Evaluation of the Anti-VEGF165 VHHs in the Human VEGF165/Human VEGFR2-Fc Blocking AlphaScreen The blocking capacity of the VHHs is also evaluated in a human VEGF165/human VEGFR2-Fc blocking AlphaScreen. Briefly, serial dilutions of purified VHHs (concentration range: 200 nM-0.7 pM) in PBS buffer containing 0.03% Tween 20 (Sigma) are added to 4 pM bio-VEGF165 and incubated for 15 min. Subsequently VEGFR2-Fc (0.4 nM) and anti-Fc VHH-coated acceptor beads (20 μg/ml) are added and this mixture is incubated for 1 hour in the dark. Finally, streptavidin donor beads (20 μg/ml) are added and after 1 hour of incubation in the dark, fluorescence is measured on the Envision microplate reader. Dose-response curves are shown in the FIG. 3. The $IC_{50}$ values for VHHs blocking the human VEGF165-human VEGFR2-Fc interaction are summarized in Table 7.

TABLE 7

| $IC_{50}$ (pM) values and % inhibition for VHHs in hVEGF165/hVEGFR2-Fc competition AlphaScreen | | |
|---|---|---|
| VHH ID | $IC_{50}$ (pM) | % inhibition |
| VEGFBII23B04 | 160 | 100 |
| VEGFBII23A06 | 250 | 100 |
| VEGFBII24C04 | 250 | 100 |
| Ranibizumab | 860 | 100 |

Figure 4:
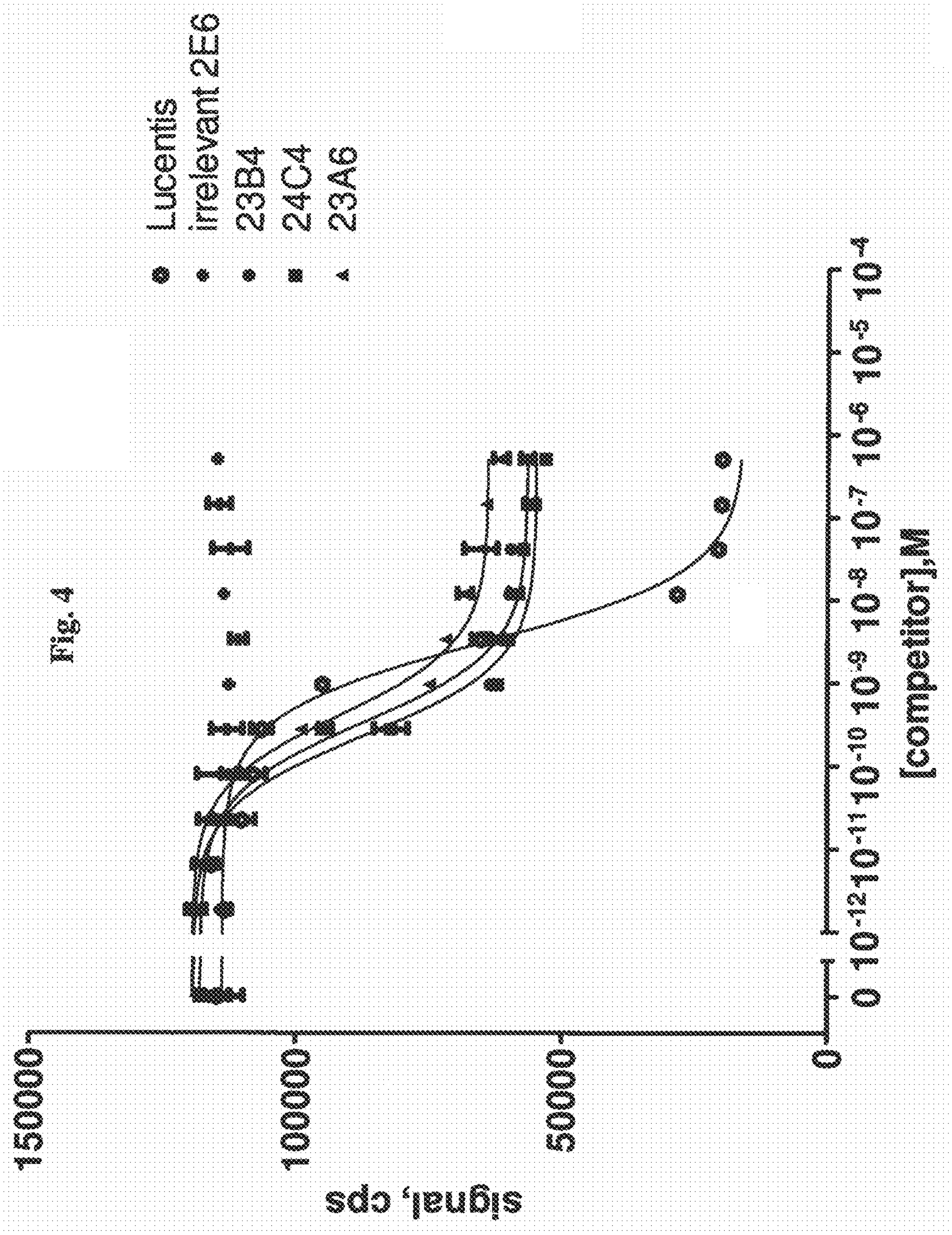
FIG. 4: Purified monovalent VHHs block the hVEGF165/hVEGFR1-Fc interaction (AlphaScreen)

5.4 Evaluation of the Anti-VEGF165 VHHs in the Human VEGF165/Human VEGFR1-Fc Blocking AlphaScreen The blocking capacity of the VHHs is also evaluated in a human VEGF165/human VEGFR1-Fc blocking AlphaScreen. Briefly, serial dilutions of purified VHHs (concentration range: 500 nM-1.8 pM)) in PBS buffer containing 0.03% Tween 20 (Sigma) are added to 0.4 nM bio-VEGF165 and incubated for 15 min. Subsequently VEGFR1-Fc (1 nM) and anti-Fc VHH-coated acceptor beads (20 μg/ml) are added and this mixture is incubated for 1 hour in the dark. Finally, streptavidin donor beads (20 μg/ml) are added and after 1 hour of incubation in the dark, fluorescence is measured on the Envision microplate reader. Dose-response curves are shown in the FIG. 4. The $IC_{50}$ values and % inhibition for VHHs blocking the human VEGF165-human VEGFR1-Fc interaction are summarized in Table 8.

TABLE 8

| $IC_{50}$ (nM) values for VHHs in hVEGF165/hVEGFR1-Fc competition AlphaScreen | | |
|---|---|---|
| VHH ID | $IC_{50}$ (nM) | % inhibition |
| VEGFBII23B04 | 0.9 | 41 |
| VEGFBII23A06 | 0.4 | 46 |
| VEGFBII24C04 | 0.2 | 53 |
| Ranibizumab | 3.3 | 79 |

5.5 Determination of the Affinity of the Human VEGF165-VHH Interaction

Binding kinetics of VHH VEGFBII23B04 with hVEGF165 is analyzed by SPR on a Biacore T100 instrument. Recombinant human VEGF165 is immobilized directly on a CM5 chip via amine coupling (using EDC and NHS). VHHs are analyzed at different concentrations between 10 and 360 nM. Samples are injected for 2 min and allowed to dissociate up to 20 min at a flow rate of 45 μl/min. In between sample injections, the chip surface is regenerated with 100 mM HCl. HBS-EP+(Hepes buffer pH7.4+EDTA) is used as running buffer. Binding curves are fitted using a Two State Reaction model by Biacore T100 Evaluation Software v2.0.1. The calculated affinities of the anti-VEGF VHHs are listed in Table 9.

TABLE 9

| Affinity $K_D$ (nM) of purified VHHs for recombinant human VEGF165 | | | | | | | |
|---|---|---|---|---|---|---|---|
| | VEGF165 | | | | | | |
| VHH ID | $k_a$ ($M^{-1} \cdot s^{-1}$) | $k_{a1}$ ($M^{-1} \cdot s^{-1}$) | $k_{a2}$ ($M^{-1} \cdot s^{-1}$) | $k_d$ ($s^{-1}$) | $k_{d1}$ ($s^{-1}$) | $k_{d2}$ ($s^{-1}$) | $K_D$ (nm) |
| VEGFBII23B04[(a)] | — | 2.1E+05 | 1.4E−02 | — | 8.6E−03 | 2.4E−04 | 0.7 |
| VEGFBII23A06[(a)] | — | 4.2E+05 | 2.0E−02 | — | 5.7E−02 | 1.0E−04 | 0.7 |
| VEGFBII24C04[(a)] | — | 3.2E+05 | 1.8E−02 | — | 2.6E−02 | 9.6E−05 | 0.4 |

[(a)]Heterogeneous binding curve resulting in no 1:1 fit, curves are fitted using a Two State Reaction model by Biacore T100 Evaluation Software v2.0.1

5.6 Binding to Mouse VEGF164

Figure 5:
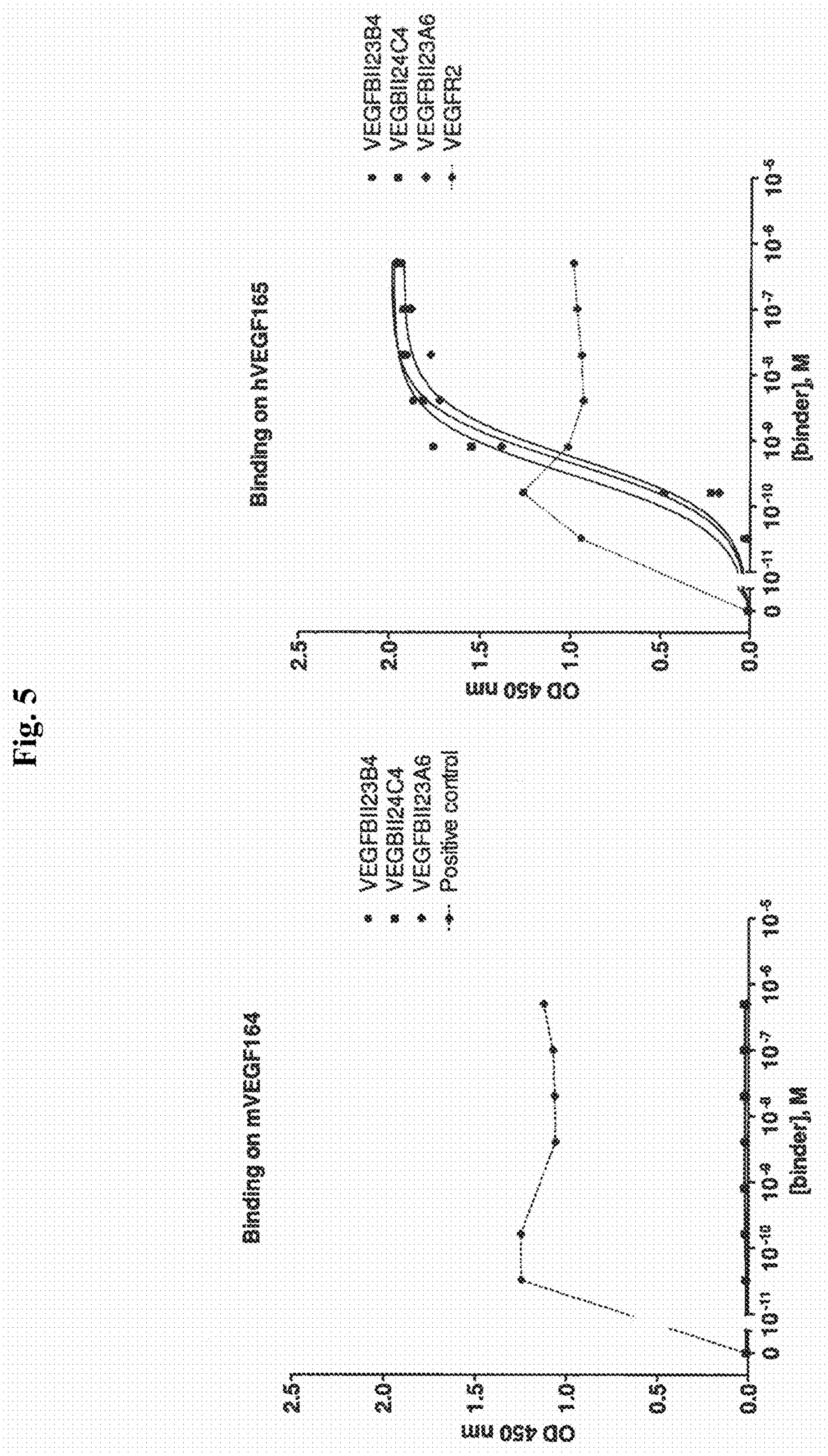
FIG. 5: Binding of monovalent VHHs to recombinant human and mouse VEGF (ELISA)

Cross-reactivity to mouse VEGF164 is determined using a binding ELISA. In brief, recombinant mouse VEGF164 (R&D Systems, Minneapolis, Miss., USA) is coated overnight at 4° C. at 1 μg/mL in a 96-well MaxiSorp plate (Nunc, Wiesbaden, Germany). Wells are blocked with a casein solution (1% in PBS). VHHs are applied as dilution series (concentration range: 500 nM-32 pM) in PBS buffer containing 0.1% casein and 0.05% Tween 20 (Sigma) and binding is detected using a mouse anti-myc (Roche) and an anti-mouse-HRP conjugate (DAKO) and a subsequent enzymatic reaction in the presence of the substrate TMB (3,3',5,5'-tetramentylbenzidine) (Pierce, Rockford, Ill., USA) (FIG. 5). A mouse VEGF164 reactive mAb is included as positive control. As reference, binding to human VEGF165 is also measured. $EC_{50}$ values are summarized in Table 10.

TABLE 10

$EC_{50}$ (pM) values for VHHs in a recombinant human VEGF165 and mouse VEGF164 binding ELISA

| VHH ID | rhVEGF165 $EC_{50}$ (pM) | rmVEGF164 $EC_{50}$ (pM) |
|---|---|---|
| VEGFBII23B04 | 297 | NB |
| VEGFBII24C04 | 453 | NB |
| VEGFBII23A06 | 531 | NB |

NB, no binding 5.7 Binding to VEGF121

Figure 6:
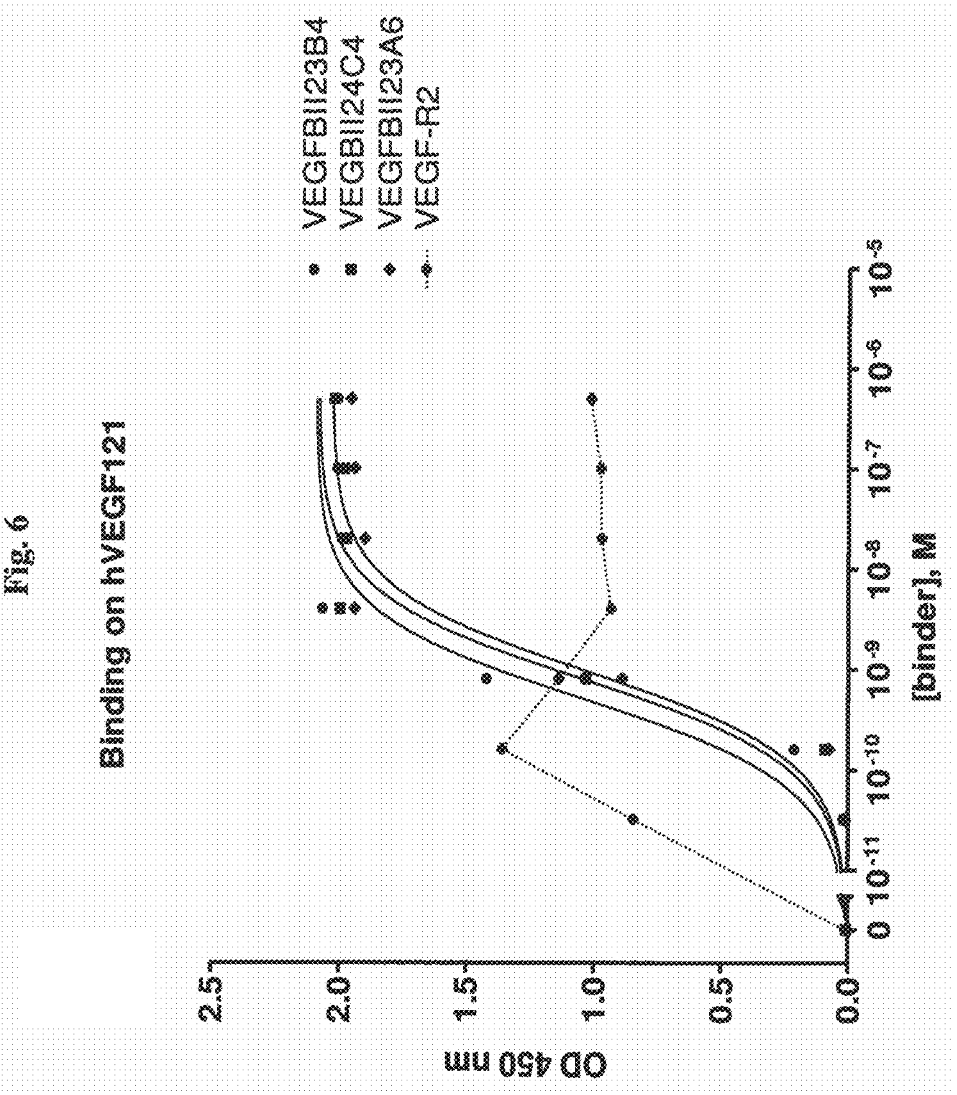
FIG. 6: Binding of monovalent VHHs to human VEGF121

Binding to recombinant human VEGF121 is assessed via a solid phase binding ELISA. Briefly, recombinant human VEGF121 (R&D Systems, Minneapolis, Miss., USA) is coated overnight at 4° C. at 1 μg/mL in a 96-well MaxiSorp plate (Nunc, Wiesbaden, Germany). Wells are blocked with a casein solution (1% in PBS). VHHs are applied as dilution series (concentration range: 500 nM-32 pM) in PBS buffer containing 0.1% casein and 0.05% Tween 20 (Sigma) and binding is detected using a mouse anti-myc (Roche) and an anti-mouse-HRP conjugate (DAKO) and a subsequent enzymatic reaction in the presence of the substrate TMB (3,3',5,5'-tetramentylbenzidine) (Pierce, Rockford, Ill., USA) (FIG. 6). As positive control serial dilutions of the VEGFR2 is taken along. $EC_{50}$ values are summarized in Table 11.

TABLE 11

$EC_{50}$ (pM) values for monovalent VHHs in a recombinant human VEGF121 binding ELISA

| VHH ID | $EC_{50}$ (pM) |
|---|---|
| VEGFBII23B04 | 510 |
| VEGFBII24C04 | 792 |
| VEGFBII23A06 | 928 |

5.8 Binding to VEGF Family Members VEGFB, VEGFC, VEGFD and PIGF

Figure 7:
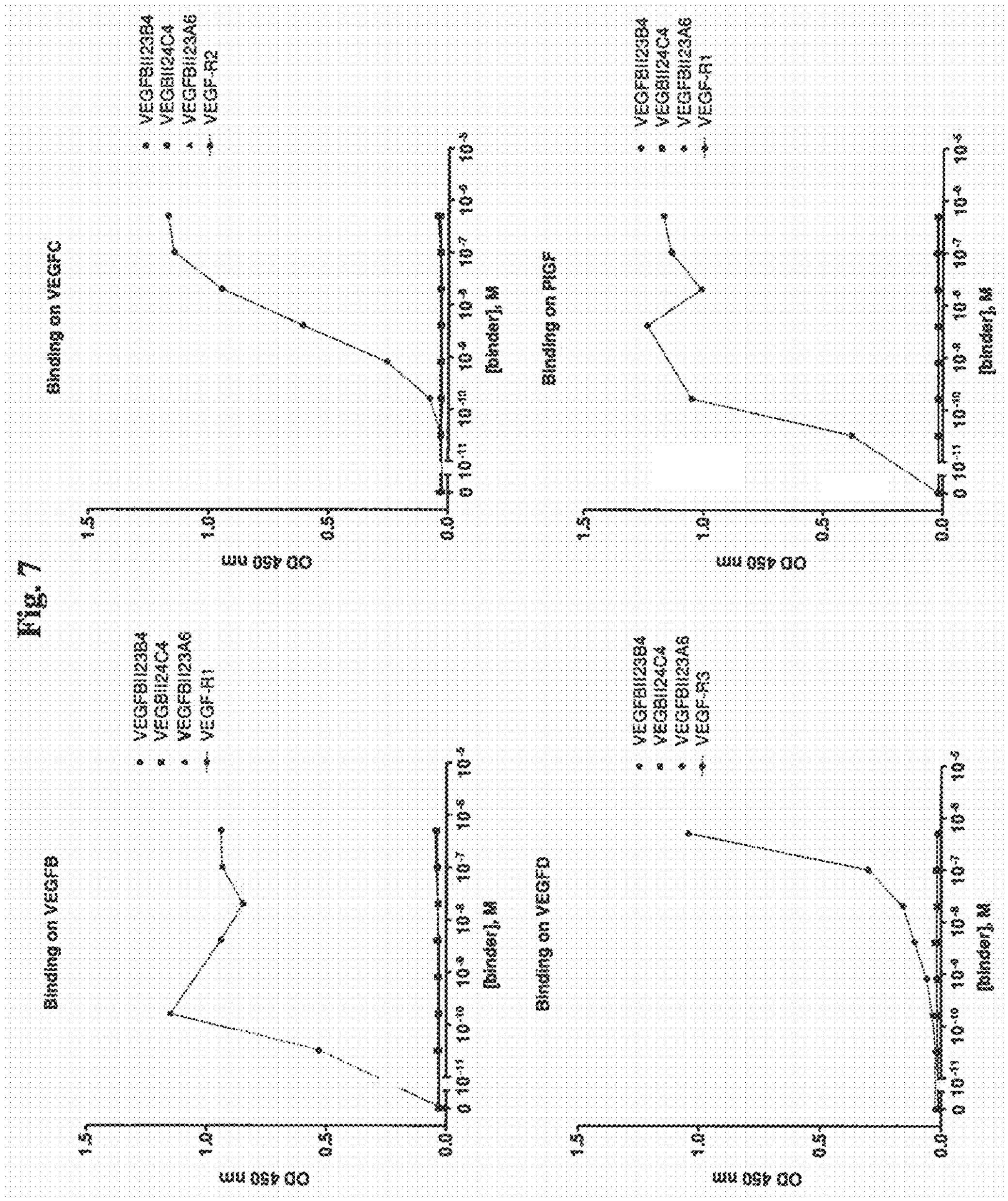
FIG. 7: Purified VHHs do not bind to VEGFB, VEGFC, VEGFD and PlGF

Binding to VEGFB, VEGFC, VEGFD and PIGF is assessed via a solid phase binding ELISA. In brief, VEGFB, VEGFC, VEGFD and PIGF (R&D Systems, Minneapolis, Miss., USA) are coated overnight at 4° C. at 1 μg/mL in a 96-well MaxiSorp plate (Nunc, Wiesbaden, Germany). Wells are blocked with a casein solution (1% in PBS). VHHs are applied as dilution series (concentration range: 500 nM-32 pM) and binding is detected using a mouse anti-myc (Roche) and an anti-mouse-AP conjugate (Sigma, St Louis, Mo., USA). As positive controls serial dilutions of the appropriate receptors are taken along and detected with horseradish peroxidase (HRP)-conjugated goat anti-human IgG, Fc specific antibody (Jackson Immuno Research Laboratories Inc., West Grove, Pa., USA) and a subsequent enzymatic reaction in the presence of the substrate TMB (3,3',5,5'-tetramentylbenzidine) (Pierce, Rockford, Ill., USA). Dose-response curves of VHHs and controls are shown in FIG. 7. The results show that there was no detectable binding of the selected VHHs to VEGFB, VEGFC, VEGFD or PIGF.

5.9 Epitope Binning

Biacore-based epitope binning experiments are performed to investigate which VEGF binders bind to a similar or overlapping epitope as VEGFBII23B04. To this end, VEGFBII23B04 is immobilized on a CM5 sensor chip. For each sample, human VEGF165 is passed over the chip surface and reversibly captured by VEGFBII23B4. Purified VHHs (100 nM) or periplasmic extracts (1/10 diluted) are then injected with a surface contact time of 240 seconds and a flow rate of 10 uL/minute. Between different samples, the surface is regenerated with regeneration buffer (100 mM HCl). Processed curves are evaluated with Biacore T100 Evaluation software. VHHs could be divided within two groups: group one which gave additional binding to VEGFBII23B04 captured VEGF165 and a second group which is not able to simultaneously bind to VEGFBII23B04 captured VEGF165. Table 12-A summarizes the binding epitopes of the tested VHHs.

The same assay set-up is used to assess whether VEGFR1, VEGFR2, Ranibizumab and Bevacizumab are able to bind to human VEGF-165 simultaneously with VEGFBII23B04. Table 12-B presents the additional binding responses to VEGFBII23B04-captured VEGF165. Only VEGFR2 is not able to bind to VEGFBII23B04-captured VEGF165, underscoring the blocking capacity of VEGFBII23B04 for the VEGF-VEGFR2 interaction. In addition, these data show that the VEGFBII23B04 epitope is different from the Bevacizumab and Ranibizumab epitope.

TABLE 12-A

Epitope binning of anti-VEGF VHHs—simultaneous binding with VEGFBII23604

| | | | | | | | | | | |
|---|---|---|---|---|---|---|---|---|---|---|
| No or low additional binding to 23B04-captured VEGF165* | 1C02 | 1E07 | 4B08 | 8E07 | 8F07 | 12A07 | 12B01 | 86C11 | 86F11 | 86G08 |
| | 86G10 | 86G11 | 87B07 | 88A01 | 88A02 | 88B02 | 88E02 | 88G03 | 88G05 | 88G11 |
| | 88H01 | 89B04 | 89D04 | 89F09 | 89G09 | 89H08 | 24C04 | 23A6 | 27G07 | 23B04 |
| Additional binding to 23B04-captured VEGF165 | 3D12 | 5B02 | 5B03 | 5B05 | 6G02 | 7D08 | 8D09 | 8F06 | 10C07 | 10E07 |
| | 10G04 | 10G05 | 11C08 | 11D09 | 11E04 | 11E05 | 11F12 | 86H09 | 41C05 | |

*indicating same or overlapping epitopes

TABLE 12-B

Epitope binning of VEGFBII23B04 - binding of benchmark inhibitors or cognate receptors on VEGFBII23B04 captured VEGF165

| Injection step | Binding | [sample] | Binding level (RU) |
|---|---|---|---|
| 1 | VEGF165 | 100 nM | 1727 |
| 2 | VEGFBII23B04 | 100 nM | — |
| 3 | Ranibizumab | 100 nM | 763 |

TABLE 12-B-continued

Epitope binning of VEGFBII23B04 - binding of benchmark inhibitors or cognate receptors on VEGFBII23B04 captured VEGF165

| Injection step | Binding | [sample] | Binding level (RU) |
|---|---|---|---|
| 4 | Bevacizumab | 100 nM | 1349 |
| 5 | VEGFR1 | 100 nM | 1011 |
| 6 | VEGFR2 | 100 nM | — |

5.10 Characterization of the Anti-VEGF VHHs in the HUVEC Proliferation Assay

The potency of the selected VHHs is evaluated in a proliferation assay. In brief, primary HUVEC cells (Technoclone) are supplement-starved over night and then 4000 cells/well are seeded in quadruplicate in 96-well tissue culture plates. Cells are stimulated in the absence or presence of VHHs with 33 ng/mL VEGF. The proliferation rates are measured by [$^3$H] Thymidine incorporation on day 4. The results of the HUVEC proliferation assay are shown in Table.

TABLE 13

$IC_{50}$ (nM) values and % inhibition of monovalent VEGFBII23B04, VEGFBII23A06 and VEGFBII24C04 in VEGF HUVEC proliferation assay

| VHH ID | $IC_{50}$ (nM) | % inhibition |
|---|---|---|
| VEGFBII23B04 | 0.36 | 91 |
| Bevacizumab | 0.21 | 92 |
| VEGFBII23A06 | 4.29 | 73 |
| VEGFBII24C04 | 3.8 | 79 |
| Bevacizumab | 0.78 | 78 |

5.11 Characterization of the Anti-VEGF VHHs in the HUVEC Erk Phosphorylation Assay The potency of the selected VHHs is assessed in the HUVEC Erk phosphorylation assay. In brief, primary HUVE cells are serum-starved over night and then stimulated in the absence or presence of VHHs with 10 ng/mL VEGF for 5 min. Cells are fixed with 4% Formaldehyde in PBS and ERK phosphorylation levels are measured by ELISA using phosphoERK-specific antibodies (anti-phosphoMAP Kinase pERK1&2, M8159, Sigma) and polyclonal Rabbit Anti-Mouse-Immunoglobulin-HRP conjugate (P0161, Dako). As shown in Table 14, VEGFBII23B04 and Bevacizumab inhibit the VEGF induced Erk phosphorylation by at least 90%, with $IC_{50}$s<1 nM.

TABLE 14

$IC_{50}$ (nM) values and % inhibition of monovalent VEGFBII23B04 in VEGF HUVEC Erk phosphorylation assay

| VHH ID | $IC_{50}$ (nM) | % inhibition |
|---|---|---|
| VEGFBII23B04 | 0.37 | 90 |
| Bevacizumab | 0.63 | 98 |

Example 6

Generation of Multivalent Anti-VEGF Blocking VHHs

VHH VEGFBII23B04 is genetically fused to either VEGFBII23B04 resulting in a homodimeric VHH (AA sequence see Table 15) or different VEGF binding VHHs resulting in heterodimeric VHHs. To generate the heterodimeric VHHs, a panel of 10 unique VEGF binding VHHs are linked via a 9 or 40 Gly-Ser flexible linker (SEQ ID NOS 170 and 171, respectively) in two different orientations to VEGFBII23B04 (AA sequences see Table 15). Homodimeric VEGFBII23B04 (VEGFBII010) and the 40 heterodimeric bivalent' VHHs are expressed in *E. coli* TG1 as c-myc, His6-tagged proteins ("His6" disclosed as SEQ ID NO: 283). Expression is induced by addition of 1 mM IPTG and allowed to continue for 4 hours at 3TC. After spinning the cell cultures, periplasmic extracts are prepared by freeze-thawing the pellets. These extracts are used as starting material and VHHs are purified via IMAC and desalting resulting in 90% purity as assessed via SDS-PAGE.

TABLE 15

Sequence ID, VHH ID and AA sequence of bivalent anti-VEGF VHHs (each of the used linkers is highlighted in one relevant sequence)

| Sequence ID/ SEQ ID NO: | VHH ID | AA sequence |
|---|---|---|
| VEGFBII23604-35GS-23B04/128 | VEGFBII010 | EVQLVESGGGLVQTGDSLRLSCEVSGRTFSSYSMGWFRQAQGKEREFVVAISKGGYKYDSVS LEGRFTISKDNAKNTVYLQINSLKPEDTAVYYCASSRAYGSSRLRLADTYEYWGQGTQVTVSS **GGGGSGGGGSGGGGSGGGGSGGGGSGGGGSGGGGS**EVQLVESGGGLVQTGDSLRLSCE VSGRTFSSYSMGWFRQAQGKEREFVVAISKGGYKYDSVSLEGRFTISKDNAKNTVYLQINSLK PEDTAVYYCASSRAYGSSRLRLADTYEYWGQGTQVTVSS |
| VEGFBII23B04-9GS-4B08/129 | | EVQLVESGGGLVQTGDSLRLSCEVSGRTFSSYSMGWFRQAQGKEREFVVAISKGGYKYDSVS LEGRFTISKDNAKNTVYLQINSLKPEDTAVYYCASSRAYGSSRLRLADTYEYWGQGTQVTVSS **GGGGSGGGS**EVQLVESGGGLVQPGGSLRLSCAASGSAVGDITVAWYRQAPGIQRQLVATITP SGYTYYWDFVKGRFTISRDNSKNIVYLQMNSLKPEDTAAYYCNTQFYWGQGTQVTVSS |
| VEGFBII23B04-9GS-5B03/130 | | EVQLVESGGGLVQTGDSLRLSCEVSGRTFSSYSMGWFRQAQGKEREFVVAISKGGYKYDSVS LEGRFTISKDNAKNTVYLQINSLKPEDTAVYYCASSRAYGSSRLRLADTYEYWGQGTQVTVSS GGGGSGGGSEVQLVESGGGLAQAGDSLRLSCAASGRSFSHYNMGWFRQAPGKEREFVASIR GGGGSTTYANSVKDRFTISRENAKNTVYLQMNSLKPEDTAVYYCAATAFYRGPYDYDYWGQG TQVTVSS |
| VEGFBII23B04-9GS-5B05/131 | VEGFBII022 | EVQLVESGGGLVQTGDSLRLSCEVSGRTFSSYSMGWFRQAQGKEREFVVAISKGGYKYDSVS LEGRFTISKDNAKNTVYLQINSLKPEDTAVYYCASSRAYGSSRLRLADTYEYWGQGTQVTVSS GGGGSGGGSEVQLVESGGGLVQPGGSLRLSCVASGIRFMSMAWYRQAPGKHRELVARISSG GTTAYVDSVKGRFTISRDNSKNTVYLQMNSLKAEDTAVYYCNTFSSRPNPWGAGTQVTVSS |

TABLE 15-continued

Sequence ID, VHH ID and AA sequence of bivalent anti-VEGF VHHs (each of the used linkers is highlighted in one relevant sequence)

| Sequence ID/<br>SEQ ID NO: | VHH ID | AA sequence |
|---|---|---|
| VEGFBII23B04-<br>9GS-6G02/132 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGSEVQLVESGGGLVQPGGSLRLSCAASGNIFSNNAMAWYRQAPGKQRELVARIS<br>GGGFTYYLDSVKGRFTVSRDNAKNTVYLQMNSLKPEDTAVYYCNAAYRTYNYWGQGTQVTV<br>SS |
| VEGFBII23B04-<br>9GS-10E07/133 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGSEVQLVESGGGLVQAGGSLRLSCAASGRTFSNYAMGWFRQAPGKERVLVADIS<br>SSGINTYVADAVKGRFTISRDNAKNTVYLQMNSLKPEDTAVYYCAASAWWYSQMARDNYRYW<br>GQGTQVTVSS |
| VEGFBII23B04-<br>9GS-12B01/134 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGSEVQLVESGGGLVQPGGSLRLACAASGFTLSSSWMYWVRQAPGKGLEWVSRI<br>SPGGLFTYYVDSVKGRFSVSTDNANNTLYLQMNSLKPEDTALYSCAKGGAPNYTPRGRGTQV<br>TVSS |
| VEGFBII23B04-<br>9GS-86C11/135 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGSEVQLVESGGGLVQAGDSLRLSCTASGRTFNSYAMGWFRQAPGKERESVAHIN<br>RSGSSTYYADSVKGRFTISRDNAKNTVYLQLNSLKPEDTAVYYCAAGRYYSSDGVPSASFNYW<br>GQGTQVTVSS |
| VEGFBII23B04-<br>9GS-86H09/136 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGSEVQLVESGGGLVQAGGSLRLSCTASGSAFKSYRMGWFRRTPGKEDEFVASIS<br>WTYGSTFYADSVKGRFTMSRDKAKNAGYLQMNSLKPEDTALYYCAAGAQSDRYNIRSYDYW<br>GQGTQVTVSS |
| VEGFBII23B04-<br>9GS-87B07/137 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGSEVQLVESGGGLVQPGGSLKLSCTASGFTFSTSWMHWVRQAPGKGLEWVSSIP<br>PVGHFANYAPSVKGRFTISRDNAKNTLFLQMNSLKSEDTAVYYCAKDSAGRTKGQGTQVTVSS |
| VEGFBII23B04-<br>9GS-88A01/138 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGSEVQLVESGGGLVQAGGSLRLSCAASERTFSNYAMDWFRQAPGKEREFVAAIT<br>RSGGGTYYADSVKGRFTISRDNAKNTVYLQMNSLKPEDTAVYYCAATRSSTIVVGVGGMEYW<br>GKGTQVTVSS |
| VEGFBII23B04-<br>40GS-4608/139 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>**GGGGSGGGGSGGGGSGGGGSGGGGSGGGGSGGGGSGGGGS**EVOLVESGGGLVQPGGS<br>LRLSCAASGSAVGDITVAWYRQAPGIQRQLVATITPSGYTYYWDFVKGRFTISRDNSKNIVYLQ<br>MNSLKPEDTAAYYCNTQFYWGQGTQVTVSS |
| VEGFBII23B04-<br>40GS-5B03/140 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGGSGGGGSGGGGSGGGGSGGGGSGGGGSGGGGSEVQLVESGGGLAQAGDSL<br>RLSCAASGRSFSHYNMGWFRQAPGKEREFVASIRGGGGSTTYANSVKDRFTISRENAKNTVY<br>LQMNSLKPEDTAVYYCAATAFYRGPYDYDYWGQGTQVTVSS |
| VEGFBII23B04-<br>40GS-5B05/141 | VEGFBII021 | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGGSGGGGSGGGGSGGGGSGGGGSGGGGSGGGGSEVQLVESGGGLVQPGGS<br>LRLSCVASGIRFMSMAWYRQAPGKHRELVARISSGGTTAYVDSVKGRFTISRDNSKNTVYLQM<br>NSLKAEDTAVYYCNTFSSRPNPWGAGTQVTVSS |
| VEGFBII23B04-<br>40GS-6G02/142 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGGSGGGGSGGGGSGGGGSGGGGSGGGGSGGGGSEVQLVESGGGLVQPGGS<br>LRLSCAASGNIFSNNAMAWYRQAPGKQRELVARISSGGGFTYYLDSVKGRFTVSRDNAKNTVY<br>LQMNSLKPEDTAVYYCNAAYRTYNYWGQGTQVTVSS |
| VEGFBII23B04-<br>40GS-10E07/143 | VEGFBII023 | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGGSGGGGSGGGGSGGGGSGGGGSGGGGSGGGGSEVQLVESGGGLVQAGGS<br>LRLSCAASGRTFSNYAMGWFRQAPGKERVLVADISSSGINTYVADAVKGRFTISRDNAKNTVYL<br>QMNSLKPEDTAVYYCAASAWWYSQMARDNYRYWGQGTQVTVSS |

TABLE 15-continued

Sequence ID, VHH ID and AA sequence of bivalent anti-VEGF VHHs (each of the used linkers is highlighted in one relevant sequence)

| Sequence ID/<br>SEQ ID NO: | VHH ID | AA sequence |
|---|---|---|
| VEGFBII23B04-<br>40GS-12B01/144 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGGSGGGGSGGGGSGGGGSGGGGSGGGGSGGGGSEVQLVESGGGLVQPGGS<br>LRLACAASGFTLSSSWMYWVRQAPGKGLEWVSRISPGGLFTYYVDSVKGRFSVSTDNANNTL<br>YLQMNSLKPEDTALYSCAKGGAPNYTPRGRGTQVTVSS |
| VEGFBII23B04-<br>40GS-86C11/145 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGGSGGGGSGGGGSGGGGSGGGGSGGGGSGGGGSEVQLVESGGGLVQAGDSL<br>RLSCTASGRTFNSYAMGWFRQAPGKERESVAHINRSGSSTYYADSVKGRFTISRDNAKNTVYL<br>QLNSLKPEDTAVYYCAAGRYYSSDGVPSASFNYWGQGTQVTVSS |
| VEGFBII23B04-<br>40GS-86H09/146 | VEGFBII024 | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGGSGGGGSGGGGSGGGGSGGGGSGGGGSGGGGSEVQLVESGGGLVQAGGS<br>LRLSCTASGSAFKSYRMGWFRRTPGKEDEFVASISWTYGSTFYADSVKGRFTMSRDKAKNAG<br>YLQMNSLKPEDTALYYCAAGAQSDRYNIRSYDYWGQGTQVTVSS |
| VEGFBII23B04-<br>40GS-87B07/147 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGGSGGGGSGGGGSGGGGSGGGGSGGGGSGGGGSEVQLVESGGGLVQPGGS<br>LKLSCTASGFTFSTSWMHWVRQAPGKGLEWVSSIPPVGHFANYAPSVKGRFTISRDNAKNTLF<br>LQMNSLKSEDTAVYYCAKDSAGRTKGQGTQVTVSS |
| VEGFBII23B04-<br>40GS-88A01/148 | | EVQLVESGGGLVQTGDSLRLSCEVSGRTFSSYSMGWFRQAQGKEREFVVAISKGGYKYDSVS<br>LEGRFTISKDNAKNTVYLQINSLKPEDTAVYYCASSRAYGSSRLRLADTYEYWGQGTQVTVSS<br>GGGGSGGGGSGGGGSGGGGSGGGGSGGGGSGGGGSGGGGSEVQLVESGGGLVQAGGS<br>LRLSCAASERTFSNYAMDWFRQAPGKEREFVAAITRSGGGTYYADSVKGRFTISRDNAKNTVY<br>LQMNSLKPEDTAVYYCAATRSSTIVVGVGGMEYWGKGTQVTVSS |
| VEGFBII4B08-9GS-<br>23B04/149 | | EVQLVESGGGLVQPGGSLRLSCAASGSAVGDITVAWYRQAPGIQRQLVATITPSGYTYYWDFV<br>KGRFTISRDNSKNIVYLQMNSLKPEDTAAYYCNTQFYWGQGTQVTVSSGGGGSGGGSEVQLV<br>ESGGGLVQTGDSLRLSCEVSGRTFSSYSMGWFRQAQGKEREFVVAISKGGYKYDSVSLEGRF<br>TISKDNAKNTVYLQINSLKPEDTAVYYCASSRAYGSSRLRLADTYEYWGQGTQVTVSS |
| VEGFBII5B03-9GS-<br>23B04/150 | | EVQLVESGGGLAQAGDSLRLSCAASGRSFSHYNMGWFRQAPGKEREFVASIRGGGGSTTYA<br>NSVKDRFTISRENAKNTVYLQMNSLKPEDTAVYYCAATAFYRGPYDYDYWGQGTQVTVSSGG<br>GGSGGGSEVQLVESGGGLVQTGDSLRLSCEVSGRTFSSYSMGWFRQAQGKEREFVVAISKG<br>GYKYDSVSLEGRFTISKDNAKNTVYLQINSLKPEDTAVYYCASSRAYGSSRLRLADTYEYWGQ<br>GTQVTVSS |
| VEGFBII5B05-9GS-<br>23B04/151 | | EVQLVESGGGLVQPGGSLRLSCVASGIRFMSMAWYRQAPGKHRELVARISSGGTTAYVDSVK<br>GRFTISRDNSKNTVYLQMNSLKAEDTAVYYCNTFSSRPNPWGAGTQVTVSSGGGGSGGGSE<br>VQLVESGGGLVQTGDSLRLSCEVSGRTFSSYSMGWFRQAQGKEREFVVAISKGGYKYDSVSL<br>EGRFTISKDNAKNTVYLQINSLKPEDTAVYYCASSRAYGSSRLRLADTYEYWGQGTQVTVSS |
| VEGFBII6G02-9GS-<br>23B04/152 | | EVQLVESGGGLVQPGGSLRLSCAASGNIFSNNAMAWYRQAPGKQRELVARISSGGGFTYYLD<br>SVKGRFTVSRDNAKNTVYLQMNSLKPEDTAVYYCNAAYRTYNYWGQGTQVTVSSGGGGSGG<br>GSEVQLVESGGGLVQTGDSLRLSCEVSGRTFSSYSMGWFRQAQGKEREFVVAISKGGYKYDS<br>VSLEGRFTISKDNAKNTVYLQINSLKPEDTAVYYCASSRAYGSSRLRLADTYEYWGQGTQVTVSS |
| VEGFBII10E07-<br>9GS-23B04/153 | | EVQLVESGGGLVQAGGSLRLSCAASGRTFSNYAMGWFRQAPGKERVLVADISSSGINTYVAD<br>AVKGRFTISRDNAKNTVYLQMNSLKPEDTAVYYCAASAWWYSQMARDNYRYWGQGTQVTVS<br>SGGGGSGGGSEVQLVESGGGLVQTGDSLRLSCEVSGRTFSSYSMGWFRQAQGKEREFVVAI<br>SKGGYKYDSVSLEGRFTISKDNAKNTVYLQINSLKPEDTAVYYCASSRAYGSSRLRLADTYEYW<br>GQGTQVTVSS |
| VEGFBII12B01-<br>9GS-23B04/154 | | EVQLVESGGGLVQPGGSLRLACAASGFTLSSSWMYWVRQAPGKGLEWVSRISPGGLFTYYV<br>DSVKGRFSVSTDNANNTLYLQMNSLKPEDTALYSCAKGGAPNYTPRGRGTQVTVSSGGGGS<br>GGGSEVQLVESGGGLVQTGDSLRLSCEVSGRTFSSYSMGWFRQAQGKEREFVVAISKGGYK<br>YDSVSLEGRFTISKDNAKNTVYLQINSLKPEDTAVYYCASSRAYGSSRLRLADTYEYWGQGTQ<br>VTVSS |
| VEGFBII86C11-<br>9GS-23B04/155 | | EVQLVESGGGLVQAGDSLRLSCTASGRTFNSYAMGWFRQAPGKERESVAHINRSGSSTYYAD<br>SVKGRFTISRDNAKNTVYLQLNSLKPEDTAVYYCAAGRYYSSDGVPSASFNYWGQGTQVTVS<br>SGGGGSGGGSEVQLVESGGGLVQTGDSLRLSCEVSGRTFSSYSMGWFRQAQGKEREFVVAI<br>SKGGYKYDSVSLEGRFTISKDNAKNTVYLQINSLKPEDTAVYYCASSRAYGSSRLRLADTYEYW<br>GQGTQVTVSS |
| VEGFBII86H09-<br>9GS-23B04/156 | | EVQLVESGGGLVQAGGSLRLSCTASGSAFKSYRMGWFRRTPGKEDEFVASISWTYGSTFYAD<br>SVKGRFTMSRDKAKNAGYLQMNSLKPEDTALYYCAAGAQSDRYNIRSYDYWGQGTQVTVSS<br>GGGGSGGGSEVQLVESGGGLVQTGDSLRLSCEVSGRTFSSYSMGWFRQAQGKEREFVVAIS<br>KGGYKYDSVSLEGRFTISKDNAKNTVYLQINSLKPEDTAVYYCASSRAYGSSRLRLADTYEYW<br>GQGTQVTVSS |

TABLE 15-continued

Sequence ID, VHH ID and AA sequence of bivalent anti-VEGF VHHs (each of the used linkers is highlighted in one relevant sequence)

| Sequence ID/ SEQ ID NO: | VHH ID | AA sequence |
|---|---|---|
| VEGFBII87B07-9GS-23B04/157 | | EVQLVESGGGLVQPGGSLKLSCTASGFTFSTSWMHWVRQAPGKGLEWVSSIPPVGHFANYA<br>PSVKGRFTISRDNAKNTLFLQMNSLKSEDTAVYYCAKDSAGRTKGQGTQVTVSSGGGGSGGG<br>SEVQLVESGGGLVQTGDSLRLSCEVSGRTFSSYSMGWFRQAQGKEREFVVAISKGGYKYDSV<br>SLEGRFTISKDNAKNTVYLQINSLKPEDTAVYYCASSRAYGSSRLRLADTYEYWGQGTQVTVSS |
| VEGFBII88A01-9GS-23B04/158 | | EVQLVESGGGLVQAGGSLRLSCAASERTFSNYAMDWFRQAPGKEREFVAAITRSGGGTYYAD<br>SVKGRFTISRDNAKNTVYLQMNSLKPEDTAVYYCAATRSSTIVVGVGGMEYWGKGTQVTVSS<br>GGGGSGGGSEVQLVESGGGLVQTGDSLRLSCEVSGRTFSSYSMGWFRQAQGKEREFVVAIS<br>KGGYKYDSVSLEGRFTISKDNAKNTVYLQINSLKPEDTAVYYCASSRAYGSSRLRLADTYEYW<br>GQGTQVTVSS |
| VEGFBII4B08-40GS-23B04/159 | | EVQLVESGGGLVQPGGSLRLSCAASGSAVGDITVAWYRQAPGIQRQLVATITPSGYTYYWDFV<br>KGRFTISRDNSKNIVYLQMNSLKPEDTAAYYCNTQFYWGQGTQVTVSSGGGGSGGGGSGGG<br>GSGGGGSGGGGSGGGGSGGGGSGGGGSEVQLVESGGGLVQTGDSLRLSCEVSGRTFSSY<br>SMGWFRQAQGKEREFVVAISKGGYKYDSVSLEGRFTISKDNAKNTVYLQINSLKPEDTAVYYC<br>ASSRAYGSSRLRLADTYEYWGQGTQVTVSS |
| VEGFBII5B03-40GS-23B04/160 | | EVQLVESGGGLAQAGDSLRLSCAASGRSFSHYNMGWFRQAPGKEREFVASIRGGGGSTTYA<br>NSVKDRFTISRENAKNTVYLQMNSLKPEDTAVYYCAATAFYRGPYDYDYWGQGTQVTVSSGG<br>GGSGGGGSGGGGSGGGGSGGGGSGGGGSGGGGSGGGGSEVQLVESGGGLVQTGDSLRL<br>SCEVSGRTFSSYSMGWFRQAQGKEREFVVAISKGGYKYDSVSLEGRFTISKDNAKNTVYLQIN<br>SLKPEDTAVYYCASSRAYGSSRLRLADTYEYWGQGTQVTVSS |
| VEGFBII5B05-40GS-23B04/161 | | EVQLVESGGGLVQPGGSLRLSCVASGIRFMSMAWYRQAPGKHRELVARISSGGTTAYVDSVK<br>GRFTISRDNSKNTVYLQMNSLKAEDTAVYYCNTFSSRPNPWGAGTQVTVSSGGGGSGGGGS<br>GGGGSGGGGSGGGGSGGGGSGGGGSGGGGSEVQLVESGGGLVQTGDSLRLSCEVSGRTF<br>SSYSMGWFRQAQGKEREFVVAISKGGYKYDSVSLEGRFTISKDNAKNTVYLQINSLKPEDTAV<br>YYCASSRAYGSSRLRLADTYEYWGQGTQVTVSS |
| VEGFBII6G02-40GS-23B04/162 | | EVQLVESGGGLVQPGGSLRLSCAASGNIFSNNAMAWYRQAPGKQRELVARISSGGGFTYYLD<br>SVKGRFTVSRDNAKNTVYLQMNSLKPEDTAVYYCNAAYRTYNYWGQGTQVTVSSGGGGSGG<br>GGSGGGGSGGGGSGGGGSGGGGSGGGGSGGGGSEVQLVESGGGLVQTGDSLRLSCEVS<br>GRTFSSYSMGWFRQAQGKEREFVVAISKGGYKYDSVSLEGRFTISKDNAKNTVYLQINSLKPE<br>DTAVYYCASSRAYGSSRLRLADTYEYWGQGTQVTVSS |
| VEGFBII10E07-40GS-23B04/163 | VEGFBII025 | EVQLVESGGGLVQAGGSLRLSCAASGRTFSNYAMGWFRQAPGKERVLVADISSSGINTYVAD<br>AVKGRFTISRDNAKNTVYLQMNSLKPEDTAVYYCAASAWWYSQMARDNYRYWGQGTQVTVS<br>SGGGGSGGGGSGGGGSGGGGSGGGGSGGGGSGGGGSGGGGSEVQLVESGGGLVQTGD<br>SLRLSCEVSGRTFSSYSMGWFRQAQGKEREFVVAISKGGYKYDSVSLEGRFTISKDNAKNTVY<br>LQINSLKPEDTAVYYCASSRAYGSSRLRLADTYEYWGQGTQVTVSS |
| VEGFBII12B01-40GS-23B04/164 | | EVQLVESGGGLVQPGGSLRLACAASGFTLSSSWMYWVRQAPGKGLEWVSRISPGGLFTYYV<br>DSVKGRFSVSTDNANNTLYLQMNSLKPEDTALYSCAKGGAPNYTPRGRGTQVTVSSGGGGS<br>GGGGSGGGGSGGGGSGGGGSGGGGSGGGGSGGGGSEVQLVESGGGLVQTGDSLRLSCE<br>VSGRTFSSYSMGWFRQAQGKEREFVVAISKGGYKYDSVSLEGRFTISKDNAKNTVYLQINSLK<br>PEDTAVYYCASSRAYGSSRLRLADTYEYWGQGTQVTVSS |
| VEGFBII86C11-40GS-23B04/165 | | EVQLVESGGGLVQAGDSLRLSCTASGRTFNSYAMGWFRQAPGKERESVAHINRSGSSTYYAD<br>SVKGRFTISRDNAKNTVYLQLNSLKPEDTAVYYCAAGRYYSSDGVPSASFNYWGQGTQVTVS<br>SGGGGSGGGGSGGGGSGGGGSGGGGSGGGGSGGGGSGGGGSEVQLVESGGGLVQTGD<br>SLRLSCEVSGRTFSSYSMGWFRQAQGKEREFVVAISKGGYKYDSVSLEGRFTISKDNAKNTVY<br>LQINSLKPEDTAVYYCASSRAYGSSRLRLADTYEYWGQGTQVTVSS |
| VEGFBII86H09-40GS-23B04/166 | | EVQLVESGGGLVQAGGSLRLSCTASGSAFKSYRMGWFRRTPGKEDEFVASISWTYGSTFYAD<br>SVKGRFTMSRDKAKNAGYLQMNSLKPEDTALYYCAAGAQSDRYNIRSYDYWGQGTQVTVSS<br>GGGGSGGGGSGGGGSGGGGSGGGGSGGGGSGGGGSGGGGSEVQLVESGGGLVQTGDSL<br>RLSCEVSGRTFSSYSMGWFRQAQGKEREFVVAISKGGYKYDSVSLEGRFTISKDNAKNTVYLQ<br>INSLKPEDTAVYYCASSRAYGSSRLRLADTYEYWGQGTQVTVSS |
| VEGFBII87B07-40GS-23B04/167 | | EVQLVESGGGLVQPGGSLKLSCTASGFTFSTSWMHWVRQAPGKGLEWVSSIPPVGHFANYA<br>PSVKGRFTISRDNAKNTLFLQMNSLKSEDTAVYYCAKDSAGRTKGQGTQVTVSSGGGGSGGG<br>GSGGGGSGGGGSGGGGSGGGGSGGGGSGGGGSEVQLVESGGGLVQTGDSLRLSCEVSGR<br>TFSSYSMGWFRQAQGKEREFVVAISKGGYKYDSVSLEGRFTISKDNAKNTVYLQINSLKPEDTA<br>VYYCASSRAYGSSRLRLADTYEYWGQGTQVTVSS |
| VEGFBII88A01-40GS-23B04/168 | | EVQLVESGGGLVQAGGSLRLSCAASERTFSNYAMDWFRQAPGKEREFVAAITRSGGGTYYAD<br>SVKGRFTISRDNAKNTVYLQMNSLKPEDTAVYYCAATRSSTIVVGVGGMEYWGKGTQVTVSS<br>GGGGSGGGGSGGGGSGGGGSGGGGSGGGGSGGGGSGGGGSEVQLVESGGGLVQTGDSL<br>RLSCEVSGRTFSSYSMGWFRQAQGKEREFVVAISKGGYKYDSVSLEGRFTISKDNAKNTVYLQ<br>INSLKPEDTAVYYCASSRAYGSSRLRLADTYEYWGQGTQVTVSS |

The panel of 40 bivalent VHHs is tested in the VEGFR2 and VEGFR1 blocking AlphaScreen assay, as described in Example 5.3 and 5.4, respectively. Based on potency and maximum level of inhibition, the 5 best bivalent VHHs (VEGFBII021, VEGFBII022, VEGFBI023, VEGFBI024 and VEGFBII025) are chosen for further characterization. An overview of the screening results for the 5 selected bivalent VHHs in the competitive VEGFR2 and VEGFR1 AlphaScreen is shown in Table 16.

TABLE 16

Potency and efficacy of 5 best bivalent VHHs in the VEGF/VEGFR1 and VEGF/VEGFR2 competition AlphaScreen assay

| | VEGFR2 | VEGFR1 | |
|---|---|---|---|
| VHH ID | $IC_{50}$ (pM) | $IC_{50}$ (pM) | % inhibition |
| VEGFBII021 | 9 | 16 | 100 |
| VEGFBII022 | 7 | 8 | 100 |
| VEGFBII023 | 38 | 44 | 91 |
| VEGFBII024 | 12 | 46 | 100 |
| VEGFBII025 | 51 | 39 | 82 |

Example 7

Characterization of Formatted Anti-VEGF VHHs

Figure 8:
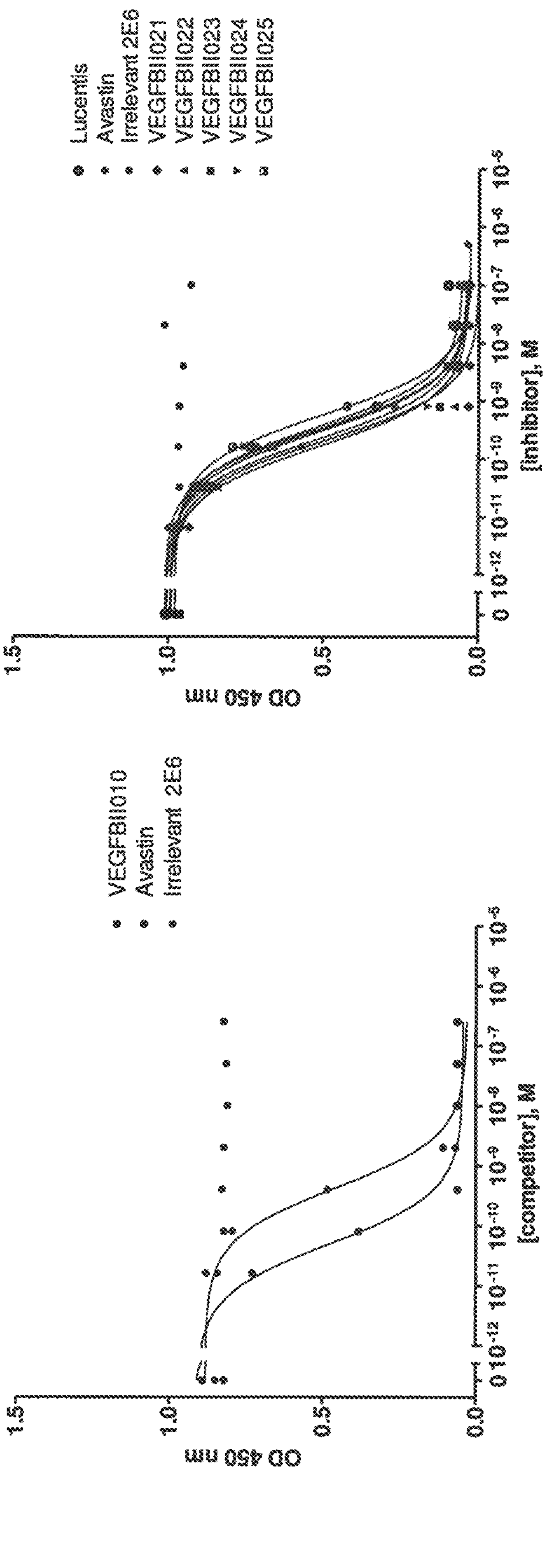
FIG. 8: Formatted VHHs block hVEGF165/hVEGFR2-Fc interaction (ELISA)
Figure 9:
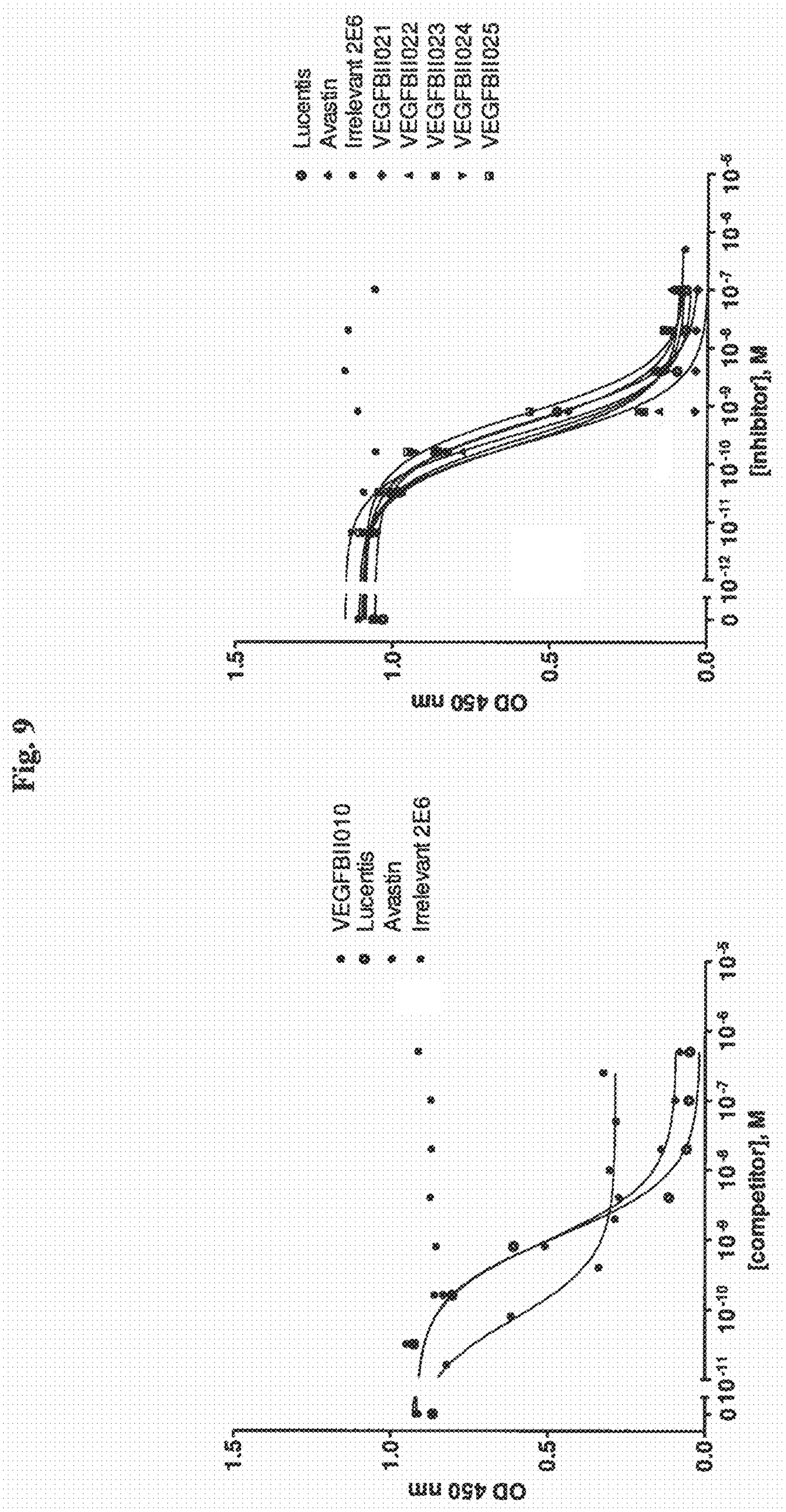
FIG. 9: Formatted VHHs block hVEGF165/hVEGFR1-Fc interaction (ELISA)
Figure 10:
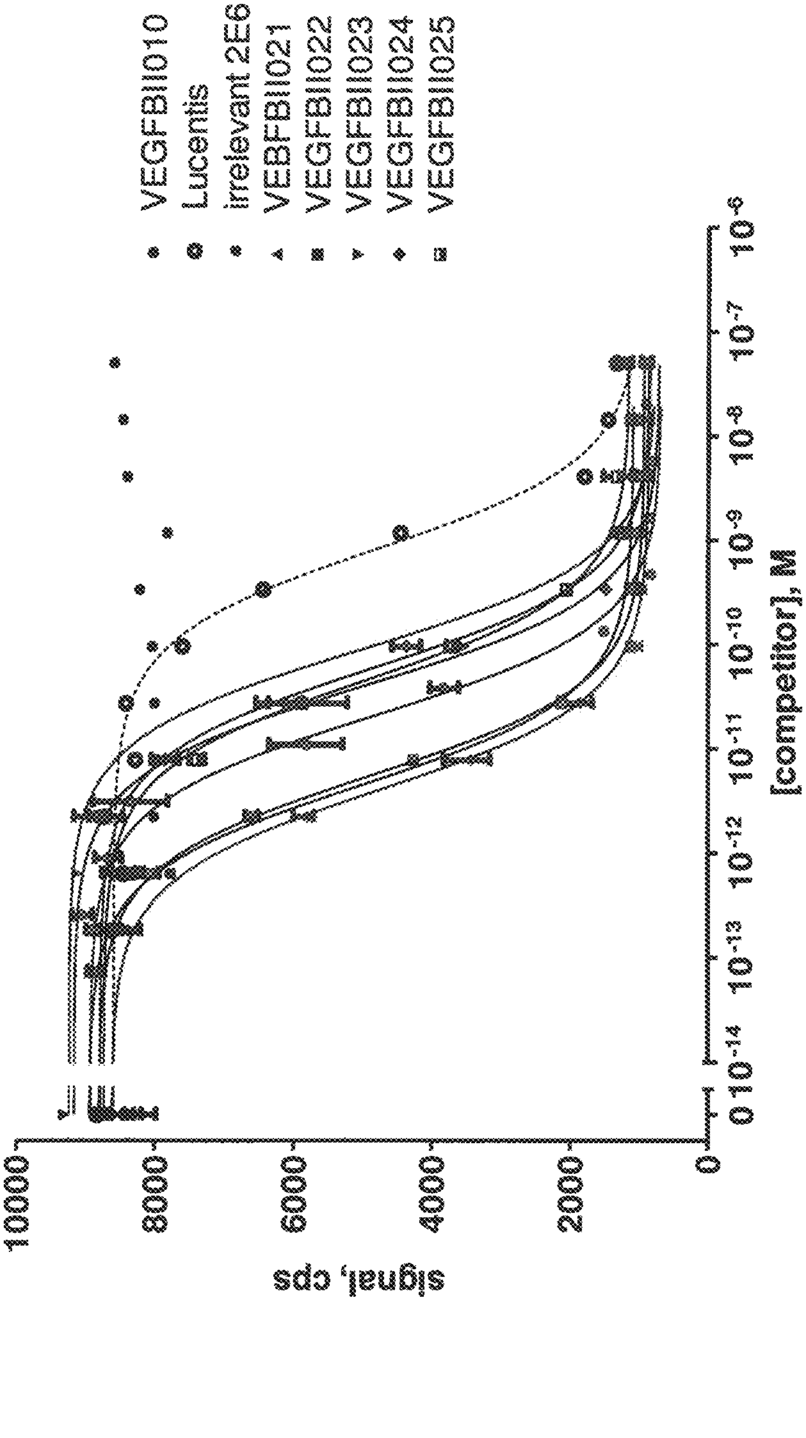
FIG. 10: Formatted VHHs block hVEGF165/hVEGFR2-Fc interaction (AlphaScreen)
Figure 11:
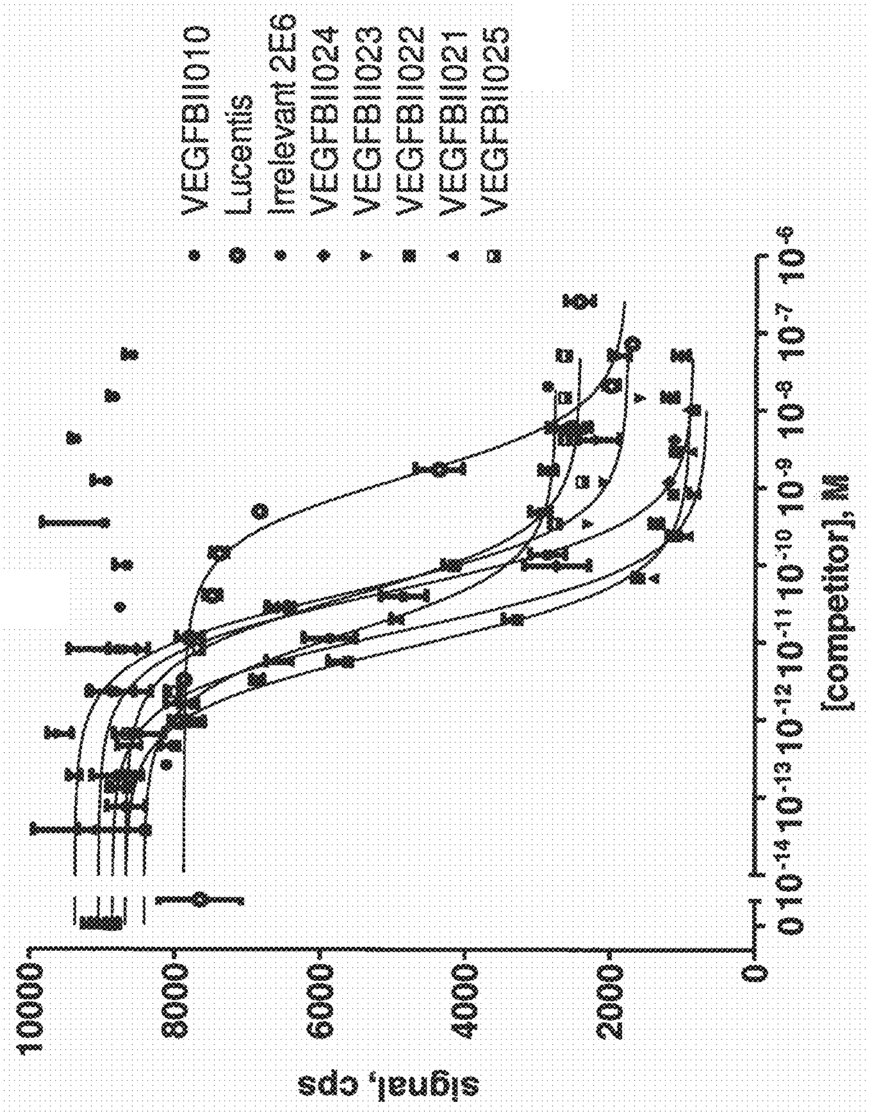
FIG. 11: Formatted VHHs block hVEGF165/hVEGFR1-Fc interaction (AlphaScreen)

VHHs VEGFBII010, VEGFBII021, VEGFBII022, VEGFBII023, VEGFBII024 and VEGFBII025 are compared side-by-side in the VEGFR2 and VEGFR1 blocking ELISA (FIGS. 8 and 9, Table 17 and Table 18 respectively) and AlphaScreen assay (FIGS. 10 and 11, Table 19 and 20) as described in Examples 5.1, 5.2, 5.3 and 5.4, respectively.

TABLE 17

$IC_{50}$ (pM) values and % inhibition for formatted VHHs in hVEGF165/hVEGFR2-Fc competition ELISA

| VHH ID | $IC_{50}$ (pM) | % inhibition |
|---|---|---|
| VEGFBII010 | 49 | 100 |
| VEGFBII021 | 204 | 100 |
| VEGFBII022 | 164 | 100 |
| VEGFBII023 | 213 | 100 |
| VEGFBII024 | 292 | 100 |
| VEGFBII025 | 577 | 100 |
| Bevacizumab | 315 | 100 |
| Ranibizumab | 349 | 100 |

TABLE 18

$IC_{50}$ (pM) values and % inhibition of formatted VHHs in VEGF165/hVEGFR1-Fc competition ELISA

| VHH ID | $IC_{50}$ (pM) | % inhibition |
|---|---|---|
| VEGFBII010 | 73.5 | 67 |
| VEGFBII021 | 254 | 97 |
| VEGFBII022 | 225 | 89 |
| VEGFBII023 | 279 | 91 |
| VEGFBII024 | 326 | 92 |
| VEGFBII025 | 735 | 91 |
| Bevacizumab | 484 | 91 |
| Ranibizumab | 594 | 96 |

TABLE 19

$IC_{50}$ (pM) values and % inhibition for formatted VHHs in hVEGF165/hVEGFR2-Fc competition AlphaScreen

| VHH ID | $IC_{50}$ (pM) | % inhibition |
|---|---|---|
| VEGFBII010 | 16 | 100 |
| VEGFBII021 | 7 | 100 |

TABLE 19-continued $IC_{50}$ (pM) values and % inhibition for formatted VHHs in hVEGF165/hVEGFR2-Fc competition AlphaScreen

| VHH ID | $IC_{50}$ (pM) | % inhibition |
|---|---|---|
| VEGFBII022 | 7 | 100 |
| VEGFBII023 | 46 | 100 |
| VEGFBII024 | 50 | 100 |
| VEGFBII025 | 51 | 100 |
| Ranibizumab | 600 | 100 |

TABLE 20

$IC_{50}$ (pM) values and % inhibition of formatted VHHs in VEGF165/hVEGFR1-Fc competition AlphaScreen

| VHH ID | $IC_{50}$ (pM) | % inhibition |
|---|---|---|
| VEGFBII010 | 21 | 70 |
| VEGFBII021 | 12 | 100 |
| VEGFBII022 | 9 | 98 |
| VEGFBII023 | 48 | 87 |
| VEGFBII024 | 69 | 98 |
| VEGFBII025 | 71 | 82 |
| Ranibizumab | 1300 | 87 |

Figure 12:
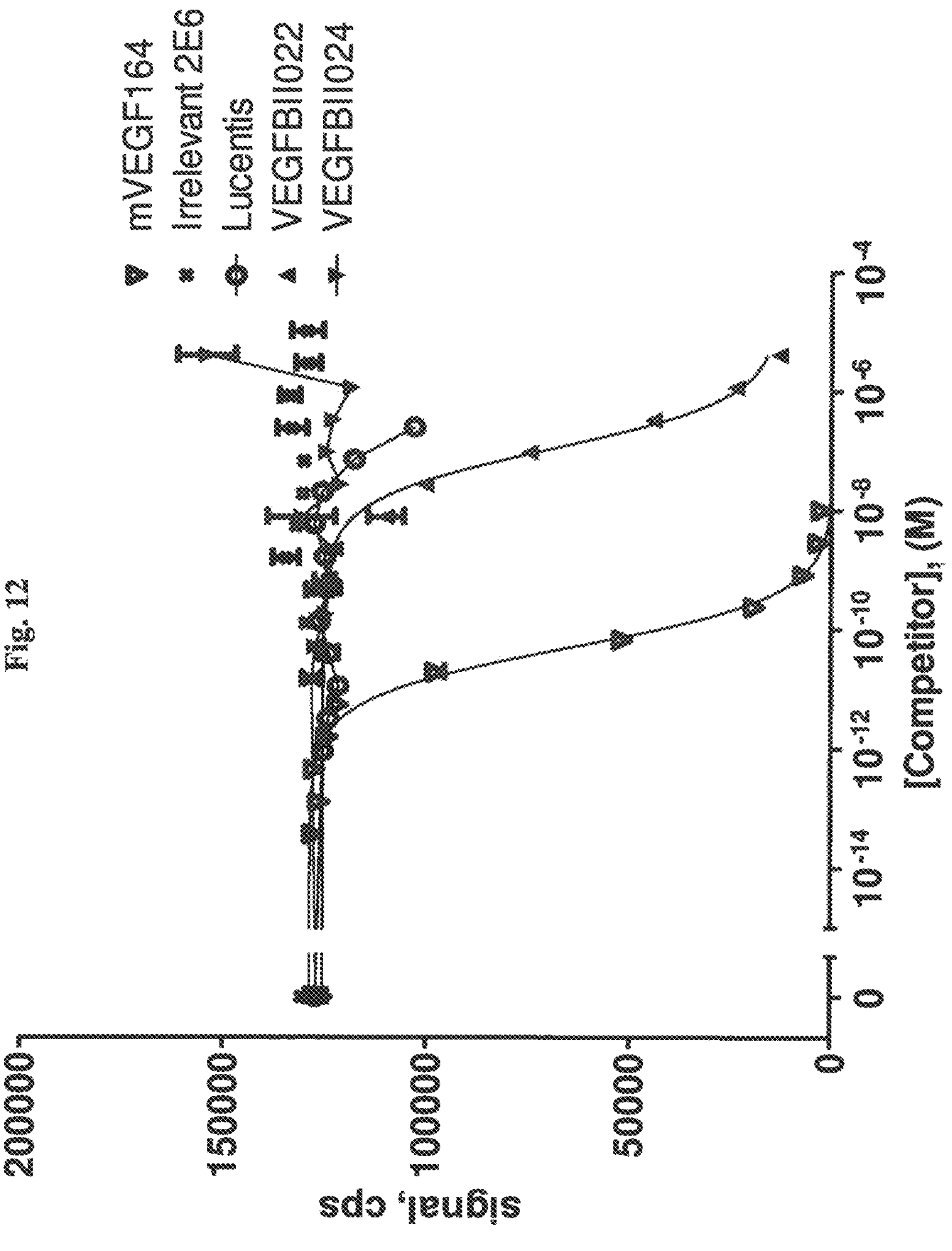
FIG. 12: Formatted VHHs block mVEGF164/mVEGFR2-Fc interaction (AlphaScreen)

In addition, formatted VHHs are also tested for their capacity to block the mVEGF164/mVEGFR2-huFc interaction. In brief, serial dilutions of purified VHHs (concentration range: 4 µM-14.5 pM) in PBS buffer containing 0.03% Tween 20 (Sigma) are added to 0.1 nM biotinylated mVEGF164 and incubated for 15 min. Subsequently mouse VEGFR2-huFc (0.1 nM) and anti-huFc VHH-coated acceptor beads (20 µg/ml) are added and this mixture is incubated for 1 hour. Finally, streptavidin donor beads (20 µg/ml) are added and after 1 hour of incubation fluorescence is measured on the Envision microplate reader. Dose-response curves are shown in FIG. 12. The $IC_{50}$ values for VHHs blocking the mouse VEGF164/VEGFR2-hFC interaction are summarized in Table 21.

TABLE 21

$IC_{50}$ (pM) values and % inhibition for formatted VHHs in mVEGF164/mVEGFR2-hFc competition AlphaScreen

| VHH ID | $IC_{50}$ (nM) | % inhibition |
|---|---|---|
| VEGFBII022 | 108 | 100 |
| VEGFBII024 | — | — |
| mVEGF164 | 0.05 | 100 |
| Ranibizumab | — | — |

Figure 13:
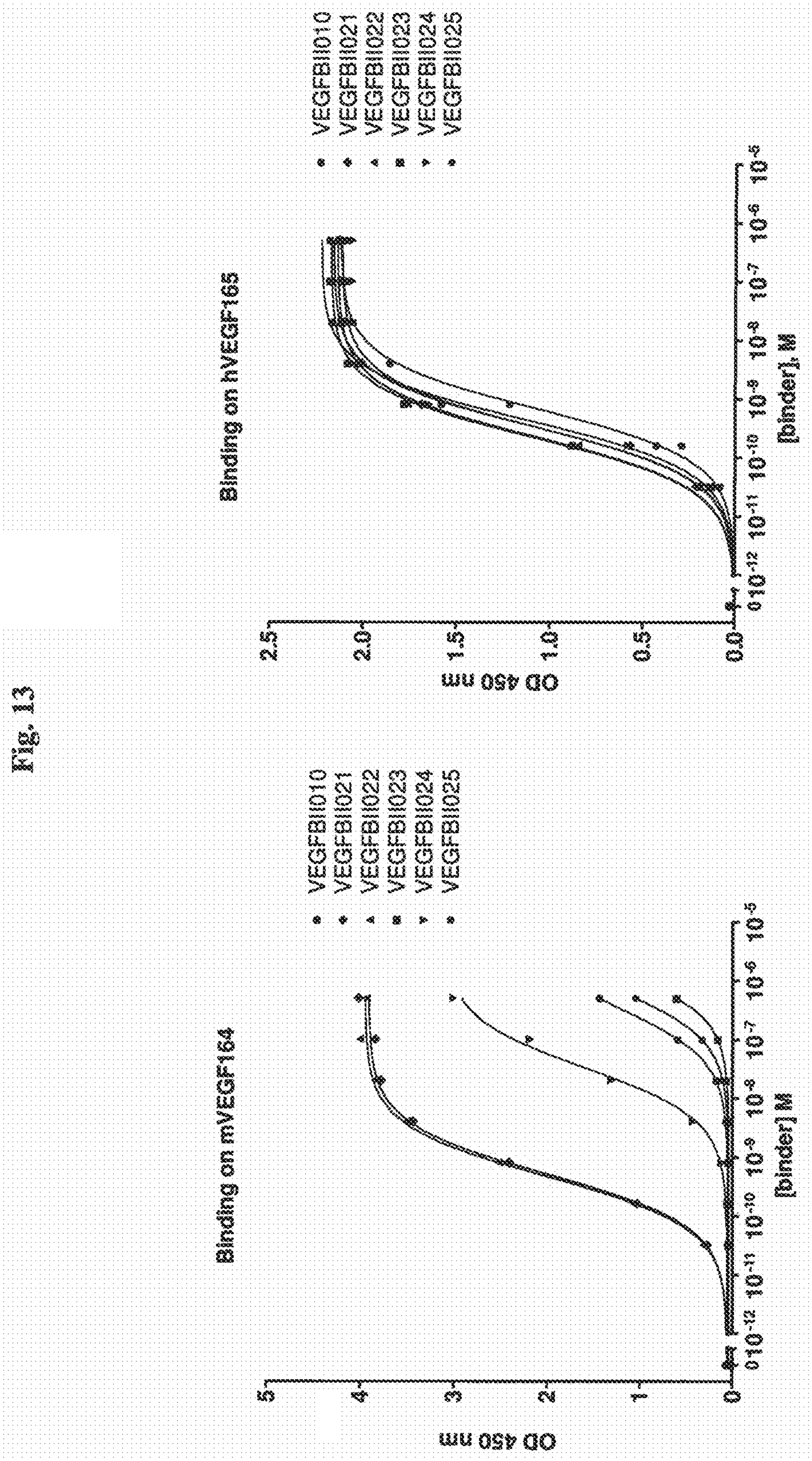
FIG. 13: Formatted VHHs bind to mouse and human VEGF
Figure 14A:
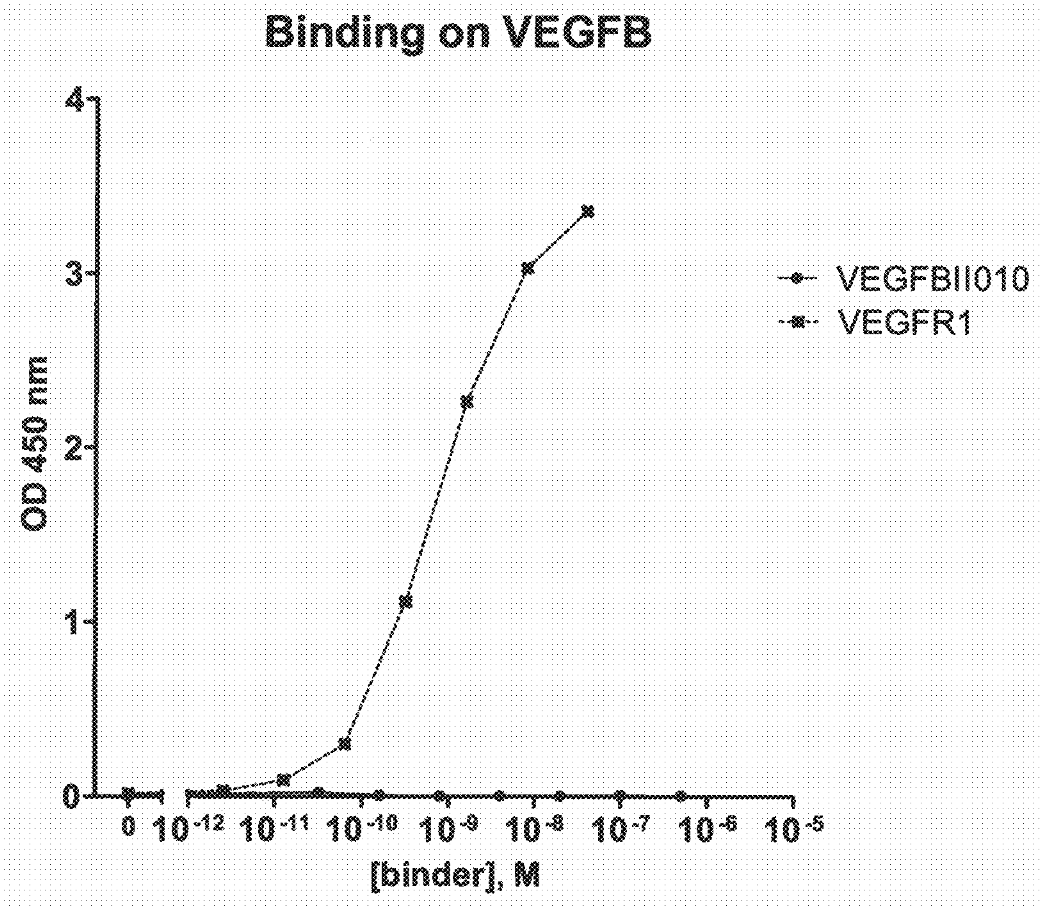
FIG. 14A-14H: Formatted VHHs do not bind to VEGFB, VEGFC, VEGFD and PlGF
Figure 14B:
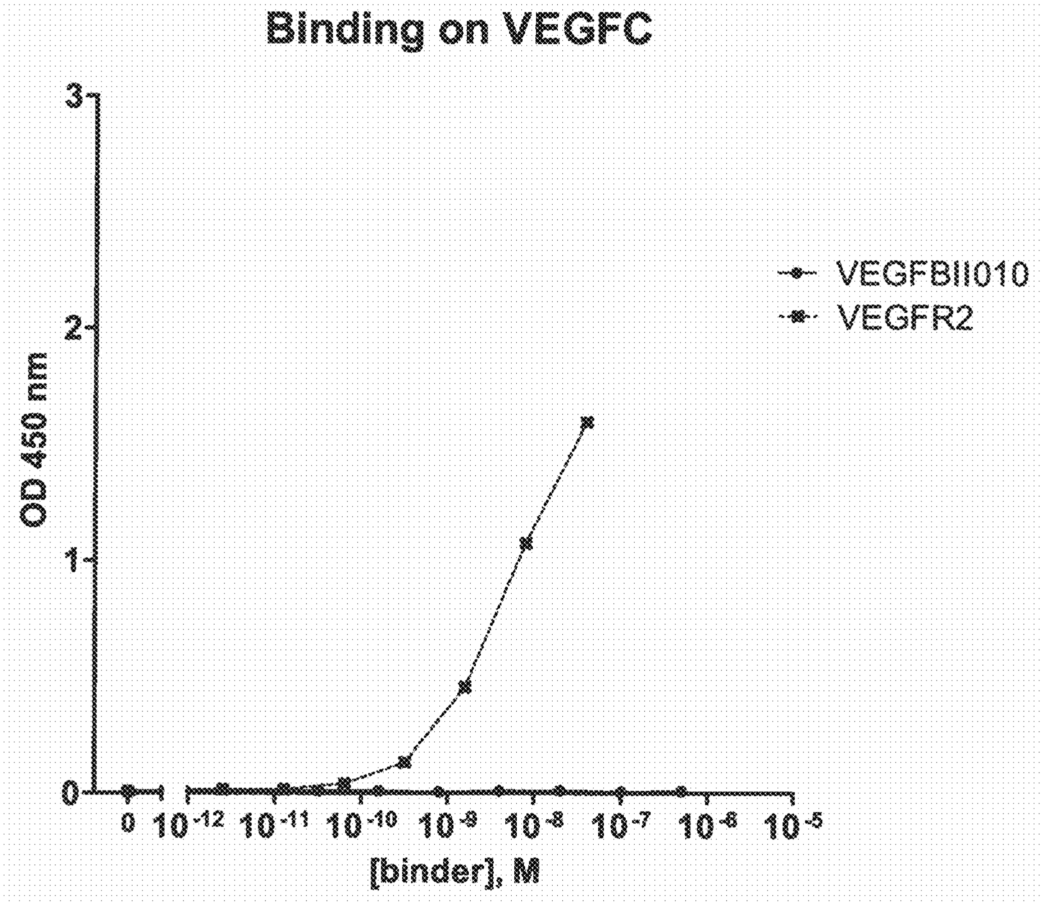
Figure 14C:
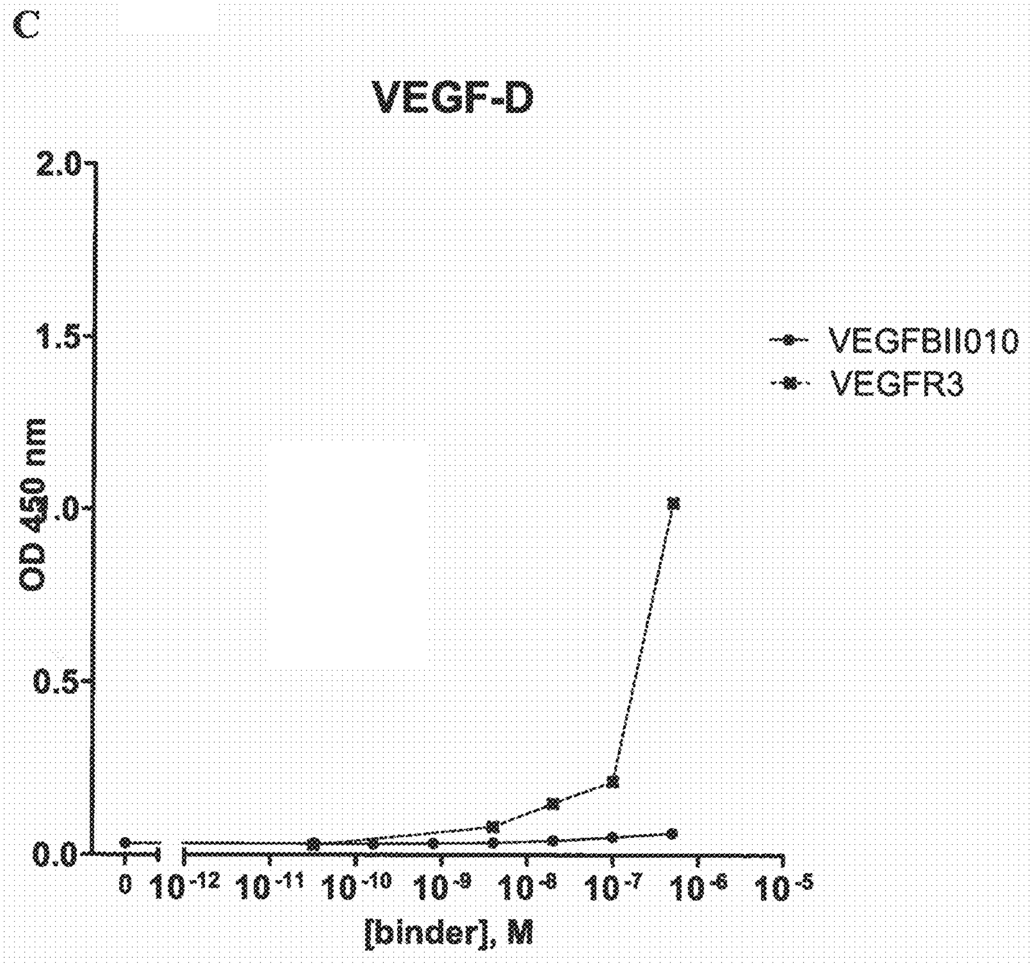
Figure 14D:
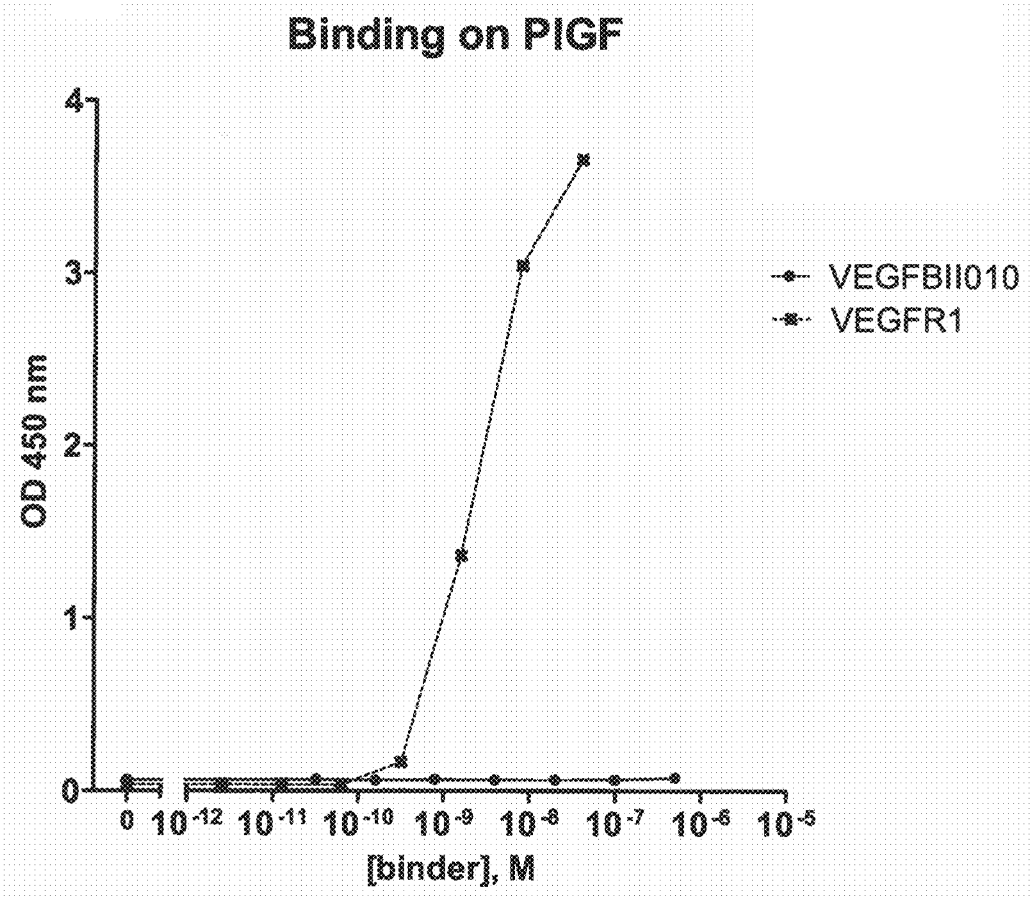
Figure 14E:
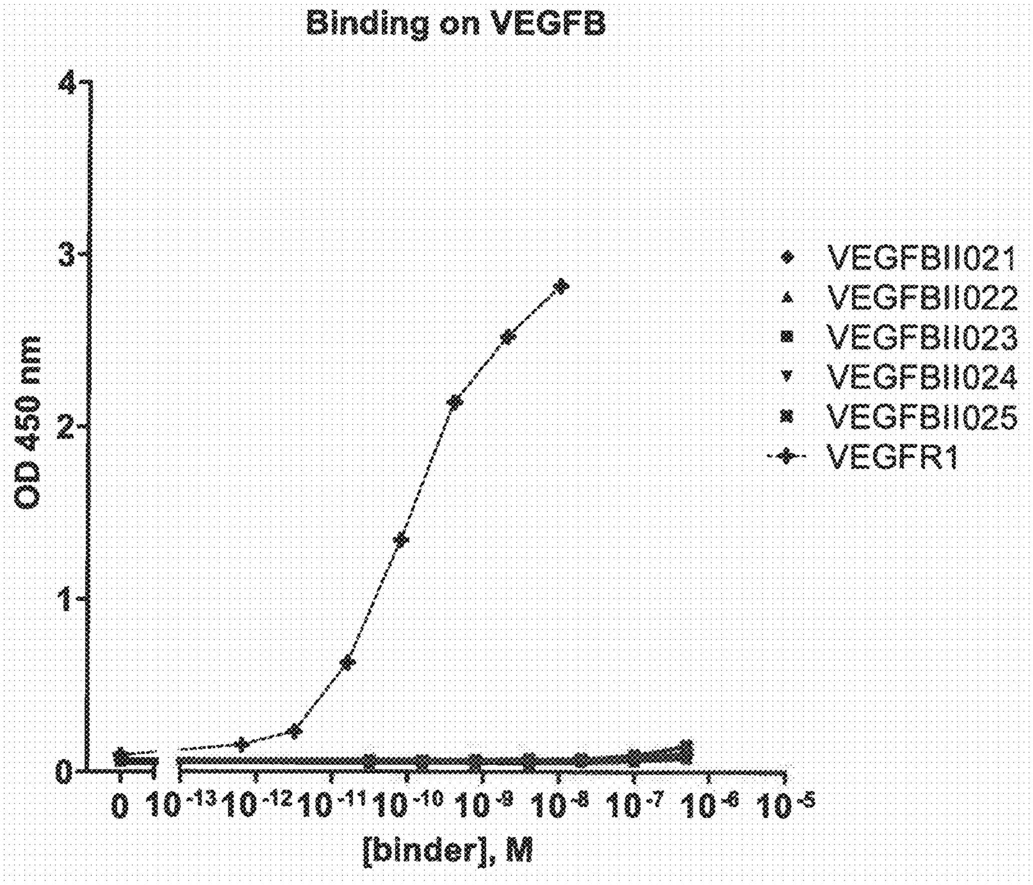
Figure 14F:
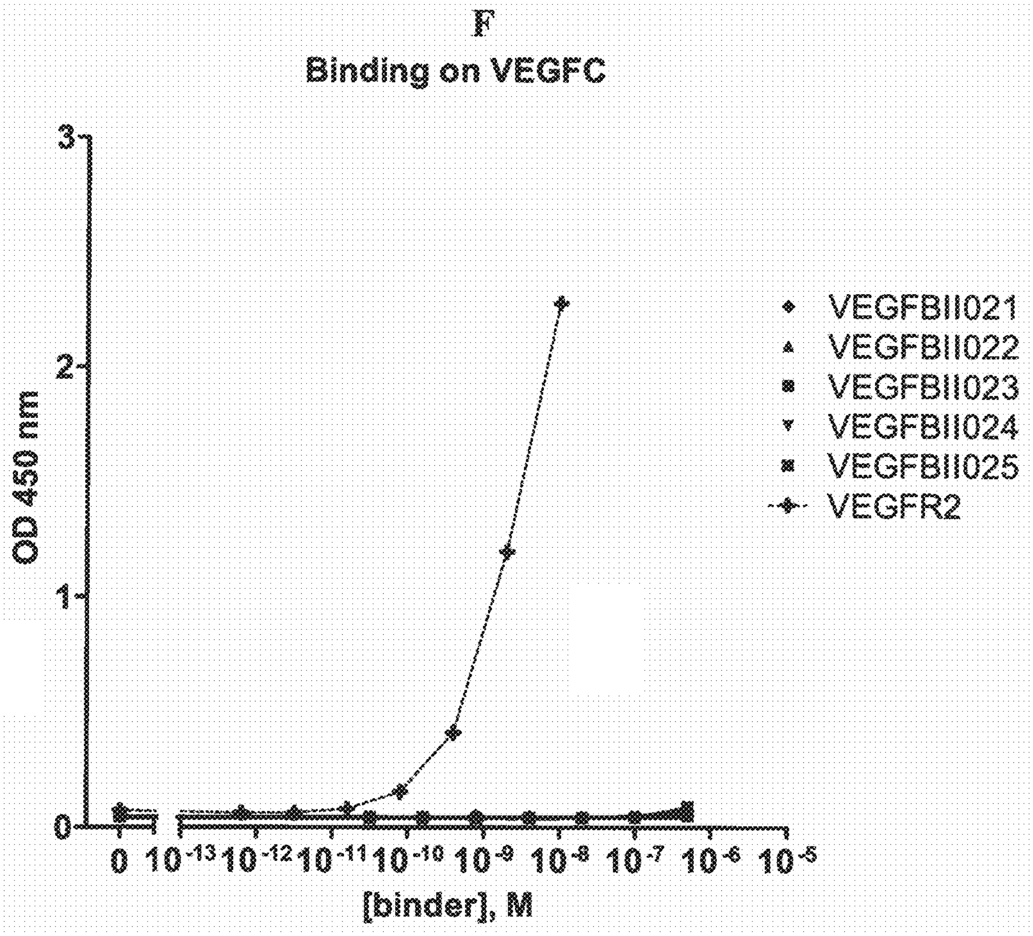
Figure 14G:
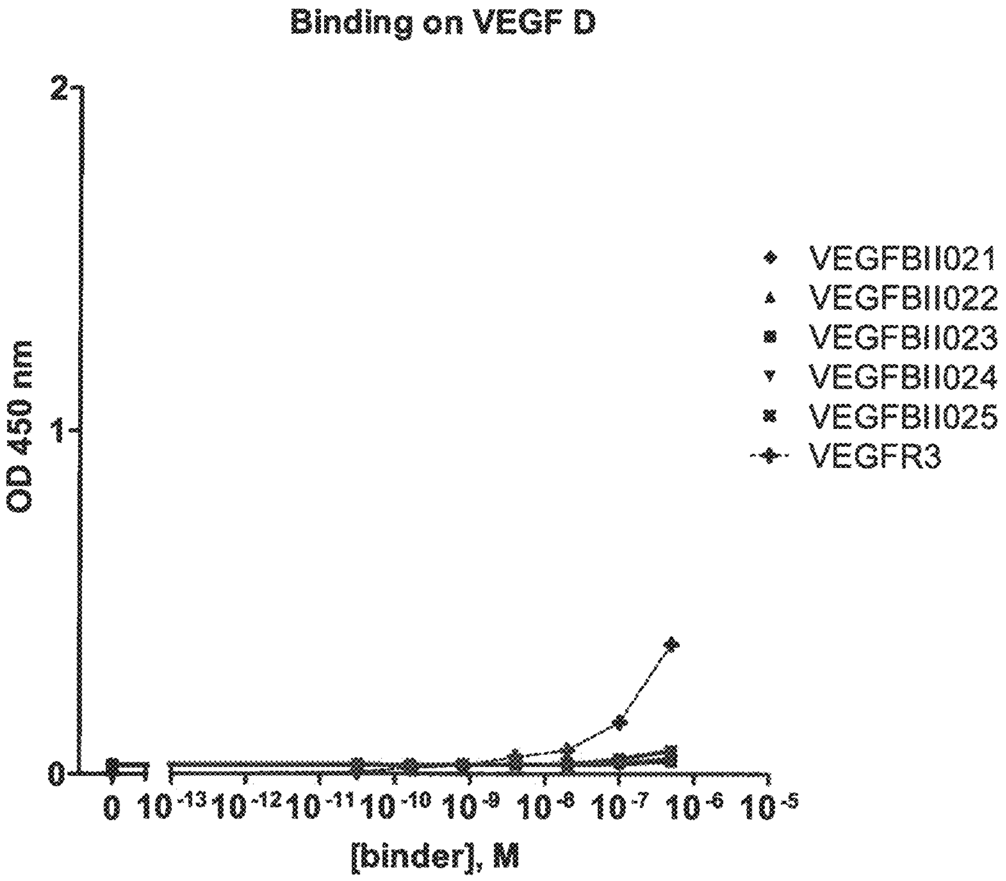
Figure 14H:
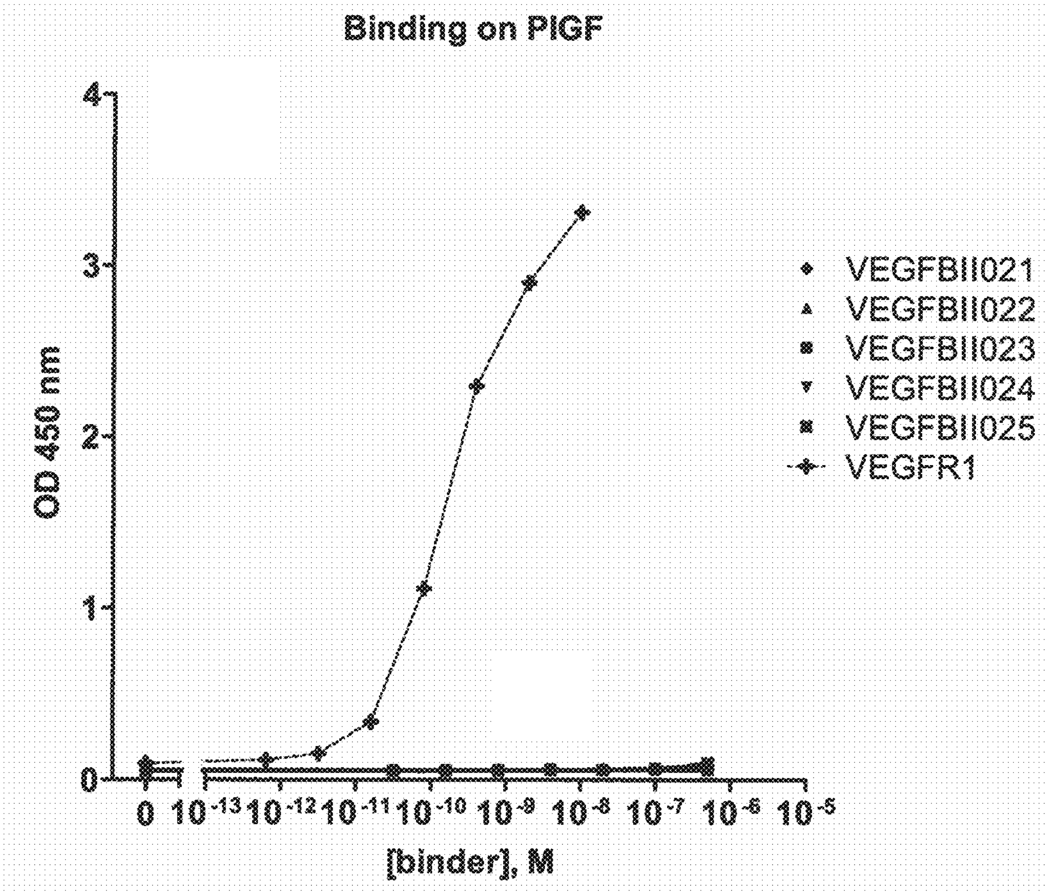
Figure 15:
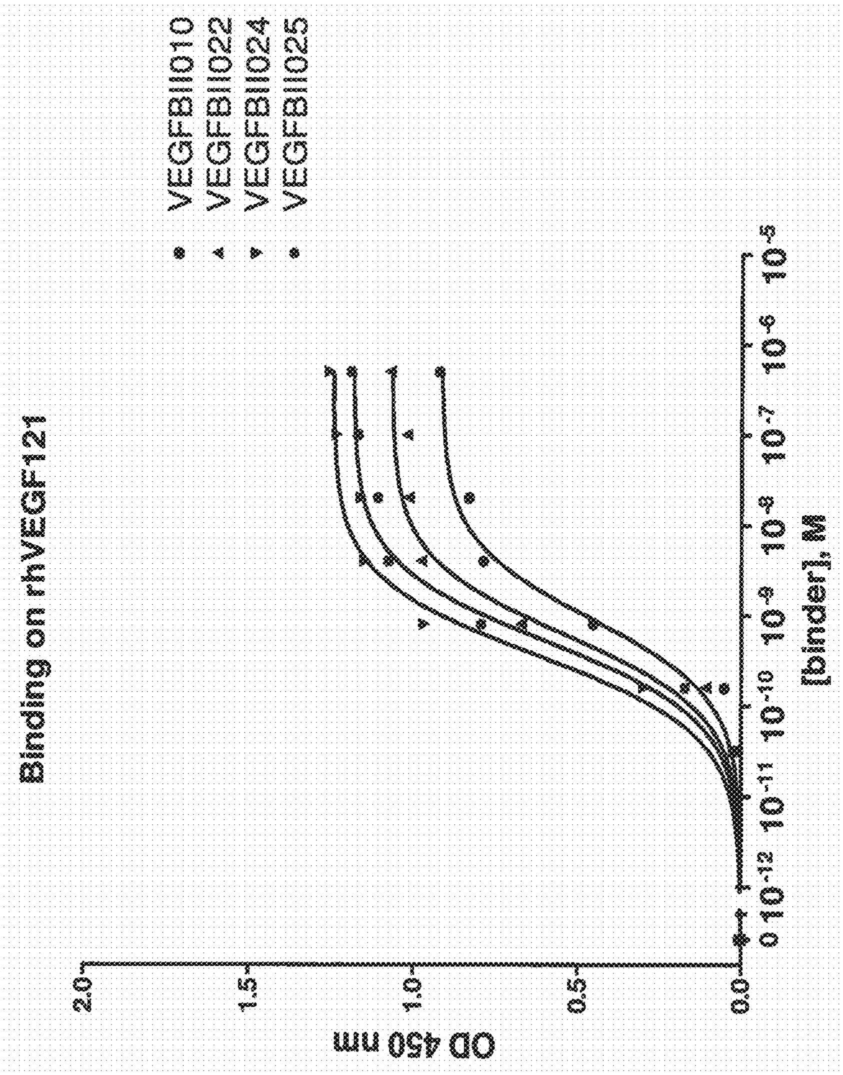
FIG. 15: Formatted VHHs bind to VEGF121

The formatted VHHs are also tested in ELISA for their ability to bind mVEGF164 and human VEGF165 (Example 5.6; FIG. 13; Table 22); VEGF121 (Example 5.7; FIG. 15; Table 23) and the VEGF family members VEGFB, VEGFC, VEGFD and PIGF (Example 5.8; FIG. 14). Binding kinetics for human VEGF165 are analyzed as described in Example 5.5. The $K_D$ values are listed in Table 24.

TABLE 22

$EC_{50}$ (pM) values for formatted VHHs in a recombinant human VEGF165 and mouse VEGF164 binding ELISA

| VHH ID | rhVEGF165 $EC_{50}$ (pM) | rmVEGF164 $EC_{50}$ (pM) |
|---|---|---|
| VEGFBII010 | 428 | — |
| VEGFBII021 | 334 | 502 |

TABLE 22-continued

EC$_{50}$ (pM) values for formatted VHHs in a recombinant human VEGF165 and mouse VEGF164 binding ELISA

| VHH ID | rhVEGF165 EC$_{50}$ (pM) | rmVEGF164 EC$_{50}$ (pM) |
|---|---|---|
| VEGFBII022 | 224 | 464 |
| VEGFBII023 | 221 | — |
| VEGFBII024 | 320 | — |
| VEGFBII025 | 668 | — |

TABLE 23

EC$_{50}$ (pM) values for formatted VHHs in a recombinant human VEGF121 binding ELISA

| VHH ID | rhVEGF121 EC$_{50}$ (pM) |
|---|---|
| VEGFBII010 | 920 |
| VEGFBII022 | 540 |
| VEGFBII024 | 325 |
| VEGFBII025 | 475 |

TABLE 24

Affinity $K_D$ (nM) of purified formatted VHHs for recombinant human VEGF165

| VHH ID | $k_{a1}$ (1/Ms) | $k_{d1}$ (1/s) | $k_{a2}$ (1/s) | $k_{d2}$ (1/s) | $K_D$ (nM)[a] |
|---|---|---|---|---|---|
| VEGFBII010[b] | 4.5E+05 | 1.7E−02 | 2.9E−02 | 1.3E−04 | 0.16 |
| VEGFBII021[b] | 1.2E+06 | 1.1E−02 | 2.3E−02 | 1.9E−04 | 0.07 |
| VEGFBII022[b] | 1.2E+06 | 9.1E−03 | 1.4E−02 | 2.6E−04 | 0.14 |
| VEGFBII023[b] | 3.0E+05 | 1.8E−02 | 2.4E−02 | 2.7E−04 | 0.69 |
| VEGFBII024[b] | 3.0E+05 | 1.3E−02 | 2.6E−02 | 2.8E−04 | 0.47 |
| VEGFBII025[b] | 3.3E+05 | 1.7E−02 | 1.8E−02 | 3.7E−04 | 1.1 |

[a] $K_D = k_{d1}/k_{a1}*(k_{d2}/(k_{d2} + k_{a2}))$

[b] Curves are fitted using a Two State Reaction model by Biacore T100 Evaluation Software v2.0.1

VHHs VEGFBII010, VEGFBII022, VEGFBII024 and VEGFBII025 are also tested in the VEGF-mediated HUVEC proliferation and Erk phosphorylation assay.

The potency of the selected formatted VHHs is evaluated in a proliferation assay. In brief, primary HUVEC cells (Technoclone) are supplement-starved over night and then 4000 cells/well are seeded in quadruplicate in 96-well tissue culture plates. Cells are stimulated in the absence or presence of VHHs with 33 ng/mL VEGF. The proliferation rates are measured by [$^3$H] Thymidine incorporation on day 4. The results shown in Table 25 demonstrate that the formatted VHHs and Bevacizumab inhibit the VEGF-induced HUVEC proliferation by more than 90%, with IC$_{50}$s<1 nM.

TABLE 25

IC$_{50}$ (nM) values and % inhibition of formatted VHHs in VEGF HUVEC proliferation assay

| VHH ID | IC$_{50}$ (nM) | % inhibition |
|---|---|---|
| VEGFBII010 | 0.22 | 95 |
| VEGFBII021 | 0.40 | 98 |
| VEGFBII022 | 0.34 | 100 |
| VEGFBII023 | 0.52 | 98 |
| VEGFBII024 | 0.38 | 96 |
| VEGFBII025 | 0.41 | 104 |
| Bevacizumab | 0.21 | 92 |

The potency of the selected formatted VHHs is assessed in the HUVEC Erk phosphorylation assay. In brief, primary HUVE cells are serum-starved over night and then stimulated in the absence or presence of VHHs with 10 ng/mL VEGF for 5 min. Cells are fixed with 4% Formaldehyde in PBS and ERK phosphorylation levels are measured by ELISA using phosphoERK-specific antibodies (anti-phosphoMAP Kinase pERK1&2, M8159, Sigma) and polyclonal Rabbit Anti-Mouse-Immunoglobulin-HRP conjugate (P0161, Dako). As shown in Table 26, the formatted VHHs and Bevacizumab inhibit the VEGF induced Erk phosphoryaltion by more than 90%, with IC$_{50}$s<1 nM.

TABLE 26

IC$_{50}$ (nM) values and % inhibition of formatted VHHs in VEGF HUVEC Erk phosphorylation assay

| VHH ID | IC$_{50}$ (nM) | % inhibition |
|---|---|---|
| VEGFBII010 | 0.19 | 92 |
| VEGFBII021 | 0.21 | 103 |
| VEGFBII022 | 0.18 | 94 |
| VEGFBII023 | 0.25 | 100 |
| VEGFBII024 | 0.23 | 94 |
| VEGFBII025 | 0.23 | 99 |
| Bevacizumab | 0.63 | 98 |

Example 8

Sequence Optimization 8.1 Sequence Optimization of VEGFBII23B04

The amino acid sequence of VEGFBII23B04 is aligned to the human germline sequence VH3-23/JH5, see FIG. 16 (SEQ ID NO: 179)

The alignment shows that VEGFBII23B04 contains 19 framework mutations relative to the reference germline sequence. Non-human residues at positions 14, 16, 23, 24, 41, 71, 82, 83 and 108 are selected for substitution with their human germline counterparts. A set of 8 VEGFBII23B04 variants is generated carrying different combinations of human residues at these positions (AA sequences are listed in Table 27). One additional variant is constructed in which the potential isomerization site at position D59S60 (CDR2 region, see FIG. 16, indicated as bold italic residues) is removed by introduction of a S60A mutation.

TABLE 27

AA sequence of sequence-optimized variants of VHH VEGFBII23B04 (FR, framework; CDR, complementary determining region)

| VHH ID/ SEQ ID NO: | FR1/SEQ ID NO: | CDR1/ SEQ ID NO: | FR2/SEQ ID NO: | CDR2/ SEQ ID NO: | FR3/SEQ ID NO: | CDR3/ SEQ ID NO: | FR4/SEQ ID NO: |
|---|---|---|---|---|---|---|---|
| VEGFBII 111D05/47 | EVQLVESGG GLVQTGGSL RLSCEASGRT FS/653 | SYSM G/450 | WFRQAPGKERE FVV/659 | AISKGGY KYDSVSL EG/459 | RFTISRDNAKNTVYLQI NSLRPEDTAVYYCAS/660 | SRAYGS SRLRLAD TYEY/4 | WGQGTLVTV SS/664 |

TABLE 27-continued

AA sequence of sequence-optimized variants of VHH VEGFBII23B04 (FR, framework; CDR, complementary determining region)

| VHH ID/ SEQ ID NO: | FR1/SEQ ID NO: | CDR1/ SEQ ID NO: | FR2/SEQ ID NO: | CDR2/ SEQ ID NO: | FR3/SEQ ID NO: | CDR3/ SEQ ID NO: | FR4/SEQ ID NO: |
|---|---|---|---|---|---|---|---|
| VEGFBII 111G06/48 | EVQLVESGG GLVQPGGSL RLSCAASGRT FS/654 | SYSM G/450 | WFRQAPGKERE FVV/659 | AISKGGY KYDSVSL EG/459 | RFTISRDNAKNTVYLQ MNSLRPEDTAVYYCAS/ 661 | SRAYGS SRLRLAD TYEY/4 | WGQGTLVTV SS/664 |
| VEGFBII 112D11/49 | EVQLVESGG GLVQPGGSL RLSCEASGRT FS/655 | SYSM G/450 | WFRQAPGKERE FVV/659 | AISKGGY KYDSVSL EG/459 | RFTISRDNAKNTVYLQI NSLRPEDTAVYYCAS/660 | SRAYGS SRLRLAD TYEY/4 | WGQGTLVTV SS/664 |
| VEGFBII 113A08/50 | EVQLVESGG GLVQTGGSL RLSCEVSGRT FS/656 | SYSM G/450 | WFRQAPGKERE FVV/659 | AISKGGY KYDSVSL EG/459 | RFTISKDNAKNTVYLQI NSLRPEDTAVYYCAS/662 | SRAYGS SRLRLAD TYEY4 | WGQGTLVTV SS/664 |
| VEGFBII 113E03/51 | EVQLVESGG GLVQTGDSL RLSCEVSGRT FS/690 | SYSM G/450 | WFRQAQGKERE FVV/691 | AISKGGY KYDSVSL EG/459 | RFTISKDNAKNTVYLQ MNSLRPEDTAVYYCAS/ 663 | SRAYGS SRLRLAD TYEY/4 | WGQGTLVTV SS/664 |
| VEGFBII 114C09/52 | EVQLVESGG GLVQPGDSL RLSCEVSGRT FS/657 | SYSM G/450 | WFRQAPGKERE FVV/659 | AISKGGY KYDSVSL EG/459 | RFTISKDNAKNTVYLQI NSLRPEDTAVYYCAS/662 | SRAYGS SRLRLAD TYEY/4 | WGQGTLVTV SS/664 |
| VEGFBII 114D02/53 | EVQLVESGG GLVQTGGSL RLSCEVSGRT FS/656 | SYSM G/450 | WFRQAPGKERE FVV/659 | AISKGGY KYDSVSL EG/459 | RFTISRDNAKNTVYLQI NSLRPEDTAVYYCAS/660 | SRAYGS SRLRLAD TYEY/4 | WGQGTLVTV SS/664 |
| VEGFBII 114D03/54 | EVQLVESGG GLVQTGDSL RLSCAVSGRT FS/658 | SYSM G/450 | WFRQAQGKERE FVV/691 | AISKGGY KYDSVSL EG/459 | RFTISKDNAKNTVYLQI NSLRPEDTAVYYCAS/662 | SRAYGS SRLRLAD TYEY/4 | WGQGTLVTV SS/664 |
| VEGFBII 118E10/55 | EVQLVESGG GLVQTGDSL RLSCEVSGRT FS/690 | SYSM G/450 | WFRQAQGKERE FVV/691 | AISKGGY KYDAVSL EG/465 | RFTISKDNAKNTVYLQI NSLKPEDTAVYYCAS/692 | SRAYGS SRLRLAD TYEY/4 | WGQGTQVT VSS/665 |

Figure 17:
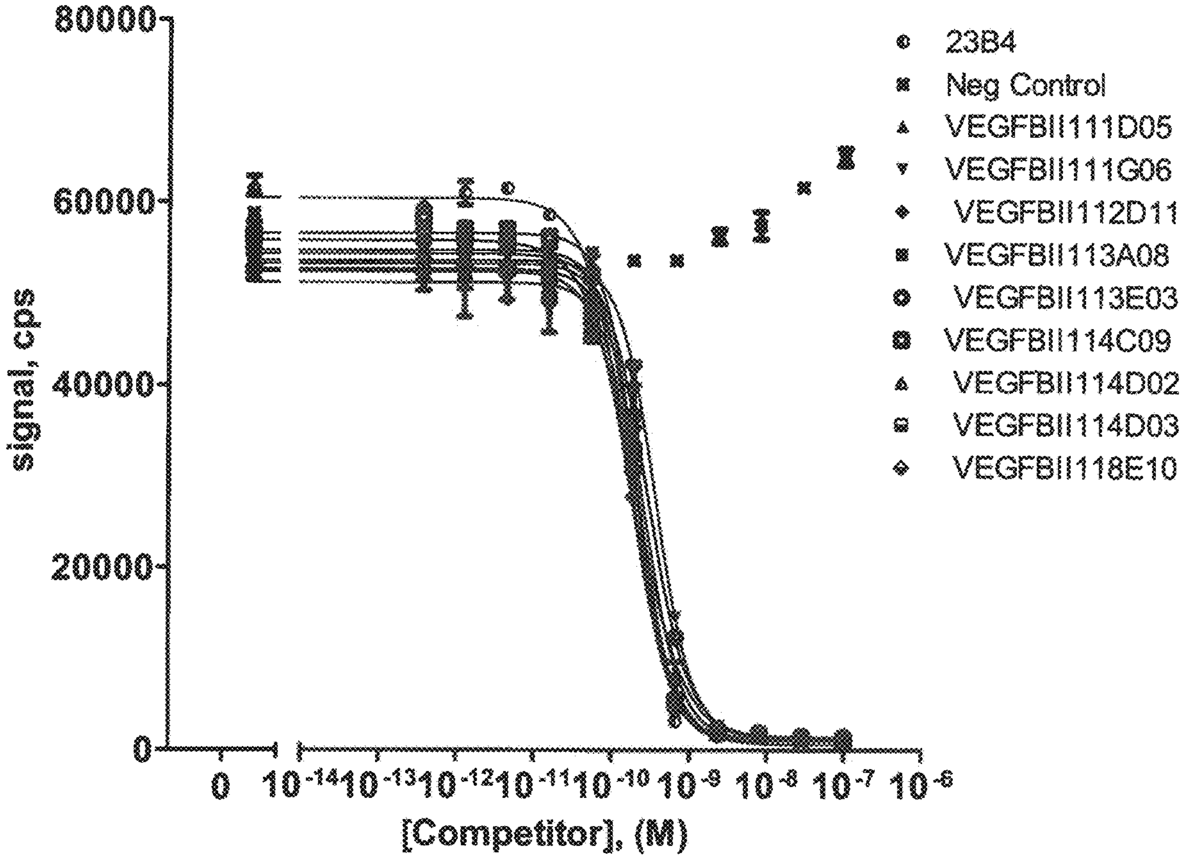
FIG. 17: VHH variants of VEGFBII23B04 block hVEGF165/hVEGFR2-Fc interaction (AlphaScreen)

These variants are characterized as purified proteins in the VEGF165/VEGFR2 AlphaScreen (Example 5.3, FIG. 17). The melting temperature ($T_m$) of each clone is determined in a thermal shift assay, which is based on the increase in fluorescence signal upon incorporation of Sypro Orange (Invitrogen) (Ericsson et al, Anal. Biochem. 357 (2006), pp 289-298). All variants displayed comparable $IC_{50}$ when compared to VEGFBII23B04 and $T_m$ values which are similar or higher when compared to the parental VEGFBII23B04. Table 28 summarizes the $IC_{50}$ values and $T_m$ values at pH 7 for the 9 clones tested.

TABLE 28

$IC_{50}$ (pM) values, % inhibition and melting temperature (@pH 7) of sequence-optimized variants of VEGFBII23B04

| VHH ID | $IC_{50}$ (pM) | % inhibition | $T_m$ @ pH 7 (° C.) |
|---|---|---|---|
| VEGFBII23B04 (wt) | 169 | 100 | 63 |
| VEGFBII111D05 | 209 | 100 | 68 |
| VEGFBII111G06 | 366 | 100 | 71 |
| VEGFBII112D11 | 221 | 100 | 70 |
| VEGFBII113A08 | 253 | 100 | 69 |
| VEGFBII113E03 | 290 | 100 | 68 |
| VEGFBII114C09 | 215 | 100 | 71 |

TABLE 28-continued $IC_{50}$ (pM) values, % inhibition and melting temperature (@pH 7) of sequence-optimized variants of VEGFBII23B04

| VHH ID | $IC_{50}$ (pM) | % inhibition | $T_m$ @ pH 7 (° C.) |
|---|---|---|---|
| VEGFBII114D02 | 199 | 100 | 74 |
| VEGFBII114D03 | 227 | 100 | 64 |
| VEGFBII118E10 | 189 | 100 | 62 |

Figure 18:
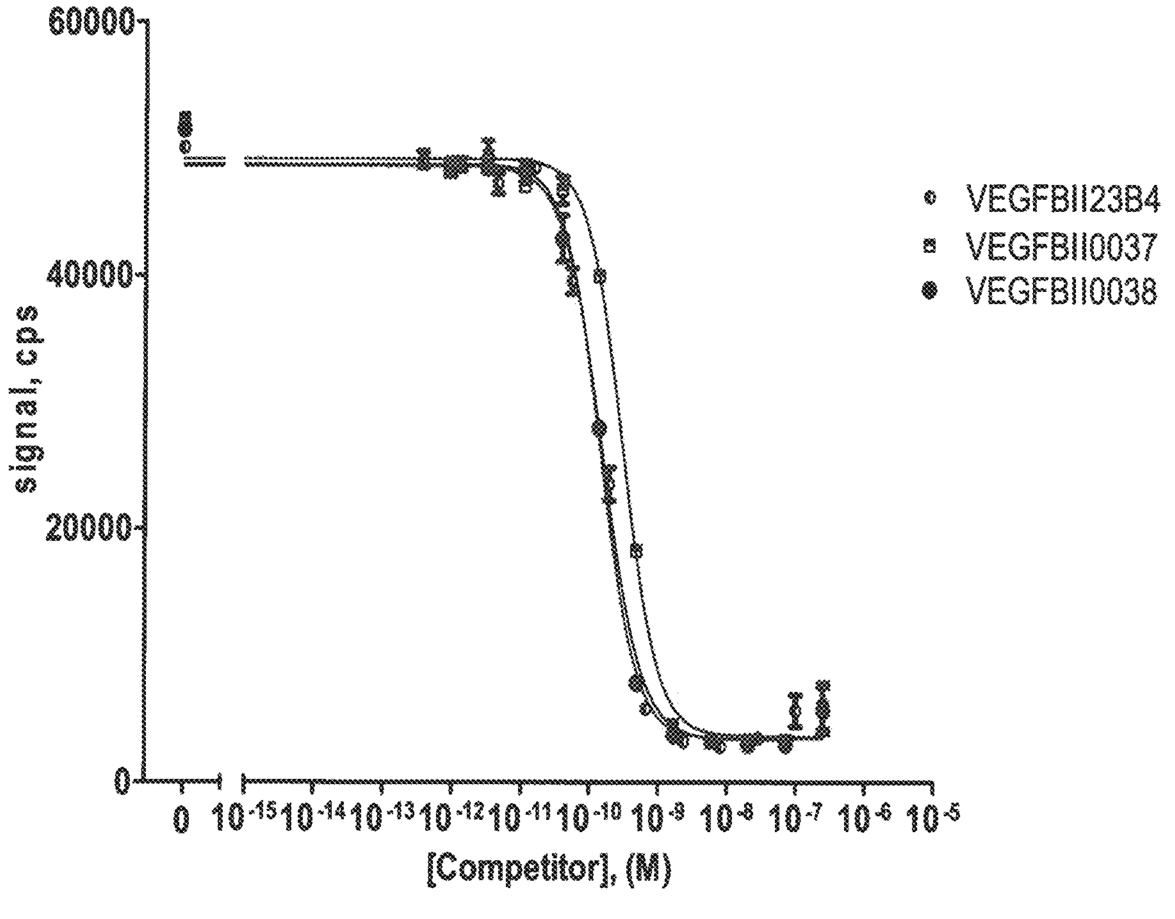
FIG. 18: Sequence-optimized clones of VEGFBII23B04 block the hVEGF165/hVEGFR2-Fc interaction (AlphaScreen)
Figure 20A:
Figure 20A:
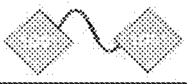
Figure 20A:
Figure 20A:
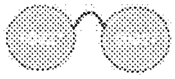
Figure 20A:
Figure 20A:
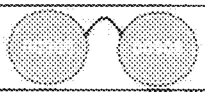
Figure 20A:
Figure 20A:
Figure 20A:
Figure 20A:
Figure 20A:
Figure 20A:
Figure 20B:
Figure 20B:
Figure 20B:
Figure 20B:
Figure 20B:
Figure 20B:
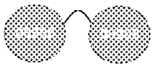
Figure 20C:
Figure 20C:
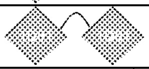
Figure 20C:
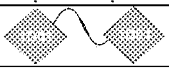
Figure 20C:
Figure 20C:
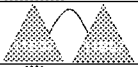
Figure 20C:
Figure 20C:
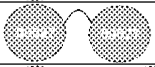
Figure 20C:
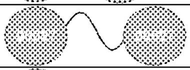
Figure 20C:
Figure 20C:
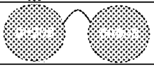

In a second cycle, tolerated mutations from the humanization effort (VEGFBII111G06) and mutations to avoid potential posttranslational modification at selected sites (the D16G, the S60A substitution and an E1D mutation) are combined resulting in a sequence-optimized clone derived from VEGFBII23B04: VEGFBII0037. One extra sequence-optimized variant (VEGFBII038) is anticipated which contains the same substitutions as VEGFBII0037, with the exception of the 182M mutation, as this mutation may be associated with a minor drop in potency. The sequences from both sequence-optimized clones are listed in Table 29. VEGFBII0037 and VEGFBII0038 are characterized in the VEGF165/VEGFR2 blocking AlphaScreen (Example 5.3, FIG. 18), the melting temperature is determined in the thermal shift assay as described above and the affinity for binding on VEGF165 is determined in Biacore (Example 5.5). An overview of the characteristics of the 2 sequence-optimized VHHs is presented in Table 30.

TABLE 29

AA sequences of sequence-optimized variants of VHH VEGFBII23B04

| VHH ID/ SEQ ID NO: | FR 1/SEQ ID NO: | CDR 1/ SEQ ID NO: | FR2/SEQ ID NO: | CDR 2/ SEQ ID NO: | FR3/SEQ ID NO: | CDR 3/SEQ ID NO: | FR 4/SEQ ID NO: |
|---|---|---|---|---|---|---|---|
| VEGFBII037 56 | DVQLVES GGGLVQP GGSLRLS CAASGRT FS/666 | SYSM G/450 | WFRQAP GKEREF VV/659 | AISKG GYKYD AVSLE G/465 | RFTISRDNAKNT VYLQMNSLRPE DTAVYYCAS/661 | SRAYGSSR LRLADTYE Y/4 | WGQG TLVTVS S/664 |
| VEGFBII038 57 | DVQLVES GGGLVQP GGSLRLS CAASGRT FS/666 | SYSM G/450 | WFRQAP GKEREF VV/659 | AISKG GYKYD AVSLE G/465 | RFTISRDNAKNT VYLQINSLRPED TAVYYCAS/660 | SRAYGSSR LRLADTYE Y/4 | WGQG TLVTVS S/664 |

TABLE 30

$IC_{50}$ (pM) values, % inhibition, melting temperature (@pH 7) and affinity (pM) of sequence-optimized clones VEGFBII037 and VEGFBII038

| VHH ID | $IC_{50}$ (pM) | % inhibition | $T_m$ (° C.) @ pH 7 | $K_D$ (pM) |
|---|---|---|---|---|
| VEGFBII23B04 | 152 | 100 | 63 | 560 |
| VEGFBII037 | 300 | 100 | 72 | 270 |
| VEGFBII038 | 143 | 100 | 71 | 360 |

8.2 Sequence Optimization of VEGFBII5B05

The amino acid sequence of VEGFBII5B05 is aligned to the human germline sequence VH3-23/JH5, see FIG. 19 (SEQ ID:NO: 179 The alignment shows that VEGFBII5B05 contains 15 framework mutations relative to the reference germline sequence. Non-human residues at positions 23, 60, 83, 105, 108 are selected for substitution with their human germline counterparts while the histidine at position 44 is selected for substitution by glutamine. One humanization variant is constructed carrying the 6 described mutations (AA sequence is listed in Table 31).

TABLE 31

AA sequences of sequence-optimized variants of VHH VEGFBII5B05 (FR, framework; CDR, complementary determining region)

| VHH ID/ SEQ ID NO: | FR1/SEQ ID NO: | CDR1/ SEQ ID NO: | FR2/SEQ ID NO: | CDR2/ SEQ ID NO: | FR3/SEQ ID NO: | CDR3/ SEQ ID NO: | FR4/SEQ ID NO: |
|---|---|---|---|---|---|---|---|
| VEGFBII119G11/ 125 | EVQLVES GGGLVQ PGGSLRL SCAASGI RFM/667 | SM A/ 290 | WYRQAP GKQRELV A/669 | RISSG GTTA YADS VKG/ 404 | RFTISRDNS KNTVYLQMN SLRAEDTAV YYCNT/671 | FSSR PNP/ 395 | WGQGTL VTVSS/664 |
| VEGFBII120E10/ 126 | EVQLVES GGGLVQ PGGSLRL SCVASGI RFI/668 | SM A/ 290 | WYRQAP GKHRELV A/670 | RISSG GTTA YVDS VKG/ 336 | RFTISRDNS KNTVYLQMN SLKAEDTAV YYCNT/672 | FSSR PNP/395 | WGAGT QVTVSS/ 673 |

One additional variant is constructed in which the potential oxidation site at position M30 (CDR1 region, see FIG. 19 indicated as bold italic residue) is removed by introduction of a M301 mutation. Both variants are tested for their ability to bind hVEGF165 using the ProteOn. In brief, a GLC ProteOn Sensor chip is coated with human VEGF165. Periplasmic extracts of the variants are diluted 1/10 and injected across the chip coated with human VEGF165. Off-rates are calculated and compared to the off-rates of the parental VEGFBII5B05. Off-rates from the 2 variants are in the same range as the off-rates from the parental VEGFBII5B05 indicating that all mutations are tolerated (Table 32).

TABLE 32

Off-rates sequence-optimized variants VEGFBII5B05

| VHH ID | binding level (RU) | $k_d$ (1/s) |
|---|---|---|
| VEGFBII5B05 | 242 | 6.15E−02 |
| VEGFBII119G11 | 234 | 7.75E−02 |
| VEGFBII120E10 | 257 | 4.68E−02 |

In a second cycle, mutations from the humanization effort and the M301 substitution are combined resulting in a sequence-optimized clone of VEGFBII5B05, designated VEGFBII032. The sequence is listed in Table 33. Affinity of VEGFBII032 is determined by Biacore (see Example 5.5) and the melting temperature is determined in the thermal shift assay as described above. An overview of the characteristics of the sequence-optimized VHH VEGFBII032 is presented in Table 34.

TABLE 33

AA sequence of sequence-optimized clone VEGFBII032 (FR, framework; CDR, complementary determining region)

| VHH ID/ SEQ ID NO: | FR1/SEQ ID NO: | CDR1/ SEQ ID NO: | FR2/SEQ ID NO: | CDR2/ SEQ ID NO: | FR3/SEQ ID NO: | CDR3/ SEQ ID NO: | FR4/SEQ ID NO: |
|---|---|---|---|---|---|---|---|
| VEGFBII032/ 127 | EVOLVES GGGLVQ PGGSLRL SCAASGI RFI/674 | SM A/ 290 | WYRQAP GKQRELV A/675 | RISSG GTTA YADS VKG/ 404 | RFTISRDNS KNTVYLQMN SLRAEDTAV YYCNT/671 | FSSR PNP/ 395 | WGQGTL VTVSS/664 |

TABLE 34

Melting temperature (@pH 7) and affinity (nM) of sequence-optimized clone VEGFBII032

| VHH ID | $T_m$ (° C.) @ pH 7 | $K_D$ (nM) |
|---|---|---|
| VEGFBII5B05(wt) | 69 | 32 |
| VEGFBII0032 | 71 | 44 |

The potency of the sequence-optimized clones VEGFBII037 and VEGFBII038 is evaluated in a proliferation assay. In brief, primary HUVEC cells (Technoclone) are supplement-starved over night and then 4000 cells/well are seeded in quadruplicate in 96-well tissue culture plates. Cells are stimulated in the absence or presence of VHHs with 33 ng/mL VEGF. The proliferation rates are measured by [$^3$H] Thymidine incorporation on day 4. The results shown in Table 35, demonstrate that the activity (potency and degree of inhibition) of the parental VHH VEGFBII23B04 is conserved in the sequence optimized clone VEGFBII038.

TABLE 35

$IC_{50}$ (nM) values and % inhibition of the sequence optimized clones VEGFBII037 and VEGFBII038 in VEGF HUVEC proliferation assay

| VHH ID | $IC_{50}$ (nM) | % inhibition |
|---|---|---|
| VEGFBII23B04 | 0.68 | 92 |
| VEGFBII037 | 1.54 | 78 |
| VEGFBII038 | 0.60 | 92 |
| Bevacizumab | 0.29 | 94 |

Example 9

Construction, Production and Characterization of Bivalent VHHs Targeting Ang2

VHHs 1D01 (SEQ ID No:214), 11B07, 00908 and 00027 (SEQ ID No:216) are genetically fused to 1D01 (SEQ ID No: 214), 11B07, 00908 and 00027 (SEQ ID No:216), respectively, resulting in homodimeric VHHs. The bivalent VHHs are linked via a 9-GlySer (SEQ ID NO: 170) or 40-GlySer (SEQ ID NO: 171) flexible linker. The encoding DNA sequences of the formatted VHHs are cloned in the expression vector pAX172. VHHs are expressed in Pichia pastoris as c-terminally myc-His6 tagged proteins ("His6" disclosed as SEQ ID NO: 283). In brief, BGCM cultures are started from a single colony streak incubated over weekend at 30° C. (250 rpm). After medium switch to BMCM, cultures are incubated until evening at 30° C. (250 rpm) and followed by an induction with 100% methanol. The next day the cultures are induced an additional 3 times (morning, afternoon, evening). The next day cultures are centrifuged for 20 min at 4° C. (1,500×g). The His6-tagged VHHs ("His6" disclosed as SEQ ID NO: 283) present in the supernatant are purified through immobilized metal affinity chromatography (IMAC) followed by desalting (DS) and finally gel filtration (GF) to remove any endotoxins/impurities. An overview of the format and sequence of all bivalent VHHs is depicted in FIG. 20 A and Table 36 (linker sequences underlined), SEQ ID Nos 180-185. Expression levels are indicated in FIG. 20 B.

Figures 1A, 21:
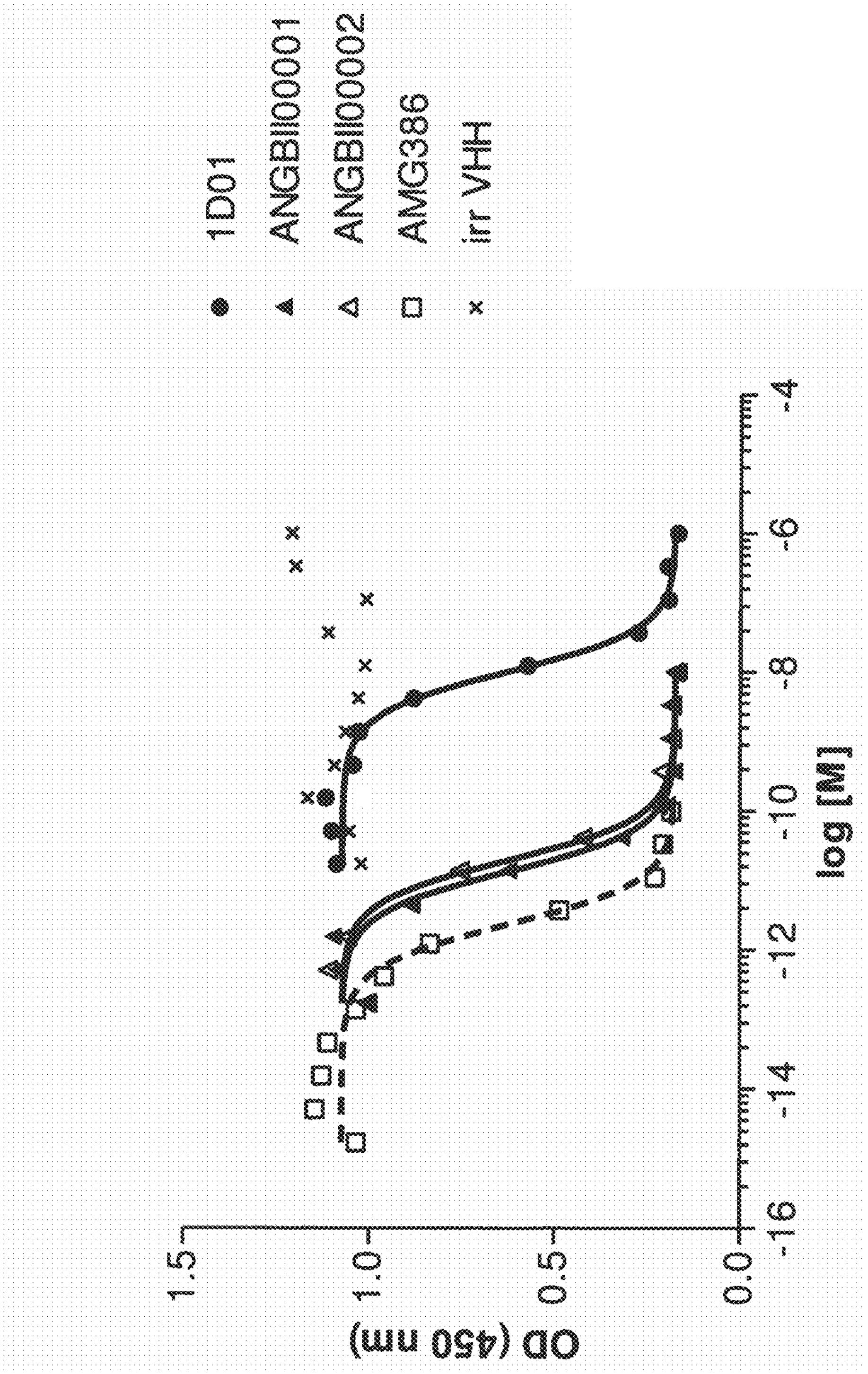
FIG. 21-1A to 21-1D; 21-2A to 21-2D; 21-3A to 21-3D: Purified bivalent Ang2 VHHs blocking hAng2-hTie2 (25-1), mAng2-mTie2 (25-2) and cAng2-cTie2 (25-3) interaction (ELISA)
Figures 1B, 21:
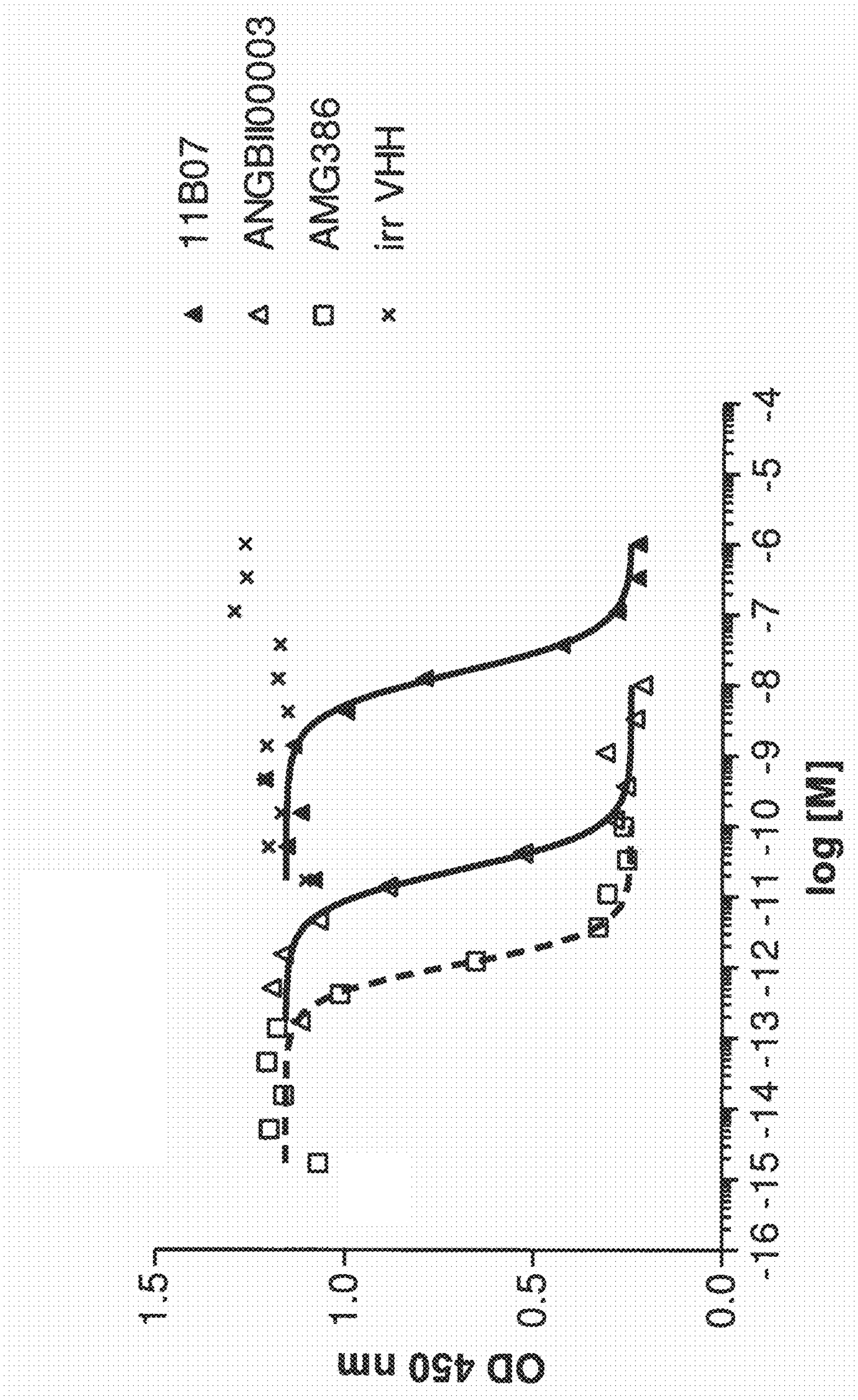
Figures 1C, 21:
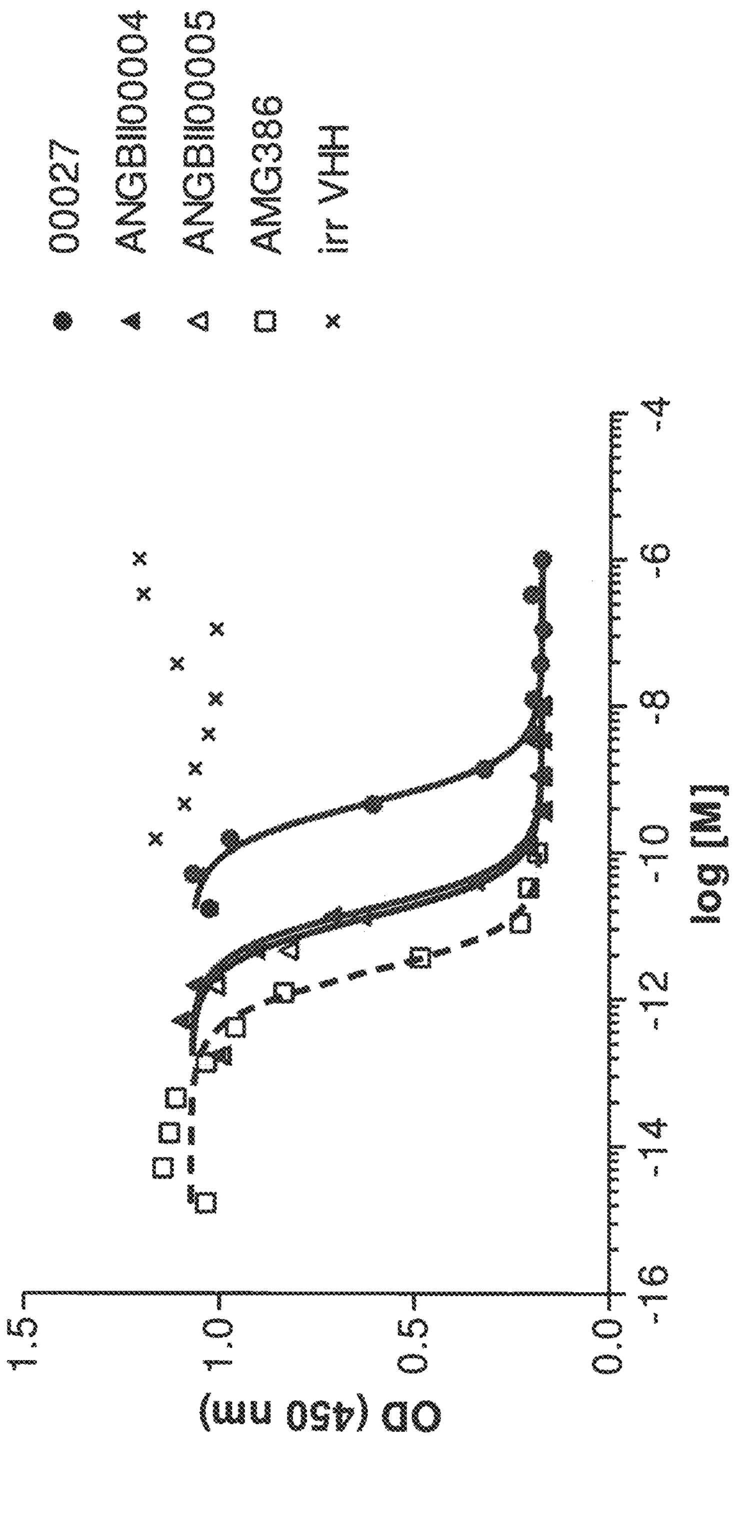
Figures 1D, 21:
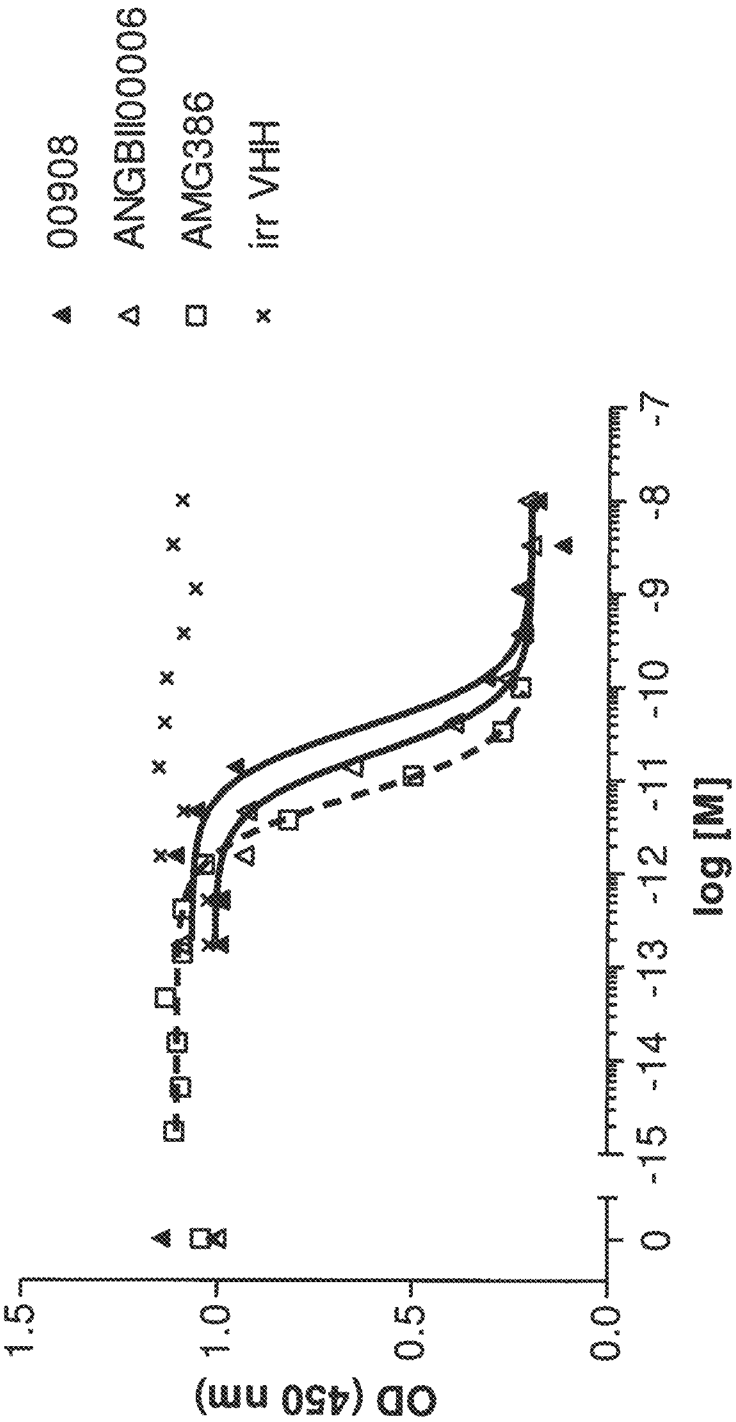
Figures 2A, 21:
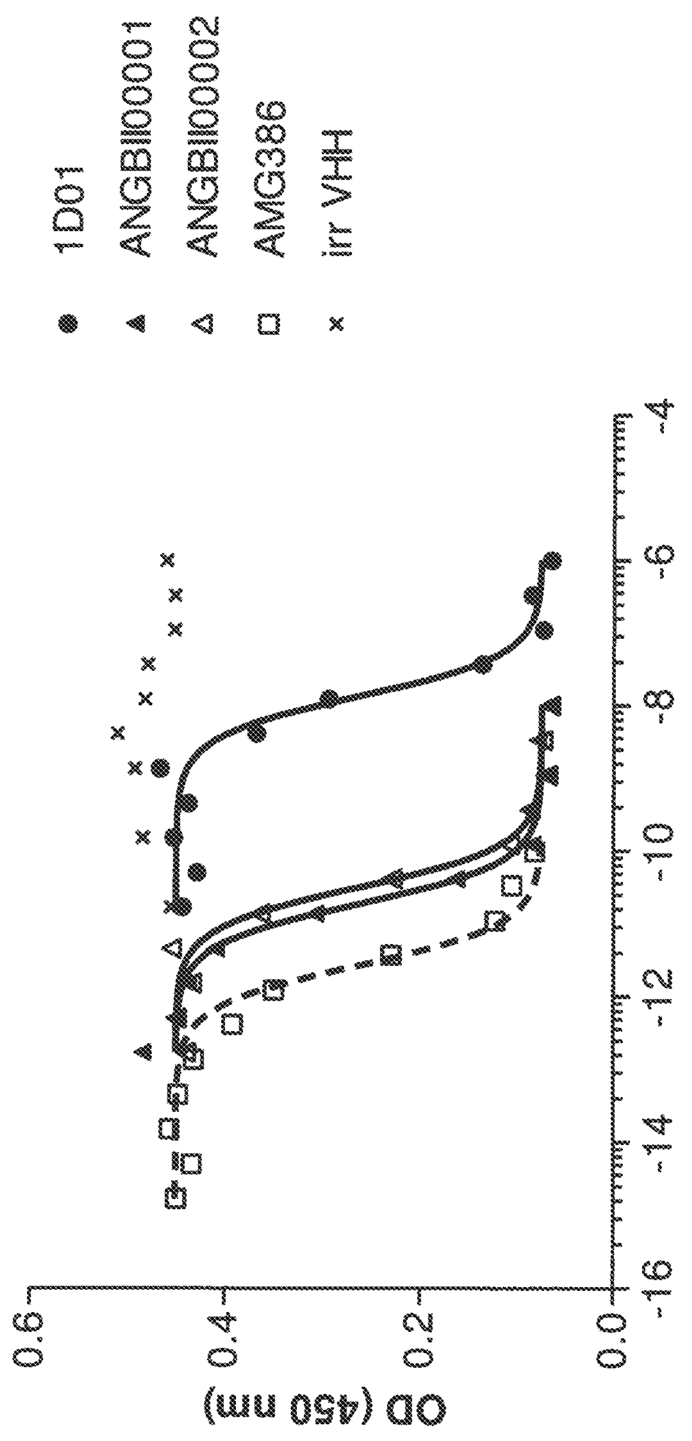
Figures 2B, 21:
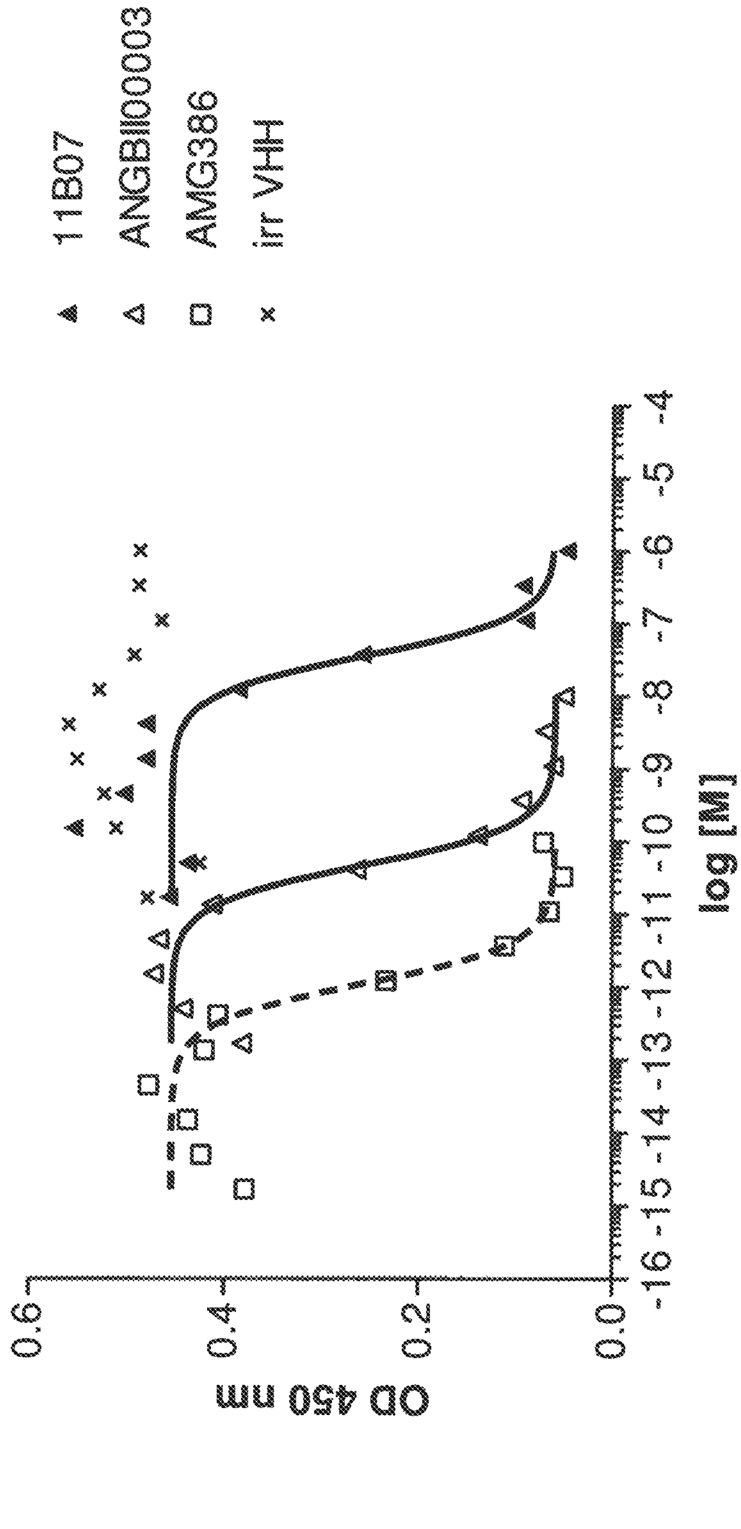
Figures 2C, 21:
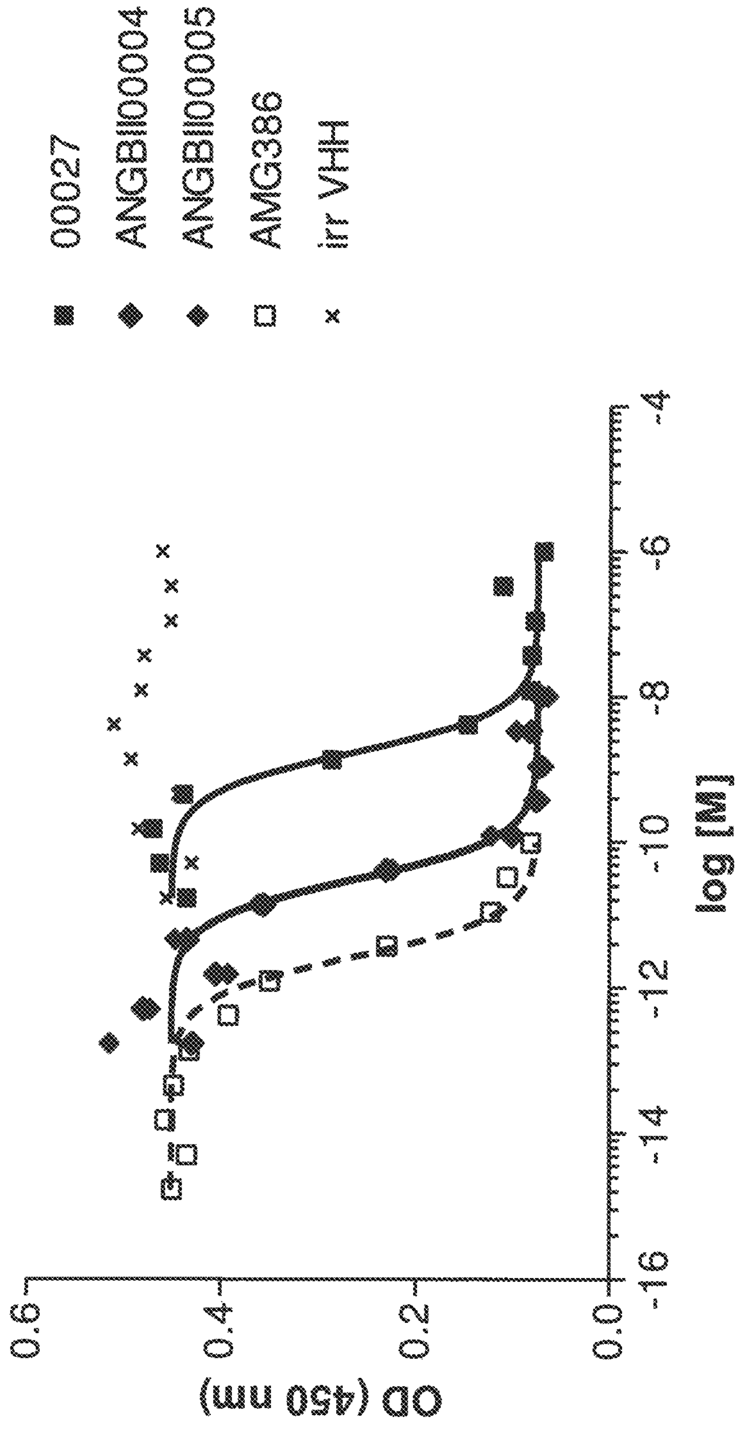
Figures 2D, 21:
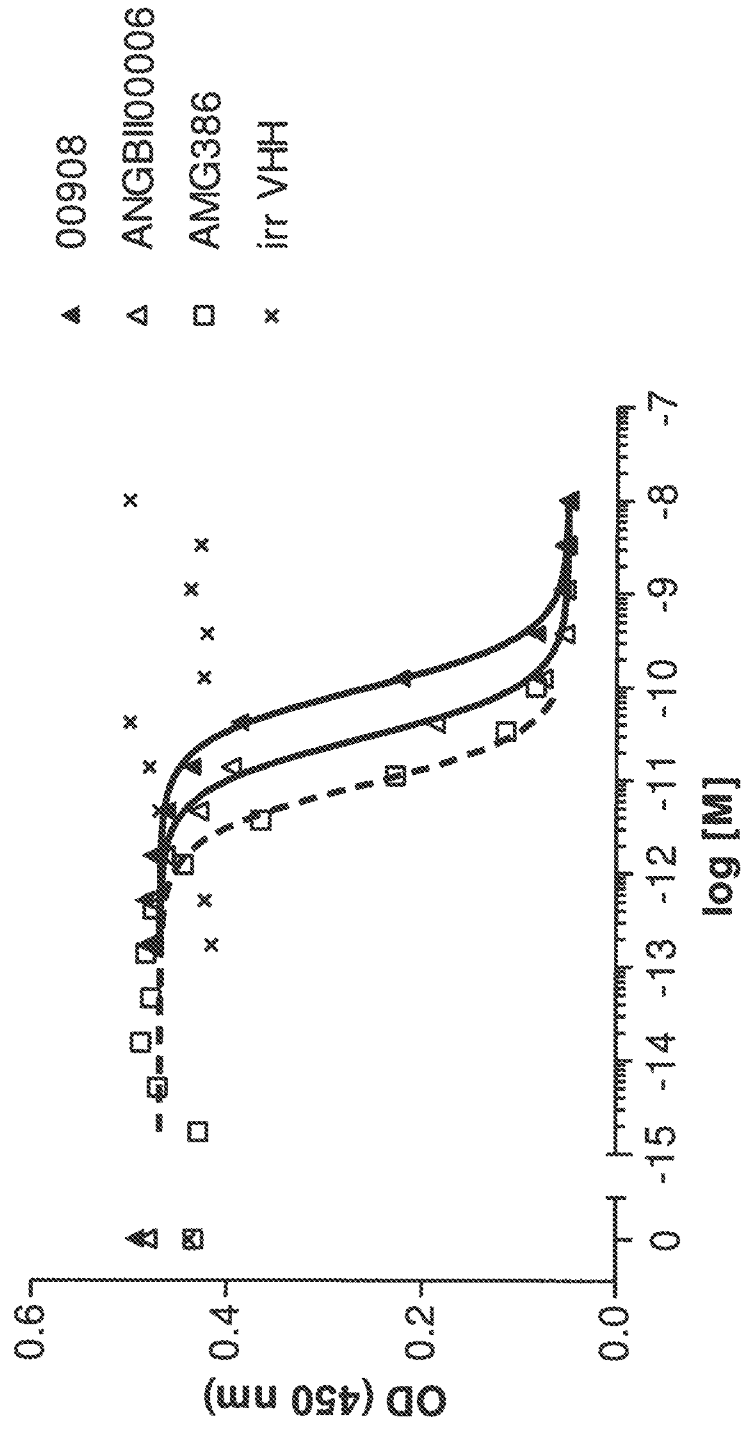
Figures 3A, 21:
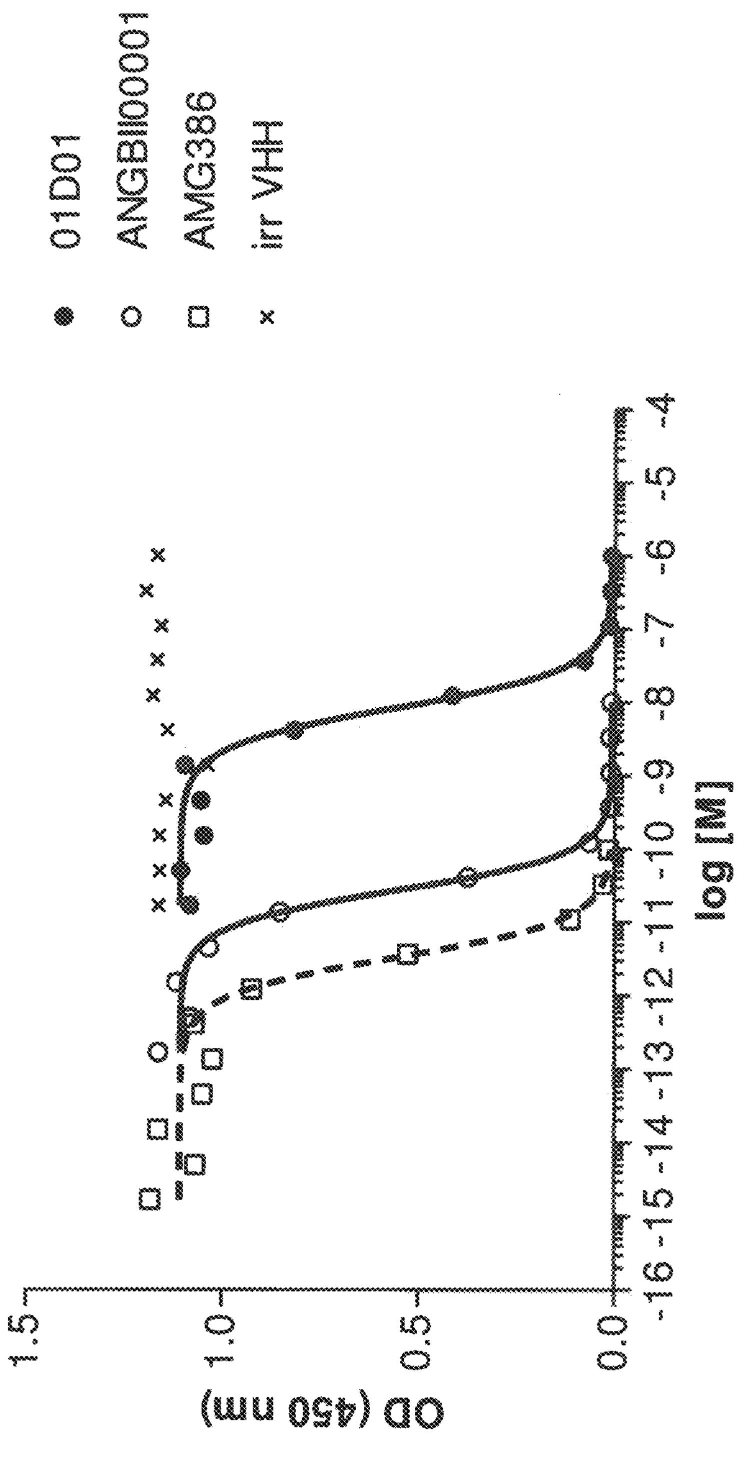
Figures 3B, 21:
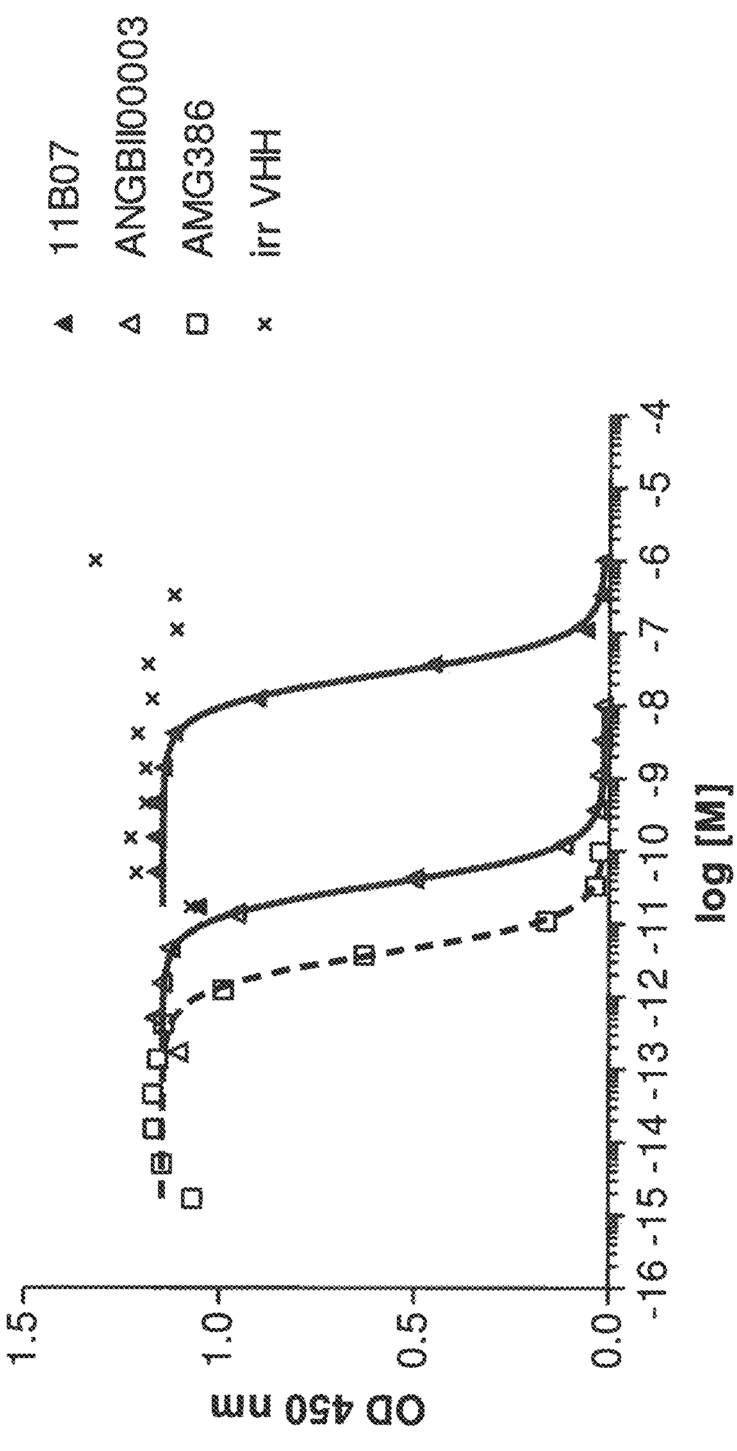
Figures 3C, 21:
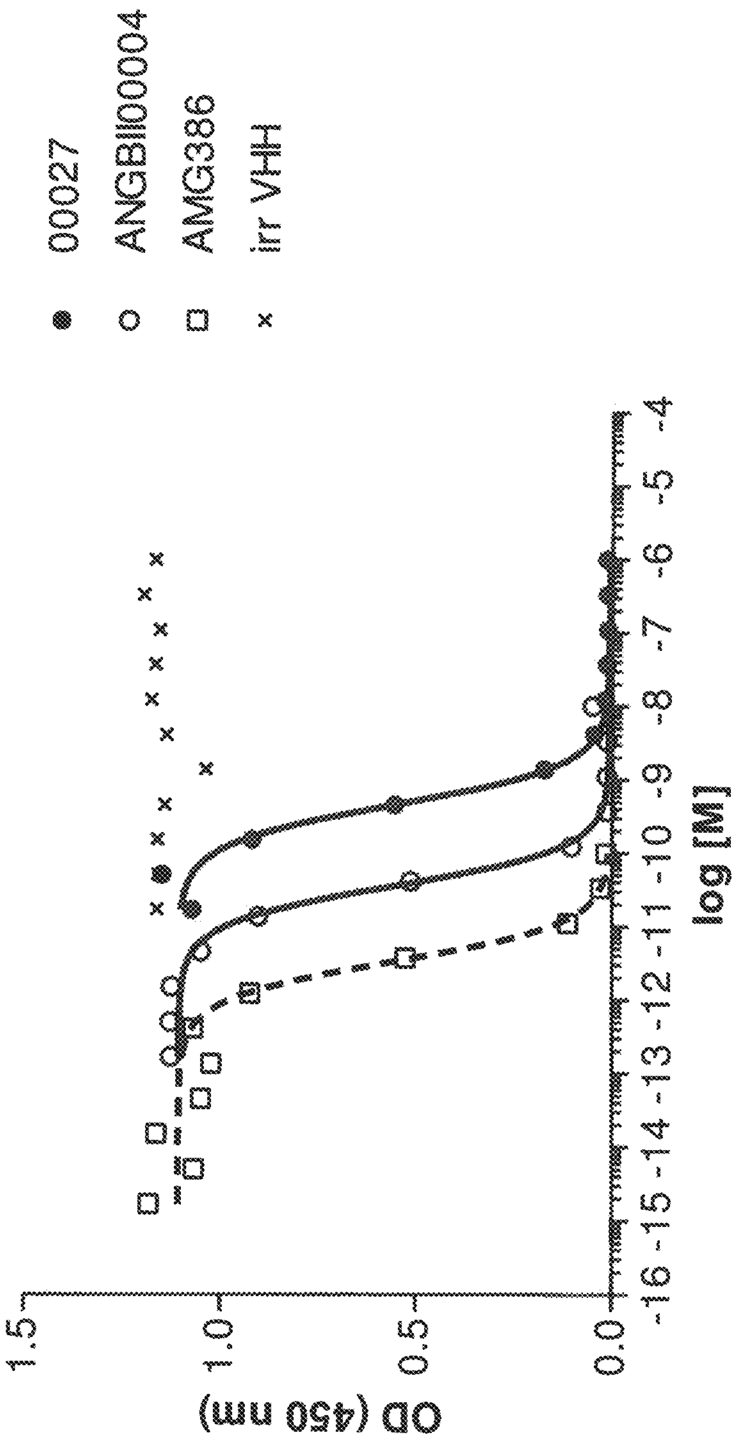
Figures 3D, 21:
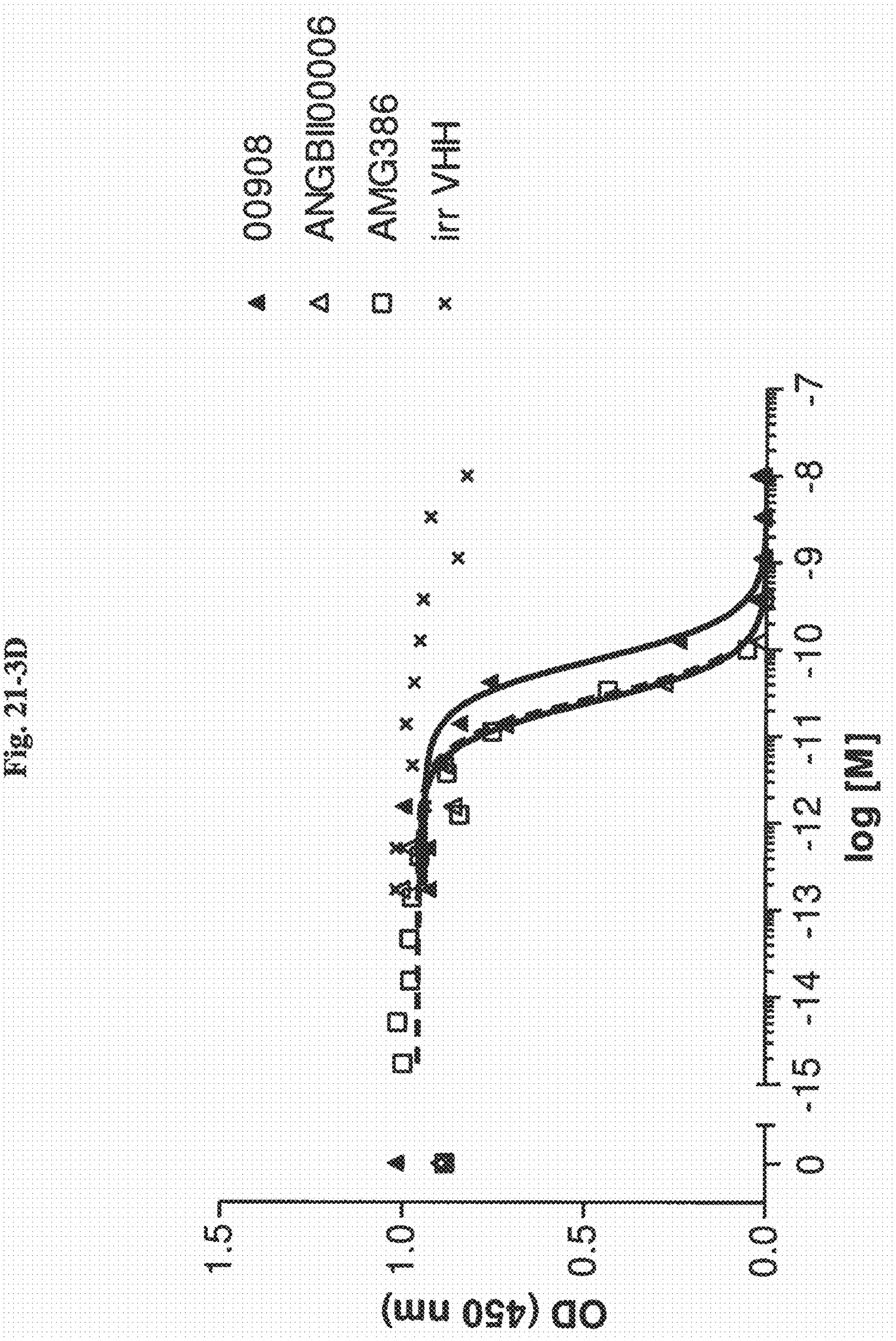
Figure 22:
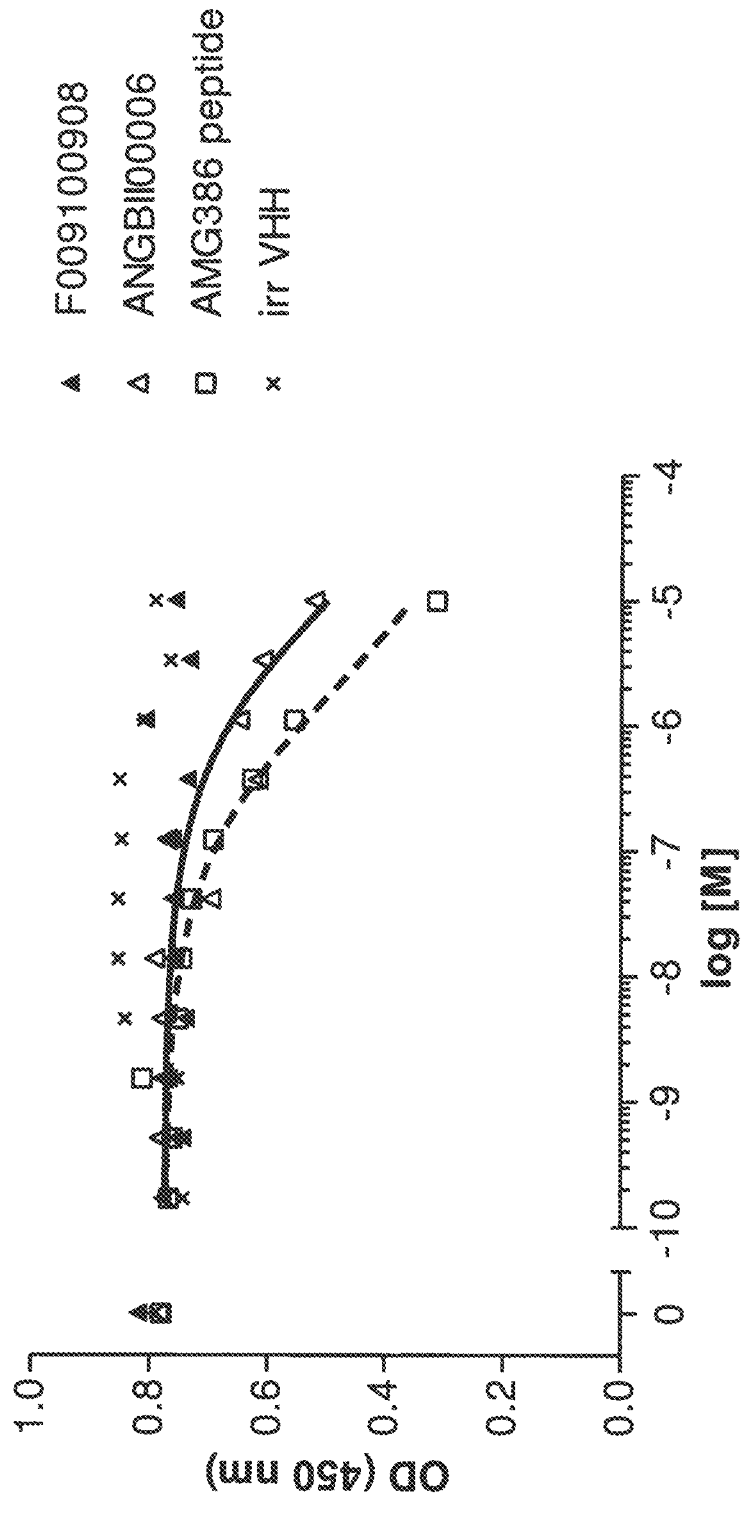
FIG. 22: Purified bivalent Ang2 VHHs blocking hAng1-hTie2 interaction (ELISA)

To explore the anti-Ang2 blocking properties in comparison with the monovalent building blocks, bivalent VHHs are analyzed in a human Ang2/hTie2 (FIG. 21-1), mouse Ang2/mTie2 (FIG. 21-2), cyno Ang2/cTie2 (FIG. 21-3) and human Ang1/hTie2 (FIG. 22) competition ELISA. A summary of $IC_{50}$ values is shown in FIG. 20 C.

TABLE 36

Sequences of bivalent VHH targeting Ang2

| VHH ID | AA sequence |
|---|---|
| ANGBII00001 | EVQLVESGGGLVQAGGSLRLSCAASGFTFDDYALGWFRQAAGKEREGVSCIRCSDGSTYYADSVKGR FTISSDNAKNTVYLQMNSLKPEDTAVYYCAASIVPRSKLEPYEYDAWGQGTLVTVSS<u>GGGGSGGGS</u>E VQLVESGGGLVQAGGSLRLSCAASGFTFDDYALGWFRQAAGKEREGVSCIRCSDGSTYYADSVKGRF TISSDNAKNTVYLQMNSLKPEDTAVYYCAASIVPRSKLEPYEYDAWGQGTLVTVSS (SEQ ID NO: 180) |

TABLE 36-continued

| Sequences of bivalent VHH targeting Ang2 | |
|---|---|
| VHH ID | AA sequence |
| ANGBII00002 | EVQLVESGGGLVQAGGSLRLSCAASGFTFDDYALGWFRQAAGKEREGVSCIRCSDGSTYYADSVKGRFTISSDNAKNTVYLQMNSLKPEDTAVYYCAASIVPRSKLEPYEYDAWGQGTLVTVSSGGGGSGGGGSGGGGSGGGGSGGGGSGGGGSGGGGSGGGGSEVQLVESGGGLVQAGGSLRLSCAASGFTFDDYALGWFRQAAGKEREGVSCIRCSDGSTYYADSVKGRFTISSDNAKNTVYLQMNSLKPEDTAVYYCAASIVPRSKLEPYEYDAWGQGTLVTVSS (SEQ ID NO: 181) |
| ANGBII00003 | EVQLVESGGGLVQVGDSLRLSCAASGRTFSTYLMVGWFRQAPGKEREFAAGIWSSGDTAYADSVRGRFTISRDNAKNTVYLQMNSLKTEDTAVYYCAGSYDGNYYIPGFYKDWGQGTLVTVSSGGGGSGGGSEVQLVESGGGLVQVGDSLRLSCAASGRTFSTYLMVGWFRQAPGKEREFAAGIWSSGDTAYADSVRGRFTISRDNAKNTVYLQMNSLKTEDTAVYYCAGSYDGNYYIPGFYKDWGQGTLVTVSS (SEQ ID NO: 182) |
| ANGBII00004 | EVQLVESGGGLVQAGGSLRLSCAASGFTLDDYAIGWFRQAPGKEREGVSSIRDNDGSTYYADSVKGRFTISSDNDKNTVYLQMNSLKPEDTAVYYCAAVPAGRLRFGEQWYPLYEYDAWGQGTLVTVSSGGGGSGGGSEVQLVESGGGLVQAGGSLRLSCAASGFTLDDYAIGWFRQAPGKEREGVSSIRDNDGSTYYADSVKGRFTISSDNDKNTVYLQMNSLKPEDTAVYYCAAVPAGRLRFGEQWYPLYEYDAWGQGTLVTVSS (SEQ ID NO: 183) |
| ANGBII00005 | EVQLVESGGGLVQAGGSLRLSCAASGFTLDDYAIGWFRQAPGKEREGVSSIRDNDGSTYYADSVKGRFTISSDNDKNTVYLQMNSLKPEDTAVYYCAAVPAGRLRFGEQWYPLYEYDAWGQGTLVTVSSGGGGSGGGGSGGGGSGGGGSGGGGSGGGGSGGGGSGGGGSEVQLVESGGGLVQAGGSLRLSCAASGFTLDDYAIGWFRQAPGKEREGVSSIRDNDGSTYYADSVKGRFTISSDNDKNTVYLQMNSLKPEDTAVYYCAAVPAGRLRFGEQWYPLYEYDAWGQGTLVTVSS (SEQ ID NO: 184) |
| ANGBII00006 | EVQLVESGGGLVQPGGSLRLSCAASGITLDDYAIGWFRQAPGKEREGVSSIRDNGGSTYYADSVKGRFTISSDNSKNTVYLQMNSLRPEDTAVYYCAAVPAGRLRYGEQWYPIYEYDAWGQGTLVTVSSGGGGSGGGSEVQLLESGGGLVQPGGSLRLSCAASGITLDDYAIGWFRQAPGKEREGVSSIRDNGGSTYYADSVKGRFTISSDNSKNTVYLQMNSLRPEDTAVYYCAAVPAGRLRYGEQWYPIYEYDAWGQGTLVTVSS (SEQ ID NO: 185) |

Example 10

Figure 23:
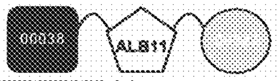
FIG. 23A-23D: A. Description trivalent VEGFxAng2 bispecific VHHs (FIG. 23 discloses "9GS" and "9 GlySer" as SEQ ID NO: 170); B. Expression levels are indicated for all four bispecific VHHs depicted in FIG. 23 A; C. $IC_{50}$ values (nM) in human VEGF165/human VEGFR2 competition AlphaScreen: D. $IC_{50}$ values (pM) in human Ang2/human Tie2 competition ELISA***
Figure 23:
Figure 23:
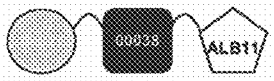
Figure 23:
Figure 23:
Figure 23:
Figure 23:
Figure 23:
Figure 23:
Figure 23:
Figure 23:
Figure 23:
Figure 23:
Figure 23:
Figure 23:
Figure 23:
Figure 23:
Figure 23:
Figure 23:
Figure 23:
Figure 23:
Figure 23:
Figure 24A:
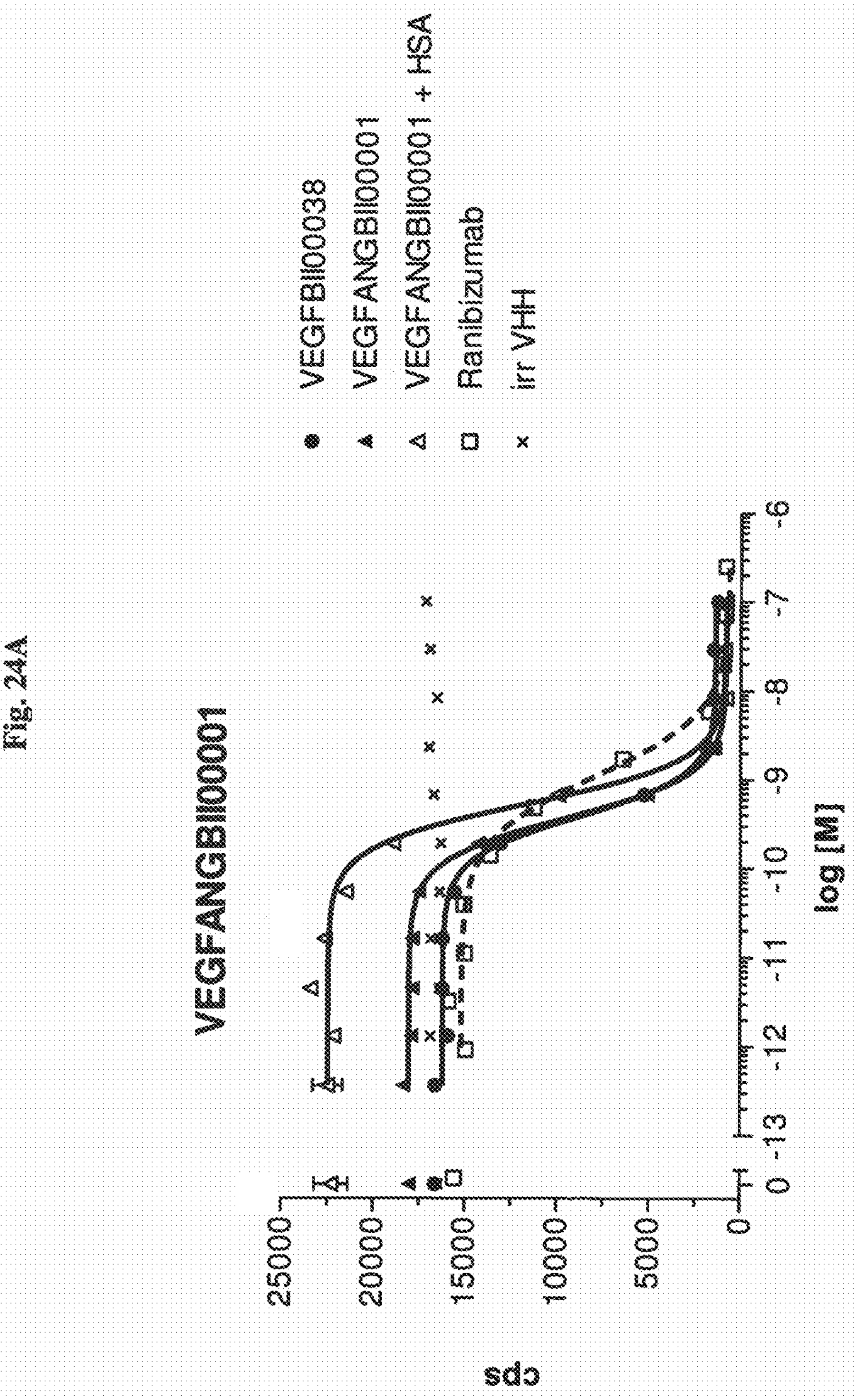
FIG. 24A-24D: Purified trivalent VEGFxAng2 Nanobodies blocking hVEGF-hVEGFR2 interaction (AlphaScreen)
Figure 24B:
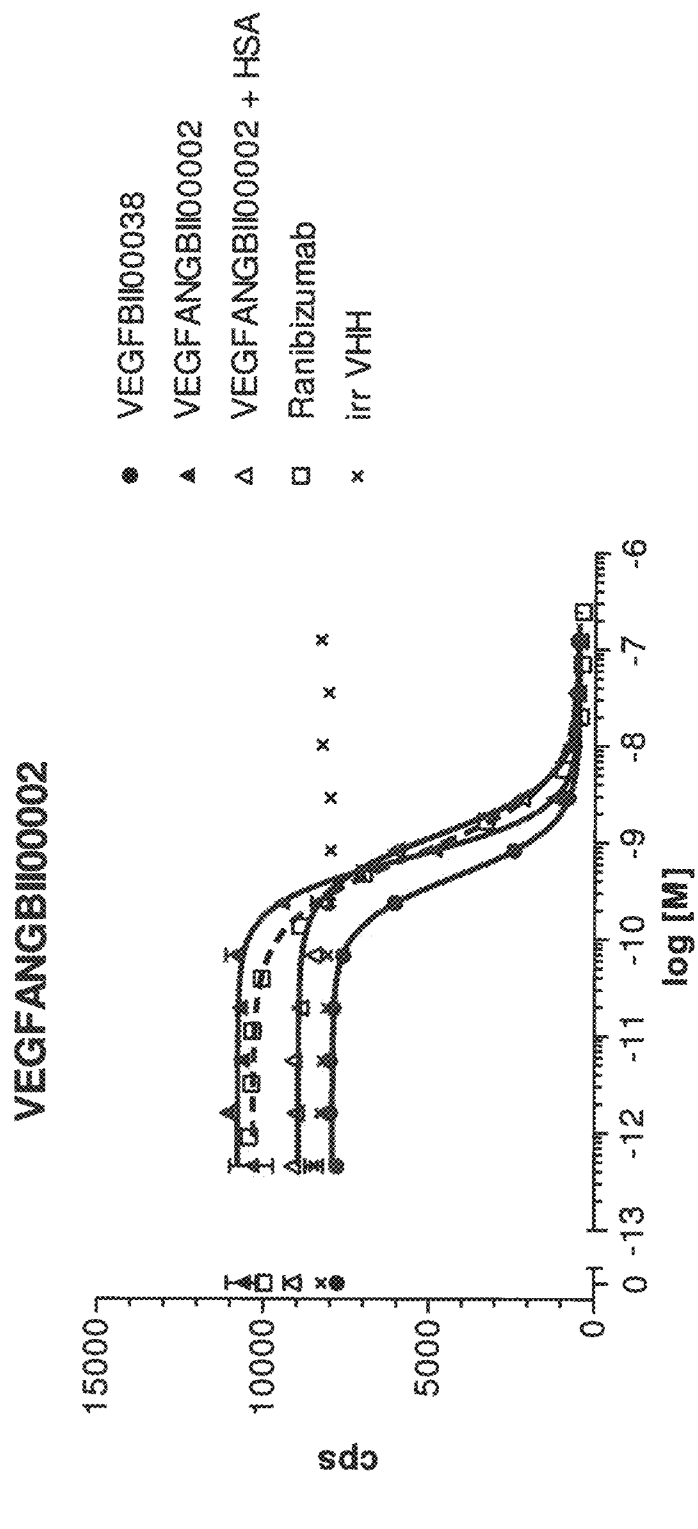
Figure 24C:
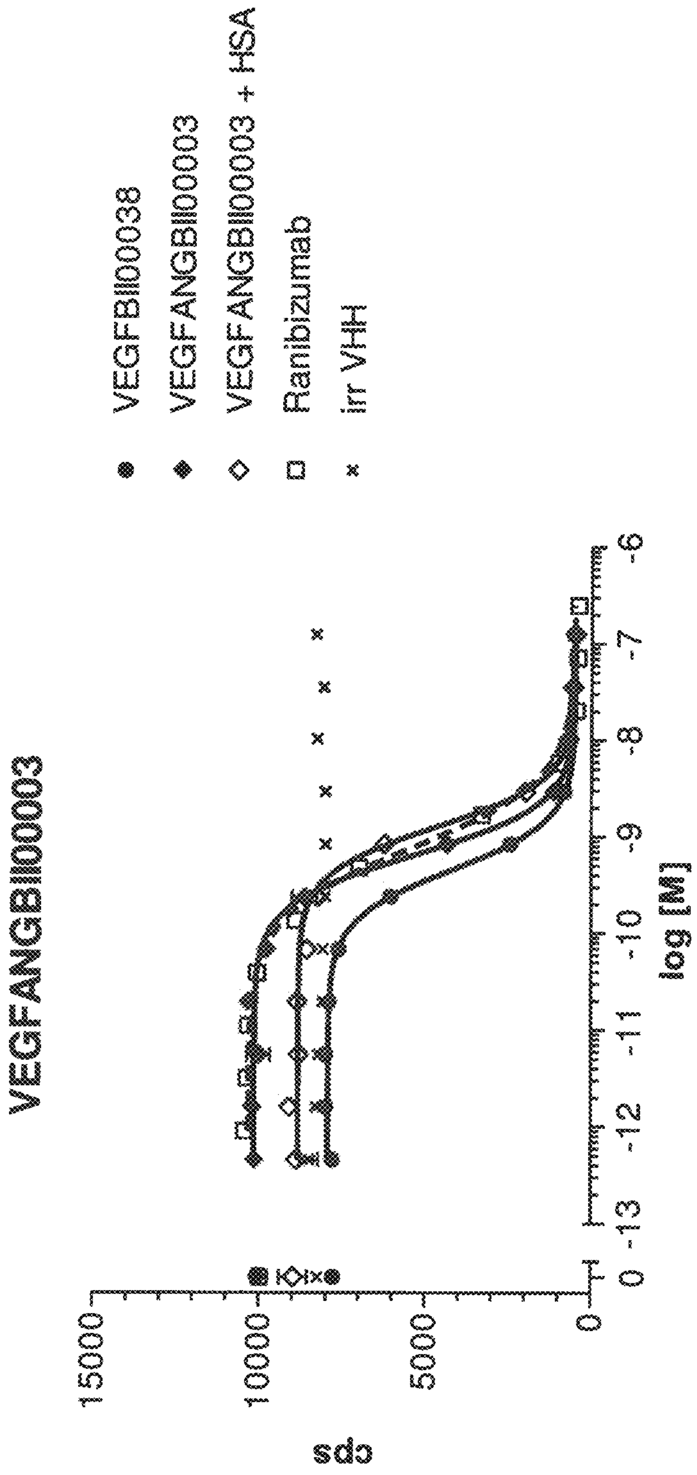
Figure 24D:
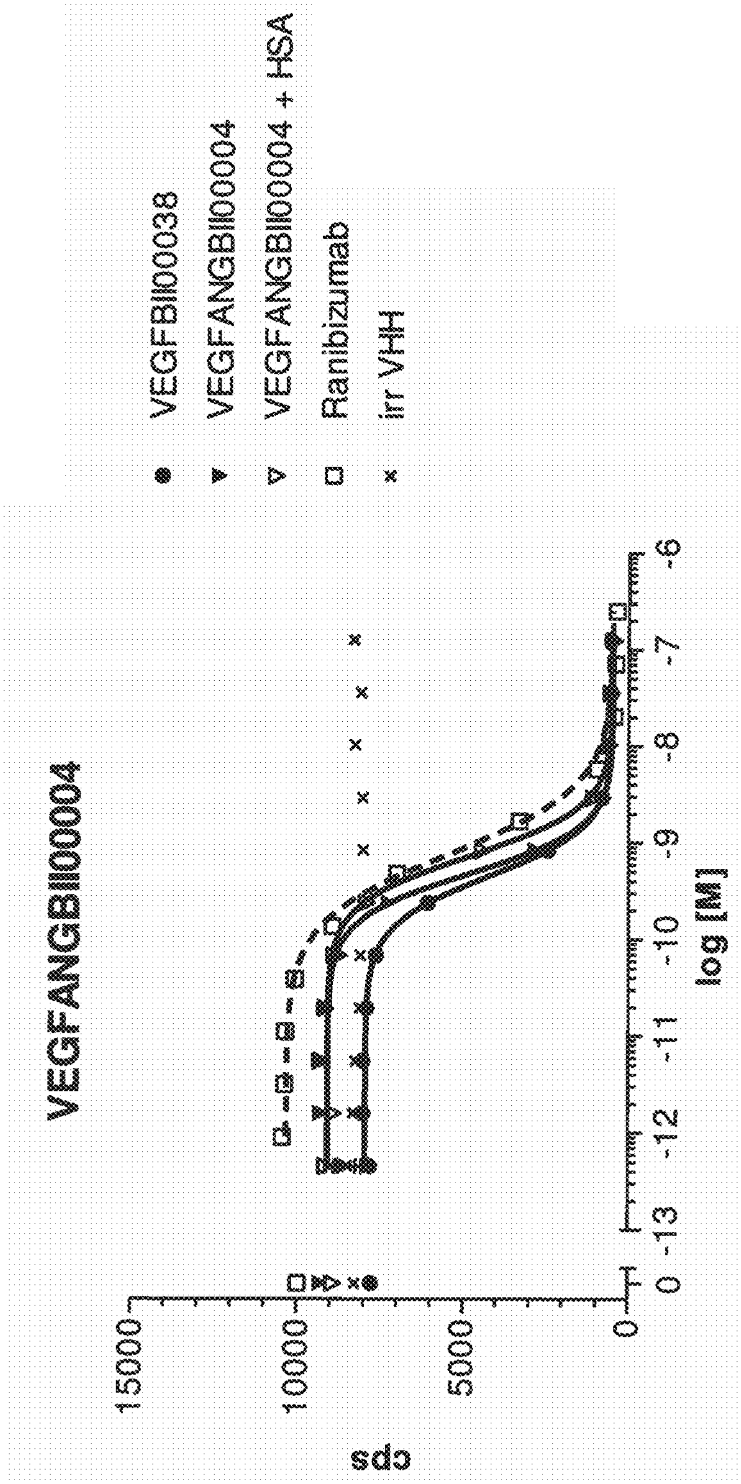
Figure 25A:
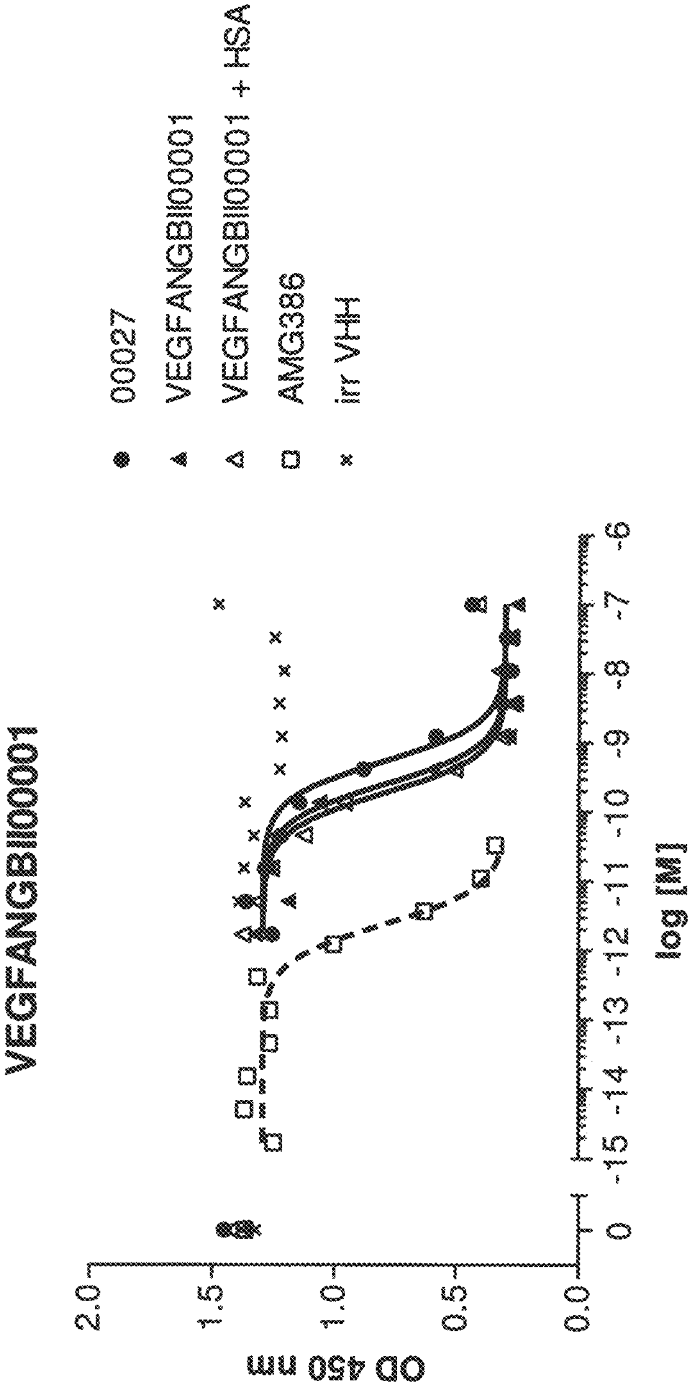
FIG. 25A-25D: Purified trivalent VEGFxAng2 VHHs blocking hAng2-hTie2 interaction (ELISA)
Figure 25B:
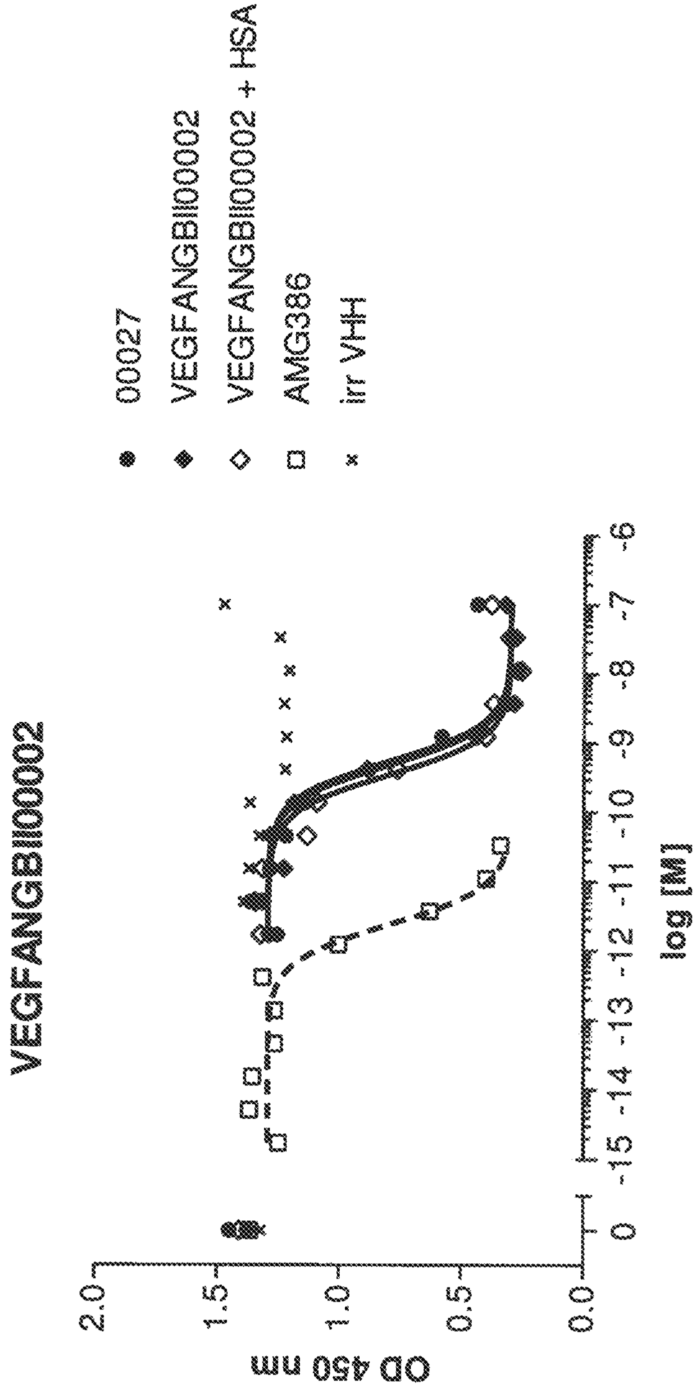
Figure 25C:
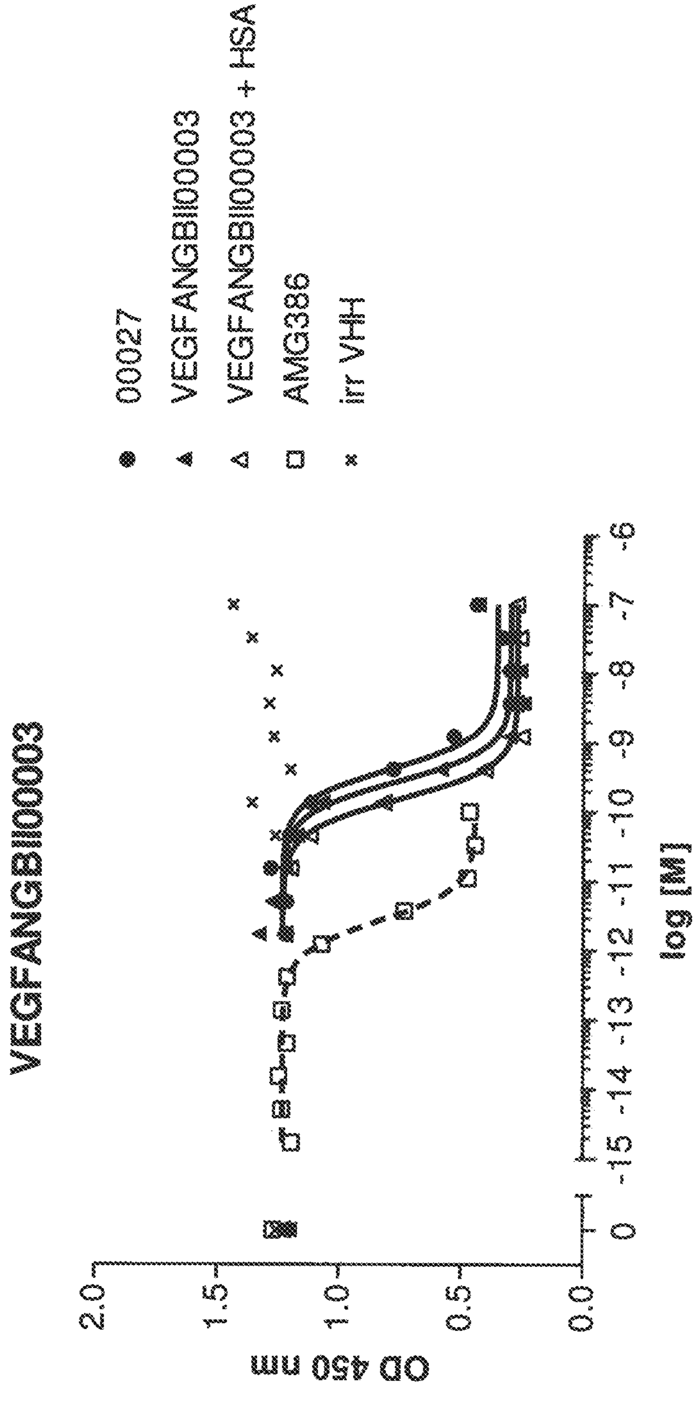
Figure 25D:
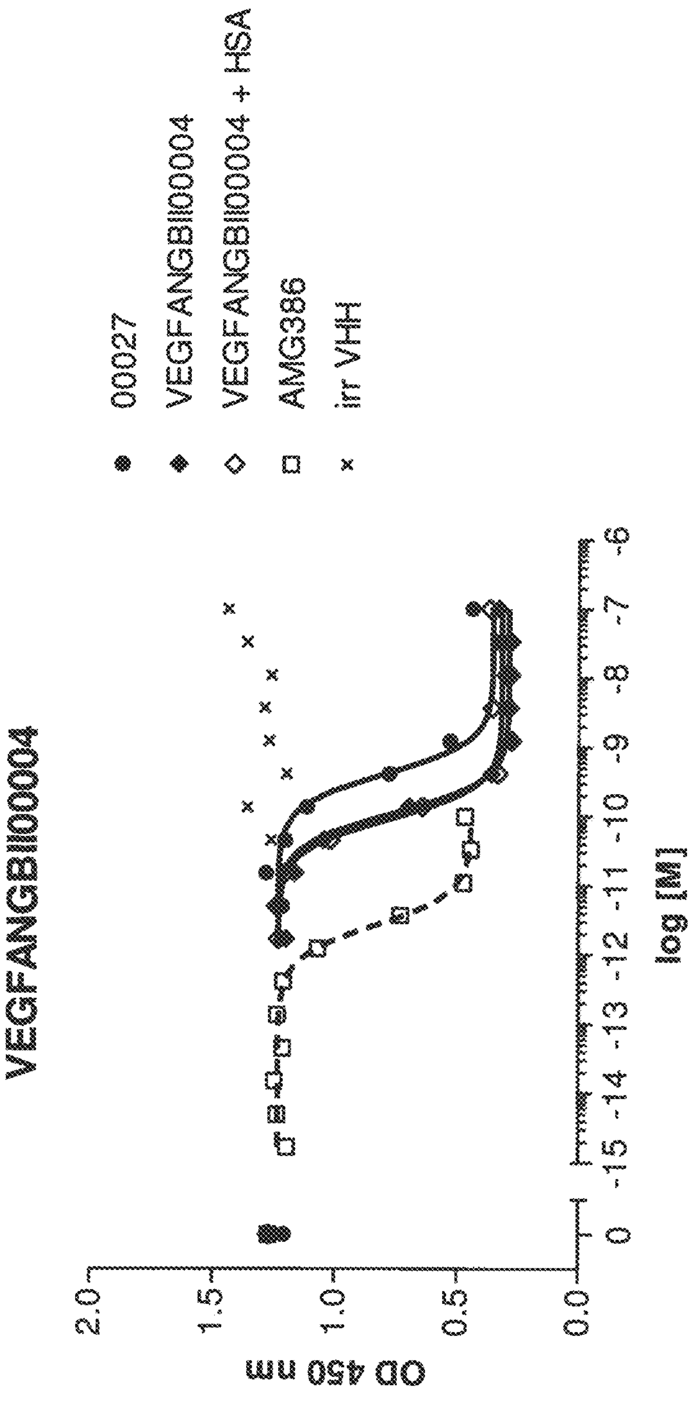

Construction, Production and Characterization of Trivalent Bispecific VHHs Targeting VEGF and Ang2 Using Anti-Serum Abumin as Half-Life Extension The anti-VEGF VHH VEGFBII00038 (US 2011/0172398 A1) and the anti-Ang2 VHH 00027 (SEQ ID No:216) are used as building blocks to generate bispecific VHHs VEGFANGBII00001-00004. A genetic fusion to a serum albumin binding VHH is used as half-life extension methodology. Building blocks are linked via a triple Ala or 9 Gly-Ser flexible linker (SEQ ID NO: 170). VHHs are produced and purified as described in Example 9. An overview of the format and sequence of all four bispecific VHHs is depicted in FIG. 23 A and Table 38 (linker sequences underlined), SEQ ID Nos 186-189. Expression levels are indicated in FIG. 23 B.

TABLE 38

| Sequences of bispecific VHH targeting VEGF and Ang2 | |
|---|---|
| VHH ID | AA sequence |
| VEGFANGBII00001 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQAGGSLRLSCAASGFTLDDYAIGWFRQAPGKEREGVSSIRDNDGSTYYADSVKGRFTISSDNDKNTVYLQMNSLKPEDTAVYYCAAVPAGRLRFGEQWYPLYEYDAWGQGTLVTVSS (SEQ ID NO: 186) |
| VEGFANGBII00002 | EVQLVESGGGLVQAGGSLRLSCAASGFTLDDYAIGWFRQAPGKEREGVSSIRDNDGSTYYADSVKGRFTISSDNDKNTVYLQMNSLKPEDTAVYYCAAVPAGRLRFGEQWYPLYEYDAWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSDVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSS (SEQ ID NO: 187) |
| VEGFANGBII00003 | EVQLVESGGGLVQAGGSLRLSCAASGFTLDDYAIGWFRQAPGKEREGVSSIRDNDGSTYYADSVKGRFTISSDNDKNTVYLQMNSLKPEDTAVYYCAAVPAGRLRFGEQWYPLYEYDAWGQGTLVTVSSGGGGSGGGSDVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS (SEQ ID NO: 188) |

TABLE 38-continued

| Sequences of bispecific VHH targeting VEGF and Ang2 | |
|---|---|
| VHH ID | AA sequence |
| VEGFANGBII00004 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSAAAEVQLVE<br>SGGGLVQPGNSLRLSCAASGFTFSSFGMSWVRQAPGKGLEWVSSISGSGSDTLYADSVKGRFTISRD<br>NAKTTLYLQMNSLRPEDTAVYYCTIGGSLSRSSQGTLVTVSSAAAEVQLVESGGGLVQAGGSLRLSC<br>AASGFTLDDYAIGWFRQAPGKEREGVSSIRDNDGSTYYADSVKGRFTISSDNDKNTVYLQMNSLKPE<br>DTAVYYCAAVPAGRLRFGEQWYPLYEYDAWGQGTLVTVSS (SEQ ID NO: 189) |

To explore the anti-VEGF blocking properties in comparison with the monovalent building block VEGFBII00038, all four bispecific VHHs are analyzed in the VEGF/VEGFR2-Fc (FIG. 22) competition AlphaScreen. The assay is slightly adjusted compared to Example 12.3 described in patent US 2011/0172398 A1. Both human VEGF165 and human VEGFR2-Fc are added at 0.05 nM. This competition assay is also performed after preincubation of the VHH with 25 μM human serum albumin. A summary of $IC_{50}$ values and % inhibition is shown in FIG. 23 C.

To explore the anti-Ang2 blocking properties in comparison with the monovalent building block 00027 (SEQ ID No:216), all four bispecific VHHs are analyzed in a human Ang2/hTie2-Fc (FIG. 25) competition ELISA. This assay is also performed after incubation of the VHH with 0.5 μM human serum albumin. A summary of $IC_{50}$ values is shown in FIG. 23 D.

Example 11

Figure 26:
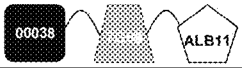
FIG. 26A-26C: A. Description trivalent and tetravalent VEGFxAng2 bispecific VHHs (FIG. 26 discloses "9GS" and "9 GlySer" as SEQ ID NO: 170); B. Expression levels all ten bispecific VHHs as depicted in FIG. 26A are shown; C. $IC_{50}$ values (nM) in human VEGF165/human VEGFR2 and human VEGF165/human VEGFR1 competition AlphaScreen FIG. 27-1A to 27-1H; 27-2A to 27-2H: Purified trivalent and tetravalent VEGFxAng2 VHHs blocking hVEGF-hVEGFR2 (31-1) and hVEGF-hVEGFR1 (31-2) interaction (AlphaScreen)
Figure 26:
Figure 26:
Figure 26:
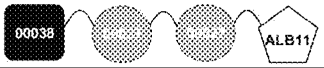
Figure 26:
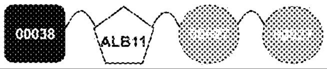
Figure 26:
Figure 26:
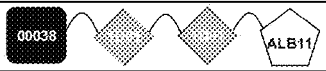
Figure 26:
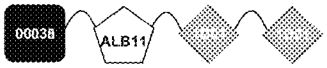
Figure 26:
Figure 26:
Figure 26:
Figure 26:
Figure 26:
Figure 26:
Figure 26:
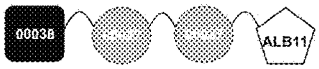
Figure 26:
Figure 26:
Figure 26:
Figure 26:
Figure 26:
Figure 26:
Figure 26:

Construction, Production and Characterization of Trivalent and Tetravalent Bispecific VHHs Targeting VEGF and Ang2 Using Anti-Serum Albumin Binding as Half-Life Extension Ten bispecific VHHs targeting VEGF and Ang2 are constructed (VEGFANGBII00005-00015). In these constructs monovalent and bivalent 1 D01 (SEQ ID NO:214), monovalent and bivalent 7G08 (SEQ ID NO:215) and bivalent 00027 (SEQ ID NO:216) anti-Ang2 building blocks are included. A genetic fusion to a serum albumin binding VHH is used as half-life extension methodology. Building blocks are linked via a 9 Gly-Ser flexible linker (SEQ ID NO: 170). VHHs are produced and purified as described in Example 8. An overview of the format and sequence of all ten bispecific VHHs is depicted in FIG. 26 A and Table 41 (linker sequences underlined), SEQ ID Nos 190-199. Expression levels are indicated in FIG. 26 B.

TABLE 41

| Sequences of bispecific VHH targeting VEGF and Ang2 | |
|---|---|
| VHH ID | AA sequence |
| VEGFANGBII00005 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGGSLRLSCAASGFALDYYAIGWERQVPGKEREGVSCISSSDGITYYVDSVKGR<br>FTISRDNAKNTVYLQMNSLKPEDTAVYYCATDSGGYIDYDCMGLGYDYWGQGTLVTVSSGGGGSGGG<br>SEVQLVESGGGLVQPGNSLRLSCAASGFTFSSFGMSWVRQAPGKGLEWVSSISGSGSDTLYADSVKG<br>RFTISRDNAKTTLYLQMNSLRPEDTAVYYCTIGGSLSRSSQGTLVTVSS (SEQ ID NO: 190) |
| VEGFANGBII00006 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGNSLRLSCAASGFTFSSFGMSWVRQAPGKGLEWVSSISGSGSDTLYADSVKGR<br>FTISRDNAKTTLYLQMNSLRPEDTAVYYCTIGGSLSRSSQGTLVTVSSGGGGSGGGSEVQLVESGGG<br>LVQPGGSLRLSCAASGFALDYYAIGWFRQVPGKEREGVSCISSSDGITYYVDSVKGRFTISRDNAKN<br>TVYLQMNSLKPEDTAVYYCATDSGGYIDYDCMGLGYDYWGQGTLVTVSS (SEQ ID NO: 191) |
| VEGFANGBII00007 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGGSLRLSCAASGFALDYYAIGWFRQVPGKEREGVSCISSSDGITYYVDSVKGR<br>FTISRDNAKNTVYLQMNSLKPEDTAVYYCATDSGGYIDYDCMGLGYDYWGQGTLVTVSSGGGGSGGG<br>SEVQLVESGGGLVQPGNSLRLSCAASGFTFSSFGMSWVRQAPGKGLEWVSSISGSGSDTLYADSVKG<br>RFTISRDNAKTTLYLQMNSLRPEDTAVYYCTIGGSLSRSSQGTLVTVSSGGGGSGGGSEVQLVESGG<br>GLVQPGGSLRLSCAASGFALDYYAIGWFRQVPGKEREGVSCISSSDGITYYVDSVKGRFTISRDNAK<br>NTVYLQMNSLKPEDTAVYYCATDSGGYIDYDCMGLGYDYWGQGTLVTVSS (SEQ ID NO: 192) |
| VEGFANGBII00008 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQAGGSLRLSCAASGFTLDDYAIGWFRQAPGKEREGVSSIRDNDGSTYYADSVKGR<br>FTISSDNDKNTVYLQMNSLKPEDTAVYYCAAVPAGRLRFGEQWYPLYEYDAWGQGTLVTVSSGGGGS<br>GGGSEVQLVESGGGLVQAGGSLRLSCAASGFTLDDYAIGWFRQAPGKEREGVSSIRDNDGSTYYADS<br>VKGRFTISSDNDKNTVYLQMNSLKPEDTAVYYCAAVPAGRLRFGEQWYPLYEYDAWGQGTLVTVSSG<br>GGGSGGGSEVQLVESGGGLVQPGNSLRLSCAASGFTFSSFGMSWVRQAPGKGLEWVSSISGSGSDTL<br>YADSVKGRFTISRDNAKTTLYLQMNSLRPEDTAVYYCTIGGSLSRSSQGTLVTVSS (SEQ ID<br>NO: 193) |
| VEGFANGBII00009 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGNSLRLSCAASGFTFSSFGMSWVRQAPGKGLEWVSSISGSGSDTLYADSVKGR |

TABLE 41-continued

| Sequences of bispecific VHH targeting VEGF and Ang2 | |
|---|---|
| VHH ID | AA sequence |
| | FTISRDNAKTTLYLQMNSLREEDTAVYYCTIGGSLSRSSQGTLVTVSSGGGGSGGGSEVQLVESGGG<br>LVQAGGSLRLSCAASGFTLDDYAIGWFRQAPGKEREGVSSIRDNDGSTYYADSVKGRFTISSDNDKN<br>TVYLQMNSLKPEDTAVYYCAAVPAGRLRFGEQWYPLYEYDAWGQGTLVTVSSGGGGSGGGSEVQLVE<br>SGGGLVQAGGSLRLSCAASGFTLDDYAIGWFRQAPGKEREGVSSIRDNDGSTYYADSVKGRFTISSD<br>NDKNTVYLQMNSLKPEDTAVYYCAAVPAGRLRFGEQWYPLYEYDAWGQGTLVTVSS (SEQ ID<br>NO: 194) |
| VEGFANGBII00010 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQAGGSLRLSCAASGFTLDDYAIGWFRQAPGKEREGVSSIRDNDGSTYYADSVKGR<br>FTISSDNDKNTVYLQMNSLKPEDTAVYYCAAVPAGRLRFGEQWYPLYEYDAWGQGTLVTVSSGGGGS<br>GGGSEVQLVESGGGLVQPGNSLRLSCAASGFTFSSFGMSWVRQAPGKGLEWVSSISGSGSDTLYADS<br>VKGRFTISRDNAKTTLYLQMNSLREEDTAVYYCTIGGSLSRSSQGTLVTVSSGGGGSGGGSEVQLVE<br>SGGGLVQAGGSLRLSCAASGFTLDDYAIGWFRQAPGKEREGVSSIRDNDGSTYYADSVKGRFTISSD<br>NDKNTVYLQMNSLKPEDTAVYYCAAVPAGRLRFGEQWYPLYEYDAWGQGTLVTVSS (SEQ ID<br>NO: 195) |
| VEGFANGBII00011 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQAGGSLRLSCAASGFTFDDYALGWERQAAGKEREGVSCIRCSDGSTYYADSVKGR<br>FTISSDNAKNTVYLQMNSLKPEDTAVYYCAASIVERSKLEPYEYDAWGQGTLVTVSSGGGGSGGGSE<br>VQLVESGGGLVQAGGSLRLSCAASGFTFDDYALGWFRQAAGKEREGVSCIRCSDGSTYYADSVKGRF<br>TISSDNAKNTVYLQMNSLKPEDTAVYYCAASIVPRSKLEPYEYDAWGQGTLVTVSSGGGGSGGGSEV<br>QLVESGGGLVQPGNSLRLSCAASGFTFSSFGMSWVRQAPGKGLEWVSSISGSGSDTLYADSVKGRFT<br>ISRDNAKTTLYLQMNSLRPEDTAVYYCTIGGSLSRSSQGTLVTVSS (SEQ ID NO: 196) |
| VEGFANGBII00012 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGNSLRLSCAASGFTFSSFGMSWVRQAPGKGLEWVSSISGSGSDTLYADSVKGR<br>FTISRDNAKTTLYLQMNSLRPEDTAVYYCTIGGSLSRSSQGTLVTVSSGGGGSGGGSEVQLVESGGG<br>LVQAGGSLRLSCAASGFTEDDYALGWFRQAAGKEREGVSCIRCSDGSTYYADSVKGRFTISSDNAKN<br>TVYLQMNSLKPEDTAVYYCAASIVPRSKLEPYEYDAWGQGTLVTVSSGGGGSGGGSEVQLVESGGGL<br>VQAGGSLRLSCAASGFTFDDYALGWFRQAAGKEREGVSCIRCSDGSTYYADSVKGRFTISSDNAKNT<br>VYLQMNSLKPEDTAVYYCAASIVPRSKLEPYEYDAWGQGTLVTVSS (SEQ ID NO: 197) |
| VEGFANGBII00013 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQAGGSLRLSCAASGFTFDDYALGWERQAAGKEREGVSCIRCSDGSTYYADSVKGR<br>FTISSDNAKNTVYLQMNSLKPEDTAVYYCAASIVPRSKLEPYEYDAWGQGTLVTVSSGGGGSGGGSE<br>VQLVESGGGLVQPGNSLRLSCAASGFTFSSFGMSWVRQAPGKGLEWVSSISGSGSDTLYADSVKGRF<br>TISRDNAKTTLYLQMNSLRPEDTAVYYCTIGGSLSRSSQGTLVTVSSGGGGSGGGSEVQLVESGGGL<br>VQAGGSLRLSCAASGFTFDDYALGWFRQAAGKEREGVSCTRCSDGSTYYADSVKGRFTISSDNAKNT<br>VYLQMNSLKPEDTAVYYCAASIVPRSKLEPYEYDAWGQGTLVTVSS (SEQ ID NO: 198) |
| VEGFANGBII00014 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGNSLRLSCAASGFTFSSFGMSWVRQAPGKGLEWVSSISGSGSDTLYADSVKGR<br>FTISRDNAKTTLYLQMNSLRPEDTAVYYCTIGGSLSRSSQGTLVTVSSGGGGSGGGSEVQLVESGGG<br>LVQAGGSLRLSCAASGFTFDDYALGWFRQAAGKEREGVSCIRCSDGSTYYADSVKGRFTISSDNAKN<br>TVYLQMNSLKPEDTAVYYCAASIVPRSKLEPYEYDAWGQGTLVTVSS (SEQ ID NO: 199) |

Figures 1A, 27:
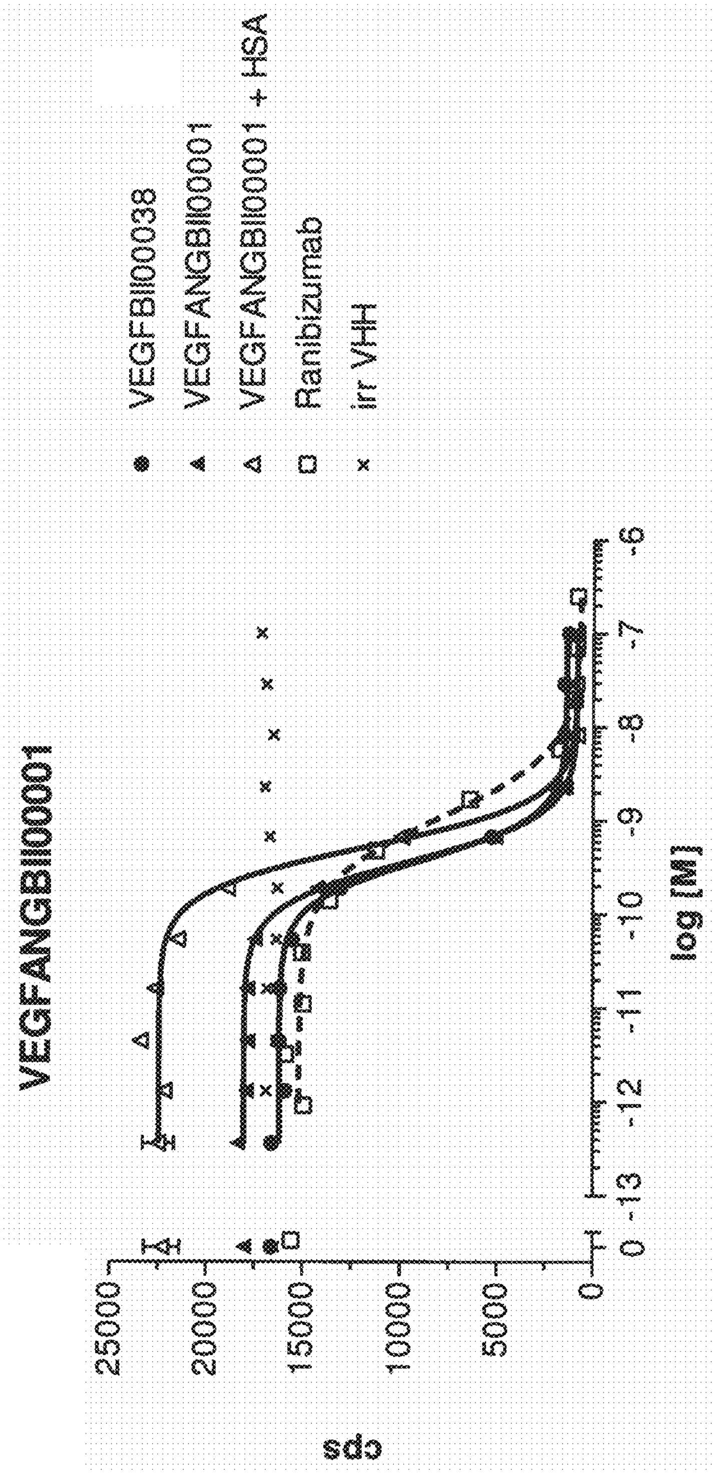
Figures 1B, 27:
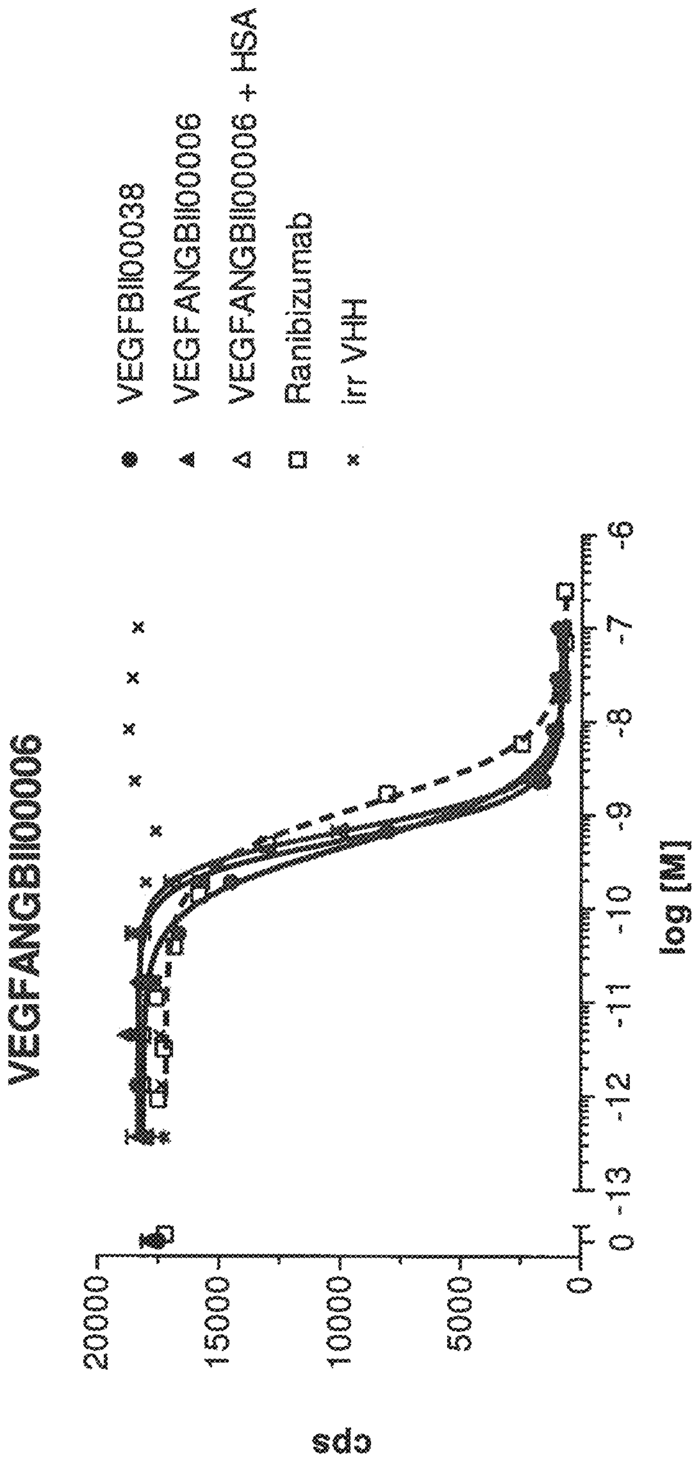
Figures 1C, 27:
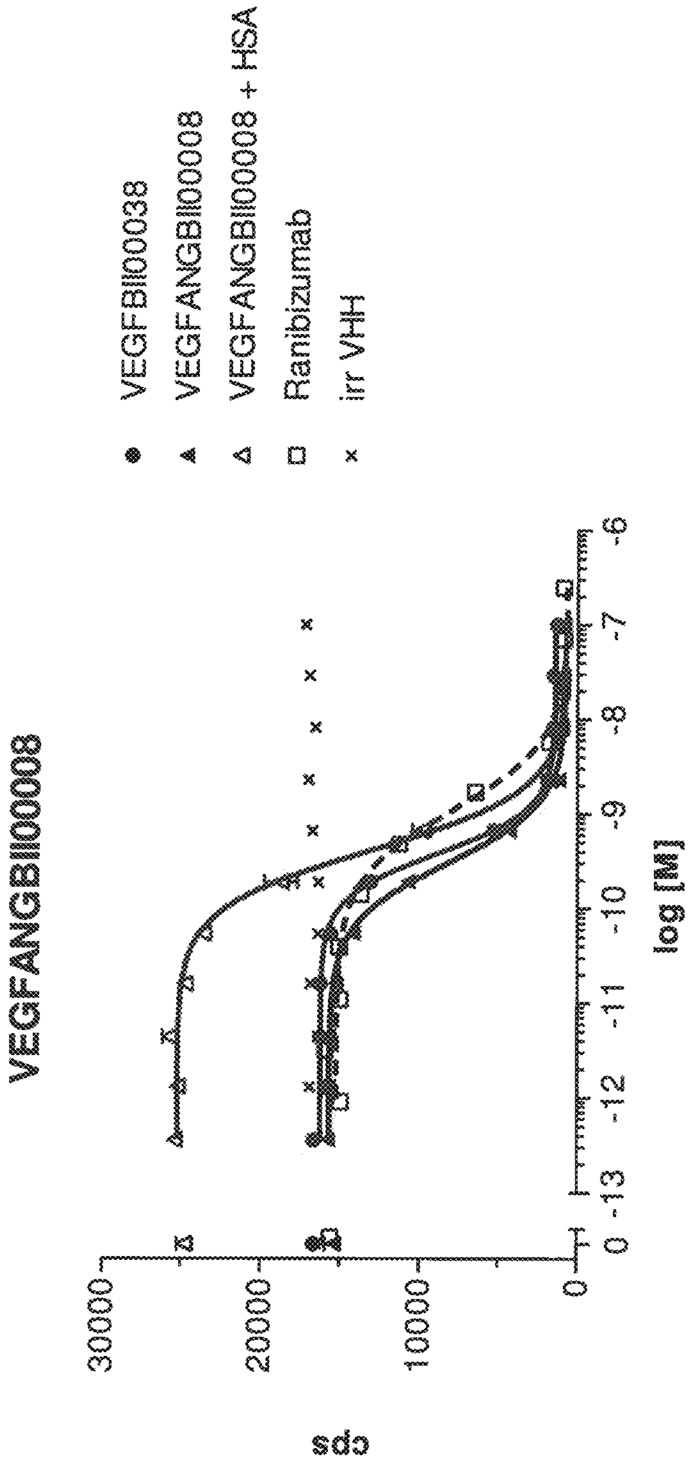
Figures 1D, 27:
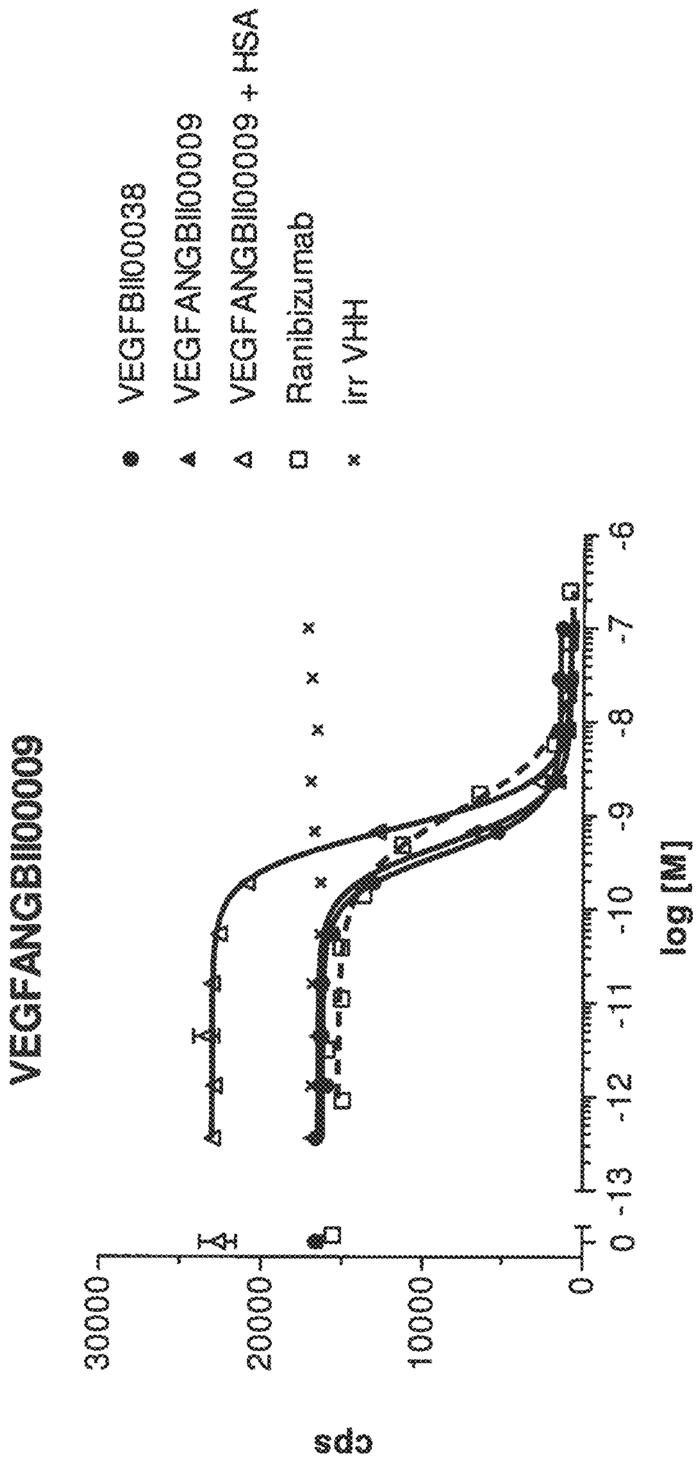
Figures 1E, 27:
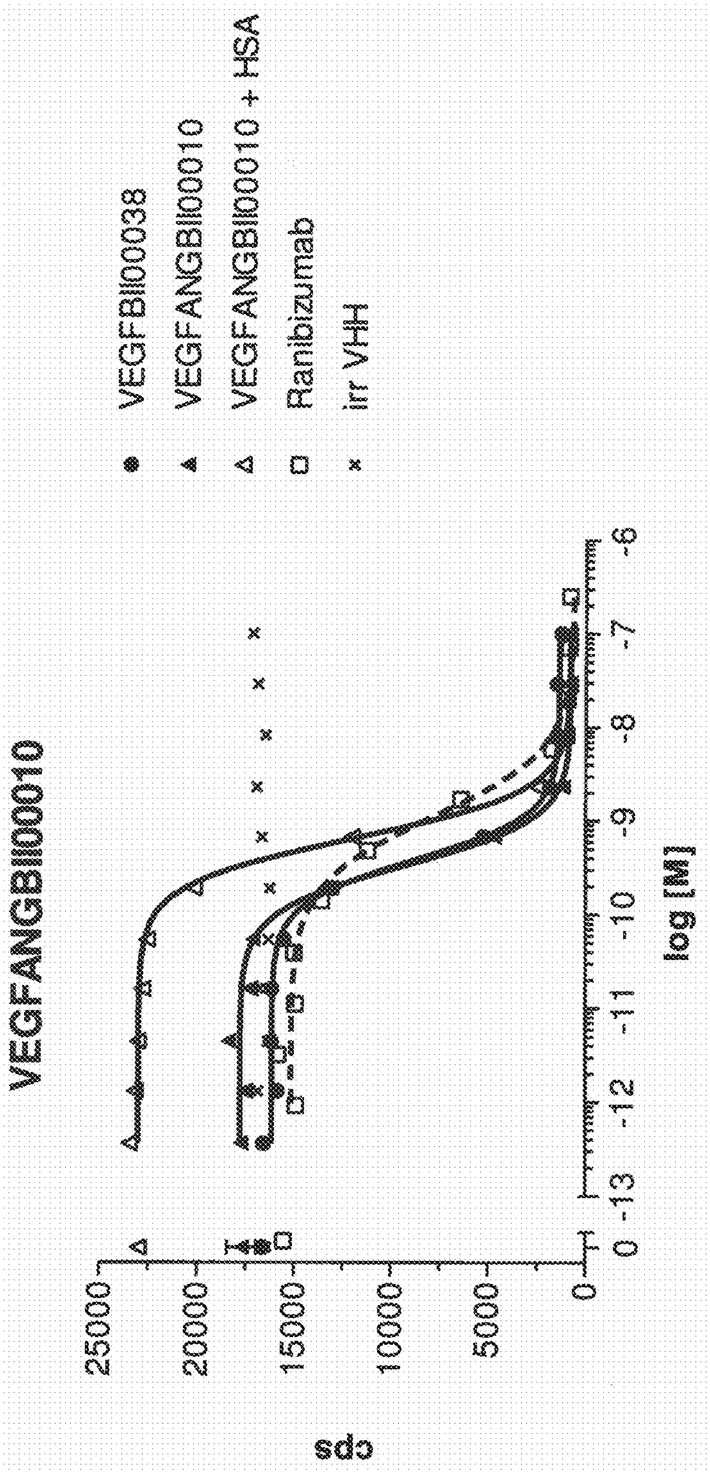
Figures 1F, 27:
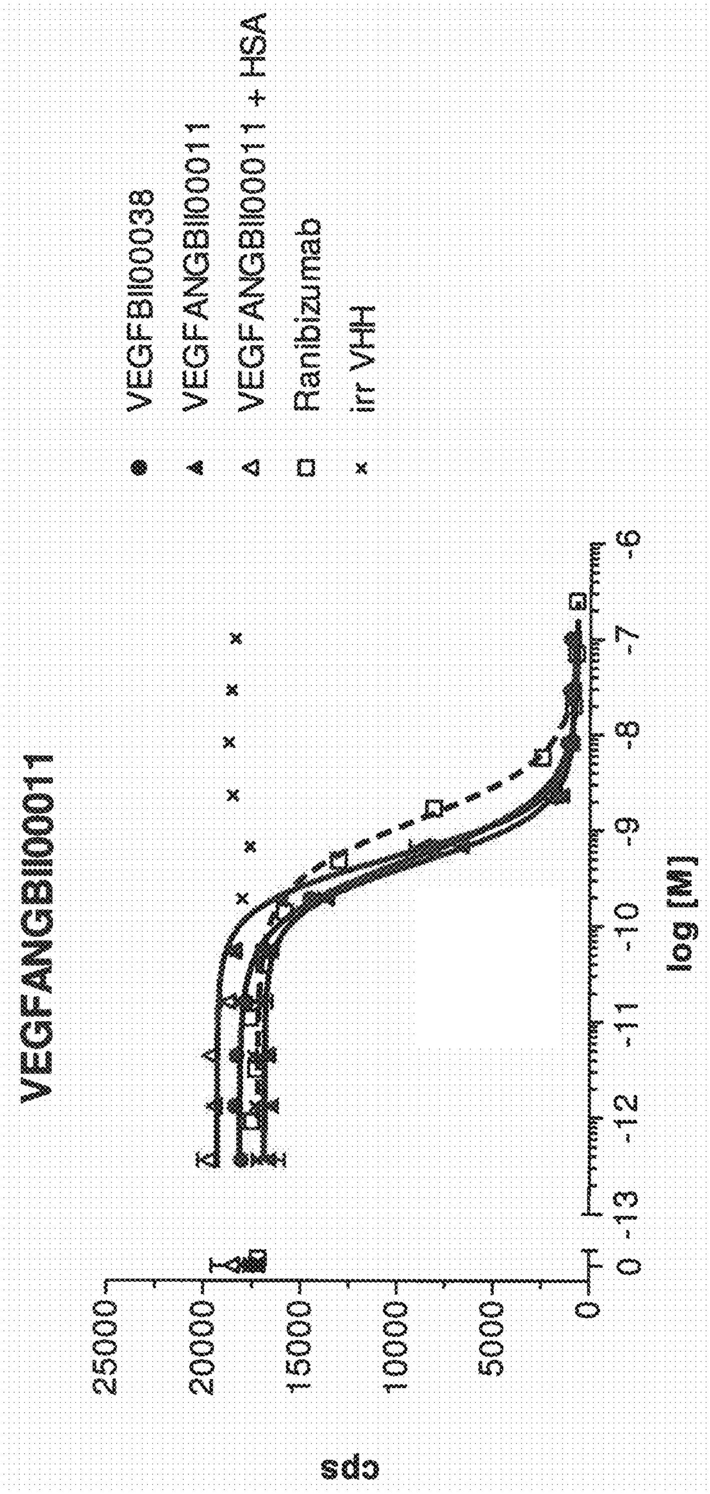
Figures 1G, 27:
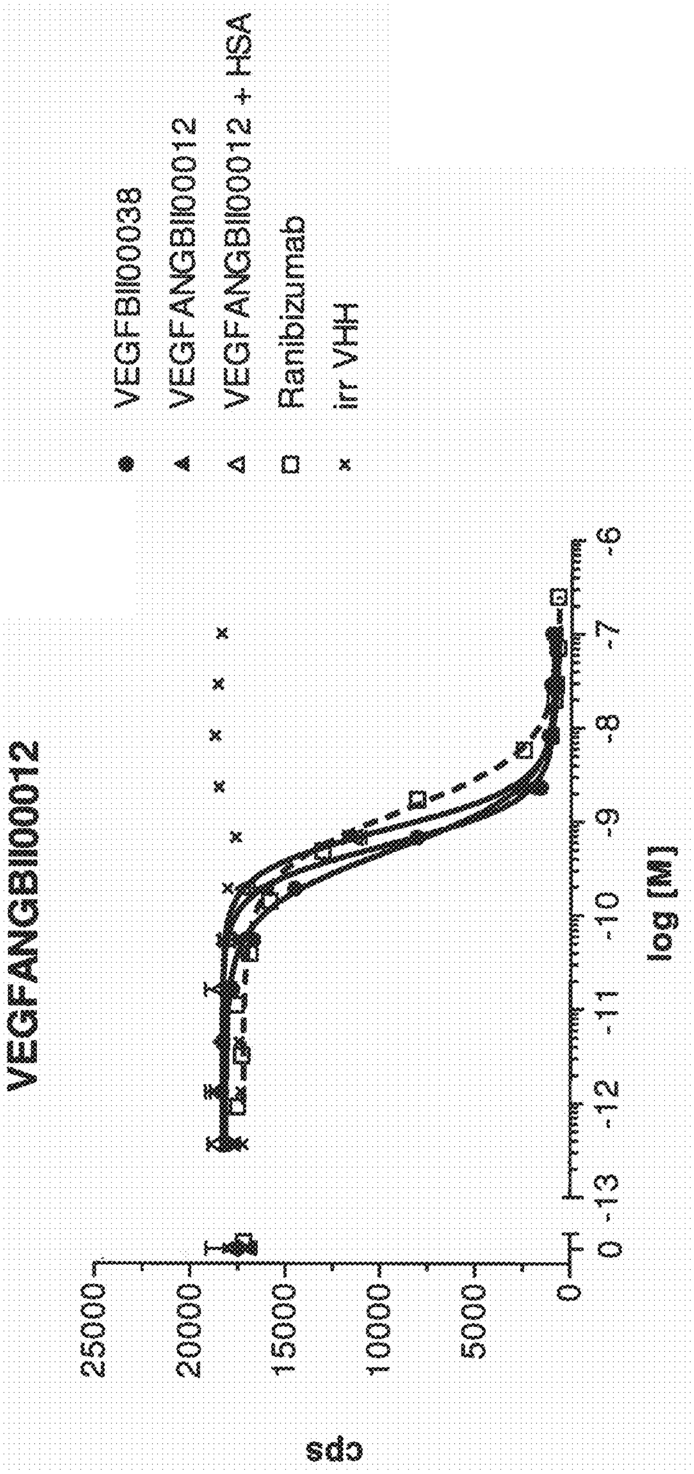
Figures 1H, 27:
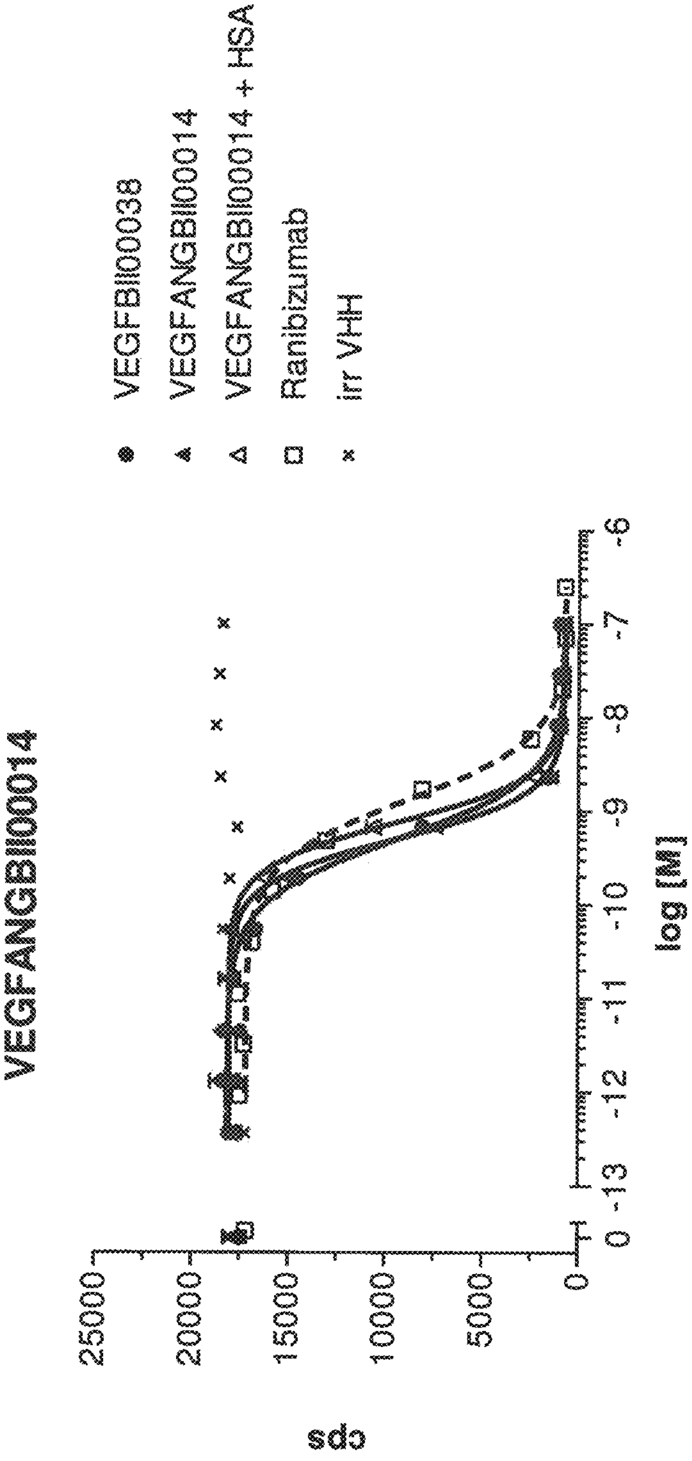
Figures 2A, 27:
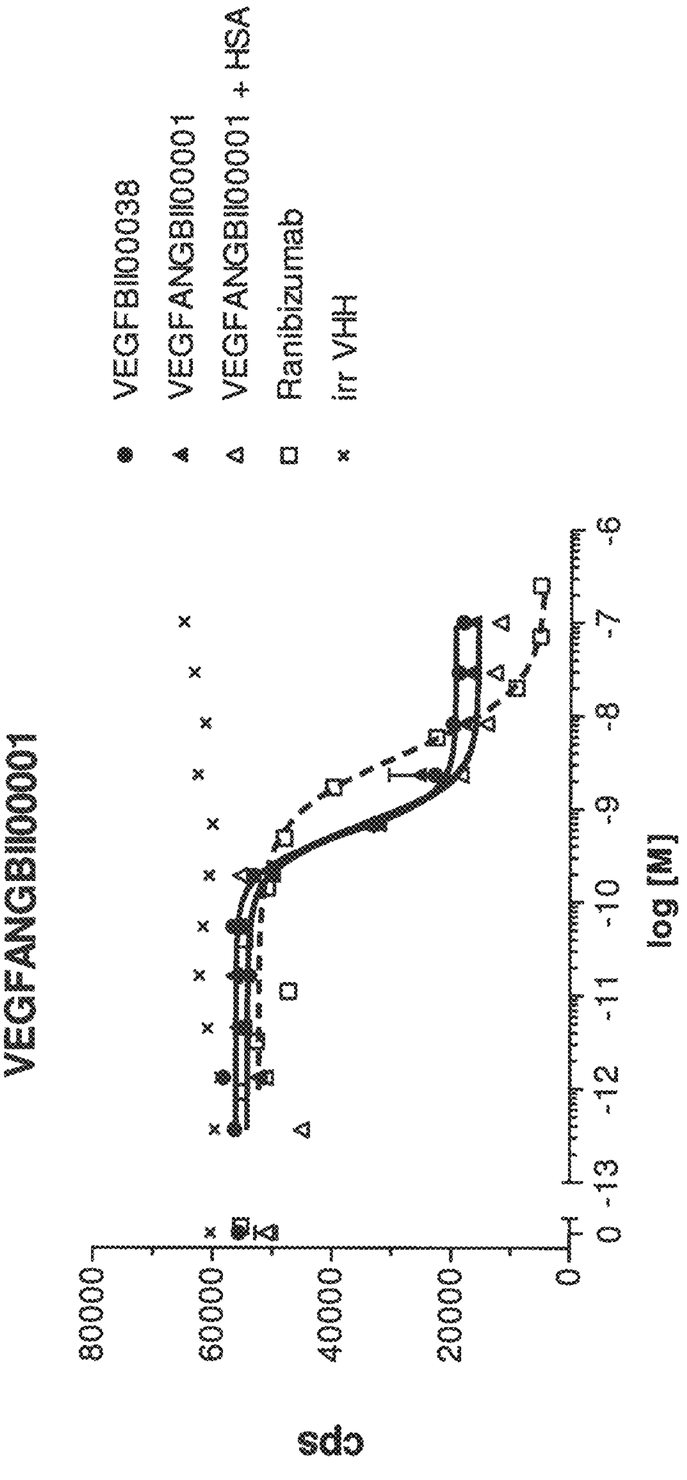
Figures 2B, 27:
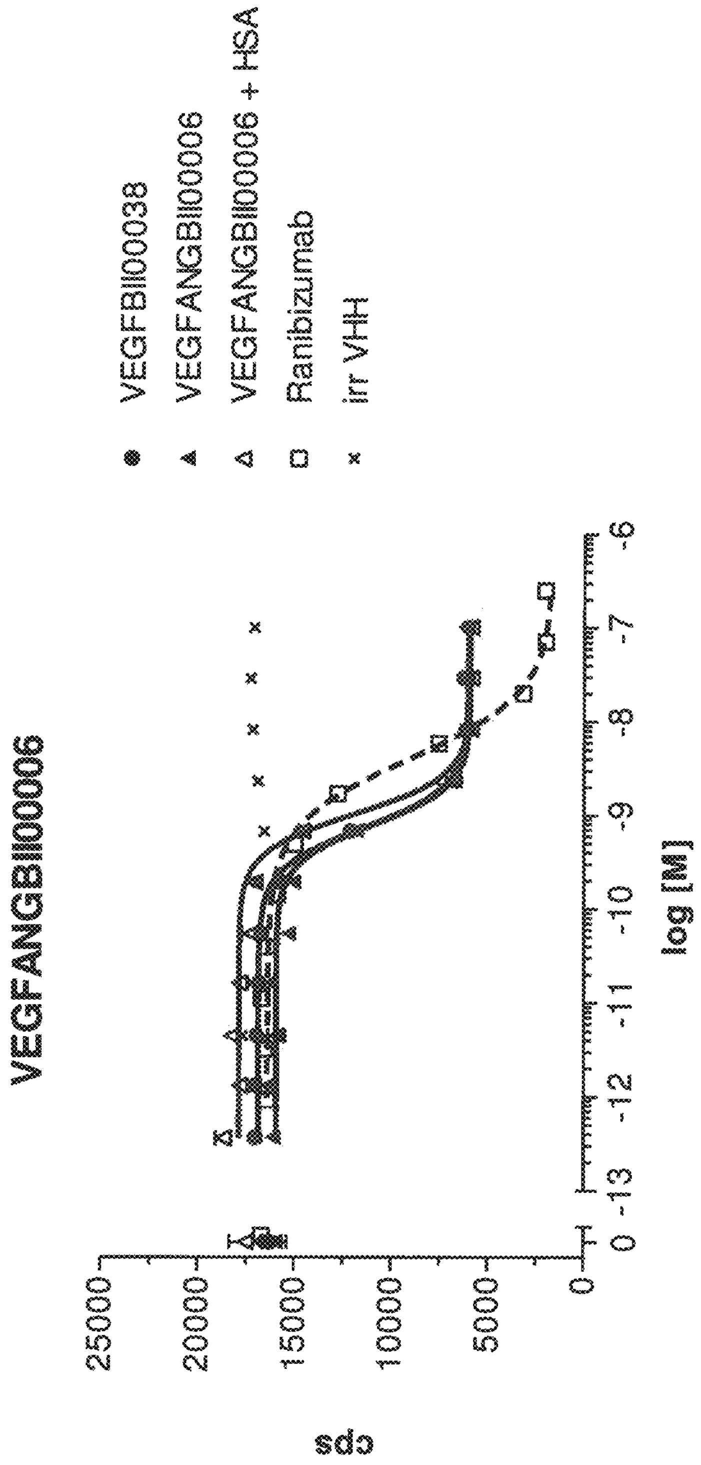
Figures 2C, 27:
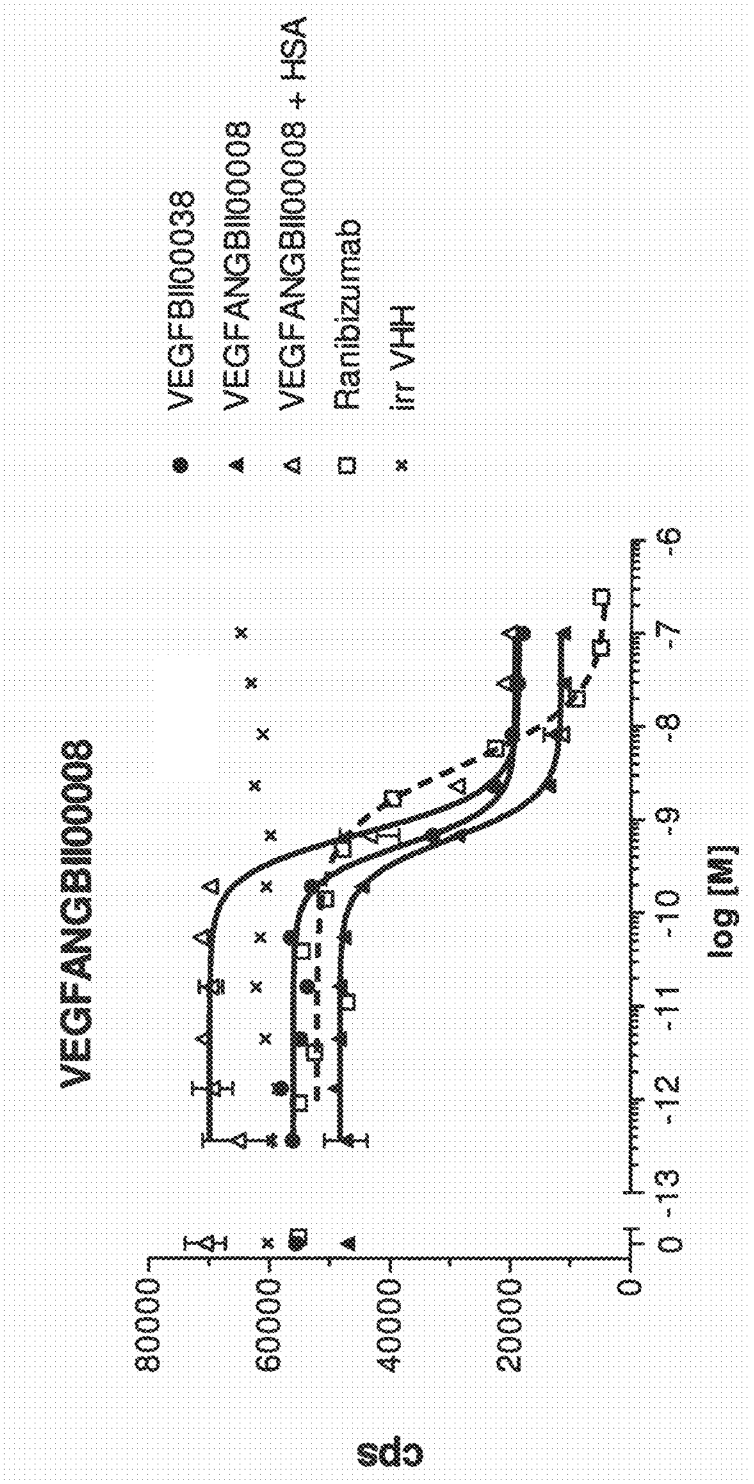
Figures 2D, 27:
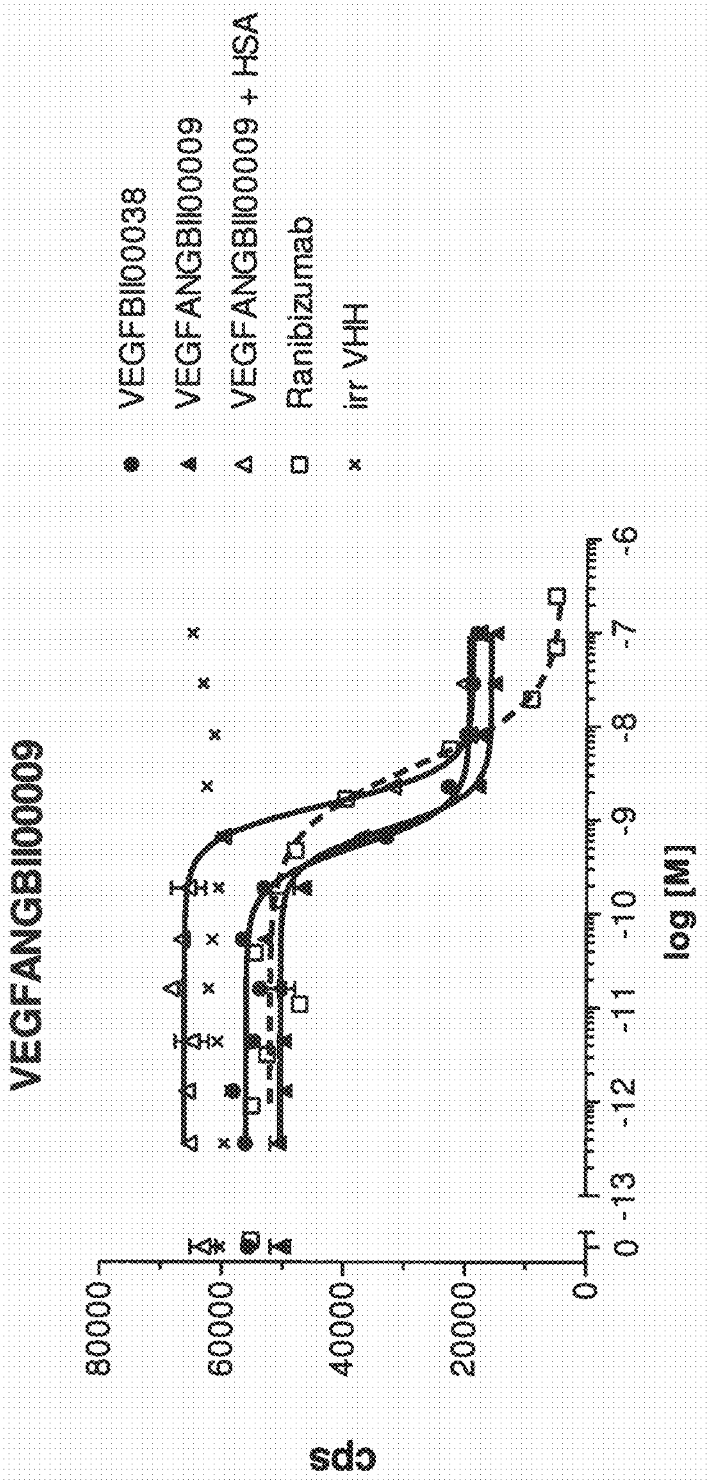
Figures 2E, 27:
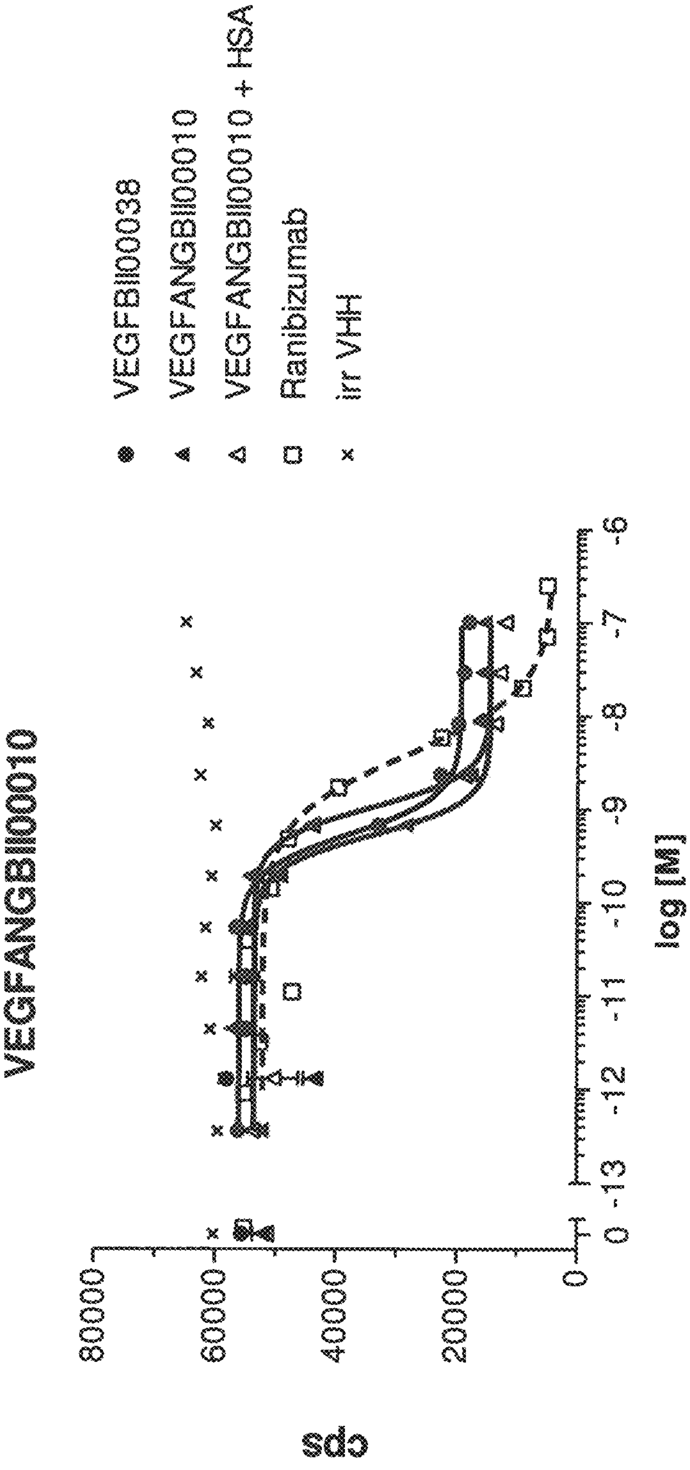
Figures 2F, 27:
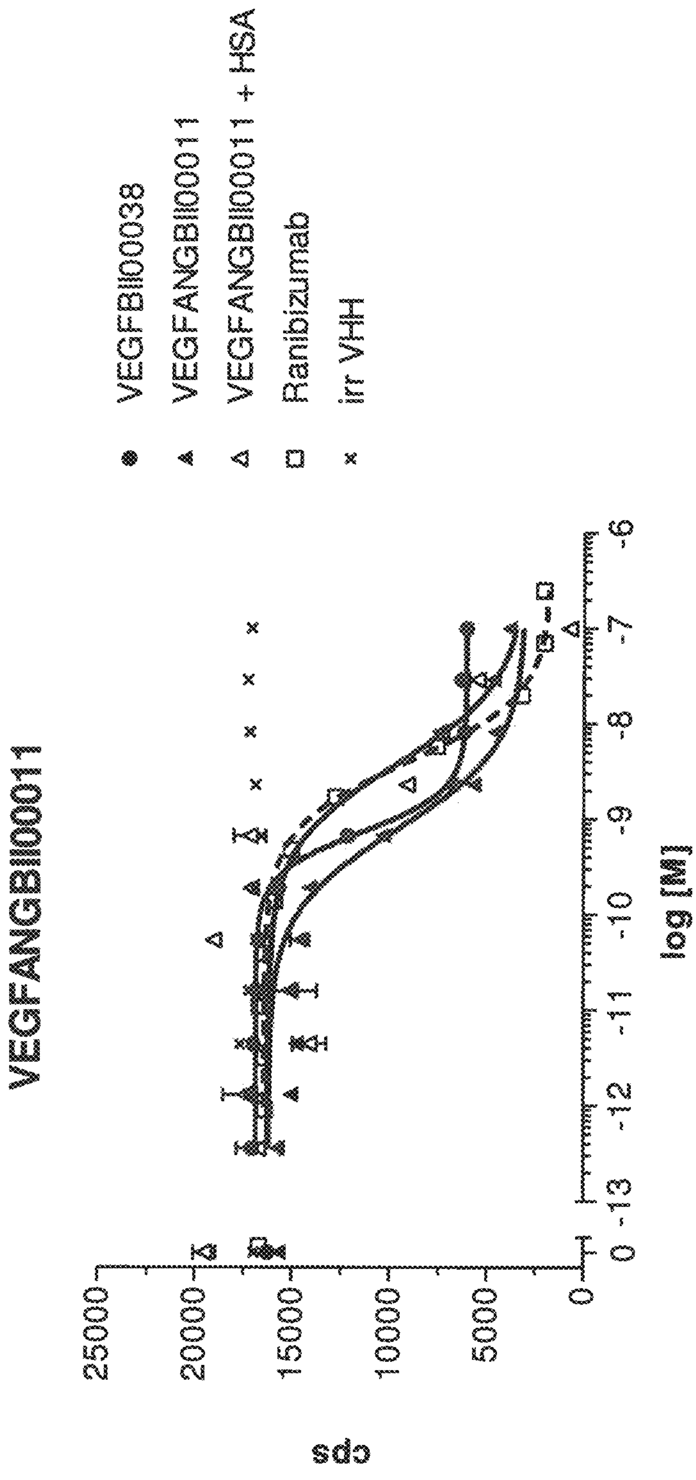
Figures 2G, 27:
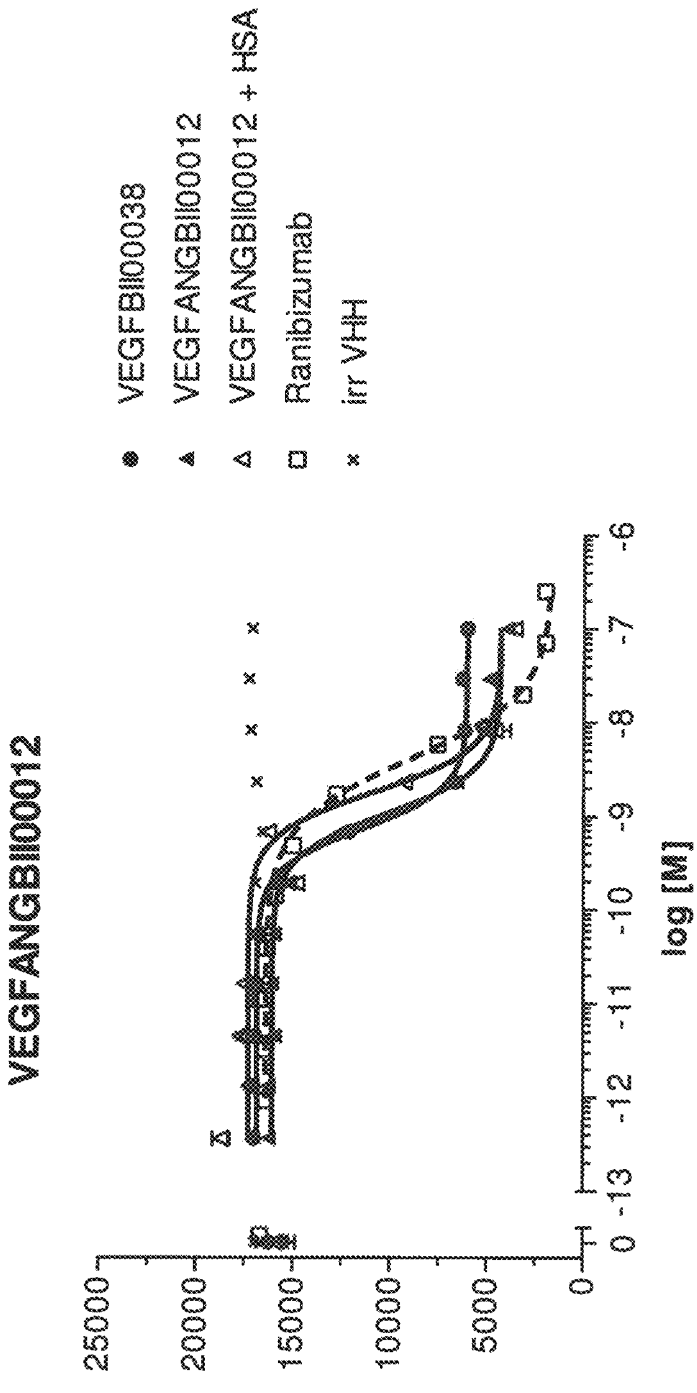
Figures 2H, 27:
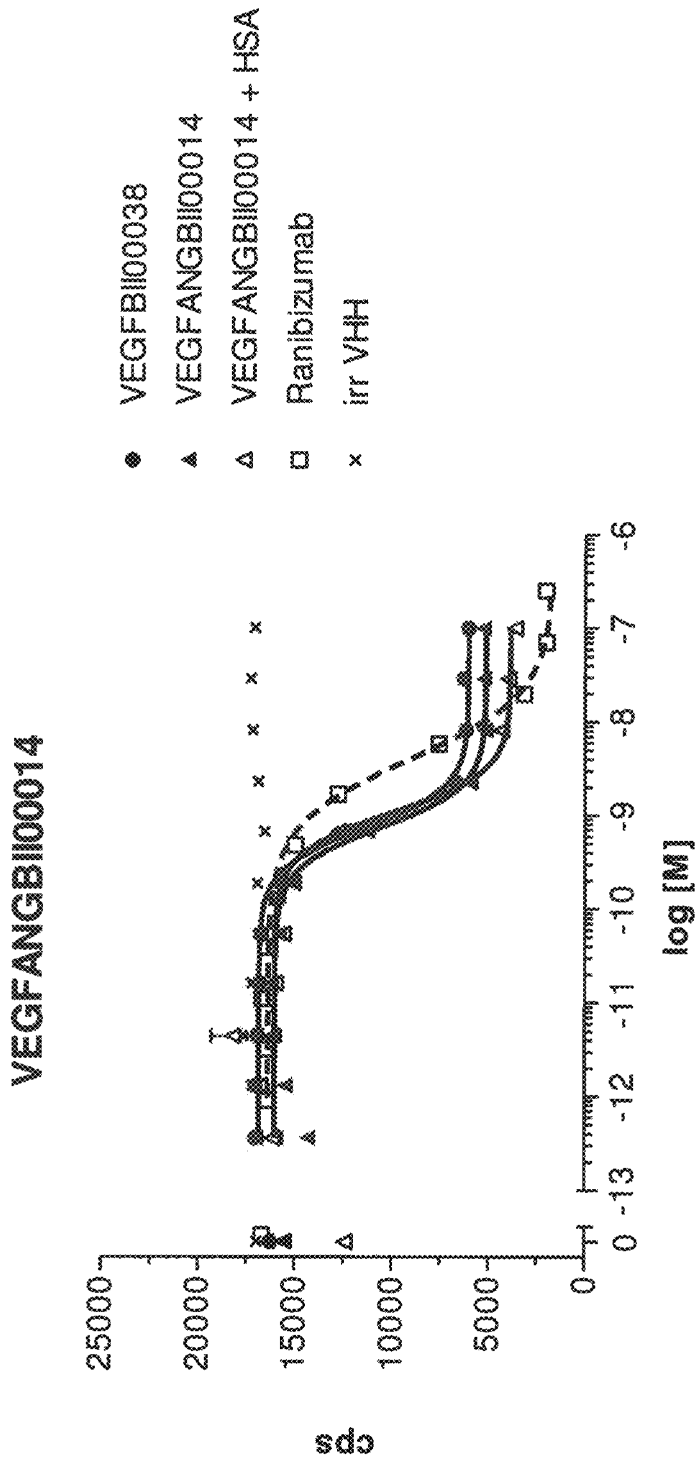

To explore the anti-VEGF blocking properties in comparison with the monovalent building block VEGFBII00038, all ten bispecific VHHs are analyzed in the VEGF/VEGFR2-Fc (Example 10; FIG. 27-1) and VEGF/VEGFR1 (FIG. 27-2) competition AlphaScreen. The VEGFR1 assay is slightly adjusted compared to Example 12.4 as described in patent US 2011/0172398 A1. Human VEGF165 and human VEGFR1-Fc are added at 0.05 nM. These competition assays are also performed after preincubation of the VHH with 25 μM human serum albumin. A summary of $IC_{50}$ values is shown in FIG. 26 C.

Figure 3:
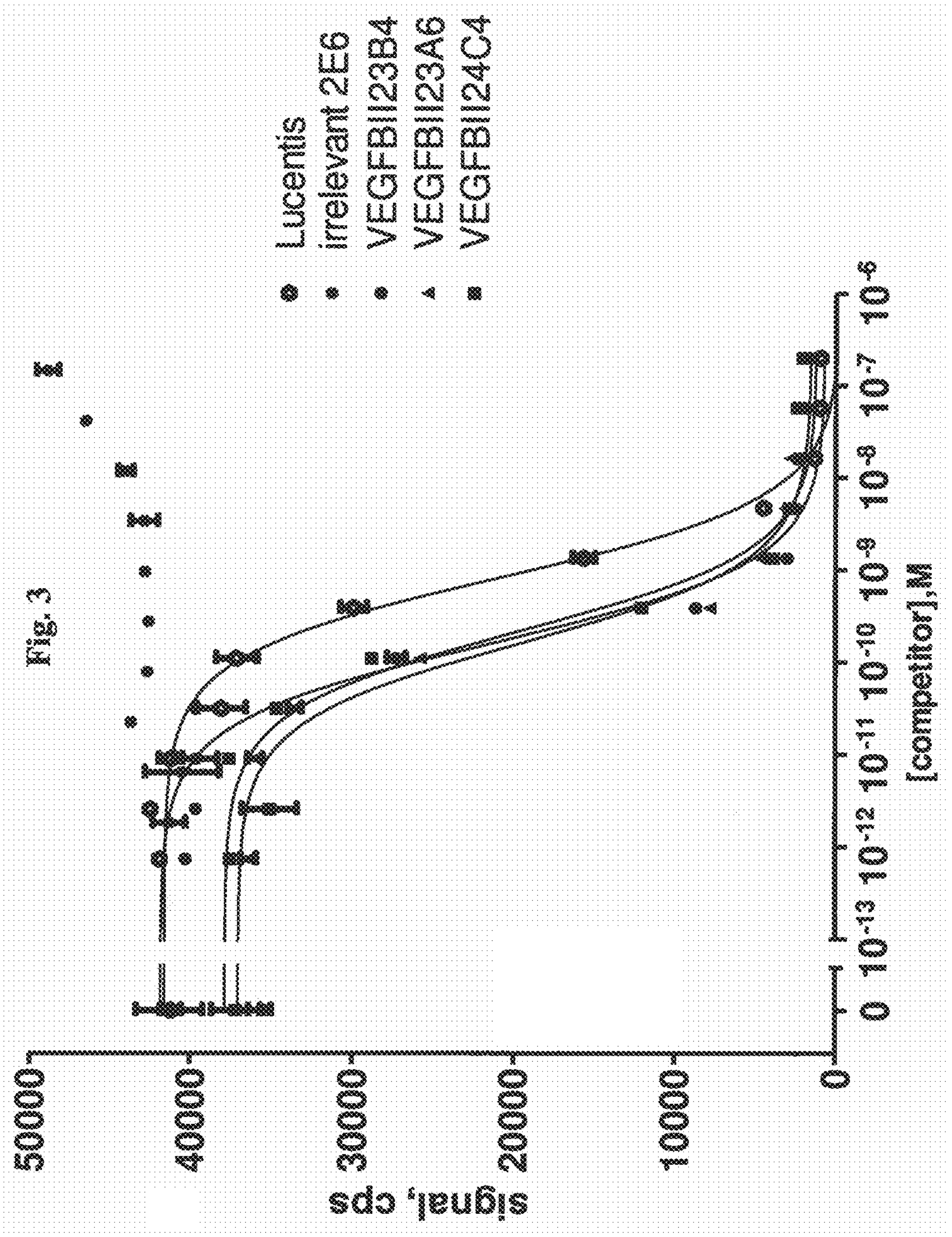
FIG. 3: Purified monovalent VHHs block the hVEGF165/hVEGFR2-Fc interaction (AlphaScreen)
Figures 1A, 28:
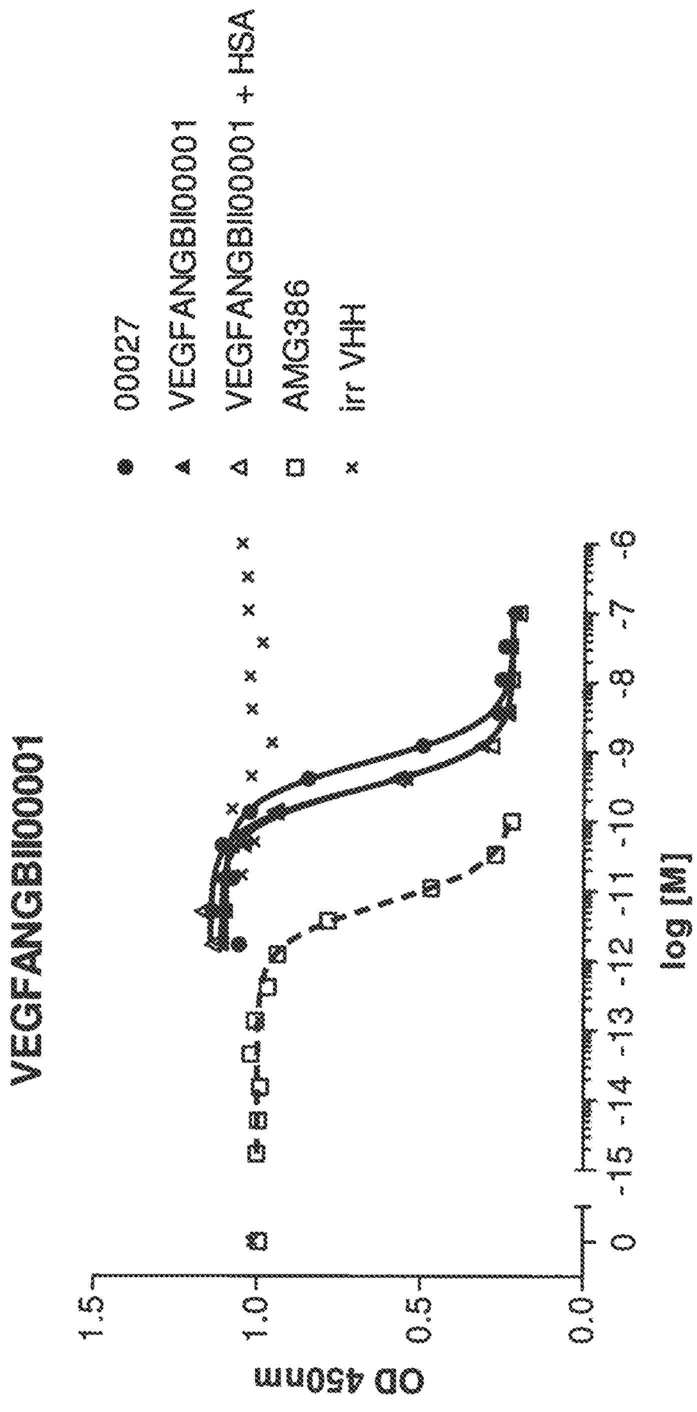
Figures 1B, 28:
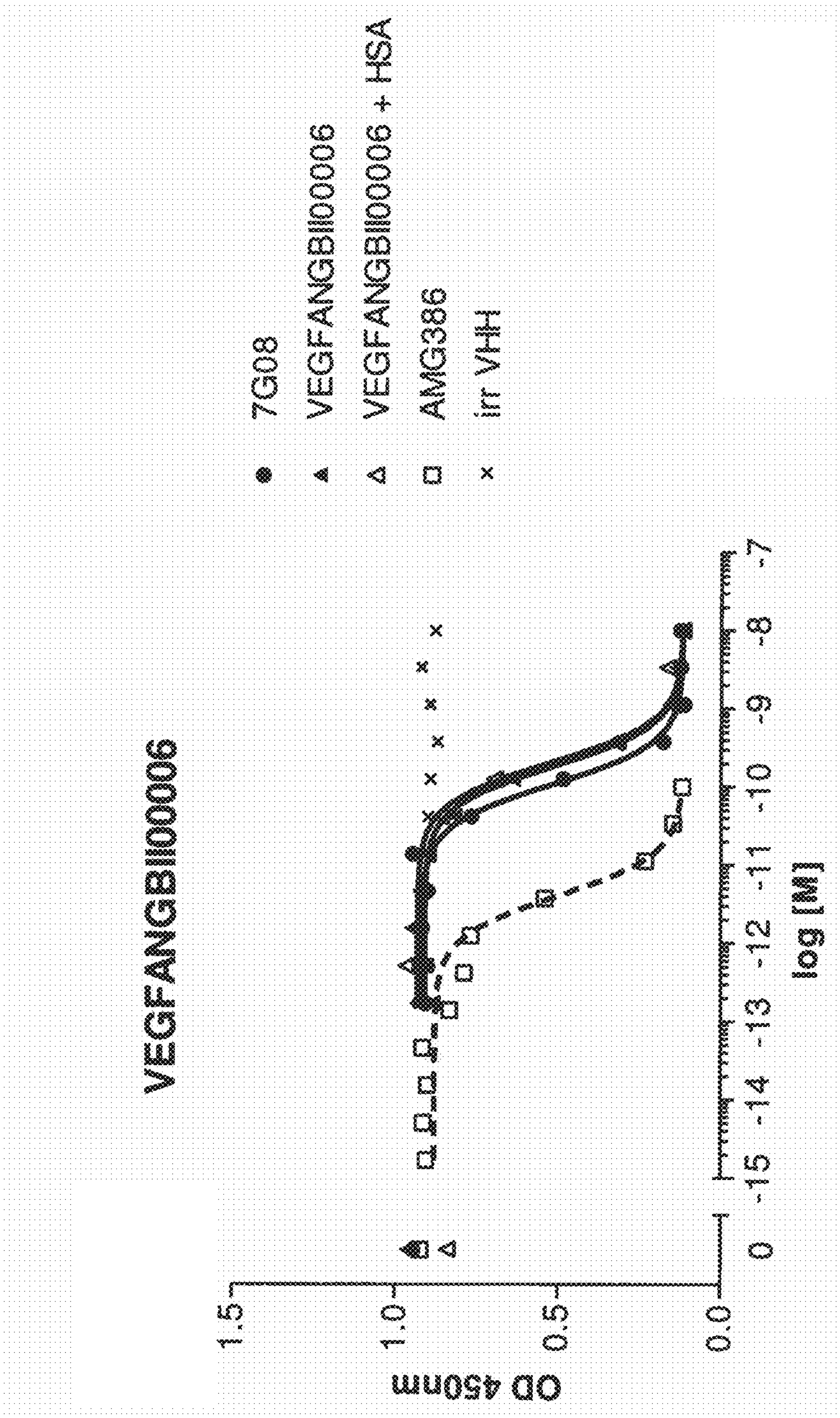
Figures 1C, 28:
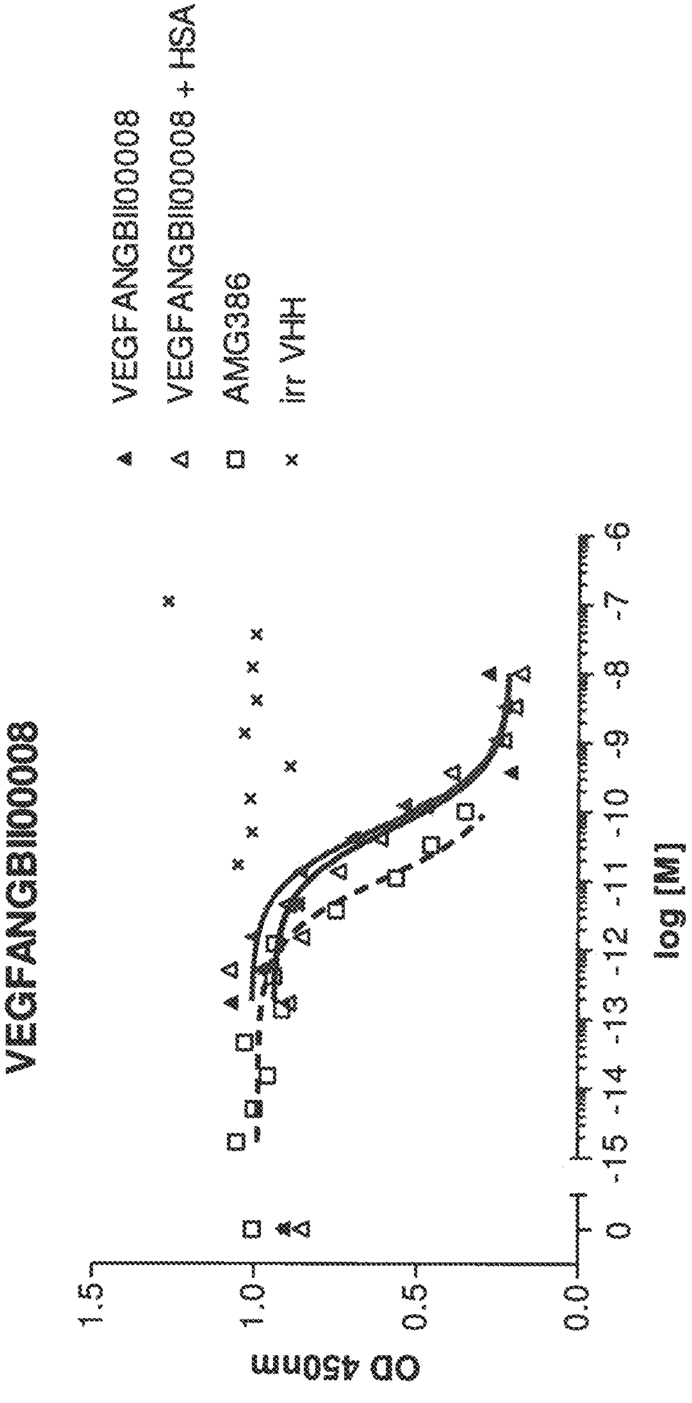
Figures 1D, 28:
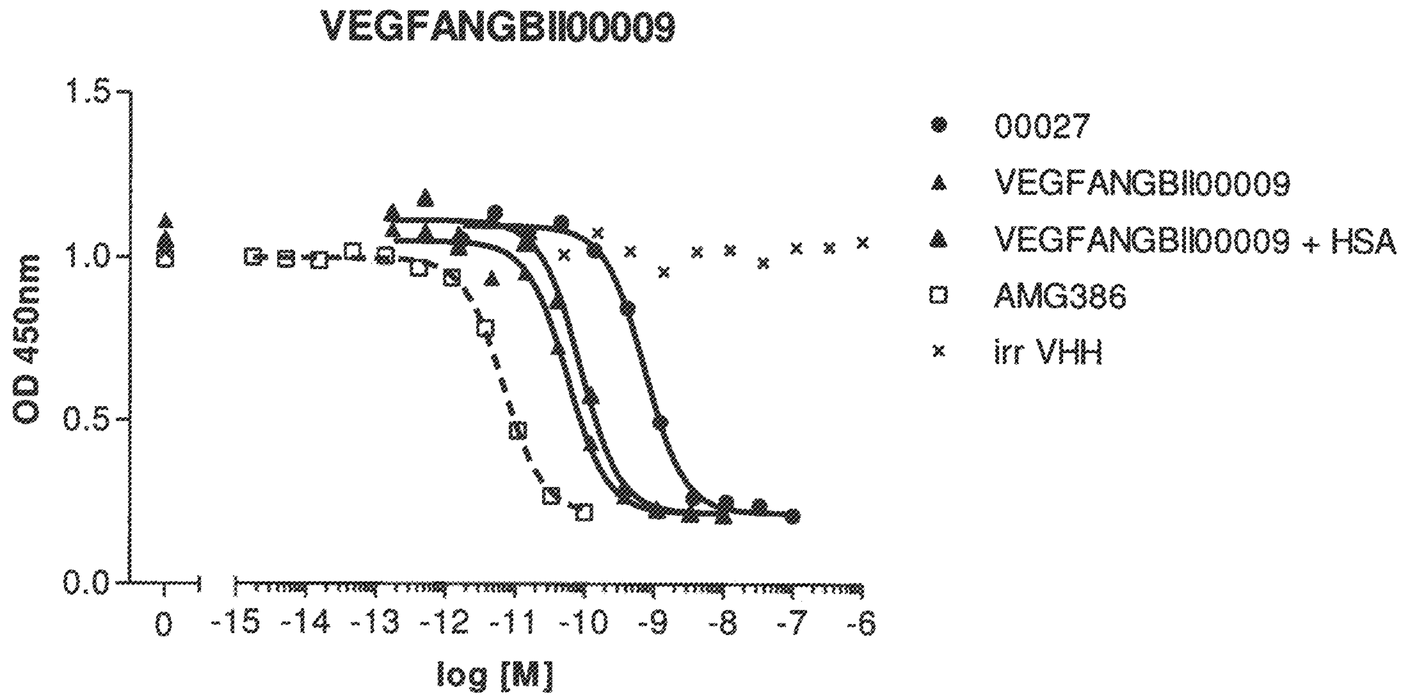
Figures 1E, 28:
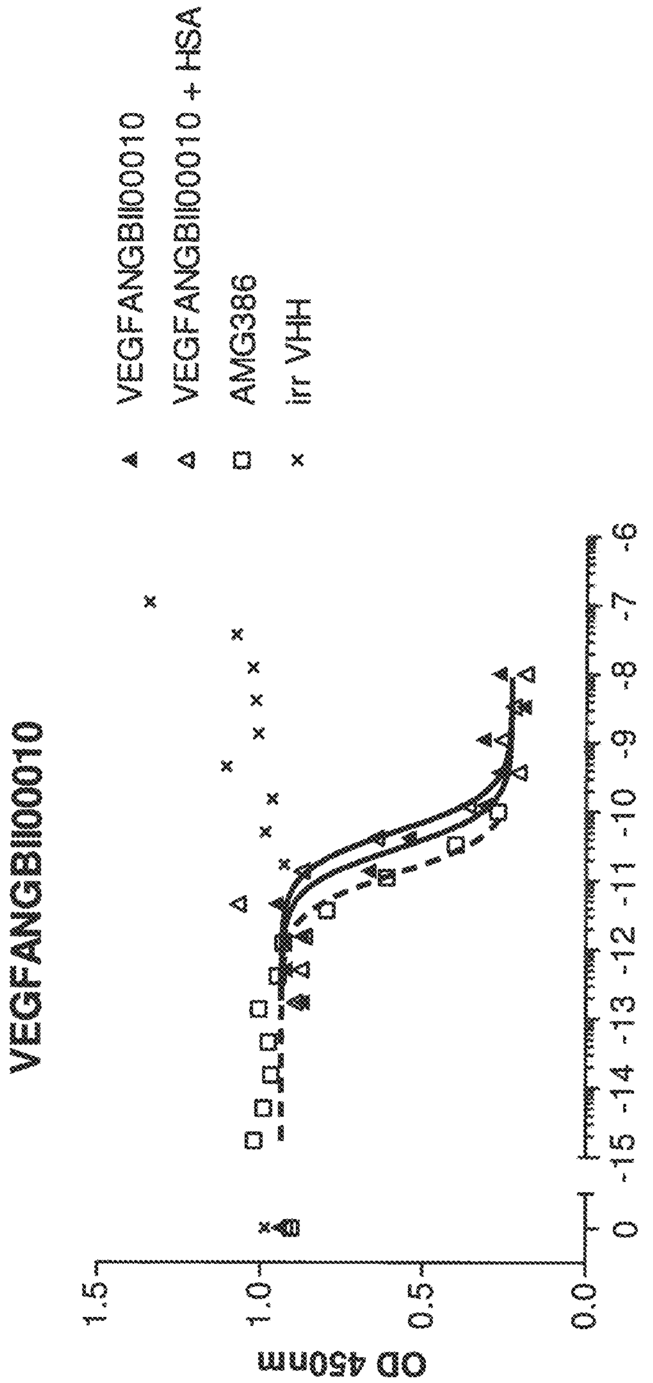
Figures 1F, 28:
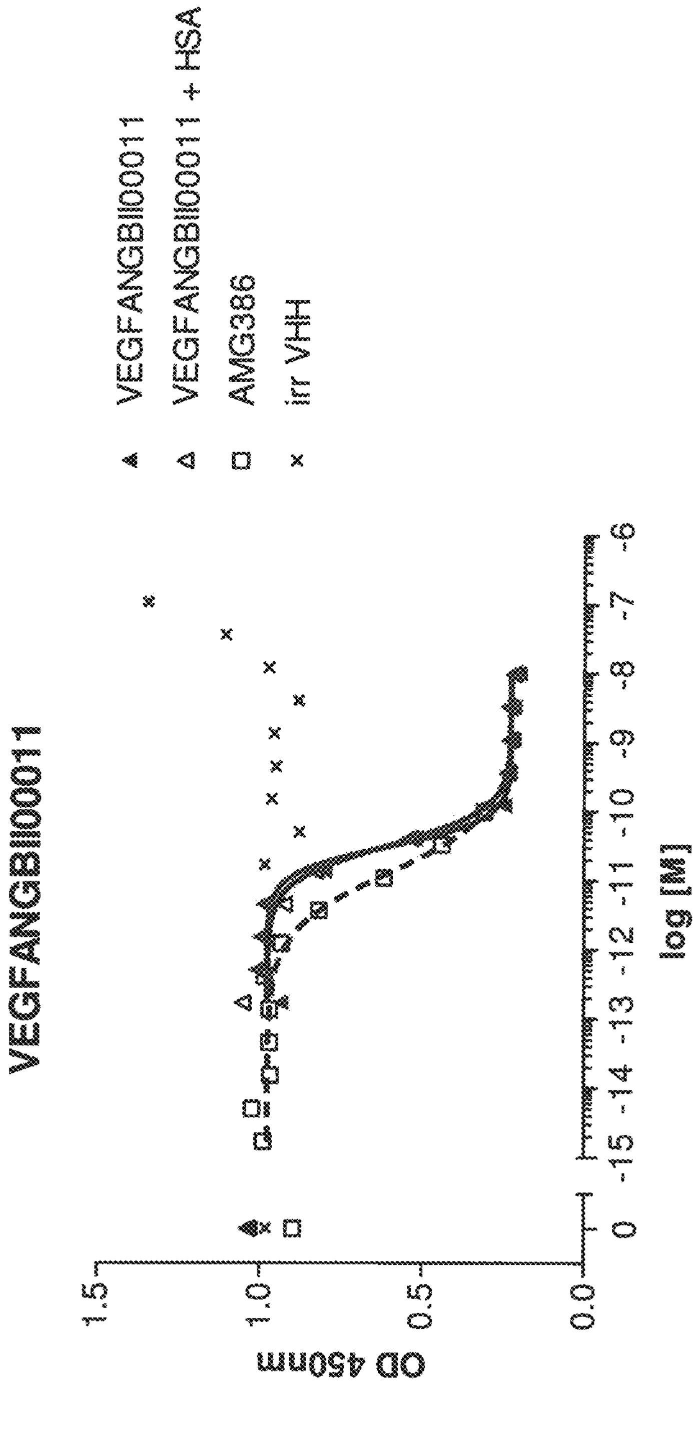
Figures 1G, 28:
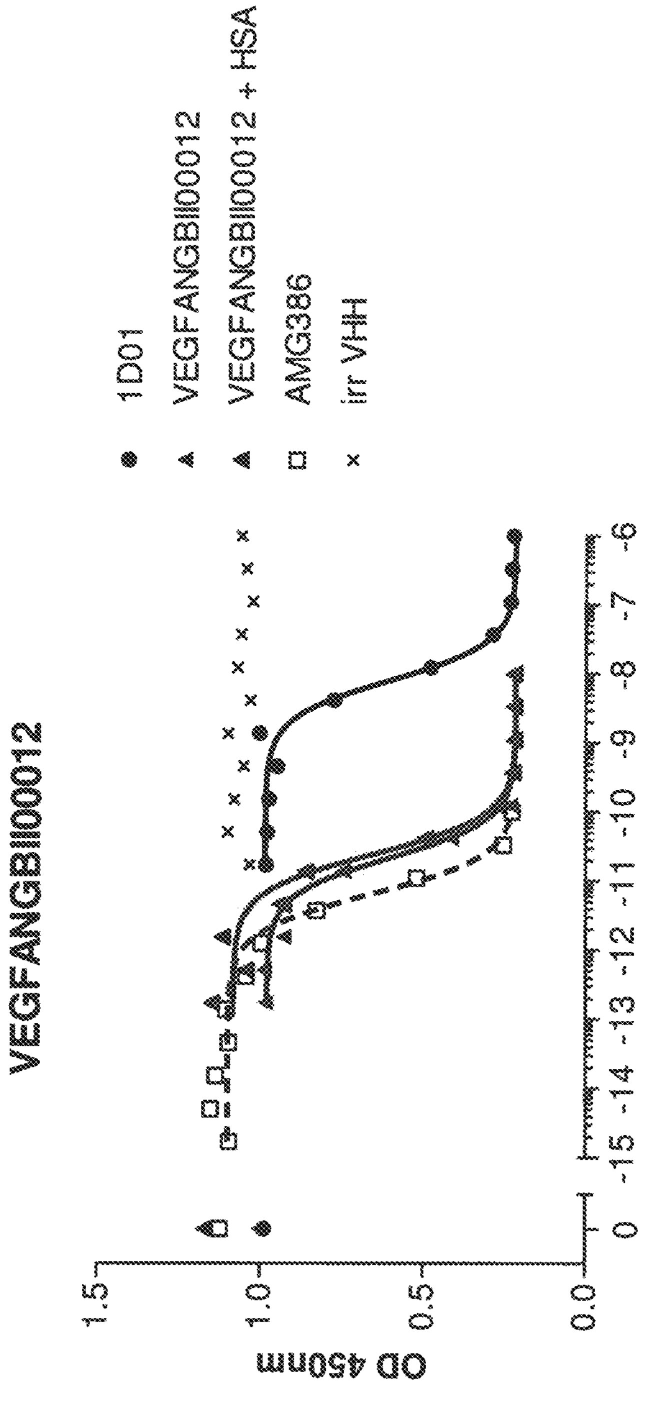
Figures 1H, 28:
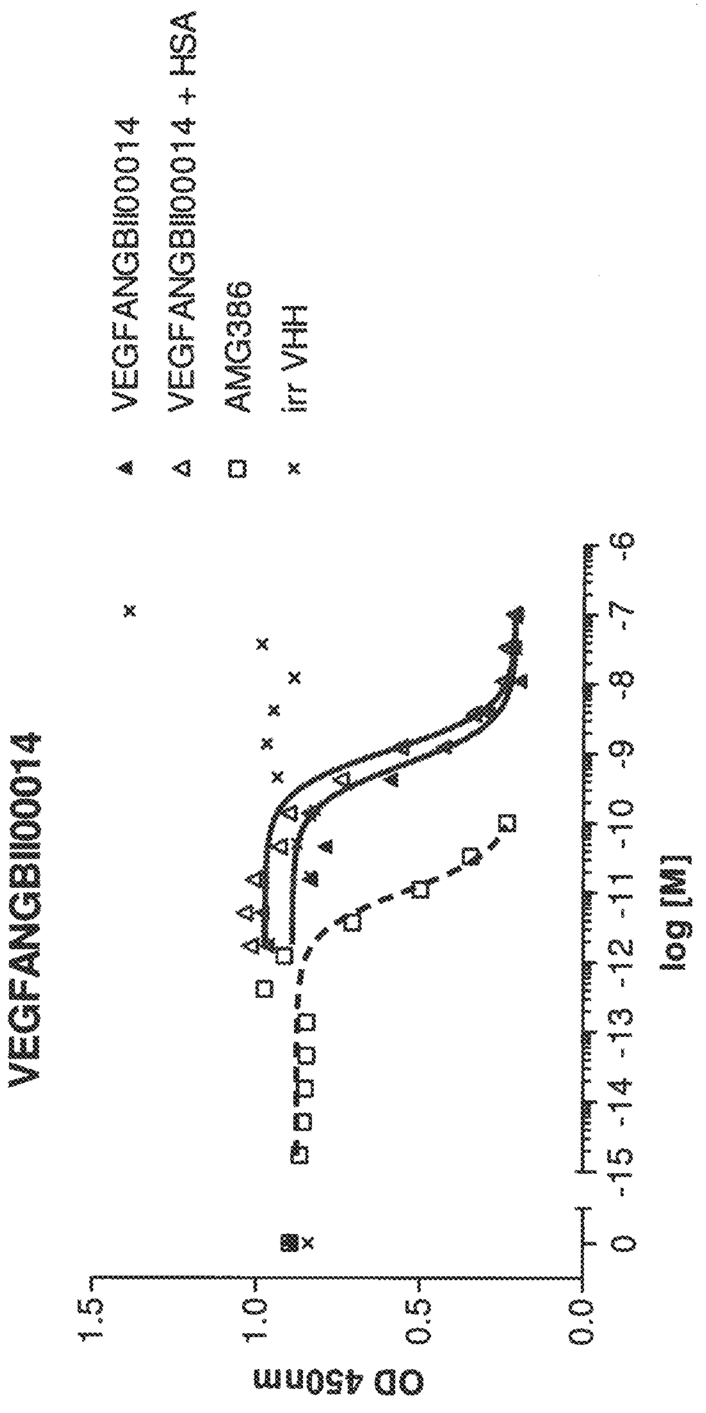
Figures 2A, 28:
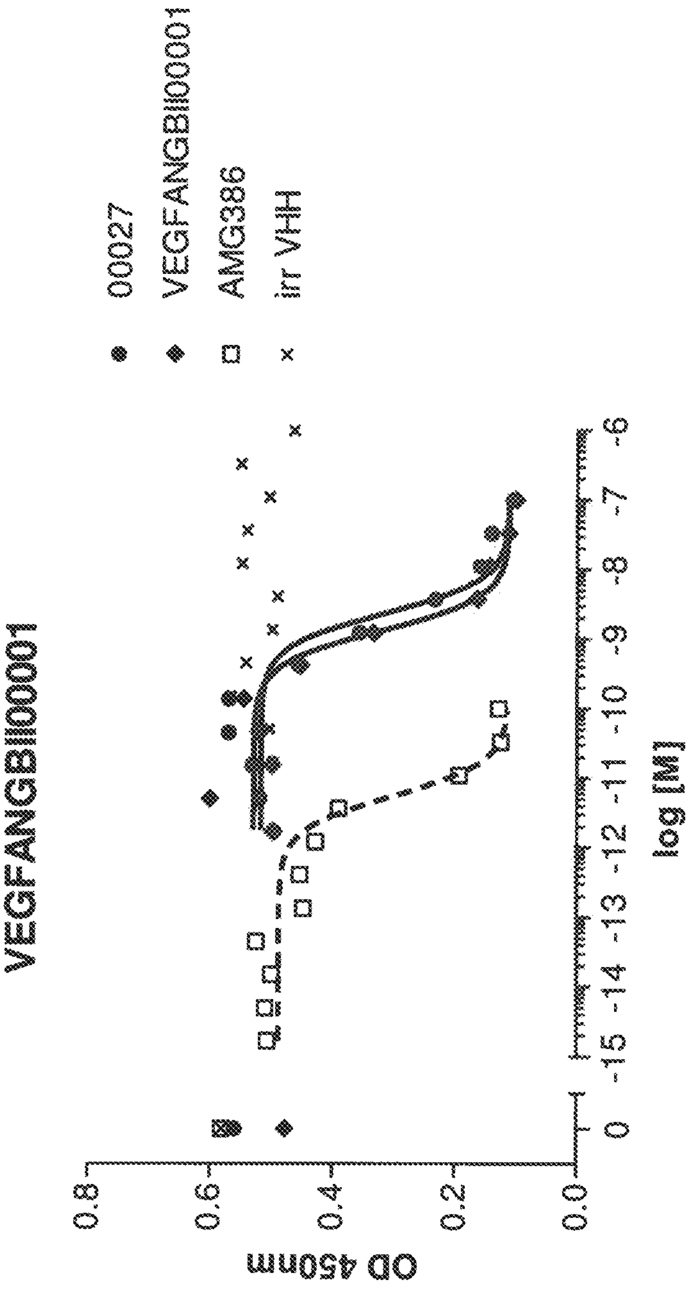
Figures 2B, 28:
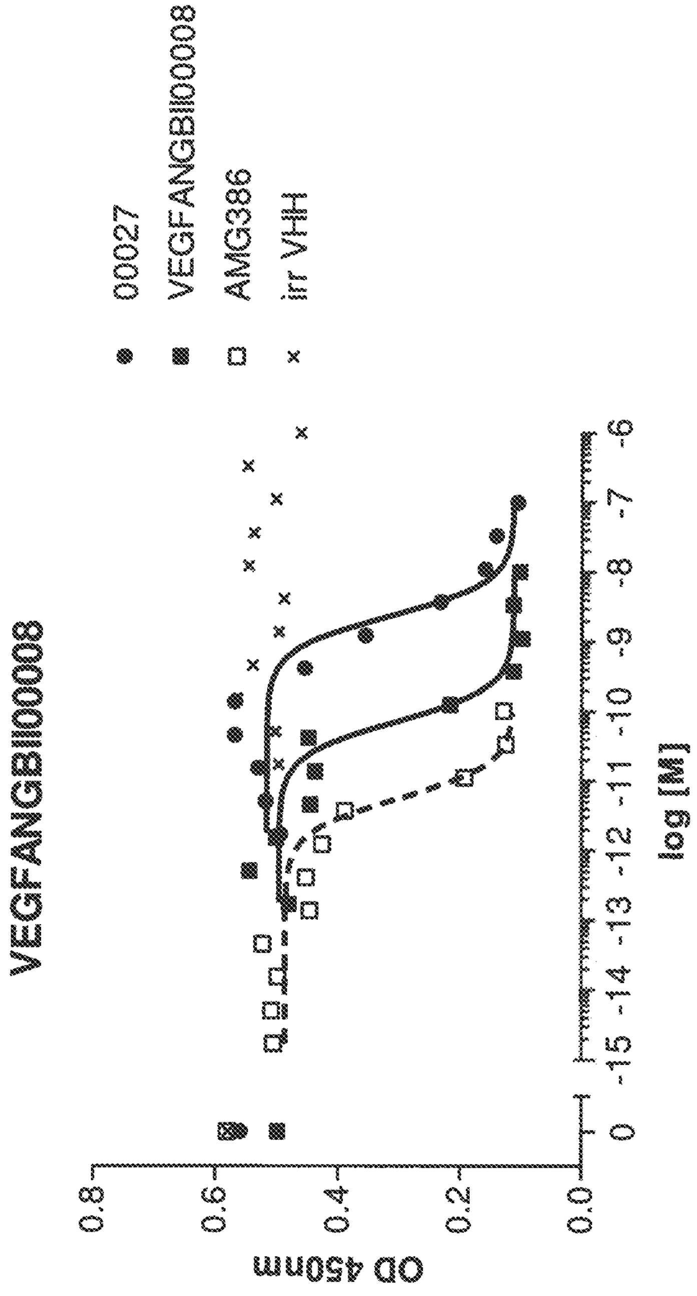
Figures 2C, 28:
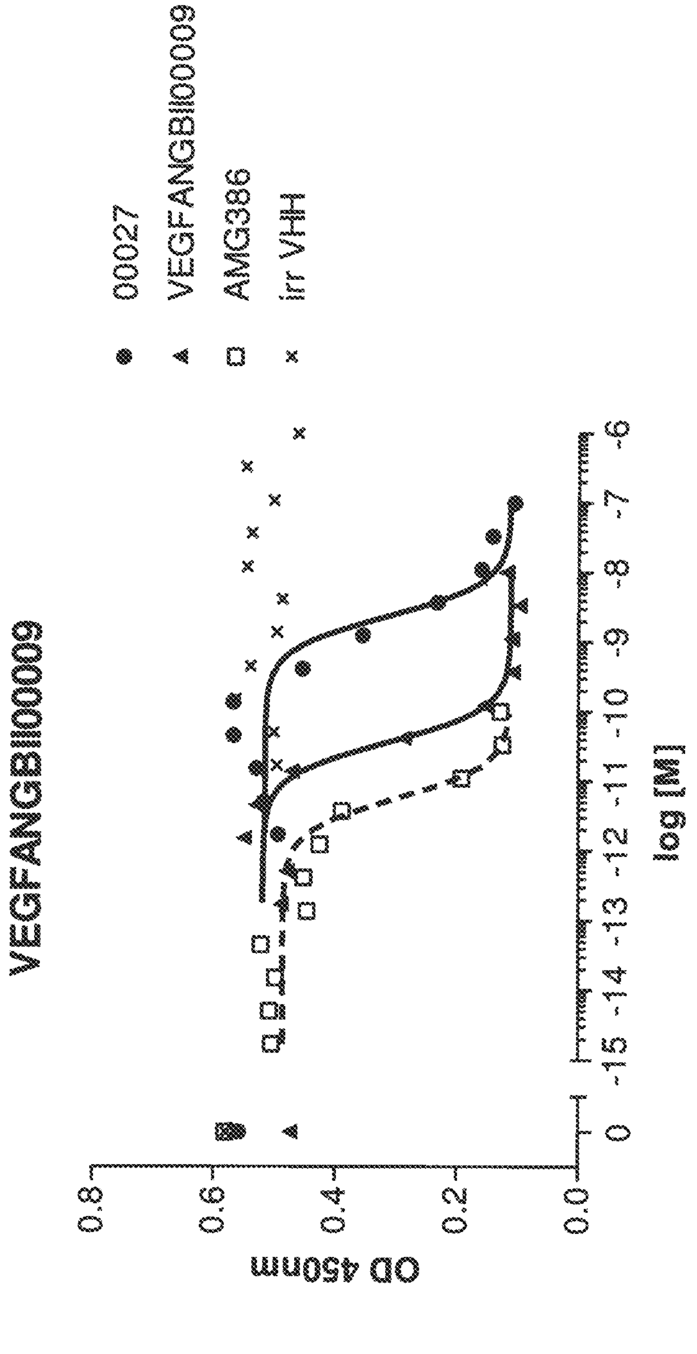
Figures 2D, 28:
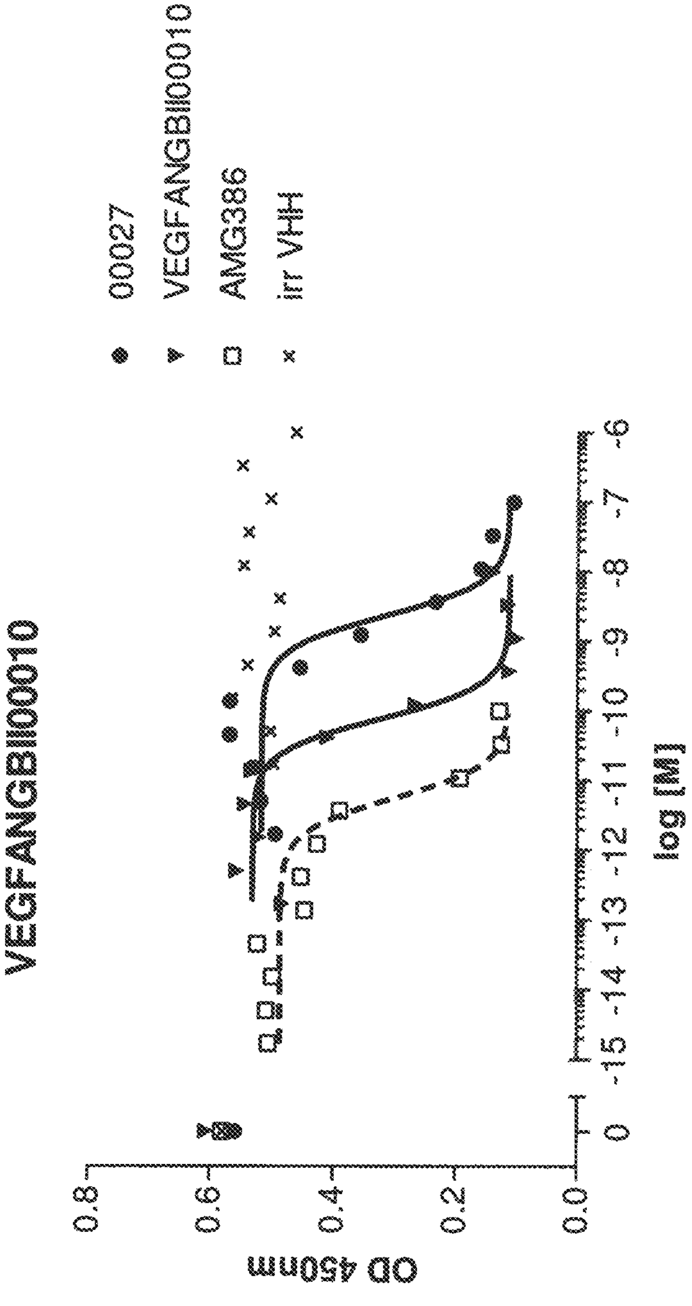
Figures 2E, 28:
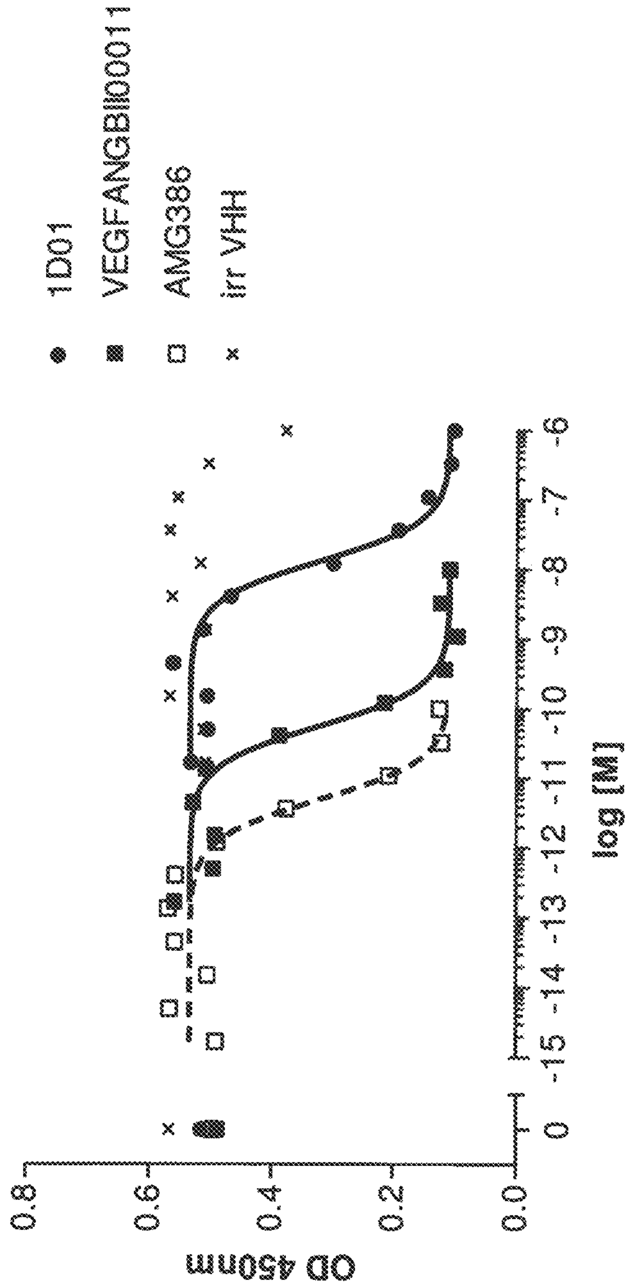
Figures 2F, 28:
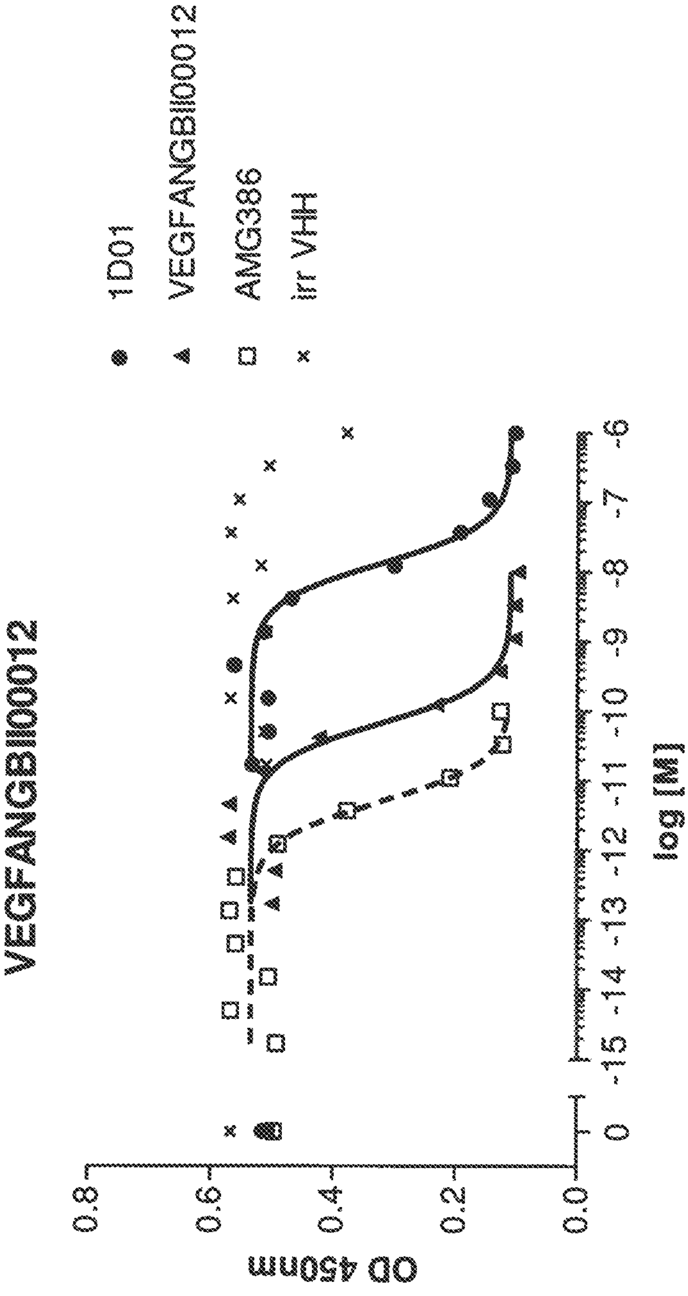
Figures 2G, 28:
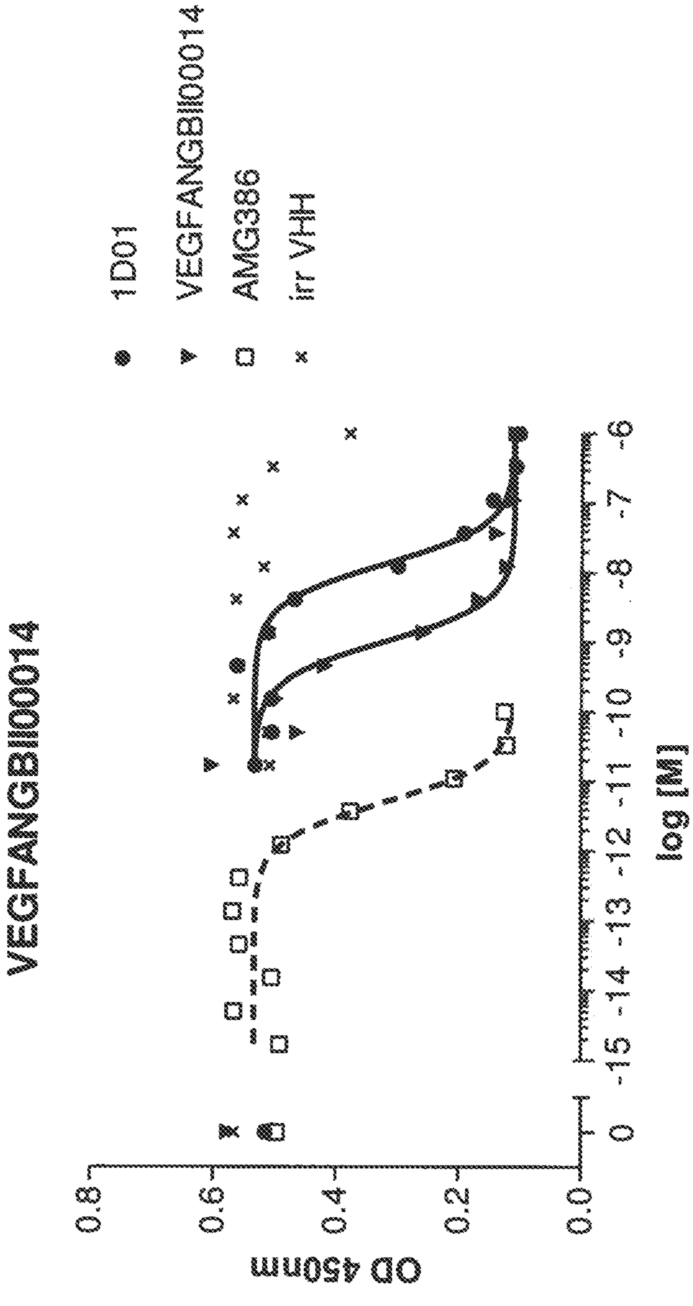
Figures 3A, 28:
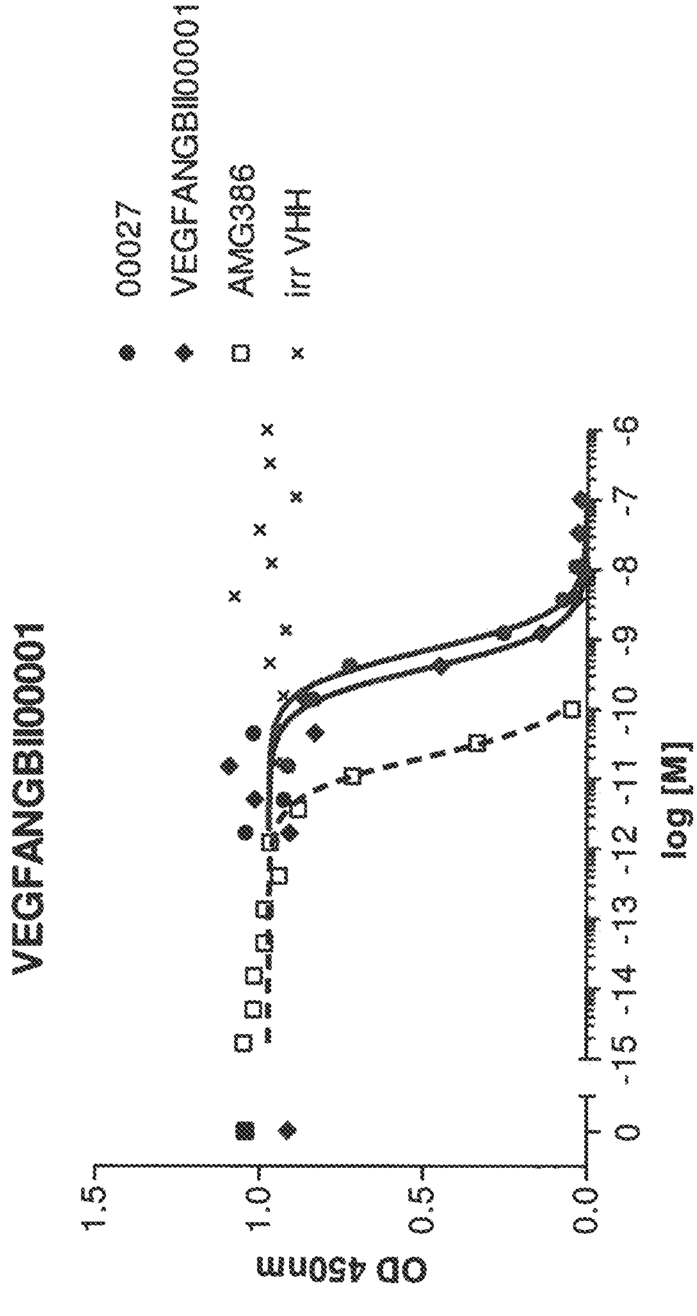
Figures 3B, 28:
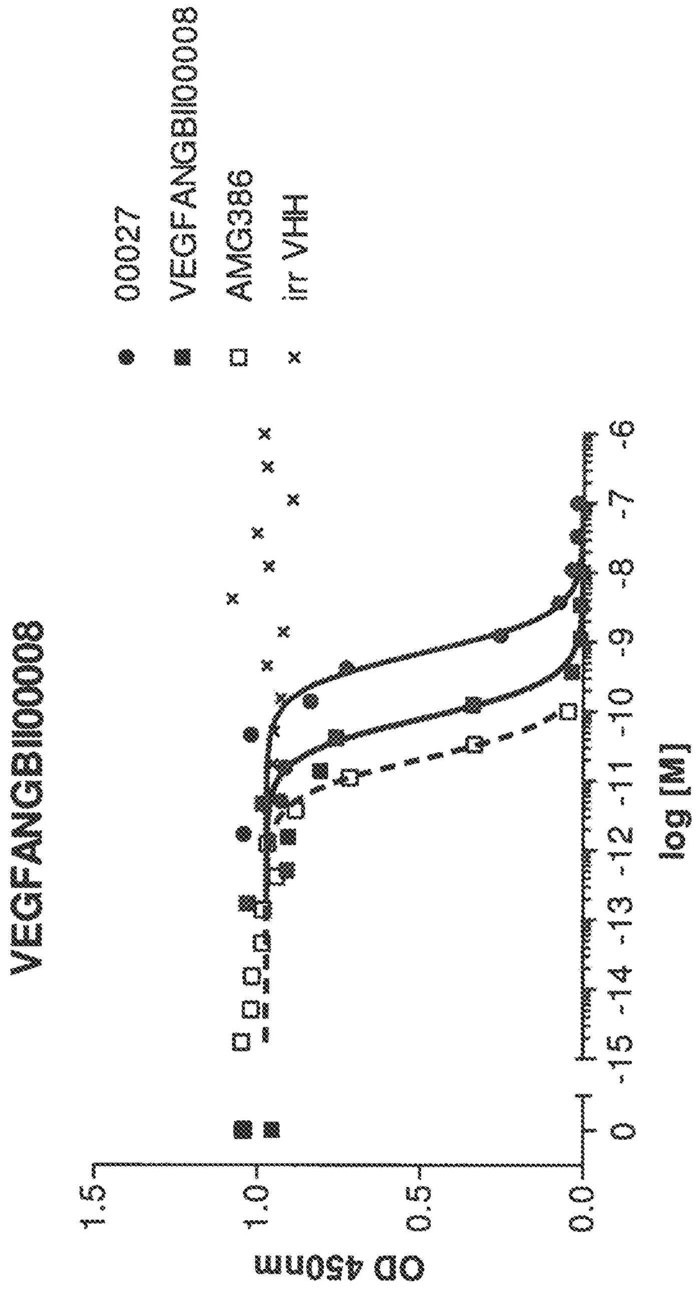
Figures 3C, 28:
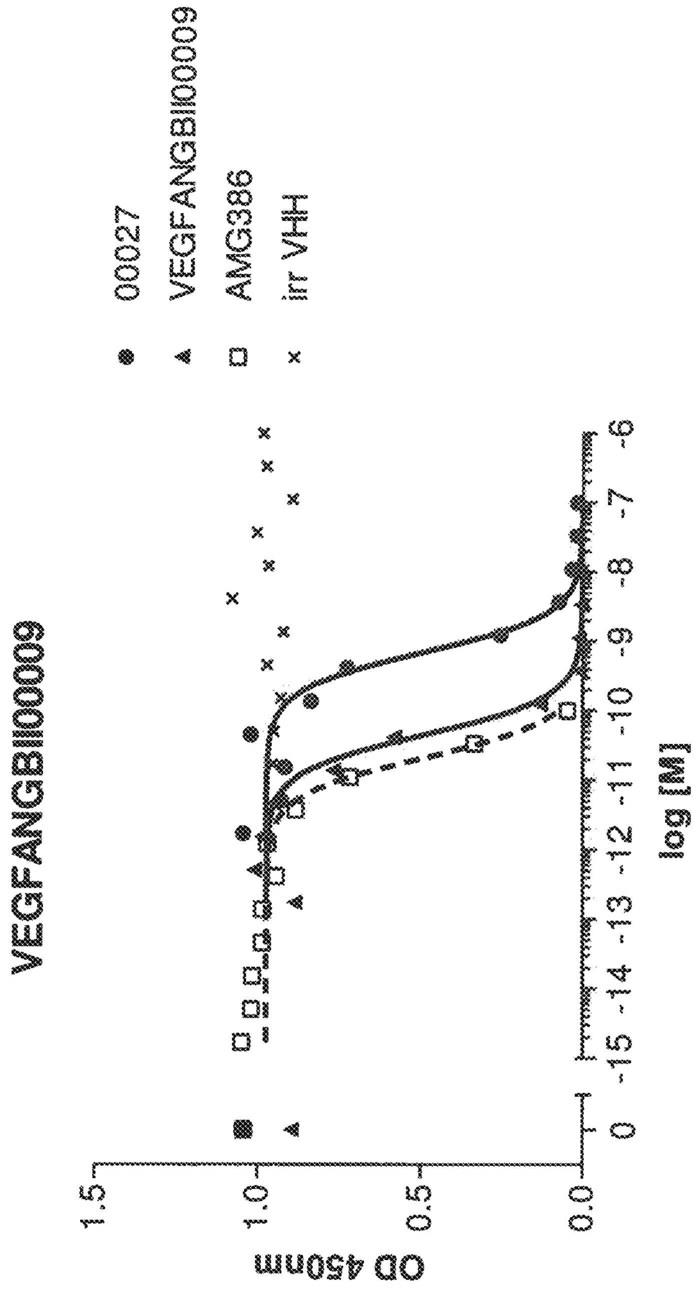
Figures 3D, 28:
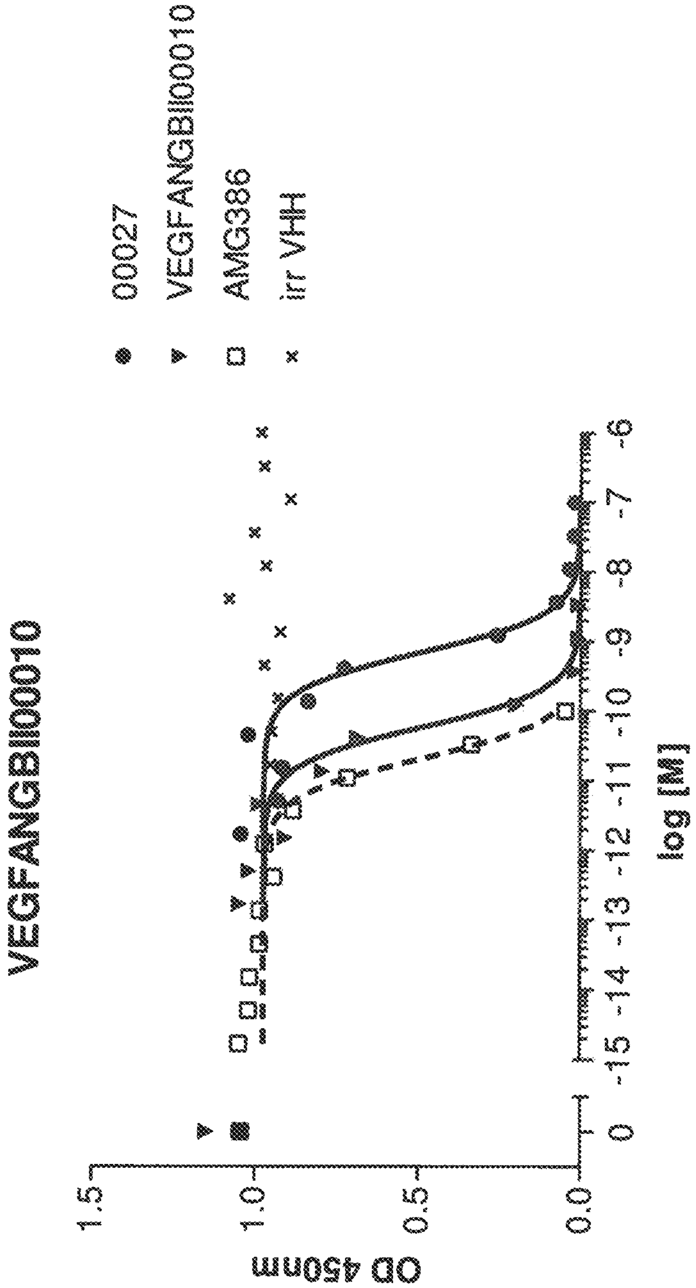
Figures 3E, 28:
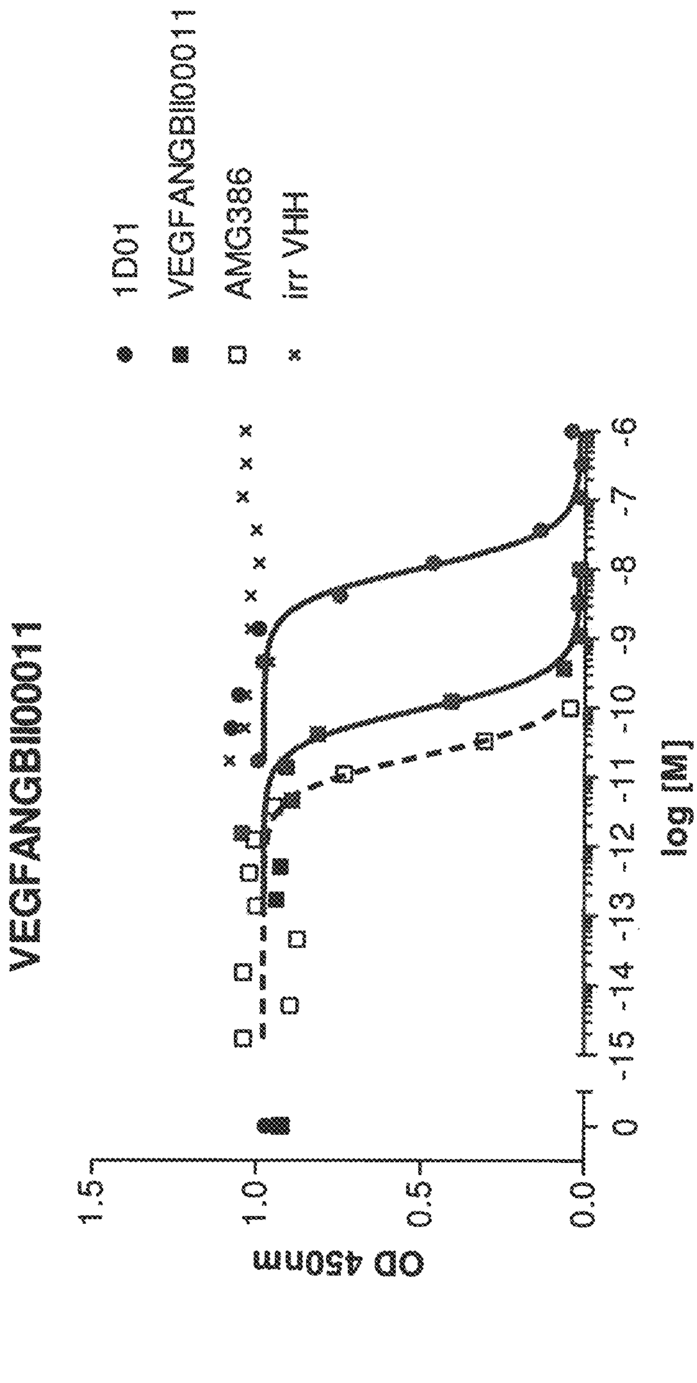
Figures 3F, 28:
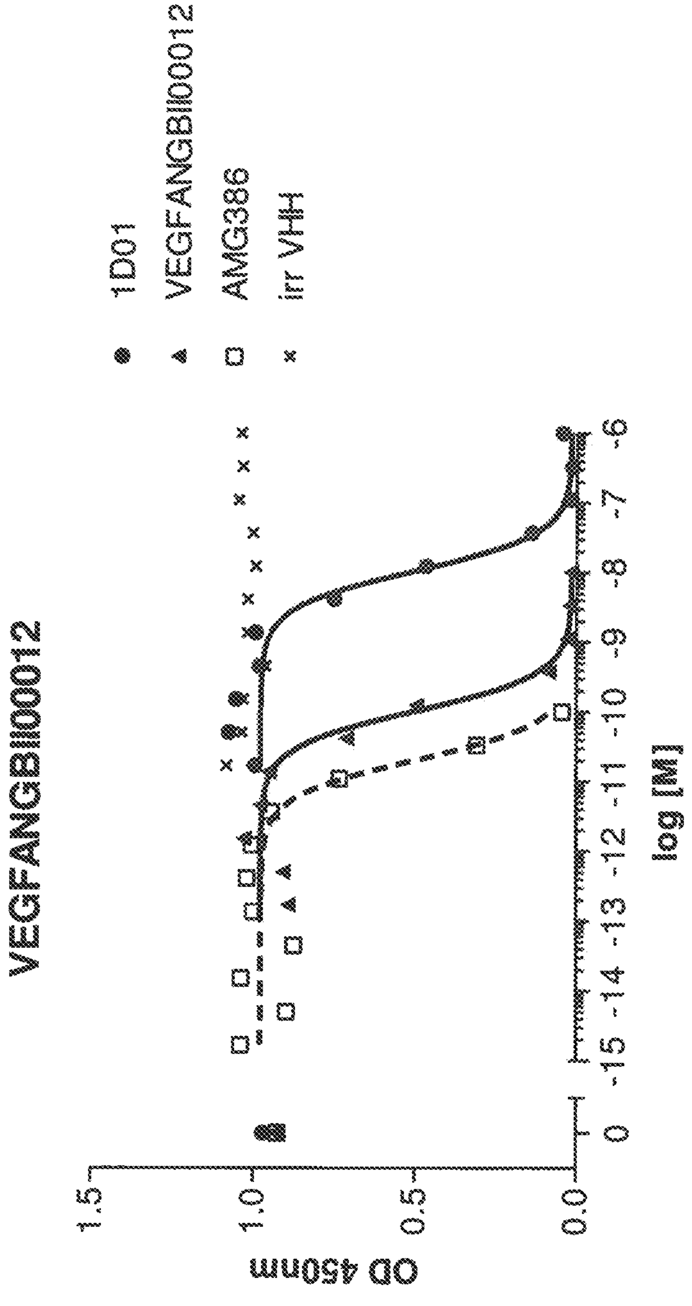
Figures 3G, 28:
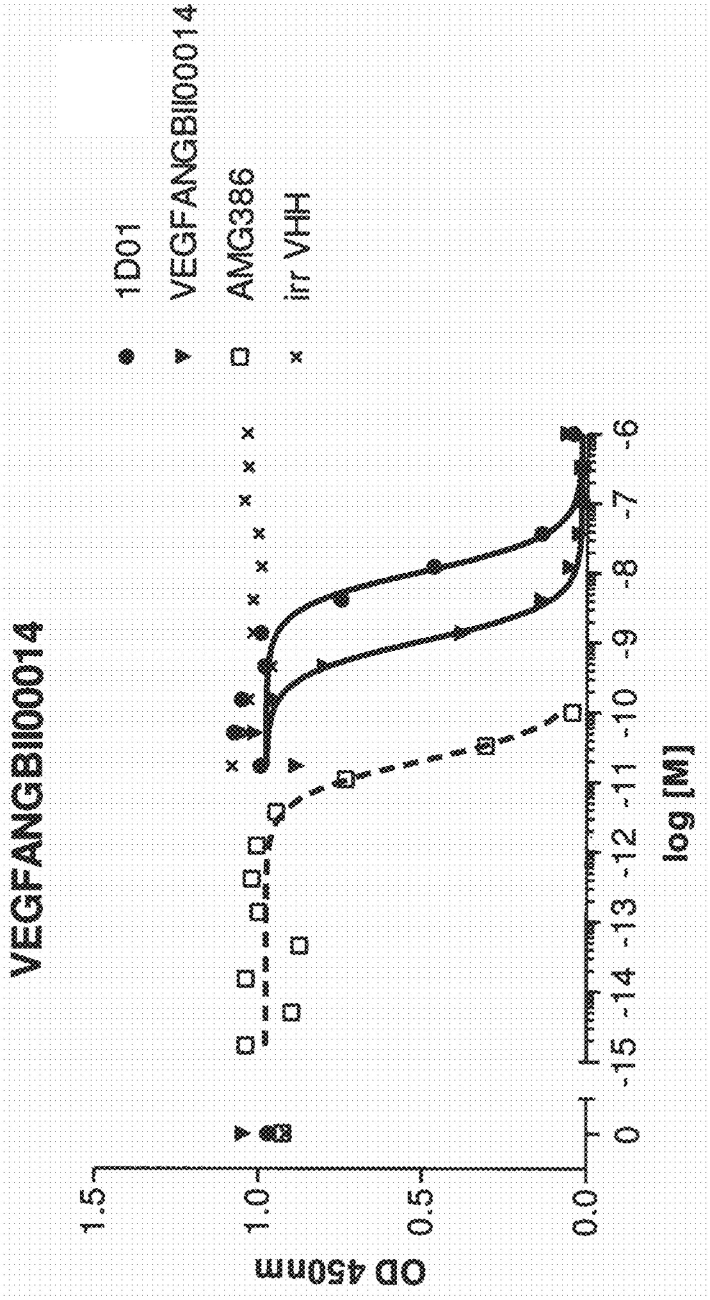
Figure 29A:
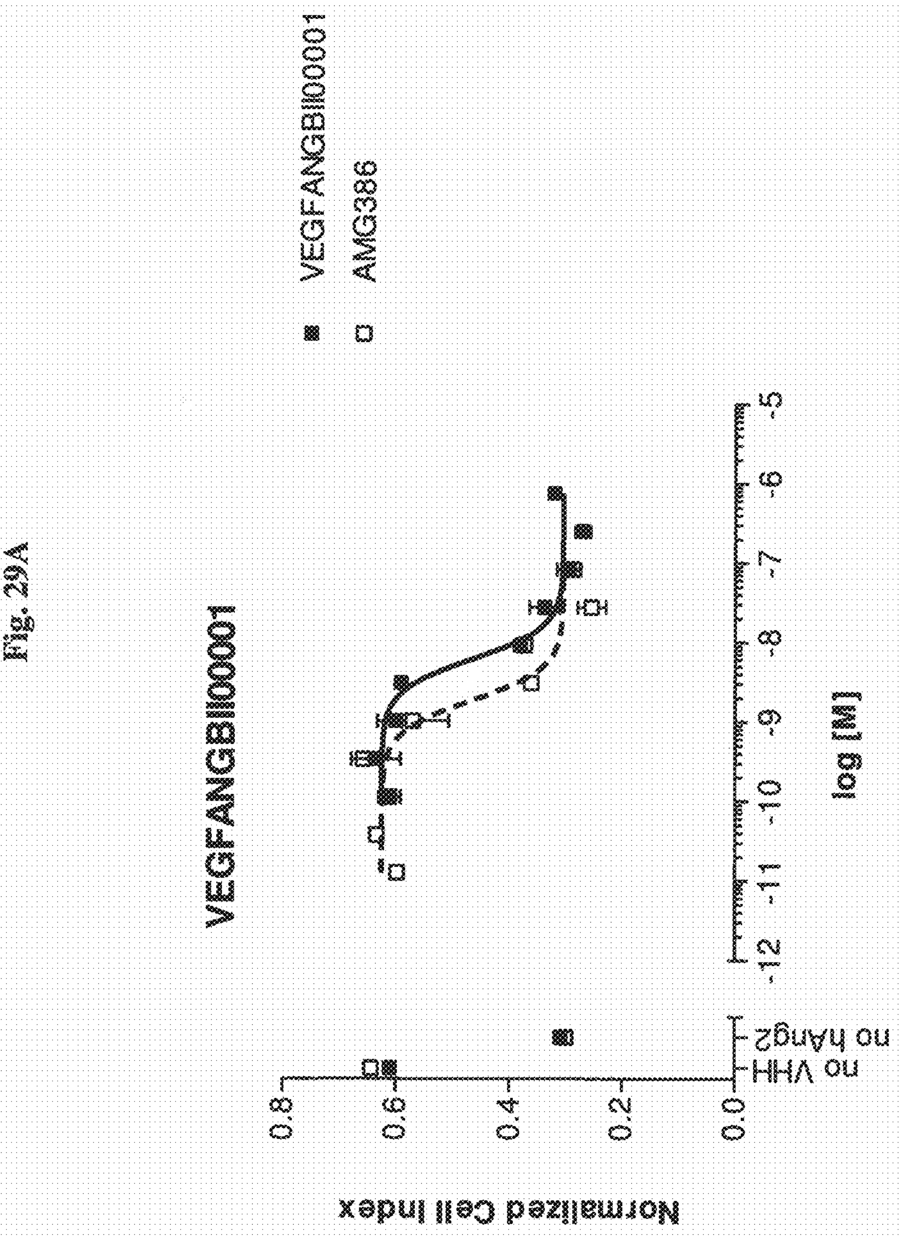
FIG. 29A-29G: A-F. Purified trivalent and tetravalent VEGFxAng2 VHHs blocking hAng2 mediated HUVEC survival; G. $IC_{50}$ values (pM) and % inhibition in human Ang2/human Tie2, mouse Ang2/mouse Tie2 and cyno Ang2/cyno Tie2 competition ELISA and $IC_{50}$ (nM) values and % inhibition in hAng2 mediated HUVEC survival.
Figure 29B:
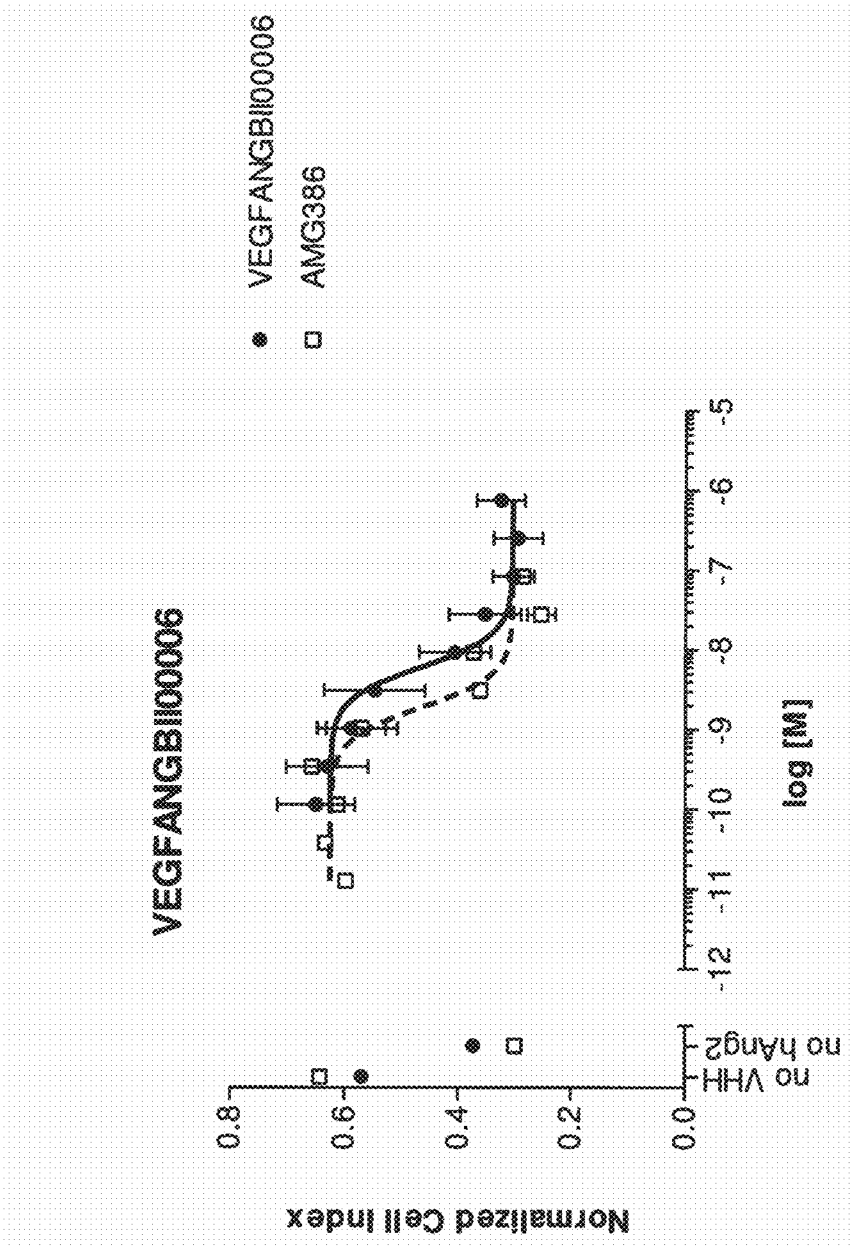
Figure 29C:
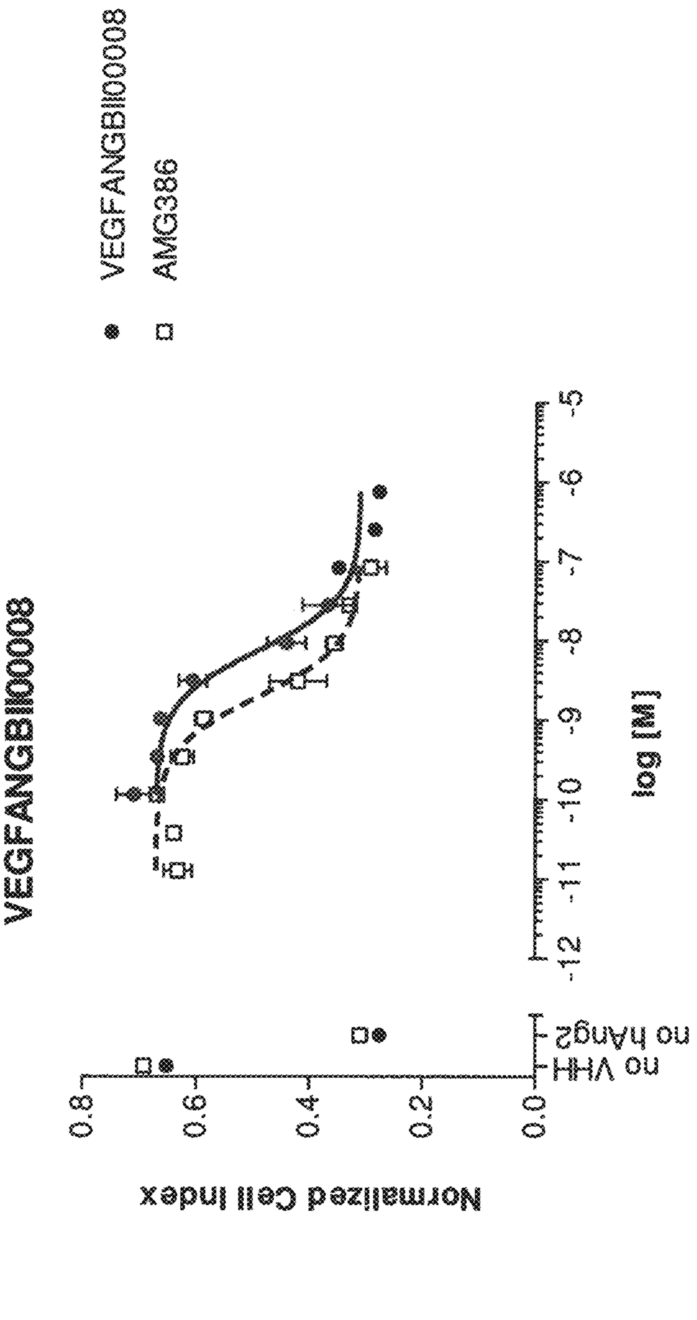
Figure 29D:
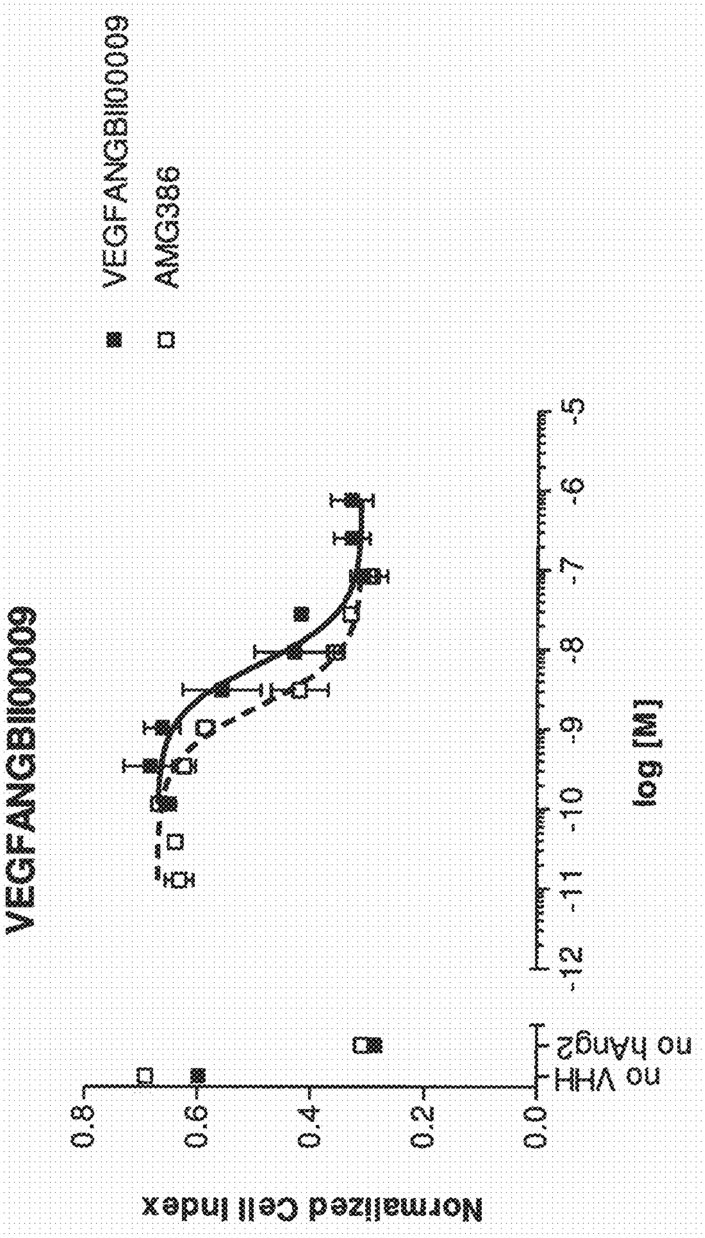
Figure 29E:
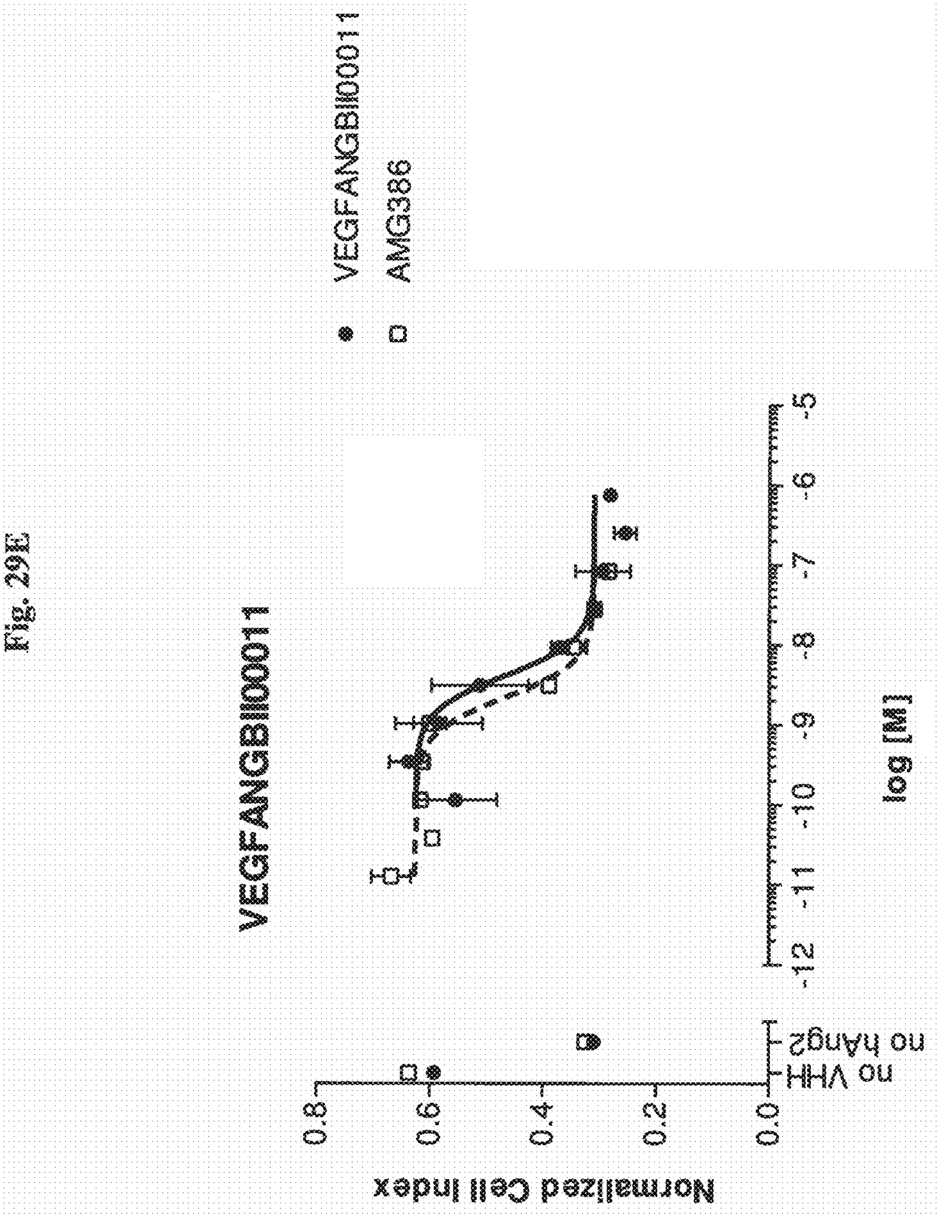
Figure 29F:
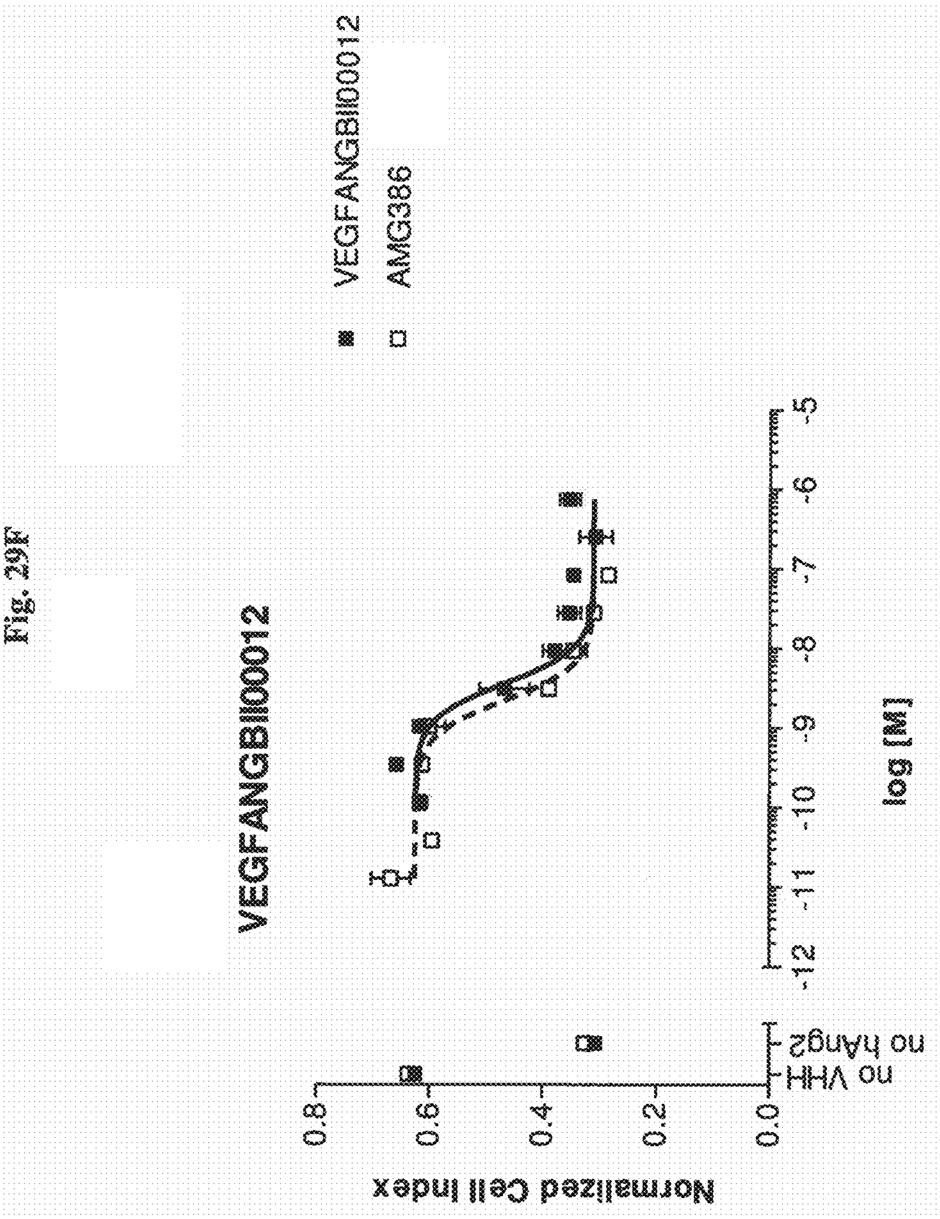
Figure 29:
Figure 29:
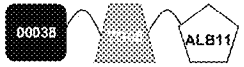
Figure 29:
Figure 29:
Figure 29:
Figure 29:
Figure 29:
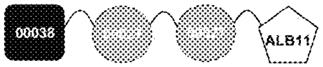
Figure 29:
Figure 29:
Figure 29:
Figure 29:
Figure 29:
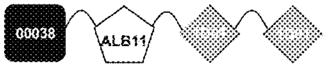
Figure 29:
Figure 29:

To explore the anti-Ang2 blocking properties in comparison with their respective monovalent building block 7G08 (SEQ ID No:215), 1D01 (SEQ ID No:214) and 00027 (SEQ ID No:216), all ten bispecific VHHs are analyzed in the human Ang2/hTie2-Fc (see Example 5.1; FIG. 28-1), mouse Ang2/mTie2-Fc (see Example 5.2; FIG. 28-2) and cyno Ang2/cTie2-Fc (see Example 5.2; FIG. 28-3) competition ELISA. The human assay is also performed after incubation of the VHH with 0.5 μM human serum albumin. Additionally, a hAng2 mediated HUVEC survival assay is performed (see Example 5.5; FIG. 29 A-F). A summary of $IC_{50}$ values and % inhibition is shown in FIG. 29 G.

Affinities of for human serum albumin have been determined and are shown in Table 44. Briefly, human serum albumin (Sigma, St Louis, Mo., USA) is immobilized on a CM5 chip via amine coupling. A multicycle kinetic approach is used: increasing concentrations of VHH (2-8-31-125-500 nM) are injected and allowed to associate for 2 min and to dissociate for 10 min at a flow rate of 100 μL/min. Between VHH injections, the surfaces are regenerated with a 10 sec pulse of 10 mM Glycine-HCl pH 1.5 and 60 sec stabilization period. Association/dissociation data are evaluated by fitting a 1:1 interaction model (Langmuir binding) or Heterogeneous Ligand model. The affinity constant $K_D$ is calculated from resulting association and dissociation rate constants $k_a$ and $k_d$ (Table 44)

TABLE 44

Affinity $K_D$ of purified VHHs for human (HSA), cyno (CSA) and mouse serum albumin (MSA)

| | HSA | | | CSA | | | MSA | | |
|---|---|---|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) |
| ALB11 | 4.5E+05 | 1.8E−03 | 4 | 4.3E+05 | 1.6E−03 | 4 | 6.6E+05 | 3.2E−02 | 49 |
| VEGFANGBII00001 | 2.3E+05 | 4.8E−03 | 22 | 1.8E+05 | 4.3E−03 | 24 | n.d. | n.d. | n.d. |
| VEGFANGBII00005 | n.d. | n.d. | n.d. | n.d. | n.d. | n.d. | n.d. | n.d. | n.d. |
| VEGFANGBII00006 | 2.0E+05 | 4.6E−03 | 22 | 1.5E+05 | 4.5E−03 | 30 | 1.7E+05 | 6.0E−02 | 360 |
| VEGFANGBII00007 | n.d. | n.d. | n.d. | n.d. | n.d. | n.d. | n.d. | n.d. | n.d. |
| VEGFANGBII00008 | 1.3E+05 | 4.3E−03 | 34 | n.d. | n.d. | n.d. | n.d. | n.d. | n.d. |
| VEGFANGBII00009 | 1.5E+05 | 4.6E−03 | 30 | 1.1E+05 | 4.2E−03 | 39 | 1.2E+05 | 4.0E−02 | 340 |
| VEGFANGBII00010 | n.d. | n.d. | n.d. | n.d. | n.d. | n.d. | n.d. | n.d. | n.d. |
| VEGFANGBII00011 | 1.3E+05 | 4.0E−03 | 31 | n.d. | n.d. | n.d. | n.d. | n.d. | n.d. |
| VEGFANGBII00012 | 1.5E+05 | 4.3E−03 | 31 | 1.2E+05 | 4.2E−03 | 24 | 1.0E+05 | 2.5E−02 | 240 |
| VEGFANGBII0013 | n.d. | n.d. | n.d. | n.d. | n.d. | n.d. | n.d. | n.d. | n.d. |
| VEGFANGBII0014 | n.d. | n.d. | n.d. | n.d. | n.d. | n.d. | n.d. | n.d. | n.d. |

n.d., not determined

Example 12

Construction, Production and Characterization of Sequence Optimized and Affinity Matured Bispecific VHHs Targeting VEGF and Ang2 Using Anti-Serum Albumin Binding as Half-Life Extension 14 bispecific VHHs targeting VEGF and Ang2 are constructed (VEGFANGBII00015-00028). In these constructs bivalent 00921 (a sequence optimized 1 D01 variant) (SEQ ID No:220), monovalent VHHs 00908-00932-00933-00934-00935-00936-00937-00938 (sequence optimized/affinity matured 28D10 variants) (SEQ ID No:222), bivalent 00956 (SEQ ID NO:223) (sequence optimized 28D10 variant) and monovalent 00928 (SEQ ID NO:221) (sequence optimized 37F02 variant) anti-Ang2 building blocks are included. A genetic fusion to a serum albumin binding VHH is used as half-life extension methodology. Building blocks are linked via a 9 Gly-Ser flexible linker (SEQ ID NO: 170). An overview of the format and sequence of all 14 bispecific VHHs is depicted in FIG. 30A and Table 45 (linker sequences underlined), SEQ ID Nos 200-213.

Expression levels are indicated in FIG. 30B.

TABLE 45

Sequences of bispecific VHH targeting VEGF and Ang2

| VHH ID | AA sequence |
|---|---|
| VEGFANGBII00015 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGNSLRLSCAASGFTFSSFGMSWVRQAPGKGLEWVSSISGSGSDTLYADSVKGR<br>FTISRDNAKTTLYLQMNSLRPEDTAVYYCTIGGSLSRSSQGTLVTVSSGGGGSGGGSEVQLVESGGG<br>LVQPGGSLRLSCAASGITLDDYAIGWFRQAPGKEREGVSSIRDNGGSTYYADSVKGRFTISSDNSKN<br>TVYLQMNSLRPEDTAVYYCAAVPAGRLRYGEQWYPIYEYDAWGQGTLVTVSS (SEQ ID NO:<br>200) |
| VEGFANGBII00016 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGNSLRLSCAASGFTFSSFGMSWVRQAPGKGLEWVSSISGSGSDTLYADSVKGR<br>FTISRDNAKTTLYLQMNSLRPEDTAVYYCTIGGSLSRSSQGTLVTVSSGGGGSGGGSEVQLVESGGG<br>LVQPGGSLRLSCAVSGITLDDYAIGWFRQAPGKEREGVSSIRDNGGSTYYADSVKGRFTISSDNSKN<br>TVYLQMNSLRPEDTAVYYCAAVPAGRLRYGEQWYPIYEYDAWGQGTLVTVSS SEQ ID NO:<br>201) |
| VEGFANGBII00017 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGNSLRLSCAASGFTFSSFGMSWVRQAPGKGLEWVSSISGSGSDTLYADSVKGR<br>FTISRDNAKTTLYLQMNSLRPEDTAVYYCTIGGSLSRSSQGTLVTVSSGGGGSGGGSEVQLVESGGG<br>LVQPGGSLRLSCAASGITLDDYAIGWFRQAPGKEREGVSAIRDNGGSTYYADSVKGRFTISSDNSKN<br>TVYLQMNSLRPEDTAVYYCAAVPAGRLRYGEQWYPIYEYDAWGQGTLVTVSS SEQ ID NO:<br>202) |
| VEGFANGBII00018 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGNSLRLSCAASGFTFSSFGMSWVRQAPGKGLEWVSSISGSGSDTLYADSVKGR<br>FTISRDNAKTTLYLQMNSLRPEDTAVYYCTIGGSLSRSSQGTLVTVSSGGGGSGGGSEVQLVESGGG<br>LVQPGGSLRLSCAASGITLDDYAIGWFRQAPGKEREGVSAIRESGGSTYYADSVKGRFTISSDNSKN<br>TVYLQMNSLRPEDTAVYYCAAVPAGRLRYGEQWYPIYEYDAWGQGTLVTVSS SEQ ID NO:<br>203) |
| VEGFANGBII00019 | DVQLVESGGGLVQPGGSLRLSCAASGRTFSSYSMGWFRQAPGKEREFVVAISKGGYKYDAVSLEGRF<br>TISRDNAKNTVYLQINSLRPEDTAVYYCASSRAYGSSRLRLADTYEYWGQGTLVTVSSGGGGSGGGS<br>EVQLVESGGGLVQPGNSLRLSCAASGFTFSSFGMSWVRQAPGKGLEWVSSISGSGSDTLYADSVKGR<br>FTISRDNAKTTLYLQMNSLRPEDTAVYYCTIGGSLSRSSQGTLVTVSSGGGGSGGGSEVQLVESGGG |

TABLE 45-continued

Sequences of bispecific VHH targeting VEGF and Ang2

| VHH ID | AA sequence |
|---|---|
| | LVQPGGSLRLSCAASGITLDDYAIGWFRQAPGKEREGVSAIRSSGGSTYYADSVKGRFTISSDNSKNTVYLQMNSLRPEDTAVYYCAAVPAGRLRYGEQWYPIYEYDAWGQGTLVTVSS SEQ ID NO: 204) |
| VEGFANGBII00020 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAVSGITLDDYAIGWFRQAPGKEREGVSAIRDNGGSTYYADSVKGRFTISSDNSKNTVYLQMNSLRPEDTAVYYCAAVPAGRLRYGEQWYPIYEYDAWGQGTLVTVSS SEQ ID NO: 205) |
| VEGFANGBII00021 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAVSGITLDDYAIGWFRQAPGKEREGVSAIRESGGSTYYADSVKGRFTISSDNSKNTVYLQMNSLRPEDTAVYYCAAVPAGRLRYGEQWYPIYEYDAWGQGTLVTVSS SEQ ID NO: 206) |
| VEGFANGBII00022 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAVSGITLDDYAIGWFRQAPGKEREGVSAIRSSGGSTYYADSVKGRFTISSDNSKNTVYLQMNSLRPEDTAVYYCAAVPAGRLRYGEQWYPIYEYDAWGQGTLVTVSS SEQ ID NO: 207) |
| VEGFANGBII00023 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAASGFTLDDYAIGWFRQAPGKEREGVSAIRDNGGSTYYADSVKGRFTISSDNSKNTVYLQMNSLRPEDTAVYYCAAVPAGRLRFGEQWYPLYEYDAWGQGTLVTVSSGGGGSGGGSEVQLVESGGGLVQPGGSLRLSCAASGFTLDDYAIGWFRQAPGKEREGVSAIRDNGGSTYYADSVKGRFTISSDNSKNTVYLQMNSLRPEDTAVYYCAAVPAGRLRFGEQWYPLYEYDAWGQGTLVTVSS SEQ ID NO: 208) |
| VEGFANGBII00024 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGGSLRLSCAASGFTLDDYAIGWFRQAPGKEREGVSAIRDNGGSTYYADSVKGRFTISSDNSKNTVYLQMNSLRPEDTAVYYCAAVPAGRLRFGEQWYPLYEYDAWGQGTLVTVSSGGGGSGGGSEVQLVESGGGLVQPGGSLRLSCAASGFTLDDYAIGWFRQAPGKEREGVSAIRDNGGSTYYADSVKGRFTISSDNSKNTVYLQMNSLRPEDTAVYYCAAVPAGRLRFGEQWYPLYEYDAWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS SEQ ID NO: 209) |
| VEGFANGBII00025 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAASGFTFDDYALGWFRQAPGKEREGVSCIRCSGGSTYYADSVKGRFTISSDNSKNTVYLQMNSLRPEDTAVYYCAASIVPRSKLEPYEYDAWGQGTLVTVSSGGGGSGGGSEVQLVESGGGLVQPGGSLRLSCAASGFTFDDYALGWFRQAPGKEREGVSCIRCSGGSTYYADSVKGRFTISSDNSKNTVYLQMNSLRPEDTAVYYCAASIVPRSKLEPYEYDAWGQGTLVTVSS SEQ ID NO: 210) |
| VEGFANGBII00026 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGGSLRLSCAASGFTFDDYALGWFRQAPGKEREGVSCIRCSGGSTYYADSVKGRFTISSDNSKNTVYLQMNSLRPEDTAVYYCAASIVPRSKLEPYEYDAWGQGTLVTVSSGGGGSGGGSEVQLVESGGGLVQPGGSLRLSCAASGFTFDDYALGWFRQAPGKEREGVSCIRCSGGSTYYADSVKGRFTISSDNSKNTVYLQMNSLRPEDTAVYYCAASIVPRSKLEPYEYDAWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS SEQ ID NO: 211) |
| VEGFANGBII00027 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAASGFALDYYAIGWFRQAPGKEREGVSCISSSGGITYYADSVKGRFTISRDNSKNTVYLQMNSLRPEDTAVYYCATDSGGYIDYDCSGLGYDYWGQGTLVTVSS SEQ ID NO: 212) |
| VEGFANGBII00028 | DVQLVESGGGLVQPGGSLRLSCAASGRTFSSYSMGWFRQAPGKEREFVVAISKGGYKYDAVSLEGRFTISRDNAKNTVYLQINSLRPEDTAVYYCASSRAYGSSRLRLADTYEYWGQGTLVTVSSGGGGSGGGSEVQLVESGGGLVQPGNSLRLSCAASGFTFSSFGMSWVRQAPGKGLEWVSSISGSGSDTLYADSVKGR |

TABLE 45-continued

Sequences of bispecific VHH targeting VEGF and Ang2

| VHH ID | AA sequence |
|---|---|
| | FTISRDNAKTTLYLQMNSLRPEDTAVYYCTIGGSLSRSSQGTLVTVSS<u>GGGGSGGGS</u>EVQLVESGGG<br>LVQPGGSLRLSCAASGFTLDDYAIGWFRQAPGKEREGVSAIRSSGGSTYYADSVKGRFTISSDNSKN<br>TVYLQMNSLRPEDTAVYYCAAVPAGRLRFGEQWYPLYEYDAWGQGTLVTVSS<u>GGGGSGGGS</u>EVQLVE<br>SGGGLVQPGGSLRLSCAASGFTLDDYAIGWFRQAPGKEREGVSAIRSSGGSTYYADSVKGRFTISSD<br>NSKNTVYLQMNSLRPEDTAVYYCAAVPAGRLRFGEQWYPLYEYDAWGQGTLVTVSS SEQ ID NO:<br>213) |

T

Figure 30:
FIG. 30A-30D: A. Description sequence optimized and affinity VEGFxAng2 bispecific VHHs (FIG. 30 discloses "9GS" and "9 GlySer" as SEQ ID NO: 170); B. Expression levels of all 14 bispecific VHHs as depicted in (A); C. $IC_{50}$ values (nM) in human VEGF165/human VEGFR2 and human VEGF165/human VEGFR1 competition AlphaScreen; D. Overview of kinetic parameters of the bispecific VHHs on human VEGF165 in hVEGF165 Biacore assay.
Figure 30:
Figure 30:
Figure 30:
Figure 30:
Figure 30:
Figure 30:
Figure 30:
Figure 30:
Figure 30:
Figure 30:
Figure 30:
Figure 30:
Figure 30:
Figure 30:
Figure 30:
Figure 30:
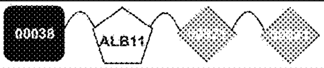
Figure 30:
Figure 30:
Figure 30:
Figure 30:
Figure 30:
Figures 1A, 31:
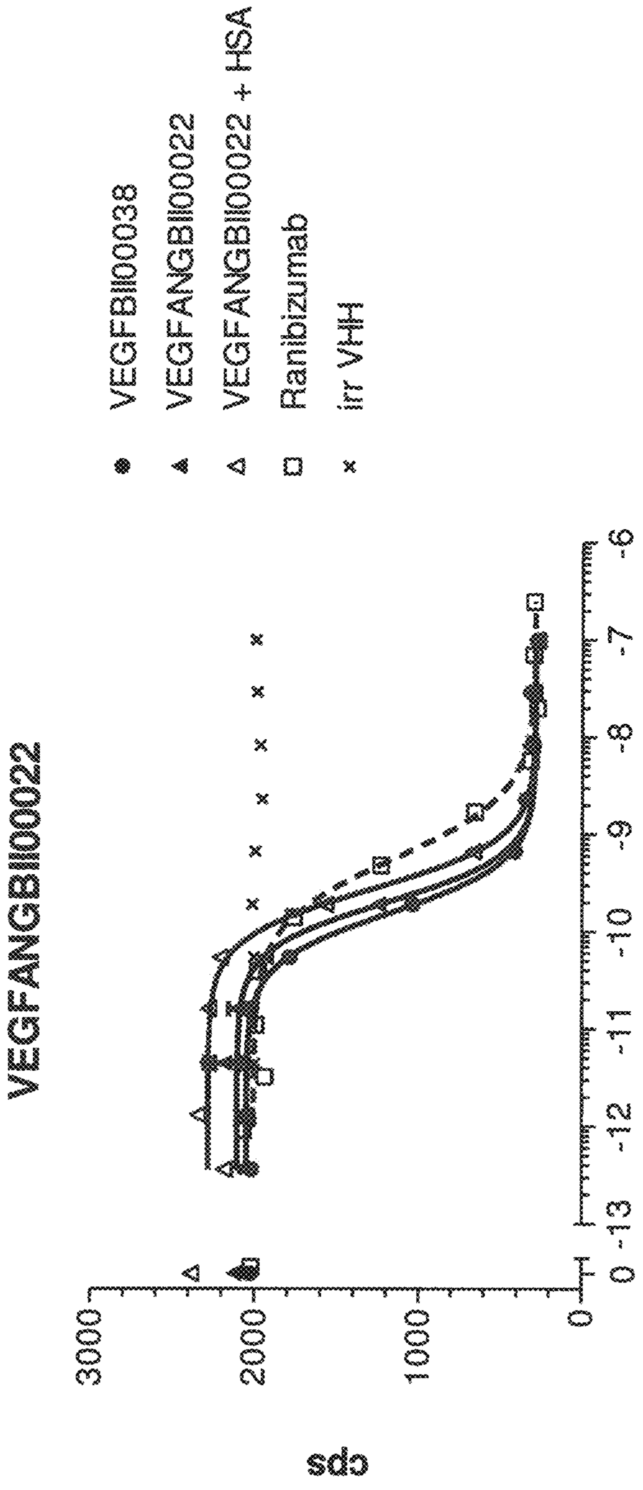
Figures 1B, 31:
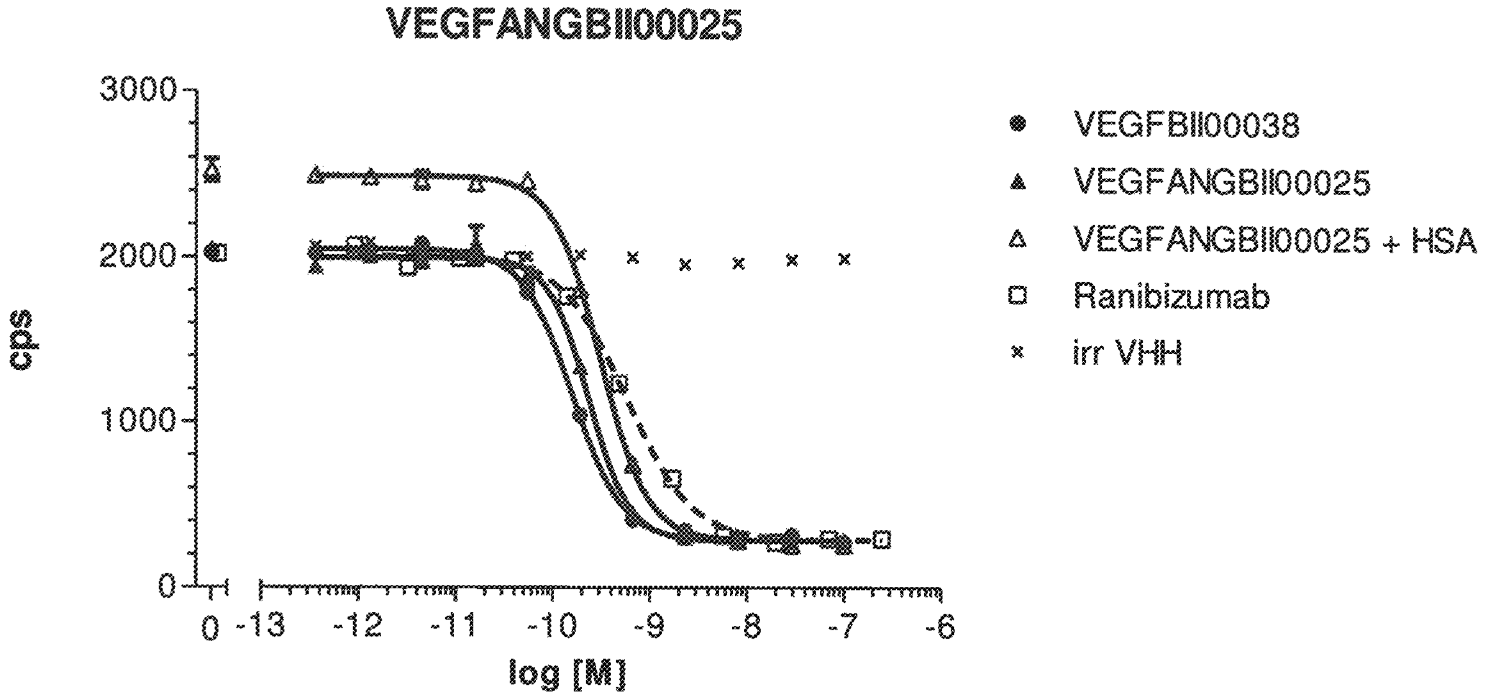
Figures 1C, 31:
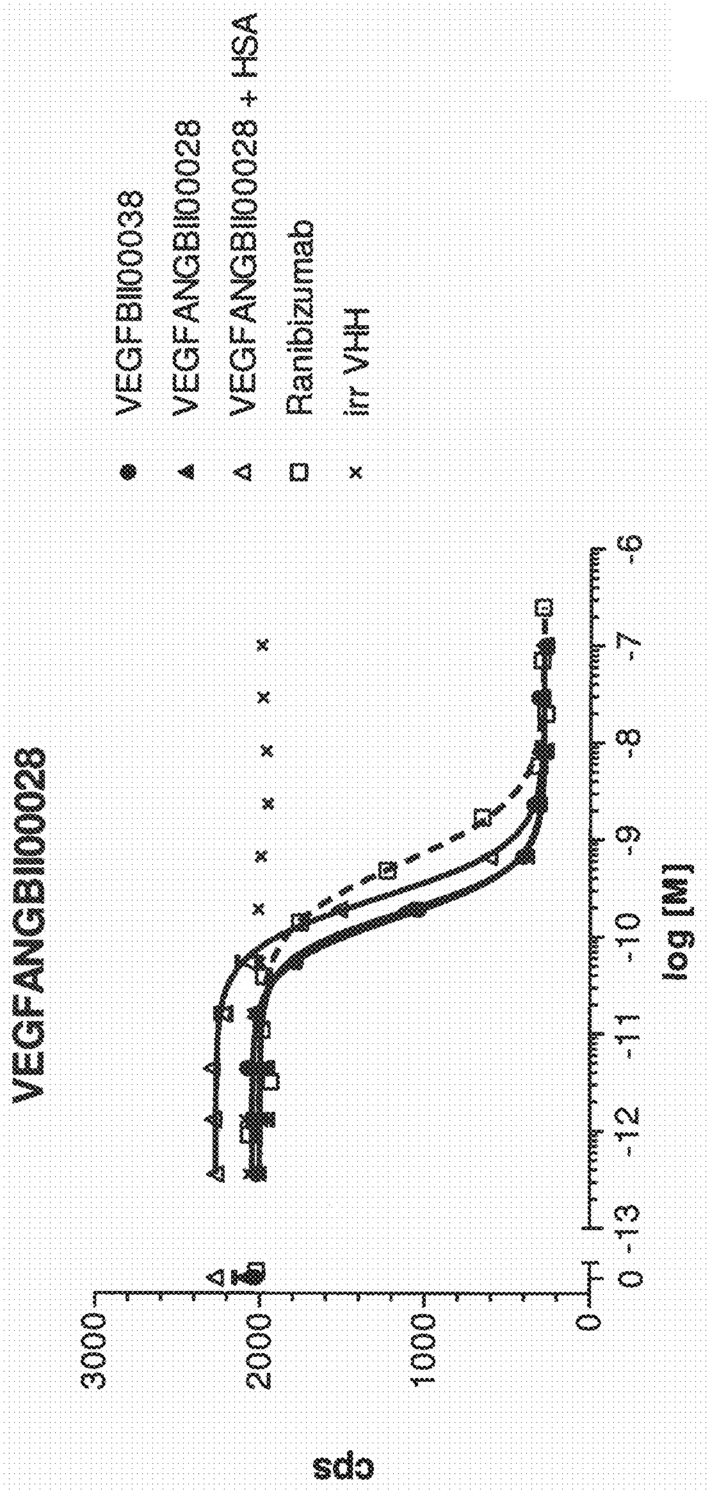
Figures 2A, 31:
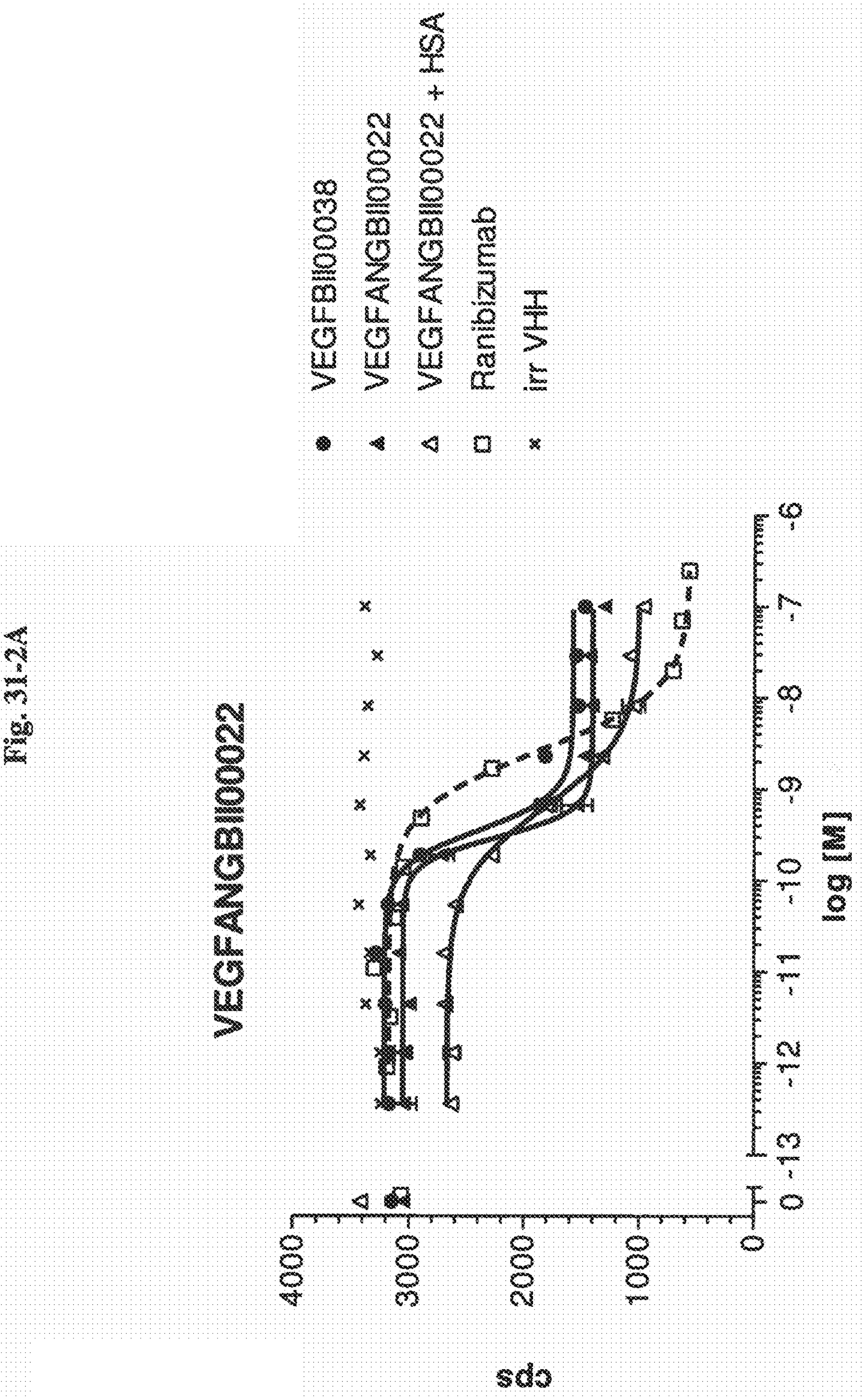
Figures 2B, 31:
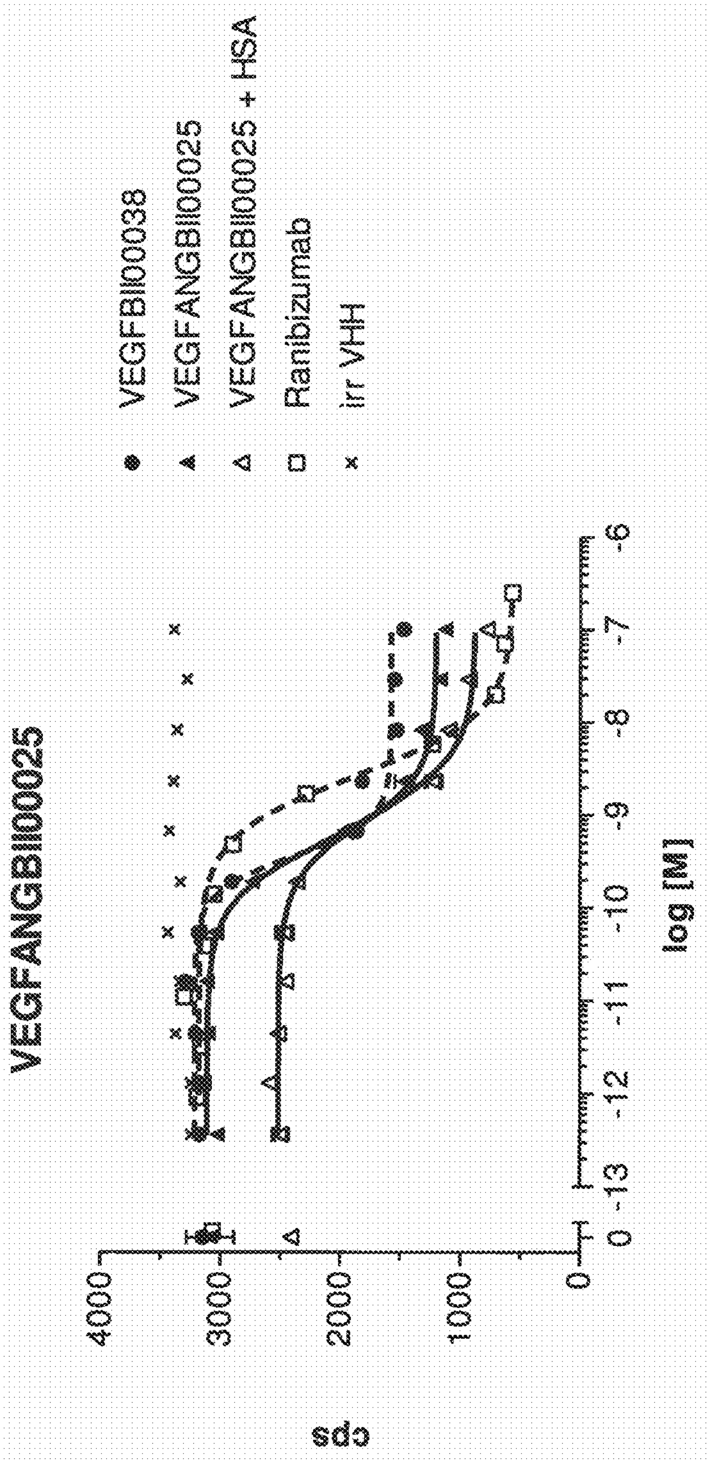
Figures 2C, 31:
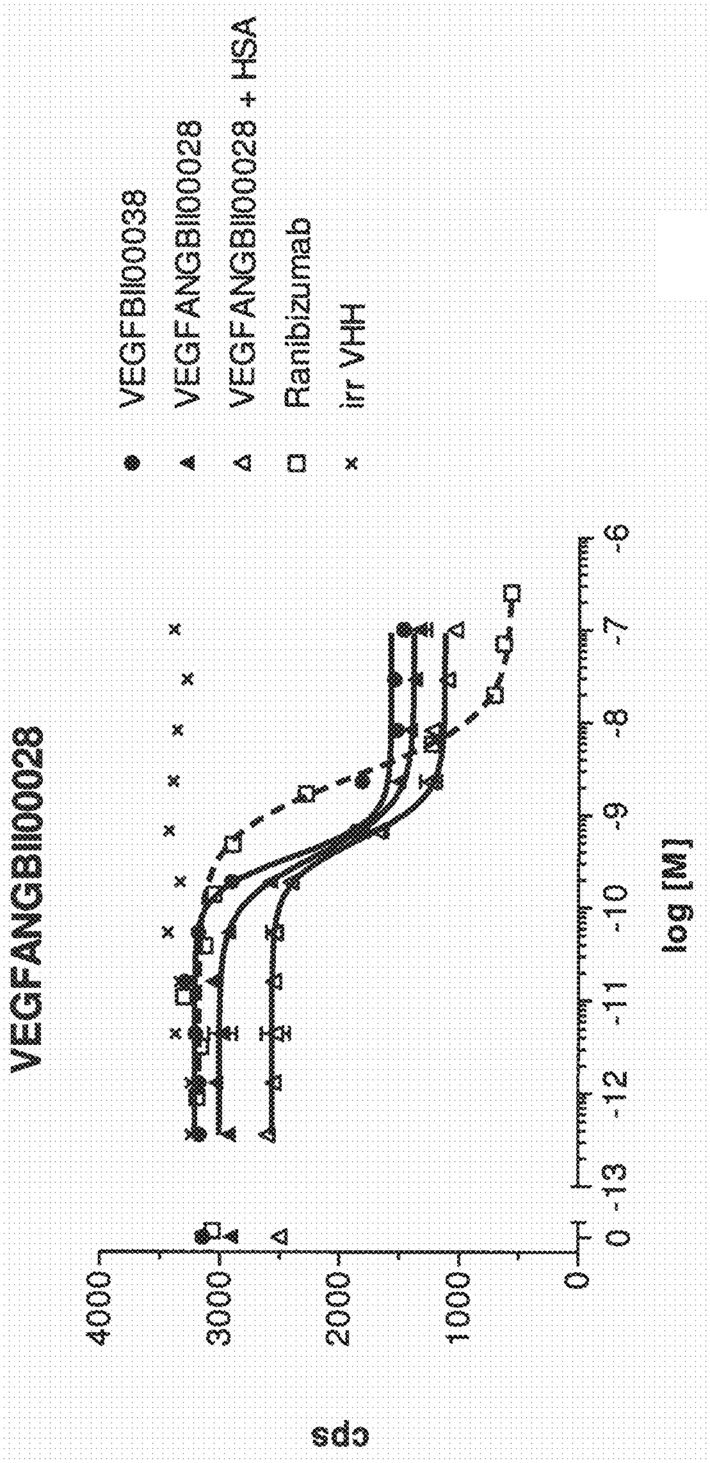
Figure 32A:
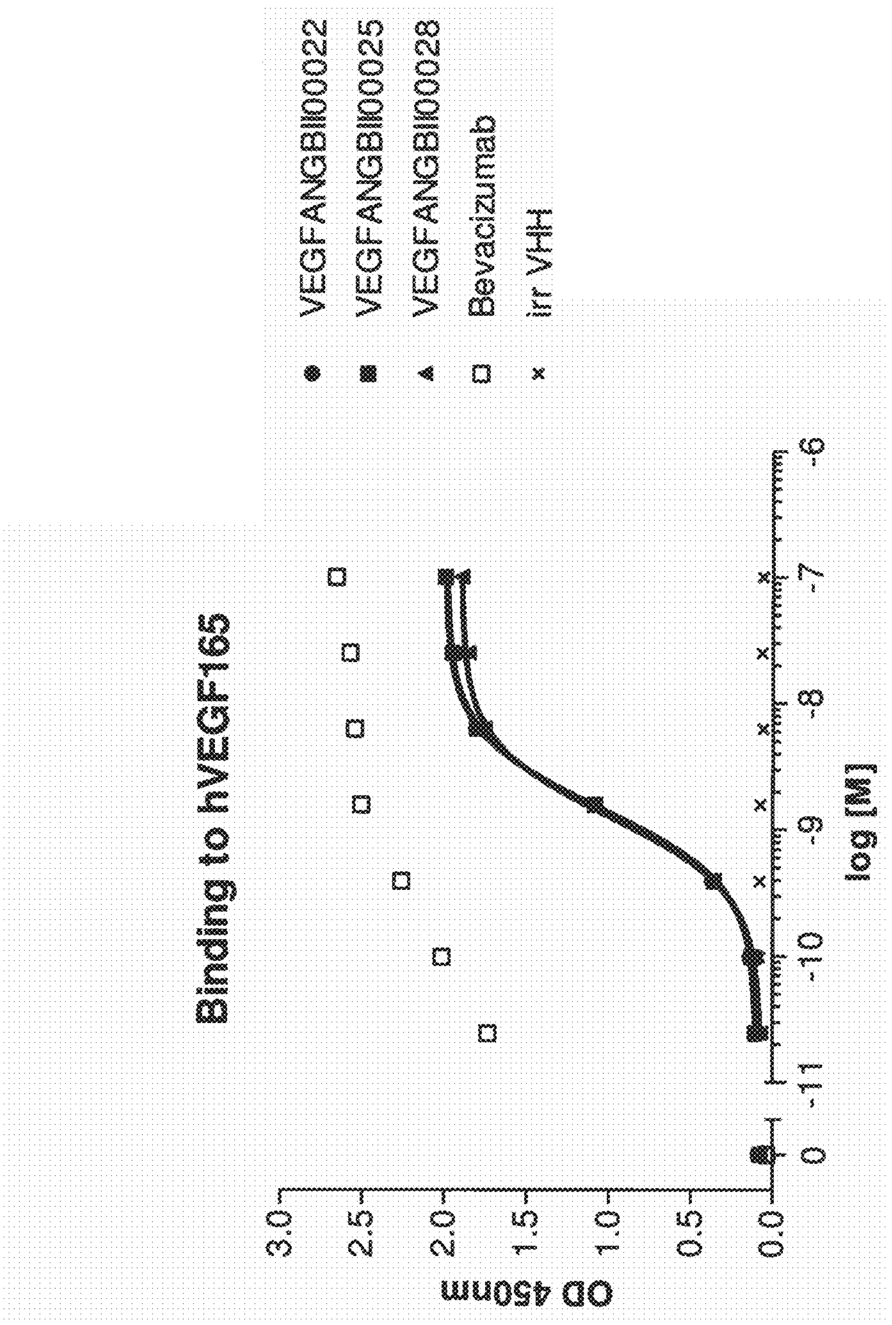
FIG. 32A-32B: Purified VEGFANGBII00022-25-28 VEGFxAng2 VHHs binding to human VEGF165 (36-1) and hVEGF121 (36-2) (ELISA)
Figure 32B:
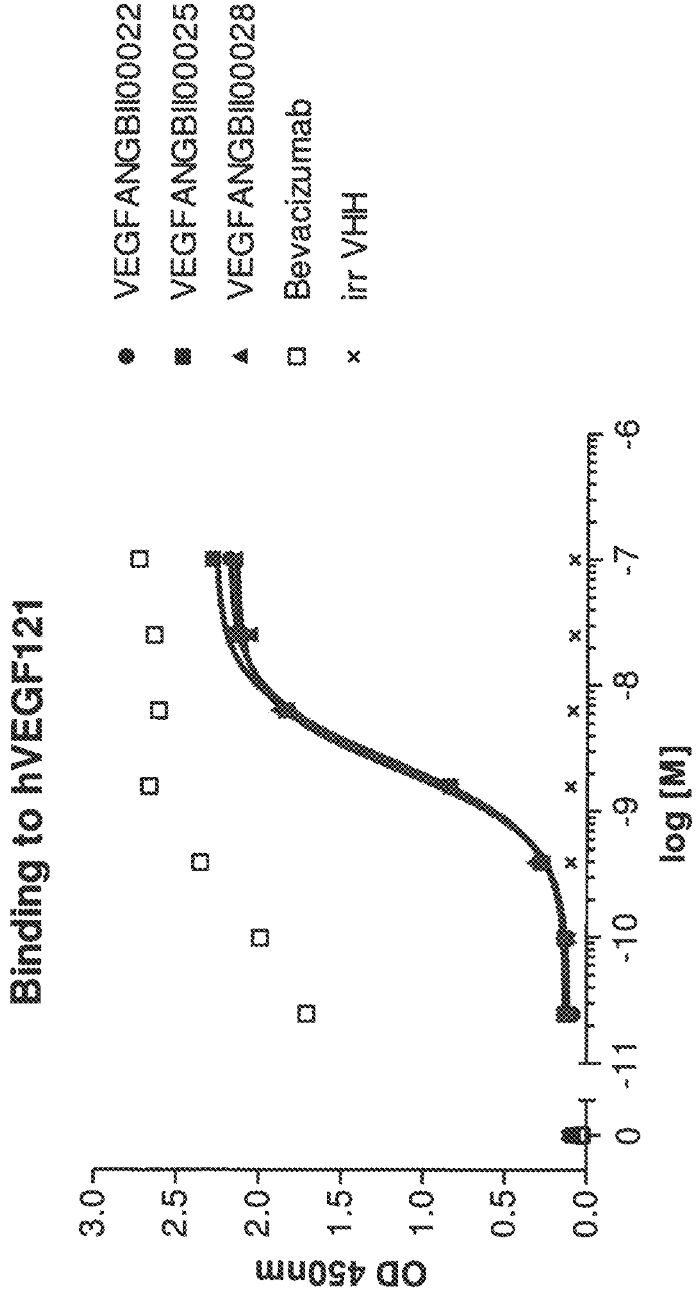

To explore the anti-VEGF blocking properties in comparison with the monovalent building block VEGFBII00038, the bispecific VHHs are analyzed in the VEGF/VEGFR2-Fc (Example 10; FIG. 31-1) and VEGF/VEGFR1 (Example 11; FIG. 31-2) competition AlphaScreen. These competition assays are also performed after preincubation of the VHH with 25 µM human serum albumin. A summary of $IC_{50}$ values is shown in FIG. 30 C.

Binding kinetics of the bispecific VHHs on human VEGF165 is analyzed by SPR on a Biacore T100 instrument (see Example 12.5 described in patent US 2011/0172398 A1). Monovalent Nanobody VEGFBII00038 is taken along as reference (FIG. 30 D).

TABLE 46-B

Overview of kinetic parameters in hVEGF165 Biacore assay.

| | ka1<br>(1/Ms) | kd1<br>(1/s) | ka2<br>(1/s) | kd2<br>(1/s) | KD1<br>(M) |
|---|---|---|---|---|---|
| VEGFBII00038 | 2.6E+05 | 1.3E-02 | 1.3E-02 | 1.9E-04 | 7.5E-10 |
| VEGFANGBII00022 | 1.6E+05 | 1.4E-02 | 1.4E-02 | 2.2E-04 | 1.4E-09 |
| VEGFANGBII00025 | 1.1E+05 | 1.4E-02 | 1.4E-02 | 2.1E-04 | 1.9E-09 |
| VEGFANGBII00028 | 1.7E+05 | 1.3E-02 | 1.3E-02 | 2.1E-04 | 1.1E-09 |

The ability of the VHHs to bind to human isoform VEGF121 is determined in a binding ELISA. Binding of a dilution series of VHH to 1 µg/mL directly coated human VEGF121 (R&D) (human VEGF165 as reference) is detected using biotinylated anti-VHH 1A4 followed by extravidin-HRP. 1A4 is a anti-VHH VHH (generated in-house by Ablynx Nev.). The benchmark Avastin serves as positive control and is detected using a HRP conjugated anti-human Fc antibody. An irrelevant VHH serves as negative control. Representative binding response curves on VEGF165 and VEGF121 are shown in FIG. 46 corresponding $EC_{50}$ values are summarized in Table 46-C.

TABLE 46-C

Overview of $EC_{50}$ values in hVEGF165
and hVEGF121 binding ELISA.

| | hVEGF165<br>$EC_{50}$ (M) | hVEGF121<br>$EC_{50}$ (M) |
|---|---|---|
| VEGFANGBII00022 | 1.4E-09 | 2.3E-09 |
| VEGFANGBII00025 | 1.5E-09 | 2.5E-09 |
| VEGFANGBII00028 | 1.2E-09 | 2.1E-09 |

Figure 33A:
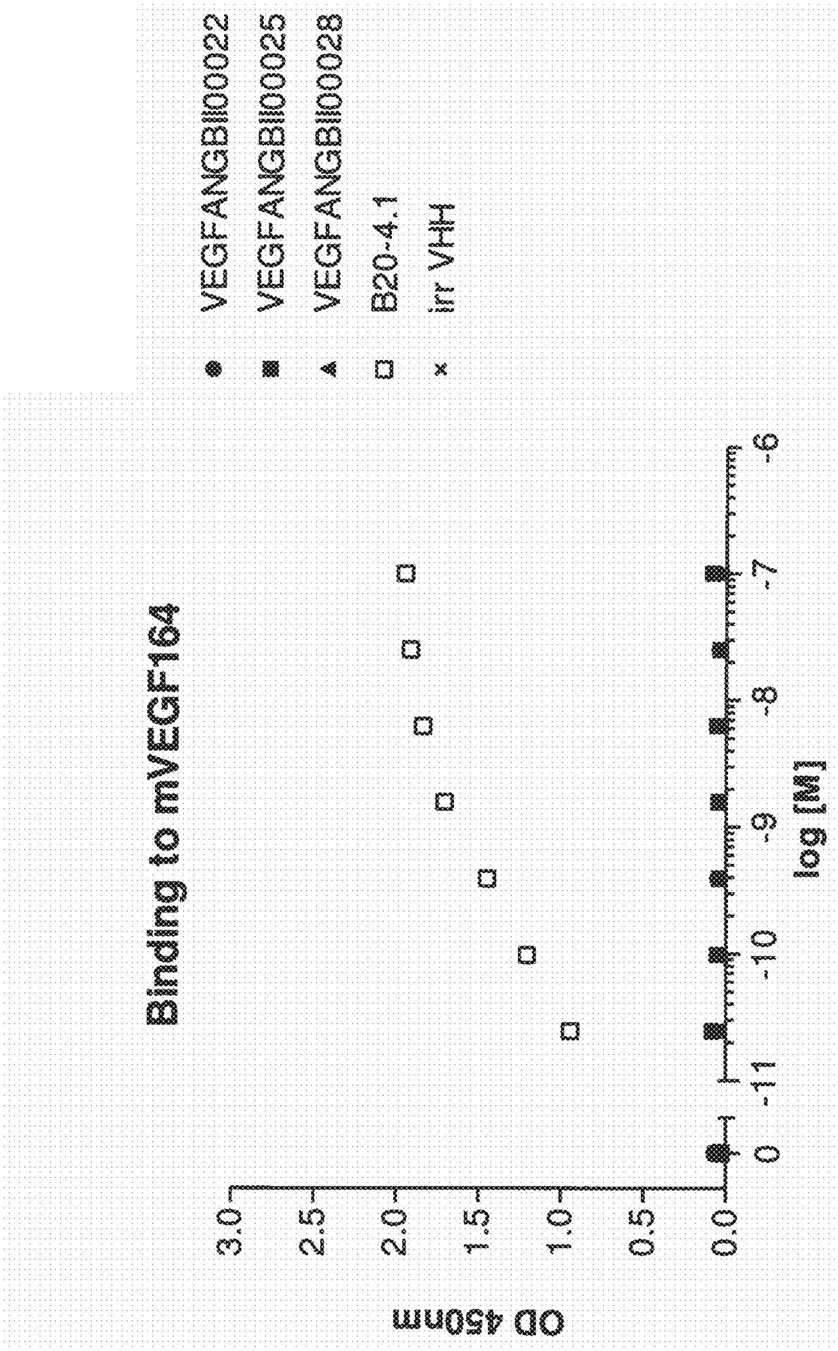
FIG. 33A-33B: Purified VEGFANGBII00022-25-28 VEGFxAng2 VHHs binding to (A) mouse and (B) rat VEGF164 (ELISA)
Figure 33B:
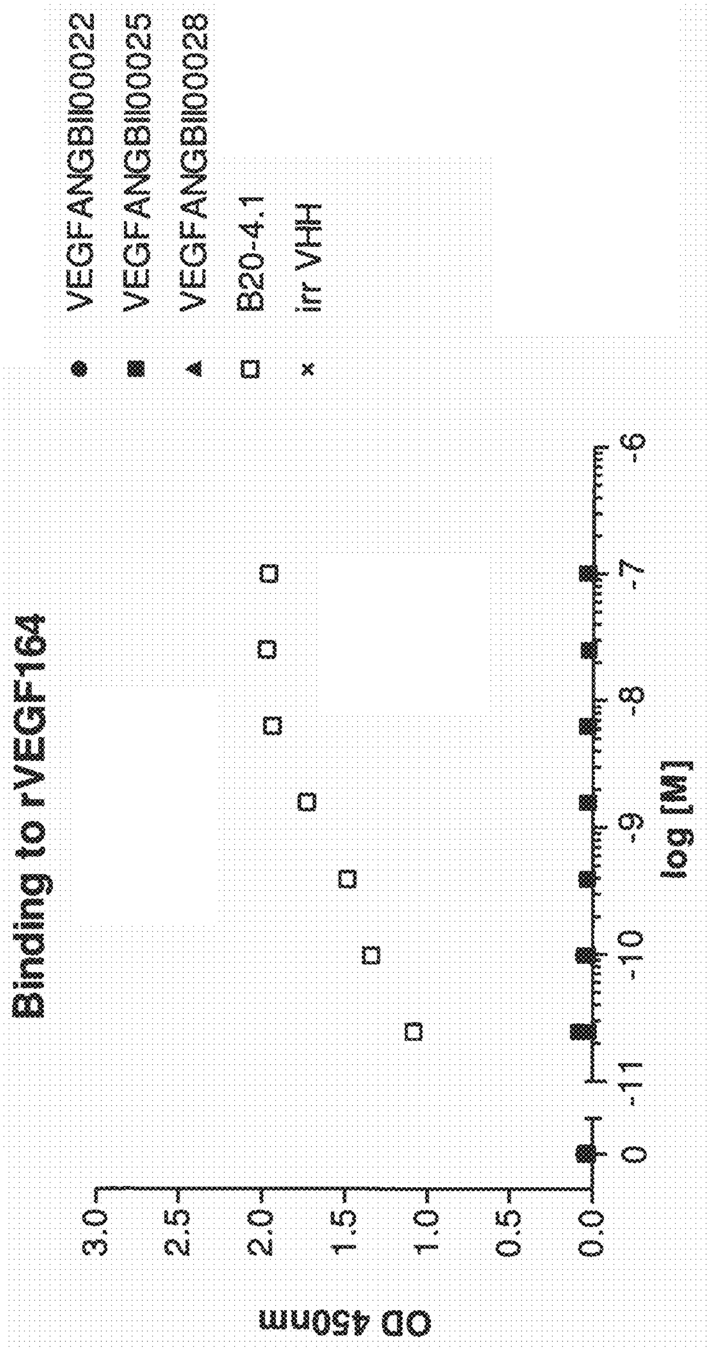
Figure 34A:
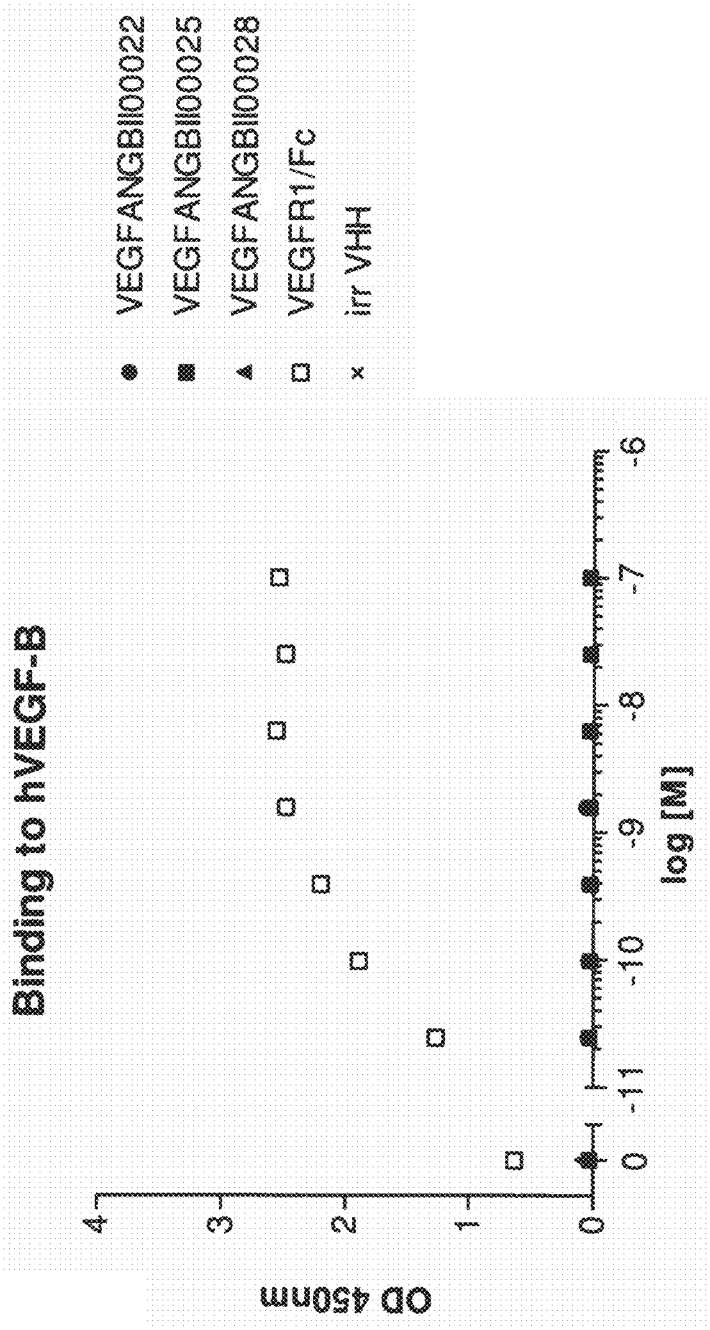
FIG. 34A-34D: Purified VEGFANGBII00022-25-28 VEGFxAng2 VHHs binding to (A) human VEGF-B, (B) human VEGF-C, (C) human VEGF-D and (D) human PIGF (ELISA)
Figure 34B:
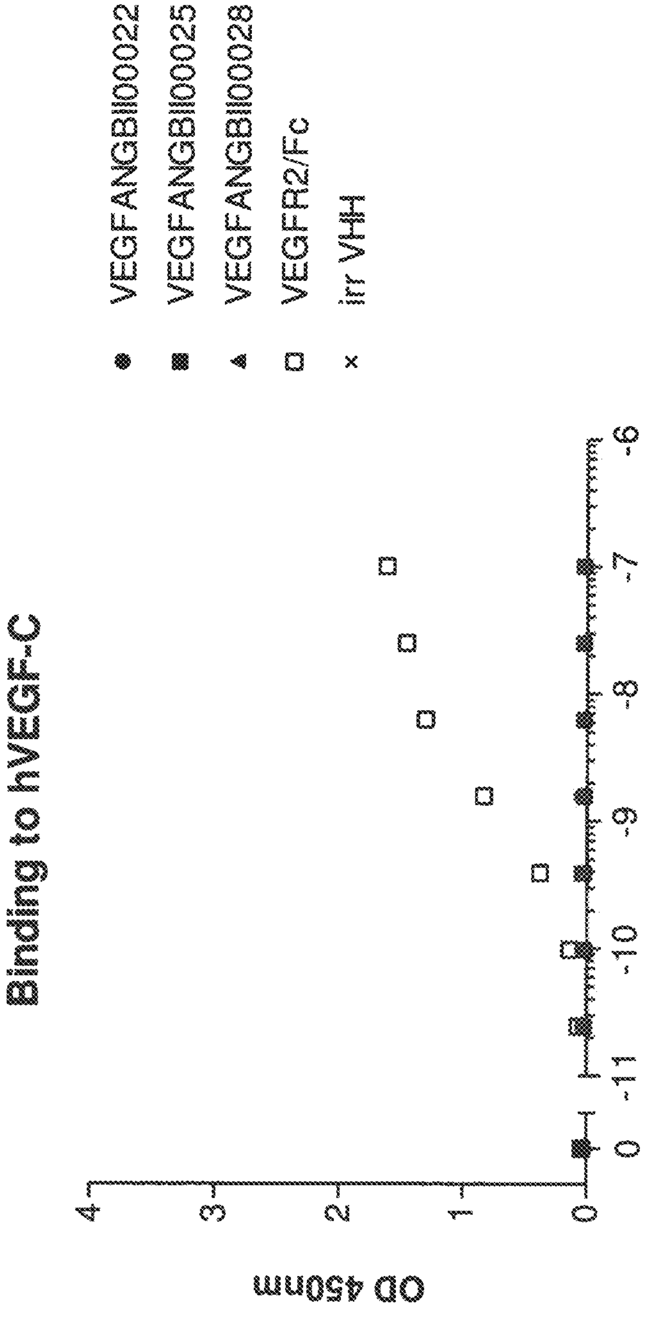
Figure 34C:
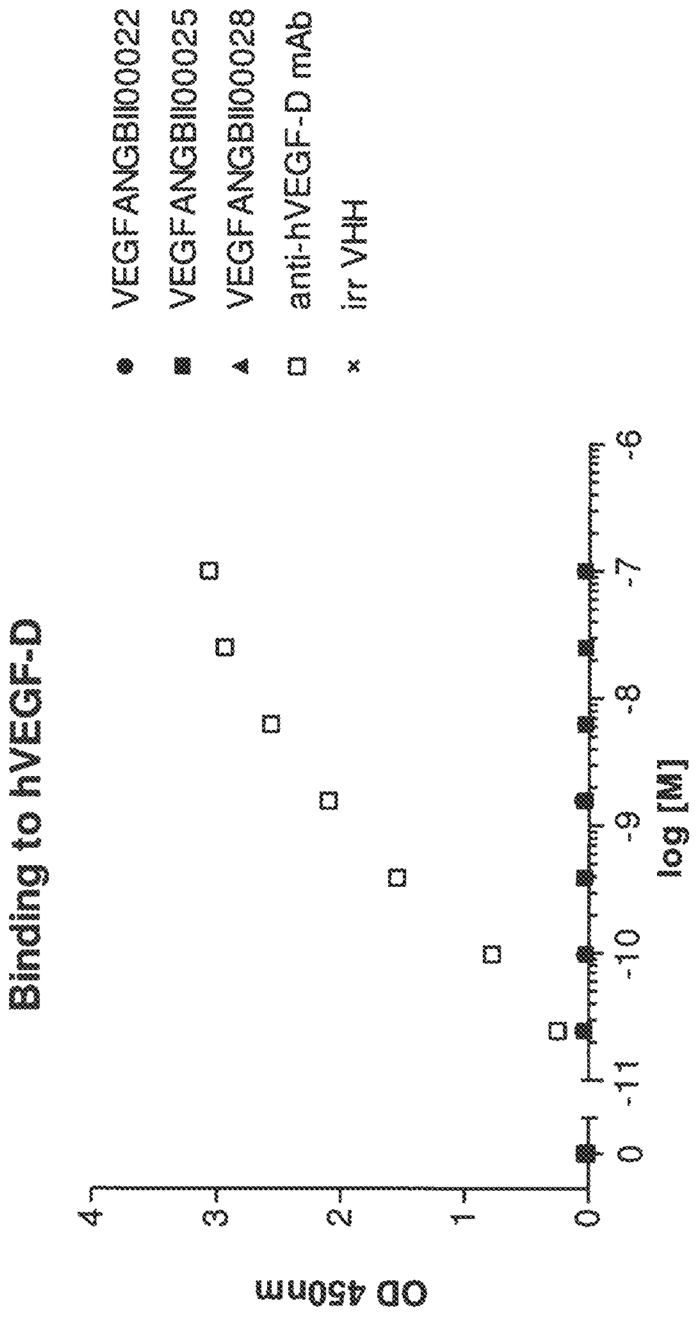
Figure 34D:
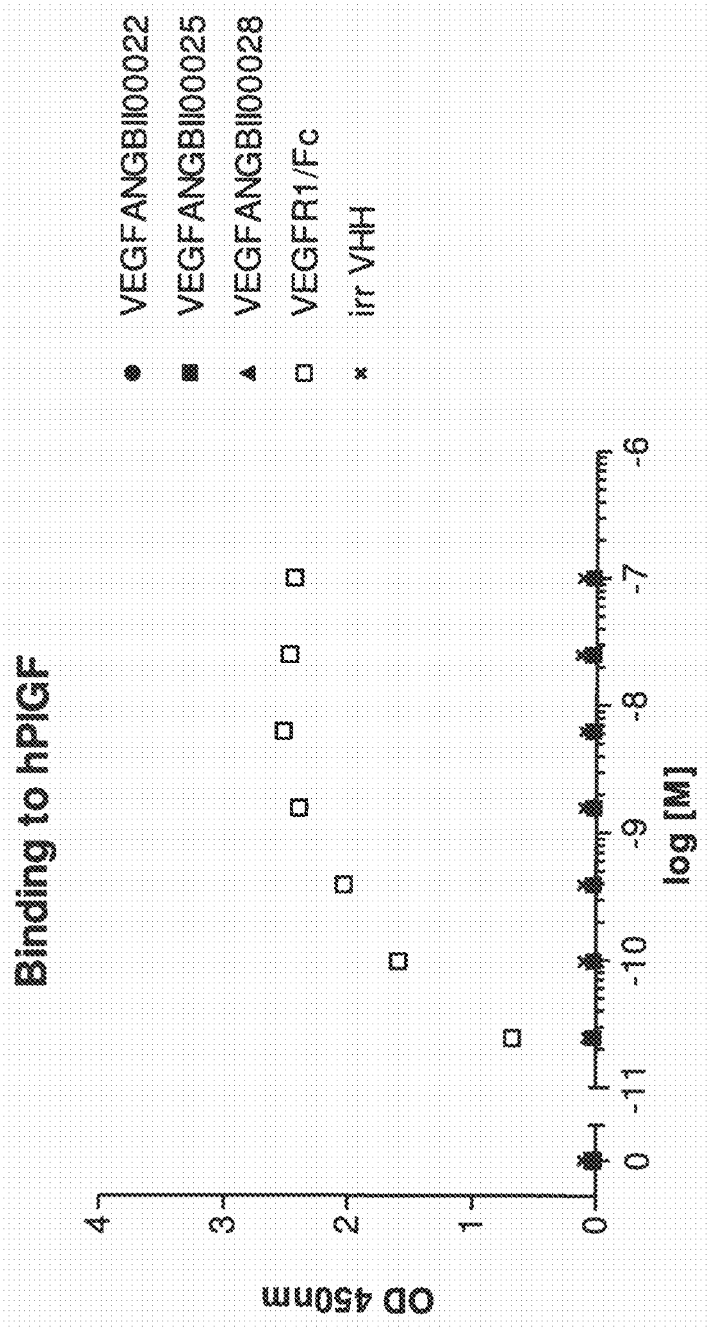

Binding to rat and mouse VEGF164 is assessed in a binding ELISA. VHHs binding to 1 µg/mL directly coated murine or rat VEGF164 (R&D) are detected using biotinylated anti-VHH 1A4 followed by extravidin-HRP. As positive control the mouse/rat cross-reactive monoclonal antibody B20-4.1 (Genentech) is titrated and detected with an HRP conjugated anti-human Fc antibody. An irrelevant VHH serves as negative control. Results are shown in FIG. 33. All 3 bispecific VHH are not cross-reactive to mouse and rat VEGF.

Binding to human VEGF-B, VEGF-C, VEGF-D and PlGF is assessed via a binding ELISA. Binding of VHHs to 1 µg/mL directly coated VEGF-B (R&D), VEGF-C(R&D), VEGF-D (R&D) and PlGF (R&D) was detected using biotinylated anti-VHH 1A4 followed by extravidin-HRP. As positive controls a series of dilutions of the appropriate receptors (hVEGFR1-Fc for hVEGF-B and hPlGF, hVEGFR2-Fc for hVEGF-C, anti-hVEGF-D mAb (R&D) for hVEGF-D) are taken along. An irrelevant VHH serves as negative control. Results are shown in FIG. 34. All 3 bispecific VHH are not binding to VEGF family members.

Figures 1A, 35:
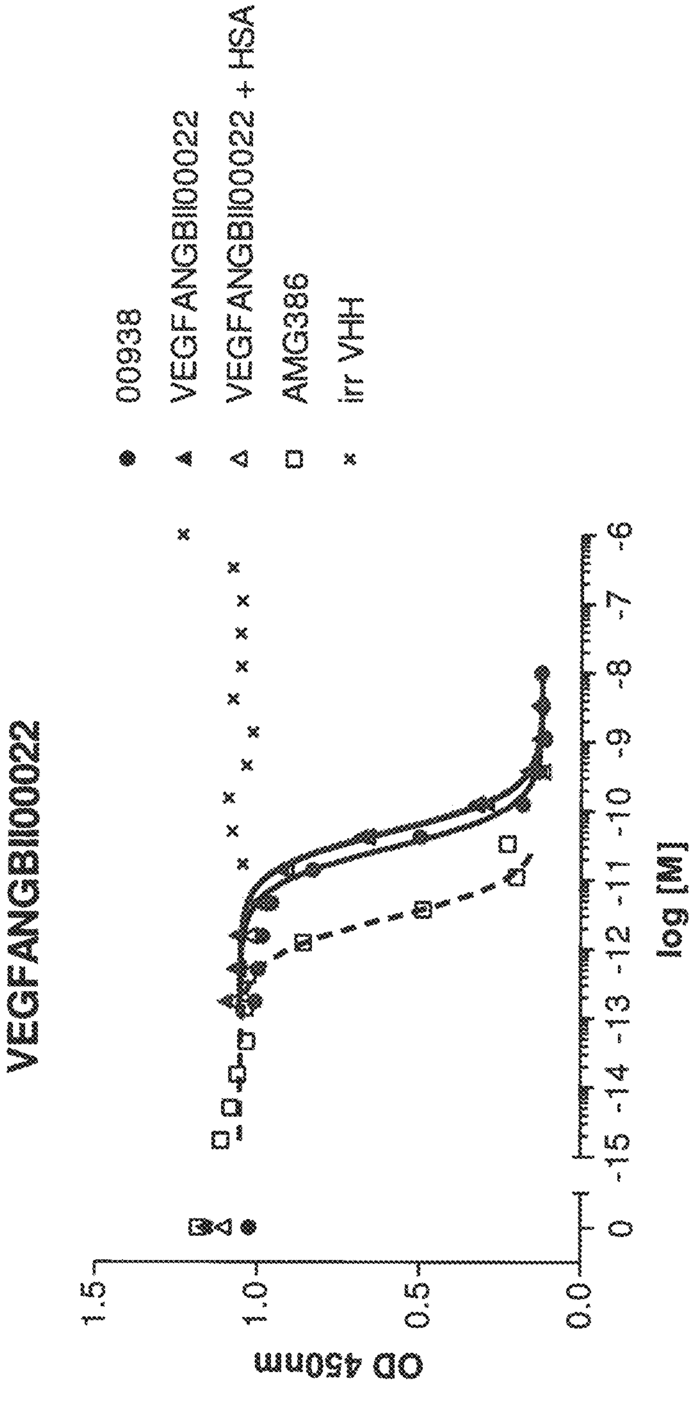
Figures 1B, 35:
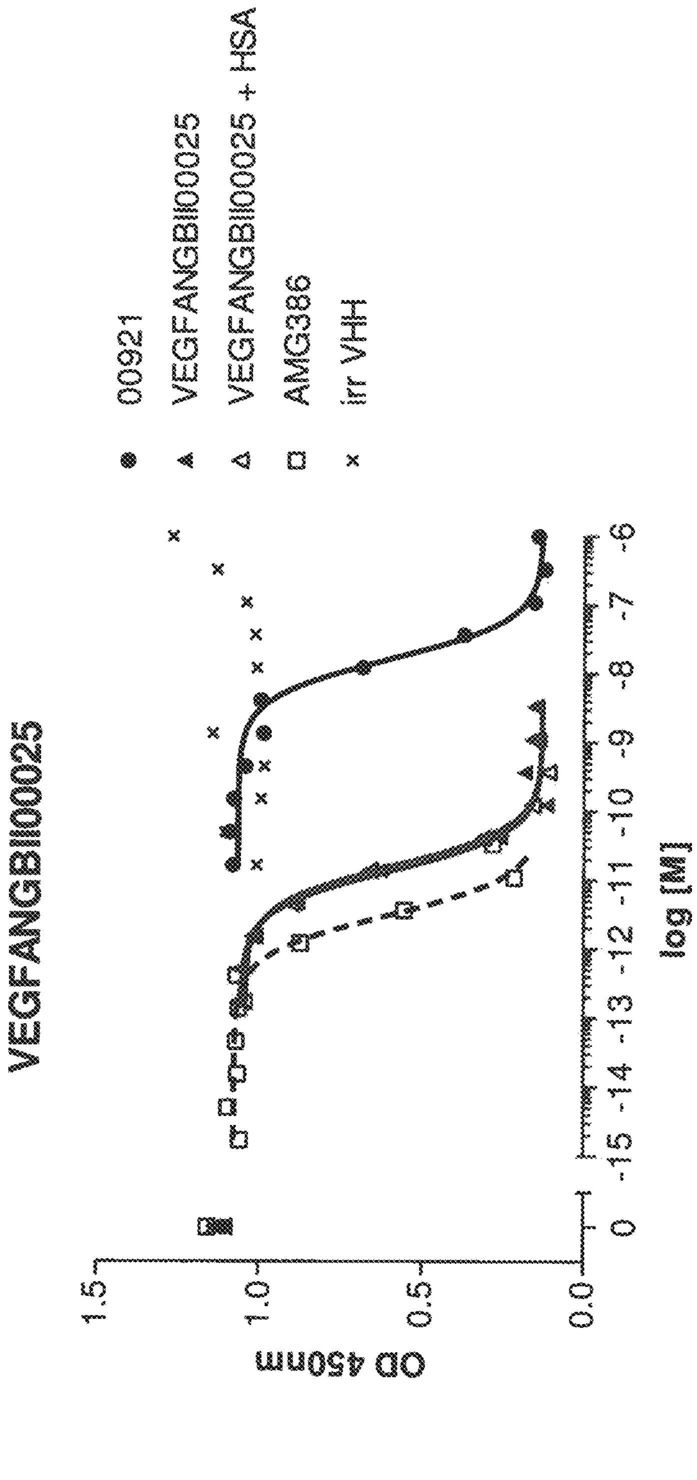
Figures 1C, 35:
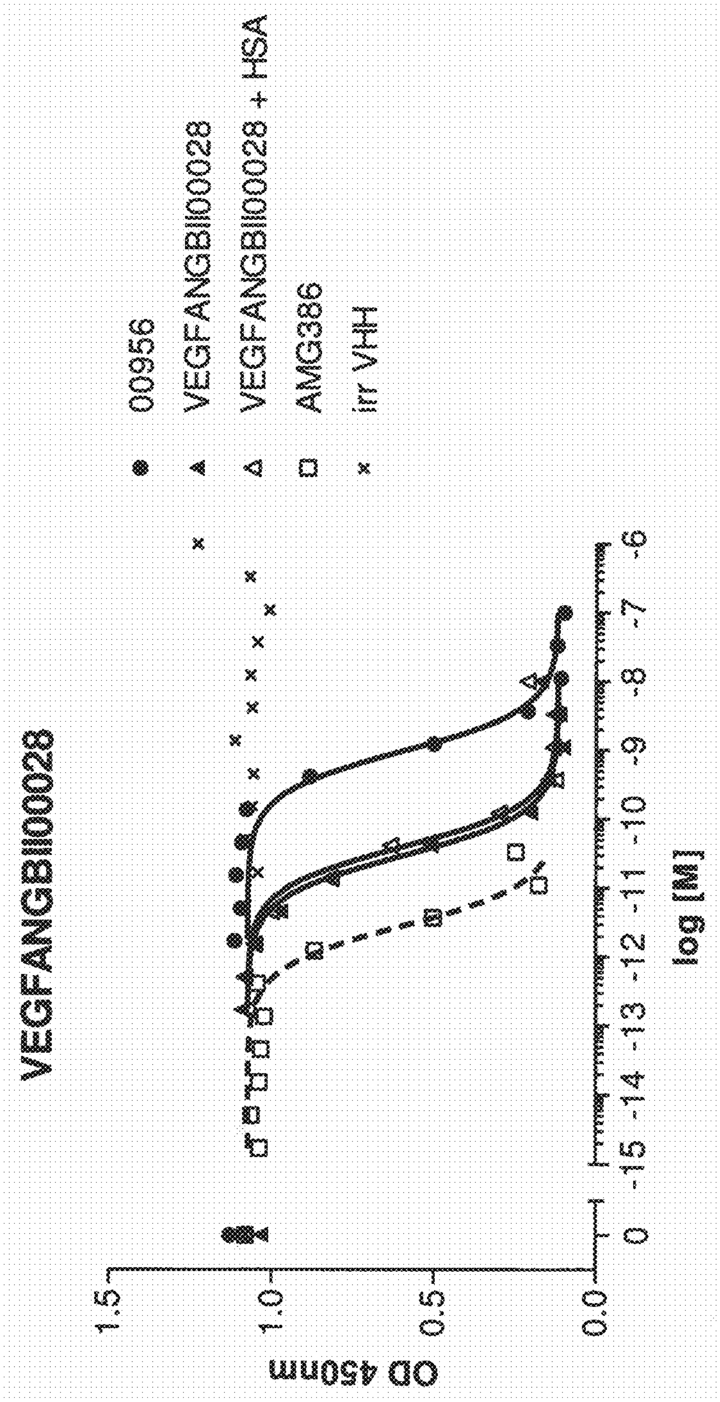
Figures 2A, 35:
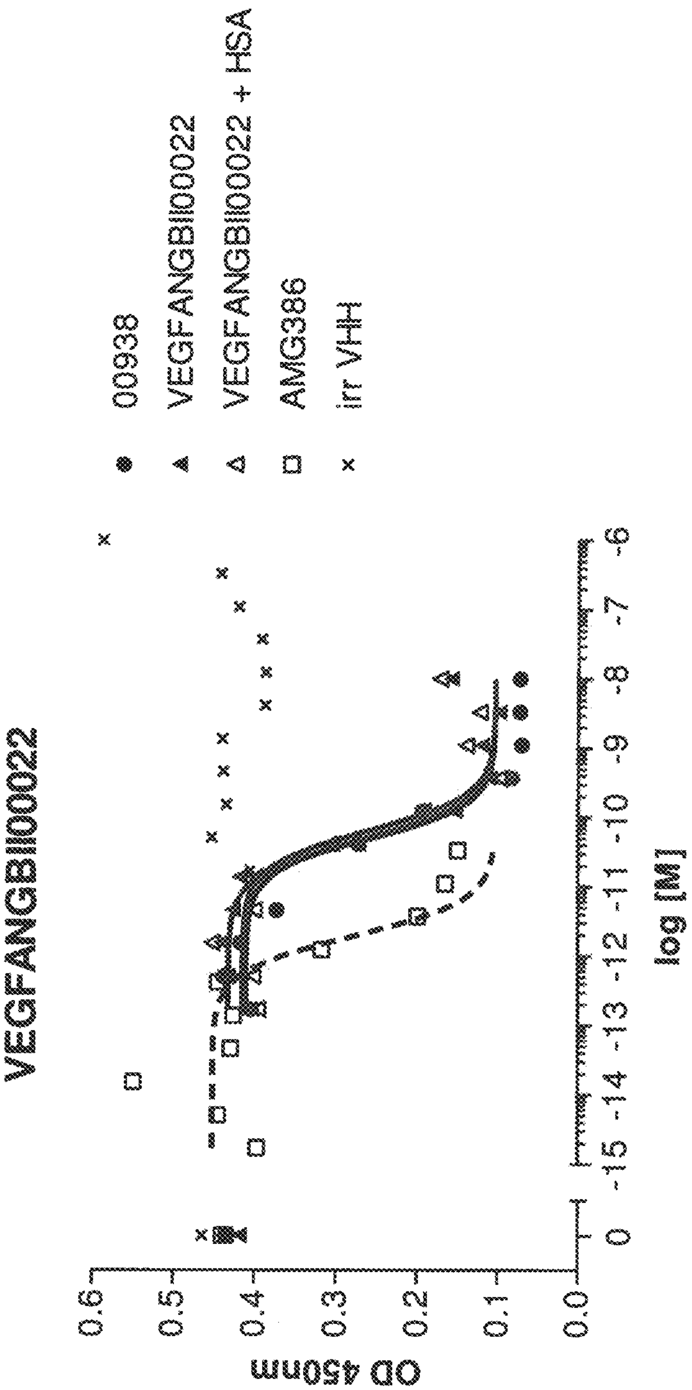
Figures 2B, 35:
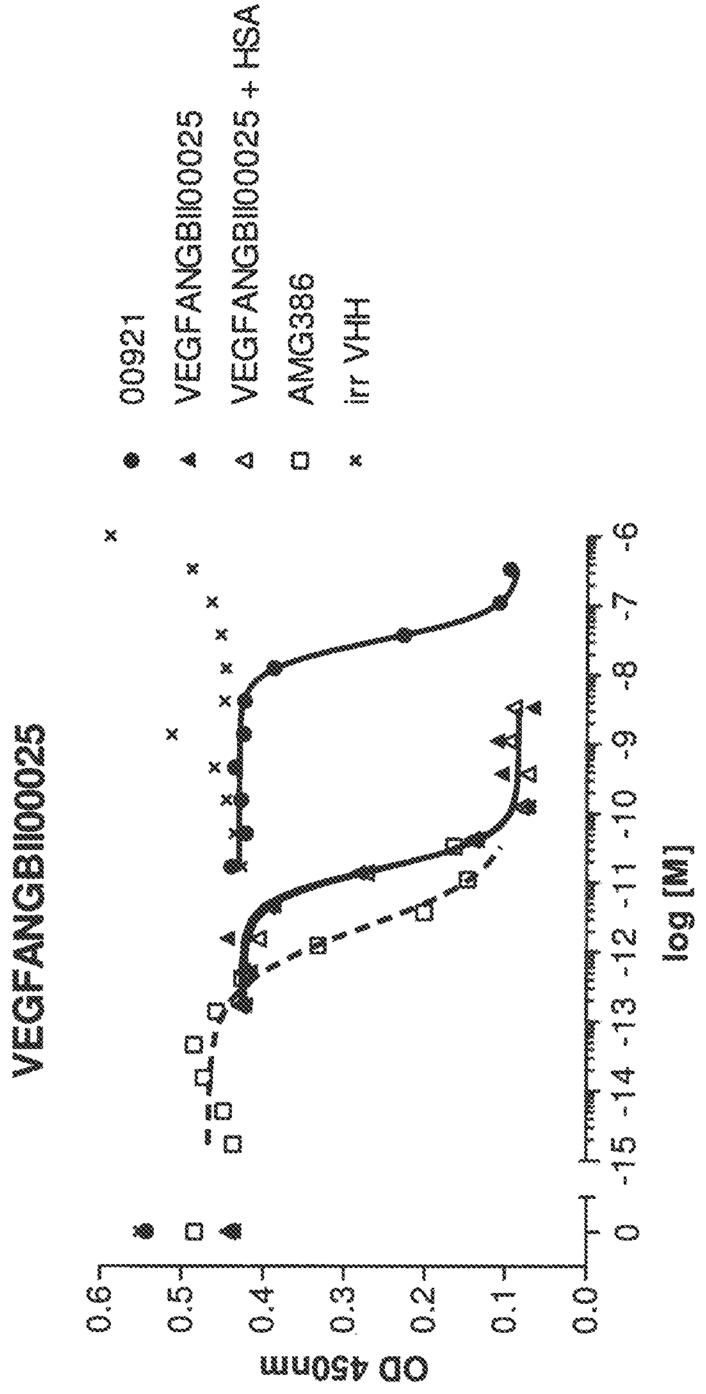
Figures 2C, 35:
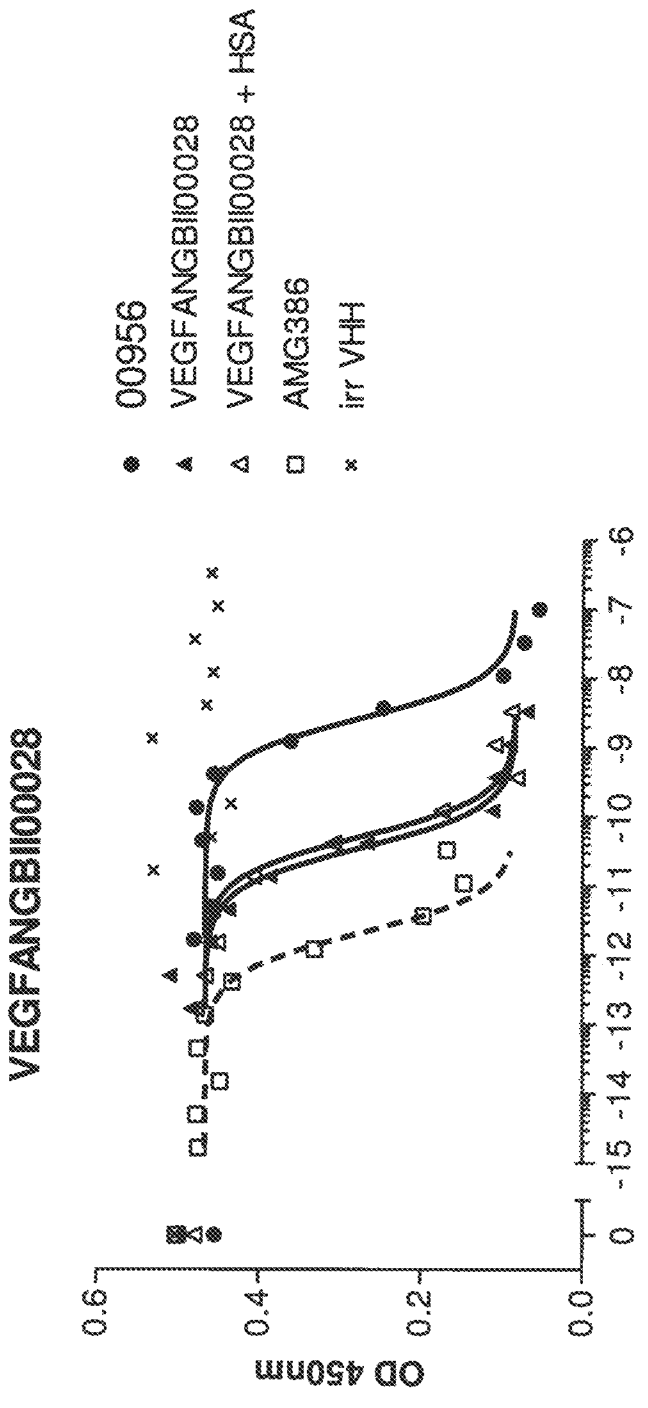
Figures 3A, 35:
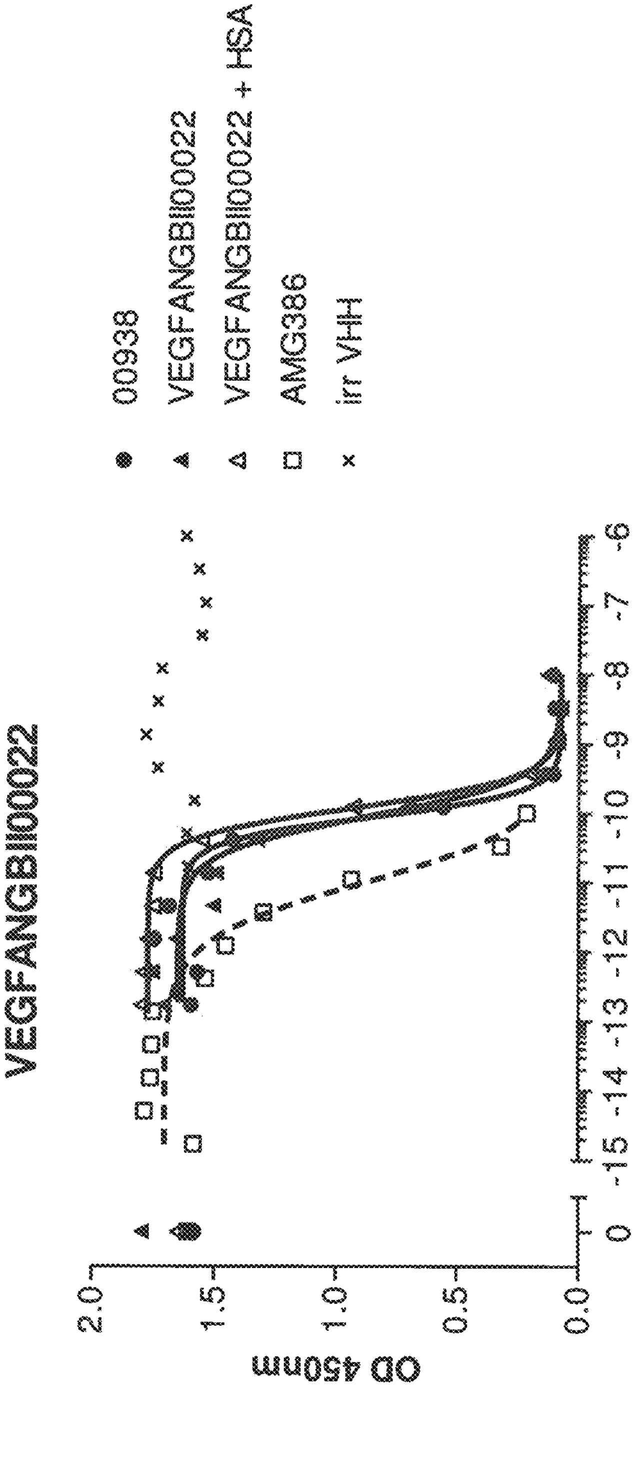
Figures 3B, 35:
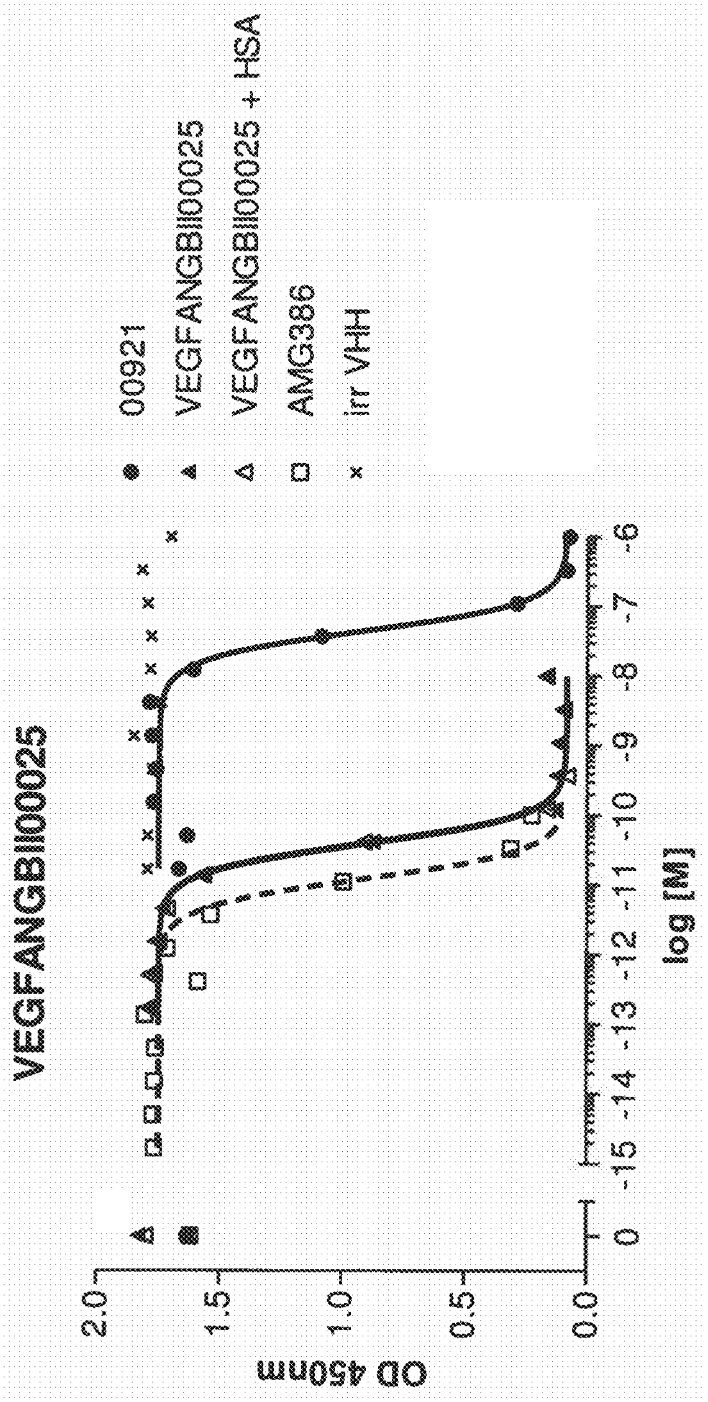
Figures 3C, 35:
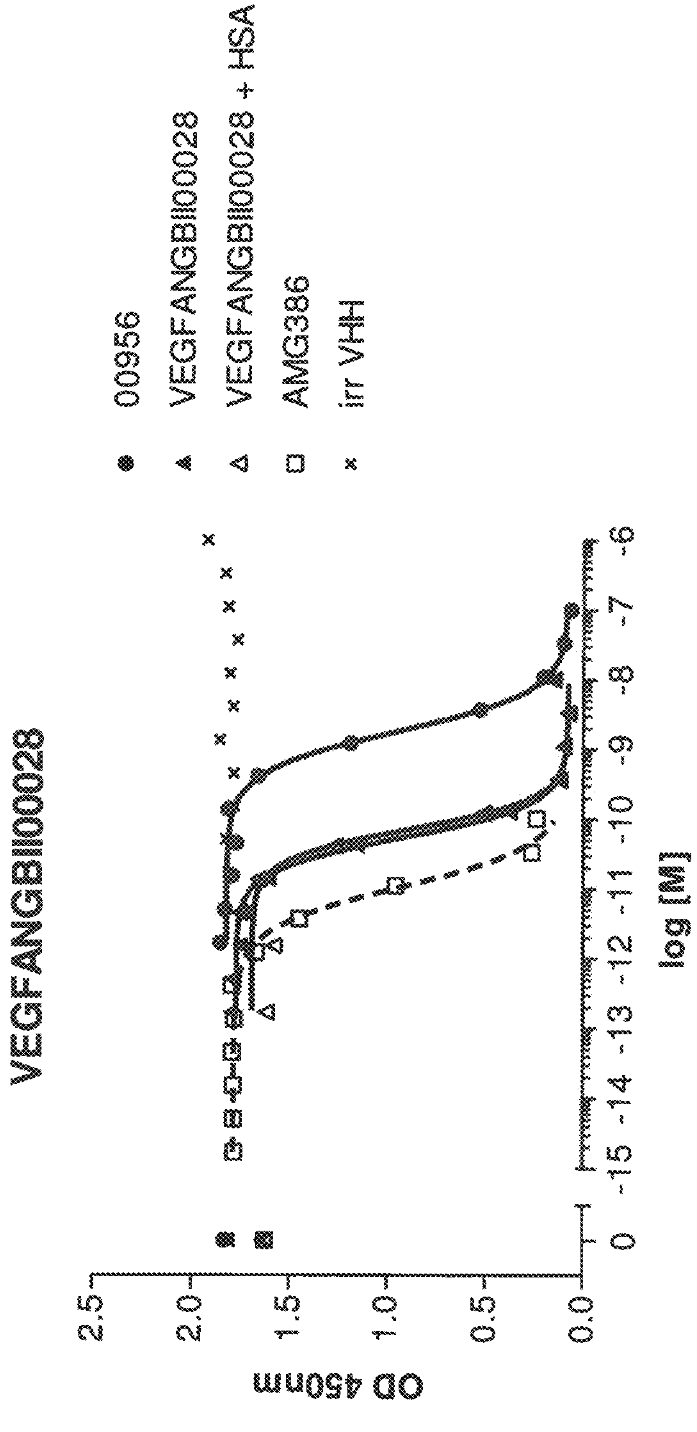
Figure 36A:
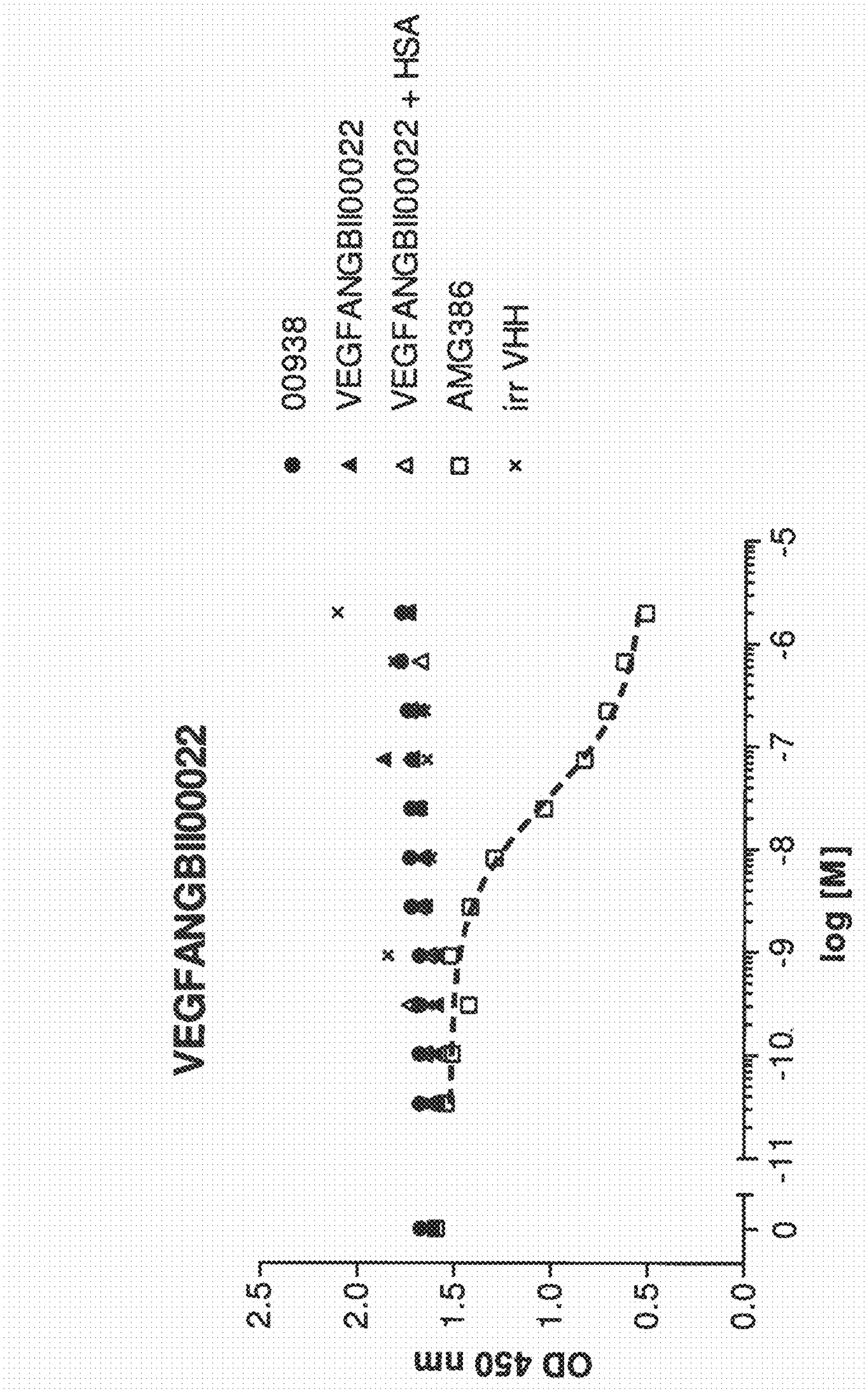
FIG. 36A-36C: Purified VEGFANGBII00022-25-28 VEGFxAng2 VHHs blocking hAng1-hTie2 interaction (ELISA)
Figure 36B:
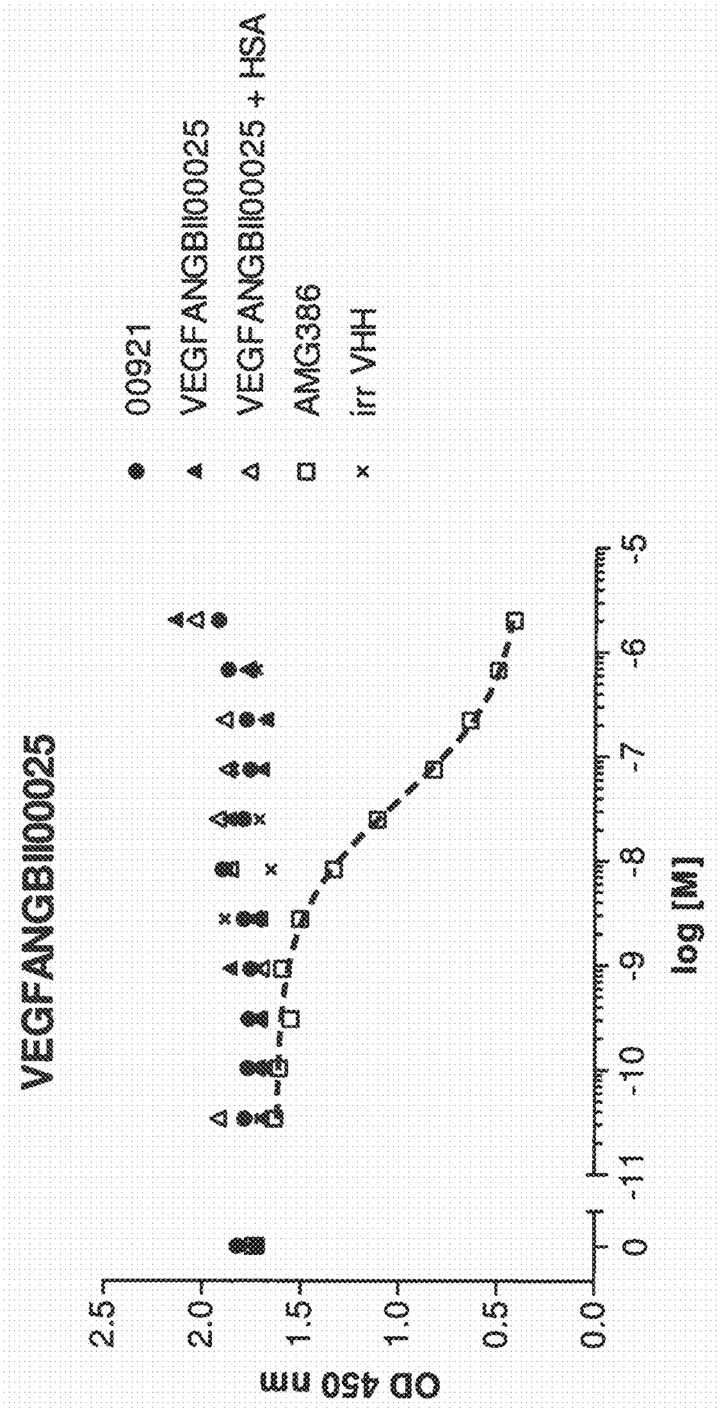
Figure 36C:
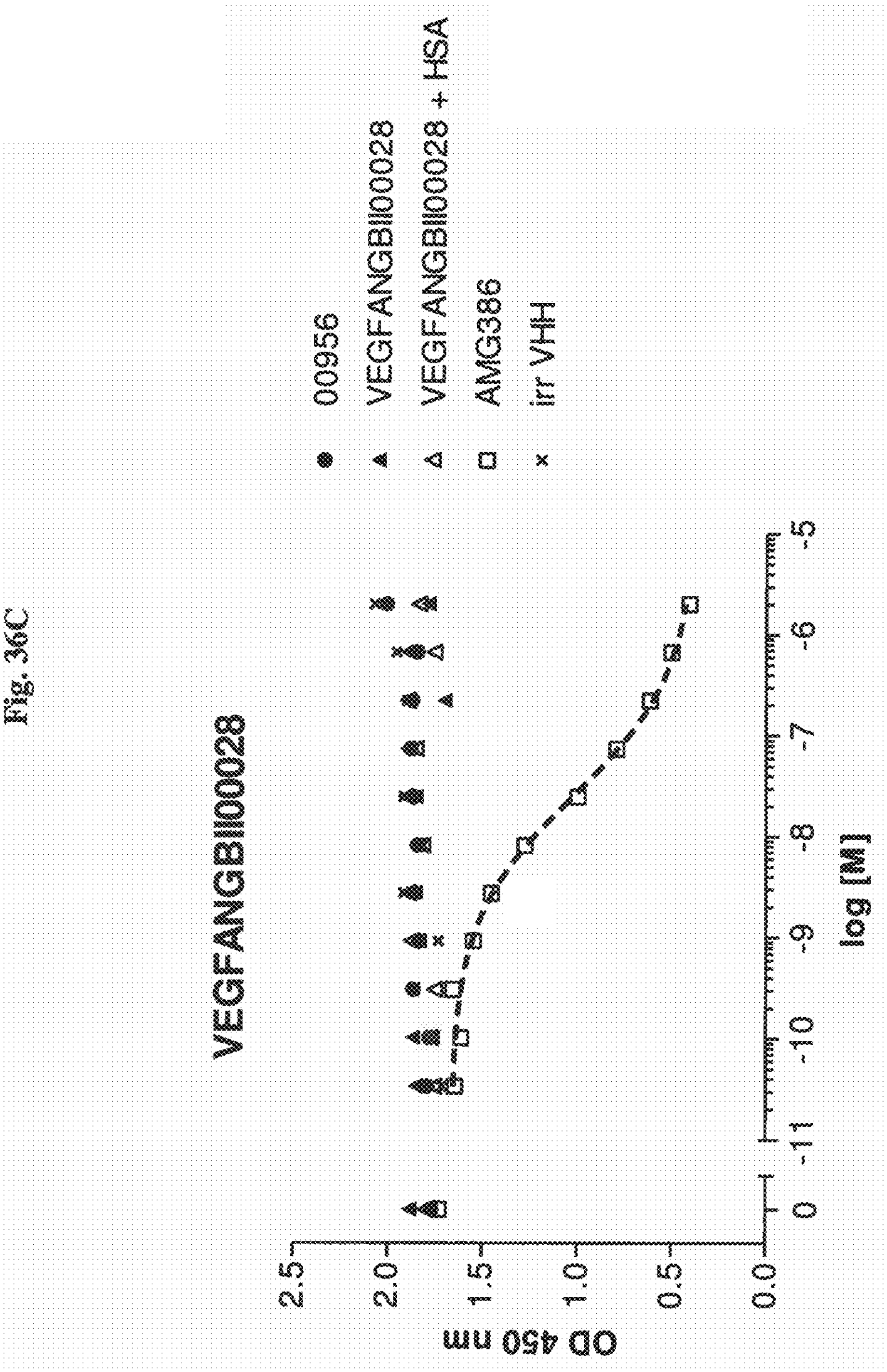
Figure 37A:
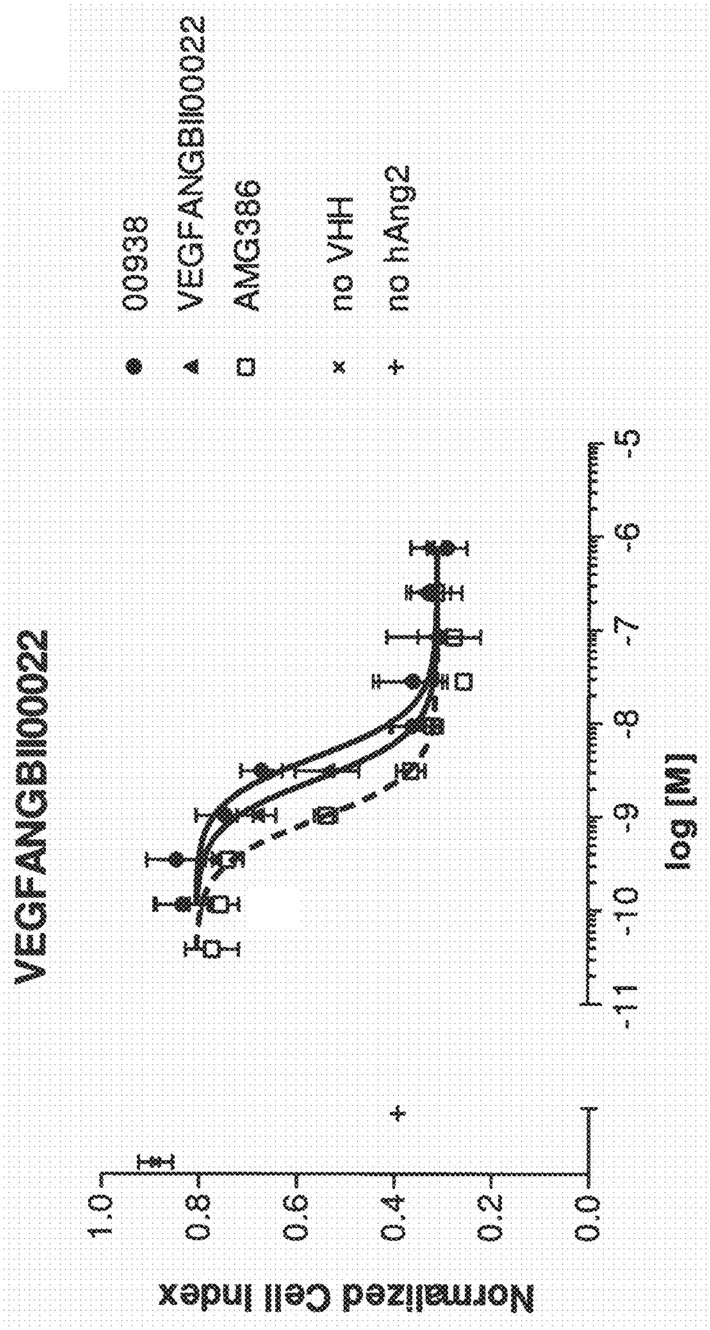
FIG. 37A-37C: Purified VEGFANGBII00022-25-28 VEGFxAng2 VHHs blocking hAng2 mediated HUVEC survival.
Figure 37B:
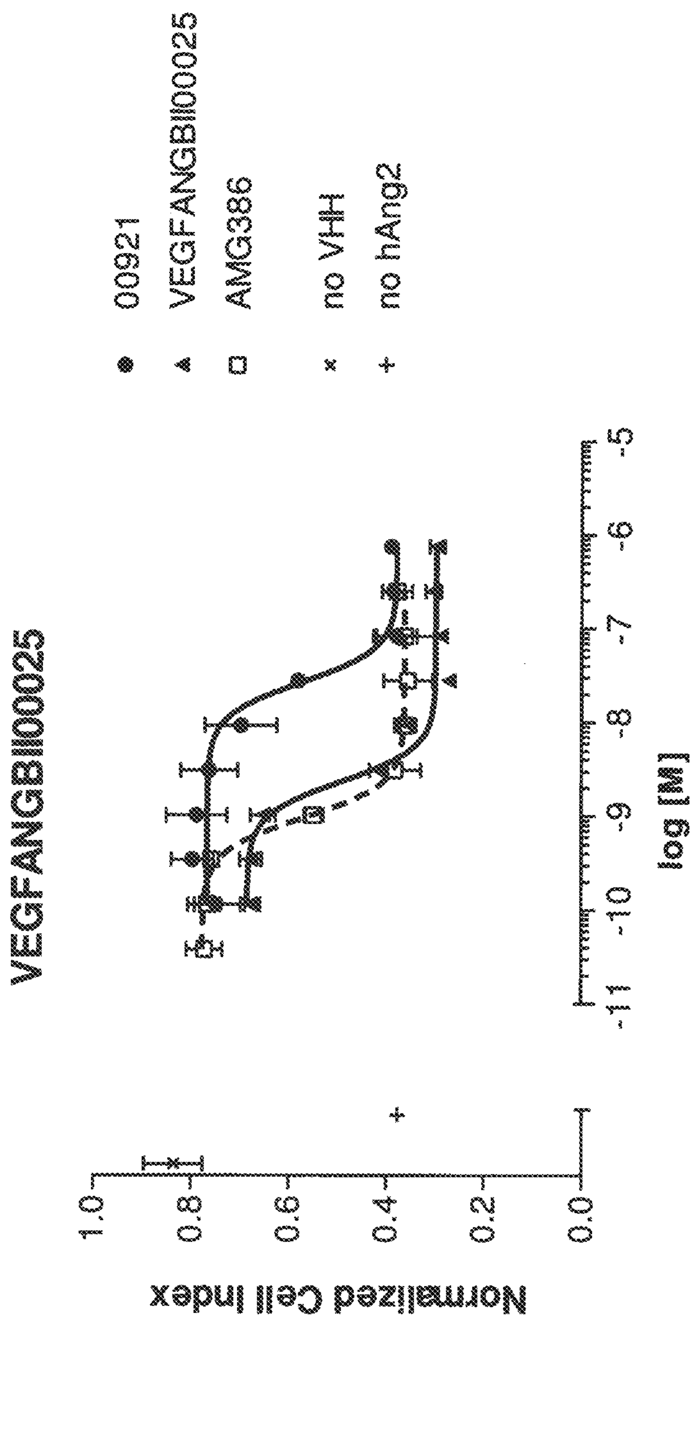
Figure 37C:
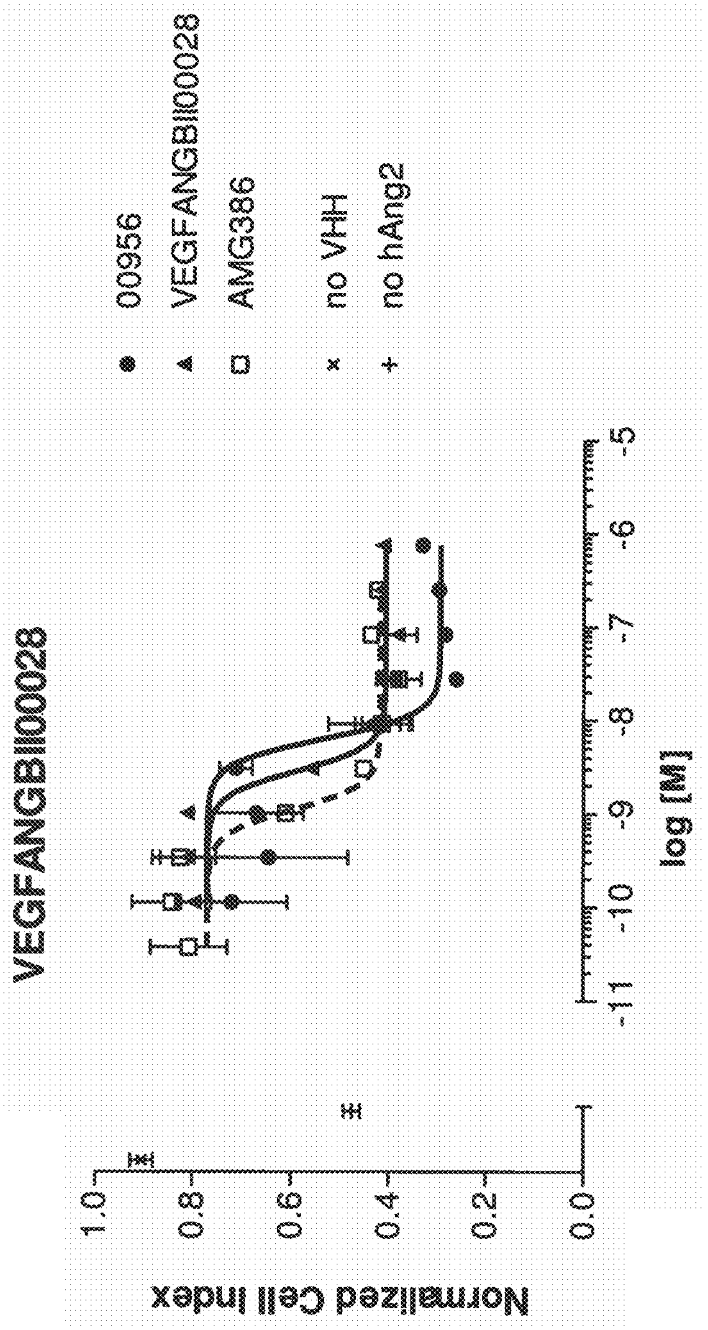
Figure 38:
FIG. 38: A summary of $IC_{50}$ values and % inhibition: IC50 values (pM) in human Ang2/human Tie2, mouse Ang2/mouse Tie2 and cyno Ang2/cyno Tie2 competition ELISA, hAng1 ELISA and IC50 values (nM) in hAng2 mediated HUVEC survival assay.
Figure 38:
Figure 38:
Figure 38:
Figure 38:
Figure 38:

To explore the anti-Ang2 blocking properties in comparison with their respective monovalent building block 00921 (SEQ ID NO:220) and 00938 (SEQ ID NO:222), all 3 bispecific VHHs are analyzed in the human Ang2/hTie2-Fc (see Example 5.1; FIG. 35-1), mouse Ang2/mTie2-Fc (see Example 5.2; FIG. 35-2) and cyno Ang2/cTie2-Fc (see Example 5.2; FIG. 35-3) competition ELISA. The human assay is also performed after incubation of the VHH with 0.5 µM human serum albumin. Additionally, bispecific VHHs are tested in the hAng 1/hTie2 competition ELISA (see Example 5.3; FIG. 36) and the Ang2 mediated HUVEC survival assay (see Example 5.5; FIG. 37). A summary of $IC_{50}$ values and % inhibition is shown in FIG. 38.

Affinities of VEGFANGBII00022-25-28 for human, mouse, cyno and rat Ang2 (see Example 5.4) have been determined and are shown in Table 47.

TABLE 47

| Affinity KD of purified VHHs for recombinant human, cyno, mouse and rat Ang2 | | | | | | |
|---|---|---|---|---|---|---|
| | $k_a$ (1/Ms) | $k_d$ (1/s) | $K_D$ (M) | $k_a$ (1/Ms) | $k_d$ (1/s) | $K_D$ (M) |
| | human Ang2-FLD | | | cyno Ang2-FLD | | |
| VEGFANGBII00022 | 9.7E+05 | 1.5E−05 | 1.6E−11 | 1.5E+06 | 1.3E−05 | 8.1E−12 |
| VEGFANGBII00025 | 2.7E+06 | 1.2E−02 | 4.5E−09 | 4.3E+06 | 1.1E−02 | 2.7E−09 |
| VEGFANGBII00028 | 5.9E+05 | 9.6E−04 | 1.6E−09 | 8.4E+05 | 8.7E−04 | 1.0E−09 |
| | mouse Ang2-FLD | | | rat Ang2-FLD | | |
| VEGFANGBII00022 | 5.5E+05 | 2.8E−05 | 5.1E−11 | 3.9E+05 | 3.8E−05 | 9.9E−11 |
| VEGFANGBII00025 | 1.3E+06 | 1.4E−02 | 1.1E−08 | 8.7E+05 | 2.9E−02 | 3.3E−08 |
| VEGFANGBII00028 | 3.6E+05 | 2.0E−03 | 5.6E−09 | 2.5E+05 | 3.1E−03 | 1.2E−08 |

Affinities of VEGFANGBII00022-25-28 for human, mouse and cyno serum albumin have been determined (Example 11) and are shown in Table 48. The affinity constant $K_D$ is calculated from resulting association and dissociation rate constants $k_a$ and $k_d$ (Table 48).

TABLE 48

Affinity KD (nM) of purified VHHs for recombinant human, mouse and cyno serum albumin using (A) 1:1 interaction model or (B) heterogeneous ligand model (A)

| | HSA | | | CSA | | | MSA | | |
|---|---|---|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) |
| ALB11 | 5.6E+05 | 1.9E−03 | 4 | 4.5E+05 | 1.7E−03 | 4 | 5.9E+05 | 3.0E−02 | 51 |
| VEGFANGBII00022 | 6.7E+05 | 6.0E−03 | 9 | 6.2E+05 | 5.4E−03 | 9 | 5.2E+05 | 5.4E−03 | 150 |
| VEGFANGBII00025 | 5.6E+05 | 5.6E−03 | 12 | 4.3E+05 | 5.1E−03 | 12 | — | — | — |
| VEGFANGBII00028 | 5.6E+05 | 5.8E−03 | 10 | 5.2E+05 | 5.3E−03 | 10 | — | — | — |

(B)

| | MSA | | | | | |
|---|---|---|---|---|---|---|
| | $k_{a1}$ (1/Ms) | $k_{d1}$ (1/s) | $k_{a2}$ (1/s) | $k_{d2}$ (1/s) | $K_{D1}$ (nM) | $K_{D2}$ (nM) |
| VEGFANGBII00025 | 6.2E+05 | 9.9E−02 | 4.7E+04 | 5.7E−04 | 160 * | 12 |
| VEGFANGBII00028 | 5.9E+04 | 6.9E−04 | 5.7E+05 | 9.4E−02 | 12 | 160 * |

* describes 70% or more of the interaction

TABLE 49

Ang2-binding components
(1D01 (SEQ ID No: 214 (CDRs 1-3 disclosed as SEQ ID NOS 224-226, respectively) (FRs 1-4 disclosed as SEQ ID NOS 689, 676, 677 and 603, respectively)); 7G08 (SEQ ID No: 215 (CDRs 1-3 disclosed as SEQ ID NOS 227-229, respectively) (FRs 1-4 disclosed as SEQ ID NOS 678, 679, 680 and 603, respectively)); 027 (SEQ ID No: 216 (CDRs 1-3 disclosed as SEQ ID NOS 230-232, respectively) (FRs 1-4 disclosed as SEQ ID NOS 681, 682, 683 and 603, respectively)); 00042 (SEQ ID No: 217 (CDRs 1-3 disclosed as SEQ ID NOS 233-235, respectively) (FRs 1-4 disclosed as SEQ ID NOS 684, 694, 685 and 664, respectively)); 00050 (SEQ DI No: 218 (CDRs 1-3 disclosed as SEQ ID NOS 224, 237, and 226, respectively) (FRs 1-4 disclosed as SEQ ID NOS 686, 694, 685 and 664, respectively); 00045 (SEQ ID No: 219 (CDRs 1-3 disclosed as SEQ ID NOS 227, 240, and 241, respectively) (FRs 1-4 disclosed as SEQ ID NOS 693, 694, 687 and 664, respectively)); 00921 (SEQ ID No: 220 (CDRs 1-3 disclosed as SEQ ID NOS 242-244, respectively) (FRs 1-4 disclosed as SEQ ID NOS 686, 694, 685 and 664, respectively)); 00928 (SEQ ID No: 221 (CDRs 1-3 disclosed as SEQ ID NOS 245-247, respectively) (FRs 1-4 disclosed as SEQ ID NOS 693, 694, 687 and 664, respectively)); 00938 (SEQ ID No: 222 (CDRs 1-3 disclosed as SEQ ID NOS 248-250, respectively) (FRs 1-4 disclosed as SEQ ID NOS 688, 694, 685 and 664, respectively)); 00956 (SEQ ID No: 223 (CDRs 1-3 disclosed as SEQ ID NOS 251-253, respectively) (FRs 1-4 disclosed as SEQ ID NOS 684, 694, 685 and 664, respectively)).

| | FR1 | CDR1 | FR2 | CDR2 |
|---|---|---|---|---|
| 1D01 | EVQLVESGGGLVQAGGSLRLSCAASGFTFD | DYALG | WFRQAAGKEREGVS | CIRCSDGSTYYADSVKG |
| 7G08 | EVQLVESGGGLVQPGGSLRLSCAASGFALD | YYAIG | WFRQVPGKEREGVS | CISSSDGITYYVDSVKG |
| 027 | EVQLVESGGGLVQAGGSLRLSCAASGFTLD | DYAIG | WFRQAPGKEREGVS | CIRDSDGSTYYADSVKG |

| | FR3 | CDR3 | FR4 |
|---|---|---|---|
| 1D01 | RFTISSDNAKNTVYLQMNSLKPEDTAVYYCAA | SIVPRSKLEPYEYDA | WGQGTQVTVSS |
| 7G08 | RFTISRDNAKNTVYLQMNSLKPEDTAVYYCAT | DSGGYIDYDCMGLGYDY | WGQGTQVTVSS |
| 027 | RFTISSDNDKNTVYLQMNSLKPEDTAVYYCAA | VPAGRLRFGEQWYPLYEYDA | WGQGTQVTVSS |

| | FR1 | CDR1 | FR2 | CDR2 |
|---|---|---|---|---|
| 00042 | EVQLVESGGGLVQPGGSLRLSCAASGFTLD | DYAIG | WFRQAPGKEREGVS | SIRDNDGSTYYADSVKG |
| 00050 | EVQLVESGGGLVQPGGSLRLSCAASGFTFD | DYALG | WFRQAPGKEREGVS | CIRCSDGSTYYADSVKG |
| 00045 | EVQLVESGGGLVQPGGSLRLSCAASGFALD | YYAIG | WFRQAPGKEREGVS | CISSSDGITYYADSVKG |

| | FR3 | CDR3 | FR4 |
|---|---|---|---|
| 00042 | RFTISSDNSKNTVYLQMNSLRPEDTAVYYCAA | VPAGRLRFGEQWYPLYEYDA | WGQGTLVTVSS |
| 00050 | RFTISSDNSKNTVYLQMNSLRPEDTAVYYCAA | SIVPRSKLEPYEYDA | WGQGTLVTVSS |
| 00045 | RFTISRDNSKNTVYLQMNSLRPEDTAVYYCAT | DSGGYIDYDCMGLGYDY | WGQGTLVTVSS |

| | FR1 | CDR1 | FR2 | CDR2 |
|---|---|---|---|---|
| 00921 | EVQLVESGGGLVQPGGSLRLSCAASGFTFD | DYALG | WFRQAPGKEREGVS | CIRCSGGSTYYADSVKG |
| 00928 | EVQLVESGGGLVQPGGSLRLSCAASGFALD | YYAIG | WFRQAPGKEREGVS | CISSSGGITYYADSVKG |
| 00938 | EVQLVESGGGLVQPGGSLRLSCAVSGITLD | DYAIG | WFRQAPGKEREGVS | AIRSSGGSTYYADSVKG |
| 00956 | EVQLVESGGGLVQPGGSLRLSCAASGFTLD | DYAIG | WFRQAPGKEREGVS | AIRSSGGSTYYADSVKG |

| | FR3 | CDR3 | FR4 |
|---|---|---|---|
| 00921 | RFTISSDNSKNTVYLQMNSLRPEDTAVYYCAA | SIVPRSKLEPYEYDA | WGQGTLVTVSS |
| 00928 | RFTISRDNSKNTVYLQMNSLRPEDTAVYYCAT | DSGGYIDYDCSGLGYDY | WGQGTLVTVSS |
| 00938 | RFTISSDNSKNTVYLQMNSLRPEDTAVYYCAA | VPAGRLRYGEQWYPIYEYDA | WGQGTLVTVSS |
| 00956 | RFTISSDNSKNTVYLQMNSLRPEDTAVYYCAA | VPAGRLRFGEQWYPLYEYDA | WGQGTLVTVSS |

The invention claimed is:

1. A method of inhibiting VEGF- and Ang2-mediated effects on angiogenesis comprising administering to a patient an effective amount of a pharmaceutical composition comprising a binding molecule comprising:

at least one VEGF-binding component, at least one serum albumin binding component, and at least one Angiopoietin-2 (Ang2) binding component, wherein said VEGF-, serum albumin and Ang2-binding components are immunoglobulin single variable domains, each immunoglobulin single variable domain consisting of four framework regions and three complementarity determining regions (CDRs), and wherein:

said VEGF binding immunoglobulin single variable domain (VEGF-binding VHH), comprises the following CDR sequences:

CDR1: SYSMG (SEQ ID NO: 450)

CDR2: AISKGGYKYDAVSLEG (SEQ ID NO: 465)

CDR3: SRAYGSSRLRLADTYEY (SEQ ID NO: 4)

said serum albumin binding immunoglobulin single variable domain (serum albumin-binding VHH), comprises the following CDR sequences:

CDR1: SFGMS (SEQ ID NO:255)

CDR2: SISGSGSDTLYADSVKG (SEQ ID NO:256)

CDR3: GGSLSR (SEQ ID NO:257); and said Ang2-binding immunoglobulin single variable domain (Ang2-binding VHH), comprises the following CDR sequences:

CDR1: DYAIG (SEQ ID NO:248)

CDR2: AIRSSGGSTYYADSVKG (SEQ ID NO:249)

CDR3: VPAGRLRYGEQWYPIYEYDA (SEQ ID NO:250).

2. The method of claim 1, wherein said VEGF-binding VHH has the amino acid sequence shown in SEQ ID NO: 57.

3. The method of claim 1, wherein said serum albumin-binding VHH has the amino acid sequence shown in SEQ ID NO: 254.

4. The method of claim 1, wherein said Ang2-binding VHH has the amino acid sequence shown in SEQ ID NO: 222.

5. The method of claim 1, wherein said serum albumin binding VHH has the amino acid sequence shown in SEQ ID NO: 254 and wherein said Ang2-binding VHH has the amino acid sequence shown in SEQ ID NO: 222.

* * * * *

SEQUENCE LISTING

<160> NUMBER OF SEQ ID NOS: 694

<210> SEQ ID NO 1
<211> LENGTH: 17
<212> TYPE: PRT
<213> ORGANISM: Lama glama
<220> FEATURE:
<221> NAME/KEY: MOD_RES
<222> LOCATION: (5)..(5)
<223> OTHER INFORMATION: Gly or Ala
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (12)..(12)
<223> OTHER INFORMATION: Gly, Ala or Pro
<220> FEATURE:
<221> NAME/KEY: MOD_RES
<222> LOCATION: (13)..(13)
<223> OTHER INFORMATION: Asp or Gly
<220> FEATURE:
<221> NAME/KEY: MOD_RES
<222> LOCATION: (16)..(16)
<223> OTHER INFORMATION: Asp or Glu

<400> SEQUENCE: 1

```
Ser Arg Ala Tyr Xaa Ser Xaa Arg Leu Arg Leu Xaa Xaa Thr Tyr Xaa
1               5                   10                  15

Tyr
```

<210> SEQ ID NO 2
<211> LENGTH: 17
<212> TYPE: PRT
<213> ORGANISM: Lama glama

<400> SEQUENCE: 2

```
Ser Arg Ala Tyr Gly Ser Ser Arg Leu Arg Leu Gly Asp Thr Tyr Asp
1               5                   10                  15

Tyr
```

<210> SEQ ID NO 3
<211> LENGTH: 17
<212> TYPE: PRT
<213> ORGANISM: Lama glama

<400> SEQUENCE: 3

```
Ser Arg Ala Tyr Gly Ser Ser Arg Leu Arg Leu Ala Asp Thr Tyr Asp
1               5                   10                  15

Tyr
```

<210> SEQ ID NO 4
<211> LENGTH: 17
<212> TYPE: PRT
<213> ORGANISM: Lama glama

<400> SEQUENCE: 4

```
Ser Arg Ala Tyr Gly Ser Ser Arg Leu Arg Leu Ala Asp Thr Tyr Glu
1               5                   10                  15

Tyr
```

<210> SEQ ID NO 5
<211> LENGTH: 17
<212> TYPE: PRT
<213> ORGANISM: Lama glama

<400> SEQUENCE: 5

Ser Arg Ala Tyr Gly Ser Gly Arg Leu Arg Leu Ala Asp Thr Tyr Asp
1 5 10 15

Tyr

<210> SEQ ID NO 6
<211> LENGTH: 17
<212> TYPE: PRT
<213> ORGANISM: Lama glama

<400> SEQUENCE: 6

Ser Arg Ala Tyr Ala Ser Ser Arg Leu Arg Leu Ala Asp Thr Tyr Asp
1 5 10 15

Tyr

<210> SEQ ID NO 7
<211> LENGTH: 17
<212> TYPE: PRT
<213> ORGANISM: Lama glama

<400> SEQUENCE: 7

Ser Arg Ala Tyr Gly Ser Ser Arg Leu Arg Leu Pro Asp Thr Tyr Asp
1 5 10 15

Tyr

<210> SEQ ID NO 8
<211> LENGTH: 17
<212> TYPE: PRT
<213> ORGANISM: Lama glama

<400> SEQUENCE: 8

Ser Arg Ala Tyr Gly Ser Ser Arg Leu Arg Leu Pro Gly Thr Tyr Asp
1 5 10 15

Tyr

<210> SEQ ID NO 9
<211> LENGTH: 126
<212> TYPE: PRT
<213> ORGANISM: Lama glama

<400> SEQUENCE: 9

Glu Val Gln Leu Val Glu Ser Gly Gly Gly Leu Val Gln Pro Gly Asp
1 5 10 15

Ser Leu Lys Leu Ser Cys Ala Phe Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Ser Ser Gly Gly Tyr Ile Tyr Asp Ser Val Ser Leu
50 55 60

Glu Gly Arg Phe Thr Ile Ser Arg Asp Asn Thr Lys Asn Thr Val Tyr
65 70 75 80

Leu Gln Thr Pro Ser Leu Lys Pro Glu Asp Thr Ala Asp Tyr Tyr Cys
85 90 95

Ala Ala Ser Arg Ala Tyr Gly Ser Ser Arg Leu Arg Leu Ala Asp Thr
100 105 110

Tyr Asp Tyr Trp Gly Gln Gly Thr Gln Val Thr Val Ser Ser
115 120 125

<210> SEQ ID NO 10
<211> LENGTH: 125
<212> TYPE: PRT
<213> ORGANISM: Lama glama

<400> SEQUENCE: 10

```
Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Ala Trp Phe Arg Gln Ala Gln Gly Lys Glu Arg Glu Phe Val
        35                  40                  45

Val Ala Ile Ser Ser Gly Gly Phe Ile Tyr Asp Ala Val Ser Leu Glu
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
        115                 120                 125
```

<210> SEQ ID NO 11
<211> LENGTH: 126
<212> TYPE: PRT
<213> ORGANISM: Lama glama

<400> SEQUENCE: 11

```
Glu Val Gln Leu Val Glu Ser Gly Gly Gly Leu Val Gln Pro Gly Asp
1               5                   10                  15

Ser Leu Lys Leu Ser Cys Ala Ala Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Thr Pro Ser Leu Lys Pro Glu Asp Thr Ala Val Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125
```

<210> SEQ ID NO 12
<211> LENGTH: 126
<212> TYPE: PRT
<213> ORGANISM: Lama glama

<400> SEQUENCE: 12

```
Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Gln Gly Lys Glu Arg Glu Phe Val
```

```
        35                  40                  45

Val Ala Ile Ser Ser Ser Gly Asn Tyr Lys Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Ile Asn Ser Leu Lys Pro Glu Asp Thr Ala Val Tyr Tyr Cys
                85                  90                  95

Ala Ala Ser Arg Ala Tyr Gly Ser Ser Arg Leu Arg Leu Gly Asp Thr
            100                 105                 110

Tyr Asp Tyr Trp Gly Gln Gly Thr Gln Val Thr Val Ser Ser
        115                 120                 125


<210> SEQ ID NO 13
<211> LENGTH: 125
<212> TYPE: PRT
<213> ORGANISM: Lama glama

<400> SEQUENCE: 13

Glu Val Gln Leu Val Glu Ser Gly Gly Gly Leu Val Gln Pro Gly Asp
1               5                   10                  15

Ser Leu Lys Leu Ser Cys Val Ala Ser Gly Arg Thr Ser Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Gly Gly Ser Ile Tyr Asp Ser Val Ser Leu Gln
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Ala Ser Ser Arg Leu Arg Leu Ala Asp Thr Tyr
            100                 105                 110

Asp Tyr Trp Gly Gln Gly Thr Gln Val Thr Val Ser Ser
        115                 120                 125


<210> SEQ ID NO 14
<211> LENGTH: 125
<212> TYPE: PRT
<213> ORGANISM: Lama glama

<400> SEQUENCE: 14

Glu Val Gln Leu Val Glu Ser Gly Gly Gly Leu Val Gln Pro Gly Asp
1               5                   10                  15

Ser Leu Lys Leu Ser Cys Val Ala Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Gly Gly Tyr Ile Tyr Asp Ser Val Ser Leu Gln
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
```

115 120 125

<210> SEQ ID NO 15
<211> LENGTH: 125
<212> TYPE: PRT
<213> ORGANISM: Lama glama

<400> SEQUENCE: 15

Glu Val Gln Leu Val Glu Ser Gly Gly Gly Leu Val Gln Pro Gly Asp
1 5 10 15

Ser Leu Lys Leu Ser Cys Ala Phe Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Ser Gly Gly Phe Ile Tyr Asp Ala Val Ser Leu Glu
50 55 60

Gly Arg Phe Thr Ile Ser Arg Asp Asn Thr Lys Asn Thr Val Tyr Leu
65 70 75 80

Gln Thr Pro Ser Leu Lys Pro Glu Asp Thr Ala Val Tyr Tyr Cys Ala
85 90 95

Ala Ser Arg Ala Tyr Gly Ser Ser Arg Leu Arg Leu Ala Asp Thr Tyr
100 105 110

Asp Tyr Trp Gly Gln Gly Thr Gln Val Thr Val Ser Ser
115 120 125

<210> SEQ ID NO 16
<211> LENGTH: 125
<212> TYPE: PRT
<213> ORGANISM: Lama glama

<400> SEQUENCE: 16

Glu Val Gln Leu Val Glu Ser Gly Gly Gly Leu Val Gln Thr Gly Asp
1 5 10 15

Ser Leu Arg Leu Ser Cys Val Ala Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Asn Gly Gly Tyr Lys Tyr Asp Ser Val Ser Leu Glu
50 55 60

Gly Arg Phe Thr Ile Ser Arg Asp Asn Thr Lys Asn Thr Val Tyr Leu
65 70 75 80

Gln Ile Asn Ser Leu Lys Pro Glu Asp Thr Ala Val Tyr Tyr Cys Ala
85 90 95

Ala Ser Arg Ala Tyr Gly Ser Ser Arg Leu Arg Leu Ala Asp Thr Tyr
100 105 110

Asp Tyr Trp Gly Gln Gly Thr Gln Val Thr Val Ser Ser
115 120 125

<210> SEQ ID NO 17
<211> LENGTH: 126
<212> TYPE: PRT
<213> ORGANISM: Lama glama

<400> SEQUENCE: 17

Glu Val Gln Leu Val Glu Ser Gly Gly Gly Leu Val Gln Pro Gly Asp
1 5 10 15

Ser Leu Lys Leu Ser Cys Ala Phe Ser Gly Arg Thr Phe Gly Ser Tyr
20 25 30

```
Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Ser Lys Asn Thr Val Tyr
65                  70                  75                  80

Leu Gln Thr Pro Ser Leu Lys Pro Glu Asp Thr Ala Val Tyr Tyr Cys
                85                  90                  95

Ala Ala Ser Arg Ala Tyr Gly Ser Ser Arg Leu Arg Leu Pro Asp Thr
            100                 105                 110

Tyr Asp Tyr Trp Gly Gln Gly Thr Gln Val Thr Val Ser Ser
        115                 120                 125


<210> SEQ ID NO 18
<211> LENGTH: 125
<212> TYPE: PRT
<213> ORGANISM: Lama glama

<400> SEQUENCE: 18

Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser
        115                 120                 125


<210> SEQ ID NO 19
<211> LENGTH: 125
<212> TYPE: PRT
<213> ORGANISM: Lama glama

<400> SEQUENCE: 19

Glu Val Gln Leu Val Glu Ser Gly Gly Gly Leu Val Gln Pro Gly Asp
1               5                   10                  15

Ser Leu Arg Leu Ser Cys Ala Phe Ser Gly Arg Thr Phe Ser Ser Tyr
            20                  25                  30

Ser Met Ala Trp Phe Arg Gln Ala Gln Gly Lys Glu Arg Glu Phe Val
        35                  40                  45

Val Ala Ile Ser Ser Gly Gly Phe Ile Tyr Asp Ala Val Ser Leu Glu
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110
```

```
Asp Tyr Trp Gly Gln Gly Thr Gln Val Thr Val Ser Ser
        115                 120                 125


<210> SEQ ID NO 20
<211> LENGTH: 125
<212> TYPE: PRT
<213> ORGANISM: Lama glama

<400> SEQUENCE: 20

Glu Val Gln Leu Val Glu Ser Glu Gly Gly Leu Val Gln Pro Gly Asp
1               5                   10                  15

Ser Leu Lys Leu Ser Cys Val Ala Ser Gly Arg Thr Ser Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Gly Gly Tyr Ile Tyr Asp Ser Val Ser Leu Gln
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
        115                 120                 125


<210> SEQ ID NO 21
<211> LENGTH: 126
<212> TYPE: PRT
<213> ORGANISM: Lama glama

<400> SEQUENCE: 21

Glu Met Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Thr Pro Ser Leu Lys Pro Glu Asp Thr Ala Asp Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125


<210> SEQ ID NO 22
<211> LENGTH: 126
<212> TYPE: PRT
<213> ORGANISM: Lama glama

<400> SEQUENCE: 22

Glu Val Gln Leu Val Glu Ser Gly Gly Gly Leu Val Gln Ala Gly Asp
1               5                   10                  15
```

```
Ser Leu Arg Leu Ser Cys Ala Ala Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Asn Tyr Lys Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Ile Asn Ser Leu Lys Pro Lys Asp Thr Ala Val Tyr Tyr Cys
                85                  90                  95

Ala Ala Ser Arg Ala Tyr Gly Ser Ser Arg Leu Arg Leu Gly Asp Thr
            100                 105                 110

Tyr Asp Tyr Trp Gly Gln Gly Thr Gln Val Thr Val Ser Ser
        115                 120                 125


<210> SEQ ID NO 23
<211> LENGTH: 126
<212> TYPE: PRT
<213> ORGANISM: Lama glama

<400> SEQUENCE: 23

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Gly Gly Gly Tyr Ile Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Thr Pro Ser Leu Lys Pro Glu Asp Thr Ala Asp Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125


<210> SEQ ID NO 24
<211> LENGTH: 126
<212> TYPE: PRT
<213> ORGANISM: Lama glama

<400> SEQUENCE: 24

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Gly Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Ser Lys Asn Thr Val Tyr
65                  70                  75                  80

Leu Gln Thr Pro Ser Leu Lys Pro Glu Asp Thr Ala Val Tyr Tyr Cys
                85                  90                  95
```

```
Ala Ala Ser Arg Ala Tyr Gly Ser Ser Arg Leu Arg Leu Pro Gly Thr
            100                 105                 110

Tyr Asp Tyr Trp Gly Gln Gly Thr Gln Val Thr Val Ser Ser
        115                 120                 125


<210> SEQ ID NO 25
<211> LENGTH: 125
<212> TYPE: PRT
<213> ORGANISM: Lama glama

<400> SEQUENCE: 25

Glu Val Gln Leu Val Glu Ser Gly Gly Gly Leu Val Gln Pro Gly Asp
1               5                   10                  15

Ser Leu Lys Leu Ser Cys Val Ala Ser Gly Arg Thr Ser Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Gly Gly Tyr Ile Tyr Asp Ser Val Ser Leu Gln
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
        115                 120                 125


<210> SEQ ID NO 26
<211> LENGTH: 125
<212> TYPE: PRT
<213> ORGANISM: Lama glama

<400> SEQUENCE: 26

Glu Val Gln Leu Val Glu Ser Gly Gly Gly Leu Val Gln Thr Gly Asp
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Gly Gly Tyr Lys Tyr Asp Ser Val Ser Leu Glu
    50                  55                  60

Gly Arg Phe Thr Ile Ser Arg Asp Asn Thr Gln Asn Thr Val Tyr Leu
65                  70                  75                  80

Gln Ile Asn Ser Leu Lys Pro Glu Asp Thr Ala Val Tyr Tyr Cys Ala
                85                  90                  95

Ala Ser Arg Ala Tyr Gly Ser Gly Arg Leu Arg Leu Ala Asp Thr Tyr
            100                 105                 110

Asp Tyr Trp Gly Gln Gly Thr Gln Val Thr Val Ser Ser
        115                 120                 125


<210> SEQ ID NO 27
<211> LENGTH: 125
<212> TYPE: PRT
<213> ORGANISM: Lama glama

<400> SEQUENCE: 27

Glu Val Gln Leu Val Glu Ser Gly Gly Gly Leu Val Gln Pro Gly Asp
```

```
1               5                   10                  15

Ser Leu Lys Leu Ser Cys Val Ala Ser Gly Arg Thr Ser Ser Ser Tyr
            20                  25                  30

Ser Met Gly Trp Phe Arg Gln Ala Gln Gly Gln Glu Arg Glu Phe Val
        35                  40                  45

Val Ala Ile Ser Ser Gly Gly Tyr Ile Tyr Asp Ser Val Ser Leu Gln
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
        115                 120                 125


<210> SEQ ID NO 28
<211> LENGTH: 125
<212> TYPE: PRT
<213> ORGANISM: Lama glama

<400> SEQUENCE: 28

Glu Val Gln Leu Val Glu Ser Gly Gly Gly Leu Val Gln Pro Gly Asp
1               5                   10                  15

Ser Leu Lys Leu Ser Cys Ile Ala Ser Gly Arg Thr Ser Ser Ser Tyr
            20                  25                  30

Ser Met Gly Trp Phe Arg Gln Ala Gln Gly Gln Glu Arg Glu Phe Val
        35                  40                  45

Val Ala Ile Ser Ser Gly Gly Tyr Ile Tyr Asp Ser Val Ser Leu Gln
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
        115                 120                 125


<210> SEQ ID NO 29
<211> LENGTH: 126
<212> TYPE: PRT
<213> ORGANISM: Lama glama

<400> SEQUENCE: 29

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Asn Tyr Lys Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Ile Asn Ser Leu Lys Pro Glu Asp Thr Ala Val Tyr Tyr Cys
```

```
                85                  90                  95

Ala Ala Ser Arg Ala Tyr Gly Ser Ser Arg Leu Arg Leu Gly Asp Thr
            100                 105                 110

Tyr Asp Tyr Trp Gly Gln Gly Thr Arg Val Thr Val Ser Ser
        115                 120                 125


<210> SEQ ID NO 30
<211> LENGTH: 126
<212> TYPE: PRT
<213> ORGANISM: Lama glama

<400> SEQUENCE: 30

Glu Val Gln Leu Val Glu Ser Gly Gly Gly Leu Val Gln Thr Gly Asp
1               5                   10                  15

Ser Leu Arg Leu Ser Cys Ala Ala Ser Gly Gly Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Thr Pro Ser Leu Lys Pro Glu Asp Thr Ala Asp Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125


<210> SEQ ID NO 31
<211> LENGTH: 126
<212> TYPE: PRT
<213> ORGANISM: Lama glama

<400> SEQUENCE: 31

Glu Val Gln Leu Val Glu Ser Gly Gly Gly Leu Val Gln Pro Gly Asp
1               5                   10                  15

Pro Leu Lys Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Thr Pro Ser Leu Lys Pro Glu Asp Thr Ala Asp Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125


<210> SEQ ID NO 32
<211> LENGTH: 126
<212> TYPE: PRT
<213> ORGANISM: Lama glama

<400> SEQUENCE: 32
```

```
Glu Val Pro Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Asn Tyr Lys Tyr Asp Ser Ala Ser Leu
    50                  55                  60

Glu Gly Arg Phe Thr Ile Ser Arg Asp Asn Thr Lys Asn Thr Val Tyr
65                  70                  75                  80

Leu Gln Ile Asn Ser Leu Lys Pro Glu Asp Thr Ala Val Tyr Tyr Cys
                85                  90                  95

Ala Ala Ser Arg Ala Tyr Gly Ser Ser Arg Leu Arg Leu Gly Asp Thr
            100                 105                 110

Tyr Asp Tyr Trp Gly Gln Gly Thr Gln Val Thr Val Ser Ser
        115                 120                 125


<210> SEQ ID NO 33
<211> LENGTH: 125
<212> TYPE: PRT
<213> ORGANISM: Lama glama

<400> SEQUENCE: 33

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Ala Trp Phe Arg Gln Ala Gln Gly Lys Glu Arg Glu Phe Val
        35                  40                  45

Val Ala Ile Ser Ser Gly Gly Phe Ile Tyr Asp Ala Val Ser Leu Glu
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Gly Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
        115                 120                 125


<210> SEQ ID NO 34
<211> LENGTH: 126
<212> TYPE: PRT
<213> ORGANISM: Lama glama

<400> SEQUENCE: 34

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Thr Lys Asn Ala Val Tyr
65                  70                  75                  80
```

```
Leu Gln Thr Pro Ser Leu Lys Pro Glu Asp Thr Ala Asp Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125


<210> SEQ ID NO 35
<211> LENGTH: 126
<212> TYPE: PRT
<213> ORGANISM: Lama glama

<400> SEQUENCE: 35

Glu Val Gln Leu Met Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Thr Pro Ser Leu Lys Pro Glu Asp Thr Ala Asp Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125


<210> SEQ ID NO 36
<211> LENGTH: 125
<212> TYPE: PRT
<213> ORGANISM: Lama glama

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Gly Gly Phe Ile Tyr Asp Ala Val Ser Leu Glu
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
        115                 120                 125


<210> SEQ ID NO 37
<211> LENGTH: 125
<212> TYPE: PRT
<213> ORGANISM: Lama glama
```

<400> SEQUENCE: 37

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Ala Trp Phe Arg Gln Ala Gln Gly Lys Glu Arg Glu Phe Val
        35                  40                  45

Val Ala Ile Ser Ser Gly Gly Phe Ile Tyr Asp Ala Val Ser Leu Glu
    50                  55                  60

Gly Arg Phe Thr Ile Ser Arg Glu Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
        115                 120                 125

<210> SEQ ID NO 38
<211> LENGTH: 126
<212> TYPE: PRT
<213> ORGANISM: Lama glama

<400> SEQUENCE: 38

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Met Pro Ser Leu Lys Pro Glu Asp Thr Ala Asp Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125

<210> SEQ ID NO 39
<211> LENGTH: 126
<212> TYPE: PRT
<213> ORGANISM: Lama glama

<400> SEQUENCE: 39

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

```
Glu Gly Arg Phe Thr Ile Ser Arg Asp Asn Thr Lys Asn Thr Val Tyr
65                  70                  75                  80

Leu Gln Thr Pro Ser Leu Lys Pro Glu Asp Thr Ala Val Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125


<210> SEQ ID NO 40
<211> LENGTH: 125
<212> TYPE: PRT
<213> ORGANISM: Lama glama

<400> SEQUENCE: 40

Glu Val Gln Leu Val Glu Ser Gly Gly Gly Leu Val Gln Pro Gly Asp
1               5                   10                  15

Ser Leu Lys Leu Ser Cys Val Ala Ser Gly Arg Thr Ser Ser Ser Tyr
            20                  25                  30

Ser Val Gly Trp Phe Arg Gln Ala Gln Gly Lys Glu Arg Glu Phe Val
        35                  40                  45

Val Ala Ile Ser Ser Gly Gly Tyr Ile Tyr Asp Ser Val Ser Leu Gln
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Gly Ser Ser Arg Leu Arg Leu Ala Asp Thr Tyr
            100                 105                 110

Asp Tyr Trp Gly Gln Gly Thr Gln Val Thr Val Ser Ser
        115                 120                 125


<210> SEQ ID NO 41
<211> LENGTH: 126
<212> TYPE: PRT
<213> ORGANISM: Lama glama

<400> SEQUENCE: 41

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Thr Lys Asn Thr Val Tyr
65                  70                  75                  80

Leu Gln Thr Pro Ser Leu Lys Pro Glu Asp Ala Ala Asp Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125


<210> SEQ ID NO 42
<211> LENGTH: 126
```

<212> TYPE: PRT
<213> ORGANISM: Lama glama

<400> SEQUENCE: 42

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu
    50                  55                  60

Glu Gly Arg Phe Thr Ile Ser Arg Asp Asn Thr Arg Asn Thr Val Tyr
65                  70                  75                  80

Leu Gln Thr Pro Ser Leu Lys Pro Glu Asp Thr Ala Asp Tyr Tyr Cys
                85                  90                  95

Ala Ala Ser Arg Ala Tyr Gly Ser Ser Arg Leu Arg Leu Ala Asp Thr
            100                 105                 110

Tyr Asp Tyr Trp Gly Gln Gly Thr Gln Val Thr Val Ser Ser
        115                 120                 125

<210> SEQ ID NO 43
<211> LENGTH: 125
<212> TYPE: PRT
<213> ORGANISM: Lama glama

<400> SEQUENCE: 43

Glu Val Gln Leu Val Glu Ser Gly Gly Gly Leu Val Gln Ala Gly Gly
1               5                   10                  15

Ser Leu Arg Leu Ser Cys Ala Phe Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Gly Gly Tyr Lys Tyr Asp Ala Val Ser Leu Glu
    50                  55                  60

Gly Arg Phe Thr Ile Ser Arg Asp Asn Thr Lys Asn Thr Val Tyr Leu
65                  70                  75                  80

Gln Thr Pro Ser Leu Lys Pro Glu Asp Thr Ala Val Tyr Tyr Cys Ala
                85                  90                  95

Ala Ser Arg Ala Tyr Ala Ser Ser Arg Leu Arg Leu Ala Asp Thr Tyr
            100                 105                 110

Asp Tyr Trp Gly Gln Gly Thr Gln Val Thr Val Ser Ser
        115                 120                 125

<210> SEQ ID NO 44
<211> LENGTH: 126
<212> TYPE: PRT
<213> ORGANISM: Lama glama

<400> SEQUENCE: 44

Glu Val Gln Leu Val Glu Ser Gly Gly Asp Leu Val Gln Pro Gly Asp
1               5                   10                  15

Ser Leu Lys Leu Ser Cys Ala Ala Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Ser Ser Gly Gly Tyr Ile Tyr Asp Ser Val Ser Leu 50 55 60

Glu Gly Arg Phe Thr Ile Ser Arg Asp Asn Thr Lys Asn Thr Val Tyr
65 70 75 80

Leu Gln Thr Pro Ser Leu Lys Pro Glu Asp Thr Ala Val Tyr Tyr Cys
85 90 95

Ala Ala Ser Arg Ala Tyr Gly Ser Ser Arg Leu Arg Leu Ala Asp Thr
100 105 110

Tyr Asp Tyr Trp Gly Gln Gly Thr Gln Val Thr Val Ser Ser
115 120 125

<210> SEQ ID NO 45
<211> LENGTH: 126
<212> TYPE: PRT
<213> ORGANISM: Lama glama

<400> SEQUENCE: 45

Glu Val Gln Leu Val Glu Ser Glu Gly Gly Leu Val Gln Ala Gly Asp
1 5 10 15

Ser Leu Arg Leu Ser Cys Ala Ala Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Ser Ser Gly Asn Tyr Lys Tyr Asp Ser Val Ser Leu
50 55 60

Glu Gly Arg Phe Thr Ile Ser Arg Asp Asn Thr Lys Asn Thr Val Tyr
65 70 75 80

Leu Gln Ile Asn Ser Leu Lys Pro Glu Asp Thr Ala Val Tyr Tyr Cys
85 90 95

Ala Ala Ser Arg Ala Tyr Gly Ser Ser Arg Leu Arg Leu Gly Asp Thr
100 105 110

Tyr Asp Tyr Trp Gly Gln Gly Thr Gln Val Thr Val Ser Ser
115 120 125

<210> SEQ ID NO 46
<211> LENGTH: 125
<212> TYPE: PRT
<213> ORGANISM: Lama glama

<400> SEQUENCE: 46

Glu Val Gln Leu Val Glu Ser Gly Gly Gly Leu Val Gln Pro Gly Asp
1 5 10 15

Ser Leu Lys Leu Ser Cys Ala Phe Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ala Ser Gly Gly Tyr Ile Tyr Asp Ala Val Ser Leu Glu
50 55 60

Gly Arg Phe Thr Ile Ser Arg Asp Asn Thr Lys Asp Thr Val Tyr Leu
65 70 75 80

Gln Thr Pro Ser Leu Lys Pro Glu Asp Thr Ala Val Tyr Tyr Cys Ala
85 90 95

Ala Ser Arg Ala Tyr Gly Ser Ser Arg Leu Arg Leu Ala Asp Thr Tyr
100 105 110

Asp Tyr Trp Gly Gln Gly Thr Gln Val Thr Val Ser Ser
115 120 125

```
<210> SEQ ID NO 47
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama glama sequence

<400> SEQUENCE: 47

Glu Val Gln Leu Val Glu Ser Gly Gly Gly Leu Val Gln Thr Gly Gly
1               5                   10                  15

Ser Leu Arg Leu Ser Cys Glu Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser
        115                 120                 125


<210> SEQ ID NO 48
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama glama sequence

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser
        115                 120                 125


<210> SEQ ID NO 49
<211> LENGTH: 125
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: Mutated lama glama sequence

<400> SEQUENCE: 49

```
Glu Val Gln Leu Val Glu Ser Gly Gly Gly Leu Val Gln Pro Gly Gly
1               5                   10                  15

Ser Leu Arg Leu Ser Cys Glu Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser
        115                 120                 125
```

<210> SEQ ID NO 50
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama glama sequence

<400> SEQUENCE: 50

```
Glu Val Gln Leu Val Glu Ser Gly Gly Gly Leu Val Gln Thr Gly Gly
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser
        115                 120                 125
```

<210> SEQ ID NO 51
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama glama sequence

<400> SEQUENCE: 51

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Met Asn Ser Leu Arg Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Leu Val Thr Val Ser Ser
115 120 125

<210> SEQ ID NO 52
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama glama sequence

<400> SEQUENCE: 52

Glu Val Gln Leu Val Glu Ser Gly Gly Gly Leu Val Gln Pro Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Pro Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Arg Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Leu Val Thr Val Ser Ser
115 120 125

<210> SEQ ID NO 53
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama glama sequence

<400> SEQUENCE: 53

Glu Val Gln Leu Val Glu Ser Gly Gly Gly Leu Val Gln Thr Gly Gly
1 5 10 15

-continued

```
Ser Leu Arg Leu Ser Cys Glu Val Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser
        115                 120                 125
```

<210> SEQ ID NO 54
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama glama sequence

<400> SEQUENCE: 54

```
Glu Val Gln Leu Val Glu Ser Gly Gly Gly Leu Val Gln Thr Gly Asp
1               5                   10                  15

Ser Leu Arg Leu Ser Cys Ala Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser
        115                 120                 125
```

<210> SEQ ID NO 55
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama glama sequence

<400> SEQUENCE: 55

```
Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45
```

```
Val Ala Ile Ser Lys Gly Gly Tyr Lys Tyr Asp Ala Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser
        115                 120                 125


<210> SEQ ID NO 56
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama glama sequence

<400> SEQUENCE: 56

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser
        115                 120                 125


<210> SEQ ID NO 57
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama glama sequence

<400> SEQUENCE: 57

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
```

```
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser
        115                 120                 125


<210> SEQ ID NO 58
<211> LENGTH: 122
<212> TYPE: PRT
<213> ORGANISM: Lama glama

<400> SEQUENCE: 58

Glu Val Gln Leu Val Glu Ser Gly Gly Gly Leu Val Gln Ala Gly Gly
1               5                   10                  15

Ser Leu Arg Leu Ser Cys Thr Ala Ser Gly Gly Ser Phe Ser Ser Tyr
            20                  25                  30

Gly Met Gly Trp Phe Arg Gln Ser Pro Gly Lys Glu Arg Glu Phe Val
        35                  40                  45

Ser Ala Ile Ser Glu Tyr Ser Asn Thr Tyr Cys Ser Asp Ser Val Arg
    50                  55                  60

Gly Arg Phe Thr Ile Ser Arg Asp Asn Thr Lys Asn Thr Val Tyr Leu
65                  70                  75                  80

Gln Met Asn Ser Leu Thr Pro Asp Asp Thr Ala Ile Tyr Tyr Cys Ala
                85                  90                  95

Ala Ser Pro Thr Ile Leu Leu Thr Thr Glu Gln Trp Tyr Lys Tyr Trp
            100                 105                 110

Gly Gln Gly Thr Gln Val Thr Val Ser Ser
        115                 120


<210> SEQ ID NO 59
<211> LENGTH: 126
<212> TYPE: PRT
<213> ORGANISM: Lama glama

<400> SEQUENCE: 59

Glu Val Gln Leu Val Glu Ser Gly Gly Gly Leu Val Gln Ala Gly Asp
1               5                   10                  15

Ser Leu Arg Leu Ser Cys Val Ala Thr Gly Arg Thr Phe Arg Ala Ser
            20                  25                  30

Asp Met Gly Trp Phe Arg Gln Ala Pro Gly Lys Glu Arg Glu Phe Val
        35                  40                  45

Ala Ala Ile Asn Trp Ser Gly Leu Ser Thr Phe Tyr Thr Asp Ser Val
    50                  55                  60

Lys Gly Arg Phe Thr Ile Ser Arg Asp Asn Asp Asn Gly Ala Leu Tyr
65                  70                  75                  80

Leu Gln Met Asn Thr Leu Lys Pro Glu Asp Thr Ala Val Tyr Ser Cys
                85                  90                  95

Ala Ala Gly Arg Ile Pro Ser Ser Ser Arg Phe Ser Ser Pro Ala Ala
            100                 105                 110

Tyr Ala Ser Trp Gly Gln Gly Thr Gln Val Thr Val Ser Ser
        115                 120                 125


<210> SEQ ID NO 60
<211> LENGTH: 125
<212> TYPE: PRT
```

<213> ORGANISM: Lama glama

<400> SEQUENCE: 60

Glu Val Gln Leu Val Glu Ser Gly Gly Gly Leu Val Gln Ala Gly Gly
1 5 10 15

Ser Leu Arg Leu Ser Cys Thr Ala Ser Thr Ser Ile Tyr Thr Ile Thr
20 25 30

Val Met Ala Trp Phe Arg Gln Ala Pro Gly Lys Glu Arg Glu Phe Val
35 40 45

Ala Ala Ile Thr Trp Ser Ala Pro Thr Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Arg Met Asn Ser Leu Lys Pro Glu Asp Ser Ala Ile Tyr Tyr Cys
85 90 95

Ala Ala Asp Arg Phe Lys Gly Arg Ser Ile Val Thr Pro Ser Asp Tyr
100 105 110

Arg Tyr Trp Gly Gln Gly Thr Gln Val Thr Val Ser Ser
115 120 125

<210> SEQ ID NO 61
<211> LENGTH: 111
<212> TYPE: PRT
<213> ORGANISM: Lama glama

<400> SEQUENCE: 61

Glu Val Gln Leu Val Glu Ser Gly Gly Gly Leu Val Gln Pro Gly Gly
1 5 10 15

Ser Leu Arg Leu Ser Cys Ala Ala Ser Gly Ser Ala Val Gly Asp Ile
20 25 30

Thr Val Ala Trp Tyr Arg Gln Ala Pro Gly Ile Gln Arg Gln Leu Val
35 40 45

Ala Thr Ile Thr Pro Ser Gly Tyr Thr Tyr Tyr Trp Asp Phe Val Lys
50 55 60

Gly Arg Phe Thr Ile Ser Arg Asp Asn Ser Lys Asn Ile Val Tyr Leu
65 70 75 80

Gln Met Asn Ser Leu Lys Pro Glu Asp Thr Ala Ala Tyr Tyr Cys Asn
85 90 95

Thr Gln Phe Tyr Trp Gly Gln Gly Thr Gln Val Thr Val Ser Ser
100 105 110

<210> SEQ ID NO 62
<211> LENGTH: 128
<212> TYPE: PRT
<213> ORGANISM: Lama glama

<400> SEQUENCE: 62

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser Thr Asp
20 25 30

Asp Val Gly Trp Phe Arg Gln Ala Pro Gly Lys Glu Arg Glu Phe Val
35 40 45

Ala Val Ile Arg Trp Ser Thr Gly Gly Thr Tyr Thr Ser Asp Ser Val
50 55 60

Lys Gly Arg Phe Thr Leu Ser Arg Asp Asn Ala Lys Asn Thr Met Tyr
65 70 75 80

```
Leu Gln Met Asn Ser Leu Lys Pro Glu Asp Thr Ala Val Tyr Tyr Cys
                85                  90                  95

Ala Ala Arg Ser Arg Pro Leu Gly Ala Gly Ala Trp Tyr Ser Gly Glu
            100                 105                 110

Lys His Tyr Asn Tyr Trp Gly Gln Gly Thr Gln Val Thr Val Ser Ser
        115                 120                 125


<210> SEQ ID NO 63
<211> LENGTH: 121
<212> TYPE: PRT
<213> ORGANISM: Lama glama

<400> SEQUENCE: 63

Glu Val Gln Leu Val Glu Ser Gly Gly Gly Leu Ala Gln Ala Gly Asp
1               5                   10                  15

Ser Leu Arg Leu Ser Cys Ala Ala Ser Gly Arg Ser Phe Ser His Tyr
            20                  25                  30

Asn Met Gly Trp Phe Arg Gln Ala Pro Gly Lys Glu Arg Glu Phe Val
        35                  40                  45

Ala Ser Ile Arg Gly Gly Gly Gly Ser Thr Thr Tyr Ala Asn Ser Val
    50                  55                  60

Lys Asp Arg Phe Thr Ile Ser Arg Glu Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Ala Phe Tyr Arg Gly Pro Tyr Asp Tyr Asp Tyr Trp Gly
            100                 105                 110

Gln Gly Thr Gln Val Thr Val Ser Ser
        115                 120


<210> SEQ ID NO 64
<211> LENGTH: 113
<212> TYPE: PRT
<213> ORGANISM: Lama glama

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Val Ala Ser Gly Ile Arg Phe Met Ser Met
            20                  25                  30

Ala Trp Tyr Arg Gln Ala Pro Gly Lys His Arg Glu Leu Val Ala Arg
        35                  40                  45

Ile Ser Ser Gly Gly Thr Thr Ala Tyr Val Asp Ser Val Lys Gly Arg
    50                  55                  60

Phe Thr Ile Ser Arg Asp Asn Ser Lys Asn Thr Val Tyr Leu Gln Met
65                  70                  75                  80

Asn Ser Leu Lys Ala Glu Asp Thr Ala Val Tyr Tyr Cys Asn Thr Phe
                85                  90                  95

Ser Ser Arg Pro Asn Pro Trp Gly Ala Gly Thr Gln Val Thr Val Ser
            100                 105                 110

Ser


<210> SEQ ID NO 65
<211> LENGTH: 116
<212> TYPE: PRT
<213> ORGANISM: Lama glama
```

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Phe Ser Asn Asn
            20                  25                  30

Ala Met Ala Trp Tyr Arg Gln Ala Pro Gly Lys Gln Arg Glu Leu Val
        35                  40                  45

Ala Arg Ile Ser Ser Gly Gly Gly Phe Thr Tyr Tyr Leu Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Ala Tyr Arg Thr Tyr Asn Tyr Trp Gly Gln Gly Thr Gln Val
            100                 105                 110

Thr Val Ser Ser
        115

<210> SEQ ID NO 66
<211> LENGTH: 125
<212> TYPE: PRT
<213> ORGANISM: Lama glama

<400> SEQUENCE: 66

Glu Val Gln Leu Val Glu Ser Gly Gly Gly Leu Val Gln Ala Gly Gly
1               5                   10                  15

Ser Leu Arg Leu Ser Cys Ala Ala Ser Thr Ser Ile Tyr Ser Ile Thr
            20                  25                  30

Val Met Ala Trp Phe Arg Gln Ala Pro Gly Lys Glu Ser Glu Phe Val
        35                  40                  45

Ala Ala Ile Thr Trp Ser Ala Pro Ser Ser Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Ser Ala Ile Tyr Tyr Cys
                85                  90                  95

Ala Ala Asp Arg Phe Lys Gly Arg Ser Ile Val Thr Arg Ser Asp Tyr
            100                 105                 110

Lys Tyr Trp Gly Gln Gly Thr Gln Val Thr Val Ser Ser
        115                 120                 125

<210> SEQ ID NO 67
<211> LENGTH: 125
<212> TYPE: PRT
<213> ORGANISM: Lama glama

<400> SEQUENCE: 67

Glu Val Gln Leu Val Glu Ser Gly Gly Gly Leu Val Gln Ala Gly Gly
1               5                   10                  15

Ser Leu Arg Leu Ser Cys Ala Val Ser Thr Ser Ile Tyr Ser Ile Ser
            20                  25                  30

Val Met Ala Trp Phe Arg Gln Ala Pro Gly Lys Glu Arg Ala Phe Val
        35                  40                  45

Ala Ala Ile Thr Trp Ser Ala Pro Thr Thr Tyr Tyr Ala Asp Ser Val
    50                  55                  60

Lys Gly Arg Phe Thr Ile Ser Arg Asp Asn Ala Lys Asn Thr Val Tyr 65 70 75 80

Leu Gln Thr Asn Ser Leu Lys Pro Glu Asp Ser Ala Ile Tyr Tyr Cys
85 90 95

Ala Ala Asp Arg Phe Lys Gly Arg Ser Ile Val Thr Arg Ser Asp Tyr
100 105 110

Arg Tyr Trp Gly Gln Gly Thr Gln Val Thr Val Ser Ser
115 120 125

<210> SEQ ID NO 68
<211> LENGTH: 126
<212> TYPE: PRT
<213> ORGANISM: Lama glama

<400> SEQUENCE: 68

Glu Val Gln Leu Val Glu Ser Gly Gly Gly Leu Val Gln Thr Gly Gly
1 5 10 15

Ser Leu Arg Leu Ser Cys Ala Ala Ser Gly Arg Thr Phe Ser Asn Tyr
20 25 30

Ala Met Ala Trp Phe Arg Gln Ala Pro Gly Lys Glu Arg Glu Phe Val
35 40 45

Ser Ala Ile Asn Gln Arg Gly Ser Asn Thr Asn Tyr Ala Asp Ser Val
50 55 60

Lys Gly Arg Phe Thr Ile Ser Arg Asp Ser Ala Lys Asn Ser Val Phe
65 70 75 80

Leu Gln Met Asn Ser Leu Lys Pro Glu Asp Thr Ala Val Tyr Tyr Cys
85 90 95

Ala Ala Ser Thr Trp Tyr Gly Tyr Ser Thr Tyr Ala Arg Arg Glu Glu
100 105 110

Tyr Arg Tyr Trp Gly Gln Gly Thr Gln Val Thr Val Ser Ser
115 120 125

<210> SEQ ID NO 69
<211> LENGTH: 123
<212> TYPE: PRT
<213> ORGANISM: Lama glama

<400> SEQUENCE: 69

Glu Val Gln Leu Val Glu Ser Gly Gly Gly Leu Val Gln Ala Gly Gly
1 5 10 15

Ser Leu Arg Leu Ser Cys Ala Ala Ser Gly Arg Ser Phe Ser Asp Asn
20 25 30

Val Met Gly Trp Phe Arg Gln Ala Ala Gly Lys Glu Arg Glu Phe Val
35 40 45

Ala His Ile Ser Arg Gly Gly Ser Arg Thr Glu Tyr Ala Glu Ser Val
50 55 60

Lys Gly Arg Phe Thr Ile Ser Arg Asp Asn Thr Lys Lys Thr Met Tyr
65 70 75 80

Leu Gln Met Asn Ser Leu Lys Pro Glu Asp Thr Ala Val Tyr Tyr Cys
85 90 95

Ala Ala Ser Arg Ser Val Ala Leu Ala Thr Ala Arg Pro Tyr Asp Tyr
100 105 110

Trp Gly Gln Gly Thr Gln Val Thr Val Ser Ser
115 120

<210> SEQ ID NO 70
<211> LENGTH: 121
<212> TYPE: PRT

<213> ORGANISM: Lama glama

<400> SEQUENCE: 70

```
Glu Val Gln Leu Val Glu Ser Gly Gly Gly Leu Ala Gln Ala Gly Gly
1               5                   10                  15

Ser Leu Arg Leu Ser Cys Thr Thr Ser Gly Leu Thr Phe Ser Ser Tyr
            20                  25                  30

Tyr Met Gly Trp Phe Arg Gln Ala Pro Gly Lys Glu Arg Glu Phe Val
        35                  40                  45

Ala Thr Ile Ser Trp Asn Lys Ile Ser Thr Ile Tyr Thr Asp Ser Val
    50                  55                  60

Lys Gly Arg Phe Thr Val Ser Arg Asp Asn Asn Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Ala Ser Arg Pro Thr Leu Arg Ile Pro Gln Tyr Trp Gly
            100                 105                 110

Gln Gly Thr Gln Val Thr Val Ser Ser
        115                 120
```

<210> SEQ ID NO 71
<211> LENGTH: 115
<212> TYPE: PRT
<213> ORGANISM: Lama glama

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Val Arg Ser Asp
            20                  25                  30

Val Met Gly Trp Tyr Arg Gln Ala Pro Gly Lys Gln Arg Glu Leu Val
        35                  40                  45

Ala Phe Ile Arg Ser Leu Gly Ser Thr Tyr Tyr Ala Gly Ser Val Lys
    50                  55                  60

Gly Arg Phe Thr Ile Ser Arg Asp Asp Ala Ala Asn Thr Val Tyr Leu
65                  70                  75                  80

Gln Met Asn Asn Leu Lys Pro Glu Asp Thr Ala Val Tyr Tyr Cys Asn
                85                  90                  95

Ala Arg Phe Ser Gly Glu Ser Tyr Trp Gly Gln Gly Thr Pro Val Thr
            100                 105                 110

Val Ser Ser
        115
```

<210> SEQ ID NO 72
<211> LENGTH: 124
<212> TYPE: PRT
<213> ORGANISM: Lama glama

<400> SEQUENCE: 72

```
Glu Val Gln Leu Val Glu Ser Gly Gly Gly Leu Val Gln Ala Gly Gly
1               5                   10                  15

Ser Leu Arg Leu Ser Cys Ala Val Ser Gly Ser Thr Phe Gly Leu Tyr
            20                  25                  30

Ala Met Gly Trp Phe Arg Gln Ala Pro Gly Arg Glu Arg Glu Phe Leu
        35                  40                  45

Ser Ala Ile Thr Trp Ser Ala Gly Asp Thr Gln Tyr Ala Asp Ser Val
    50                  55                  60
```

Lys Gly Arg Phe Thr Ile Ser Arg Asp Asn Ala Arg Asn Thr Val Asn
65 70 75 80

Leu Gln Met Asn Gly Leu Lys Pro Glu Asp Thr Ala Val Tyr Tyr Cys
85 90 95

Ala Gly Arg Gln Trp Gly Gly Thr Tyr Tyr Tyr His Gly Ser Tyr Ala
100 105 110

Tyr Trp Gly Gln Gly Thr Gln Val Thr Val Ser Ser
115 120

<210> SEQ ID NO 73
<211> LENGTH: 113
<212> TYPE: PRT
<213> ORGANISM: Lama glama

<400> SEQUENCE: 73

Glu Val Gln Leu Val Glu Ser Gly Gly Gly Leu Val Gln Pro Gly Gly
1 5 10 15

Ser Leu Arg Leu Ser Cys Val Ala Ser Gly Ile Arg Phe Met Ser Met
20 25 30

Ala Trp Tyr Arg Gln Ala Pro Gly Lys His Arg Glu Leu Val Ala Arg
35 40 45

Ile Ser Ser Glu Gly Thr Thr Ala Tyr Val Asp Ser Val Lys Gly Arg
50 55 60

Phe Thr Ile Ser Arg Asp Asn Ser Lys Asn Thr Val Tyr Leu Gln Met
65 70 75 80

Asn Ser Leu Lys Ala Glu Asp Thr Ala Val Tyr Tyr Cys Asn Thr Phe
85 90 95

Ser Ser Arg Pro Asn Pro Trp Gly Ala Gly Thr Thr Val Thr Val Ser
100 105 110

Ser

<210> SEQ ID NO 74
<211> LENGTH: 128
<212> TYPE: PRT
<213> ORGANISM: Lama glama

<400> SEQUENCE: 74

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser Thr Asp
20 25 30

Asp Val Gly Trp Phe Arg Gln Ala Pro Gly Lys Glu Arg Glu Phe Val
35 40 45

Ala Val Ile Arg Trp Ser Thr Gly Gly Thr Tyr Thr Ser Asp Ser Val
50 55 60

Ala Gly Arg Phe Thr Leu Ser Arg Asp Asn Ala Lys Asn Thr Met Tyr
65 70 75 80

Leu Gln Met Asn Ser Leu Lys Pro Glu Asp Thr Ala Val Tyr Tyr Cys
85 90 95

Ala Ala Arg Ser Arg Pro Leu Gly Ala Gly Ala Trp Tyr Thr Gly Glu
100 105 110

Thr Arg Tyr Asp Ser Trp Gly Gln Gly Thr Gln Val Thr Val Ser Ser
115 120 125

<210> SEQ ID NO 75
<211> LENGTH: 122

<212> TYPE: PRT
<213> ORGANISM: Lama glama

<400> SEQUENCE: 75

Glu Val Gln Leu Val Glu Ser Gly Gly Gly Leu Val Gln Pro Gly Asp
1 5 10 15

Ser Leu Arg Leu Ser Cys Ala Ala Ser Gly Leu Ser Phe Ser Arg Tyr
20 25 30

Gly Met Gly Trp Phe Arg Gln Ala Pro Gly Lys Glu Arg Glu Phe Val
35 40 45

Ile Ala Ile Ser Glu Tyr Asp Asn Val Tyr Thr Ala Asp Ser Val Arg
50 55 60

Gly Arg Phe Thr Ile Ser Arg Asp Asn Ser Lys Ser Thr Val Tyr Leu
65 70 75 80

Gln Met Asn Ser Leu Lys Ser Glu Asp Thr Ala Val Tyr Tyr Cys Ala
85 90 95

Ala Ser Pro Thr Ile Leu Leu Ser Thr Asp Glu Trp Tyr Lys Tyr Trp
100 105 110

Gly Arg Gly Thr Gln Val Thr Val Ser Ser
115 120

<210> SEQ ID NO 76
<211> LENGTH: 128
<212> TYPE: PRT
<213> ORGANISM: Lama glama

<400> SEQUENCE: 76

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser Thr Asp
20 25 30

Asp Val Gly Trp Phe Arg Gln Ala Pro Gly Lys Glu Arg Glu Phe Val
35 40 45

Ala Val Ile Arg Trp Ser Thr Gly Gly Thr Tyr Thr Ser Asp Ser Val
50 55 60

Lys Gly Arg Phe Thr Leu Ser Arg Asp Asn Ala Lys Asn Thr Met Tyr
65 70 75 80

Leu Gln Met Asn Ser Leu Lys Pro Glu Asp Thr Ala Val Tyr Tyr Cys
85 90 95

Ala Ala Arg Ser Arg Pro Leu Gly Ala Gly Ala Trp Tyr Thr Gly Glu
100 105 110

Thr Arg Tyr Asn Tyr Trp Gly Gln Gly Thr Gln Val Thr Val Ser Ser
115 120 125

<210> SEQ ID NO 77
<211> LENGTH: 127
<212> TYPE: PRT
<213> ORGANISM: Lama glama

<400> SEQUENCE: 77

Glu Val Gln Leu Val Glu Ser Gly Gly Gly Leu Val Gln Ala Gly Gly
1 5 10 15

Ser Leu Ser Leu Ser Cys Ala Ala Ser Ala Arg Ala Phe Ser Asn Tyr
20 25 30

Ala Met Gly Trp Phe Arg Gln Val Pro Gly Arg Glu Arg Glu Phe Val
35 40 45

Ala Val Ile Thr Arg Ser Pro Ser Asn Thr Tyr Tyr Thr Asp Ser Val 50 55 60

Lys Gly Arg Phe Thr Ile Ser Arg Asp Asn Ala Lys Asn Ile Val Tyr
65 70 75 80

Leu Gln Met Asn Ser Leu Lys Pro Glu Asp Thr Ala Val Tyr Tyr Cys
85 90 95

Ala Ala His Tyr Trp Asn Ser Asp Ser Tyr Thr Tyr Thr Asp Ser Arg
100 105 110

Trp Tyr Asn Tyr Trp Gly Gln Gly Thr Gln Val Thr Val Ser Ser
115 120 125

<210> SEQ ID NO 78
<211> LENGTH: 124
<212> TYPE: PRT
<213> ORGANISM: Lama glama

<400> SEQUENCE: 78

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser Asn Tyr
20 25 30

Ala Met Gly Trp Phe Arg Gln Ala Pro Gly Lys Glu Arg Val Leu Val
35 40 45

Ala Asp Ile Ser Ser Ser Gly Ile Asn Thr Tyr Val Ala Asp Ala Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Ser Ala Trp Trp Tyr Ser Gln Met Ala Arg Asp Asn Tyr Arg
100 105 110

Tyr Trp Gly Gln Gly Thr Gln Val Thr Val Ser Ser
115 120

<210> SEQ ID NO 79
<211> LENGTH: 125
<212> TYPE: PRT
<213> ORGANISM: Lama glama

<400> SEQUENCE: 79

Glu Val Gln Leu Val Glu Ser Gly Gly Gly Leu Val Gln Ala Gly Gly
1 5 10 15

Ser Leu Arg Leu Ser Cys Ala Ala Ser Gly Asp Thr Leu Ser Arg Tyr
20 25 30

Ala Met Gly Trp Phe Arg Gln Ala Pro Gly Lys Glu Arg Glu Phe Val
35 40 45

Ala Ser Ile Asn Thr Ser Gly Lys Arg Thr Ser Tyr Ala Asp Ser Met
50 55 60

Lys Gly Arg Phe Ala Val Ser Arg Asp Asn Ala Lys Asn Thr Gly Tyr
65 70 75 80

Leu Gln Met Asn Ser Leu Lys Leu Glu Asp Thr Ala Thr Tyr Tyr Cys
85 90 95

Ala Ala Asp Arg Phe Phe Gly Ser Asp Ser Asn Glu Pro Arg Ala Tyr
100 105 110

Arg Tyr Trp Gly Gln Gly Thr Gln Val Thr Val Ser Ser
115 120 125

<210> SEQ ID NO 80
<211> LENGTH: 123
<212> TYPE: PRT
<213> ORGANISM: Lama glama

<400> SEQUENCE: 80

```
Glu Val Gln Leu Val Glu Ser Gly Gly Gly Leu Val Gln Ala Gly Glu
1               5                   10                  15

Ser Leu Arg Leu Ser Cys Val Ala Ser Gly Ile Thr Phe Ser Asn Tyr
            20                  25                  30

Asn Met Gly Trp Phe Arg Gln Ala Pro Gly Lys Glu Arg Glu Phe Val
        35                  40                  45

Ala Thr Ile Arg His His Gly Tyr Asp Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Ser Cys
                85                  90                  95

Ala Lys Lys Leu Phe Trp Asp Met Asp Pro Lys Thr Gly Phe Ser Ser
            100                 105                 110

Trp Gly Gln Gly Thr Gln Val Thr Val Ser Ser
        115                 120
```

<210> SEQ ID NO 81
<211> LENGTH: 126
<212> TYPE: PRT
<213> ORGANISM: Lama glama

<400> SEQUENCE: 81

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Ser Tyr
            20                  25                  30

Gly Leu Gly Trp Phe Arg Gln Ala Pro Gly Lys Glu Arg Glu Phe Val
        35                  40                  45

Ala Ala Ile Gly Trp Ser Gly Ser Ser Thr Tyr Tyr Ala Asp Ser Val
    50                  55                  60

Lys Gly Arg Phe Thr Val Ser Val Asp Asn Ala Lys Asn Thr Val Tyr
65                  70                  75                  80

Leu Lys Met Asn Ser Leu Glu Pro Glu Asp Thr Ala Val Tyr Tyr Cys
                85                  90                  95

Ala Ala Lys Val Arg Asn Phe Asn Ser Asp Trp Asp Leu Leu Thr Ser
            100                 105                 110

Tyr Asn Tyr Trp Gly Gln Gly Thr Gln Val Thr Val Ser Ser
        115                 120                 125
```

<210> SEQ ID NO 82
<211> LENGTH: 125
<212> TYPE: PRT
<213> ORGANISM: Lama glama

<400> SEQUENCE: 82

```
Glu Val Gln Leu Val Glu Ser Gly Gly Gly Leu Val Gln Ala Gly Gly
1               5                   10                  15

Ser Leu Met Leu Ser Cys Ala Ala Ser Gly Arg Ala Leu Ser Ser Tyr
            20                  25                  30

Ala Ile Gly Trp Phe Arg Gln Ala Pro Gly Arg Glu Arg Glu Phe Val
        35                  40                  45
```

```
Ala Arg Ile Ser Trp Ser Gly Ala Asn Thr Tyr Tyr Ala Asp Ser Val
    50                  55                  60

Lys Gly Arg Phe Thr Ile Ser Arg Gly Asn Ala Lys Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Gln Thr Thr Ser Lys Tyr Asp Asn Tyr Asp Ala Arg Ala Tyr
            100                 105                 110

Gly Tyr Trp Gly Gln Gly Thr Gln Val Thr Val Ser Ser
        115                 120                 125
```

<210> SEQ ID NO 83
<211> LENGTH: 125
<212> TYPE: PRT
<213> ORGANISM: Lama glama

<400> SEQUENCE: 83

```
Glu Glu Gln Leu Val Glu Ser Gly Gly Gly Leu Val Gln Ala Gly Gly
1               5                   10                  15

Ser Leu Met Leu Ser Cys Ala Ala Ser Gly Arg Ala Leu Ser Ser Tyr
            20                  25                  30

Ala Ile Gly Trp Phe Arg Gln Ala Pro Gly Arg Glu Arg Glu Phe Val
        35                  40                  45

Ala Arg Ile Ser Trp Ser Gly Ala Asn Thr Tyr Tyr Ala Asp Ser Val
    50                  55                  60

Lys Gly Arg Phe Thr Ile Ser Arg Gly Asn Ala Lys Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Gln Thr Thr Ser Lys Tyr Asp Asn Tyr Asp Ala Arg Ala Tyr
            100                 105                 110

Gly Tyr Trp Gly Gln Gly Thr Gln Val Thr Val Ser Ser
        115                 120                 125
```

<210> SEQ ID NO 84
<211> LENGTH: 123
<212> TYPE: PRT
<213> ORGANISM: Lama glama

<400> SEQUENCE: 84

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Thr Ile Ser Gln Ser Gly Tyr Ser Thr Tyr Tyr Ala Asp Ser Val
    50                  55                  60

Lys Gly Arg Phe Thr Ile Ser Arg Asp Asn Ala Lys Asn Thr Val Asn
65                  70                  75                  80

Leu Gln Met Asn Ser Leu Lys Pro Glu Asp Thr Ala Val Tyr Tyr Cys
                85                  90                  95

Ala Ala Asp Pro Phe Tyr Ser Tyr Gly Ser Pro Ser Pro Tyr Arg Tyr
            100                 105                 110

Trp Gly Gln Gly Thr Gln Val Thr Val Ser Ser
        115                 120
```

<210> SEQ ID NO 85
<211> LENGTH: 125
<212> TYPE: PRT
<213> ORGANISM: Lama glama

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ser Ser Gly Arg Leu Phe Ser Phe Ser
            20                  25                  30

Ala Met Gly Trp Phe Arg Gln Ala Pro Gly Lys Glu Arg Glu Phe Val
        35                  40                  45

Ala Ala Phe Lys Trp Ser Gly Ser Thr Thr Tyr Tyr Ala Asp Tyr Val
    50                  55                  60

Lys Gly Arg Phe Thr Ile Ser Thr Asp Asn Ala Lys Asn Ile Leu Phe
65                  70                  75                  80

Leu Gln Met Asn Ser Leu Lys Pro Glu Asp Thr Ala Ile Tyr Tyr Cys
                85                  90                  95

Ala Val Asp Arg Phe Tyr Thr Gly Arg Tyr Tyr Ser Ser Asp Glu Tyr
            100                 105                 110

Asp Tyr Trp Gly Gln Gly Thr Gln Val Thr Val Ser Ser
        115                 120                 125

<210> SEQ ID NO 86
<211> LENGTH: 125
<212> TYPE: PRT
<213> ORGANISM: Lama glama

<400> SEQUENCE: 86

Glu Val Gln Leu Val Glu Ser Gly Gly Gly Leu Val Gln Ala Gly Gly
1               5                   10                  15

Ser Leu Arg Leu Ser Cys Ala Ala Ser Thr Ser Ile Tyr Ser Ile Thr
            20                  25                  30

Val Met Ala Trp Phe Arg Gln Ala Pro Gly Lys Glu Arg Glu Phe Val
        35                  40                  45

Ala Ala Ile Thr Trp Ser Ala Pro Ser Ser Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Val Asn Ser Leu Lys Pro Glu Asp Ser Ala Ile Tyr Tyr Cys
                85                  90                  95

Ala Ala Asp Arg Phe Lys Gly Arg Ser Ile Val Thr Arg Ser Asp Tyr
            100                 105                 110

Arg Tyr Trp Gly Gln Gly Thr Gln Val Thr Val Ser Ser
        115                 120                 125

<210> SEQ ID NO 87
<211> LENGTH: 125
<212> TYPE: PRT
<213> ORGANISM: Lama glama

<400> SEQUENCE: 87

Glu Val Gln Leu Val Glu Ser Gly Gly Gly Leu Val Gln Ser Gly Gly
1               5                   10                  15

Ser Leu Arg Leu Ser Cys Ala Ala Ser Gly Arg Ser Phe Ser Ser Leu
            20                  25                  30

-continued

```
Ala Met Gly Trp Phe Arg Gln Val Pro Gly Lys Asp Arg Glu Phe Val
        35                  40                  45

Ala Ser Ile Ser Gln Ser Gly Ile Thr Thr Ser Tyr Ala Asp Ser Val
    50                  55                  60

Lys Ser Arg Phe Thr Ile Ser Arg Asp Ser Ala Lys Asn Thr Val Tyr
65                  70                  75                  80

Leu Gln Met Asn Leu Leu Lys Pro Glu Asp Thr Ala Val Tyr Tyr Cys
                85                  90                  95

Ala Thr Ser Val Phe Tyr Ser Thr Ala Leu Thr Arg Pro Val Asp Tyr
            100                 105                 110

Arg Tyr Trp Gly Gln Gly Thr Gln Val Thr Val Ser Ser
        115                 120                 125


<210> SEQ ID NO 88
<211> LENGTH: 125
<212> TYPE: PRT
<213> ORGANISM: Lama glama

<400> SEQUENCE: 88

Glu Val Gln Leu Val Glu Ser Gly Gly Gly Leu Val Gln Ala Gly Gly
1               5                   10                  15

Ser Leu Arg Leu Ser Cys Ala Ala Ser Thr Ser Ile Tyr Ser Ile Thr
            20                  25                  30

Val Met Ala Trp Phe Arg Gln Ala Pro Gly Lys Glu Arg Glu Phe Val
        35                  40                  45

Ala Ala Ile Thr Trp Ser Ala Pro Thr Thr Tyr Ser Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Ser Ala Ile Tyr Tyr Cys
                85                  90                  95

Ala Ala Asp Arg Phe Lys Gly Arg Ser Ile Val Thr Arg Ser Asp Tyr
            100                 105                 110

Arg Tyr Trp Gly Gln Gly Thr Gln Val Thr Val Ser Ser
        115                 120                 125


<210> SEQ ID NO 89
<211> LENGTH: 129
<212> TYPE: PRT
<213> ORGANISM: Lama glama

<400> SEQUENCE: 89

Glu Val Gln Leu Val Glu Ser Gly Gly Gly Leu Val Gln Ala Gly Gly
1               5                   10                  15

Ser Leu Arg Leu Ser Cys Ser Val Thr Gly Arg Thr Phe Asn Lys Tyr
            20                  25                  30

Val Met Gly Trp Phe Arg Gln Ala Pro Gly Asn Asp Arg Glu Phe Val
        35                  40                  45

Ala Ala Ile Thr Ser Arg Asp Gly Pro Thr Tyr Tyr Ala Asp Ser Val
    50                  55                  60

Lys Gly Arg Phe Thr Ile Ser Gly Asp Asn Thr Lys Asn Lys Ile Phe
65                  70                  75                  80

Leu Gln Met Asn Ser Leu Met Pro Glu Asp Thr Ala Val Tyr Tyr Cys
                85                  90                  95

Ala Ile Asp Glu Asp Leu Tyr His Tyr Ser Ser Tyr His Phe Thr Arg
            100                 105                 110
```

```
Val Asp Leu Tyr His Tyr Trp Gly Gln Gly Thr Gln Val Thr Val Ser
        115                 120                 125

Ser


<210> SEQ ID NO 90
<211> LENGTH: 117
<212> TYPE: PRT
<213> ORGANISM: Lama glama

<400> SEQUENCE: 90

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Leu Ser Ser Ser
            20                  25                  30

Trp Met Tyr Trp Val Arg Gln Ala Pro Gly Lys Gly Leu Glu Trp Val
        35                  40                  45

Ser Arg Ile Ser Pro Gly Gly Leu Phe Thr Tyr Tyr Val Asp Ser Val
    50                  55                  60

Lys Gly Arg Phe Ser Val Ser Thr Asp Asn Ala Asn Asn Thr Leu Tyr
65                  70                  75                  80

Leu Gln Met Asn Ser Leu Lys Pro Glu Asp Thr Ala Leu Tyr Ser Cys
                85                  90                  95

Ala Lys Gly Gly Ala Pro Asn Tyr Thr Pro Arg Gly Arg Gly Thr Gln
            100                 105                 110

Val Thr Val Ser Ser
        115


<210> SEQ ID NO 91
<211> LENGTH: 115
<212> TYPE: PRT
<213> ORGANISM: Lama glama

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Val Arg Ser Asp
            20                  25                  30

Val Met Gly Trp Tyr Arg Gln Ala Pro Gly Lys Gln Arg Glu Leu Val
        35                  40                  45

Ala Phe Ile Arg Ser Leu Gly Ser Thr Tyr Tyr Ala Gly Ser Val Lys
    50                  55                  60

Gly Arg Phe Thr Ile Ser Arg Asp Asn Ala Ala Asn Thr Val Tyr Leu
65                  70                  75                  80

Gln Met Asn Asn Leu Lys Pro Glu Asp Thr Ala Val Tyr Tyr Cys Asn
                85                  90                  95

Ala Arg Phe Ser Gly Glu Ser Tyr Trp Gly Gln Gly Thr Pro Val Thr
            100                 105                 110

Val Ser Ser
        115


<210> SEQ ID NO 92
<211> LENGTH: 129
<212> TYPE: PRT
<213> ORGANISM: Lama glama

<400> SEQUENCE: 92

Glu Val Gln Leu Val Glu Ser Gly Gly Gly Leu Ala Gln Ala Gly Gly
1               5                   10                  15
```

Ser Leu Arg Leu Ser Cys Thr Ala Ser Gly Arg Thr Phe Asn Asn Tyr
20 25 30

Val Met Gly Trp Phe Arg Gln Ala Pro Gly Asn Glu Arg Glu Phe Val
35 40 45

Ala Ala Ile Thr Ser Thr Asn Gly Pro Thr Tyr Tyr Ala Asp Ser Val
50 55 60

Lys Gly Arg Phe Thr Ile Ser Gly Asp Asn Thr Lys Asn Lys Val Phe
65 70 75 80

Leu Gln Met Asp Ser Leu Arg Pro Glu Asp Thr Ala Val Tyr Tyr Cys
85 90 95

Ala Ile Asp Glu Asp Leu Tyr His Tyr Ser Ser Tyr His Tyr Thr Arg
100 105 110

Val Ala Leu Tyr His Tyr Trp Gly Gln Gly Thr Gln Val Thr Val Ser
115 120 125

Ser

<210> SEQ ID NO 93
<211> LENGTH: 124
<212> TYPE: PRT
<213> ORGANISM: Lama glama

<400> SEQUENCE: 93

Glu Val Gln Leu Val Glu Ser Gly Gly Gly Leu Val Gln Ser Gly Asp
1 5 10 15

Ser Leu Arg Leu Ser Cys Ala Val Ser Gly Asn Thr Phe Gly Leu Tyr
20 25 30

Ala Met Gly Trp Phe Arg Gln Ala Pro Gly Arg Glu Arg Glu Phe Val
35 40 45

Ser Ala Ile Thr Trp Ser Ala Gly Asp Thr Gln Tyr Ala Asp Ser Val
50 55 60

Lys Gly Arg Phe Thr Ile Ser Arg Asp Asn Ala Arg Asn Thr Val Asn
65 70 75 80

Leu Gln Met Asn Gly Leu Lys Pro Glu Asp Thr Ala Val Tyr Tyr Cys
85 90 95

Ala Gly Arg Gln Trp Gly Gly Thr Tyr Tyr Tyr His Gly Ser Tyr Ala
100 105 110

Trp Trp Gly Gln Gly Thr Gln Val Thr Val Ser Ser
115 120

<210> SEQ ID NO 94
<211> LENGTH: 128
<212> TYPE: PRT
<213> ORGANISM: Lama glama

<400> SEQUENCE: 94

Glu Val Gln Leu Val Glu Ser Glu Gly Gly Leu Val Gln Ala Gly Gly
1 5 10 15

Ser Leu Arg Leu Ser Cys Ala Ala Ser Gly Arg Thr Phe Ser Thr Asp
20 25 30

Asp Val Gly Trp Phe Arg Gln Ala Pro Gly Lys Glu Arg Glu Phe Val
35 40 45

Ala Val Ile Arg Trp Ser Thr Gly Gly Thr Tyr Thr Ser Asp Ser Val
50 55 60

Lys Gly Arg Phe Thr Leu Ser Arg Asp Asn Ala Lys Asn Thr Met Tyr
65 70 75 80

```
Leu Gln Met Asn Ser Leu Lys Pro Glu Asp Thr Ala Val Tyr Tyr Cys
                85                  90                  95

Ala Ala Arg Ser Arg Pro Leu Gly Ala Gly Ala Trp Tyr Thr Gly Glu
            100                 105                 110

Asn Tyr Tyr Asn Tyr Trp Gly Gln Gly Thr Gln Val Thr Val Ser Ser
        115                 120                 125


<210> SEQ ID NO 95
<211> LENGTH: 126
<212> TYPE: PRT
<213> ORGANISM: Lama glama

<400> SEQUENCE: 95

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Gly Tyr
            20                  25                  30

Asp Met Gly Trp Phe Arg Gln Ala Pro Gly Lys Glu Arg Glu Phe Val
        35                  40                  45

Thr Ala Ile Thr Trp Ser Gly Gly Ser Thr Tyr Ser Pro Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Thr Pro Glu Asp Thr Ala Val Tyr Tyr Cys
                85                  90                  95

Ala Ser Gly Arg Ile Trp Arg Ser Arg Asp Tyr Asp Ser Glu Lys Tyr
            100                 105                 110

Tyr Asp Ile Trp Gly His Gly Thr Gln Val Thr Val Ser Ser
        115                 120                 125


<210> SEQ ID NO 96
<211> LENGTH: 129
<212> TYPE: PRT
<213> ORGANISM: Lama glama

<400> SEQUENCE: 96

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ala Tyr
            20                  25                  30

Asp Met Gly Trp Phe Arg Gln Ala Pro Gly Lys Glu Arg Glu Phe Val
        35                  40                  45

Ala Val Ile Ser Trp Thr Asn Ser Met Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Val Asp Arg Arg Arg Thr Tyr Ser Arg Trp Arg Phe Tyr Thr Gly
            100                 105                 110

Val Asn Asp Tyr Asp Tyr Trp Gly Gln Gly Thr Gln Val Thr Val Ser
        115                 120                 125

Ser


<210> SEQ ID NO 97
<211> LENGTH: 129
<212> TYPE: PRT
```

<213> ORGANISM: Lama glama

<400> SEQUENCE: 97

```
Glu Val Gln Leu Val Glu Ser Gly Gly Gly Leu Val Gln Thr Gly Gly
1               5                   10                  15

Ser Leu Arg Leu Ser Cys Ala Ala Ser Gly Arg Thr Phe Ser Ala Tyr
            20                  25                  30

Asp Met Gly Trp Phe Arg Gln Ala Pro Gly Lys Glu Arg Glu Phe Val
        35                  40                  45

Ala Val Ile Ser Trp Ser Gly Gly Met Thr Tyr Tyr Ala Asp Ser Val
    50                  55                  60

Gln Gly Arg Phe Thr Ile Ser Arg Asp Asn Ala Lys Ser Thr Val Tyr
65                  70                  75                  80

Leu Gln Met Asn Ser Pro Lys Pro Glu Asp Thr Ala Val Tyr Tyr Cys
                85                  90                  95

Ala Val Asp Arg Arg Arg Ala Tyr Ser Arg Trp Arg Tyr Tyr Thr Gly
            100                 105                 110

Val Asn Asp Tyr Glu Phe Trp Gly Gln Gly Thr Gln Val Thr Val Ser
        115                 120                 125

Ser
```

<210> SEQ ID NO 98
<211> LENGTH: 129
<212> TYPE: PRT
<213> ORGANISM: Lama glama

<400> SEQUENCE: 98

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ala Tyr
            20                  25                  30

Asp Met Gly Trp Phe Arg Gln Ala Pro Gly Lys Glu Arg Glu Phe Val
        35                  40                  45

Ala Val Ile Ser Trp Ser Gly Gly Met Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Val Asp Arg Arg Arg Leu Tyr Ser Arg Trp Arg Tyr Tyr Thr Gly
            100                 105                 110

Val Asn Asp Tyr Asp Tyr Trp Gly Gln Gly Thr Gln Val Thr Val Ser
        115                 120                 125

Ser
```

<210> SEQ ID NO 99
<211> LENGTH: 129
<212> TYPE: PRT
<213> ORGANISM: Lama glama

<400> SEQUENCE: 99

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ala Tyr
            20                  25                  30

Asp Met Gly Trp Phe Arg Gln Ala Pro Gly Lys Glu Arg Glu Phe Val
```

```
        35                  40                  45

Ala Val Ile Ser Trp Thr Gly Gly Met Thr Tyr Tyr Ala Asp Ser Val
    50                  55                  60

Lys Gly Arg Phe Thr Ile Ser Arg Asp Lys Ala Lys Asn Thr Val Ser
65                  70                  75                  80

Leu Gln Met Asn Ser Leu Lys Pro Glu Asp Thr Ala Val Tyr Tyr Cys
                85                  90                  95

Ala Val Asp Arg Arg Arg Thr Tyr Ser Arg Trp Arg Tyr Tyr Thr Gly
            100                 105                 110

Val Asn Glu Tyr Glu Tyr Trp Gly Gln Gly Thr Gln Val Thr Val Ser
        115                 120                 125

Ser


<210> SEQ ID NO 100
<211> LENGTH: 129
<212> TYPE: PRT
<213> ORGANISM: Lama glama

<400> SEQUENCE: 100

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ala Tyr
            20                  25                  30

Asp Met Gly Trp Phe Arg Gln Ala Pro Gly Lys Glu Arg Glu Phe Val
        35                  40                  45

Ala Val Ile Ser Trp Thr Gly Asp Met Thr Tyr Tyr Ala Asp Ser Val
    50                  55                  60

Lys Gly Arg Phe Thr Ile Ser Arg Asp Lys Ala Lys Asn Thr Val Ser
65                  70                  75                  80

Leu Gln Met Asn Ser Leu Lys Pro Glu Asp Thr Ala Val Tyr Tyr Cys
                85                  90                  95

Ala Ala Asp Arg Arg Arg Thr Tyr Ser Arg Trp Arg Tyr Tyr Thr Gly
            100                 105                 110

Val Asn Glu Tyr Glu Tyr Trp Gly Gln Gly Thr Gln Val Thr Val Ser
        115                 120                 125

Ser


<210> SEQ ID NO 101
<211> LENGTH: 123
<212> TYPE: PRT
<213> ORGANISM: Lama glama

<400> SEQUENCE: 101

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Val Tyr
            20                  25                  30

Thr Met Gly Trp Phe Arg Gln Ala Pro Gly Lys Glu Arg Glu Phe Val
        35                  40                  45

Ala Thr Ile Ser Arg Thr Gly Asp Arg Thr Ser Tyr Ala Asn Ser Val
    50                  55                  60

Lys Gly Arg Phe Thr Ile Ser Arg Glu Asn Ala Lys Asn Thr Val Tyr
65                  70                  75                  80

Leu Gln Met Asn Ser Leu Lys Pro Glu Asp Thr Ala Val Tyr Ser Cys
                85                  90                  95
```

```
Ala Ala Gly Pro Ile Ala Pro Ser Pro Arg Pro Arg Glu Tyr Tyr Tyr
            100                 105                 110

Trp Gly Gln Gly Thr Gln Val Thr Val Ser Ser
        115                 120


<210> SEQ ID NO 102
<211> LENGTH: 129
<212> TYPE: PRT
<213> ORGANISM: Lama glama

<400> SEQUENCE: 102

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Ser Ala Tyr
            20                  25                  30

Asp Met Gly Trp Phe Arg Gln Ala Pro Gly Lys Glu Arg Glu Phe Val
        35                  40                  45

Ala Val Ile Ser Trp Thr Gly Gly Met Thr Tyr Tyr Ala Asp Ser Val
    50                  55                  60

Lys Gly Arg Phe Thr Ile Ser Arg Asp Lys Ala Lys Asn Thr Val Ser
65                  70                  75                  80

Leu Gln Met Asn Ser Leu Lys Pro Glu Asp Thr Ala Val Tyr Tyr Cys
                85                  90                  95

Ala Val Asp Arg Arg Arg Thr Tyr Ser Arg Trp Arg Tyr Tyr Thr Gly
            100                 105                 110

Val Asn Glu Tyr Glu Tyr Trp Gly Gln Gly Thr Gln Val Thr Val Ser
        115                 120                 125

Ser


<210> SEQ ID NO 103
<211> LENGTH: 129
<212> TYPE: PRT
<213> ORGANISM: Lama glama

<400> SEQUENCE: 103

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ala Tyr
            20                  25                  30

Asp Met Gly Trp Phe Arg Gln Ala Pro Gly Lys Glu Arg Glu Phe Val
        35                  40                  45

Ala Val Ile Ser Trp Ser Gly Gly Met Thr Asp Tyr Ala Asp Ser Val
    50                  55                  60

Lys Gly Arg Phe Thr Ile Ser Arg Glu Asn Ala Lys Asn Thr Gln Phe
65                  70                  75                  80

Leu Gln Met Asn Ser Leu Lys Pro Glu Asp Thr Ala Val Tyr Tyr Cys
                85                  90                  95

Ala Val Gly Arg Arg Arg Ala Tyr Ser Arg Trp Arg Tyr Tyr Thr Gly
            100                 105                 110

Val Asn Glu Tyr Asp Tyr Trp Gly Gln Gly Thr Gln Val Thr Val Ser
        115                 120                 125

Ser


<210> SEQ ID NO 104
<211> LENGTH: 125
<212> TYPE: PRT
<213> ORGANISM: Lama glama
```

<400> SEQUENCE: 104

Glu Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Asn Ser Tyr
            20                  25                  30

Ala Met Gly Trp Phe Arg Gln Ala Pro Gly Lys Glu Arg Glu Ser Val
        35                  40                  45

Ala His Ile Asn Arg Ser Gly Ser Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Gly Arg Tyr Tyr Ser Ser Asp Gly Val Pro Ser Ala Ser Phe
            100                 105                 110

Asn Tyr Trp Gly Gln Gly Thr Gln Val Thr Val Ser Ser
        115                 120                 125

<210> SEQ ID NO 105
<211> LENGTH: 128
<212> TYPE: PRT
<213> ORGANISM: Lama glama

<400> SEQUENCE: 105

Glu Val Gln Leu Val Glu Ser Gly Gly Gly Leu Val Gln Ala Gly Asp
1               5                   10                  15

Ser Leu Arg Leu Ser Cys Phe Thr Ser Ala Arg Thr Phe Asp Thr Trp
            20                  25                  30

Ala Met Ala Trp Phe Arg Gln Ala Pro Gly Lys Glu Arg Glu Phe Ile
        35                  40                  45

Ser Ala Ile Ser Trp Ser Gly Ser Met Thr Tyr Tyr Thr Asp Ser Val
    50                  55                  60

Lys Gly Arg Phe Ile Ile Ser Arg Asp Asn Ala Gln Asn Thr Leu Phe
65                  70                  75                  80

Leu Gln Met Asn Asn Thr Ala Pro Glu Asp Thr Ala Val Tyr Tyr Cys
                85                  90                  95

Ala Ala Lys Thr Val Asp Tyr Cys Ser Ala Tyr Glu Cys Tyr Ala Arg
            100                 105                 110

Leu Glu Tyr Asp Tyr Trp Gly Arg Gly Ala Gln Val Thr Val Ser Ser
        115                 120                 125

<210> SEQ ID NO 106
<211> LENGTH: 126
<212> TYPE: PRT
<213> ORGANISM: Lama glama

<400> SEQUENCE: 106

Glu Val Gln Leu Val Glu Ser Gly Gly Gly Leu Met Gln Thr Gly Asp
1               5                   10                  15

Ser Leu Arg Leu Ser Cys Ala Ala Ser Gly Leu Arg Phe Thr Ser Thr
            20                  25                  30

Asn Met Gly Trp Phe Arg Gln Gly Pro Gly Lys Glu Arg Glu Phe Val
        35                  40                  45

Ala Ala Ile Thr Leu Ser Gly Thr Thr Tyr Tyr Ala Glu Ala Val Lys
    50                  55                  60

```
Gly Arg Phe Thr Ile Ser Arg Asp Asn Asp Lys Asn Thr Val Ala Leu
65                  70                  75                  80

Gln Met Asn Ser Leu Lys Pro Glu Asp Thr Ala Val Tyr Tyr Cys Gly
                85                  90                  95

Ala Asp Pro Ser Tyr Tyr Ser Thr Ser Arg Tyr Thr Lys Ala Thr Glu
            100                 105                 110

Tyr Asp Tyr Trp Gly Gln Gly Thr Gln Val Thr Val Ser Ser
        115                 120                 125


<210> SEQ ID NO 107
<211> LENGTH: 126
<212> TYPE: PRT
<213> ORGANISM: Lama glama

<400> SEQUENCE: 107

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asn Thr Tyr
            20                  25                  30

Thr Met Gly Trp Phe Arg Gln Thr Pro Gly Thr Glu Arg Glu Phe Val
        35                  40                  45

Ala Ala Ile Arg Trp Thr Val Asn Ile Thr Tyr Tyr Ala Asp Ser Val
    50                  55                  60

Lys Gly Arg Phe Thr Ile Ser Arg Asp Ile Val Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Thr Ser Ala Pro Arg Ser Leu Ile Arg Met Ser Asn Glu
            100                 105                 110

Tyr Pro Tyr Trp Gly Gln Gly Thr Gln Val Thr Val Ser Ser
        115                 120                 125


<210> SEQ ID NO 108
<211> LENGTH: 123
<212> TYPE: PRT
<213> ORGANISM: Lama glama

<400> SEQUENCE: 108

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Leu Tyr
            20                  25                  30

Thr Val Gly Trp Phe Arg Gln Ala Pro Gly Lys Glu Arg Glu Phe Val
        35                  40                  45

Ala Tyr Ile Ser Arg Ser Gly Ser Asn Arg Tyr Tyr Val Asp Ser Val
    50                  55                  60

Lys Gly Arg Phe Thr Leu Ser Arg Asp Asn Ala Lys Asn Thr Val Asp
65                  70                  75                  80

Leu Gln Met Asn Ser Leu Lys Thr Glu Asp Thr Ala Val Tyr Tyr Cys
                85                  90                  95

Ala Ala Thr Ser Arg Gly Leu Ser Ser Leu Ala Gly Glu Tyr Asn Tyr
            100                 105                 110

Trp Gly Arg Gly Thr Gln Val Thr Val Ser Ser
        115                 120


<210> SEQ ID NO 109
<211> LENGTH: 123
```

<212> TYPE: PRT
<213> ORGANISM: Lama glama

<400> SEQUENCE: 109

Glu Val Gln Leu Val Glu Ser Gly Gly Gly Leu Val Gln Ala Gly Gly
1 5 10 15

Ser Leu Arg Leu Ser Cys Thr Ala Ser Gly Ser Ala Phe Lys Ser Tyr
20 25 30

Arg Met Gly Trp Phe Arg Arg Thr Pro Gly Lys Glu Asp Glu Phe Val
35 40 45

Ala Ser Ile Ser Trp Thr Tyr Gly Ser Thr Phe Tyr Ala Asp Ser Val
50 55 60

Lys Gly Arg Phe Thr Met Ser Arg Asp Lys Ala Lys Asn Ala Gly Tyr
65 70 75 80

Leu Gln Met Asn Ser Leu Lys Pro Glu Asp Thr Ala Leu Tyr Tyr Cys
85 90 95

Ala Ala Gly Ala Gln Ser Asp Arg Tyr Asn Ile Arg Ser Tyr Asp Tyr
100 105 110

Trp Gly Gln Gly Thr Gln Val Thr Val Ser Ser
115 120

<210> SEQ ID NO 110
<211> LENGTH: 115
<212> TYPE: PRT
<213> ORGANISM: Lama glama

<400> SEQUENCE: 110

Glu Val Gln Leu Val Glu Ser Gly Gly Gly Leu Val Gln Pro Gly Gly
1 5 10 15

Ser Leu Lys Leu Ser Cys Thr Ala Ser Gly Phe Thr Phe Ser Thr Ser
20 25 30

Trp Met His Trp Val Arg Gln Ala Pro Gly Lys Gly Leu Glu Trp Val
35 40 45

Ser Ser Ile Pro Pro Val Gly His Phe Ala Asn Tyr Ala Pro Ser Val
50 55 60

Lys Gly Arg Phe Thr Ile Ser Arg Asp Asn Ala Lys Asn Thr Leu Phe
65 70 75 80

Leu Gln Met Asn Ser Leu Lys Ser Glu Asp Thr Ala Val Tyr Tyr Cys
85 90 95

Ala Lys Asp Ser Ala Gly Arg Thr Lys Gly Gln Gly Thr Gln Val Thr
100 105 110

Val Ser Ser
115

<210> SEQ ID NO 111
<211> LENGTH: 124
<212> TYPE: PRT
<213> ORGANISM: Lama glama

<400> SEQUENCE: 111

Lys Val Gln Leu Val Glu Ser Gly Gly Gly Leu Val Gln Ala Gly Gly
1 5 10 15

Ser Leu Arg Leu Ser Cys Ala Ala Ser Glu Arg Thr Phe Ser Asn Tyr
20 25 30

Ala Met Asp Trp Phe Arg Gln Ala Pro Gly Lys Glu Arg Glu Phe Val
35 40 45

Ala Ala Ile Thr Arg Ser Gly Gly Gly Thr Tyr Tyr Ala Asp Ser Val

```
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Arg Ser Ser Thr Ile Val Val Gly Val Gly Gly Met Glu
            100                 105                 110

Tyr Trp Gly Lys Gly Thr Leu Val Thr Val Ser Ser
        115                 120


<210> SEQ ID NO 112
<211> LENGTH: 128
<212> TYPE: PRT
<213> ORGANISM: Lama glama

<400> SEQUENCE: 112

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Gly Asp Tyr
            20                  25                  30

Asp Ile Gly Trp Phe Arg Gln Ala Pro Gly Asn Glu Arg Glu Gly Val
        35                  40                  45

Ser Cys Ile Thr Thr Asp Val Gly Thr Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Ile Asn Asp Leu Lys Pro Glu Asp Thr Ala Ile Tyr Tyr Cys
                85                  90                  95

Ala Val Asp Thr Gln Asp Leu Gly Leu Asp Ile Phe Cys Arg Gly Asn
            100                 105                 110

Gly Pro Phe Asp Gly Trp Gly Gln Gly Thr Gln Val Thr Val Ser Ser
        115                 120                 125


<210> SEQ ID NO 113
<211> LENGTH: 134
<212> TYPE: PRT
<213> ORGANISM: Lama glama

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Thr Ala Ser Gly Leu Asn Leu Asp Asp Tyr
            20                  25                  30

Ala Ile Gly Trp Phe Arg Gln Ala Pro Gly Lys Glu Arg Glu Gly Val
        35                  40                  45

Ser Cys Ile Ser Ser Tyr Asp Ser Val Thr Tyr Tyr Ala Asp His Val
    50                  55                  60

Lys Gly Arg Phe Thr Ile Ser Arg Asp Ser Ala Lys Asn Thr Leu Tyr
65                  70                  75                  80

Leu Gln Met Asn Ser Leu Ser Ile Glu Asp Thr Gly Val Tyr Tyr Cys
                85                  90                  95

Ala Ala Glu Arg Glu Gln Leu Arg Arg Arg Glu Ser Pro His Asp Glu
            100                 105                 110

Leu Leu Arg Leu Cys Phe Tyr Gly Met Arg Tyr Ser Gly Lys Gly Thr
        115                 120                 125

Leu Val Thr Val Ser Ser
```

130

<210> SEQ ID NO 114
<211> LENGTH: 123
<212> TYPE: PRT
<213> ORGANISM: Lama glama

<400> SEQUENCE: 114

Glu Val Gln Leu Val Glu Ser Gly Gly Gly Leu Val Gln Pro Gly Gly
1 5 10 15

Ser Leu Arg Leu Ser Cys Val Ala Ser Gly Phe Arg Leu Asp Asp Tyr
20 25 30

Ala Ile Gly Trp Phe Arg Gln Ala Pro Gly Lys Glu Arg Glu Ala Val
35 40 45

Ser Cys Ile Ser Ser Ser Asp Thr Ser Ile Asp Tyr Thr Asn Ser Val
50 55 60

Lys Gly Arg Phe Thr Phe Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Ala Phe Arg Cys Ser Gly Tyr Glu Leu Arg Gly Phe Pro Thr
100 105 110

Trp Gly Gln Gly Thr Gln Val Thr Val Ser Ser
115 120

<210> SEQ ID NO 115
<211> LENGTH: 126
<212> TYPE: PRT
<213> ORGANISM: Lama glama

<400> SEQUENCE: 115

Glu Val Gln Leu Val Glu Ser Gly Gly Gly Leu Val Gln Ala Gly Gly
1 5 10 15

Ser Leu Arg Leu Ser Cys Ala Ala Ser Gly Gly Thr Phe Ser Ser Leu
20 25 30

Ala Val Gly Trp Phe Arg Gln Ala Pro Gly Lys Glu Arg Glu Phe Val
35 40 45

Ala Arg Ile Thr Trp Ser Gly Ala Thr Thr Tyr Tyr Ala Asp Ala Val
50 55 60

Lys Asp Arg Phe Thr Ile Ser Arg Asp Asn Ala Lys Asn Thr Met Tyr
65 70 75 80

Leu Gln Met Asn Ser Leu Lys Pro Glu Asp Thr Ala Val Tyr Tyr Cys
85 90 95

Ala Ala Asp Arg Ser Pro Asn Ile Ile Asn Val Val Thr Ala Tyr Glu
100 105 110

Tyr Asp Tyr Trp Gly Gln Gly Thr Gln Val Thr Val Ser Ser
115 120 125

<210> SEQ ID NO 116
<211> LENGTH: 126
<212> TYPE: PRT
<213> ORGANISM: Lama glama

<400> SEQUENCE: 116

Glu Val Gln Leu Val Glu Ser Gly Gly Gly Leu Val Gln Pro Gly Ala
1 5 10 15

Ser Leu Arg Leu Ser Cys Ala Ala Ser Gly Asp Gly Phe Thr Leu Tyr
20 25 30

```
Asn Met Gly Trp Phe Arg Gln Ala Pro Gly Lys Glu Arg Glu Phe Val
        35                  40                  45

Ala Ala Ile Thr Ser Ser Pro Met Ser Thr Tyr Tyr Ala Asp Ser Val
    50                  55                  60

Lys Gly Arg Phe Ser Ile Ser Ile Asn Asn Asp Lys Thr Thr Gly Phe
65                  70                  75                  80

Leu Gln Met Asn Val Leu Lys Pro Glu Asp Thr Gly Val Tyr Phe Cys
                85                  90                  95

Ala Ala Pro Glu Gly Ser Phe Arg Arg Gln Tyr Ala Asp Arg Ala Met
            100                 105                 110

Tyr Asp Tyr Trp Gly Gln Gly Thr Gln Val Thr Val Ser Ser
        115                 120                 125


<210> SEQ ID NO 117
<211> LENGTH: 127
<212> TYPE: PRT
<213> ORGANISM: Lama glama

<400> SEQUENCE: 117

Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Thr Phe Ser Gly Ser
            20                  25                  30

Asp Met Gly Trp Phe Arg Gln Ser Pro Gly Lys Glu Arg Glu Ile Val
        35                  40                  45

Ala Ala Ile Arg Leu Ser Gly Ser Ile Thr Tyr Tyr Pro Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ser Thr Tyr Ser Tyr Tyr Leu Ala Leu Ala Asp Arg Gly
            100                 105                 110

Gly Tyr Asp Tyr Trp Gly Gln Gly Thr Gln Val Thr Val Ser Ser
        115                 120                 125


<210> SEQ ID NO 118
<211> LENGTH: 125
<212> TYPE: PRT
<213> ORGANISM: Lama glama

<400> SEQUENCE: 118

Glu Val Gln Leu Val Glu Ser Gly Gly Gly Leu Val Gln Ala Gly Gly
1               5                   10                  15

Ser Leu Arg Leu Ser Cys Val Ala Ser Gly Phe Thr Leu Gly Thr Tyr
            20                  25                  30

Ala Ile Gly Trp Phe Arg Gln Ala Pro Gly Lys Glu Arg Glu Ala Val
        35                  40                  45

Ser Cys Met Ser Ala Gly Asp Ser Ile Pro Trp Tyr Thr Ala Ser Val
    50                  55                  60

Lys Gly Arg Phe Thr Thr Ser Thr Asp Asn Ala Arg Asn Thr Val Tyr
65                  70                  75                  80

Leu Gln Met Asn Ser Leu Lys Pro Glu Asp Thr Ala His Tyr Tyr Cys
                85                  90                  95

Ala Ala Ala Arg Tyr His Gly Asp Tyr Cys Tyr Tyr Glu Gly Tyr Tyr
            100                 105                 110
```

```
Pro Phe Trp Gly Gln Gly Thr Gln Val Thr Val Ser Ser
        115                 120                 125


<210> SEQ ID NO 119
<211> LENGTH: 117
<212> TYPE: PRT
<213> ORGANISM: Lama glama

<400> SEQUENCE: 119

Glu Val Gln Leu Val Glu Ser Gly Gly Gly Leu Val Gln Ala Gly Gly
1               5                   10                  15

Ser Leu Arg Leu Ser Cys Ala Ala Ser Thr Ser Ile Ser Ser Thr Asn
            20                  25                  30

Phe Met Gly Trp Tyr Arg Gln Ala Pro Gly Lys Gln Arg Glu Leu Val
        35                  40                  45

Ala Thr Ile Thr Ser Ser Ser Ile Thr Asn Tyr Val Asp Ser Val Lys
    50                  55                  60

Gly Arg Phe Thr Ile Ser Arg Asp Asn Ala Lys Asn Thr Val Tyr Leu
65                  70                  75                  80

Gln Met Thr Ser Leu Lys Pro Glu Asp Thr Ala Val Tyr Tyr Cys His
                85                  90                  95

Ala Arg Trp Arg Trp Ser Asp Val Glu Tyr Trp Gly Lys Gly Thr Leu
            100                 105                 110

Val Thr Val Ser Ser
        115


<210> SEQ ID NO 120
<211> LENGTH: 121
<212> TYPE: PRT
<213> ORGANISM: Lama glama

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Ser Ser Ile Phe
            20                  25                  30

Ala Met Arg Trp Tyr Arg Gln Ala Pro Gly Lys Gln Arg Glu Leu Val
        35                  40                  45

Ala Ser Ile Thr Arg Ser Ser Ile Thr Thr Tyr Ala Asp Ser Val Lys
    50                  55                  60

Gly Arg Phe Thr Pro Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Asn
                85                  90                  95

Ala Ala Ile Arg Pro Glu Leu Tyr Ser Val Val Asn Asp Tyr Trp Gly
            100                 105                 110

Gln Gly Thr Gln Val Thr Val Ser Ser
        115                 120


<210> SEQ ID NO 121
<211> LENGTH: 127
<212> TYPE: PRT
<213> ORGANISM: Lama glama

<400> SEQUENCE: 121

Glu Val Gln Leu Val Glu Ser Gly Gly Gly Leu Val Gln Pro Gly Gly
1               5                   10                  15
```

-continued

```
Ser Leu Arg Leu Ser Cys Ala Thr Ser Gly Leu Thr Phe Ser Asp Tyr
            20                  25                  30

Asn Leu Gly Trp Phe Arg Gln Ala Pro Gly Lys Glu Arg Gln Phe Val
        35                  40                  45

Ala Val Ile Ser Trp Arg Asp Ser Phe Ala Tyr Tyr Ala Glu Pro Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Arg Val Ser Ser Arg Leu Val Leu Pro Asn Thr Ser Pro
            100                 105                 110

Asp Phe Gly Ser Trp Gly Gln Gly Thr Gln Val Thr Val Ser Ser
        115                 120                 125


<210> SEQ ID NO 122
<211> LENGTH: 129
<212> TYPE: PRT
<213> ORGANISM: Lama glama

<400> SEQUENCE: 122

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Asn Asn Ala
            20                  25                  30

Ile Met Gly Trp Phe Arg Gln Ala Pro Gly Gln Glu Arg Glu Phe Val
        35                  40                  45

Ala Ala Met Asn Trp Arg Gly Gly Pro Thr Tyr Tyr Ala Asp Ser Val
    50                  55                  60

Lys Gly Arg Phe Thr Ile Ser Gly Asp Asn Thr Lys Asn Thr Val Phe
65                  70                  75                  80

Leu Gln Met Asn Phe Leu Lys Pro Glu Asp Thr Ala Val Tyr Tyr Cys
                85                  90                  95

Ala Ala Asp Glu Asp Leu Tyr His Tyr Ser Ser Tyr His Tyr Ser Arg
            100                 105                 110

Val Asp Leu Tyr His Tyr Trp Gly Gln Gly Thr Gln Val Thr Val Ser
        115                 120                 125

Ser


<210> SEQ ID NO 123
<211> LENGTH: 121
<212> TYPE: PRT
<213> ORGANISM: Lama glama

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Ser Ser Ile Phe
            20                  25                  30

Ala Met Arg Trp Tyr Arg Gln Ala Pro Gly Lys Gln Arg Glu Leu Val
        35                  40                  45

Ala Ser Ile Thr Arg Ser Ser Ile Thr Thr Tyr Ala Asp Ser Val Lys
    50                  55                  60

Gly Arg Phe Thr Leu Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Asn
```

```
                85                  90                  95

Ala Ala Ile Arg Pro Glu Leu Tyr Ser Val Val Asn Asp Tyr Trp Gly
            100                 105                 110

Gln Gly Thr Gln Val Thr Val Ser Ser
        115                 120


<210> SEQ ID NO 124
<211> LENGTH: 123
<212> TYPE: PRT
<213> ORGANISM: Lama glama

<400> SEQUENCE: 124

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Ser Phe Ser Ser Tyr
            20                  25                  30

Ala Pro Gly Trp Phe Arg Gln Ala Pro Gly Lys Glu Arg Glu Phe Val
        35                  40                  45

Ala Ala Phe Thr Arg Ser Ser Asn Ile Pro Tyr Tyr Lys Asp Ser Val
    50                  55                  60

Lys Gly Arg Phe Thr Ile Ser Arg Asp Asn Ala His Thr Val Tyr Leu
65                  70                  75                  80

Gln Met Asn Ser Leu Lys Pro Glu Asp Thr Ala Ile Tyr Tyr Cys Ala
                85                  90                  95

Val Asn Leu Gly Ser Thr Trp Ser Arg Asp Gln Arg Thr Tyr Asp Tyr
            100                 105                 110

Trp Gly Gln Gly Thr Gln Val Thr Val Ser Ser
        115                 120


<210> SEQ ID NO 125
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama glama sequence

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Arg Phe Met Ser Met
            20                  25                  30

Ala Trp Tyr Arg Gln Ala Pro Gly Lys Gln Arg Glu Leu Val Ala Arg
        35                  40                  45

Ile Ser Ser Gly Gly Thr Thr Ala Tyr Ala Asp Ser Val Lys Gly Arg
    50                  55                  60

Phe Thr Ile Ser Arg Asp Asn Ser Lys Asn Thr Val Tyr Leu Gln Met
65                  70                  75                  80

Asn Ser Leu Arg Ala Glu Asp Thr Ala Val Tyr Tyr Cys Asn Thr Phe
                85                  90                  95

Ser Ser Arg Pro Asn Pro Trp Gly Gln Gly Thr Leu Val Thr Val Ser
            100                 105                 110

Ser


<210> SEQ ID NO 126
<211> LENGTH: 113
```

<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama glama sequence

<400> SEQUENCE: 126

```
Glu Val Gln Leu Val Glu Ser Gly Gly Gly Leu Val Gln Pro Gly Gly
1               5                   10                  15

Ser Leu Arg Leu Ser Cys Val Ala Ser Gly Ile Arg Phe Ile Ser Met
            20                  25                  30

Ala Trp Tyr Arg Gln Ala Pro Gly Lys His Arg Glu Leu Val Ala Arg
        35                  40                  45

Ile Ser Ser Gly Gly Thr Thr Ala Tyr Val Asp Ser Val Lys Gly Arg
    50                  55                  60

Phe Thr Ile Ser Arg Asp Asn Ser Lys Asn Thr Val Tyr Leu Gln Met
65                  70                  75                  80

Asn Ser Leu Lys Ala Glu Asp Thr Ala Val Tyr Tyr Cys Asn Thr Phe
                85                  90                  95

Ser Ser Arg Pro Asn Pro Trp Gly Ala Gly Thr Gln Val Thr Val Ser
            100                 105                 110

Ser
```

<210> SEQ ID NO 127
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama glama sequence

<400> SEQUENCE: 127

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Arg Phe Ile Ser Met
            20                  25                  30

Ala Trp Tyr Arg Gln Ala Pro Gly Lys Gln Arg Glu Leu Val Ala Arg
        35                  40                  45

Ile Ser Ser Gly Gly Thr Thr Ala Tyr Ala Asp Ser Val Lys Gly Arg
    50                  55                  60

Phe Thr Ile Ser Arg Asp Asn Ser Lys Asn Thr Val Tyr Leu Gln Met
65                  70                  75                  80

Asn Ser Leu Arg Ala Glu Asp Thr Ala Val Tyr Tyr Cys Asn Thr Phe
                85                  90                  95

Ser Ser Arg Pro Asn Pro Trp Gly Gln Gly Thr Leu Val Thr Val Ser
            100                 105                 110

Ser
```

<210> SEQ ID NO 128
<211> LENGTH: 285
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 128

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Gly Gly Gly Gly Ser Gly Gly Gly Gly Ser
145 150 155 160

Glu Val Gln Leu Val Glu Ser Gly Gly Gly Leu Val Gln Thr Gly Asp
165 170 175

Ser Leu Arg Leu Ser Cys Glu Val Ser Gly Arg Thr Phe Ser Ser Tyr
180 185 190

Ser Met Gly Trp Phe Arg Gln Ala Gln Gly Lys Glu Arg Glu Phe Val
195 200 205

Val Ala Ile Ser Lys Gly Gly Tyr Lys Tyr Asp Ser Val Ser Leu Glu
210 215 220

Gly Arg Phe Thr Ile Ser Lys Asp Asn Ala Lys Asn Thr Val Tyr Leu
225 230 235 240

Gln Ile Asn Ser Leu Lys Pro Glu Asp Thr Ala Val Tyr Tyr Cys Ala
245 250 255

Ser Ser Arg Ala Tyr Gly Ser Ser Arg Leu Arg Leu Ala Asp Thr Tyr
260 265 270

Glu Tyr Trp Gly Gln Gly Thr Gln Val Thr Val Ser Ser
275 280 285

<210> SEQ ID NO 129
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 129

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val

```
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Ser Ala Val Gly Asp Ile Thr Val Ala Trp Tyr Arg Gln Ala Pro Gly
                165                 170                 175

Ile Gln Arg Gln Leu Val Ala Thr Ile Thr Pro Ser Gly Tyr Thr Tyr
            180                 185                 190

Tyr Trp Asp Phe Val Lys Gly Arg Phe Thr Ile Ser Arg Asp Asn Ser
        195                 200                 205

Lys Asn Ile Val Tyr Leu Gln Met Asn Ser Leu Lys Pro Glu Asp Thr
    210                 215                 220

Ala Ala Tyr Tyr Cys Asn Thr Gln Phe Tyr Trp Gly Gln Gly Thr Gln
225                 230                 235                 240

Val Thr Val Ser Ser
                245


<210> SEQ ID NO 130
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 130

Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125
```

Gly Ser Gly Gly Gly Ser Glu Val Gln Leu Val Glu Ser Gly Gly Gly
130 135 140

Leu Ala Gln Ala Gly Asp Ser Leu Arg Leu Ser Cys Ala Ala Ser Gly
145 150 155 160

Arg Ser Phe Ser His Tyr Asn Met Gly Trp Phe Arg Gln Ala Pro Gly
165 170 175

Lys Glu Arg Glu Phe Val Ala Ser Ile Arg Gly Gly Gly Gly Ser Thr
180 185 190

Thr Tyr Ala Asn Ser Val Lys Asp Arg Phe Thr Ile Ser Arg Glu Asn
195 200 205

Ala Lys Asn Thr Val Tyr Leu Gln Met Asn Ser Leu Lys Pro Glu Asp
210 215 220

Thr Ala Val Tyr Tyr Cys Ala Ala Thr Ala Phe Tyr Arg Gly Pro Tyr
225 230 235 240

Asp Tyr Asp Tyr Trp Gly Gln Gly Thr Gln Val Thr Val Ser Ser
245 250 255

<210> SEQ ID NO 131
<211> LENGTH: 247
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 131

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Gly Ser Leu Arg Leu Ser Cys Val Ala Ser Gly
145 150 155 160

Ile Arg Phe Met Ser Met Ala Trp Tyr Arg Gln Ala Pro Gly Lys His
165 170 175

Arg Glu Leu Val Ala Arg Ile Ser Ser Gly Gly Thr Thr Ala Tyr Val
180 185 190

Asp Ser Val Lys Gly Arg Phe Thr Ile Ser Arg Asp Asn Ser Lys Asn
195 200 205

Thr Val Tyr Leu Gln Met Asn Ser Leu Lys Ala Glu Asp Thr Ala Val
210 215 220

```
Tyr Tyr Cys Asn Thr Phe Ser Ser Arg Pro Asn Pro Trp Gly Ala Gly
225                 230                 235                 240

Thr Gln Val Thr Val Ser Ser
                245


<210> SEQ ID NO 132
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 132

Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Asn Ile Phe Ser Asn Asn Ala Met Ala Trp Tyr Arg Gln Ala Pro Gly
                165                 170                 175

Lys Gln Arg Glu Leu Val Ala Arg Ile Ser Ser Gly Gly Gly Phe Thr
            180                 185                 190

Tyr Tyr Leu Asp Ser Val Lys Gly Arg Phe Thr Val Ser Arg Asp Asn
        195                 200                 205

Ala Lys Asn Thr Val Tyr Leu Gln Met Asn Ser Leu Lys Pro Glu Asp
    210                 215                 220

Thr Ala Val Tyr Tyr Cys Asn Ala Ala Tyr Arg Thr Tyr Asn Tyr Trp
225                 230                 235                 240

Gly Gln Gly Thr Gln Val Thr Val Ser Ser
                245                 250


<210> SEQ ID NO 133
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
```

sequences

<400> SEQUENCE: 133

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Ala Gly Gly Ser Leu Arg Leu Ser Cys Ala Ala Ser Gly
145 150 155 160

Arg Thr Phe Ser Asn Tyr Ala Met Gly Trp Phe Arg Gln Ala Pro Gly
165 170 175

Lys Glu Arg Val Leu Val Ala Asp Ile Ser Ser Ser Gly Ile Asn Thr
180 185 190

Tyr Val Ala Asp Ala Val Lys Gly Arg Phe Thr Ile Ser Arg Asp Asn
195 200 205

Ala Lys Asn Thr Val Tyr Leu Gln Met Asn Ser Leu Lys Pro Glu Asp
210 215 220

Thr Ala Val Tyr Tyr Cys Ala Ala Ser Ala Trp Trp Tyr Ser Gln Met
225 230 235 240

Ala Arg Asp Asn Tyr Arg Tyr Trp Gly Gln Gly Thr Gln Val Thr Val
245 250 255

Ser Ser

<210> SEQ ID NO 134
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 134

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Gly Ser Leu Arg Leu Ala Cys Ala Ala Ser Gly
145 150 155 160

Phe Thr Leu Ser Ser Ser Trp Met Tyr Trp Val Arg Gln Ala Pro Gly
165 170 175

Lys Gly Leu Glu Trp Val Ser Arg Ile Ser Pro Gly Gly Leu Phe Thr
180 185 190

Tyr Tyr Val Asp Ser Val Lys Gly Arg Phe Ser Val Ser Thr Asp Asn
195 200 205

Ala Asn Asn Thr Leu Tyr Leu Gln Met Asn Ser Leu Lys Pro Glu Asp
210 215 220

Thr Ala Leu Tyr Ser Cys Ala Lys Gly Gly Ala Pro Asn Tyr Thr Pro
225 230 235 240

Arg Gly Arg Gly Thr Gln Val Thr Val Ser Ser
245 250

<210> SEQ ID NO 135
<211> LENGTH: 259
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 135

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Ala Gly Asp Ser Leu Arg Leu Ser Cys Thr Ala Ser Gly

```
145                 150                 155                 160

Arg Thr Phe Asn Ser Tyr Ala Met Gly Trp Phe Arg Gln Ala Pro Gly
                165                 170                 175

Lys Glu Arg Glu Ser Val Ala His Ile Asn Arg Ser Gly Ser Ser Thr
            180                 185                 190

Tyr Tyr Ala Asp Ser Val Lys Gly Arg Phe Thr Ile Ser Arg Asp Asn
        195                 200                 205

Ala Lys Asn Thr Val Tyr Leu Gln Leu Asn Ser Leu Lys Pro Glu Asp
    210                 215                 220

Thr Ala Val Tyr Tyr Cys Ala Ala Gly Arg Tyr Tyr Ser Ser Asp Gly
225                 230                 235                 240

Val Pro Ser Ala Ser Phe Asn Tyr Trp Gly Gln Gly Thr Gln Val Thr
                245                 250                 255

Val Ser Ser


<210> SEQ ID NO 136
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 136

Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Ala Gly Gly Ser Leu Arg Leu Ser Cys Thr Ala Ser Gly
145                 150                 155                 160

Ser Ala Phe Lys Ser Tyr Arg Met Gly Trp Phe Arg Arg Thr Pro Gly
                165                 170                 175

Lys Glu Asp Glu Phe Val Ala Ser Ile Ser Trp Thr Tyr Gly Ser Thr
            180                 185                 190

Phe Tyr Ala Asp Ser Val Lys Gly Arg Phe Thr Met Ser Arg Asp Lys
        195                 200                 205

Ala Lys Asn Ala Gly Tyr Leu Gln Met Asn Ser Leu Lys Pro Glu Asp
    210                 215                 220

Thr Ala Leu Tyr Tyr Cys Ala Ala Gly Ala Gln Ser Asp Arg Tyr Asn
```

225 230 235 240

Ile Arg Ser Tyr Asp Tyr Trp Gly Gln Gly Thr Gln Val Thr Val Ser
245 250 255

Ser

<210> SEQ ID NO 137
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 137

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Gly Ser Leu Lys Leu Ser Cys Thr Ala Ser Gly
145 150 155 160

Phe Thr Phe Ser Thr Ser Trp Met His Trp Val Arg Gln Ala Pro Gly
165 170 175

Lys Gly Leu Glu Trp Val Ser Ser Ile Pro Pro Val Gly His Phe Ala
180 185 190

Asn Tyr Ala Pro Ser Val Lys Gly Arg Phe Thr Ile Ser Arg Asp Asn
195 200 205

Ala Lys Asn Thr Leu Phe Leu Gln Met Asn Ser Leu Lys Ser Glu Asp
210 215 220

Thr Ala Val Tyr Tyr Cys Ala Lys Asp Ser Ala Gly Arg Thr Lys Gly
225 230 235 240

Gln Gly Thr Gln Val Thr Val Ser Ser
245

<210> SEQ ID NO 138
<211> LENGTH: 258
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 138

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Ala Gly Gly Ser Leu Arg Leu Ser Cys Ala Ala Ser Glu
145 150 155 160

Arg Thr Phe Ser Asn Tyr Ala Met Asp Trp Phe Arg Gln Ala Pro Gly
165 170 175

Lys Glu Arg Glu Phe Val Ala Ala Ile Thr Arg Ser Gly Gly Gly Thr
180 185 190

Tyr Tyr Ala Asp Ser Val Lys Gly Arg Phe Thr Ile Ser Arg Asp Asn
195 200 205

Ala Lys Asn Thr Val Tyr Leu Gln Met Asn Ser Leu Lys Pro Glu Asp
210 215 220

Thr Ala Val Tyr Tyr Cys Ala Ala Thr Arg Ser Ser Thr Ile Val Val
225 230 235 240

Gly Val Gly Gly Met Glu Tyr Trp Gly Lys Gly Thr Gln Val Thr Val
245 250 255

Ser Ser

<210> SEQ ID NO 139
<211> LENGTH: 276
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 139

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Gly Gly Gly Gly Ser Gly Gly Gly Gly Ser
145 150 155 160

Gly Gly Gly Gly Ser Glu Val Gln Leu Val Glu Ser Gly Gly Gly Leu
165 170 175

Val Gln Pro Gly Gly Ser Leu Arg Leu Ser Cys Ala Ala Ser Gly Ser
180 185 190

Ala Val Gly Asp Ile Thr Val Ala Trp Tyr Arg Gln Ala Pro Gly Ile
195 200 205

Gln Arg Gln Leu Val Ala Thr Ile Thr Pro Ser Gly Tyr Thr Tyr Tyr
210 215 220

Trp Asp Phe Val Lys Gly Arg Phe Thr Ile Ser Arg Asp Asn Ser Lys
225 230 235 240

Asn Ile Val Tyr Leu Gln Met Asn Ser Leu Lys Pro Glu Asp Thr Ala
245 250 255

Ala Tyr Tyr Cys Asn Thr Gln Phe Tyr Trp Gly Gln Gly Thr Gln Val
260 265 270

Thr Val Ser Ser
275

<210> SEQ ID NO 140
<211> LENGTH: 286
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 140

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly

```
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Ala Gln Ala Gly Asp Ser Leu Arg Leu Ser Cys Ala Ala Ser Gly Arg
            180                 185                 190

Ser Phe Ser His Tyr Asn Met Gly Trp Phe Arg Gln Ala Pro Gly Lys
        195                 200                 205

Glu Arg Glu Phe Val Ala Ser Ile Arg Gly Gly Gly Gly Ser Thr Thr
    210                 215                 220

Tyr Ala Asn Ser Val Lys Asp Arg Phe Thr Ile Ser Arg Glu Asn Ala
225                 230                 235                 240

Lys Asn Thr Val Tyr Leu Gln Met Asn Ser Leu Lys Pro Glu Asp Thr
                245                 250                 255

Ala Val Tyr Tyr Cys Ala Ala Thr Ala Phe Tyr Arg Gly Pro Tyr Asp
            260                 265                 270

Tyr Asp Tyr Trp Gly Gln Gly Thr Gln Val Thr Val Ser Ser
        275                 280                 285


<210> SEQ ID NO 141
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 141

Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175
```

```
Val Gln Pro Gly Gly Ser Leu Arg Leu Ser Cys Val Ala Ser Gly Ile
            180                 185                 190

Arg Phe Met Ser Met Ala Trp Tyr Arg Gln Ala Pro Gly Lys His Arg
        195                 200                 205

Glu Leu Val Ala Arg Ile Ser Ser Gly Gly Thr Thr Ala Tyr Val Asp
    210                 215                 220

Ser Val Lys Gly Arg Phe Thr Ile Ser Arg Asp Asn Ser Lys Asn Thr
225                 230                 235                 240

Val Tyr Leu Gln Met Asn Ser Leu Lys Ala Glu Asp Thr Ala Val Tyr
                245                 250                 255

Tyr Cys Asn Thr Phe Ser Ser Arg Pro Asn Pro Trp Gly Ala Gly Thr
            260                 265                 270

Gln Val Thr Val Ser Ser
        275
```

<210> SEQ ID NO 142
<211> LENGTH: 281
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 142

```
Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Pro Gly Gly Ser Leu Arg Leu Ser Cys Ala Ala Ser Gly Asn
            180                 185                 190

Ile Phe Ser Asn Asn Ala Met Ala Trp Tyr Arg Gln Ala Pro Gly Lys
        195                 200                 205

Gln Arg Glu Leu Val Ala Arg Ile Ser Ser Gly Gly Phe Thr Tyr
    210                 215                 220

Tyr Leu Asp Ser Val Lys Gly Arg Phe Thr Val Ser Arg Asp Asn Ala
225                 230                 235                 240
```

```
Lys Asn Thr Val Tyr Leu Gln Met Asn Ser Leu Lys Pro Glu Asp Thr
                245                 250                 255

Ala Val Tyr Tyr Cys Asn Ala Ala Tyr Arg Thr Tyr Asn Tyr Trp Gly
            260                 265                 270

Gln Gly Thr Gln Val Thr Val Ser Ser
        275                 280


<210> SEQ ID NO 143
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 143

Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Ala Gly Gly Ser Leu Arg Leu Ser Cys Ala Ala Ser Gly Arg
            180                 185                 190

Thr Phe Ser Asn Tyr Ala Met Gly Trp Phe Arg Gln Ala Pro Gly Lys
        195                 200                 205

Glu Arg Val Leu Val Ala Asp Ile Ser Ser Ser Gly Ile Asn Thr Tyr
    210                 215                 220

Val Ala Asp Ala Val Lys Gly Arg Phe Thr Ile Ser Arg Asp Asn Ala
225                 230                 235                 240

Lys Asn Thr Val Tyr Leu Gln Met Asn Ser Leu Lys Pro Glu Asp Thr
                245                 250                 255

Ala Val Tyr Tyr Cys Ala Ala Ser Ala Trp Trp Tyr Ser Gln Met Ala
            260                 265                 270

Arg Asp Asn Tyr Arg Tyr Trp Gly Gln Gly Thr Gln Val Thr Val Ser
        275                 280                 285

Ser
```

<210> SEQ ID NO 144
<211> LENGTH: 282
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Artificial polypeptide comprising lama glama
sequences

<400> SEQUENCE: 144

```
Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Pro Gly Gly Ser Leu Arg Leu Ala Cys Ala Ala Ser Gly Phe
            180                 185                 190

Thr Leu Ser Ser Ser Trp Met Tyr Trp Val Arg Gln Ala Pro Gly Lys
        195                 200                 205

Gly Leu Glu Trp Val Ser Arg Ile Ser Pro Gly Gly Leu Phe Thr Tyr
    210                 215                 220

Tyr Val Asp Ser Val Lys Gly Arg Phe Ser Val Ser Thr Asp Asn Ala
225                 230                 235                 240

Asn Asn Thr Leu Tyr Leu Gln Met Asn Ser Leu Lys Pro Glu Asp Thr
                245                 250                 255

Ala Leu Tyr Ser Cys Ala Lys Gly Gly Ala Pro Asn Tyr Thr Pro Arg
            260                 265                 270

Gly Arg Gly Thr Gln Val Thr Val Ser Ser
        275                 280
```

<210> SEQ ID NO 145
<211> LENGTH: 290
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Artificial polypeptide comprising lama glama sequences

<400> SEQUENCE: 145

```
Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Ala Gly Asp Ser Leu Arg Leu Ser Cys Thr Ala Ser Gly Arg
            180                 185                 190

Thr Phe Asn Ser Tyr Ala Met Gly Trp Phe Arg Gln Ala Pro Gly Lys
        195                 200                 205

Glu Arg Glu Ser Val Ala His Ile Asn Arg Ser Gly Ser Ser Thr Tyr
    210                 215                 220

Tyr Ala Asp Ser Val Lys Gly Arg Phe Thr Ile Ser Arg Asp Asn Ala
225                 230                 235                 240

Lys Asn Thr Val Tyr Leu Gln Leu Asn Ser Leu Lys Pro Glu Asp Thr
                245                 250                 255

Ala Val Tyr Tyr Cys Ala Ala Gly Arg Tyr Tyr Ser Ser Asp Gly Val
            260                 265                 270

Pro Ser Ala Ser Phe Asn Tyr Trp Gly Gln Gly Thr Gln Val Thr Val
        275                 280                 285

Ser Ser
    290
```

<210> SEQ ID NO 146
<211> LENGTH: 288
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 146

```
Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
```

```
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80

Gln Ile Asn Ser Leu Lys Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Gln Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Ala Gly Gly Ser Leu Arg Leu Ser Cys Thr Ala Ser Gly Ser
            180                 185                 190

Ala Phe Lys Ser Tyr Arg Met Gly Trp Phe Arg Arg Thr Pro Gly Lys
        195                 200                 205

Glu Asp Glu Phe Val Ala Ser Ile Ser Trp Thr Tyr Gly Ser Thr Phe
    210                 215                 220

Tyr Ala Asp Ser Val Lys Gly Arg Phe Thr Met Ser Arg Asp Lys Ala
225                 230                 235                 240

Lys Asn Ala Gly Tyr Leu Gln Met Asn Ser Leu Lys Pro Glu Asp Thr
                245                 250                 255

Ala Leu Tyr Tyr Cys Ala Ala Gly Ala Gln Ser Asp Arg Tyr Asn Ile
            260                 265                 270

Arg Ser Tyr Asp Tyr Trp Gly Gln Gly Thr Gln Val Thr Val Ser Ser
        275                 280                 285


<210> SEQ ID NO 147
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 147

Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser Ser Tyr
            20                  25                  30

Ser Met Gly Trp Phe Arg Gln Ala Gln Gly Lys Glu Arg Glu Phe Val
        35                  40                  45

Val Ala Ile Ser Lys Gly Gly Tyr Lys Tyr Asp Ser Val Ser Leu Glu
    50                  55                  60

Gly Arg Phe Thr Ile Ser Lys Asp Asn Ala Lys Asn Thr Val Tyr Leu
65                  70                  75                  80
```

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Gly Gly Gly Gly Ser Gly Gly Gly Gly Ser
145 150 155 160

Gly Gly Gly Gly Ser Glu Val Gln Leu Val Glu Ser Gly Gly Gly Leu
165 170 175

Val Gln Pro Gly Gly Ser Leu Lys Leu Ser Cys Thr Ala Ser Gly Phe
180 185 190

Thr Phe Ser Thr Ser Trp Met His Trp Val Arg Gln Ala Pro Gly Lys
195 200 205

Gly Leu Glu Trp Val Ser Ser Ile Pro Pro Val Gly His Phe Ala Asn
210 215 220

Tyr Ala Pro Ser Val Lys Gly Arg Phe Thr Ile Ser Arg Asp Asn Ala
225 230 235 240

Lys Asn Thr Leu Phe Leu Gln Met Asn Ser Leu Lys Ser Glu Asp Thr
245 250 255

Ala Val Tyr Tyr Cys Ala Lys Asp Ser Ala Gly Arg Thr Lys Gly Gln
260 265 270

Gly Thr Gln Val Thr Val Ser Ser
275 280

<210> SEQ ID NO 148
<211> LENGTH: 289
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 148

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser Ser Tyr
20 25 30

Ser Met Gly Trp Phe Arg Gln Ala Gln Gly Lys Glu Arg Glu Phe Val
35 40 45

Val Ala Ile Ser Lys Gly Gly Tyr Lys Tyr Asp Ser Val Ser Leu Glu
50 55 60

Gly Arg Phe Thr Ile Ser Lys Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Gln Val Thr Val Ser Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Gly Gly Gly Gly Ser Gly Gly Gly Gly Ser
145 150 155 160

Gly Gly Gly Gly Ser Glu Val Gln Leu Val Glu Ser Gly Gly Gly Leu
165 170 175

Val Gln Ala Gly Gly Ser Leu Arg Leu Ser Cys Ala Ala Ser Glu Arg
180 185 190

Thr Phe Ser Asn Tyr Ala Met Asp Trp Phe Arg Gln Ala Pro Gly Lys
195 200 205

Glu Arg Glu Phe Val Ala Ala Ile Thr Arg Ser Gly Gly Gly Thr Tyr
210 215 220

Tyr Ala Asp Ser Val Lys Gly Arg Phe Thr Ile Ser Arg Asp Asn Ala
225 230 235 240

Lys Asn Thr Val Tyr Leu Gln Met Asn Ser Leu Lys Pro Glu Asp Thr
245 250 255

Ala Val Tyr Tyr Cys Ala Ala Thr Arg Ser Ser Thr Ile Val Val Gly
260 265 270

Val Gly Gly Met Glu Tyr Trp Gly Lys Gly Thr Gln Val Thr Val Ser
275 280 285

Ser

<210> SEQ ID NO 149
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 149

Glu Val Gln Leu Val Glu Ser Gly Gly Gly Leu Val Gln Pro Gly Gly
1 5 10 15

Ser Leu Arg Leu Ser Cys Ala Ala Ser Gly Ser Ala Val Gly Asp Ile
20 25 30

Thr Val Ala Trp Tyr Arg Gln Ala Pro Gly Ile Gln Arg Gln Leu Val
35 40 45

Ala Thr Ile Thr Pro Ser Gly Tyr Thr Tyr Tyr Trp Asp Phe Val Lys
50 55 60

Gly Arg Phe Thr Ile Ser Arg Asp Asn Ser Lys Asn Ile Val Tyr Leu
65 70 75 80

Gln Met Asn Ser Leu Lys Pro Glu Asp Thr Ala Ala Tyr Tyr Cys Asn
85 90 95

Thr Gln Phe Tyr Trp Gly Gln Gly Thr Gln Val Thr Val Ser Ser Gly
100 105 110

Gly Gly Gly Ser Gly Gly Gly Ser Glu Val Gln Leu Val Glu Ser Gly
115 120 125

Gly Gly Leu Val Gln Thr Gly Asp Ser Leu Arg Leu Ser Cys Glu Val
130 135 140

Ser Gly Arg Thr Phe Ser Ser Tyr Ser Met Gly Trp Phe Arg Gln Ala
145 150 155 160

Gln Gly Lys Glu Arg Glu Phe Val Val Ala Ile Ser Lys Gly Gly Tyr
165 170 175

Lys Tyr Asp Ser Val Ser Leu Glu Gly Arg Phe Thr Ile Ser Lys Asp
180 185 190

Asn Ala Lys Asn Thr Val Tyr Leu Gln Ile Asn Ser Leu Lys Pro Glu
195 200 205

Asp Thr Ala Val Tyr Tyr Cys Ala Ser Ser Arg Ala Tyr Gly Ser Ser
210 215 220

Arg Leu Arg Leu Ala Asp Thr Tyr Glu Tyr Trp Gly Gln Gly Thr Gln
225 230 235 240

Val Thr Val Ser Ser
245

<210> SEQ ID NO 150
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 150

Glu Val Gln Leu Val Glu Ser Gly Gly Gly Leu Ala Gln Ala Gly Asp
1 5 10 15

Ser Leu Arg Leu Ser Cys Ala Ala Ser Gly Arg Ser Phe Ser His Tyr
20 25 30

Asn Met Gly Trp Phe Arg Gln Ala Pro Gly Lys Glu Arg Glu Phe Val
35 40 45

Ala Ser Ile Arg Gly Gly Gly Gly Ser Thr Thr Tyr Ala Asn Ser Val
50 55 60

Lys Asp Arg Phe Thr Ile Ser Arg Glu Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Thr Ala Phe Tyr Arg Gly Pro Tyr Asp Tyr Asp Tyr Trp Gly
100 105 110

Gln Gly Thr Gln Val Thr Val Ser Ser Gly Gly Gly Gly Ser Gly Gly
115 120 125

Gly Ser Glu Val Gln Leu Val Glu Ser Gly Gly Gly Leu Val Gln Thr
130 135 140

Gly Asp Ser Leu Arg Leu Ser Cys Glu Val Ser Gly Arg Thr Phe Ser
145 150 155 160

Ser Tyr Ser Met Gly Trp Phe Arg Gln Ala Gln Gly Lys Glu Arg Glu
165 170 175

Phe Val Val Ala Ile Ser Lys Gly Gly Tyr Lys Tyr Asp Ser Val Ser
180 185 190

Leu Glu Gly Arg Phe Thr Ile Ser Lys Asp Asn Ala Lys Asn Thr Val
195 200 205

Tyr Leu Gln Ile Asn Ser Leu Lys Pro Glu Asp Thr Ala Val Tyr Tyr
210 215 220

Cys Ala Ser Ser Arg Ala Tyr Gly Ser Ser Arg Leu Arg Leu Ala Asp
225 230 235 240

Thr Tyr Glu Tyr Trp Gly Gln Gly Thr Gln Val Thr Val Ser Ser
245 250 255

<210> SEQ ID NO 151
<211> LENGTH: 247
<212> TYPE: PRT

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 151

```
Glu Val Gln Leu Val Glu Ser Gly Gly Gly Leu Val Gln Pro Gly Gly
1               5                   10                  15

Ser Leu Arg Leu Ser Cys Val Ala Ser Gly Ile Arg Phe Met Ser Met
            20                  25                  30

Ala Trp Tyr Arg Gln Ala Pro Gly Lys His Arg Glu Leu Val Ala Arg
        35                  40                  45

Ile Ser Ser Gly Gly Thr Thr Ala Tyr Val Asp Ser Val Lys Gly Arg
    50                  55                  60

Phe Thr Ile Ser Arg Asp Asn Ser Lys Asn Thr Val Tyr Leu Gln Met
65                  70                  75                  80

Asn Ser Leu Lys Ala Glu Asp Thr Ala Val Tyr Tyr Cys Asn Thr Phe
                85                  90                  95

Ser Ser Arg Pro Asn Pro Trp Gly Ala Gly Thr Gln Val Thr Val Ser
            100                 105                 110

Ser Gly Gly Gly Gly Ser Gly Gly Gly Ser Glu Val Gln Leu Val Glu
        115                 120                 125

Ser Gly Gly Gly Leu Val Gln Thr Gly Asp Ser Leu Arg Leu Ser Cys
    130                 135                 140

Glu Val Ser Gly Arg Thr Phe Ser Ser Tyr Ser Met Gly Trp Phe Arg
145                 150                 155                 160

Gln Ala Gln Gly Lys Glu Arg Glu Phe Val Val Ala Ile Ser Lys Gly
                165                 170                 175

Gly Tyr Lys Tyr Asp Ser Val Ser Leu Glu Gly Arg Phe Thr Ile Ser
            180                 185                 190

Lys Asp Asn Ala Lys Asn Thr Val Tyr Leu Gln Ile Asn Ser Leu Lys
        195                 200                 205

Pro Glu Asp Thr Ala Val Tyr Tyr Cys Ala Ser Ser Arg Ala Tyr Gly
    210                 215                 220

Ser Ser Arg Leu Arg Leu Ala Asp Thr Tyr Glu Tyr Trp Gly Gln Gly
225                 230                 235                 240

Thr Gln Val Thr Val Ser Ser
                245
```

<210> SEQ ID NO 152
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 152

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Phe Ser Asn Asn
            20                  25                  30

Ala Met Ala Trp Tyr Arg Gln Ala Pro Gly Lys Gln Arg Glu Leu Val
```

```
        35                  40                  45

Ala Arg Ile Ser Ser Gly Gly Gly Phe Thr Tyr Tyr Leu Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Ala Tyr Arg Thr Tyr Asn Tyr Trp Gly Gln Gly Thr Gln Val
            100                 105                 110

Thr Val Ser Ser Gly Gly Gly Gly Ser Gly Gly Gly Ser Glu Val Gln
        115                 120                 125

Leu Val Glu Ser Gly Gly Gly Leu Val Gln Thr Gly Asp Ser Leu Arg
    130                 135                 140

Leu Ser Cys Glu Val Ser Gly Arg Thr Phe Ser Ser Tyr Ser Met Gly
145                 150                 155                 160

Trp Phe Arg Gln Ala Gln Gly Lys Glu Arg Glu Phe Val Val Ala Ile
                165                 170                 175

Ser Lys Gly Gly Tyr Lys Tyr Asp Ser Val Ser Leu Glu Gly Arg Phe
            180                 185                 190

Thr Ile Ser Lys Asp Asn Ala Lys Asn Thr Val Tyr Leu Gln Ile Asn
        195                 200                 205

Ser Leu Lys Pro Glu Asp Thr Ala Val Tyr Tyr Cys Ala Ser Ser Arg
    210                 215                 220

Ala Tyr Gly Ser Ser Arg Leu Arg Leu Ala Asp Thr Tyr Glu Tyr Trp
225                 230                 235                 240

Gly Gln Gly Thr Gln Val Thr Val Ser Ser
                245                 250
```

<210> SEQ ID NO 153
<211> LENGTH: 258
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 153

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Val Leu Val
        35                  40                  45

Ala Asp Ile Ser Ser Ser Gly Ile Asn Thr Tyr Val Ala Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Ala Trp Trp Tyr Ser Gln Met Ala Arg Asp Asn Tyr Arg
            100                 105                 110

Tyr Trp Gly Gln Gly Thr Gln Val Thr Val Ser Ser Gly Gly Gly Gly
        115                 120                 125
```

```
Ser Gly Gly Gly Ser Glu Val Gln Leu Val Glu Ser Gly Gly Gly Leu
    130                 135                 140

Val Gln Thr Gly Asp Ser Leu Arg Leu Ser Cys Glu Val Ser Gly Arg
145                 150                 155                 160

Thr Phe Ser Ser Tyr Ser Met Gly Trp Phe Arg Gln Ala Gln Gly Lys
                165                 170                 175

Glu Arg Glu Phe Val Val Ala Ile Ser Lys Gly Gly Tyr Lys Tyr Asp
            180                 185                 190

Ser Val Ser Leu Glu Gly Arg Phe Thr Ile Ser Lys Asp Asn Ala Lys
        195                 200                 205

Asn Thr Val Tyr Leu Gln Ile Asn Ser Leu Lys Pro Glu Asp Thr Ala
    210                 215                 220

Val Tyr Tyr Cys Ala Ser Ser Arg Ala Tyr Gly Ser Ser Arg Leu Arg
225                 230                 235                 240

Leu Ala Asp Thr Tyr Glu Tyr Trp Gly Gln Gly Thr Gln Val Thr Val
                245                 250                 255

Ser Ser


<210> SEQ ID NO 154
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 154

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Leu Ser Ser Ser
            20                  25                  30

Trp Met Tyr Trp Val Arg Gln Ala Pro Gly Lys Gly Leu Glu Trp Val
        35                  40                  45

Ser Arg Ile Ser Pro Gly Gly Leu Phe Thr Tyr Tyr Val Asp Ser Val
    50                  55                  60

Lys Gly Arg Phe Ser Val Ser Thr Asp Asn Ala Asn Asn Thr Leu Tyr
65                  70                  75                  80

Leu Gln Met Asn Ser Leu Lys Pro Glu Asp Thr Ala Leu Tyr Ser Cys
                85                  90                  95

Ala Lys Gly Gly Ala Pro Asn Tyr Thr Pro Arg Gly Arg Gly Thr Gln
            100                 105                 110

Val Thr Val Ser Ser Gly Gly Gly Gly Ser Gly Gly Gly Ser Glu Val
        115                 120                 125

Gln Leu Val Glu Ser Gly Gly Gly Leu Val Gln Thr Gly Asp Ser Leu
    130                 135                 140

Arg Leu Ser Cys Glu Val Ser Gly Arg Thr Phe Ser Ser Tyr Ser Met
145                 150                 155                 160

Gly Trp Phe Arg Gln Ala Gln Gly Lys Glu Arg Glu Phe Val Val Ala
                165                 170                 175

Ile Ser Lys Gly Gly Tyr Lys Tyr Asp Ser Val Ser Leu Glu Gly Arg
            180                 185                 190

Phe Thr Ile Ser Lys Asp Asn Ala Lys Asn Thr Val Tyr Leu Gln Ile
        195                 200                 205
```

-continued

```
Asn Ser Leu Lys Pro Glu Asp Thr Ala Val Tyr Tyr Cys Ala Ser Ser
    210                 215                 220

Arg Ala Tyr Gly Ser Ser Arg Leu Arg Leu Ala Asp Thr Tyr Glu Tyr
225                 230                 235                 240

Trp Gly Gln Gly Thr Gln Val Thr Val Ser Ser
                245                 250


<210> SEQ ID NO 155
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 155

Glu Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Asn Ser Tyr
            20                  25                  30

Ala Met Gly Trp Phe Arg Gln Ala Pro Gly Lys Glu Arg Glu Ser Val
        35                  40                  45

Ala His Ile Asn Arg Ser Gly Ser Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Gly Arg Tyr Tyr Ser Ser Asp Gly Val Pro Ser Ala Ser Phe
            100                 105                 110

Asn Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Thr Gly Asp Ser Leu Arg Leu Ser Cys Glu Val Ser Gly
145                 150                 155                 160

Arg Thr Phe Ser Ser Tyr Ser Met Gly Trp Phe Arg Gln Ala Gln Gly
                165                 170                 175

Lys Glu Arg Glu Phe Val Val Ala Ile Ser Lys Gly Gly Tyr Lys Tyr
            180                 185                 190

Asp Ser Val Ser Leu Glu Gly Arg Phe Thr Ile Ser Lys Asp Asn Ala
        195                 200                 205

Lys Asn Thr Val Tyr Leu Gln Ile Asn Ser Leu Lys Pro Glu Asp Thr
    210                 215                 220

Ala Val Tyr Tyr Cys Ala Ser Ser Arg Ala Tyr Gly Ser Ser Arg Leu
225                 230                 235                 240

Arg Leu Ala Asp Thr Tyr Glu Tyr Trp Gly Gln Gly Thr Gln Val Thr
                245                 250                 255

Val Ser Ser


<210> SEQ ID NO 156
<211> LENGTH: 257
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<223> OTHER INFORMATION: Artificial polypeptide comprising lama glama
sequences

<400> SEQUENCE: 156

Glu Val Gln Leu Val Glu Ser Gly Gly Gly Leu Val Gln Ala Gly Gly
1 5 10 15

Ser Leu Arg Leu Ser Cys Thr Ala Ser Gly Ser Ala Phe Lys Ser Tyr
20 25 30

Arg Met Gly Trp Phe Arg Arg Thr Pro Gly Lys Glu Asp Glu Phe Val
35 40 45

Ala Ser Ile Ser Trp Thr Tyr Gly Ser Thr Phe Tyr Ala Asp Ser Val
50 55 60

Lys Gly Arg Phe Thr Met Ser Arg Asp Lys Ala Lys Asn Ala Gly Tyr
65 70 75 80

Leu Gln Met Asn Ser Leu Lys Pro Glu Asp Thr Ala Leu Tyr Tyr Cys
85 90 95

Ala Ala Gly Ala Gln Ser Asp Arg Tyr Asn Ile Arg Ser Tyr Asp Tyr
100 105 110

Trp Gly Gln Gly Thr Gln Val Thr Val Ser Ser Gly Gly Gly Gly Ser
115 120 125

Gly Gly Gly Ser Glu Val Gln Leu Val Glu Ser Gly Gly Gly Leu Val
130 135 140

Gln Thr Gly Asp Ser Leu Arg Leu Ser Cys Glu Val Ser Gly Arg Thr
145 150 155 160

Phe Ser Ser Tyr Ser Met Gly Trp Phe Arg Gln Ala Gln Gly Lys Glu
165 170 175

Arg Glu Phe Val Val Ala Ile Ser Lys Gly Gly Tyr Lys Tyr Asp Ser
180 185 190

Val Ser Leu Glu Gly Arg Phe Thr Ile Ser Lys Asp Asn Ala Lys Asn
195 200 205

Thr Val Tyr Leu Gln Ile Asn Ser Leu Lys Pro Glu Asp Thr Ala Val
210 215 220

Tyr Tyr Cys Ala Ser Ser Arg Ala Tyr Gly Ser Ser Arg Leu Arg Leu
225 230 235 240

Ala Asp Thr Tyr Glu Tyr Trp Gly Gln Gly Thr Gln Val Thr Val Ser
245 250 255

Ser

<210> SEQ ID NO 157
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Artificial polypeptide comprising lama glama
sequences

<400> SEQUENCE: 157

Glu Val Gln Leu Val Glu Ser Gly Gly Gly Leu Val Gln Pro Gly Gly
1 5 10 15

Ser Leu Lys Leu Ser Cys Thr Ala Ser Gly Phe Thr Phe Ser Thr Ser
20 25 30

Trp Met His Trp Val Arg Gln Ala Pro Gly Lys Gly Leu Glu Trp Val

```
        35                  40                  45

Ser Ser Ile Pro Pro Val Gly His Phe Ala Asn Tyr Ala Pro Ser Val
    50                  55                  60

Lys Gly Arg Phe Thr Ile Ser Arg Asp Asn Ala Lys Asn Thr Leu Phe
65                  70                  75                  80

Leu Gln Met Asn Ser Leu Lys Ser Glu Asp Thr Ala Val Tyr Tyr Cys
                85                  90                  95

Ala Lys Asp Ser Ala Gly Arg Thr Lys Gly Gln Gly Thr Gln Val Thr
            100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Thr Gly Asp Ser Leu Arg Leu
    130                 135                 140

Ser Cys Glu Val Ser Gly Arg Thr Phe Ser Ser Tyr Ser Met Gly Trp
145                 150                 155                 160

Phe Arg Gln Ala Gln Gly Lys Glu Arg Glu Phe Val Val Ala Ile Ser
                165                 170                 175

Lys Gly Gly Tyr Lys Tyr Asp Ser Val Ser Leu Glu Gly Arg Phe Thr
            180                 185                 190

Ile Ser Lys Asp Asn Ala Lys Asn Thr Val Tyr Leu Gln Ile Asn Ser
        195                 200                 205

Leu Lys Pro Glu Asp Thr Ala Val Tyr Tyr Cys Ala Ser Ser Arg Ala
    210                 215                 220

Tyr Gly Ser Ser Arg Leu Arg Leu Ala Asp Thr Tyr Glu Tyr Trp Gly
225                 230                 235                 240

Gln Gly Thr Gln Val Thr Val Ser Ser
                245


<210> SEQ ID NO 158
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 158

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Phe Ser Asn Tyr
            20                  25                  30

Ala Met Asp Trp Phe Arg Gln Ala Pro Gly Lys Glu Arg Glu Phe Val
        35                  40                  45

Ala Ala Ile Thr Arg Ser Gly Gly Gly Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Arg Ser Ser Thr Ile Val Val Gly Val Gly Gly Met Glu
            100                 105                 110

Tyr Trp Gly Lys Gly Thr Gln Val Thr Val Ser Ser Gly Gly Gly Gly
        115                 120                 125
```

```
Ser Gly Gly Gly Ser Glu Val Gln Leu Val Glu Ser Gly Gly Gly Leu
    130                 135                 140

Val Gln Thr Gly Asp Ser Leu Arg Leu Ser Cys Glu Val Ser Gly Arg
145                 150                 155                 160

Thr Phe Ser Ser Tyr Ser Met Gly Trp Phe Arg Gln Ala Gln Gly Lys
                165                 170                 175

Glu Arg Glu Phe Val Val Ala Ile Ser Lys Gly Gly Tyr Lys Tyr Asp
            180                 185                 190

Ser Val Ser Leu Glu Gly Arg Phe Thr Ile Ser Lys Asp Asn Ala Lys
        195                 200                 205

Asn Thr Val Tyr Leu Gln Ile Asn Ser Leu Lys Pro Glu Asp Thr Ala
    210                 215                 220

Val Tyr Tyr Cys Ala Ser Ser Arg Ala Tyr Gly Ser Ser Arg Leu Arg
225                 230                 235                 240

Leu Ala Asp Thr Tyr Glu Tyr Trp Gly Gln Gly Thr Gln Val Thr Val
                245                 250                 255

Ser Ser


<210> SEQ ID NO 159
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ala Val Gly Asp Ile
            20                  25                  30

Thr Val Ala Trp Tyr Arg Gln Ala Pro Gly Ile Gln Arg Gln Leu Val
        35                  40                  45

Ala Thr Ile Thr Pro Ser Gly Tyr Thr Tyr Tyr Trp Asp Phe Val Lys
    50                  55                  60

Gly Arg Phe Thr Ile Ser Arg Asp Asn Ser Lys Asn Ile Val Tyr Leu
65                  70                  75                  80

Gln Met Asn Ser Leu Lys Pro Glu Asp Thr Ala Ala Tyr Tyr Cys Asn
                85                  90                  95

Thr Gln Phe Tyr Trp Gly Gln Gly Thr Gln Val Thr Val Ser Ser Gly
            100                 105                 110

Gly Gly Gly Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Glu Val Gln Leu Val Glu Ser Gly Gly
145                 150                 155                 160

Gly Leu Val Gln Thr Gly Asp Ser Leu Arg Leu Ser Cys Glu Val Ser
                165                 170                 175

Gly Arg Thr Phe Ser Ser Tyr Ser Met Gly Trp Phe Arg Gln Ala Gln
            180                 185                 190

Gly Lys Glu Arg Glu Phe Val Val Ala Ile Ser Lys Gly Gly Tyr Lys
        195                 200                 205
```

-continued

```
Tyr Asp Ser Val Ser Leu Glu Gly Arg Phe Thr Ile Ser Lys Asp Asn
    210                 215                 220

Ala Lys Asn Thr Val Tyr Leu Gln Ile Asn Ser Leu Lys Pro Glu Asp
225                 230                 235                 240

Thr Ala Val Tyr Tyr Cys Ala Ser Ser Arg Ala Tyr Gly Ser Ser Arg
                245                 250                 255

Leu Arg Leu Ala Asp Thr Tyr Glu Tyr Trp Gly Gln Gly Thr Gln Val
            260                 265                 270

Thr Val Ser Ser
        275


<210> SEQ ID NO 160
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 160

Glu Val Gln Leu Val Glu Ser Gly Gly Gly Leu Ala Gln Ala Gly Asp
1               5                   10                  15

Ser Leu Arg Leu Ser Cys Ala Ala Ser Gly Arg Ser Phe Ser His Tyr
            20                  25                  30

Asn Met Gly Trp Phe Arg Gln Ala Pro Gly Lys Glu Arg Glu Phe Val
        35                  40                  45

Ala Ser Ile Arg Gly Gly Gly Gly Ser Thr Thr Tyr Ala Asn Ser Val
    50                  55                  60

Lys Asp Arg Phe Thr Ile Ser Arg Glu Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Ala Phe Tyr Arg Gly Pro Tyr Asp Tyr Asp Tyr Trp Gly
            100                 105                 110

Gln Gly Thr Gln Val Thr Val Ser Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Thr Gly
                165                 170                 175

Asp Ser Leu Arg Leu Ser Cys Glu Val Ser Gly Arg Thr Phe Ser Ser
            180                 185                 190

Tyr Ser Met Gly Trp Phe Arg Gln Ala Gln Gly Lys Glu Arg Glu Phe
        195                 200                 205

Val Val Ala Ile Ser Lys Gly Gly Tyr Lys Tyr Asp Ser Val Ser Leu
    210                 215                 220

Glu Gly Arg Phe Thr Ile Ser Lys Asp Asn Ala Lys Asn Thr Val Tyr
225                 230                 235                 240

Leu Gln Ile Asn Ser Leu Lys Pro Glu Asp Thr Ala Val Tyr Tyr Cys
                245                 250                 255

Ala Ser Ser Arg Ala Tyr Gly Ser Ser Arg Leu Arg Leu Ala Asp Thr
            260                 265                 270
```

```
Tyr Glu Tyr Trp Gly Gln Gly Thr Gln Val Thr Val Ser Ser
        275                 280                 285
```

<210> SEQ ID NO 161
<211> LENGTH: 278
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 161

```
Glu Val Gln Leu Val Glu Ser Gly Gly Gly Leu Val Gln Pro Gly Gly
1               5                   10                  15

Ser Leu Arg Leu Ser Cys Val Ala Ser Gly Ile Arg Phe Met Ser Met
            20                  25                  30

Ala Trp Tyr Arg Gln Ala Pro Gly Lys His Arg Glu Leu Val Ala Arg
        35                  40                  45

Ile Ser Ser Gly Gly Thr Thr Ala Tyr Val Asp Ser Val Lys Gly Arg
    50                  55                  60

Phe Thr Ile Ser Arg Asp Asn Ser Lys Asn Thr Val Tyr Leu Gln Met
65                  70                  75                  80

Asn Ser Leu Lys Ala Glu Asp Thr Ala Val Tyr Tyr Cys Asn Thr Phe
                85                  90                  95

Ser Ser Arg Pro Asn Pro Trp Gly Ala Gly Thr Gln Val Thr Val Ser
            100                 105                 110

Ser Gly Gly Gly Gly Ser Gly Gly Gly Gly Ser Gly Gly Gly Gly Ser
        115                 120                 125

Gly Gly Gly Gly Ser Gly Gly Gly Gly Ser Gly Gly Gly Gly Ser Gly
    130                 135                 140

Gly Gly Gly Ser Gly Gly Gly Gly Ser Glu Val Gln Leu Val Glu Ser
145                 150                 155                 160

Gly Gly Gly Leu Val Gln Thr Gly Asp Ser Leu Arg Leu Ser Cys Glu
                165                 170                 175

Val Ser Gly Arg Thr Phe Ser Ser Tyr Ser Met Gly Trp Phe Arg Gln
            180                 185                 190

Ala Gln Gly Lys Glu Arg Glu Phe Val Val Ala Ile Ser Lys Gly Gly
        195                 200                 205

Tyr Lys Tyr Asp Ser Val Ser Leu Glu Gly Arg Phe Thr Ile Ser Lys
    210                 215                 220

Asp Asn Ala Lys Asn Thr Val Tyr Leu Gln Ile Asn Ser Leu Lys Pro
225                 230                 235                 240

Glu Asp Thr Ala Val Tyr Tyr Cys Ala Ser Ser Arg Ala Tyr Gly Ser
                245                 250                 255

Ser Arg Leu Arg Leu Ala Asp Thr Tyr Glu Tyr Trp Gly Gln Gly Thr
            260                 265                 270

Gln Val Thr Val Ser Ser
        275
```

<210> SEQ ID NO 162
<211> LENGTH: 281
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<223> OTHER INFORMATION: Artificial polypeptide comprising lama glama
      sequences

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Phe Ser Asn Asn
            20                  25                  30

Ala Met Ala Trp Tyr Arg Gln Ala Pro Gly Lys Gln Arg Glu Leu Val
        35                  40                  45

Ala Arg Ile Ser Ser Gly Gly Gly Phe Thr Tyr Tyr Leu Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Ala Tyr Arg Thr Tyr Asn Tyr Trp Gly Gln Gly Thr Gln Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Glu Val Gln Leu
145                 150                 155                 160

Val Glu Ser Gly Gly Gly Leu Val Gln Thr Gly Asp Ser Leu Arg Leu
                165                 170                 175

Ser Cys Glu Val Ser Gly Arg Thr Phe Ser Ser Tyr Ser Met Gly Trp
            180                 185                 190

Phe Arg Gln Ala Gln Gly Lys Glu Arg Glu Phe Val Val Ala Ile Ser
        195                 200                 205

Lys Gly Gly Tyr Lys Tyr Asp Ser Val Ser Leu Glu Gly Arg Phe Thr
    210                 215                 220

Ile Ser Lys Asp Asn Ala Lys Asn Thr Val Tyr Leu Gln Ile Asn Ser
225                 230                 235                 240

Leu Lys Pro Glu Asp Thr Ala Val Tyr Tyr Cys Ala Ser Ser Arg Ala
                245                 250                 255

Tyr Gly Ser Ser Arg Leu Arg Leu Ala Asp Thr Tyr Glu Tyr Trp Gly
            260                 265                 270

Gln Gly Thr Gln Val Thr Val Ser Ser
        275                 280


<210> SEQ ID NO 163
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 163

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
```

```
            20                  25                  30

Ala Met Gly Trp Phe Arg Gln Ala Pro Gly Lys Glu Arg Val Leu Val
        35                  40                  45

Ala Asp Ile Ser Ser Ser Gly Ile Asn Thr Tyr Val Ala Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Ala Trp Trp Tyr Ser Gln Met Ala Arg Asp Asn Tyr Arg
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160

Gly Gly Gly Ser Glu Val Gln Leu Val Glu Ser Gly Gly Gly Leu Val
                165                 170                 175

Gln Thr Gly Asp Ser Leu Arg Leu Ser Cys Glu Val Ser Gly Arg Thr
            180                 185                 190

Phe Ser Ser Tyr Ser Met Gly Trp Phe Arg Gln Ala Gln Gly Lys Glu
        195                 200                 205

Arg Glu Phe Val Val Ala Ile Ser Lys Gly Gly Tyr Lys Tyr Asp Ser
    210                 215                 220

Val Ser Leu Glu Gly Arg Phe Thr Ile Ser Lys Asp Asn Ala Lys Asn
225                 230                 235                 240

Thr Val Tyr Leu Gln Ile Asn Ser Leu Lys Pro Glu Asp Thr Ala Val
                245                 250                 255

Tyr Tyr Cys Ala Ser Ser Arg Ala Tyr Gly Ser Ser Arg Leu Arg Leu
            260                 265                 270

Ala Asp Thr Tyr Glu Tyr Trp Gly Gln Gly Thr Gln Val Thr Val Ser
        275                 280                 285

Ser


<210> SEQ ID NO 164
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 164

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Leu Ser Ser Ser
            20                  25                  30

Trp Met Tyr Trp Val Arg Gln Ala Pro Gly Lys Gly Leu Glu Trp Val
        35                  40                  45

Ser Arg Ile Ser Pro Gly Gly Leu Phe Thr Tyr Tyr Val Asp Ser Val
    50                  55                  60

Lys Gly Arg Phe Ser Val Ser Thr Asp Asn Ala Asn Asn Thr Leu Tyr
```

```
65                  70                  75                  80

Leu Gln Met Asn Ser Leu Lys Pro Glu Asp Thr Ala Leu Tyr Ser Cys
                85                  90                  95

Ala Lys Gly Gly Ala Pro Asn Tyr Thr Pro Arg Gly Arg Gly Thr Gln
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Val Glu Ser Gly Gly Gly Leu Val Gln Thr Gly Asp Ser Leu Arg
                165                 170                 175

Leu Ser Cys Glu Val Ser Gly Arg Thr Phe Ser Ser Tyr Ser Met Gly
            180                 185                 190

Trp Phe Arg Gln Ala Gln Gly Lys Glu Arg Glu Phe Val Val Ala Ile
        195                 200                 205

Ser Lys Gly Gly Tyr Lys Tyr Asp Ser Val Ser Leu Glu Gly Arg Phe
    210                 215                 220

Thr Ile Ser Lys Asp Asn Ala Lys Asn Thr Val Tyr Leu Gln Ile Asn
225                 230                 235                 240

Ser Leu Lys Pro Glu Asp Thr Ala Val Tyr Tyr Cys Ala Ser Ser Arg
                245                 250                 255

Ala Tyr Gly Ser Ser Arg Leu Arg Leu Ala Asp Thr Tyr Glu Tyr Trp
            260                 265                 270

Gly Gln Gly Thr Gln Val Thr Val Ser Ser
        275                 280
```

<210> SEQ ID NO 165
<211> LENGTH: 290
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 165

```
Glu Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Asn Ser Tyr
            20                  25                  30

Ala Met Gly Trp Phe Arg Gln Ala Pro Gly Lys Glu Arg Glu Ser Val
        35                  40                  45

Ala His Ile Asn Arg Ser Gly Ser Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Gly Arg Tyr Tyr Ser Ser Asp Gly Val Pro Ser Ala Ser Phe
            100                 105                 110

Asn Tyr Trp Gly Gln Gly Thr Gln Val Thr Val Ser Ser Gly Gly Gly
        115                 120                 125
```

-continued

```
Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Thr Gly Asp Ser Leu Arg Leu Ser Cys Glu Val Ser Gly Arg
            180                 185                 190

Thr Phe Ser Ser Tyr Ser Met Gly Trp Phe Arg Gln Ala Gln Gly Lys
        195                 200                 205

Glu Arg Glu Phe Val Val Ala Ile Ser Lys Gly Gly Tyr Lys Tyr Asp
    210                 215                 220

Ser Val Ser Leu Glu Gly Arg Phe Thr Ile Ser Lys Asp Asn Ala Lys
225                 230                 235                 240

Asn Thr Val Tyr Leu Gln Ile Asn Ser Leu Lys Pro Glu Asp Thr Ala
                245                 250                 255

Val Tyr Tyr Cys Ala Ser Ser Arg Ala Tyr Gly Ser Ser Arg Leu Arg
            260                 265                 270

Leu Ala Asp Thr Tyr Glu Tyr Trp Gly Gln Gly Thr Gln Val Thr Val
        275                 280                 285

Ser Ser
    290


<210> SEQ ID NO 166
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial polypeptide comprising lama glama
      sequences

<400> SEQUENCE: 166

Glu Val Gln Leu Val Glu Ser Gly Gly Gly Leu Val Gln Ala Gly Gly
1               5                   10                  15

Ser Leu Arg Leu Ser Cys Thr Ala Ser Gly Ser Ala Phe Lys Ser Tyr
            20                  25                  30

Arg Met Gly Trp Phe Arg Arg Thr Pro Gly Lys Glu Asp Glu Phe Val
        35                  40                  45

Ala Ser Ile Ser Trp Thr Tyr Gly Ser Thr Phe Tyr Ala Asp Ser Val
    50                  55                  60

Lys Gly Arg Phe Thr Met Ser Arg Asp Lys Ala Lys Asn Ala Gly Tyr
65                  70                  75                  80

Leu Gln Met Asn Ser Leu Lys Pro Glu Asp Thr Ala Leu Tyr Tyr Cys
                85                  90                  95

Ala Ala Gly Ala Gln Ser Asp Arg Tyr Asn Ile Arg Ser Tyr Asp Tyr
            100                 105                 110

Trp Gly Gln Gly Thr Gln Val Thr Val Ser Ser Gly Gly Gly Gly Ser
        115                 120                 125

Gly Gly Gly Gly Ser Gly Gly Gly Gly Ser Gly Gly Gly Gly Ser Gly
    130                 135                 140

Gly Gly Gly Ser Gly Gly Gly Gly Ser Gly Gly Gly Gly Ser Gly Gly
145                 150                 155                 160

Gly Gly Ser Glu Val Gln Leu Val Glu Ser Gly Gly Gly Leu Val Gln
                165                 170                 175
```

Thr Gly Asp Ser Leu Arg Leu Ser Cys Glu Val Ser Gly Arg Thr Phe
180 185 190

Ser Ser Tyr Ser Met Gly Trp Phe Arg Gln Ala Gln Gly Lys Glu Arg
195 200 205

Glu Phe Val Val Ala Ile Ser Lys Gly Gly Tyr Lys Tyr Asp Ser Val
210 215 220

Ser Leu Glu Gly Arg Phe Thr Ile Ser Lys Asp Asn Ala Lys Asn Thr
225 230 235 240

Val Tyr Leu Gln Ile Asn Ser Leu Lys Pro Glu Asp Thr Ala Val Tyr
245 250 255

Tyr Cys Ala Ser Ser Arg Ala Tyr Gly Ser Ser Arg Leu Arg Leu Ala
260 265 270

Asp Thr Tyr Glu Tyr Trp Gly Gln Gly Thr Gln Val Thr Val Ser Ser
275 280 285

<210> SEQ ID NO 167
<211> LENGTH: 280
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 167

Glu Val Gln Leu Val Glu Ser Gly Gly Gly Leu Val Gln Pro Gly Gly
1 5 10 15

Ser Leu Lys Leu Ser Cys Thr Ala Ser Gly Phe Thr Phe Ser Thr Ser
20 25 30

Trp Met His Trp Val Arg Gln Ala Pro Gly Lys Gly Leu Glu Trp Val
35 40 45

Ser Ser Ile Pro Pro Val Gly His Phe Ala Asn Tyr Ala Pro Ser Val
50 55 60

Lys Gly Arg Phe Thr Ile Ser Arg Asp Asn Ala Lys Asn Thr Leu Phe
65 70 75 80

Leu Gln Met Asn Ser Leu Lys Ser Glu Asp Thr Ala Val Tyr Tyr Cys
85 90 95

Ala Lys Asp Ser Ala Gly Arg Thr Lys Gly Gln Gly Thr Gln Val Thr
100 105 110

Val Ser Ser Gly Gly Gly Gly Ser Gly Gly Gly Gly Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Gly Gly Gly Gly Ser Glu Val Gln Leu Val
145 150 155 160

Glu Ser Gly Gly Gly Leu Val Gln Thr Gly Asp Ser Leu Arg Leu Ser
165 170 175

Cys Glu Val Ser Gly Arg Thr Phe Ser Ser Tyr Ser Met Gly Trp Phe
180 185 190

Arg Gln Ala Gln Gly Lys Glu Arg Glu Phe Val Val Ala Ile Ser Lys
195 200 205

Gly Gly Tyr Lys Tyr Asp Ser Val Ser Leu Glu Gly Arg Phe Thr Ile
210 215 220

Ser Lys Asp Asn Ala Lys Asn Thr Val Tyr Leu Gln Ile Asn Ser Leu 225 230 235 240

Lys Pro Glu Asp Thr Ala Val Tyr Tyr Cys Ala Ser Ser Arg Ala Tyr
245 250 255

Gly Ser Ser Arg Leu Arg Leu Ala Asp Thr Tyr Glu Tyr Trp Gly Gln
260 265 270

Gly Thr Gln Val Thr Val Ser Ser
275 280

<210> SEQ ID NO 168
<211> LENGTH: 289
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Artificial polypeptide comprising lama glama sequences

<400> SEQUENCE: 168

Glu Val Gln Leu Val Glu Ser Gly Gly Gly Leu Val Gln Ala Gly Gly
1 5 10 15

Ser Leu Arg Leu Ser Cys Ala Ala Ser Glu Arg Thr Phe Ser Asn Tyr
20 25 30

Ala Met Asp Trp Phe Arg Gln Ala Pro Gly Lys Glu Arg Glu Phe Val
35 40 45

Ala Ala Ile Thr Arg Ser Gly Gly Gly Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Thr Arg Ser Ser Thr Ile Val Val Gly Val Gly Gly Met Glu
100 105 110

Tyr Trp Gly Lys Gly Thr Gln Val Thr Val Ser Ser Gly Gly Gly Gly
115 120 125

Ser Gly Gly Gly Gly Ser Gly Gly Gly Gly Ser Gly Gly Gly Gly Ser
130 135 140

Gly Gly Gly Gly Ser Gly Gly Gly Gly Ser Gly Gly Gly Gly Ser Gly
145 150 155 160

Gly Gly Gly Ser Glu Val Gln Leu Val Glu Ser Gly Gly Gly Leu Val
165 170 175

Gln Thr Gly Asp Ser Leu Arg Leu Ser Cys Glu Val Ser Gly Arg Thr
180 185 190

Phe Ser Ser Tyr Ser Met Gly Trp Phe Arg Gln Ala Gln Gly Lys Glu
195 200 205

Arg Glu Phe Val Val Ala Ile Ser Lys Gly Gly Tyr Lys Tyr Asp Ser
210 215 220

Val Ser Leu Glu Gly Arg Phe Thr Ile Ser Lys Asp Asn Ala Lys Asn
225 230 235 240

Thr Val Tyr Leu Gln Ile Asn Ser Leu Lys Pro Glu Asp Thr Ala Val
245 250 255

Tyr Tyr Cys Ala Ser Ser Arg Ala Tyr Gly Ser Ser Arg Leu Arg Leu
260 265 270

Ala Asp Thr Tyr Glu Tyr Trp Gly Gln Gly Thr Gln Val Thr Val Ser
275 280 285

Ser

<210> SEQ ID NO 169
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Synthetic linker

<400> SEQUENCE: 169

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Synthetic linker

<400> SEQUENCE: 170

```
Gly Gly Gly Gly Ser Gly Gly Gly Ser
1               5
```

<210> SEQ ID NO 171
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Synthetic linker

<400> SEQUENCE: 171

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40
```

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Synthetic linker

<400> SEQUENCE: 172

```
Gly Gly Gly Gly Cys Gly Gly Gly Ser
1               5
```

<210> SEQ ID NO 173
<211> LENGTH: 25
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Synthetic linker

<400> SEQUENCE: 173

```
Gly Gly Gly Gly Cys Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 174
<211> LENGTH: 27
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Synthetic linker

<400> SEQUENCE: 174

```
Gly Gly Gly Ser Gly Gly Gly Gly Ser Gly Gly Gly Gly Cys Gly Gly
1               5                   10                  15

Gly Gly Ser Gly Gly Gly Gly Ser Gly Gly Gly
            20                  25
```

<210> SEQ ID NO 175
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Synthetic linker

<400> SEQUENCE: 175

```
Gly Gly Gly Gly Ser Gly Gly Gly Gly Ser Gly Gly Gly Gly Cys Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 176
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Synthetic linker

<400> SEQUENCE: 176

```
Gly Gly Gly Gly Cys Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
```

35

<210> SEQ ID NO 177
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama glama sequence

<400> SEQUENCE: 177

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Ser Phe
20 25 30

Gly Met Ser Trp Val Arg Gln Ala Pro Gly Lys Gly Leu Glu Trp Val
35 40 45

Ser Ser Ile Ser Gly Ser Gly Ser Asp Thr Leu Tyr Ala Asp Ser Val
50 55 60

Lys Gly Arg Phe Thr Ile Ser Arg Asp Asn Ala Lys Thr Thr Leu Tyr
65 70 75 80

Leu Gln Met Asn Ser Leu Arg Pro Glu Asp Thr Ala Val Tyr Tyr Cys
85 90 95

Thr Ile Gly Gly Ser Leu Ser Arg Ser Ser Gln Gly Thr Leu Val Thr
100 105 110

Val Ser Ser
115

<210> SEQ ID NO 178
<211> LENGTH: 585
<212> TYPE: PRT
<213> ORGANISM: Homo sapiens

<400> SEQUENCE: 178

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Cys Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

-continued

```
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 179
<211> LENGTH: 109
<212> TYPE: PRT
<213> ORGANISM: Homo sapiens

<400> SEQUENCE: 179

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
            100                 105
```

<210> SEQ ID NO 180
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated Lama sequence

<400> SEQUENCE: 180

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Leu Gly Trp Phe Arg Gln Ala Ala Gly Lys Glu Arg Glu Gly Val
        35                  40                  45

Ser Cys Ile Arg Cys Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Ile Val Pro Arg Ser Lys Leu Glu Pro Tyr Glu Tyr Asp
            100                 105                 110

Ala Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Ala Gly Gly Ser Leu Arg Leu Ser Cys Ala Ala Ser Gly Phe
145                 150                 155                 160

Thr Phe Asp Asp Tyr Ala Leu Gly Trp Phe Arg Gln Ala Ala Gly Lys
                165                 170                 175

Glu Arg Glu Gly Val Ser Cys Ile Arg Cys Ser Asp Gly Ser Thr Tyr
            180                 185                 190

Tyr Ala Asp Ser Val Lys Gly Arg Phe Thr Ile Ser Ser Asp Asn Ala
```

```
        195                 200                 205

Lys Asn Thr Val Tyr Leu Gln Met Asn Ser Leu Lys Pro Glu Asp Thr
    210                 215                 220

Ala Val Tyr Tyr Cys Ala Ala Ser Ile Val Pro Arg Ser Lys Leu Glu
225                 230                 235                 240

Pro Tyr Glu Tyr Asp Ala Trp Gly Gln Gly Thr Leu Val Thr Val Ser
                245                 250                 255

Ser


<210> SEQ ID NO 181
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 181

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Leu Gly Trp Phe Arg Gln Ala Ala Gly Lys Glu Arg Glu Gly Val
        35                  40                  45

Ser Cys Ile Arg Cys Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Ile Val Pro Arg Ser Lys Leu Glu Pro Tyr Glu Tyr Asp
            100                 105                 110

Ala Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160

Gly Gly Gly Ser Glu Val Gln Leu Val Glu Ser Gly Gly Gly Leu Val
                165                 170                 175

Gln Ala Gly Gly Ser Leu Arg Leu Ser Cys Ala Ala Ser Gly Phe Thr
            180                 185                 190

Phe Asp Asp Tyr Ala Leu Gly Trp Phe Arg Gln Ala Ala Gly Lys Glu
        195                 200                 205

Arg Glu Gly Val Ser Cys Ile Arg Cys Ser Asp Gly Ser Thr Tyr Tyr
    210                 215                 220

Ala Asp Ser Val Lys Gly Arg Phe Thr Ile Ser Ser Asp Asn Ala Lys
225                 230                 235                 240

Asn Thr Val Tyr Leu Gln Met Asn Ser Leu Lys Pro Glu Asp Thr Ala
                245                 250                 255

Val Tyr Tyr Cys Ala Ala Ser Ile Val Pro Arg Ser Lys Leu Glu Pro
            260                 265                 270

Tyr Glu Tyr Asp Ala Trp Gly Gln Gly Thr Leu Val Thr Val Ser Ser
        275                 280                 285
```

<210> SEQ ID NO 182
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 182

Glu Val Gln Leu Val Glu Ser Gly Gly Gly Leu Val Gln Val Gly Asp
1 5 10 15

Ser Leu Arg Leu Ser Cys Ala Ala Ser Gly Arg Thr Phe Ser Thr Tyr
20 25 30

Leu Met Val Gly Trp Phe Arg Gln Ala Pro Gly Lys Glu Arg Glu Phe
35 40 45

Ala Ala Gly Ile Trp Ser Ser Gly Asp Thr Ala Tyr Ala Asp Ser Val
50 55 60

Arg Gly Arg Phe Thr Ile Ser Arg Asp Asn Ala Lys Asn Thr Val Tyr
65 70 75 80

Leu Gln Met Asn Ser Leu Lys Thr Glu Asp Thr Ala Val Tyr Tyr Cys
85 90 95

Ala Gly Ser Tyr Asp Gly Asn Tyr Tyr Ile Pro Gly Phe Tyr Lys Asp
100 105 110

Trp Gly Gln Gly Thr Leu Val Thr Val Ser Ser Gly Gly Gly Gly Ser
115 120 125

Gly Gly Gly Ser Glu Val Gln Leu Val Glu Ser Gly Gly Gly Leu Val
130 135 140

Gln Val Gly Asp Ser Leu Arg Leu Ser Cys Ala Ala Ser Gly Arg Thr
145 150 155 160

Phe Ser Thr Tyr Leu Met Val Gly Trp Phe Arg Gln Ala Pro Gly Lys
165 170 175

Glu Arg Glu Phe Ala Ala Gly Ile Trp Ser Ser Gly Asp Thr Ala Tyr
180 185 190

Ala Asp Ser Val Arg Gly Arg Phe Thr Ile Ser Arg Asp Asn Ala Lys
195 200 205

Asn Thr Val Tyr Leu Gln Met Asn Ser Leu Lys Thr Glu Asp Thr Ala
210 215 220

Val Tyr Tyr Cys Ala Gly Ser Tyr Asp Gly Asn Tyr Tyr Ile Pro Gly
225 230 235 240

Phe Tyr Lys Asp Trp Gly Gln Gly Thr Leu Val Thr Val Ser Ser
245 250 255

<210> SEQ ID NO 183
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 183

Glu Val Gln Leu Val Glu Ser Gly Gly Gly Leu Val Gln Ala Gly Gly
1 5 10 15

Ser Leu Arg Leu Ser Cys Ala Ala Ser Gly Phe Thr Leu Asp Asp Tyr

```
            20                  25                  30

Ala Ile Gly Trp Phe Arg Gln Ala Pro Gly Lys Glu Arg Glu Gly Val
        35                  40                  45

Ser Ser Ile Arg Asp Asn Asp Gly Ser Thr Tyr Tyr Ala Asp Ser Val
    50                  55                  60

Lys Gly Arg Phe Thr Ile Ser Ser Asp Asn Asp Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Pro Ala Gly Arg Leu Arg Phe Gly Glu Gln Trp Tyr Pro
            100                 105                 110

Leu Tyr Glu Tyr Asp Ala Trp Gly Gln Gly Thr Leu Val Thr Val Ser
        115                 120                 125

Ser Gly Gly Gly Gly Ser Gly Gly Gly Ser Glu Val Gln Leu Val Glu
    130                 135                 140

Ser Gly Gly Gly Leu Val Gln Ala Gly Gly Ser Leu Arg Leu Ser Cys
145                 150                 155                 160

Ala Ala Ser Gly Phe Thr Leu Asp Asp Tyr Ala Ile Gly Trp Phe Arg
                165                 170                 175

Gln Ala Pro Gly Lys Glu Arg Glu Gly Val Ser Ser Ile Arg Asp Asn
            180                 185                 190

Asp Gly Ser Thr Tyr Tyr Ala Asp Ser Val Lys Gly Arg Phe Thr Ile
        195                 200                 205

Ser Ser Asp Asn Asp Lys Asn Thr Val Tyr Leu Gln Met Asn Ser Leu
    210                 215                 220

Lys Pro Glu Asp Thr Ala Val Tyr Tyr Cys Ala Ala Val Pro Ala Gly
225                 230                 235                 240

Arg Leu Arg Phe Gly Glu Gln Trp Tyr Pro Leu Tyr Glu Tyr Asp Ala
                245                 250                 255

Trp Gly Gln Gly Thr Leu Val Thr Val Ser Ser
            260                 265
```

<210> SEQ ID NO 184
<211> LENGTH: 298
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 184

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Asp Asp Tyr
            20                  25                  30

Ala Ile Gly Trp Phe Arg Gln Ala Pro Gly Lys Glu Arg Glu Gly Val
        35                  40                  45

Ser Ser Ile Arg Asp Asn Asp Gly Ser Thr Tyr Tyr Ala Asp Ser Val
    50                  55                  60

Lys Gly Arg Phe Thr Ile Ser Ser Asp Asn Asp Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Pro Ala Gly Arg Leu Arg Phe Gly Glu Gln Trp Tyr Pro
```

100 105 110

Leu Tyr Glu Tyr Asp Ala Trp Gly Gln Gly Thr Leu Val Thr Val Ser
115 120 125

Ser Gly Gly Gly Gly Ser Gly Gly Gly Gly Ser Gly Gly Gly Gly Ser
130 135 140

Gly Gly Gly Gly Ser Gly Gly Gly Gly Ser Gly Gly Gly Gly Ser Gly
145 150 155 160

Gly Gly Gly Ser Gly Gly Gly Gly Ser Glu Val Gln Leu Val Glu Ser
165 170 175

Gly Gly Gly Leu Val Gln Ala Gly Gly Ser Leu Arg Leu Ser Cys Ala
180 185 190

Ala Ser Gly Phe Thr Leu Asp Asp Tyr Ala Ile Gly Trp Phe Arg Gln
195 200 205

Ala Pro Gly Lys Glu Arg Glu Gly Val Ser Ser Ile Arg Asp Asn Asp
210 215 220

Gly Ser Thr Tyr Tyr Ala Asp Ser Val Lys Gly Arg Phe Thr Ile Ser
225 230 235 240

Ser Asp Asn Asp Lys Asn Thr Val Tyr Leu Gln Met Asn Ser Leu Lys
245 250 255

Pro Glu Asp Thr Ala Val Tyr Tyr Cys Ala Ala Val Pro Ala Gly Arg
260 265 270

Leu Arg Phe Gly Glu Gln Trp Tyr Pro Leu Tyr Glu Tyr Asp Ala Trp
275 280 285

Gly Gln Gly Thr Leu Val Thr Val Ser Ser
290 295

<210> SEQ ID NO 185
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 185

Glu Val Gln Leu Val Glu Ser Gly Gly Gly Leu Val Gln Pro Gly Gly
1 5 10 15

Ser Leu Arg Leu Ser Cys Ala Ala Ser Gly Ile Thr Leu Asp Asp Tyr
20 25 30

Ala Ile Gly Trp Phe Arg Gln Ala Pro Gly Lys Glu Arg Glu Gly Val
35 40 45

Ser Ser Ile Arg Asp Asn Gly Gly Ser Thr Tyr Tyr Ala Asp Ser Val
50 55 60

Lys Gly Arg Phe Thr Ile Ser Ser Asp Asn Ser Lys Asn Thr Val Tyr
65 70 75 80

Leu Gln Met Asn Ser Leu Arg Pro Glu Asp Thr Ala Val Tyr Tyr Cys
85 90 95

Ala Ala Val Pro Ala Gly Arg Leu Arg Tyr Gly Glu Gln Trp Tyr Pro
100 105 110

Ile Tyr Glu Tyr Asp Ala Trp Gly Gln Gly Thr Leu Val Thr Val Ser
115 120 125

Ser Gly Gly Gly Gly Ser Gly Gly Gly Ser Glu Val Gln Leu Leu Glu
130 135 140

Ser Gly Gly Gly Leu Val Gln Pro Gly Gly Ser Leu Arg Leu Ser Cys

```
145                 150                 155                 160

Ala Ala Ser Gly Ile Thr Leu Asp Asp Tyr Ala Ile Gly Trp Phe Arg
                165                 170                 175

Gln Ala Pro Gly Lys Glu Arg Glu Gly Val Ser Ser Ile Arg Asp Asn
            180                 185                 190

Gly Gly Ser Thr Tyr Tyr Ala Asp Ser Val Lys Gly Arg Phe Thr Ile
        195                 200                 205

Ser Ser Asp Asn Ser Lys Asn Thr Val Tyr Leu Gln Met Asn Ser Leu
    210                 215                 220

Arg Pro Glu Asp Thr Ala Val Tyr Tyr Cys Ala Ala Val Pro Ala Gly
225                 230                 235                 240

Arg Leu Arg Tyr Gly Glu Gln Trp Tyr Pro Ile Tyr Glu Tyr Asp Ala
                245                 250                 255

Trp Gly Gln Gly Thr Leu Val Thr Val Ser Ser
            260                 265


<210> SEQ ID NO 186
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 186

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
```

```
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Ala
            260                 265                 270

Gly Gly Ser Leu Arg Leu Ser Cys Ala Ala Ser Gly Phe Thr Leu Asp
        275                 280                 285

Asp Tyr Ala Ile Gly Trp Phe Arg Gln Ala Pro Gly Lys Glu Arg Glu
    290                 295                 300

Gly Val Ser Ser Ile Arg Asp Asn Asp Gly Ser Thr Tyr Tyr Ala Asp
305                 310                 315                 320

Ser Val Lys Gly Arg Phe Thr Ile Ser Ser Asp Asn Asp Lys Asn Thr
                325                 330                 335

Val Tyr Leu Gln Met Asn Ser Leu Lys Pro Glu Asp Thr Ala Val Tyr
            340                 345                 350

Tyr Cys Ala Ala Val Pro Ala Gly Arg Leu Arg Phe Gly Glu Gln Trp
        355                 360                 365

Tyr Pro Leu Tyr Glu Tyr Asp Ala Trp Gly Gln Gly Thr Leu Val Thr
    370                 375                 380

Val Ser Ser
385


<210> SEQ ID NO 187
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 187

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Asp Asp Tyr
            20                  25                  30

Ala Ile Gly Trp Phe Arg Gln Ala Pro Gly Lys Glu Arg Glu Gly Val
        35                  40                  45

Ser Ser Ile Arg Asp Asn Asp Gly Ser Thr Tyr Tyr Ala Asp Ser Val
    50                  55                  60

Lys Gly Arg Phe Thr Ile Ser Ser Asp Asn Asp Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Pro Ala Gly Arg Leu Arg Phe Gly Glu Gln Trp Tyr Pro
            100                 105                 110

Leu Tyr Glu Tyr Asp Ala Trp Gly Gln Gly Thr Leu Val Thr Val Ser
        115                 120                 125

Ser Gly Gly Gly Gly Ser Gly Gly Gly Ser Glu Val Gln Leu Val Glu
    130                 135                 140

Ser Gly Gly Gly Leu Val Gln Pro Gly Asn Ser Leu Arg Leu Ser Cys
145                 150                 155                 160

Ala Ala Ser Gly Phe Thr Phe Ser Ser Phe Gly Met Ser Trp Val Arg
                165                 170                 175

Gln Ala Pro Gly Lys Gly Leu Glu Trp Val Ser Ser Ile Ser Gly Ser
```

```
            180                 185                 190

Gly Ser Asp Thr Leu Tyr Ala Asp Ser Val Lys Gly Arg Phe Thr Ile
        195                 200                 205

Ser Arg Asp Asn Ala Lys Thr Thr Leu Tyr Leu Gln Met Asn Ser Leu
    210                 215                 220

Arg Pro Glu Asp Thr Ala Val Tyr Tyr Cys Thr Ile Gly Gly Ser Leu
225                 230                 235                 240

Ser Arg Ser Ser Gln Gly Thr Leu Val Thr Val Ser Ser Gly Gly Gly
                245                 250                 255

Gly Ser Gly Gly Gly Ser Asp Val Gln Leu Val Glu Ser Gly Gly Gly
            260                 265                 270

Leu Val Gln Pro Gly Gly Ser Leu Arg Leu Ser Cys Ala Ala Ser Gly
        275                 280                 285

Arg Thr Phe Ser Ser Tyr Ser Met Gly Trp Phe Arg Gln Ala Pro Gly
    290                 295                 300

Lys Glu Arg Glu Phe Val Val Ala Ile Ser Lys Gly Gly Tyr Lys Tyr
305                 310                 315                 320

Asp Ala Val Ser Leu Glu Gly Arg Phe Thr Ile Ser Arg Asp Asn Ala
                325                 330                 335

Lys Asn Thr Val Tyr Leu Gln Ile Asn Ser Leu Arg Pro Glu Asp Thr
            340                 345                 350

Ala Val Tyr Tyr Cys Ala Ser Ser Arg Ala Tyr Gly Ser Ser Arg Leu
        355                 360                 365

Arg Leu Ala Asp Thr Tyr Glu Tyr Trp Gly Gln Gly Thr Leu Val Thr
    370                 375                 380

Val Ser Ser
385
```

<210> SEQ ID NO 188
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 188

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Asp Asp Tyr
            20                  25                  30

Ala Ile Gly Trp Phe Arg Gln Ala Pro Gly Lys Glu Arg Glu Gly Val
        35                  40                  45

Ser Ser Ile Arg Asp Asn Asp Gly Ser Thr Tyr Tyr Ala Asp Ser Val
    50                  55                  60

Lys Gly Arg Phe Thr Ile Ser Ser Asp Asn Asp Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Pro Ala Gly Arg Leu Arg Phe Gly Glu Gln Trp Tyr Pro
            100                 105                 110

Leu Tyr Glu Tyr Asp Ala Trp Gly Gln Gly Thr Leu Val Thr Val Ser
        115                 120                 125

Ser Gly Gly Gly Gly Ser Gly Gly Gly Ser Asp Val Gln Leu Val Glu
```

```
    130                 135                 140

Ser Gly Gly Gly Leu Val Gln Pro Gly Gly Ser Leu Arg Leu Ser Cys
145                 150                 155                 160

Ala Ala Ser Gly Arg Thr Phe Ser Ser Tyr Ser Met Gly Trp Phe Arg
                165                 170                 175

Gln Ala Pro Gly Lys Glu Arg Glu Phe Val Val Ala Ile Ser Lys Gly
            180                 185                 190

Gly Tyr Lys Tyr Asp Ala Val Ser Leu Glu Gly Arg Phe Thr Ile Ser
        195                 200                 205

Arg Asp Asn Ala Lys Asn Thr Val Tyr Leu Gln Ile Asn Ser Leu Arg
    210                 215                 220

Pro Glu Asp Thr Ala Val Tyr Tyr Cys Ala Ser Ser Arg Ala Tyr Gly
225                 230                 235                 240

Ser Ser Arg Leu Arg Leu Ala Asp Thr Tyr Glu Tyr Trp Gly Gln Gly
                245                 250                 255

Thr Leu Val Thr Val Ser Ser Gly Gly Gly Gly Ser Gly Gly Gly Ser
            260                 265                 270

Glu Val Gln Leu Val Glu Ser Gly Gly Gly Leu Val Gln Pro Gly Asn
        275                 280                 285

Ser Leu Arg Leu Ser Cys Ala Ala Ser Gly Phe Thr Phe Ser Ser Phe
    290                 295                 300

Gly Met Ser Trp Val Arg Gln Ala Pro Gly Lys Gly Leu Glu Trp Val
305                 310                 315                 320

Ser Ser Ile Ser Gly Ser Gly Ser Asp Thr Leu Tyr Ala Asp Ser Val
                325                 330                 335

Lys Gly Arg Phe Thr Ile Ser Arg Asp Asn Ala Lys Thr Thr Leu Tyr
            340                 345                 350

Leu Gln Met Asn Ser Leu Arg Pro Glu Asp Thr Ala Val Tyr Tyr Cys
        355                 360                 365

Thr Ile Gly Gly Ser Leu Ser Arg Ser Ser Gln Gly Thr Leu Val Thr
    370                 375                 380

Val Ser Ser
385
```

<210> SEQ ID NO 189
<211> LENGTH: 375
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 189

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
```

```
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Ala Ala Ala
        115                 120                 125

Glu Val Gln Leu Val Glu Ser Gly Gly Gly Leu Val Gln Pro Gly Asn
    130                 135                 140

Ser Leu Arg Leu Ser Cys Ala Ala Ser Gly Phe Thr Phe Ser Ser Phe
145                 150                 155                 160

Gly Met Ser Trp Val Arg Gln Ala Pro Gly Lys Gly Leu Glu Trp Val
                165                 170                 175

Ser Ser Ile Ser Gly Ser Gly Ser Asp Thr Leu Tyr Ala Asp Ser Val
            180                 185                 190

Lys Gly Arg Phe Thr Ile Ser Arg Asp Asn Ala Lys Thr Thr Leu Tyr
        195                 200                 205

Leu Gln Met Asn Ser Leu Arg Pro Glu Asp Thr Ala Val Tyr Tyr Cys
    210                 215                 220

Thr Ile Gly Gly Ser Leu Ser Arg Ser Ser Gln Gly Thr Leu Val Thr
225                 230                 235                 240

Val Ser Ser Ala Ala Ala Glu Val Gln Leu Val Glu Ser Gly Gly Gly
                245                 250                 255

Leu Val Gln Ala Gly Gly Ser Leu Arg Leu Ser Cys Ala Ala Ser Gly
            260                 265                 270

Phe Thr Leu Asp Asp Tyr Ala Ile Gly Trp Phe Arg Gln Ala Pro Gly
        275                 280                 285

Lys Glu Arg Glu Gly Val Ser Ser Ile Arg Asp Asn Asp Gly Ser Thr
    290                 295                 300

Tyr Tyr Ala Asp Ser Val Lys Gly Arg Phe Thr Ile Ser Ser Asp Asn
305                 310                 315                 320

Asp Lys Asn Thr Val Tyr Leu Gln Met Asn Ser Leu Lys Pro Glu Asp
                325                 330                 335

Thr Ala Val Tyr Tyr Cys Ala Ala Val Pro Ala Gly Arg Leu Arg Phe
            340                 345                 350

Gly Glu Gln Trp Tyr Pro Leu Tyr Glu Tyr Asp Ala Trp Gly Gln Gly
        355                 360                 365

Thr Leu Val Thr Val Ser Ser
    370                 375


<210> SEQ ID NO 190
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 190

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
```

```
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ala Leu Asp Tyr Tyr Ala Ile Gly Trp Phe Arg Gln Val Pro Gly
                165                 170                 175

Lys Glu Arg Glu Gly Val Ser Cys Ile Ser Ser Ser Asp Gly Ile Thr
            180                 185                 190

Tyr Tyr Val Asp Ser Val Lys Gly Arg Phe Thr Ile Ser Arg Asp Asn
        195                 200                 205

Ala Lys Asn Thr Val Tyr Leu Gln Met Asn Ser Leu Lys Pro Glu Asp
    210                 215                 220

Thr Ala Val Tyr Tyr Cys Ala Thr Asp Ser Gly Gly Tyr Ile Asp Tyr
225                 230                 235                 240

Asp Cys Met Gly Leu Gly Tyr Asp Tyr Trp Gly Gln Gly Thr Leu Val
                245                 250                 255

Thr Val Ser Ser Gly Gly Gly Gly Ser Gly Gly Gly Ser Glu Val Gln
            260                 265                 270

Leu Val Glu Ser Gly Gly Gly Leu Val Gln Pro Gly Asn Ser Leu Arg
        275                 280                 285

Leu Ser Cys Ala Ala Ser Gly Phe Thr Phe Ser Ser Phe Gly Met Ser
    290                 295                 300

Trp Val Arg Gln Ala Pro Gly Lys Gly Leu Glu Trp Val Ser Ser Ile
305                 310                 315                 320

Ser Gly Ser Gly Ser Asp Thr Leu Tyr Ala Asp Ser Val Lys Gly Arg
                325                 330                 335

Phe Thr Ile Ser Arg Asp Asn Ala Lys Thr Thr Leu Tyr Leu Gln Met
            340                 345                 350

Asn Ser Leu Arg Pro Glu Asp Thr Ala Val Tyr Tyr Cys Thr Ile Gly
        355                 360                 365

Gly Ser Leu Ser Arg Ser Ser Gln Gly Thr Leu Val Thr Val Ser Ser
    370                 375                 380


<210> SEQ ID NO 191
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 191

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
```

```
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Phe Ala Leu Asp
        275                 280                 285

Tyr Tyr Ala Ile Gly Trp Phe Arg Gln Val Pro Gly Lys Glu Arg Glu
    290                 295                 300

Gly Val Ser Cys Ile Ser Ser Ser Asp Gly Ile Thr Tyr Tyr Val Asp
305                 310                 315                 320

Ser Val Lys Gly Arg Phe Thr Ile Ser Arg Asp Asn Ala Lys Asn Thr
                325                 330                 335

Val Tyr Leu Gln Met Asn Ser Leu Lys Pro Glu Asp Thr Ala Val Tyr
            340                 345                 350

Tyr Cys Ala Thr Asp Ser Gly Gly Tyr Ile Asp Tyr Asp Cys Met Gly
        355                 360                 365

Leu Gly Tyr Asp Tyr Trp Gly Gln Gly Thr Leu Val Thr Val Ser Ser
    370                 375                 380
```

<210> SEQ ID NO 192
<211> LENGTH: 519
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 192

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ala Leu Asp Tyr Tyr Ala Ile Gly Trp Phe Arg Gln Val Pro Gly
                165                 170                 175

Lys Glu Arg Glu Gly Val Ser Cys Ile Ser Ser Ser Asp Gly Ile Thr
            180                 185                 190

Tyr Tyr Val Asp Ser Val Lys Gly Arg Phe Thr Ile Ser Arg Asp Asn
        195                 200                 205

Ala Lys Asn Thr Val Tyr Leu Gln Met Asn Ser Leu Lys Pro Glu Asp
    210                 215                 220

Thr Ala Val Tyr Tyr Cys Ala Thr Asp Ser Gly Gly Tyr Ile Asp Tyr
225                 230                 235                 240

Asp Cys Met Gly Leu Gly Tyr Asp Tyr Trp Gly Gln Gly Thr Leu Val
                245                 250                 255

Thr Val Ser Ser Gly Gly Gly Gly Ser Gly Gly Gly Ser Glu Val Gln
            260                 265                 270

Leu Val Glu Ser Gly Gly Gly Leu Val Gln Pro Gly Asn Ser Leu Arg
        275                 280                 285

Leu Ser Cys Ala Ala Ser Gly Phe Thr Phe Ser Ser Phe Gly Met Ser
    290                 295                 300

Trp Val Arg Gln Ala Pro Gly Lys Gly Leu Glu Trp Val Ser Ser Ile
305                 310                 315                 320

Ser Gly Ser Gly Ser Asp Thr Leu Tyr Ala Asp Ser Val Lys Gly Arg
                325                 330                 335

Phe Thr Ile Ser Arg Asp Asn Ala Lys Thr Thr Leu Tyr Leu Gln Met
            340                 345                 350

Asn Ser Leu Arg Pro Glu Asp Thr Ala Val Tyr Tyr Cys Thr Ile Gly
        355                 360                 365

Gly Ser Leu Ser Arg Ser Ser Gln Gly Thr Leu Val Thr Val Ser Ser
    370                 375                 380

Gly Gly Gly Gly Ser Gly Gly Gly Ser Glu Val Gln Leu Val Glu Ser
385                 390                 395                 400

Gly Gly Gly Leu Val Gln Pro Gly Gly Ser Leu Arg Leu Ser Cys Ala
                405                 410                 415

Ala Ser Gly Phe Ala Leu Asp Tyr Tyr Ala Ile Gly Trp Phe Arg Gln
420 425 430

Val Pro Gly Lys Glu Arg Glu Gly Val Ser Cys Ile Ser Ser Ser Asp
435 440 445

Gly Ile Thr Tyr Tyr Val Asp Ser Val Lys Gly Arg Phe Thr Ile Ser
450 455 460

Arg Asp Asn Ala Lys Asn Thr Val Tyr Leu Gln Met Asn Ser Leu Lys
465 470 475 480

Pro Glu Asp Thr Ala Val Tyr Tyr Cys Ala Thr Asp Ser Gly Gly Tyr
485 490 495

Ile Asp Tyr Asp Cys Met Gly Leu Gly Tyr Asp Tyr Trp Gly Gln Gly
500 505 510

Thr Leu Val Thr Val Ser Ser
515

<210> SEQ ID NO 193
<211> LENGTH: 525
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Muttaed lama sequence

<400> SEQUENCE: 193

Asp Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser Ser Tyr
20 25 30

Ser Met Gly Trp Phe Arg Gln Ala Pro Gly Lys Glu Arg Glu Phe Val
35 40 45

Val Ala Ile Ser Lys Gly Gly Tyr Lys Tyr Asp Ala Val Ser Leu Glu
50 55 60

Gly Arg Phe Thr Ile Ser Arg Asp Asn Ala Lys Asn Thr Val Tyr Leu
65 70 75 80

Gln Ile Asn Ser Leu Arg Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Leu Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Ala Gly Gly Ser Leu Arg Leu Ser Cys Ala Ala Ser Gly
145 150 155 160

Phe Thr Leu Asp Asp Tyr Ala Ile Gly Trp Phe Arg Gln Ala Pro Gly
165 170 175

Lys Glu Arg Glu Gly Val Ser Ser Ile Arg Asp Asn Asp Gly Ser Thr
180 185 190

Tyr Tyr Ala Asp Ser Val Lys Gly Arg Phe Thr Ile Ser Ser Asp Asn
195 200 205

Asp Lys Asn Thr Val Tyr Leu Gln Met Asn Ser Leu Lys Pro Glu Asp
210 215 220

Thr Ala Val Tyr Tyr Cys Ala Ala Val Pro Ala Gly Arg Leu Arg Phe
225 230 235 240

```
Gly Glu Gln Trp Tyr Pro Leu Tyr Glu Tyr Asp Ala Trp Gly Gln Gly
                245                 250                 255

Thr Leu Val Thr Val Ser Ser Gly Gly Gly Gly Ser Gly Gly Gly Ser
            260                 265                 270

Glu Val Gln Leu Val Glu Ser Gly Gly Gly Leu Val Gln Ala Gly Gly
        275                 280                 285

Ser Leu Arg Leu Ser Cys Ala Ala Ser Gly Phe Thr Leu Asp Asp Tyr
    290                 295                 300

Ala Ile Gly Trp Phe Arg Gln Ala Pro Gly Lys Glu Arg Glu Gly Val
305                 310                 315                 320

Ser Ser Ile Arg Asp Asn Asp Gly Ser Thr Tyr Tyr Ala Asp Ser Val
                325                 330                 335

Lys Gly Arg Phe Thr Ile Ser Ser Asp Asn Asp Lys Asn Thr Val Tyr
            340                 345                 350

Leu Gln Met Asn Ser Leu Lys Pro Glu Asp Thr Ala Val Tyr Tyr Cys
        355                 360                 365

Ala Ala Val Pro Ala Gly Arg Leu Arg Phe Gly Glu Gln Trp Tyr Pro
    370                 375                 380

Leu Tyr Glu Tyr Asp Ala Trp Gly Gln Gly Thr Leu Val Thr Val Ser
385                 390                 395                 400

Ser Gly Gly Gly Gly Ser Gly Gly Gly Ser Glu Val Gln Leu Val Glu
                405                 410                 415

Ser Gly Gly Gly Leu Val Gln Pro Gly Asn Ser Leu Arg Leu Ser Cys
            420                 425                 430

Ala Ala Ser Gly Phe Thr Phe Ser Ser Phe Gly Met Ser Trp Val Arg
        435                 440                 445

Gln Ala Pro Gly Lys Gly Leu Glu Trp Val Ser Ser Ile Ser Gly Ser
    450                 455                 460

Gly Ser Asp Thr Leu Tyr Ala Asp Ser Val Lys Gly Arg Phe Thr Ile
465                 470                 475                 480

Ser Arg Asp Asn Ala Lys Thr Thr Leu Tyr Leu Gln Met Asn Ser Leu
                485                 490                 495

Arg Pro Glu Asp Thr Ala Val Tyr Tyr Cys Thr Ile Gly Gly Ser Leu
            500                 505                 510

Ser Arg Ser Ser Gln Gly Thr Leu Val Thr Val Ser Ser
        515                 520                 525
```

<210> SEQ ID NO 194
<211> LENGTH: 525
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 194

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60
```

```
Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Ala
            260                 265                 270

Gly Gly Ser Leu Arg Leu Ser Cys Ala Ala Ser Gly Phe Thr Leu Asp
        275                 280                 285

Asp Tyr Ala Ile Gly Trp Phe Arg Gln Ala Pro Gly Lys Glu Arg Glu
    290                 295                 300

Gly Val Ser Ser Ile Arg Asp Asn Asp Gly Ser Thr Tyr Tyr Ala Asp
305                 310                 315                 320

Ser Val Lys Gly Arg Phe Thr Ile Ser Ser Asp Asn Asp Lys Asn Thr
                325                 330                 335

Val Tyr Leu Gln Met Asn Ser Leu Lys Pro Glu Asp Thr Ala Val Tyr
            340                 345                 350

Tyr Cys Ala Ala Val Pro Ala Gly Arg Leu Arg Phe Gly Glu Gln Trp
        355                 360                 365

Tyr Pro Leu Tyr Glu Tyr Asp Ala Trp Gly Gln Gly Thr Leu Val Thr
    370                 375                 380

Val Ser Ser Gly Gly Gly Gly Ser Gly Gly Gly Ser Glu Val Gln Leu
385                 390                 395                 400

Val Glu Ser Gly Gly Gly Leu Val Gln Ala Gly Gly Ser Leu Arg Leu
                405                 410                 415

Ser Cys Ala Ala Ser Gly Phe Thr Leu Asp Asp Tyr Ala Ile Gly Trp
            420                 425                 430

Phe Arg Gln Ala Pro Gly Lys Glu Arg Glu Gly Val Ser Ser Ile Arg
        435                 440                 445

Asp Asn Asp Gly Ser Thr Tyr Tyr Ala Asp Ser Val Lys Gly Arg Phe
    450                 455                 460

Thr Ile Ser Ser Asp Asn Asp Lys Asn Thr Val Tyr Leu Gln Met Asn
465                 470                 475                 480
```

```
Ser Leu Lys Pro Glu Asp Thr Ala Val Tyr Tyr Cys Ala Ala Val Pro
                485                 490                 495

Ala Gly Arg Leu Arg Phe Gly Glu Gln Trp Tyr Pro Leu Tyr Glu Tyr
            500                 505                 510

Asp Ala Trp Gly Gln Gly Thr Leu Val Thr Val Ser Ser
        515                 520                 525


<210> SEQ ID NO 195
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 195

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Ala Gly Gly Ser Leu Arg Leu Ser Cys Ala Ala Ser Gly
145                 150                 155                 160

Phe Thr Leu Asp Asp Tyr Ala Ile Gly Trp Phe Arg Gln Ala Pro Gly
                165                 170                 175

Lys Glu Arg Glu Gly Val Ser Ser Ile Arg Asp Asn Asp Gly Ser Thr
            180                 185                 190

Tyr Tyr Ala Asp Ser Val Lys Gly Arg Phe Thr Ile Ser Ser Asp Asn
        195                 200                 205

Asp Lys Asn Thr Val Tyr Leu Gln Met Asn Ser Leu Lys Pro Glu Asp
    210                 215                 220

Thr Ala Val Tyr Tyr Cys Ala Ala Val Pro Ala Gly Arg Leu Arg Phe
225                 230                 235                 240

Gly Glu Gln Trp Tyr Pro Leu Tyr Glu Tyr Asp Ala Trp Gly Gln Gly
                245                 250                 255

Thr Leu Val Thr Val Ser Ser Gly Gly Gly Gly Ser Gly Gly Gly Ser
            260                 265                 270

Glu Val Gln Leu Val Glu Ser Gly Gly Gly Leu Val Gln Pro Gly Asn
        275                 280                 285

Ser Leu Arg Leu Ser Cys Ala Ala Ser Gly Phe Thr Phe Ser Ser Phe
    290                 295                 300
```

```
Gly Met Ser Trp Val Arg Gln Ala Pro Gly Lys Gly Leu Glu Trp Val
305                 310                 315                 320

Ser Ser Ile Ser Gly Ser Gly Ser Asp Thr Leu Tyr Ala Asp Ser Val
                325                 330                 335

Lys Gly Arg Phe Thr Ile Ser Arg Asp Asn Ala Lys Thr Thr Leu Tyr
            340                 345                 350

Leu Gln Met Asn Ser Leu Arg Pro Glu Asp Thr Ala Val Tyr Tyr Cys
        355                 360                 365

Thr Ile Gly Gly Ser Leu Ser Arg Ser Ser Gln Gly Thr Leu Val Thr
    370                 375                 380

Val Ser Ser Gly Gly Gly Gly Ser Gly Gly Gly Ser Glu Val Gln Leu
385                 390                 395                 400

Val Glu Ser Gly Gly Gly Leu Val Gln Ala Gly Gly Ser Leu Arg Leu
                405                 410                 415

Ser Cys Ala Ala Ser Gly Phe Thr Leu Asp Asp Tyr Ala Ile Gly Trp
            420                 425                 430

Phe Arg Gln Ala Pro Gly Lys Glu Arg Glu Gly Val Ser Ser Ile Arg
        435                 440                 445

Asp Asn Asp Gly Ser Thr Tyr Tyr Ala Asp Ser Val Lys Gly Arg Phe
    450                 455                 460

Thr Ile Ser Ser Asp Asn Asp Lys Asn Thr Val Tyr Leu Gln Met Asn
465                 470                 475                 480

Ser Leu Lys Pro Glu Asp Thr Ala Val Tyr Tyr Cys Ala Ala Val Pro
                485                 490                 495

Ala Gly Arg Leu Arg Phe Gly Glu Gln Trp Tyr Pro Leu Tyr Glu Tyr
            500                 505                 510

Asp Ala Trp Gly Gln Gly Thr Leu Val Thr Val Ser Ser
        515                 520                 525


<210> SEQ ID NO 196
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 196

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125
```

```
Gly Ser Gly Gly Gly Ser Glu Val Gln Leu Val Glu Ser Gly Gly Gly
    130                 135                 140

Leu Val Gln Ala Gly Gly Ser Leu Arg Leu Ser Cys Ala Ala Ser Gly
145                 150                 155                 160

Phe Thr Phe Asp Asp Tyr Ala Leu Gly Trp Phe Arg Gln Ala Ala Gly
                165                 170                 175

Lys Glu Arg Glu Gly Val Ser Cys Ile Arg Cys Ser Asp Gly Ser Thr
            180                 185                 190

Tyr Tyr Ala Asp Ser Val Lys Gly Arg Phe Thr Ile Ser Ser Asp Asn
        195                 200                 205

Ala Lys Asn Thr Val Tyr Leu Gln Met Asn Ser Leu Lys Pro Glu Asp
    210                 215                 220

Thr Ala Val Tyr Tyr Cys Ala Ala Ser Ile Val Pro Arg Ser Lys Leu
225                 230                 235                 240

Glu Pro Tyr Glu Tyr Asp Ala Trp Gly Gln Gly Thr Leu Val Thr Val
                245                 250                 255

Ser Ser Gly Gly Gly Gly Ser Gly Gly Gly Ser Glu Val Gln Leu Val
            260                 265                 270

Glu Ser Gly Gly Gly Leu Val Gln Ala Gly Gly Ser Leu Arg Leu Ser
        275                 280                 285

Cys Ala Ala Ser Gly Phe Thr Phe Asp Asp Tyr Ala Leu Gly Trp Phe
    290                 295                 300

Arg Gln Ala Ala Gly Lys Glu Arg Glu Gly Val Ser Cys Ile Arg Cys
305                 310                 315                 320

Ser Asp Gly Ser Thr Tyr Tyr Ala Asp Ser Val Lys Gly Arg Phe Thr
                325                 330                 335

Ile Ser Ser Asp Asn Ala Lys Asn Thr Val Tyr Leu Gln Met Asn Ser
            340                 345                 350

Leu Lys Pro Glu Asp Thr Ala Val Tyr Tyr Cys Ala Ala Ser Ile Val
        355                 360                 365

Pro Arg Ser Lys Leu Glu Pro Tyr Glu Tyr Asp Ala Trp Gly Gln Gly
    370                 375                 380

Thr Leu Val Thr Val Ser Ser Gly Gly Gly Gly Ser Gly Gly Gly Ser
385                 390                 395                 400

Glu Val Gln Leu Val Glu Ser Gly Gly Gly Leu Val Gln Pro Gly Asn
                405                 410                 415

Ser Leu Arg Leu Ser Cys Ala Ala Ser Gly Phe Thr Phe Ser Ser Phe
            420                 425                 430

Gly Met Ser Trp Val Arg Gln Ala Pro Gly Lys Gly Leu Glu Trp Val
        435                 440                 445

Ser Ser Ile Ser Gly Ser Gly Ser Asp Thr Leu Tyr Ala Asp Ser Val
    450                 455                 460

Lys Gly Arg Phe Thr Ile Ser Arg Asp Asn Ala Lys Thr Thr Leu Tyr
465                 470                 475                 480

Leu Gln Met Asn Ser Leu Arg Pro Glu Asp Thr Ala Val Tyr Tyr Cys
                485                 490                 495

Thr Ile Gly Gly Ser Leu Ser Arg Ser Ser Gln Gly Thr Leu Val Thr
            500                 505                 510

Val Ser Ser
        515
```

<210> SEQ ID NO 197
<211> LENGTH: 515
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Mutated lama sequence

<400> SEQUENCE: 197

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Ala
            260                 265                 270

Gly Gly Ser Leu Arg Leu Ser Cys Ala Ala Ser Gly Phe Thr Phe Asp
        275                 280                 285

Asp Tyr Ala Leu Gly Trp Phe Arg Gln Ala Ala Gly Lys Glu Arg Glu
    290                 295                 300

Gly Val Ser Cys Ile Arg Cys Ser Asp Gly Ser Thr Tyr Tyr Ala Asp
305                 310                 315                 320

Ser Val Lys Gly Arg Phe Thr Ile Ser Ser Asp Asn Ala Lys Asn Thr
                325                 330                 335

Val Tyr Leu Gln Met Asn Ser Leu Lys Pro Glu Asp Thr Ala Val Tyr
            340                 345                 350

Tyr Cys Ala Ala Ser Ile Val Pro Arg Ser Lys Leu Glu Pro Tyr Glu
        355                 360                 365

Tyr Asp Ala Trp Gly Gln Gly Thr Leu Val Thr Val Ser Ser Gly Gly

```
    370                 375                 380

Gly Gly Ser Gly Gly Gly Ser Glu Val Gln Leu Val Glu Ser Gly Gly
385                 390                 395                 400

Gly Leu Val Gln Ala Gly Gly Ser Leu Arg Leu Ser Cys Ala Ala Ser
                405                 410                 415

Gly Phe Thr Phe Asp Asp Tyr Ala Leu Gly Trp Phe Arg Gln Ala Ala
            420                 425                 430

Gly Lys Glu Arg Glu Gly Val Ser Cys Ile Arg Cys Ser Asp Gly Ser
        435                 440                 445

Thr Tyr Tyr Ala Asp Ser Val Lys Gly Arg Phe Thr Ile Ser Ser Asp
    450                 455                 460

Asn Ala Lys Asn Thr Val Tyr Leu Gln Met Asn Ser Leu Lys Pro Glu
465                 470                 475                 480

Asp Thr Ala Val Tyr Tyr Cys Ala Ala Ser Ile Val Pro Arg Ser Lys
                485                 490                 495

Leu Glu Pro Tyr Glu Tyr Asp Ala Trp Gly Gln Gly Thr Leu Val Thr
            500                 505                 510

Val Ser Ser
        515


<210> SEQ ID NO 198
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 198

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Ala Gly Gly Ser Leu Arg Leu Ser Cys Ala Ala Ser Gly
145                 150                 155                 160

Phe Thr Phe Asp Asp Tyr Ala Leu Gly Trp Phe Arg Gln Ala Ala Gly
                165                 170                 175

Lys Glu Arg Glu Gly Val Ser Cys Ile Arg Cys Ser Asp Gly Ser Thr
            180                 185                 190

Tyr Tyr Ala Asp Ser Val Lys Gly Arg Phe Thr Ile Ser Ser Asp Asn
```

```
        195                 200                 205

Ala Lys Asn Thr Val Tyr Leu Gln Met Asn Ser Leu Lys Pro Glu Asp
    210                 215                 220

Thr Ala Val Tyr Tyr Cys Ala Ala Ser Ile Val Pro Arg Ser Lys Leu
225                 230                 235                 240

Glu Pro Tyr Glu Tyr Asp Ala Trp Gly Gln Gly Thr Leu Val Thr Val
                245                 250                 255

Ser Ser Gly Gly Gly Gly Ser Gly Gly Gly Ser Glu Val Gln Leu Val
            260                 265                 270

Glu Ser Gly Gly Gly Leu Val Gln Pro Gly Asn Ser Leu Arg Leu Ser
        275                 280                 285

Cys Ala Ala Ser Gly Phe Thr Phe Ser Ser Phe Gly Met Ser Trp Val
    290                 295                 300

Arg Gln Ala Pro Gly Lys Gly Leu Glu Trp Val Ser Ser Ile Ser Gly
305                 310                 315                 320

Ser Gly Ser Asp Thr Leu Tyr Ala Asp Ser Val Lys Gly Arg Phe Thr
                325                 330                 335

Ile Ser Arg Asp Asn Ala Lys Thr Thr Leu Tyr Leu Gln Met Asn Ser
            340                 345                 350

Leu Arg Pro Glu Asp Thr Ala Val Tyr Tyr Cys Thr Ile Gly Gly Ser
        355                 360                 365

Leu Ser Arg Ser Ser Gln Gly Thr Leu Val Thr Val Ser Ser Gly Gly
    370                 375                 380

Gly Gly Ser Gly Gly Gly Ser Glu Val Gln Leu Val Glu Ser Gly Gly
385                 390                 395                 400

Gly Leu Val Gln Ala Gly Gly Ser Leu Arg Leu Ser Cys Ala Ala Ser
                405                 410                 415

Gly Phe Thr Phe Asp Asp Tyr Ala Leu Gly Trp Phe Arg Gln Ala Ala
            420                 425                 430

Gly Lys Glu Arg Glu Gly Val Ser Cys Ile Arg Cys Ser Asp Gly Ser
        435                 440                 445

Thr Tyr Tyr Ala Asp Ser Val Lys Gly Arg Phe Thr Ile Ser Ser Asp
    450                 455                 460

Asn Ala Lys Asn Thr Val Tyr Leu Gln Met Asn Ser Leu Lys Pro Glu
465                 470                 475                 480

Asp Thr Ala Val Tyr Tyr Cys Ala Ala Ser Ile Val Pro Arg Ser Lys
                485                 490                 495

Leu Glu Pro Tyr Glu Tyr Asp Ala Trp Gly Gln Gly Thr Leu Val Thr
            500                 505                 510

Val Ser Ser
        515
```

<210> SEQ ID NO 199
<211> LENGTH: 382
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 199

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
```

```
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Ala
            260                 265                 270

Gly Gly Ser Leu Arg Leu Ser Cys Ala Ala Ser Gly Phe Thr Phe Asp
        275                 280                 285

Asp Tyr Ala Leu Gly Trp Phe Arg Gln Ala Ala Gly Lys Glu Arg Glu
    290                 295                 300

Gly Val Ser Cys Ile Arg Cys Ser Asp Gly Ser Thr Tyr Tyr Ala Asp
305                 310                 315                 320

Ser Val Lys Gly Arg Phe Thr Ile Ser Ser Asp Asn Ala Lys Asn Thr
                325                 330                 335

Val Tyr Leu Gln Met Asn Ser Leu Lys Pro Glu Asp Thr Ala Val Tyr
            340                 345                 350

Tyr Cys Ala Ala Ser Ile Val Pro Arg Ser Lys Leu Glu Pro Tyr Glu
        355                 360                 365

Tyr Asp Ala Trp Gly Gln Gly Thr Leu Val Thr Val Ser Ser
    370                 375                 380
```

<210> SEQ ID NO 200
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 200

Asp Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser Ser Tyr
20 25 30

Ser Met Gly Trp Phe Arg Gln Ala Pro Gly Lys Glu Arg Glu Phe Val
35 40 45

Val Ala Ile Ser Lys Gly Gly Tyr Lys Tyr Asp Ala Val Ser Leu Glu
50 55 60

Gly Arg Phe Thr Ile Ser Arg Asp Asn Ala Lys Asn Thr Val Tyr Leu
65 70 75 80

Gln Ile Asn Ser Leu Arg Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Leu Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Asn Ser Leu Arg Leu Ser Cys Ala Ala Ser Gly
145 150 155 160

Phe Thr Phe Ser Ser Phe Gly Met Ser Trp Val Arg Gln Ala Pro Gly
165 170 175

Lys Gly Leu Glu Trp Val Ser Ser Ile Ser Gly Ser Gly Ser Asp Thr
180 185 190

Leu Tyr Ala Asp Ser Val Lys Gly Arg Phe Thr Ile Ser Arg Asp Asn
195 200 205

Ala Lys Thr Thr Leu Tyr Leu Gln Met Asn Ser Leu Arg Pro Glu Asp
210 215 220

Thr Ala Val Tyr Tyr Cys Thr Ile Gly Gly Ser Leu Ser Arg Ser Ser
225 230 235 240

Gln Gly Thr Leu Val Thr Val Ser Ser Gly Gly Gly Gly Ser Gly Gly
245 250 255

Gly Ser Glu Val Gln Leu Val Glu Ser Gly Gly Gly Leu Val Gln Pro
260 265 270

Gly Gly Ser Leu Arg Leu Ser Cys Ala Ala Ser Gly Ile Thr Leu Asp
275 280 285

Asp Tyr Ala Ile Gly Trp Phe Arg Gln Ala Pro Gly Lys Glu Arg Glu
290 295 300

Gly Val Ser Ser Ile Arg Asp Asn Gly Gly Ser Thr Tyr Tyr Ala Asp
305 310 315 320

Ser Val Lys Gly Arg Phe Thr Ile Ser Ser Asp Asn Ser Lys Asn Thr
325 330 335

Val Tyr Leu Gln Met Asn Ser Leu Arg Pro Glu Asp Thr Ala Val Tyr
340 345 350

Tyr Cys Ala Ala Val Pro Ala Gly Arg Leu Arg Tyr Gly Glu Gln Trp
355 360 365

Tyr Pro Ile Tyr Glu Tyr Asp Ala Trp Gly Gln Gly Thr Leu Val Thr
370 375 380

Val Ser Ser
385

<210> SEQ ID NO 201

<211> LENGTH: 387
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Mutated lama sequence

<400> SEQUENCE: 201

Asp Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser Ser Tyr
20 25 30

Ser Met Gly Trp Phe Arg Gln Ala Pro Gly Lys Glu Arg Glu Phe Val
35 40 45

Val Ala Ile Ser Lys Gly Gly Tyr Lys Tyr Asp Ala Val Ser Leu Glu
50 55 60

Gly Arg Phe Thr Ile Ser Arg Asp Asn Ala Lys Asn Thr Val Tyr Leu
65 70 75 80

Gln Ile Asn Ser Leu Arg Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Leu Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Asn Ser Leu Arg Leu Ser Cys Ala Ala Ser Gly
145 150 155 160

Phe Thr Phe Ser Ser Phe Gly Met Ser Trp Val Arg Gln Ala Pro Gly
165 170 175

Lys Gly Leu Glu Trp Val Ser Ser Ile Ser Gly Ser Gly Ser Asp Thr
180 185 190

Leu Tyr Ala Asp Ser Val Lys Gly Arg Phe Thr Ile Ser Arg Asp Asn
195 200 205

Ala Lys Thr Thr Leu Tyr Leu Gln Met Asn Ser Leu Arg Pro Glu Asp
210 215 220

Thr Ala Val Tyr Tyr Cys Thr Ile Gly Gly Ser Leu Ser Arg Ser Ser
225 230 235 240

Gln Gly Thr Leu Val Thr Val Ser Ser Gly Gly Gly Gly Ser Gly Gly
245 250 255

Gly Ser Glu Val Gln Leu Val Glu Ser Gly Gly Gly Leu Val Gln Pro
260 265 270

Gly Gly Ser Leu Arg Leu Ser Cys Ala Val Ser Gly Ile Thr Leu Asp
275 280 285

Asp Tyr Ala Ile Gly Trp Phe Arg Gln Ala Pro Gly Lys Glu Arg Glu
290 295 300

Gly Val Ser Ser Ile Arg Asp Asn Gly Gly Ser Thr Tyr Tyr Ala Asp
305 310 315 320

Ser Val Lys Gly Arg Phe Thr Ile Ser Ser Asp Asn Ser Lys Asn Thr
325 330 335

Val Tyr Leu Gln Met Asn Ser Leu Arg Pro Glu Asp Thr Ala Val Tyr
340 345 350

Tyr Cys Ala Ala Val Pro Ala Gly Arg Leu Arg Tyr Gly Glu Gln Trp
355 360 365

```
Tyr Pro Ile Tyr Glu Tyr Asp Ala Trp Gly Gln Gly Thr Leu Val Thr
    370                 375                 380

Val Ser Ser
385
```

<210> SEQ ID NO 202
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 202

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Ile Thr Leu Asp
        275                 280                 285

Asp Tyr Ala Ile Gly Trp Phe Arg Gln Ala Pro Gly Lys Glu Arg Glu
    290                 295                 300

Gly Val Ser Ala Ile Arg Asp Asn Gly Gly Ser Thr Tyr Tyr Ala Asp
305                 310                 315                 320
```

```
Ser Val Lys Gly Arg Phe Thr Ile Ser Ser Asp Asn Ser Lys Asn Thr
                325                 330                 335

Val Tyr Leu Gln Met Asn Ser Leu Arg Pro Glu Asp Thr Ala Val Tyr
            340                 345                 350

Tyr Cys Ala Ala Val Pro Ala Gly Arg Leu Arg Tyr Gly Glu Gln Trp
        355                 360                 365

Tyr Pro Ile Tyr Glu Tyr Asp Ala Trp Gly Gln Gly Thr Leu Val Thr
    370                 375                 380

Val Ser Ser
385


<210> SEQ ID NO 203
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 203

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270
```

```
Gly Gly Ser Leu Arg Leu Ser Cys Ala Ala Ser Gly Ile Thr Leu Asp
        275                 280                 285

Asp Tyr Ala Ile Gly Trp Phe Arg Gln Ala Pro Gly Lys Glu Arg Glu
    290                 295                 300

Gly Val Ser Ala Ile Arg Glu Ser Gly Gly Ser Thr Tyr Tyr Ala Asp
305                 310                 315                 320

Ser Val Lys Gly Arg Phe Thr Ile Ser Ser Asp Asn Ser Lys Asn Thr
                325                 330                 335

Val Tyr Leu Gln Met Asn Ser Leu Arg Pro Glu Asp Thr Ala Val Tyr
            340                 345                 350

Tyr Cys Ala Ala Val Pro Ala Gly Arg Leu Arg Tyr Gly Glu Gln Trp
        355                 360                 365

Tyr Pro Ile Tyr Glu Tyr Asp Ala Trp Gly Gln Gly Thr Leu Val Thr
    370                 375                 380

Val Ser Ser
385


<210> SEQ ID NO 204
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 204

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220
```

Thr Ala Val Tyr Tyr Cys Thr Ile Gly Gly Ser Leu Ser Arg Ser Ser
225 230 235 240

Gln Gly Thr Leu Val Thr Val Ser Ser Gly Gly Gly Gly Ser Gly Gly
245 250 255

Gly Ser Glu Val Gln Leu Val Glu Ser Gly Gly Gly Leu Val Gln Pro
260 265 270

Gly Gly Ser Leu Arg Leu Ser Cys Ala Ala Ser Gly Ile Thr Leu Asp
275 280 285

Asp Tyr Ala Ile Gly Trp Phe Arg Gln Ala Pro Gly Lys Glu Arg Glu
290 295 300

Gly Val Ser Ala Ile Arg Ser Ser Gly Gly Ser Thr Tyr Tyr Ala Asp
305 310 315 320

Ser Val Lys Gly Arg Phe Thr Ile Ser Ser Asp Asn Ser Lys Asn Thr
325 330 335

Val Tyr Leu Gln Met Asn Ser Leu Arg Pro Glu Asp Thr Ala Val Tyr
340 345 350

Tyr Cys Ala Ala Val Pro Ala Gly Arg Leu Arg Tyr Gly Glu Gln Trp
355 360 365

Tyr Pro Ile Tyr Glu Tyr Asp Ala Trp Gly Gln Gly Thr Leu Val Thr
370 375 380

Val Ser Ser
385

<210> SEQ ID NO 205
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 205

Asp Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser Ser Tyr
20 25 30

Ser Met Gly Trp Phe Arg Gln Ala Pro Gly Lys Glu Arg Glu Phe Val
35 40 45

Val Ala Ile Ser Lys Gly Gly Tyr Lys Tyr Asp Ala Val Ser Leu Glu
50 55 60

Gly Arg Phe Thr Ile Ser Arg Asp Asn Ala Lys Asn Thr Val Tyr Leu
65 70 75 80

Gln Ile Asn Ser Leu Arg Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Leu Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Asn Ser Leu Arg Leu Ser Cys Ala Ala Ser Gly
145 150 155 160

Phe Thr Phe Ser Ser Phe Gly Met Ser Trp Val Arg Gln Ala Pro Gly
165 170 175

```
Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Val Ser Gly Ile Thr Leu Asp
        275                 280                 285

Asp Tyr Ala Ile Gly Trp Phe Arg Gln Ala Pro Gly Lys Glu Arg Glu
    290                 295                 300

Gly Val Ser Ala Ile Arg Asp Asn Gly Gly Ser Thr Tyr Tyr Ala Asp
305                 310                 315                 320

Ser Val Lys Gly Arg Phe Thr Ile Ser Ser Asp Asn Ser Lys Asn Thr
                325                 330                 335

Val Tyr Leu Gln Met Asn Ser Leu Arg Pro Glu Asp Thr Ala Val Tyr
            340                 345                 350

Tyr Cys Ala Ala Val Pro Ala Gly Arg Leu Arg Tyr Gly Glu Gln Trp
        355                 360                 365

Tyr Pro Ile Tyr Glu Tyr Asp Ala Trp Gly Gln Gly Thr Leu Val Thr
    370                 375                 380

Val Ser Ser
385


<210> SEQ ID NO 206
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 206

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125
```

Gly Ser Gly Gly Gly Ser Glu Val Gln Leu Val Glu Ser Gly Gly Gly
130 135 140

Leu Val Gln Pro Gly Asn Ser Leu Arg Leu Ser Cys Ala Ala Ser Gly
145 150 155 160

Phe Thr Phe Ser Ser Phe Gly Met Ser Trp Val Arg Gln Ala Pro Gly
165 170 175

Lys Gly Leu Glu Trp Val Ser Ser Ile Ser Gly Ser Gly Ser Asp Thr
180 185 190

Leu Tyr Ala Asp Ser Val Lys Gly Arg Phe Thr Ile Ser Arg Asp Asn
195 200 205

Ala Lys Thr Thr Leu Tyr Leu Gln Met Asn Ser Leu Arg Pro Glu Asp
210 215 220

Thr Ala Val Tyr Tyr Cys Thr Ile Gly Gly Ser Leu Ser Arg Ser Ser
225 230 235 240

Gln Gly Thr Leu Val Thr Val Ser Ser Gly Gly Gly Gly Ser Gly Gly
245 250 255

Gly Ser Glu Val Gln Leu Val Glu Ser Gly Gly Gly Leu Val Gln Pro
260 265 270

Gly Gly Ser Leu Arg Leu Ser Cys Ala Val Ser Gly Ile Thr Leu Asp
275 280 285

Asp Tyr Ala Ile Gly Trp Phe Arg Gln Ala Pro Gly Lys Glu Arg Glu
290 295 300

Gly Val Ser Ala Ile Arg Glu Ser Gly Gly Ser Thr Tyr Tyr Ala Asp
305 310 315 320

Ser Val Lys Gly Arg Phe Thr Ile Ser Ser Asp Asn Ser Lys Asn Thr
325 330 335

Val Tyr Leu Gln Met Asn Ser Leu Arg Pro Glu Asp Thr Ala Val Tyr
340 345 350

Tyr Cys Ala Ala Val Pro Ala Gly Arg Leu Arg Tyr Gly Glu Gln Trp
355 360 365

Tyr Pro Ile Tyr Glu Tyr Asp Ala Trp Gly Gln Gly Thr Leu Val Thr
370 375 380

Val Ser Ser
385

<210> SEQ ID NO 207
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 207

Asp Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser Ser Tyr
20 25 30

Ser Met Gly Trp Phe Arg Gln Ala Pro Gly Lys Glu Arg Glu Phe Val
35 40 45

Val Ala Ile Ser Lys Gly Gly Tyr Lys Tyr Asp Ala Val Ser Leu Glu
50 55 60

Gly Arg Phe Thr Ile Ser Arg Asp Asn Ala Lys Asn Thr Val Tyr Leu
65 70 75 80

Gln Ile Asn Ser Leu Arg Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Leu Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Asn Ser Leu Arg Leu Ser Cys Ala Ala Ser Gly
145 150 155 160

Phe Thr Phe Ser Ser Phe Gly Met Ser Trp Val Arg Gln Ala Pro Gly
165 170 175

Lys Gly Leu Glu Trp Val Ser Ser Ile Ser Gly Ser Gly Ser Asp Thr
180 185 190

Leu Tyr Ala Asp Ser Val Lys Gly Arg Phe Thr Ile Ser Arg Asp Asn
195 200 205

Ala Lys Thr Thr Leu Tyr Leu Gln Met Asn Ser Leu Arg Pro Glu Asp
210 215 220

Thr Ala Val Tyr Tyr Cys Thr Ile Gly Gly Ser Leu Ser Arg Ser Ser
225 230 235 240

Gln Gly Thr Leu Val Thr Val Ser Ser Gly Gly Gly Gly Ser Gly Gly
245 250 255

Gly Ser Glu Val Gln Leu Val Glu Ser Gly Gly Gly Leu Val Gln Pro
260 265 270

Gly Gly Ser Leu Arg Leu Ser Cys Ala Val Ser Gly Ile Thr Leu Asp
275 280 285

Asp Tyr Ala Ile Gly Trp Phe Arg Gln Ala Pro Gly Lys Glu Arg Glu
290 295 300

Gly Val Ser Ala Ile Arg Ser Ser Gly Gly Ser Thr Tyr Tyr Ala Asp
305 310 315 320

Ser Val Lys Gly Arg Phe Thr Ile Ser Ser Asp Asn Ser Lys Asn Thr
325 330 335

Val Tyr Leu Gln Met Asn Ser Leu Arg Pro Glu Asp Thr Ala Val Tyr
340 345 350

Tyr Cys Ala Ala Val Pro Ala Gly Arg Leu Arg Tyr Gly Glu Gln Trp
355 360 365

Tyr Pro Ile Tyr Glu Tyr Asp Ala Trp Gly Gln Gly Thr Leu Val Thr
370 375 380

Val Ser Ser
385

<210> SEQ ID NO 208
<211> LENGTH: 525
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Mutated lama sequence

<400> SEQUENCE: 208

Asp Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser Ser Tyr
20 25 30

```
Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Phe Thr Leu Asp
        275                 280                 285

Asp Tyr Ala Ile Gly Trp Phe Arg Gln Ala Pro Gly Lys Glu Arg Glu
    290                 295                 300

Gly Val Ser Ala Ile Arg Asp Asn Gly Gly Ser Thr Tyr Tyr Ala Asp
305                 310                 315                 320

Ser Val Lys Gly Arg Phe Thr Ile Ser Ser Asp Asn Ser Lys Asn Thr
                325                 330                 335

Val Tyr Leu Gln Met Asn Ser Leu Arg Pro Glu Asp Thr Ala Val Tyr
            340                 345                 350

Tyr Cys Ala Ala Val Pro Ala Gly Arg Leu Arg Phe Gly Glu Gln Trp
        355                 360                 365

Tyr Pro Leu Tyr Glu Tyr Asp Ala Trp Gly Gln Gly Thr Leu Val Thr
    370                 375                 380

Val Ser Ser Gly Gly Gly Gly Ser Gly Gly Gly Ser Glu Val Gln Leu
385                 390                 395                 400

Val Glu Ser Gly Gly Gly Leu Val Gln Pro Gly Gly Ser Leu Arg Leu
                405                 410                 415

Ser Cys Ala Ala Ser Gly Phe Thr Leu Asp Asp Tyr Ala Ile Gly Trp
            420                 425                 430

Phe Arg Gln Ala Pro Gly Lys Glu Arg Glu Gly Val Ser Ala Ile Arg
        435                 440                 445
```

```
Asp Asn Gly Gly Ser Thr Tyr Tyr Ala Asp Ser Val Lys Gly Arg Phe
    450                 455                 460

Thr Ile Ser Ser Asp Asn Ser Lys Asn Thr Val Tyr Leu Gln Met Asn
465                 470                 475                 480

Ser Leu Arg Pro Glu Asp Thr Ala Val Tyr Tyr Cys Ala Ala Val Pro
                485                 490                 495

Ala Gly Arg Leu Arg Phe Gly Glu Gln Trp Tyr Pro Leu Tyr Glu Tyr
            500                 505                 510

Asp Ala Trp Gly Gln Gly Thr Leu Val Thr Val Ser Ser
        515                 520                 525


<210> SEQ ID NO 209
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 209

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Thr Leu Asp Asp Tyr Ala Ile Gly Trp Phe Arg Gln Ala Pro Gly
                165                 170                 175

Lys Glu Arg Glu Gly Val Ser Ala Ile Arg Asp Asn Gly Gly Ser Thr
            180                 185                 190

Tyr Tyr Ala Asp Ser Val Lys Gly Arg Phe Thr Ile Ser Ser Asp Asn
        195                 200                 205

Ser Lys Asn Thr Val Tyr Leu Gln Met Asn Ser Leu Arg Pro Glu Asp
    210                 215                 220

Thr Ala Val Tyr Tyr Cys Ala Ala Val Pro Ala Gly Arg Leu Arg Phe
225                 230                 235                 240

Gly Glu Gln Trp Tyr Pro Leu Tyr Glu Tyr Asp Ala Trp Gly Gln Gly
                245                 250                 255

Thr Leu Val Thr Val Ser Ser Gly Gly Gly Gly Ser Gly Gly Gly Ser
            260                 265                 270
```

```
Glu Val Gln Leu Val Glu Ser Gly Gly Gly Leu Val Gln Pro Gly Gly
        275                 280                 285

Ser Leu Arg Leu Ser Cys Ala Ala Ser Gly Phe Thr Leu Asp Asp Tyr
    290                 295                 300

Ala Ile Gly Trp Phe Arg Gln Ala Pro Gly Lys Glu Arg Glu Gly Val
305                 310                 315                 320

Ser Ala Ile Arg Asp Asn Gly Gly Ser Thr Tyr Tyr Ala Asp Ser Val
                325                 330                 335

Lys Gly Arg Phe Thr Ile Ser Ser Asp Asn Ser Lys Asn Thr Val Tyr
            340                 345                 350

Leu Gln Met Asn Ser Leu Arg Pro Glu Asp Thr Ala Val Tyr Tyr Cys
        355                 360                 365

Ala Ala Val Pro Ala Gly Arg Leu Arg Phe Gly Glu Gln Trp Tyr Pro
    370                 375                 380

Leu Tyr Glu Tyr Asp Ala Trp Gly Gln Gly Thr Leu Val Thr Val Ser
385                 390                 395                 400

Ser Gly Gly Gly Gly Ser Gly Gly Gly Ser Glu Val Gln Leu Val Glu
                405                 410                 415

Ser Gly Gly Gly Leu Val Gln Pro Gly Asn Ser Leu Arg Leu Ser Cys
            420                 425                 430

Ala Ala Ser Gly Phe Thr Phe Ser Ser Phe Gly Met Ser Trp Val Arg
        435                 440                 445

Gln Ala Pro Gly Lys Gly Leu Glu Trp Val Ser Ser Ile Ser Gly Ser
    450                 455                 460

Gly Ser Asp Thr Leu Tyr Ala Asp Ser Val Lys Gly Arg Phe Thr Ile
465                 470                 475                 480

Ser Arg Asp Asn Ala Lys Thr Thr Leu Tyr Leu Gln Met Asn Ser Leu
                485                 490                 495

Arg Pro Glu Asp Thr Ala Val Tyr Tyr Cys Thr Ile Gly Gly Ser Leu
            500                 505                 510

Ser Arg Ser Ser Gln Gly Thr Leu Val Thr Val Ser Ser
        515                 520                 525


<210> SEQ ID NO 210
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 210

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95
```

```
Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Phe Thr Phe Asp
        275                 280                 285

Asp Tyr Ala Leu Gly Trp Phe Arg Gln Ala Pro Gly Lys Glu Arg Glu
    290                 295                 300

Gly Val Ser Cys Ile Arg Cys Ser Gly Gly Ser Thr Tyr Tyr Ala Asp
305                 310                 315                 320

Ser Val Lys Gly Arg Phe Thr Ile Ser Ser Asp Asn Ser Lys Asn Thr
                325                 330                 335

Val Tyr Leu Gln Met Asn Ser Leu Arg Pro Glu Asp Thr Ala Val Tyr
            340                 345                 350

Tyr Cys Ala Ala Ser Ile Val Pro Arg Ser Lys Leu Glu Pro Tyr Glu
        355                 360                 365

Tyr Asp Ala Trp Gly Gln Gly Thr Leu Val Thr Val Ser Ser Gly Gly
    370                 375                 380

Gly Gly Ser Gly Gly Gly Ser Glu Val Gln Leu Val Glu Ser Gly Gly
385                 390                 395                 400

Gly Leu Val Gln Pro Gly Gly Ser Leu Arg Leu Ser Cys Ala Ala Ser
                405                 410                 415

Gly Phe Thr Phe Asp Asp Tyr Ala Leu Gly Trp Phe Arg Gln Ala Pro
            420                 425                 430

Gly Lys Glu Arg Glu Gly Val Ser Cys Ile Arg Cys Ser Gly Gly Ser
        435                 440                 445

Thr Tyr Tyr Ala Asp Ser Val Lys Gly Arg Phe Thr Ile Ser Ser Asp
    450                 455                 460

Asn Ser Lys Asn Thr Val Tyr Leu Gln Met Asn Ser Leu Arg Pro Glu
465                 470                 475                 480

Asp Thr Ala Val Tyr Tyr Cys Ala Ala Ser Ile Val Pro Arg Ser Lys
                485                 490                 495

Leu Glu Pro Tyr Glu Tyr Asp Ala Trp Gly Gln Gly Thr Leu Val Thr
            500                 505                 510

Val Ser Ser
```

515

<210> SEQ ID NO 211
<211> LENGTH: 515
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 211

Asp Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser Ser Tyr
20 25 30

Ser Met Gly Trp Phe Arg Gln Ala Pro Gly Lys Glu Arg Glu Phe Val
35 40 45

Val Ala Ile Ser Lys Gly Gly Tyr Lys Tyr Asp Ala Val Ser Leu Glu
50 55 60

Gly Arg Phe Thr Ile Ser Arg Asp Asn Ala Lys Asn Thr Val Tyr Leu
65 70 75 80

Gln Ile Asn Ser Leu Arg Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Leu Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Gly Ser Leu Arg Leu Ser Cys Ala Ala Ser Gly
145 150 155 160

Phe Thr Phe Asp Asp Tyr Ala Leu Gly Trp Phe Arg Gln Ala Pro Gly
165 170 175

Lys Glu Arg Glu Gly Val Ser Cys Ile Arg Cys Ser Gly Gly Ser Thr
180 185 190

Tyr Tyr Ala Asp Ser Val Lys Gly Arg Phe Thr Ile Ser Ser Asp Asn
195 200 205

Ser Lys Asn Thr Val Tyr Leu Gln Met Asn Ser Leu Arg Pro Glu Asp
210 215 220

Thr Ala Val Tyr Tyr Cys Ala Ala Ser Ile Val Pro Arg Ser Lys Leu
225 230 235 240

Glu Pro Tyr Glu Tyr Asp Ala Trp Gly Gln Gly Thr Leu Val Thr Val
245 250 255

Ser Ser Gly Gly Gly Gly Ser Gly Gly Gly Ser Glu Val Gln Leu Val
260 265 270

Glu Ser Gly Gly Gly Leu Val Gln Pro Gly Gly Ser Leu Arg Leu Ser
275 280 285

Cys Ala Ala Ser Gly Phe Thr Phe Asp Asp Tyr Ala Leu Gly Trp Phe
290 295 300

Arg Gln Ala Pro Gly Lys Glu Arg Glu Gly Val Ser Cys Ile Arg Cys
305 310 315 320

Ser Gly Gly Ser Thr Tyr Tyr Ala Asp Ser Val Lys Gly Arg Phe Thr
325 330 335

Ile Ser Ser Asp Asn Ser Lys Asn Thr Val Tyr Leu Gln Met Asn Ser 340 345 350

Leu Arg Pro Glu Asp Thr Ala Val Tyr Tyr Cys Ala Ala Ser Ile Val
355 360 365

Pro Arg Ser Lys Leu Glu Pro Tyr Glu Tyr Asp Ala Trp Gly Gln Gly
370 375 380

Thr Leu Val Thr Val Ser Ser Gly Gly Gly Gly Ser Gly Gly Gly Ser
385 390 395 400

Glu Val Gln Leu Val Glu Ser Gly Gly Gly Leu Val Gln Pro Gly Asn
405 410 415

Ser Leu Arg Leu Ser Cys Ala Ala Ser Gly Phe Thr Phe Ser Ser Phe
420 425 430

Gly Met Ser Trp Val Arg Gln Ala Pro Gly Lys Gly Leu Glu Trp Val
435 440 445

Ser Ser Ile Ser Gly Ser Gly Ser Asp Thr Leu Tyr Ala Asp Ser Val
450 455 460

Lys Gly Arg Phe Thr Ile Ser Arg Asp Asn Ala Lys Thr Thr Leu Tyr
465 470 475 480

Leu Gln Met Asn Ser Leu Arg Pro Glu Asp Thr Ala Val Tyr Tyr Cys
485 490 495

Thr Ile Gly Gly Ser Leu Ser Arg Ser Ser Gln Gly Thr Leu Val Thr
500 505 510

Val Ser Ser
515

<210> SEQ ID NO 212
<211> LENGTH: 384
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Mutated lama sequence

<400> SEQUENCE: 212

Asp Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser Ser Tyr
20 25 30

Ser Met Gly Trp Phe Arg Gln Ala Pro Gly Lys Glu Arg Glu Phe Val
35 40 45

Val Ala Ile Ser Lys Gly Gly Tyr Lys Tyr Asp Ala Val Ser Leu Glu
50 55 60

Gly Arg Phe Thr Ile Ser Arg Asp Asn Ala Lys Asn Thr Val Tyr Leu
65 70 75 80

Gln Ile Asn Ser Leu Arg Pro Glu Asp Thr Ala Val Tyr Tyr Cys Ala
85 90 95

Ser Ser Arg Ala Tyr Gly Ser Ser Arg Leu Arg Leu Ala Asp Thr Tyr
100 105 110

Glu Tyr Trp Gly Gln Gly Thr Leu Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Asn Ser Leu Arg Leu Ser Cys Ala Ala Ser Gly
145 150 155 160

Phe Thr Phe Ser Ser Phe Gly Met Ser Trp Val Arg Gln Ala Pro Gly

```
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Phe Ala Leu Asp
        275                 280                 285

Tyr Tyr Ala Ile Gly Trp Phe Arg Gln Ala Pro Gly Lys Glu Arg Glu
    290                 295                 300

Gly Val Ser Cys Ile Ser Ser Ser Gly Gly Ile Thr Tyr Tyr Ala Asp
305                 310                 315                 320

Ser Val Lys Gly Arg Phe Thr Ile Ser Arg Asp Asn Ser Lys Asn Thr
                325                 330                 335

Val Tyr Leu Gln Met Asn Ser Leu Arg Pro Glu Asp Thr Ala Val Tyr
            340                 345                 350

Tyr Cys Ala Thr Asp Ser Gly Gly Tyr Ile Asp Tyr Asp Cys Ser Gly
        355                 360                 365

Leu Gly Tyr Asp Tyr Trp Gly Gln Gly Thr Leu Val Thr Val Ser Ser
    370                 375                 380
```

<210> SEQ ID NO 213
<211> LENGTH: 525
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 213

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
```

```
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Phe Thr Leu Asp
        275                 280                 285

Asp Tyr Ala Ile Gly Trp Phe Arg Gln Ala Pro Gly Lys Glu Arg Glu
    290                 295                 300

Gly Val Ser Ala Ile Arg Ser Ser Gly Gly Ser Thr Tyr Tyr Ala Asp
305                 310                 315                 320

Ser Val Lys Gly Arg Phe Thr Ile Ser Ser Asp Asn Ser Lys Asn Thr
                325                 330                 335

Val Tyr Leu Gln Met Asn Ser Leu Arg Pro Glu Asp Thr Ala Val Tyr
            340                 345                 350

Tyr Cys Ala Ala Val Pro Ala Gly Arg Leu Arg Phe Gly Glu Gln Trp
        355                 360                 365

Tyr Pro Leu Tyr Glu Tyr Asp Ala Trp Gly Gln Gly Thr Leu Val Thr
    370                 375                 380

Val Ser Ser Gly Gly Gly Gly Ser Gly Gly Gly Ser Glu Val Gln Leu
385                 390                 395                 400

Val Glu Ser Gly Gly Gly Leu Val Gln Pro Gly Gly Ser Leu Arg Leu
                405                 410                 415

Ser Cys Ala Ala Ser Gly Phe Thr Leu Asp Asp Tyr Ala Ile Gly Trp
            420                 425                 430

Phe Arg Gln Ala Pro Gly Lys Glu Arg Glu Gly Val Ser Ala Ile Arg
        435                 440                 445

Ser Ser Gly Gly Ser Thr Tyr Tyr Ala Asp Ser Val Lys Gly Arg Phe
    450                 455                 460

Thr Ile Ser Ser Asp Asn Ser Lys Asn Thr Val Tyr Leu Gln Met Asn
465                 470                 475                 480

Ser Leu Arg Pro Glu Asp Thr Ala Val Tyr Tyr Cys Ala Ala Val Pro
                485                 490                 495

Ala Gly Arg Leu Arg Phe Gly Glu Gln Trp Tyr Pro Leu Tyr Glu Tyr
            500                 505                 510

Asp Ala Trp Gly Gln Gly Thr Leu Val Thr Val Ser Ser
        515                 520                 525
```

<210> SEQ ID NO 214
<211> LENGTH: 124
<212> TYPE: PRT
<213> ORGANISM: Lama glama

<400> SEQUENCE: 214

Glu Val Gln Leu Val Glu Ser Gly Gly Gly Leu Val Gln Ala Gly Gly
1 5 10 15

Ser Leu Arg Leu Ser Cys Ala Ala Ser Gly Phe Thr Phe Asp Asp Tyr
20 25 30

Ala Leu Gly Trp Phe Arg Gln Ala Ala Gly Lys Glu Arg Glu Gly Val
35 40 45

Ser Cys Ile Arg Cys Ser Asp Gly Ser Thr Tyr Tyr Ala Asp Ser Val
50 55 60

Lys Gly Arg Phe Thr Ile Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Ser Ile Val Pro Arg Ser Lys Leu Glu Pro Tyr Glu Tyr Asp
100 105 110

Ala Trp Gly Gln Gly Thr Gln Val Thr Val Ser Ser
115 120

<210> SEQ ID NO 215
<211> LENGTH: 126
<212> TYPE: PRT
<213> ORGANISM: Lama glama

<400> SEQUENCE: 215

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ala Leu Asp Tyr Tyr
20 25 30

Ala Ile Gly Trp Phe Arg Gln Val Pro Gly Lys Glu Arg Glu Gly Val
35 40 45

Ser Cys Ile Ser Ser Ser Asp Gly Ile Thr Tyr Tyr Val Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Thr Asp Ser Gly Gly Tyr Ile Asp Tyr Asp Cys Met Gly Leu Gly
100 105 110

Tyr Asp Tyr Trp Gly Gln Gly Thr Gln Val Thr Val Ser Ser
115 120 125

<210> SEQ ID NO 216
<211> LENGTH: 129
<212> TYPE: PRT
<213> ORGANISM: Lama glama

<400> SEQUENCE: 216

Glu Val Gln Leu Val Glu Ser Gly Gly Gly Leu Val Gln Ala Gly Gly
1 5 10 15

Ser Leu Arg Leu Ser Cys Ala Ala Ser Gly Phe Thr Leu Asp Asp Tyr
20 25 30

Ala Ile Gly Trp Phe Arg Gln Ala Pro Gly Lys Glu Arg Glu Gly Val
35 40 45

Ser Cys Ile Arg Asp Ser Asp Gly Ser Thr Tyr Tyr Ala Asp Ser Val
50 55 60

Lys Gly Arg Phe Thr Ile Ser Ser Asp Asn Asp Lys Asn Thr Val Tyr
65 70 75 80

Leu Gln Met Asn Ser Leu Lys Pro Glu Asp Thr Ala Val Tyr Tyr Cys
85 90 95

Ala Ala Val Pro Ala Gly Arg Leu Arg Phe Gly Glu Gln Trp Tyr Pro
100 105 110

Leu Tyr Glu Tyr Asp Ala Trp Gly Gln Gly Thr Gln Val Thr Val Ser
115 120 125

Ser

<210> SEQ ID NO 217
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 217

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Asp Asp Tyr
20 25 30

Ala Ile Gly Trp Phe Arg Gln Ala Pro Gly Lys Glu Arg Glu Gly Val
35 40 45

Ser Ser Ile Arg Asp Asn Asp Gly Ser Thr Tyr Tyr Ala Asp Ser Val
50 55 60

Lys Gly Arg Phe Thr Ile Ser Ser Asp Asn Ser Lys Asn Thr Val Tyr
65 70 75 80

Leu Gln Met Asn Ser Leu Arg Pro Glu Asp Thr Ala Val Tyr Tyr Cys
85 90 95

Ala Ala Val Pro Ala Gly Arg Leu Arg Phe Gly Glu Gln Trp Tyr Pro
100 105 110

Leu Tyr Glu Tyr Asp Ala Trp Gly Gln Gly Thr Leu Val Thr Val Ser
115 120 125

Ser

<210> SEQ ID NO 218
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 218

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asp Asp Tyr
20 25 30

Ala Leu Gly Trp Phe Arg Gln Ala Pro Gly Lys Glu Arg Glu Gly Val
35 40 45

Ser Cys Ile Arg Cys Ser Asp Gly Ser Thr Tyr Tyr Ala Asp Ser Val
50 55 60

Lys Gly Arg Phe Thr Ile Ser Ser Asp Asn Ser Lys Asn Thr Val Tyr

```
65                  70                  75                  80

Leu Gln Met Asn Ser Leu Arg Pro Glu Asp Thr Ala Val Tyr Tyr Cys
                85                  90                  95

Ala Ala Ser Ile Val Pro Arg Ser Lys Leu Glu Pro Tyr Glu Tyr Asp
            100                 105                 110

Ala Trp Gly Gln Gly Thr Leu Val Thr Val Ser Ser
        115                 120


<210> SEQ ID NO 219
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Asp Ser Gly Gly Tyr Ile Asp Tyr Asp Cys Met Gly Leu Gly
            100                 105                 110

Tyr Asp Tyr Trp Gly Gln Gly Thr Leu Val Thr Val Ser Ser
        115                 120                 125


<210> SEQ ID NO 220
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 220

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Leu Gly Trp Phe Arg Gln Ala Pro Gly Lys Glu Arg Glu Gly Val
        35                  40                  45

Ser Cys Ile Arg Cys Ser Gly Gly Ser Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95
```

```
Ala Ala Ser Ile Val Pro Arg Ser Lys Leu Glu Pro Tyr Glu Tyr Asp
            100                 105                 110

Ala Trp Gly Gln Gly Thr Leu Val Thr Val Ser Ser
        115                 120


<210> SEQ ID NO 221
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 221

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Asp Ser Gly Gly Tyr Ile Asp Tyr Asp Cys Ser Gly Leu Gly
            100                 105                 110

Tyr Asp Tyr Trp Gly Gln Gly Thr Leu Val Thr Val Ser Ser
        115                 120                 125


<210> SEQ ID NO 222
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 222

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Thr Leu Asp Asp Tyr
            20                  25                  30

Ala Ile Gly Trp Phe Arg Gln Ala Pro Gly Lys Glu Arg Glu Gly Val
        35                  40                  45

Ser Ala Ile Arg Ser Ser Gly Gly Ser Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Val Pro Ala Gly Arg Leu Arg Tyr Gly Glu Gln Trp Tyr Pro
            100                 105                 110

Ile Tyr Glu Tyr Asp Ala Trp Gly Gln Gly Thr Leu Val Thr Val Ser
        115                 120                 125
```

Ser

<210> SEQ ID NO 223
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutated lama sequence

<400> SEQUENCE: 223

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Asp Asp Tyr
20 25 30

Ala Ile Gly Trp Phe Arg Gln Ala Pro Gly Lys Glu Arg Glu Gly Val
35 40 45

Ser Ala Ile Arg Ser Ser Gly Gly Ser Thr Tyr Tyr Ala Asp Ser Val
50 55 60

Lys Gly Arg Phe Thr Ile Ser Ser Asp Asn Ser Lys Asn Thr Val Tyr
65 70 75 80

Leu Gln Met Asn Ser Leu Arg Pro Glu Asp Thr Ala Val Tyr Tyr Cys
85 90 95

Ala Ala Val Pro Ala Gly Arg Leu Arg Phe Gly Glu Gln Trp Tyr Pro
100 105 110

Leu Tyr Glu Tyr Asp Ala Trp Gly Gln Gly Thr Leu Val Thr Val Ser
115 120 125

Ser

<210> SEQ ID NO 224
<211> LENGTH: 5
<212> TYPE: PRT
<213> ORGANISM: Lama glama

<400> SEQUENCE: 224

Asp Tyr Ala Leu Gly
1 5

<210> SEQ ID NO 225
<211> LENGTH: 17
<212> TYPE: PRT
<213> ORGANISM: Lama glama

<400> SEQUENCE: 225

Cys Ile Arg Cys Ser Asp Gly Ser Thr Tyr Tyr Ala Asp Ser Val Lys
1 5 10 15

Gly

<210> SEQ ID NO 226
<211> LENGTH: 15
<212> TYPE: PRT
<213> ORGANISM: Lama glama

<400> SEQUENCE: 226

Ser Ile Val Pro Arg Ser Lys Leu Glu Pro Tyr Glu Tyr Asp Ala
1 5 10 15

<210> SEQ ID NO 227

<211> LENGTH: 5
<212> TYPE: PRT
<213> ORGANISM: Lama glama

<400> SEQUENCE: 227

Tyr Tyr Ala Ile Gly
1               5

<210> SEQ ID NO 228
<211> LENGTH: 17
<212> TYPE: PRT
<213> ORGANISM: Lama glama

<400> SEQUENCE: 228

Cys Ile Ser Ser Ser Asp Gly Ile Thr Tyr Tyr Val Asp Ser Val Lys
1               5                   10                  15

Gly

<210> SEQ ID NO 229
<211> LENGTH: 17
<212> TYPE: PRT
<213> ORGANISM: Lama glama

<400> SEQUENCE: 229

Asp Ser Gly Gly Tyr Ile Asp Tyr Asp Cys Met Gly Leu Gly Tyr Asp
1               5                   10                  15

Tyr

<210> SEQ ID NO 230
<211> LENGTH: 5
<212> TYPE: PRT
<213> ORGANISM: Lama glama

<400> SEQUENCE: 230

Asp Tyr Ala Ile Gly
1               5

<210> SEQ ID NO 231
<211> LENGTH: 17
<212> TYPE: PRT
<213> ORGANISM: Lama glama

<400> SEQUENCE: 231

Cys Ile Arg Asp Ser Asp Gly Ser Thr Tyr Tyr Ala Asp Ser Val Lys
1               5                   10                  15

Gly

<210> SEQ ID NO 232
<211> LENGTH: 20
<212> TYPE: PRT
<213> ORGANISM: Lama glama

<400> SEQUENCE: 232

Val Pro Ala Gly Arg Leu Arg Phe Gly Glu Gln Trp Tyr Pro Leu Tyr
1               5                   10                  15

Glu Tyr Asp Ala
            20

<210> SEQ ID NO 233
<211> LENGTH: 5
<212> TYPE: PRT
<213> ORGANISM: Lama glama

<400> SEQUENCE: 233

Asp Tyr Ala Ile Gly
1 5

<210> SEQ ID NO 234
<211> LENGTH: 17
<212> TYPE: PRT
<213> ORGANISM: Lama glama

<400> SEQUENCE: 234

Ser Ile Arg Asp Asn Asp Gly Ser Thr Tyr Tyr Ala Asp Ser Val Lys
1 5 10 15

Gly

<210> SEQ ID NO 235
<211> LENGTH: 20
<212> TYPE: PRT
<213> ORGANISM: Lama glama

<400> SEQUENCE: 235

Val Pro Ala Gly Arg Leu Arg Phe Gly Glu Gln Trp Tyr Pro Leu Tyr
1 5 10 15

Glu Tyr Asp Ala
20

<210> SEQ ID NO 236
<211> LENGTH: 5
<212> TYPE: PRT
<213> ORGANISM: Lama glama

<400> SEQUENCE: 236

Asp Tyr Ala Leu Gly
1 5

<210> SEQ ID NO 237
<211> LENGTH: 17
<212> TYPE: PRT
<213> ORGANISM: Lama glama

<400> SEQUENCE: 237

Cys Ile Arg Cys Ser Asp Gly Ser Thr Tyr Tyr Ala Asp Ser Val Lys
1 5 10 15

Gly

<210> SEQ ID NO 238
<211> LENGTH: 15
<212> TYPE: PRT
<213> ORGANISM: Lama glama

<400> SEQUENCE: 238

Ser Ile Val Pro Arg Ser Lys Leu Glu Pro Tyr Glu Tyr Asp Ala
1 5 10 15

<210> SEQ ID NO 239
<211> LENGTH: 5
<212> TYPE: PRT
<213> ORGANISM: Lama glama

<400> SEQUENCE: 239

Tyr Tyr Ala Ile Gly
1 5

<210> SEQ ID NO 240
<211> LENGTH: 17
<212> TYPE: PRT
<213> ORGANISM: Lama glama

<400> SEQUENCE: 240

Cys Ile Ser Ser Ser Asp Gly Ile Thr Tyr Tyr Ala Asp Ser Val Lys
1 5 10 15

Gly

<210> SEQ ID NO 241
<211> LENGTH: 17
<212> TYPE: PRT
<213> ORGANISM: Lama glama

<400> SEQUENCE: 241

Asp Ser Gly Gly Tyr Ile Asp Tyr Asp Cys Met Gly Leu Gly Tyr Asp
1 5 10 15

Tyr

<210> SEQ ID NO 242
<211> LENGTH: 5
<212> TYPE: PRT
<213> ORGANISM: Lama glama

<400> SEQUENCE: 242

Asp Tyr Ala Leu Gly
1 5

<210> SEQ ID NO 243
<211> LENGTH: 17
<212> TYPE: PRT
<213> ORGANISM: Lama glama

<400> SEQUENCE: 243

Cys Ile Arg Cys Ser Gly Gly Ser Thr Tyr Tyr Ala Asp Ser Val Lys
1 5 10 15

Gly

<210> SEQ ID NO 244
<211> LENGTH: 15
<212> TYPE: PRT
<213> ORGANISM: Lama glama

<400> SEQUENCE: 244

Ser Ile Val Pro Arg Ser Lys Leu Glu Pro Tyr Glu Tyr Asp Ala
1 5 10 15

<210> SEQ ID NO 245
<211> LENGTH: 5
<212> TYPE: PRT
<213> ORGANISM: Lama glama

<400> SEQUENCE: 245

Tyr Tyr Ala Ile Gly
1 5

<210> SEQ ID NO 246
<211> LENGTH: 17
<212> TYPE: PRT
<213> ORGANISM: Lama glama

<400> SEQUENCE: 246

Cys Ile Ser Ser Ser Gly Gly Ile Thr Tyr Tyr Ala Asp Ser Val Lys
1 5 10 15

Gly

<210> SEQ ID NO 247
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Mutated lama sequence

<400> SEQUENCE: 247

Asp Ser Gly Gly Tyr Ile Asp Tyr Asp Cys Ser Gly Leu Gly Tyr Asp
1 5 10 15

Tyr

<210> SEQ ID NO 248
<211> LENGTH: 5
<212> TYPE: PRT
<213> ORGANISM: Lama glama

<400> SEQUENCE: 248

Asp Tyr Ala Ile Gly
1 5

<210> SEQ ID NO 249
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Mutated lama sequence

<400> SEQUENCE: 249

Ala Ile Arg Ser Ser Gly Gly Ser Thr Tyr Tyr Ala Asp Ser Val Lys
1 5 10 15

Gly

<210> SEQ ID NO 250
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Mutated lama sequence

<400> SEQUENCE: 250

Val Pro Ala Gly Arg Leu Arg Tyr Gly Glu Gln Trp Tyr Pro Ile Tyr
1 5 10 15

Glu Tyr Asp Ala
20

<210> SEQ ID NO 251
<211> LENGTH: 5
<212> TYPE: PRT
<213> ORGANISM: Lama glama

<400> SEQUENCE: 251

```
Asp Tyr Ala Ile Gly
1               5


<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated lama sequence

<400> SEQUENCE: 252

Ala Ile Arg Ser Ser Gly Gly Ser Thr Tyr Tyr Ala Asp Ser Val Lys
1               5                   10                  15

Gly


<210> SEQ ID NO 253
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated lama sequence

<400> SEQUENCE: 253

Val Pro Ala Gly Arg Leu Arg Phe Gly Glu Gln Trp Tyr Pro Leu Tyr
1               5                   10                  15

Glu Tyr Asp Ala
            20


<210> SEQ ID NO 254
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated lama sequence

<400> SEQUENCE: 254

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 255
```

<211> LENGTH: 5
<212> TYPE: PRT
<213> ORGANISM: Lama glama

<400> SEQUENCE: 255

Ser Phe Gly Met Ser
1 5

<210> SEQ ID NO 256
<211> LENGTH: 17
<212> TYPE: PRT
<213> ORGANISM: Lama glama

<400> SEQUENCE: 256

Ser Ile Ser Gly Ser Gly Ser Asp Thr Leu Tyr Ala Asp Ser Val Lys
1 5 10 15

Gly

<210> SEQ ID NO 257
<211> LENGTH: 6
<212> TYPE: PRT
<213> ORGANISM: Lama glama

<400> SEQUENCE: 257

Gly Gly Ser Leu Ser Arg
1 5

<210> SEQ ID NO 258
<211> LENGTH: 5
<212> TYPE: PRT
<213> ORGANISM: Lama glama

<400> SEQUENCE: 258

Leu Asn Leu Met Gly
1 5

<210> SEQ ID NO 259
<211> LENGTH: 16
<212> TYPE: PRT
<213> ORGANISM: Lama glama

<400> SEQUENCE: 259

Thr Ile Thr Val Gly Asp Ser Thr Asn Tyr Ala Asp Ser Val Lys Gly
1 5 10 15

<210> SEQ ID NO 260
<211> LENGTH: 8
<212> TYPE: PRT
<213> ORGANISM: Lama glama

<400> SEQUENCE: 260

Arg Arg Thr Trp His Ser Glu Leu
1 5

<210> SEQ ID NO 261
<211> LENGTH: 5
<212> TYPE: PRT
<213> ORGANISM: Lama glama

<400> SEQUENCE: 261

Ile Asn Leu Leu Gly
1 5

<210> SEQ ID NO 262

<211> LENGTH: 16
<212> TYPE: PRT
<213> ORGANISM: Lama glama

<400> SEQUENCE: 262

Thr Ile Thr Val Gly Asp Ser Thr Ser Tyr Ala Asp Ser Val Lys Gly
1 5 10 15

<210> SEQ ID NO 263
<211> LENGTH: 8
<212> TYPE: PRT
<213> ORGANISM: Lama glama

<400> SEQUENCE: 263

Arg Arg Thr Trp His Ser Glu Leu
1 5

<210> SEQ ID NO 264
<211> LENGTH: 5
<212> TYPE: PRT
<213> ORGANISM: Lama glama

<400> SEQUENCE: 264

Ser Phe Gly Met Ser
1 5

<210> SEQ ID NO 265
<211> LENGTH: 17
<212> TYPE: PRT
<213> ORGANISM: Lama glama

<400> SEQUENCE: 265

Ser Ile Asn Gly Arg Gly Asp Asp Thr Arg Tyr Ala Asp Ser Val Lys
1 5 10 15

Gly

<210> SEQ ID NO 266
<211> LENGTH: 7
<212> TYPE: PRT
<213> ORGANISM: Lama glama

<400> SEQUENCE: 266

Gly Arg Ser Val Ser Arg Ser
1 5

<210> SEQ ID NO 267
<211> LENGTH: 5
<212> TYPE: PRT
<213> ORGANISM: Lama glama

<400> SEQUENCE: 267

Ser Phe Gly Met Ser
1 5

<210> SEQ ID NO 268
<211> LENGTH: 17
<212> TYPE: PRT
<213> ORGANISM: Lama glama

<400> SEQUENCE: 268

Ala Ile Ser Ala Asp Ser Ser Asp Lys Arg Tyr Ala Asp Ser Val Lys
1 5 10 15

Gly

<210> SEQ ID NO 269
<211> LENGTH: 5
<212> TYPE: PRT
<213> ORGANISM: Lama glama

<400> SEQUENCE: 269

Gly Arg Gly Ser Pro
1               5

<210> SEQ ID NO 270
<211> LENGTH: 5
<212> TYPE: PRT
<213> ORGANISM: Lama glama

<400> SEQUENCE: 270

Ser Phe Gly Met Ser
1               5

<210> SEQ ID NO 271
<211> LENGTH: 17
<212> TYPE: PRT
<213> ORGANISM: Lama glama

<400> SEQUENCE: 271

Ala Ile Ser Ala Asp Ser Ser Asp Lys Arg Tyr Ala Asp Ser Val Lys
1               5                   10                  15

Gly

<210> SEQ ID NO 272
<211> LENGTH: 5
<212> TYPE: PRT
<213> ORGANISM: Lama glama

<400> SEQUENCE: 272

Gly Arg Gly Ser Pro
1               5

<210> SEQ ID NO 273
<211> LENGTH: 5
<212> TYPE: PRT
<213> ORGANISM: Lama glama

<400> SEQUENCE: 273

Asn Tyr Trp Met Tyr
1               5

<210> SEQ ID NO 274
<211> LENGTH: 17
<212> TYPE: PRT
<213> ORGANISM: Lama glama

<400> SEQUENCE: 274

Arg Ile Ser Thr Gly Gly Gly Tyr Ser Tyr Tyr Ala Asp Ser Val Lys
1               5                   10                  15

Gly

<210> SEQ ID NO 275
<211> LENGTH: 13
<212> TYPE: PRT
<213> ORGANISM: Lama glama

<400> SEQUENCE: 275

Asp Arg Glu Ala Gln Val Asp Thr Leu Asp Phe Asp Tyr 1 5 10

<210> SEQ ID NO 276
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Lys Glu Arg Glu
1

<210> SEQ ID NO 277
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Gly Leu Glu Trp
1

<210> SEQ ID NO 278
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Gly Gly Gly Gly Ser Gly Gly Gly Gly Ser Gly Gly Gly Gly Ser
1 5 10 15

<210> SEQ ID NO 279
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

Gly Gly Gly Gly Ser Gly Gly Gly Gly Ser Gly Gly Gly Gly Ser Gly
1 5 10 15

Gly Gly Gly Ser
20

<210> SEQ ID NO 280
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Gly Gly Gly Gly Ser
1 5

<210> SEQ ID NO 281
<211> LENGTH: 4
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 281

Gly Gly Gly Ser
1

<210> SEQ ID NO 282
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gly Gly Gly Ser Ser Gly Gly Gly Ser Ser Gly Gly Gly Ser Ser
1               5                   10                  15

<210> SEQ ID NO 283
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 283

His His His His His His
1               5

<210> SEQ ID NO 284
<211> LENGTH: 5
<212> TYPE: PRT
<213> ORGANISM: Lama glama

<400> SEQUENCE: 284

Ser Tyr Gly Met Gly
1               5

<210> SEQ ID NO 285
<211> LENGTH: 5
<212> TYPE: PRT
<213> ORGANISM: Lama glama

<400> SEQUENCE: 285

Ala Ser Asp Met Gly
1               5

<210> SEQ ID NO 286
<211> LENGTH: 5
<212> TYPE: PRT
<213> ORGANISM: Lama glama

<400> SEQUENCE: 286

Ile Thr Val Met Ala
1               5

<210> SEQ ID NO 287
<211> LENGTH: 5
<212> TYPE: PRT
<213> ORGANISM: Lama glama

<400> SEQUENCE: 287

Asp Ile Thr Val Ala
1 5

<210> SEQ ID NO 288
<211> LENGTH: 5
<212> TYPE: PRT
<213> ORGANISM: Lama glama

<400> SEQUENCE: 288

Thr Asp Asp Val Gly
1 5

<210> SEQ ID NO 289
<211> LENGTH: 5
<212> TYPE: PRT
<213> ORGANISM: Lama glama

<400> SEQUENCE: 289

His Tyr Asn Met Gly
1 5

<210> SEQ ID NO 290
<211> LENGTH: 3
<212> TYPE: PRT
<213> ORGANISM: Lama glama

<400> SEQUENCE: 290

Ser Met Ala
1

<210> SEQ ID NO 291
<211> LENGTH: 5
<212> TYPE: PRT
<213> ORGANISM: Lama glama

<400> SEQUENCE: 291

Asn Asn Ala Met Ala
1 5

<210> SEQ ID NO 292
<211> LENGTH: 5
<212> TYPE: PRT
<213> ORGANISM: Lama glama

<400> SEQUENCE: 292

Ile Ser Val Met Ala
1 5

<210> SEQ ID NO 293
<211> LENGTH: 5
<212> TYPE: PRT
<213> ORGANISM: Lama glama

<400> SEQUENCE: 293

Asn Tyr Ala Met Ala
1 5

<210> SEQ ID NO 294
<211> LENGTH: 5
<212> TYPE: PRT
<213> ORGANISM: Lama glama

<400> SEQUENCE: 294

Asp Asn Val Met Gly
1 5

<210> SEQ ID NO 295
<211> LENGTH: 5
<212> TYPE: PRT
<213> ORGANISM: Lama glama

<400> SEQUENCE: 295

Ser Tyr Tyr Met Gly
1 5

<210> SEQ ID NO 296
<211> LENGTH: 5
<212> TYPE: PRT
<213> ORGANISM: Lama glama

<400> SEQUENCE: 296

Ser Asp Val Met Gly
1 5

<210> SEQ ID NO 297
<211> LENGTH: 5
<212> TYPE: PRT
<213> ORGANISM: Lama glama

<400> SEQUENCE: 297

Leu Tyr Ala Met Gly
1 5

<210> SEQ ID NO 298
<211> LENGTH: 5
<212> TYPE: PRT
<213> ORGANISM: Lama glama

<400> SEQUENCE: 298

Arg Tyr Gly Met Gly
1 5

<210> SEQ ID NO 299
<211> LENGTH: 5
<212> TYPE: PRT
<213> ORGANISM: Lama glama

<400> SEQUENCE: 299

Asn Tyr Ala Met Gly
1 5

<210> SEQ ID NO 300
<211> LENGTH: 5
<212> TYPE: PRT
<213> ORGANISM: Lama glama

<400> SEQUENCE: 300

Arg Tyr Ala Met Gly
1 5

<210> SEQ ID NO 301
<211> LENGTH: 5
<212> TYPE: PRT
<213> ORGANISM: Lama glama

<400> SEQUENCE: 301

Asn Tyr Asn Met Gly
1 5

<210> SEQ ID NO 302
<211> LENGTH: 5
<212> TYPE: PRT
<213> ORGANISM: Lama glama

<400> SEQUENCE: 302

Ser Tyr Gly Leu Gly
1               5

<210> SEQ ID NO 303
<211> LENGTH: 5
<212> TYPE: PRT
<213> ORGANISM: Lama glama

<400> SEQUENCE: 303

Ser Tyr Ala Ile Gly
1               5

<210> SEQ ID NO 304
<211> LENGTH: 5
<212> TYPE: PRT
<213> ORGANISM: Lama glama

<400> SEQUENCE: 304

Ser Tyr Ala Met Gly
1               5

<210> SEQ ID NO 305
<211> LENGTH: 5
<212> TYPE: PRT
<213> ORGANISM: Lama glama

<400> SEQUENCE: 305

Phe Ser Ala Met Gly
1               5

<210> SEQ ID NO 306
<211> LENGTH: 5
<212> TYPE: PRT
<213> ORGANISM: Lama glama

<400> SEQUENCE: 306

Ser Leu Ala Met Gly
1               5

<210> SEQ ID NO 307
<211> LENGTH: 5
<212> TYPE: PRT
<213> ORGANISM: Lama glama

<400> SEQUENCE: 307

Lys Tyr Val Met Gly
1               5

<210> SEQ ID NO 308
<211> LENGTH: 5
<212> TYPE: PRT
<213> ORGANISM: Lama glama

<400> SEQUENCE: 308

Ser Ser Trp Met Tyr
1               5

<210> SEQ ID NO 309
<211> LENGTH: 5

<212> TYPE: PRT
<213> ORGANISM: Lama glama

<400> SEQUENCE: 309

Asn Tyr Val Met Gly
1 5

<210> SEQ ID NO 310
<211> LENGTH: 5
<212> TYPE: PRT
<213> ORGANISM: Lama glama

<400> SEQUENCE: 310

Gly Tyr Asp Met Gly
1 5

<210> SEQ ID NO 311
<211> LENGTH: 5
<212> TYPE: PRT
<213> ORGANISM: Lama glama

<400> SEQUENCE: 311

Ala Tyr Asp Met Gly
1 5

<210> SEQ ID NO 312
<211> LENGTH: 5
<212> TYPE: PRT
<213> ORGANISM: Lama glama

<400> SEQUENCE: 312

Val Tyr Thr Met Gly
1 5

<210> SEQ ID NO 313
<211> LENGTH: 5
<212> TYPE: PRT
<213> ORGANISM: Lama glama

<400> SEQUENCE: 313

Thr Trp Ala Met Ala
1 5

<210> SEQ ID NO 314
<211> LENGTH: 5
<212> TYPE: PRT
<213> ORGANISM: Lama glama

<400> SEQUENCE: 314

Ser Thr Asn Met Gly
1 5

<210> SEQ ID NO 315
<211> LENGTH: 5
<212> TYPE: PRT
<213> ORGANISM: Lama glama

<400> SEQUENCE: 315

Thr Tyr Thr Met Gly
1 5

<210> SEQ ID NO 316
<211> LENGTH: 5
<212> TYPE: PRT
<213> ORGANISM: Lama glama

<400> SEQUENCE: 316

Leu Tyr Thr Val Gly
1 5

<210> SEQ ID NO 317
<211> LENGTH: 5
<212> TYPE: PRT
<213> ORGANISM: Lama glama

<400> SEQUENCE: 317

Ser Tyr Arg Met Gly
1 5

<210> SEQ ID NO 318
<211> LENGTH: 5
<212> TYPE: PRT
<213> ORGANISM: Lama glama

<400> SEQUENCE: 318

Thr Ser Trp Met His
1 5

<210> SEQ ID NO 319
<211> LENGTH: 5
<212> TYPE: PRT
<213> ORGANISM: Lama glama

<400> SEQUENCE: 319

Asn Tyr Ala Met Asp
1 5

<210> SEQ ID NO 320
<211> LENGTH: 5
<212> TYPE: PRT
<213> ORGANISM: Lama glama

<400> SEQUENCE: 320

Asp Tyr Asp Ile Gly
1 5

<210> SEQ ID NO 321
<211> LENGTH: 5
<212> TYPE: PRT
<213> ORGANISM: Lama glama

<400> SEQUENCE: 321

Ser Leu Ala Val Gly
1 5

<210> SEQ ID NO 322
<211> LENGTH: 5
<212> TYPE: PRT
<213> ORGANISM: Lama glama

<400> SEQUENCE: 322

Leu Tyr Asn Met Gly
1 5

<210> SEQ ID NO 323
<211> LENGTH: 5
<212> TYPE: PRT
<213> ORGANISM: Lama glama

<400> SEQUENCE: 323

Gly Ser Asp Met Gly
1 5

<210> SEQ ID NO 324
<211> LENGTH: 5
<212> TYPE: PRT
<213> ORGANISM: Lama glama

<400> SEQUENCE: 324

Thr Tyr Ala Ile Gly
1 5

<210> SEQ ID NO 325
<211> LENGTH: 5
<212> TYPE: PRT
<213> ORGANISM: Lama glama

<400> SEQUENCE: 325

Thr Asn Phe Met Gly
1 5

<210> SEQ ID NO 326
<211> LENGTH: 5
<212> TYPE: PRT
<213> ORGANISM: Lama glama

<400> SEQUENCE: 326

Ile Phe Ala Met Arg
1 5

<210> SEQ ID NO 327
<211> LENGTH: 5
<212> TYPE: PRT
<213> ORGANISM: Lama glama

<400> SEQUENCE: 327

Asp Tyr Asn Leu Gly
1 5

<210> SEQ ID NO 328
<211> LENGTH: 5
<212> TYPE: PRT
<213> ORGANISM: Lama glama

<400> SEQUENCE: 328

Asn Ala Ile Met Gly
1 5

<210> SEQ ID NO 329
<211> LENGTH: 5
<212> TYPE: PRT
<213> ORGANISM: Lama glama

<400> SEQUENCE: 329

Ser Tyr Ala Pro Gly
1 5

<210> SEQ ID NO 330
<211> LENGTH: 16
<212> TYPE: PRT
<213> ORGANISM: Lama glama

<400> SEQUENCE: 330

Ala Ile Ser Glu Tyr Ser Asn Thr Tyr Cys Ser Asp Ser Val Arg Gly 1 5 10 15

<210> SEQ ID NO 331
<211> LENGTH: 17
<212> TYPE: PRT
<213> ORGANISM: Lama glama

<400> SEQUENCE: 331

Ala Ile Asn Trp Ser Gly Leu Ser Thr Phe Tyr Thr Asp Ser Val Lys
1 5 10 15

Gly

<210> SEQ ID NO 332
<211> LENGTH: 17
<212> TYPE: PRT
<213> ORGANISM: Lama glama

<400> SEQUENCE: 332

Ala Ile Thr Trp Ser Ala Pro Thr Thr Tyr Tyr Ala Asp Ser Val Lys
1 5 10 15

Gly

<210> SEQ ID NO 333
<211> LENGTH: 16
<212> TYPE: PRT
<213> ORGANISM: Lama glama

<400> SEQUENCE: 333

Thr Ile Thr Pro Ser Gly Tyr Thr Tyr Tyr Trp Asp Phe Val Lys Gly
1 5 10 15

<210> SEQ ID NO 334
<211> LENGTH: 17
<212> TYPE: PRT
<213> ORGANISM: Lama glama

<400> SEQUENCE: 334

Val Ile Arg Trp Ser Thr Gly Gly Thr Tyr Thr Ser Asp Ser Val Lys
1 5 10 15

Gly

<210> SEQ ID NO 335
<211> LENGTH: 17
<212> TYPE: PRT
<213> ORGANISM: Lama glama

<400> SEQUENCE: 335

Ser Ile Arg Gly Gly Gly Gly Ser Thr Thr Tyr Ala Asn Ser Val Lys
1 5 10 15

Asp

<210> SEQ ID NO 336
<211> LENGTH: 16
<212> TYPE: PRT
<213> ORGANISM: Lama glama

<400> SEQUENCE: 336

Arg Ile Ser Ser Gly Gly Thr Thr Ala Tyr Val Asp Ser Val Lys Gly
1 5 10 15

<210> SEQ ID NO 337
<211> LENGTH: 17

<212> TYPE: PRT
<213> ORGANISM: Lama glama

<400> SEQUENCE: 337

Arg Ile Ser Ser Gly Gly Gly Phe Thr Tyr Tyr Leu Asp Ser Val Lys
1               5                   10                  15

Gly

<210> SEQ ID NO 338
<211> LENGTH: 17
<212> TYPE: PRT
<213> ORGANISM: Lama glama

<400> SEQUENCE: 338

Ala Ile Thr Trp Ser Ala Pro Ser Ser Tyr Tyr Ala Asp Ser Val Lys
1               5                   10                  15

Gly

<210> SEQ ID NO 339
<211> LENGTH: 17
<212> TYPE: PRT
<213> ORGANISM: Lama glama

<400> SEQUENCE: 339

Ala Ile Asn Gln Arg Gly Ser Asn Thr Asn Tyr Ala Asp Ser Val Lys
1               5                   10                  15

Gly

<210> SEQ ID NO 340
<211> LENGTH: 17
<212> TYPE: PRT
<213> ORGANISM: Lama glama

<400> SEQUENCE: 340

His Ile Ser Arg Gly Gly Ser Arg Thr Glu Tyr Ala Glu Ser Val Lys
1               5                   10                  15

Gly

<210> SEQ ID NO 341
<211> LENGTH: 17
<212> TYPE: PRT
<213> ORGANISM: Lama glama

<400> SEQUENCE: 341

Thr Ile Ser Trp Asn Lys Ile Ser Thr Ile Tyr Thr Asp Ser Val Lys
1               5                   10                  15

Gly

<210> SEQ ID NO 342
<211> LENGTH: 16
<212> TYPE: PRT
<213> ORGANISM: Lama glama

<400> SEQUENCE: 342

Phe Ile Arg Ser Leu Gly Ser Thr Tyr Tyr Ala Gly Ser Val Lys Gly
1               5                   10                  15

<210> SEQ ID NO 343
<211> LENGTH: 17
<212> TYPE: PRT
<213> ORGANISM: Lama glama

<400> SEQUENCE: 343

Ala Ile Thr Trp Ser Ala Gly Asp Thr Gln Tyr Ala Asp Ser Val Lys
1 5 10 15

Gly

<210> SEQ ID NO 344
<211> LENGTH: 16
<212> TYPE: PRT
<213> ORGANISM: Lama glama

<400> SEQUENCE: 344

Arg Ile Ser Ser Glu Gly Thr Thr Ala Tyr Val Asp Ser Val Lys Gly
1 5 10 15

<210> SEQ ID NO 345
<211> LENGTH: 17
<212> TYPE: PRT
<213> ORGANISM: Lama glama

<400> SEQUENCE: 345

Val Ile Arg Trp Ser Thr Gly Gly Thr Tyr Thr Ser Asp Ser Val Ala
1 5 10 15

Gly

<210> SEQ ID NO 346
<211> LENGTH: 16
<212> TYPE: PRT
<213> ORGANISM: Lama glama

<400> SEQUENCE: 346

Ala Ile Ser Glu Tyr Asp Asn Val Tyr Thr Ala Asp Ser Val Arg Gly
1 5 10 15

<210> SEQ ID NO 347
<211> LENGTH: 17
<212> TYPE: PRT
<213> ORGANISM: Lama glama

<400> SEQUENCE: 347

Val Ile Thr Arg Ser Pro Ser Asn Thr Tyr Tyr Thr Asp Ser Val Lys
1 5 10 15

Gly

<210> SEQ ID NO 348
<211> LENGTH: 17
<212> TYPE: PRT
<213> ORGANISM: Lama glama

<400> SEQUENCE: 348

Asp Ile Ser Ser Ser Gly Ile Asn Thr Tyr Val Ala Asp Ala Val Lys
1 5 10 15

Gly

<210> SEQ ID NO 349
<211> LENGTH: 17
<212> TYPE: PRT
<213> ORGANISM: Lama glama

<400> SEQUENCE: 349

Ser Ile Asn Thr Ser Gly Lys Arg Thr Ser Tyr Ala Asp Ser Met Lys
1 5 10 15

Gly

<210> SEQ ID NO 350
<211> LENGTH: 17
<212> TYPE: PRT
<213> ORGANISM: Lama glama

<400> SEQUENCE: 350

Thr Ile Arg His His Gly Tyr Asp Thr Tyr Tyr Ala Glu Ser Val Lys
1 5 10 15

Gly

<210> SEQ ID NO 351
<211> LENGTH: 17
<212> TYPE: PRT
<213> ORGANISM: Lama glama

<400> SEQUENCE: 351

Ala Ile Gly Trp Ser Gly Ser Ser Thr Tyr Tyr Ala Asp Ser Val Lys
1 5 10 15

Gly

<210> SEQ ID NO 352
<211> LENGTH: 17
<212> TYPE: PRT
<213> ORGANISM: Lama glama

<400> SEQUENCE: 352

Arg Ile Ser Trp Ser Gly Ala Asn Thr Tyr Tyr Ala Asp Ser Val Lys
1 5 10 15

Gly

<210> SEQ ID NO 353
<211> LENGTH: 17
<212> TYPE: PRT
<213> ORGANISM: Lama glama

<400> SEQUENCE: 353

Thr Ile Ser Gln Ser Gly Tyr Ser Thr Tyr Tyr Ala Asp Ser Val Lys
1 5 10 15

Gly

<210> SEQ ID NO 354
<211> LENGTH: 17
<212> TYPE: PRT
<213> ORGANISM: Lama glama

<400> SEQUENCE: 354

Ala Phe Lys Trp Ser Gly Ser Thr Thr Tyr Tyr Ala Asp Tyr Val Lys
1 5 10 15

Gly

<210> SEQ ID NO 355
<211> LENGTH: 17
<212> TYPE: PRT
<213> ORGANISM: Lama glama

<400> SEQUENCE: 355

Ala Ile Thr Trp Ser Ala Pro Ser Ser Tyr Tyr Ala Asp Ser Val Lys
1 5 10 15

Gly

<210> SEQ ID NO 356
<211> LENGTH: 17
<212> TYPE: PRT
<213> ORGANISM: Lama glama

<400> SEQUENCE: 356

Ser Ile Ser Gln Ser Gly Ile Thr Thr Ser Tyr Ala Asp Ser Val Lys
1 5 10 15

Ser

<210> SEQ ID NO 357
<211> LENGTH: 17
<212> TYPE: PRT
<213> ORGANISM: Lama glama

<400> SEQUENCE: 357

Ala Ile Thr Trp Ser Ala Pro Thr Thr Tyr Ser Ala Asp Ser Val Lys
1 5 10 15

Gly

<210> SEQ ID NO 358
<211> LENGTH: 17
<212> TYPE: PRT
<213> ORGANISM: Lama glama

<400> SEQUENCE: 358

Ala Ile Thr Ser Arg Asp Gly Pro Thr Tyr Tyr Ala Asp Ser Val Lys
1 5 10 15

Gly

<210> SEQ ID NO 359
<211> LENGTH: 17
<212> TYPE: PRT
<213> ORGANISM: Lama glama

<400> SEQUENCE: 359

Arg Ile Ser Pro Gly Gly Leu Phe Thr Tyr Tyr Val Asp Ser Val Lys
1 5 10 15

Gly

<210> SEQ ID NO 360
<211> LENGTH: 17
<212> TYPE: PRT
<213> ORGANISM: Lama glama

<400> SEQUENCE: 360

Ala Ile Thr Ser Thr Asn Gly Pro Thr Tyr Tyr Ala Asp Ser Val Lys
1 5 10 15

Gly

<210> SEQ ID NO 361
<211> LENGTH: 17
<212> TYPE: PRT
<213> ORGANISM: Lama glama

<400> SEQUENCE: 361

Ala Ile Thr Trp Ser Gly Gly Ser Thr Tyr Ser Pro Asp Ser Val Lys
1 5 10 15

Gly

<210> SEQ ID NO 362
<211> LENGTH: 17
<212> TYPE: PRT
<213> ORGANISM: Lama glama

<400> SEQUENCE: 362

Val Ile Ser Trp Thr Asn Ser Met Thr Tyr Tyr Ala Asp Ser Val Lys
1 5 10 15

Gly

<210> SEQ ID NO 363
<211> LENGTH: 17
<212> TYPE: PRT
<213> ORGANISM: Lama glama

<400> SEQUENCE: 363

Val Ile Ser Trp Ser Gly Gly Met Thr Tyr Tyr Ala Asp Ser Val Gln
1 5 10 15

Gly

<210> SEQ ID NO 364
<211> LENGTH: 17
<212> TYPE: PRT
<213> ORGANISM: Lama glama

<400> SEQUENCE: 364

Val Ile Ser Trp Ser Gly Gly Met Thr Tyr Tyr Ala Asp Ser Val Lys
1 5 10 15

Gly

<210> SEQ ID NO 365
<211> LENGTH: 17
<212> TYPE: PRT
<213> ORGANISM: Lama glama

<400> SEQUENCE: 365

Val Ile Ser Trp Thr Gly Gly Met Thr Tyr Tyr Ala Asp Ser Val Lys
1 5 10 15

Gly

<210> SEQ ID NO 366
<211> LENGTH: 17
<212> TYPE: PRT
<213> ORGANISM: Lama glama

<400> SEQUENCE: 366

Val Ile Ser Trp Thr Gly Asp Met Thr Tyr Tyr Ala Asp Ser Val Lys
1 5 10 15

Gly

<210> SEQ ID NO 367
<211> LENGTH: 17
<212> TYPE: PRT
<213> ORGANISM: Lama glama

<400> SEQUENCE: 367

Thr Ile Ser Arg Thr Gly Asp Arg Thr Ser Tyr Ala Asn Ser Val Lys
1 5 10 15

Gly

<210> SEQ ID NO 368
<211> LENGTH: 17
<212> TYPE: PRT
<213> ORGANISM: Lama glama

<400> SEQUENCE: 368

Val Ile Ser Trp Ser Gly Gly Met Thr Asp Tyr Ala Asp Ser Val Lys
1 5 10 15

Gly

<210> SEQ ID NO 369
<211> LENGTH: 17
<212> TYPE: PRT
<213> ORGANISM: Lama glama

<400> SEQUENCE: 369

His Ile Asn Arg Ser Gly Ser Ser Thr Tyr Tyr Ala Asp Ser Val Lys
1 5 10 15

Gly

<210> SEQ ID NO 370
<211> LENGTH: 17
<212> TYPE: PRT
<213> ORGANISM: Lama glama

<400> SEQUENCE: 370

Ala Ile Ser Trp Ser Gly Ser Met Thr Tyr Tyr Thr Asp Ser Val Lys
1 5 10 15

Gly

<210> SEQ ID NO 371
<211> LENGTH: 16
<212> TYPE: PRT
<213> ORGANISM: Lama glama

<400> SEQUENCE: 371

Ala Ile Thr Leu Ser Gly Thr Thr Tyr Tyr Ala Glu Ala Val Lys Gly
1 5 10 15

<210> SEQ ID NO 372
<211> LENGTH: 17
<212> TYPE: PRT
<213> ORGANISM: Lama glama

<400> SEQUENCE: 372

Ala Ile Arg Trp Thr Val Asn Ile Thr Tyr Tyr Ala Asp Ser Val Lys
1 5 10 15

Gly

<210> SEQ ID NO 373
<211> LENGTH: 17
<212> TYPE: PRT
<213> ORGANISM: Lama glama

<400> SEQUENCE: 373

Tyr Ile Ser Arg Ser Gly Ser Asn Arg Tyr Tyr Val Asp Ser Val Lys
1 5 10 15

Gly

<210> SEQ ID NO 374
<211> LENGTH: 17
<212> TYPE: PRT

<213> ORGANISM: Lama glama

<400> SEQUENCE: 374

Ser Ile Ser Trp Thr Tyr Gly Ser Thr Phe Tyr Ala Asp Ser Val Lys
1 5 10 15

Gly

<210> SEQ ID NO 375
<211> LENGTH: 17
<212> TYPE: PRT
<213> ORGANISM: Lama glama

<400> SEQUENCE: 375

Ser Ile Pro Pro Val Gly His Phe Ala Asn Tyr Ala Pro Ser Val Lys
1 5 10 15

Gly

<210> SEQ ID NO 376
<211> LENGTH: 17
<212> TYPE: PRT
<213> ORGANISM: Lama glama

<400> SEQUENCE: 376

Ala Ile Thr Arg Ser Gly Gly Gly Thr Tyr Tyr Ala Asp Ser Val Lys
1 5 10 15

Gly

<210> SEQ ID NO 377
<211> LENGTH: 17
<212> TYPE: PRT
<213> ORGANISM: Lama glama

<400> SEQUENCE: 377

Cys Ile Thr Thr Asp Val Gly Thr Thr Tyr Tyr Ala Asp Ser Val Lys
1 5 10 15

Gly

<210> SEQ ID NO 378
<211> LENGTH: 17
<212> TYPE: PRT
<213> ORGANISM: Lama glama

<400> SEQUENCE: 378

Cys Ile Ser Ser Tyr Asp Ser Val Thr Tyr Tyr Ala Asp His Val Lys
1 5 10 15

Gly

<210> SEQ ID NO 379
<211> LENGTH: 17
<212> TYPE: PRT
<213> ORGANISM: Lama glama

<400> SEQUENCE: 379

Cys Ile Ser Ser Ser Asp Thr Ser Ile Asp Tyr Thr Asn Ser Val Lys
1 5 10 15

Gly

<210> SEQ ID NO 380
<211> LENGTH: 17
<212> TYPE: PRT
<213> ORGANISM: Lama glama

<400> SEQUENCE: 380

Arg Ile Thr Trp Ser Gly Ala Thr Thr Tyr Tyr Ala Asp Ala Val Lys
1 5 10 15

Asp

<210> SEQ ID NO 381
<211> LENGTH: 17
<212> TYPE: PRT
<213> ORGANISM: Lama glama

<400> SEQUENCE: 381

Ala Ile Thr Ser Ser Pro Met Ser Thr Tyr Tyr Ala Asp Ser Val Lys
1 5 10 15

Gly

<210> SEQ ID NO 382
<211> LENGTH: 17
<212> TYPE: PRT
<213> ORGANISM: Lama glama

<400> SEQUENCE: 382

Ala Ile Arg Leu Ser Gly Ser Ile Thr Tyr Tyr Pro Asp Ser Val Lys
1 5 10 15

Gly

<210> SEQ ID NO 383
<211> LENGTH: 17
<212> TYPE: PRT
<213> ORGANISM: Lama glama

<400> SEQUENCE: 383

Cys Met Ser Ala Gly Asp Ser Ile Pro Trp Tyr Thr Ala Ser Val Lys
1 5 10 15

Gly

<210> SEQ ID NO 384
<211> LENGTH: 16
<212> TYPE: PRT
<213> ORGANISM: Lama glama

<400> SEQUENCE: 384

Thr Ile Thr Ser Ser Ser Ile Thr Asn Tyr Val Asp Ser Val Lys Gly
1 5 10 15

<210> SEQ ID NO 385
<211> LENGTH: 16
<212> TYPE: PRT
<213> ORGANISM: Lama glama

<400> SEQUENCE: 385

Ser Ile Thr Arg Ser Ser Ile Thr Thr Tyr Ala Asp Ser Val Lys Gly
1 5 10 15

<210> SEQ ID NO 386
<211> LENGTH: 17
<212> TYPE: PRT
<213> ORGANISM: Lama glama

<400> SEQUENCE: 386

Val Ile Ser Trp Arg Asp Ser Phe Ala Tyr Tyr Ala Glu Pro Val Lys
1 5 10 15

Gly

<210> SEQ ID NO 387
<211> LENGTH: 17
<212> TYPE: PRT
<213> ORGANISM: Lama glama

<400> SEQUENCE: 387

Ala Met Asn Trp Arg Gly Gly Pro Thr Tyr Tyr Ala Asp Ser Val Lys
1 5 10 15

Gly

<210> SEQ ID NO 388
<211> LENGTH: 17
<212> TYPE: PRT
<213> ORGANISM: Lama glama

<400> SEQUENCE: 388

Ala Phe Thr Arg Ser Ser Asn Ile Pro Tyr Tyr Lys Asp Ser Val Lys
1 5 10 15

Gly

<210> SEQ ID NO 389
<211> LENGTH: 14
<212> TYPE: PRT
<213> ORGANISM: Lama glama

<400> SEQUENCE: 389

Ser Pro Thr Ile Leu Leu Thr Thr Glu Gln Trp Tyr Lys Tyr
1 5 10

<210> SEQ ID NO 390
<211> LENGTH: 17
<212> TYPE: PRT
<213> ORGANISM: Lama glama

<400> SEQUENCE: 390

Gly Arg Ile Pro Ser Ser Ser Arg Phe Ser Ser Pro Ala Ala Tyr Ala
1 5 10 15

Ser

<210> SEQ ID NO 391
<211> LENGTH: 16
<212> TYPE: PRT
<213> ORGANISM: Lama glama

<400> SEQUENCE: 391

Asp Arg Phe Lys Gly Arg Ser Ile Val Thr Pro Ser Asp Tyr Arg Tyr
1 5 10 15

<210> SEQ ID NO 392
<211> LENGTH: 3
<212> TYPE: PRT
<213> ORGANISM: Lama glama

<400> SEQUENCE: 392

Gln Phe Tyr
1

<210> SEQ ID NO 393
<211> LENGTH: 19
<212> TYPE: PRT

<213> ORGANISM: Lama glama

<400> SEQUENCE: 393

Arg Ser Arg Pro Leu Gly Ala Gly Ala Trp Tyr Ser Gly Glu Lys His
1 5 10 15

Tyr Asn Tyr

<210> SEQ ID NO 394
<211> LENGTH: 12
<212> TYPE: PRT
<213> ORGANISM: Lama glama

<400> SEQUENCE: 394

Thr Ala Phe Tyr Arg Gly Pro Tyr Asp Tyr Asp Tyr
1 5 10

<210> SEQ ID NO 395
<211> LENGTH: 7
<212> TYPE: PRT
<213> ORGANISM: Lama glama

<400> SEQUENCE: 395

Phe Ser Ser Arg Pro Asn Pro
1 5

<210> SEQ ID NO 396
<211> LENGTH: 7
<212> TYPE: PRT
<213> ORGANISM: Lama glama

<400> SEQUENCE: 396

Ala Tyr Arg Thr Tyr Asn Tyr
1 5

<210> SEQ ID NO 397
<211> LENGTH: 16
<212> TYPE: PRT
<213> ORGANISM: Lama glama

<400> SEQUENCE: 397

Asp Arg Phe Lys Gly Arg Ser Ile Val Thr Arg Ser Asp Tyr Lys Tyr
1 5 10 15

<210> SEQ ID NO 398
<211> LENGTH: 16
<212> TYPE: PRT
<213> ORGANISM: Lama glama

<400> SEQUENCE: 398

Asp Arg Phe Lys Gly Arg Ser Ile Val Thr Arg Ser Asp Tyr Arg Tyr
1 5 10 15

<210> SEQ ID NO 399
<211> LENGTH: 17
<212> TYPE: PRT
<213> ORGANISM: Lama glama

<400> SEQUENCE: 399

Ser Thr Trp Tyr Gly Tyr Ser Thr Tyr Ala Arg Arg Glu Glu Tyr Arg
1 5 10 15

Tyr

<210> SEQ ID NO 400

<211> LENGTH: 14
<212> TYPE: PRT
<213> ORGANISM: Lama glama

<400> SEQUENCE: 400

Ser Arg Ser Val Ala Leu Ala Thr Ala Arg Pro Tyr Asp Tyr
1 5 10

<210> SEQ ID NO 401
<211> LENGTH: 12
<212> TYPE: PRT
<213> ORGANISM: Lama glama

<400> SEQUENCE: 401

Asp Ala Ser Arg Pro Thr Leu Arg Ile Pro Gln Tyr
1 5 10

<210> SEQ ID NO 402
<211> LENGTH: 7
<212> TYPE: PRT
<213> ORGANISM: Lama glama

<400> SEQUENCE: 402

Arg Phe Ser Gly Glu Ser Tyr
1 5

<210> SEQ ID NO 403
<211> LENGTH: 15
<212> TYPE: PRT
<213> ORGANISM: Lama glama

<400> SEQUENCE: 403

Arg Gln Trp Gly Gly Thr Tyr Tyr Tyr His Gly Ser Tyr Ala Tyr
1 5 10 15

<210> SEQ ID NO 404
<211> LENGTH: 16
<212> TYPE: PRT
<213> ORGANISM: Lama glama

<400> SEQUENCE: 404

Arg Ile Ser Ser Gly Gly Thr Thr Ala Tyr Ala Asp Ser Val Lys Gly
1 5 10 15

<210> SEQ ID NO 405
<211> LENGTH: 19
<212> TYPE: PRT
<213> ORGANISM: Lama glama

<400> SEQUENCE: 405

Arg Ser Arg Pro Leu Gly Ala Gly Ala Trp Tyr Thr Gly Glu Thr Arg
1 5 10 15

Tyr Asp Ser

<210> SEQ ID NO 406
<211> LENGTH: 14
<212> TYPE: PRT
<213> ORGANISM: Lama glama

<400> SEQUENCE: 406

Ser Pro Thr Ile Leu Leu Ser Thr Asp Glu Trp Tyr Lys Tyr
1 5 10

<210> SEQ ID NO 407

<211> LENGTH: 19
<212> TYPE: PRT
<213> ORGANISM: Lama glama

<400> SEQUENCE: 407

Arg Ser Arg Pro Leu Gly Ala Gly Ala Trp Tyr Thr Gly Glu Thr Arg
1 5 10 15

Tyr Asn Tyr

<210> SEQ ID NO 408
<211> LENGTH: 18
<212> TYPE: PRT
<213> ORGANISM: Lama glama

<400> SEQUENCE: 408

His Tyr Trp Asn Ser Asp Ser Tyr Thr Tyr Thr Asp Ser Arg Trp Tyr
1 5 10 15

Asn Tyr

<210> SEQ ID NO 409
<211> LENGTH: 15
<212> TYPE: PRT
<213> ORGANISM: Lama glama

<400> SEQUENCE: 409

Ser Ala Trp Trp Tyr Ser Gln Met Ala Arg Asp Asn Tyr Arg Tyr
1 5 10 15

<210> SEQ ID NO 410
<211> LENGTH: 16
<212> TYPE: PRT
<213> ORGANISM: Lama glama

<400> SEQUENCE: 410

Asp Arg Phe Phe Gly Ser Asp Ser Asn Glu Pro Arg Ala Tyr Arg Tyr
1 5 10 15

<210> SEQ ID NO 411
<211> LENGTH: 14
<212> TYPE: PRT
<213> ORGANISM: Lama glama

<400> SEQUENCE: 411

Lys Leu Phe Trp Asp Met Asp Pro Lys Thr Gly Phe Ser Ser
1 5 10

<210> SEQ ID NO 412
<211> LENGTH: 17
<212> TYPE: PRT
<213> ORGANISM: Lama glama

<400> SEQUENCE: 412

Lys Val Arg Asn Phe Asn Ser Asp Trp Asp Leu Leu Thr Ser Tyr Asn
1 5 10 15

Tyr

<210> SEQ ID NO 413
<211> LENGTH: 16
<212> TYPE: PRT
<213> ORGANISM: Lama glama

<400> SEQUENCE: 413

Gln Thr Thr Ser Lys Tyr Asp Asn Tyr Asp Ala Arg Ala Tyr Gly Tyr 1 5 10 15

<210> SEQ ID NO 414
<211> LENGTH: 14
<212> TYPE: PRT
<213> ORGANISM: Lama glama

<400> SEQUENCE: 414

Asp Pro Phe Tyr Ser Tyr Gly Ser Pro Ser Pro Tyr Arg Tyr
1 5 10

<210> SEQ ID NO 415
<211> LENGTH: 16
<212> TYPE: PRT
<213> ORGANISM: Lama glama

<400> SEQUENCE: 415

Asp Arg Phe Tyr Thr Gly Arg Tyr Tyr Ser Ser Asp Glu Tyr Asp Tyr
1 5 10 15

<210> SEQ ID NO 416
<211> LENGTH: 16
<212> TYPE: PRT
<213> ORGANISM: Lama glama

<400> SEQUENCE: 416

Asp Arg Phe Lys Gly Arg Ser Ile Val Thr Arg Ser Asp Tyr Arg Tyr
1 5 10 15

<210> SEQ ID NO 417
<211> LENGTH: 16
<212> TYPE: PRT
<213> ORGANISM: Lama glama

<400> SEQUENCE: 417

Ser Val Phe Tyr Ser Thr Ala Leu Thr Arg Pro Val Asp Tyr Arg Tyr
1 5 10 15

<210> SEQ ID NO 418
<211> LENGTH: 20
<212> TYPE: PRT
<213> ORGANISM: Lama glama

<400> SEQUENCE: 418

Asp Glu Asp Leu Tyr His Tyr Ser Ser Tyr His Phe Thr Arg Val Asp
1 5 10 15

Leu Tyr His Tyr
20

<210> SEQ ID NO 419
<211> LENGTH: 8
<212> TYPE: PRT
<213> ORGANISM: Lama glama

<400> SEQUENCE: 419

Gly Gly Ala Pro Asn Tyr Thr Pro
1 5

<210> SEQ ID NO 420
<211> LENGTH: 20
<212> TYPE: PRT
<213> ORGANISM: Lama glama

<400> SEQUENCE: 420

```
Asp Glu Asp Leu Tyr His Tyr Ser Ser Tyr His Tyr Thr Arg Val Ala
1               5                   10                  15

Leu Tyr His Tyr
            20


<210> SEQ ID NO 421
<211> LENGTH: 15
<212> TYPE: PRT
<213> ORGANISM: Lama glama

<400> SEQUENCE: 421

Arg Gln Trp Gly Gly Thr Tyr Tyr Tyr His Gly Ser Tyr Ala Trp
1               5                   10                  15


<210> SEQ ID NO 422
<211> LENGTH: 19
<212> TYPE: PRT
<213> ORGANISM: Lama glama

<400> SEQUENCE: 422

Arg Ser Arg Pro Leu Gly Ala Gly Ala Trp Tyr Thr Gly Glu Asn Tyr
1               5                   10                  15

Tyr Asn Tyr


<210> SEQ ID NO 423
<211> LENGTH: 17
<212> TYPE: PRT
<213> ORGANISM: Lama glama

<400> SEQUENCE: 423

Gly Arg Ile Trp Arg Ser Arg Asp Tyr Asp Ser Glu Lys Tyr Tyr Asp
1               5                   10                  15

Ile


<210> SEQ ID NO 424
<211> LENGTH: 20
<212> TYPE: PRT
<213> ORGANISM: Lama glama

<400> SEQUENCE: 424

Asp Arg Arg Arg Thr Tyr Ser Arg Trp Arg Phe Tyr Thr Gly Val Asn
1               5                   10                  15

Asp Tyr Asp Tyr
            20


<210> SEQ ID NO 425
<211> LENGTH: 20
<212> TYPE: PRT
<213> ORGANISM: Lama glama

<400> SEQUENCE: 425

Asp Arg Arg Arg Ala Tyr Ser Arg Trp Arg Tyr Tyr Thr Gly Val Asn
1               5                   10                  15

Asp Tyr Glu Phe
            20


<210> SEQ ID NO 426
<211> LENGTH: 20
<212> TYPE: PRT
<213> ORGANISM: Lama glama

<400> SEQUENCE: 426
```

```
Asp Arg Arg Arg Leu Tyr Ser Arg Trp Arg Tyr Tyr Thr Gly Val Asn
1               5                   10                  15

Asp Tyr Asp Tyr
            20


<210> SEQ ID NO 427
<211> LENGTH: 20
<212> TYPE: PRT
<213> ORGANISM: Lama glama

<400> SEQUENCE: 427

Asp Arg Arg Arg Thr Tyr Ser Arg Trp Arg Tyr Tyr Thr Gly Val Asn
1               5                   10                  15

Glu Tyr Glu Tyr
            20


<210> SEQ ID NO 428
<211> LENGTH: 14
<212> TYPE: PRT
<213> ORGANISM: Lama glama

<400> SEQUENCE: 428

Gly Pro Ile Ala Pro Ser Pro Arg Pro Arg Glu Tyr Tyr Tyr
1               5                   10


<210> SEQ ID NO 429
<211> LENGTH: 20
<212> TYPE: PRT
<213> ORGANISM: Lama glama

<400> SEQUENCE: 429

Gly Arg Arg Arg Ala Tyr Ser Arg Trp Arg Tyr Tyr Thr Gly Val Asn
1               5                   10                  15

Glu Tyr Asp Tyr
            20


<210> SEQ ID NO 430
<211> LENGTH: 16
<212> TYPE: PRT
<213> ORGANISM: Lama glama

<400> SEQUENCE: 430

Gly Arg Tyr Tyr Ser Ser Asp Gly Val Pro Ser Ala Ser Phe Asn Tyr
1               5                   10                  15


<210> SEQ ID NO 431
<211> LENGTH: 19
<212> TYPE: PRT
<213> ORGANISM: Lama glama

<400> SEQUENCE: 431

Lys Thr Val Asp Tyr Cys Ser Ala Tyr Glu Cys Tyr Ala Arg Leu Glu
1               5                   10                  15

Tyr Asp Tyr


<210> SEQ ID NO 432
<211> LENGTH: 18
<212> TYPE: PRT
<213> ORGANISM: Lama glama

<400> SEQUENCE: 432

Asp Pro Ser Tyr Tyr Ser Thr Ser Arg Tyr Thr Lys Ala Thr Glu Tyr
1               5                   10                  15
```

Asp Tyr

<210> SEQ ID NO 433
<211> LENGTH: 17
<212> TYPE: PRT
<213> ORGANISM: Lama glama

<400> SEQUENCE: 433

Gln Thr Ser Ala Pro Arg Ser Leu Ile Arg Met Ser Asn Glu Tyr Pro
1 5 10 15

Tyr

<210> SEQ ID NO 434
<211> LENGTH: 14
<212> TYPE: PRT
<213> ORGANISM: Lama glama

<400> SEQUENCE: 434

Thr Ser Arg Gly Leu Ser Ser Leu Ala Gly Glu Tyr Asn Tyr
1 5 10

<210> SEQ ID NO 435
<211> LENGTH: 14
<212> TYPE: PRT
<213> ORGANISM: Lama glama

<400> SEQUENCE: 435

Gly Ala Gln Ser Asp Arg Tyr Asn Ile Arg Ser Tyr Asp Tyr
1 5 10

<210> SEQ ID NO 436
<211> LENGTH: 6
<212> TYPE: PRT
<213> ORGANISM: Lama glama

<400> SEQUENCE: 436

Asp Ser Ala Gly Arg Thr
1 5

<210> SEQ ID NO 437
<211> LENGTH: 15
<212> TYPE: PRT
<213> ORGANISM: Lama glama

<400> SEQUENCE: 437

Thr Arg Ser Ser Thr Ile Val Val Gly Val Gly Gly Met Glu Tyr
1 5 10 15

<210> SEQ ID NO 438
<211> LENGTH: 19
<212> TYPE: PRT
<213> ORGANISM: Lama glama

<400> SEQUENCE: 438

Asp Thr Gln Asp Leu Gly Leu Asp Ile Phe Cys Arg Gly Asn Gly Pro
1 5 10 15

Phe Asp Gly

<210> SEQ ID NO 439
<211> LENGTH: 25
<212> TYPE: PRT
<213> ORGANISM: Lama glama

<400> SEQUENCE: 439

Glu Arg Glu Gln Leu Arg Arg Arg Glu Ser Pro His Asp Glu Leu Leu
1 5 10 15

Arg Leu Cys Phe Tyr Gly Met Arg Tyr
20 25

<210> SEQ ID NO 440
<211> LENGTH: 14
<212> TYPE: PRT
<213> ORGANISM: Lama glama

<400> SEQUENCE: 440

Ala Phe Arg Cys Ser Gly Tyr Glu Leu Arg Gly Phe Pro Thr
1 5 10

<210> SEQ ID NO 441
<211> LENGTH: 17
<212> TYPE: PRT
<213> ORGANISM: Lama glama

<400> SEQUENCE: 441

Asp Arg Ser Pro Asn Ile Ile Asn Val Val Thr Ala Tyr Glu Tyr Asp
1 5 10 15

Tyr

<210> SEQ ID NO 442
<211> LENGTH: 17
<212> TYPE: PRT
<213> ORGANISM: Lama glama

<400> SEQUENCE: 442

Pro Glu Gly Ser Phe Arg Arg Gln Tyr Ala Asp Arg Ala Met Tyr Asp
1 5 10 15

Tyr

<210> SEQ ID NO 443
<211> LENGTH: 18
<212> TYPE: PRT
<213> ORGANISM: Lama glama

<400> SEQUENCE: 443

Arg Ser Thr Tyr Ser Tyr Tyr Leu Ala Leu Ala Asp Arg Gly Gly Tyr
1 5 10 15

Asp Tyr

<210> SEQ ID NO 444
<211> LENGTH: 16
<212> TYPE: PRT
<213> ORGANISM: Lama glama

<400> SEQUENCE: 444

Ala Arg Tyr His Gly Asp Tyr Cys Tyr Tyr Glu Gly Tyr Tyr Pro Phe
1 5 10 15

<210> SEQ ID NO 445
<211> LENGTH: 9
<212> TYPE: PRT
<213> ORGANISM: Lama glama

<400> SEQUENCE: 445

Arg Trp Arg Trp Ser Asp Val Glu Tyr
1 5

<210> SEQ ID NO 446
<211> LENGTH: 13
<212> TYPE: PRT
<213> ORGANISM: Lama glama

<400> SEQUENCE: 446

Ala Ile Arg Pro Glu Leu Tyr Ser Val Val Asn Asp Tyr
1 5 10

<210> SEQ ID NO 447
<211> LENGTH: 18
<212> TYPE: PRT
<213> ORGANISM: Lama glama

<400> SEQUENCE: 447

Asp Arg Val Ser Ser Arg Leu Val Leu Pro Asn Thr Ser Pro Asp Phe
1 5 10 15

Gly Ser

<210> SEQ ID NO 448
<211> LENGTH: 20
<212> TYPE: PRT
<213> ORGANISM: Lama glama

<400> SEQUENCE: 448

Asp Glu Asp Leu Tyr His Tyr Ser Ser Tyr His Tyr Ser Arg Val Asp
1 5 10 15

Leu Tyr His Tyr
20

<210> SEQ ID NO 449
<211> LENGTH: 15
<212> TYPE: PRT
<213> ORGANISM: Lama glama

<400> SEQUENCE: 449

Asn Leu Gly Ser Thr Trp Ser Arg Asp Gln Arg Thr Tyr Asp Tyr
1 5 10 15

<210> SEQ ID NO 450
<211> LENGTH: 5
<212> TYPE: PRT
<213> ORGANISM: Lama glama

<400> SEQUENCE: 450

Ser Tyr Ser Met Gly
1 5

<210> SEQ ID NO 451
<211> LENGTH: 5
<212> TYPE: PRT
<213> ORGANISM: Lama glama

<400> SEQUENCE: 451

Ser Tyr Ser Met Ala
1 5

<210> SEQ ID NO 452
<211> LENGTH: 5
<212> TYPE: PRT
<213> ORGANISM: Lama glama

<400> SEQUENCE: 452

Ser Tyr Ser Val Gly
1               5

<210> SEQ ID NO 453
<211> LENGTH: 17
<212> TYPE: PRT
<213> ORGANISM: Lama glama

<400> SEQUENCE: 453

Ala Ile Ser Ser Ser Gly Gly Tyr Ile Tyr Asp Ser Val Ser Leu Glu
1               5                   10                  15

Gly

<210> SEQ ID NO 454
<211> LENGTH: 16
<212> TYPE: PRT
<213> ORGANISM: Lama glama

<400> SEQUENCE: 454

Ala Ile Ser Ser Gly Gly Phe Ile Tyr Asp Ala Val Ser Leu Glu Gly
1               5                   10                  15

<210> SEQ ID NO 455
<211> LENGTH: 17
<212> TYPE: PRT
<213> ORGANISM: Lama glama

<400> SEQUENCE: 455

Ala Ile Ser Ser Ser Gly Asn Tyr Lys Tyr Asp Ser Val Ser Leu Glu
1               5                   10                  15

Gly

<210> SEQ ID NO 456
<211> LENGTH: 16
<212> TYPE: PRT
<213> ORGANISM: Lama glama

<400> SEQUENCE: 456

Ala Ile Ser Ser Gly Gly Ser Ile Tyr Asp Ser Val Ser Leu Gln Gly
1               5                   10                  15

<210> SEQ ID NO 457
<211> LENGTH: 16
<212> TYPE: PRT
<213> ORGANISM: Lama glama

<400> SEQUENCE: 457

Ala Ile Ser Ser Gly Gly Tyr Ile Tyr Asp Ser Val Ser Leu Gln Gly
1               5                   10                  15

<210> SEQ ID NO 458
<211> LENGTH: 16
<212> TYPE: PRT
<213> ORGANISM: Lama glama

<400> SEQUENCE: 458

Ala Ile Ser Asn Gly Gly Tyr Lys Tyr Asp Ser Val Ser Leu Glu Gly
1               5                   10                  15

<210> SEQ ID NO 459
<211> LENGTH: 16
<212> TYPE: PRT
<213> ORGANISM: Lama glama

<400> SEQUENCE: 459

Ala Ile Ser Lys Gly Gly Tyr Lys Tyr Asp Ser Val Ser Leu Glu Gly
1 5 10 15

<210> SEQ ID NO 460
<211> LENGTH: 17
<212> TYPE: PRT
<213> ORGANISM: Lama glama

<400> SEQUENCE: 460

Ala Ile Ser Ser Gly Gly Gly Tyr Ile Tyr Asp Ser Val Ser Leu Glu
1 5 10 15

Gly

<210> SEQ ID NO 461
<211> LENGTH: 16
<212> TYPE: PRT
<213> ORGANISM: Lama glama

<400> SEQUENCE: 461

Ala Ile Ser Ser Gly Gly Tyr Lys Tyr Asp Ser Val Ser Leu Glu Gly
1 5 10 15

<210> SEQ ID NO 462
<211> LENGTH: 17
<212> TYPE: PRT
<213> ORGANISM: Lama glama

<400> SEQUENCE: 462

Ala Ile Ser Ser Ser Gly Asn Tyr Lys Tyr Asp Ser Ala Ser Leu Glu
1 5 10 15

Gly

<210> SEQ ID NO 463
<211> LENGTH: 16
<212> TYPE: PRT
<213> ORGANISM: Lama glama

<400> SEQUENCE: 463

Ala Ile Ser Ser Gly Gly Tyr Lys Tyr Asp Ala Val Ser Leu Glu Gly
1 5 10 15

<210> SEQ ID NO 464
<211> LENGTH: 16
<212> TYPE: PRT
<213> ORGANISM: Lama glama

<400> SEQUENCE: 464

Ala Ile Ala Ser Gly Gly Tyr Ile Tyr Asp Ala Val Ser Leu Glu Gly
1 5 10 15

<210> SEQ ID NO 465
<211> LENGTH: 16
<212> TYPE: PRT
<213> ORGANISM: Lama glama

<400> SEQUENCE: 465

Ala Ile Ser Lys Gly Gly Tyr Lys Tyr Asp Ala Val Ser Leu Glu Gly
1 5 10 15

<210> SEQ ID NO 466
<211> LENGTH: 30

<212> TYPE: PRT
<213> ORGANISM: Lama glama

<400> SEQUENCE: 466

Glu Val Gln Leu Val Glu Ser Gly Gly Gly Leu Val Gln Ala Gly Gly
1               5                   10                  15

Ser Leu Arg Leu Ser Cys Thr Ala Ser Gly Gly Ser Phe Ser
            20                  25                  30

<210> SEQ ID NO 467
<211> LENGTH: 30
<212> TYPE: PRT
<213> ORGANISM: Lama glama

<400> SEQUENCE: 467

Glu Val Gln Leu Val Glu Ser Gly Gly Gly Leu Val Gln Ala Gly Asp
1               5                   10                  15

Ser Leu Arg Leu Ser Cys Val Ala Thr Gly Arg Thr Phe Arg
            20                  25                  30

<210> SEQ ID NO 468
<211> LENGTH: 30
<212> TYPE: PRT
<213> ORGANISM: Lama glama

<400> SEQUENCE: 468

Glu Val Gln Leu Val Glu Ser Gly Gly Gly Leu Val Gln Ala Gly Gly
1               5                   10                  15

Ser Leu Arg Leu Ser Cys Thr Ala Ser Thr Ser Ile Tyr Thr
            20                  25                  30

<210> SEQ ID NO 469
<211> LENGTH: 30
<212> TYPE: PRT
<213> ORGANISM: Lama glama

<400> SEQUENCE: 469

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ala Val Gly
            20                  25                  30

<210> SEQ ID NO 470
<211> LENGTH: 30
<212> TYPE: PRT
<213> ORGANISM: Lama glama

<400> SEQUENCE: 470

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 471
<211> LENGTH: 30
<212> TYPE: PRT
<213> ORGANISM: Lama glama

<400> SEQUENCE: 471

Glu Val Gln Leu Val Glu Ser Gly Gly Gly Leu Ala Gln Ala Gly Asp
1               5                   10                  15

Ser Leu Arg Leu Ser Cys Ala Ala Ser Gly Arg Ser Phe Ser 20 25 30

<210> SEQ ID NO 472
<211> LENGTH: 30
<212> TYPE: PRT
<213> ORGANISM: Lama glama

<400> SEQUENCE: 472

Glu Val Gln Leu Val Glu Ser Gly Gly Gly Leu Val Gln Pro Gly Gly
1 5 10 15

Ser Leu Arg Leu Ser Cys Val Ala Ser Gly Ile Arg Phe Met
20 25 30

<210> SEQ ID NO 473
<211> LENGTH: 30
<212> TYPE: PRT
<213> ORGANISM: Lama glama

<400> SEQUENCE: 473

Glu Val Gln Leu Val Glu Ser Gly Gly Gly Leu Val Gln Pro Gly Gly
1 5 10 15

Ser Leu Arg Leu Ser Cys Ala Ala Ser Gly Asn Ile Phe Ser
20 25 30

<210> SEQ ID NO 474
<211> LENGTH: 30
<212> TYPE: PRT
<213> ORGANISM: Lama glama

<400> SEQUENCE: 474

Glu Val Gln Leu Val Glu Ser Gly Gly Gly Leu Val Gln Ala Gly Gly
1 5 10 15

Ser Leu Arg Leu Ser Cys Ala Ala Ser Thr Ser Ile Tyr Ser
20 25 30

<210> SEQ ID NO 475
<211> LENGTH: 30
<212> TYPE: PRT
<213> ORGANISM: Lama glama

<400> SEQUENCE: 475

Glu Val Gln Leu Val Glu Ser Gly Gly Gly Leu Val Gln Ala Gly Gly
1 5 10 15

Ser Leu Arg Leu Ser Cys Ala Val Ser Thr Ser Ile Tyr Ser
20 25 30

<210> SEQ ID NO 476
<211> LENGTH: 30
<212> TYPE: PRT
<213> ORGANISM: Lama glama

<400> SEQUENCE: 476

Glu Val Gln Leu Val Glu Ser Gly Gly Gly Leu Val Gln Thr Gly Gly
1 5 10 15

Ser Leu Arg Leu Ser Cys Ala Ala Ser Gly Arg Thr Phe Ser
20 25 30

<210> SEQ ID NO 477
<211> LENGTH: 30
<212> TYPE: PRT
<213> ORGANISM: Lama glama

<400> SEQUENCE: 477

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser
            20                  25                  30


<210> SEQ ID NO 478
<211> LENGTH: 30
<212> TYPE: PRT
<213> ORGANISM: Lama glama

<400> SEQUENCE: 478

Glu Val Gln Leu Val Glu Ser Gly Gly Gly Leu Ala Gln Ala Gly Gly
1               5                   10                  15

Ser Leu Arg Leu Ser Cys Thr Thr Ser Gly Leu Thr Phe Ser
            20                  25                  30


<210> SEQ ID NO 479
<211> LENGTH: 30
<212> TYPE: PRT
<213> ORGANISM: Lama glama

<400> SEQUENCE: 479

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Val Arg
            20                  25                  30


<210> SEQ ID NO 480
<211> LENGTH: 30
<212> TYPE: PRT
<213> ORGANISM: Lama glama

<400> SEQUENCE: 480

Glu Val Gln Leu Val Glu Ser Gly Gly Gly Leu Val Gln Ala Gly Gly
1               5                   10                  15

Ser Leu Arg Leu Ser Cys Ala Val Ser Gly Ser Thr Phe Gly
            20                  25                  30


<210> SEQ ID NO 481
<211> LENGTH: 30
<212> TYPE: PRT
<213> ORGANISM: Lama glama

<400> SEQUENCE: 481

Glu Val Gln Leu Val Glu Ser Gly Gly Gly Leu Val Gln Pro Gly Asp
1               5                   10                  15

Ser Leu Arg Leu Ser Cys Ala Ala Ser Gly Leu Ser Phe Ser
            20                  25                  30


<210> SEQ ID NO 482
<211> LENGTH: 30
<212> TYPE: PRT
<213> ORGANISM: Lama glama

<400> SEQUENCE: 482

Glu Val Gln Leu Val Glu Ser Gly Gly Gly Leu Val Gln Ala Gly Gly
1               5                   10                  15

Ser Leu Ser Leu Ser Cys Ala Ala Ser Ala Arg Ala Phe Ser
            20                  25                  30


<210> SEQ ID NO 483
```

<211> LENGTH: 30
<212> TYPE: PRT
<213> ORGANISM: Lama glama

<400> SEQUENCE: 483

Glu Val Gln Leu Val Glu Ser Gly Gly Gly Leu Val Gln Ala Gly Gly
1 5 10 15

Ser Leu Arg Leu Ser Cys Ala Ala Ser Gly Asp Thr Leu Ser
20 25 30

<210> SEQ ID NO 484
<211> LENGTH: 30
<212> TYPE: PRT
<213> ORGANISM: Lama glama

<400> SEQUENCE: 484

Glu Val Gln Leu Val Glu Ser Gly Gly Gly Leu Val Gln Ala Gly Glu
1 5 10 15

Ser Leu Arg Leu Ser Cys Val Ala Ser Gly Ile Thr Phe Ser
20 25 30

<210> SEQ ID NO 485
<211> LENGTH: 30
<212> TYPE: PRT
<213> ORGANISM: Lama glama

<400> SEQUENCE: 485

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Leu Ser
20 25 30

<210> SEQ ID NO 486
<211> LENGTH: 30
<212> TYPE: PRT
<213> ORGANISM: Lama glama

<400> SEQUENCE: 486

Glu Val Gln Leu Val Glu Ser Gly Gly Gly Leu Val Gln Ala Gly Gly
1 5 10 15

Ser Leu Met Leu Ser Cys Ala Ala Ser Gly Arg Ala Leu Ser
20 25 30

<210> SEQ ID NO 487
<211> LENGTH: 30
<212> TYPE: PRT
<213> ORGANISM: Lama glama

<400> SEQUENCE: 487

Glu Glu Gln Leu Val Glu Ser Gly Gly Gly Leu Val Gln Ala Gly Gly
1 5 10 15

Ser Leu Met Leu Ser Cys Ala Ala Ser Gly Arg Ala Leu Ser
20 25 30

<210> SEQ ID NO 488
<211> LENGTH: 30
<212> TYPE: PRT
<213> ORGANISM: Lama glama

<400> SEQUENCE: 488

Glu Val Gln Leu Val Glu Ser Gly Gly Gly Leu Val Gln Pro Gly Gly
1 5 10 15

Ser Leu Arg Leu Ser Cys Ala Ser Ser Gly Arg Leu Phe Ser
            20                  25                  30

<210> SEQ ID NO 489
<211> LENGTH: 30
<212> TYPE: PRT
<213> ORGANISM: Lama glama

<400> SEQUENCE: 489

Glu Val Gln Leu Val Glu Ser Gly Gly Gly Leu Val Gln Ser Gly Gly
1               5                   10                  15

Ser Leu Arg Leu Ser Cys Ala Ala Ser Gly Arg Ser Phe Ser
            20                  25                  30

<210> SEQ ID NO 490
<211> LENGTH: 30
<212> TYPE: PRT
<213> ORGANISM: Lama glama

<400> SEQUENCE: 490

Glu Val Gln Leu Val Glu Ser Gly Gly Gly Leu Val Gln Ala Gly Gly
1               5                   10                  15

Ser Leu Arg Leu Ser Cys Ser Val Thr Gly Arg Thr Phe Asn
            20                  25                  30

<210> SEQ ID NO 491
<211> LENGTH: 30
<212> TYPE: PRT
<213> ORGANISM: Lama glama

<400> SEQUENCE: 491

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Leu Ser
            20                  25                  30

<210> SEQ ID NO 492
<211> LENGTH: 30
<212> TYPE: PRT
<213> ORGANISM: Lama glama

<400> SEQUENCE: 492

Glu Val Gln Leu Val Glu Ser Gly Gly Gly Leu Ala Gln Ala Gly Gly
1               5                   10                  15

Ser Leu Arg Leu Ser Cys Thr Ala Ser Gly Arg Thr Phe Asn
            20                  25                  30

<210> SEQ ID NO 493
<211> LENGTH: 30
<212> TYPE: PRT
<213> ORGANISM: Lama glama

<400> SEQUENCE: 493

Glu Val Gln Leu Val Glu Ser Gly Gly Gly Leu Val Gln Ser Gly Asp
1               5                   10                  15

Ser Leu Arg Leu Ser Cys Ala Val Ser Gly Asn Thr Phe Gly
            20                  25                  30

<210> SEQ ID NO 494
<211> LENGTH: 30
<212> TYPE: PRT
<213> ORGANISM: Lama glama

<400> SEQUENCE: 494

Glu Val Gln Leu Val Glu Ser Glu Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 495
<211> LENGTH: 30
<212> TYPE: PRT
<213> ORGANISM: Lama glama

<400> SEQUENCE: 495

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser
            20                  25                  30

<210> SEQ ID NO 496
<211> LENGTH: 30
<212> TYPE: PRT
<213> ORGANISM: Lama glama

<400> SEQUENCE: 496

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 497
<211> LENGTH: 30
<212> TYPE: PRT
<213> ORGANISM: Lama glama

<400> SEQUENCE: 497

Glu Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Asn
            20                  25                  30

<210> SEQ ID NO 498
<211> LENGTH: 30
<212> TYPE: PRT
<213> ORGANISM: Lama glama

<400> SEQUENCE: 498

Glu Val Gln Leu Val Glu Ser Gly Gly Gly Leu Val Gln Ala Gly Asp
1               5                   10                  15

Ser Leu Arg Leu Ser Cys Phe Thr Ser Ala Arg Thr Phe Asp
            20                  25                  30

<210> SEQ ID NO 499
<211> LENGTH: 30
<212> TYPE: PRT
<213> ORGANISM: Lama glama

<400> SEQUENCE: 499

Glu Val Gln Leu Val Glu Ser Gly Gly Gly Leu Met Gln Thr Gly Asp
1               5                   10                  15

Ser Leu Arg Leu Ser Cys Ala Ala Ser Gly Leu Arg Phe Thr
            20                  25                  30

<210> SEQ ID NO 500
<211> LENGTH: 30
<212> TYPE: PRT
<213> ORGANISM: Lama glama

<400> SEQUENCE: 500

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Asn
20 25 30

<210> SEQ ID NO 501
<211> LENGTH: 30
<212> TYPE: PRT
<213> ORGANISM: Lama glama

<400> SEQUENCE: 501

Glu Val Gln Leu Val Glu Ser Gly Gly Gly Leu Val Gln Ala Gly Gly
1 5 10 15

Ser Leu Arg Leu Ser Cys Ala Ala Ser Gly Leu Thr Phe Ser
20 25 30

<210> SEQ ID NO 502
<211> LENGTH: 30
<212> TYPE: PRT
<213> ORGANISM: Lama glama

<400> SEQUENCE: 502

Glu Val Gln Leu Val Glu Ser Gly Gly Gly Leu Val Gln Ala Gly Gly
1 5 10 15

Ser Leu Arg Leu Ser Cys Thr Ala Ser Gly Ser Ala Phe Lys
20 25 30

<210> SEQ ID NO 503
<211> LENGTH: 30
<212> TYPE: PRT
<213> ORGANISM: Lama glama

<400> SEQUENCE: 503

Glu Val Gln Leu Val Glu Ser Gly Gly Gly Leu Val Gln Pro Gly Gly
1 5 10 15

Ser Leu Lys Leu Ser Cys Thr Ala Ser Gly Phe Thr Phe Ser
20 25 30

<210> SEQ ID NO 504
<211> LENGTH: 30
<212> TYPE: PRT
<213> ORGANISM: Lama glama

<400> SEQUENCE: 504

Lys Val Gln Leu Val Glu Ser Gly Gly Gly Leu Val Gln Ala Gly Gly
1 5 10 15

Ser Leu Arg Leu Ser Cys Ala Ala Ser Glu Arg Thr Phe Ser
20 25 30

<210> SEQ ID NO 505
<211> LENGTH: 30
<212> TYPE: PRT
<213> ORGANISM: Lama glama

<400> SEQUENCE: 505

Glu Val Gln Leu Val Glu Ser Gly Gly Gly Leu Val Gln Ala Gly Gly
1 5 10 15

Ser Leu Arg Leu Ser Cys Ala Ala Ser Gly Phe Thr Phe Gly
20 25 30

<210> SEQ ID NO 506
<211> LENGTH: 30
<212> TYPE: PRT
<213> ORGANISM: Lama glama

<400> SEQUENCE: 506

Glu Val Gln Leu Val Glu Ser Gly Gly Gly Leu Val Gln Pro Gly Gly
1 5 10 15

Ser Leu Arg Leu Ser Cys Thr Ala Ser Gly Leu Asn Leu Asp
20 25 30

<210> SEQ ID NO 507
<211> LENGTH: 30
<212> TYPE: PRT
<213> ORGANISM: Lama glama

<400> SEQUENCE: 507

Glu Val Gln Leu Val Glu Ser Gly Gly Gly Leu Val Gln Pro Gly Gly
1 5 10 15

Ser Leu Arg Leu Ser Cys Val Ala Ser Gly Phe Arg Leu Asp
20 25 30

<210> SEQ ID NO 508
<211> LENGTH: 30
<212> TYPE: PRT
<213> ORGANISM: Lama glama

<400> SEQUENCE: 508

Glu Val Gln Leu Val Glu Ser Gly Gly Gly Leu Val Gln Ala Gly Gly
1 5 10 15

Ser Leu Arg Leu Ser Cys Ala Ala Ser Gly Gly Thr Phe Ser
20 25 30

<210> SEQ ID NO 509
<211> LENGTH: 30
<212> TYPE: PRT
<213> ORGANISM: Lama glama

<400> SEQUENCE: 509

Glu Val Gln Leu Val Glu Ser Gly Gly Gly Leu Val Gln Pro Gly Ala
1 5 10 15

Ser Leu Arg Leu Ser Cys Ala Ala Ser Gly Asp Gly Phe Thr
20 25 30

<210> SEQ ID NO 510
<211> LENGTH: 30
<212> TYPE: PRT
<213> ORGANISM: Lama glama

<400> SEQUENCE: 510

Glu Val Gln Leu Val Glu Ser Gly Gly Gly Leu Ala Gln Ala Gly Gly
1 5 10 15

Ser Leu Arg Leu Ser Cys Ala Ala Ser Gly Arg Thr Phe Ser
20 25 30

<210> SEQ ID NO 511
<211> LENGTH: 30
<212> TYPE: PRT
<213> ORGANISM: Lama glama

<400> SEQUENCE: 511

Glu Val Gln Leu Val Glu Ser Gly Gly Gly Leu Val Gln Ala Gly Gly
1 5 10 15

Ser Leu Arg Leu Ser Cys Val Ala Ser Gly Phe Thr Leu Gly
20 25 30

<210> SEQ ID NO 512
<211> LENGTH: 30
<212> TYPE: PRT
<213> ORGANISM: Lama glama

<400> SEQUENCE: 512

Glu Val Gln Leu Val Glu Ser Gly Gly Gly Leu Val Gln Ala Gly Gly
1 5 10 15

Ser Leu Arg Leu Ser Cys Ala Ala Ser Thr Ser Ile Ser Ser
20 25 30

<210> SEQ ID NO 513
<211> LENGTH: 30
<212> TYPE: PRT
<213> ORGANISM: Lama glama

<400> SEQUENCE: 513

Glu Val Gln Leu Val Glu Ser Gly Gly Gly Leu Val Gln Pro Gly Gly
1 5 10 15

Ser Leu Arg Leu Ser Cys Ala Ala Ser Gly Thr Thr Ser Ser
20 25 30

<210> SEQ ID NO 514
<211> LENGTH: 30
<212> TYPE: PRT
<213> ORGANISM: Lama glama

<400> SEQUENCE: 514

Glu Val Gln Leu Val Glu Ser Gly Gly Gly Leu Val Gln Pro Gly Gly
1 5 10 15

Ser Leu Arg Leu Ser Cys Ala Thr Ser Gly Leu Thr Phe Ser
20 25 30

<210> SEQ ID NO 515
<211> LENGTH: 30
<212> TYPE: PRT
<213> ORGANISM: Lama glama

<400> SEQUENCE: 515

Glu Val Gln Leu Val Glu Ser Gly Gly Gly Leu Val Gln Ala Gly Asp
1 5 10 15

Ser Leu Arg Leu Ser Cys Ala Ala Ser Gly Arg Thr Phe Asn
20 25 30

<210> SEQ ID NO 516
<211> LENGTH: 30
<212> TYPE: PRT
<213> ORGANISM: Lama glama

<400> SEQUENCE: 516

Glu Val Gln Leu Val Glu Ser Gly Gly Gly Leu Val Gln Ala Gly Gly
1 5 10 15

Ser Leu Arg Leu Ser Cys Ala Ala Ser Gly Gly Ser Phe Ser
20 25 30

<210> SEQ ID NO 517
<211> LENGTH: 14
<212> TYPE: PRT
<213> ORGANISM: Lama glama

<400> SEQUENCE: 517

Trp Phe Arg Gln Ser Pro Gly Lys Glu Arg Glu Phe Val Ser
1 5 10

<210> SEQ ID NO 518
<211> LENGTH: 14
<212> TYPE: PRT
<213> ORGANISM: Lama glama

<400> SEQUENCE: 518

Trp Phe Arg Gln Ala Pro Gly Lys Glu Arg Glu Phe Val Ala
1 5 10

<210> SEQ ID NO 519
<211> LENGTH: 14
<212> TYPE: PRT
<213> ORGANISM: Lama glama

<400> SEQUENCE: 519

Trp Tyr Arg Gln Ala Pro Gly Ile Gln Arg Gln Leu Val Ala
1 5 10

<210> SEQ ID NO 520
<211> LENGTH: 14
<212> TYPE: PRT
<213> ORGANISM: Lama glama

<400> SEQUENCE: 520

Trp Tyr Arg Gln Ala Pro Gly Lys His Arg Glu Leu Val Ala
1 5 10

<210> SEQ ID NO 521
<211> LENGTH: 14
<212> TYPE: PRT
<213> ORGANISM: Lama glama

<400> SEQUENCE: 521

Trp Tyr Arg Gln Ala Pro Gly Lys Gln Arg Glu Leu Val Ala
1 5 10

<210> SEQ ID NO 522
<211> LENGTH: 14
<212> TYPE: PRT
<213> ORGANISM: Lama glama

<400> SEQUENCE: 522

Trp Phe Arg Gln Ala Pro Gly Lys Glu Ser Glu Phe Val Ala
1 5 10

<210> SEQ ID NO 523
<211> LENGTH: 14
<212> TYPE: PRT
<213> ORGANISM: Lama glama

<400> SEQUENCE: 523

Trp Phe Arg Gln Ala Pro Gly Lys Glu Arg Ala Phe Val Ala
1 5 10

<210> SEQ ID NO 524

<211> LENGTH: 14
<212> TYPE: PRT
<213> ORGANISM: Lama glama

<400> SEQUENCE: 524

Trp Phe Arg Gln Ala Pro Gly Lys Glu Arg Glu Phe Val Ser
1 5 10

<210> SEQ ID NO 525
<211> LENGTH: 14
<212> TYPE: PRT
<213> ORGANISM: Lama glama

<400> SEQUENCE: 525

Trp Phe Arg Gln Ala Ala Gly Lys Glu Arg Glu Phe Val Ala
1 5 10

<210> SEQ ID NO 526
<211> LENGTH: 14
<212> TYPE: PRT
<213> ORGANISM: Lama glama

<400> SEQUENCE: 526

Trp Phe Arg Gln Ala Pro Gly Arg Glu Arg Glu Phe Leu Ser
1 5 10

<210> SEQ ID NO 527
<211> LENGTH: 14
<212> TYPE: PRT
<213> ORGANISM: Lama glama

<400> SEQUENCE: 527

Trp Phe Arg Gln Ala Pro Gly Lys Glu Arg Glu Phe Val Ile
1 5 10

<210> SEQ ID NO 528
<211> LENGTH: 14
<212> TYPE: PRT
<213> ORGANISM: Lama glama

<400> SEQUENCE: 528

Trp Phe Arg Gln Val Pro Gly Arg Glu Arg Glu Phe Val Ala
1 5 10

<210> SEQ ID NO 529
<211> LENGTH: 14
<212> TYPE: PRT
<213> ORGANISM: Lama glama

<400> SEQUENCE: 529

Trp Phe Arg Gln Ala Pro Gly Lys Glu Arg Val Leu Val Ala
1 5 10

<210> SEQ ID NO 530
<211> LENGTH: 14
<212> TYPE: PRT
<213> ORGANISM: Lama glama

<400> SEQUENCE: 530

Trp Phe Arg Gln Ala Pro Gly Arg Glu Arg Glu Phe Val Ala
1 5 10

<210> SEQ ID NO 531
<211> LENGTH: 14
<212> TYPE: PRT

<213> ORGANISM: Lama glama

<400> SEQUENCE: 531

Trp Phe Arg Gln Val Pro Gly Lys Asp Arg Glu Phe Val Ala
1               5                   10

<210> SEQ ID NO 532
<211> LENGTH: 14
<212> TYPE: PRT
<213> ORGANISM: Lama glama

<400> SEQUENCE: 532

Trp Phe Arg Gln Ala Pro Gly Asn Asp Arg Glu Phe Val Ala
1               5                   10

<210> SEQ ID NO 533
<211> LENGTH: 14
<212> TYPE: PRT
<213> ORGANISM: Lama glama

<400> SEQUENCE: 533

Trp Val Arg Gln Ala Pro Gly Lys Gly Leu Glu Trp Val Ser
1               5                   10

<210> SEQ ID NO 534
<211> LENGTH: 14
<212> TYPE: PRT
<213> ORGANISM: Lama glama

<400> SEQUENCE: 534

Trp Phe Arg Gln Ala Pro Gly Asn Glu Arg Glu Phe Val Ala
1               5                   10

<210> SEQ ID NO 535
<211> LENGTH: 14
<212> TYPE: PRT
<213> ORGANISM: Lama glama

<400> SEQUENCE: 535

Trp Phe Arg Gln Ala Pro Gly Arg Glu Arg Glu Phe Val Ser
1               5                   10

<210> SEQ ID NO 536
<211> LENGTH: 14
<212> TYPE: PRT
<213> ORGANISM: Lama glama

<400> SEQUENCE: 536

Trp Phe Arg Gln Ala Pro Gly Lys Glu Arg Glu Phe Val Thr
1               5                   10

<210> SEQ ID NO 537
<211> LENGTH: 14
<212> TYPE: PRT
<213> ORGANISM: Lama glama

<400> SEQUENCE: 537

Trp Phe Arg Gln Ala Pro Gly Lys Glu Arg Glu Ser Val Ala
1               5                   10

<210> SEQ ID NO 538
<211> LENGTH: 14
<212> TYPE: PRT
<213> ORGANISM: Lama glama

<400> SEQUENCE: 538

Trp Phe Arg Gln Ala Pro Gly Lys Glu Arg Glu Phe Ile Ser
1 5 10

<210> SEQ ID NO 539
<211> LENGTH: 14
<212> TYPE: PRT
<213> ORGANISM: Lama glama

<400> SEQUENCE: 539

Trp Phe Arg Gln Gly Pro Gly Lys Glu Arg Glu Phe Val Ala
1 5 10

<210> SEQ ID NO 540
<211> LENGTH: 14
<212> TYPE: PRT
<213> ORGANISM: Lama glama

<400> SEQUENCE: 540

Trp Phe Arg Gln Thr Pro Gly Thr Glu Arg Glu Phe Val Ala
1 5 10

<210> SEQ ID NO 541
<211> LENGTH: 14
<212> TYPE: PRT
<213> ORGANISM: Lama glama

<400> SEQUENCE: 541

Trp Phe Arg Arg Thr Pro Gly Lys Glu Asp Glu Phe Val Ala
1 5 10

<210> SEQ ID NO 542
<211> LENGTH: 14
<212> TYPE: PRT
<213> ORGANISM: Lama glama

<400> SEQUENCE: 542

Trp Phe Arg Gln Ala Pro Gly Asn Glu Arg Glu Gly Val Ser
1 5 10

<210> SEQ ID NO 543
<211> LENGTH: 14
<212> TYPE: PRT
<213> ORGANISM: Lama glama

<400> SEQUENCE: 543

Trp Phe Arg Gln Ala Pro Gly Lys Glu Arg Glu Gly Val Ser
1 5 10

<210> SEQ ID NO 544
<211> LENGTH: 14
<212> TYPE: PRT
<213> ORGANISM: Lama glama

<400> SEQUENCE: 544

Trp Phe Arg Gln Ala Pro Gly Lys Glu Arg Glu Ala Val Ser
1 5 10

<210> SEQ ID NO 545
<211> LENGTH: 14
<212> TYPE: PRT
<213> ORGANISM: Lama glama

<400> SEQUENCE: 545

Trp Phe Arg Gln Ser Pro Gly Lys Glu Arg Glu Ile Val Ala
1 5 10

<210> SEQ ID NO 546
<211> LENGTH: 14
<212> TYPE: PRT
<213> ORGANISM: Lama glama

<400> SEQUENCE: 546

Trp Phe Arg Gln Ala Pro Gly Lys Glu Arg Gln Phe Val Ala
1 5 10

<210> SEQ ID NO 547
<211> LENGTH: 14
<212> TYPE: PRT
<213> ORGANISM: Lama glama

<400> SEQUENCE: 547

Trp Phe Arg Gln Ala Pro Gly Gln Glu Arg Glu Phe Val Ala
1 5 10

<210> SEQ ID NO 548
<211> LENGTH: 32
<212> TYPE: PRT
<213> ORGANISM: Lama glama

<400> SEQUENCE: 548

Arg Phe Thr Ile Ser Arg Asp Asn Thr Lys Asn Thr Val Tyr Leu Gln
1 5 10 15

Met Asn Ser Leu Thr Pro Asp Asp Thr Ala Ile Tyr Tyr Cys Ala Ala
20 25 30

<210> SEQ ID NO 549
<211> LENGTH: 32
<212> TYPE: PRT
<213> ORGANISM: Lama glama

<400> SEQUENCE: 549

Arg Phe Thr Ile Ser Arg Asp Asn Asp Asn Gly Ala Leu Tyr Leu Gln
1 5 10 15

Met Asn Thr Leu Lys Pro Glu Asp Thr Ala Val Tyr Ser Cys Ala Ala
20 25 30

<210> SEQ ID NO 550
<211> LENGTH: 32
<212> TYPE: PRT
<213> ORGANISM: Lama glama

<400> SEQUENCE: 550

Arg Phe Thr Ile Ser Arg Asp Asn Ala Lys Asn Thr Val Tyr Leu Arg
1 5 10 15

Met Asn Ser Leu Lys Pro Glu Asp Ser Ala Ile Tyr Tyr Cys Ala Ala
20 25 30

<210> SEQ ID NO 551
<211> LENGTH: 32
<212> TYPE: PRT
<213> ORGANISM: Lama glama

<400> SEQUENCE: 551

Arg Phe Thr Ile Ser Arg Asp Asn Ser Lys Asn Ile Val Tyr Leu Gln
1 5 10 15

Met Asn Ser Leu Lys Pro Glu Asp Thr Ala Ala Tyr Tyr Cys Asn Thr 20 25 30

<210> SEQ ID NO 552
<211> LENGTH: 32
<212> TYPE: PRT
<213> ORGANISM: Lama glama

<400> SEQUENCE: 552

Arg Phe Thr Leu Ser Arg Asp Asn Ala Lys Asn Thr Met Tyr Leu Gln
1 5 10 15

Met Asn Ser Leu Lys Pro Glu Asp Thr Ala Val Tyr Tyr Cys Ala Ala
20 25 30

<210> SEQ ID NO 553
<211> LENGTH: 32
<212> TYPE: PRT
<213> ORGANISM: Lama glama

<400> SEQUENCE: 553

Arg Phe Thr Ile Ser Arg Glu Asn Ala Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 554
<211> LENGTH: 32
<212> TYPE: PRT
<213> ORGANISM: Lama glama

<400> SEQUENCE: 554

Arg Phe Thr Ile Ser Arg Asp Asn Ser Lys Asn Thr Val Tyr Leu Gln
1 5 10 15

Met Asn Ser Leu Lys Ala Glu Asp Thr Ala Val Tyr Tyr Cys Asn Thr
20 25 30

<210> SEQ ID NO 555
<211> LENGTH: 32
<212> TYPE: PRT
<213> ORGANISM: Lama glama

<400> SEQUENCE: 555

Arg Phe Thr Val Ser Arg Asp Asn Ala Lys Asn Thr Val Tyr Leu Gln
1 5 10 15

Met Asn Ser Leu Lys Pro Glu Asp Thr Ala Val Tyr Tyr Cys Asn Ala
20 25 30

<210> SEQ ID NO 556
<211> LENGTH: 32
<212> TYPE: PRT
<213> ORGANISM: Lama glama

<400> SEQUENCE: 556

Arg Phe Thr Ile Ser Arg Asp Asn Ala Lys Asn Thr Val Tyr Leu Gln
1 5 10 15

Met Asn Ser Leu Lys Pro Glu Asp Ser Ala Ile Tyr Tyr Cys Ala Ala
20 25 30

<210> SEQ ID NO 557
<211> LENGTH: 32
<212> TYPE: PRT
<213> ORGANISM: Lama glama

<400> SEQUENCE: 557

Arg Phe Thr Ile Ser Arg Asp Asn Ala Lys Asn Thr Val Tyr Leu Gln
1 5 10 15

Thr Asn Ser Leu Lys Pro Glu Asp Ser Ala Ile Tyr Tyr Cys Ala Ala
20 25 30

<210> SEQ ID NO 558
<211> LENGTH: 32
<212> TYPE: PRT
<213> ORGANISM: Lama glama

<400> SEQUENCE: 558

Arg Phe Thr Ile Ser Arg Asp Ser Ala Lys Asn Ser Val Phe Leu Gln
1 5 10 15

Met Asn Ser Leu Lys Pro Glu Asp Thr Ala Val Tyr Tyr Cys Ala Ala
20 25 30

<210> SEQ ID NO 559
<211> LENGTH: 32
<212> TYPE: PRT
<213> ORGANISM: Lama glama

<400> SEQUENCE: 559

Arg Phe Thr Ile Ser Arg Asp Asn Thr Lys Lys Thr Met Tyr Leu Gln
1 5 10 15

Met Asn Ser Leu Lys Pro Glu Asp Thr Ala Val Tyr Tyr Cys Ala Ala
20 25 30

<210> SEQ ID NO 560
<211> LENGTH: 32
<212> TYPE: PRT
<213> ORGANISM: Lama glama

<400> SEQUENCE: 560

Arg Phe Thr Val Ser Arg Asp Asn Asn Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 561
<211> LENGTH: 32
<212> TYPE: PRT
<213> ORGANISM: Lama glama

<400> SEQUENCE: 561

Arg Phe Thr Ile Ser Arg Asp Asp Ala Ala Asn Thr Val Tyr Leu Gln
1 5 10 15

Met Asn Asn Leu Lys Pro Glu Asp Thr Ala Val Tyr Tyr Cys Asn Ala
20 25 30

<210> SEQ ID NO 562
<211> LENGTH: 32
<212> TYPE: PRT
<213> ORGANISM: Lama glama

<400> SEQUENCE: 562

Arg Phe Thr Ile Ser Arg Asp Asn Ala Arg Asn Thr Val Asn Leu Gln
1 5 10 15

Met Asn Gly Leu Lys Pro Glu Asp Thr Ala Val Tyr Tyr Cys Ala Gly
20 25 30

<210> SEQ ID NO 563

<211> LENGTH: 32
<212> TYPE: PRT
<213> ORGANISM: Lama glama

<400> SEQUENCE: 563

Arg Phe Thr Ile Ser Arg Asp Asn Ser Lys Ser Thr Val Tyr Leu Gln
1 5 10 15

Met Asn Ser Leu Lys Ser Glu Asp Thr Ala Val Tyr Tyr Cys Ala Ala
20 25 30

<210> SEQ ID NO 564
<211> LENGTH: 32
<212> TYPE: PRT
<213> ORGANISM: Lama glama

<400> SEQUENCE: 564

Arg Phe Thr Ile Ser Arg Asp Asn Ala Lys Asn Ile Val Tyr Leu Gln
1 5 10 15

Met Asn Ser Leu Lys Pro Glu Asp Thr Ala Val Tyr Tyr Cys Ala Ala
20 25 30

<210> SEQ ID NO 565
<211> LENGTH: 32
<212> TYPE: PRT
<213> ORGANISM: Lama glama

<400> SEQUENCE: 565

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 566
<211> LENGTH: 32
<212> TYPE: PRT
<213> ORGANISM: Lama glama

<400> SEQUENCE: 566

Arg Phe Ala Val Ser Arg Asp Asn Ala Lys Asn Thr Gly Tyr Leu Gln
1 5 10 15

Met Asn Ser Leu Lys Leu Glu Asp Thr Ala Thr Tyr Tyr Cys Ala Ala
20 25 30

<210> SEQ ID NO 567
<211> LENGTH: 32
<212> TYPE: PRT
<213> ORGANISM: Lama glama

<400> SEQUENCE: 567

Arg Phe Thr Ile Ser Arg Asp Asn Ala Lys Asn Thr Val Tyr Leu Gln
1 5 10 15

Met Asn Ser Leu Lys Pro Glu Asp Thr Ala Leu Tyr Ser Cys Ala Lys
20 25 30

<210> SEQ ID NO 568
<211> LENGTH: 32
<212> TYPE: PRT
<213> ORGANISM: Lama glama

<400> SEQUENCE: 568

Arg Phe Thr Val Ser Val Asp Asn Ala Lys Asn Thr Val Tyr Leu Lys
1 5 10 15

Met Asn Ser Leu Glu Pro Glu Asp Thr Ala Val Tyr Tyr Cys Ala Ala
20 25 30

<210> SEQ ID NO 569
<211> LENGTH: 32
<212> TYPE: PRT
<213> ORGANISM: Lama glama

<400> SEQUENCE: 569

Arg Phe Thr Ile Ser Arg Gly Asn Ala Lys Asn Thr Val Tyr Leu Gln
1 5 10 15

Met Asn Ser Leu Lys Pro Glu Asp Thr Ala Ala Tyr Tyr Cys Ala Ala
20 25 30

<210> SEQ ID NO 570
<211> LENGTH: 32
<212> TYPE: PRT
<213> ORGANISM: Lama glama

<400> SEQUENCE: 570

Arg Phe Thr Ile Ser Arg Asp Asn Ala Lys Asn Thr Val Asn Leu Gln
1 5 10 15

Met Asn Ser Leu Lys Pro Glu Asp Thr Ala Val Tyr Tyr Cys Ala Ala
20 25 30

<210> SEQ ID NO 571
<211> LENGTH: 32
<212> TYPE: PRT
<213> ORGANISM: Lama glama

<400> SEQUENCE: 571

Arg Phe Thr Ile Ser Thr Asp Asn Ala Lys Asn Ile Leu Phe Leu Gln
1 5 10 15

Met Asn Ser Leu Lys Pro Glu Asp Thr Ala Ile Tyr Tyr Cys Ala Val
20 25 30

<210> SEQ ID NO 572
<211> LENGTH: 32
<212> TYPE: PRT
<213> ORGANISM: Lama glama

<400> SEQUENCE: 572

Arg Phe Thr Ile Ser Arg Asp Asn Ala Lys Asn Thr Val Tyr Leu Gln
1 5 10 15

Val Asn Ser Leu Lys Pro Glu Asp Ser Ala Ile Tyr Tyr Cys Ala Ala
20 25 30

<210> SEQ ID NO 573
<211> LENGTH: 32
<212> TYPE: PRT
<213> ORGANISM: Lama glama

<400> SEQUENCE: 573

Arg Phe Thr Ile Ser Arg Asp Ser Ala Lys Asn Thr Val Tyr Leu Gln
1 5 10 15

Met Asn Leu Leu Lys Pro Glu Asp Thr Ala Val Tyr Tyr Cys Ala Thr
20 25 30

<210> SEQ ID NO 574
<211> LENGTH: 32
<212> TYPE: PRT
<213> ORGANISM: Lama glama

<400> SEQUENCE: 574

Arg Phe Thr Ile Ser Gly Asp Asn Thr Lys Asn Lys Ile Phe Leu Gln
1 5 10 15

Met Asn Ser Leu Met Pro Glu Asp Thr Ala Val Tyr Tyr Cys Ala Ile
20 25 30

<210> SEQ ID NO 575
<211> LENGTH: 32
<212> TYPE: PRT
<213> ORGANISM: Lama glama

<400> SEQUENCE: 575

Arg Phe Ser Val Ser Thr Asp Asn Ala Asn Asn Thr Leu Tyr Leu Gln
1 5 10 15

Met Asn Ser Leu Lys Pro Glu Asp Thr Ala Leu Tyr Ser Cys Ala Lys
20 25 30

<210> SEQ ID NO 576
<211> LENGTH: 32
<212> TYPE: PRT
<213> ORGANISM: Lama glama

<400> SEQUENCE: 576

Arg Phe Thr Ile Ser Arg Asp Asn Ala Ala Asn Thr Val Tyr Leu Gln
1 5 10 15

Met Asn Asn Leu Lys Pro Glu Asp Thr Ala Val Tyr Tyr Cys Asn Ala
20 25 30

<210> SEQ ID NO 577
<211> LENGTH: 32
<212> TYPE: PRT
<213> ORGANISM: Lama glama

<400> SEQUENCE: 577

Arg Phe Thr Ile Ser Gly Asp Asn Thr Lys Asn Lys Val Phe Leu Gln
1 5 10 15

Met Asp Ser Leu Arg Pro Glu Asp Thr Ala Val Tyr Tyr Cys Ala Ile
20 25 30

<210> SEQ ID NO 578
<211> LENGTH: 32
<212> TYPE: PRT
<213> ORGANISM: Lama glama

<400> SEQUENCE: 578

Arg Phe Thr Ile Ser Arg Asp Asn Ala Lys Asn Thr Val Tyr Leu Gln
1 5 10 15

Met Asn Asn Leu Thr Pro Glu Asp Thr Ala Val Tyr Tyr Cys Ala Ser
20 25 30

<210> SEQ ID NO 579
<211> LENGTH: 32
<212> TYPE: PRT
<213> ORGANISM: Lama glama

<400> SEQUENCE: 579

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Tyr Cys Ala Val
20 25 30

<210> SEQ ID NO 580
<211> LENGTH: 32
<212> TYPE: PRT
<213> ORGANISM: Lama glama

<400> SEQUENCE: 580

```
Arg Phe Thr Ile Ser Arg Asp Asn Ala Lys Ser Thr Val Tyr Leu Gln
1               5                   10                  15

Met Asn Ser Pro Lys Pro Glu Asp Thr Ala Val Tyr Tyr Cys Ala Val
            20                  25                  30
```

<210> SEQ ID NO 581
<211> LENGTH: 32
<212> TYPE: PRT
<213> ORGANISM: Lama glama

<400> SEQUENCE: 581

```
Arg Phe Thr Ile Ser Arg Asp Lys Ala Lys Asn Thr Val Ser Leu Gln
1               5                   10                  15

Met Asn Ser Leu Lys Pro Glu Asp Thr Ala Val Tyr Tyr Cys Ala Val
            20                  25                  30
```

<210> SEQ ID NO 582
<211> LENGTH: 32
<212> TYPE: PRT
<213> ORGANISM: Lama glama

<400> SEQUENCE: 582

```
Arg Phe Thr Ile Ser Arg Asp Lys Ala Lys Asn Thr Val Ser Leu Gln
1               5                   10                  15

Met Asn Ser Leu Lys Pro Glu Asp Thr Ala Val Tyr Tyr Cys Ala Ala
            20                  25                  30
```

<210> SEQ ID NO 583
<211> LENGTH: 32
<212> TYPE: PRT
<213> ORGANISM: Lama glama

<400> SEQUENCE: 583

```
Arg Phe Thr Ile Ser Arg Glu Asn Ala Lys Asn Thr Val Tyr Leu Gln
1               5                   10                  15

Met Asn Ser Leu Lys Pro Glu Asp Thr Ala Val Tyr Ser Cys Ala Ala
            20                  25                  30
```

<210> SEQ ID NO 584
<211> LENGTH: 32
<212> TYPE: PRT
<213> ORGANISM: Lama glama

<400> SEQUENCE: 584

```
Arg Phe Thr Ile Ser Arg Glu Asn Ala Lys Asn Thr Gln Phe Leu Gln
1               5                   10                  15

Met Asn Ser Leu Lys Pro Glu Asp Thr Ala Val Tyr Tyr Cys Ala Val
            20                  25                  30
```

<210> SEQ ID NO 585
<211> LENGTH: 32
<212> TYPE: PRT
<213> ORGANISM: Lama glama

<400> SEQUENCE: 585

```
Arg Phe Thr Ile Ser Arg Asp Asn Ala Lys Asn Thr Val Tyr Leu Gln
1               5                   10                  15
```

Leu Asn Ser Leu Lys Pro Glu Asp Thr Ala Val Tyr Tyr Cys Ala Ala
20 25 30

<210> SEQ ID NO 586
<211> LENGTH: 32
<212> TYPE: PRT
<213> ORGANISM: Lama glama

<400> SEQUENCE: 586

Arg Phe Ile Ile Ser Arg Asp Asn Ala Gln Asn Thr Leu Phe Leu Gln
1 5 10 15

Met Asn Asn Thr Ala Pro Glu Asp Thr Ala Val Tyr Tyr Cys Ala Ala
20 25 30

<210> SEQ ID NO 587
<211> LENGTH: 32
<212> TYPE: PRT
<213> ORGANISM: Lama glama

<400> SEQUENCE: 587

Arg Phe Thr Ile Ser Arg Asp Asn Asp Lys Asn Thr Val Ala Leu Gln
1 5 10 15

Met Asn Ser Leu Lys Pro Glu Asp Thr Ala Val Tyr Tyr Cys Gly Ala
20 25 30

<210> SEQ ID NO 588
<211> LENGTH: 32
<212> TYPE: PRT
<213> ORGANISM: Lama glama

<400> SEQUENCE: 588

Arg Phe Thr Ile Ser Arg Asp Ile Val Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 589
<211> LENGTH: 32
<212> TYPE: PRT
<213> ORGANISM: Lama glama

<400> SEQUENCE: 589

Arg Phe Thr Leu Ser Arg Asp Asn Ala Lys Asn Thr Val Asp Leu Gln
1 5 10 15

Met Asn Ser Leu Lys Thr Glu Asp Thr Ala Val Tyr Tyr Cys Ala Ala
20 25 30

<210> SEQ ID NO 590
<211> LENGTH: 32
<212> TYPE: PRT
<213> ORGANISM: Lama glama

<400> SEQUENCE: 590

Arg Phe Thr Met Ser Arg Asp Lys Ala Lys Asn Ala Gly Tyr Leu Gln
1 5 10 15

Met Asn Ser Leu Lys Pro Glu Asp Thr Ala Leu Tyr Tyr Cys Ala Ala
20 25 30

<210> SEQ ID NO 591
<211> LENGTH: 32
<212> TYPE: PRT
<213> ORGANISM: Lama glama

<400> SEQUENCE: 591

Arg Phe Thr Ile Ser Arg Asp Asn Ala Lys Asn Thr Leu Phe Leu Gln
1 5 10 15

Met Asn Ser Leu Lys Ser Glu Asp Thr Ala Val Tyr Tyr Cys Ala Lys
20 25 30

<210> SEQ ID NO 592
<211> LENGTH: 32
<212> TYPE: PRT
<213> ORGANISM: Lama glama

<400> SEQUENCE: 592

Arg Phe Thr Ile Ser Ser Asp Asn Ala Lys Asn Thr Val Tyr Leu Gln
1 5 10 15

Ile Asn Asp Leu Lys Pro Glu Asp Thr Ala Ile Tyr Tyr Cys Ala Val
20 25 30

<210> SEQ ID NO 593
<211> LENGTH: 32
<212> TYPE: PRT
<213> ORGANISM: Lama glama

<400> SEQUENCE: 593

Arg Phe Thr Ile Ser Arg Asp Ser Ala Lys Asn Thr Leu Tyr Leu Gln
1 5 10 15

Met Asn Ser Leu Ser Ile Glu Asp Thr Gly Val Tyr Tyr Cys Ala Ala
20 25 30

<210> SEQ ID NO 594
<211> LENGTH: 32
<212> TYPE: PRT
<213> ORGANISM: Lama glama

<400> SEQUENCE: 594

Arg Phe Thr Phe Ser Arg Asp Asn Ala Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 595
<211> LENGTH: 32
<212> TYPE: PRT
<213> ORGANISM: Lama glama

<400> SEQUENCE: 595

Arg Phe Thr Ile Ser Arg Asp Asn Ala Lys Asn Thr Met Tyr Leu Gln
1 5 10 15

Met Asn Ser Leu Lys Pro Glu Asp Thr Ala Val Tyr Tyr Cys Ala Ala
20 25 30

<210> SEQ ID NO 596
<211> LENGTH: 32
<212> TYPE: PRT
<213> ORGANISM: Lama glama

<400> SEQUENCE: 596

Arg Phe Ser Ile Ser Ile Asn Asn Asp Lys Thr Thr Gly Phe Leu Gln
1 5 10 15

Met Asn Val Leu Lys Pro Glu Asp Thr Gly Val Tyr Phe Cys Ala Ala
20 25 30

<210> SEQ ID NO 597
<211> LENGTH: 32
<212> TYPE: PRT
<213> ORGANISM: Lama glama

<400> SEQUENCE: 597

Arg Phe Thr Thr Ser Thr Asp Asn Ala Arg Asn Thr Val Tyr Leu Gln
1 5 10 15

Met Asn Ser Leu Lys Pro Glu Asp Thr Ala His Tyr Tyr Cys Ala Ala
20 25 30

<210> SEQ ID NO 598
<211> LENGTH: 32
<212> TYPE: PRT
<213> ORGANISM: Lama glama

<400> SEQUENCE: 598

Arg Phe Thr Ile Ser Arg Asp Asn Ala Lys Asn Thr Val Tyr Leu Gln
1 5 10 15

Met Thr Ser Leu Lys Pro Glu Asp Thr Ala Val Tyr Tyr Cys His Ala
20 25 30

<210> SEQ ID NO 599
<211> LENGTH: 32
<212> TYPE: PRT
<213> ORGANISM: Lama glama

<400> SEQUENCE: 599

Arg Phe Thr Pro Ser Arg Asp Asn Ala Lys Asn Thr Val Ser Leu Gln
1 5 10 15

Met Asn Ser Leu Lys Pro Glu Asp Thr Ala Val Tyr Tyr Cys Asn Ala
20 25 30

<210> SEQ ID NO 600
<211> LENGTH: 32
<212> TYPE: PRT
<213> ORGANISM: Lama glama

<400> SEQUENCE: 600

Arg Phe Thr Ile Ser Gly Asp Asn Thr Lys Asn Thr Val Phe Leu Gln
1 5 10 15

Met Asn Phe Leu Lys Pro Glu Asp Thr Ala Val Tyr Tyr Cys Ala Ala
20 25 30

<210> SEQ ID NO 601
<211> LENGTH: 32
<212> TYPE: PRT
<213> ORGANISM: Lama glama

<400> SEQUENCE: 601

Arg Phe Thr Leu Ser Arg Asp Asn Ala Lys Asn Thr Val Ser Leu Gln
1 5 10 15

Met Asn Ser Leu Lys Pro Glu Asp Thr Ala Val Tyr Tyr Cys Asn Ala
20 25 30

<210> SEQ ID NO 602
<211> LENGTH: 31
<212> TYPE: PRT
<213> ORGANISM: Lama glama

<400> SEQUENCE: 602

Arg Phe Thr Ile Ser Arg Asp Asn Ala His Thr Val Tyr Leu Gln Met 1 5 10 15

Asn Ser Leu Lys Pro Glu Asp Thr Ala Ile Tyr Tyr Cys Ala Val
20 25 30

<210> SEQ ID NO 603
<211> LENGTH: 11
<212> TYPE: PRT
<213> ORGANISM: Lama glama

<400> SEQUENCE: 603

Trp Gly Gln Gly Thr Gln Val Thr Val Ser Ser
1 5 10

<210> SEQ ID NO 604
<211> LENGTH: 11
<212> TYPE: PRT
<213> ORGANISM: Lama glama

<400> SEQUENCE: 604

Trp Gly Ala Gly Thr Gln Val Thr Val Ser Ser
1 5 10

<210> SEQ ID NO 605
<211> LENGTH: 11
<212> TYPE: PRT
<213> ORGANISM: Lama glama

<400> SEQUENCE: 605

Trp Gly Gln Gly Thr Pro Val Thr Val Ser Ser
1 5 10

<210> SEQ ID NO 606
<211> LENGTH: 11
<212> TYPE: PRT
<213> ORGANISM: Lama glama

<400> SEQUENCE: 606

Trp Gly Ala Gly Thr Thr Val Thr Val Ser Ser
1 5 10

<210> SEQ ID NO 607
<211> LENGTH: 11
<212> TYPE: PRT
<213> ORGANISM: Lama glama

<400> SEQUENCE: 607

Trp Gly Arg Gly Thr Gln Val Thr Val Ser Ser
1 5 10

<210> SEQ ID NO 608
<211> LENGTH: 11
<212> TYPE: PRT
<213> ORGANISM: Lama glama

<400> SEQUENCE: 608

Arg Gly Arg Gly Thr Gln Val Thr Val Ser Ser
1 5 10

<210> SEQ ID NO 609
<211> LENGTH: 11
<212> TYPE: PRT
<213> ORGANISM: Lama glama

<400> SEQUENCE: 609

```
Trp Gly His Gly Thr Gln Val Thr Val Ser Ser
1               5                   10


<210> SEQ ID NO 610
<211> LENGTH: 11
<212> TYPE: PRT
<213> ORGANISM: Lama glama

<400> SEQUENCE: 610

Trp Gly Arg Gly Ala Gln Val Thr Val Ser Ser
1               5                   10


<210> SEQ ID NO 611
<211> LENGTH: 11
<212> TYPE: PRT
<213> ORGANISM: Lama glama

<400> SEQUENCE: 611

Lys Gly Gln Gly Thr Gln Val Thr Val Ser Ser
1               5                   10


<210> SEQ ID NO 612
<211> LENGTH: 11
<212> TYPE: PRT
<213> ORGANISM: Lama glama

<400> SEQUENCE: 612

Trp Gly Lys Gly Thr Leu Val Thr Val Ser Ser
1               5                   10


<210> SEQ ID NO 613
<211> LENGTH: 11
<212> TYPE: PRT
<213> ORGANISM: Lama glama

<400> SEQUENCE: 613

Ser Gly Lys Gly Thr Leu Val Thr Val Ser Ser
1               5                   10


<210> SEQ ID NO 614
<211> LENGTH: 30
<212> TYPE: PRT
<213> ORGANISM: Lama glama

<400> SEQUENCE: 614

Glu Val Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser
            20                  25                  30


<210> SEQ ID NO 615
<211> LENGTH: 30
<212> TYPE: PRT
<213> ORGANISM: Lama glama

<400> SEQUENCE: 615

Glu Val Gln Leu Val Glu Ser Gly Gly Gly Leu Val Gln Pro Gly Asp
1               5                   10                  15

Ser Leu Lys Leu Ser Cys Ala Ala Ser Gly Arg Thr Phe Ser
            20                  25                  30


<210> SEQ ID NO 616
<211> LENGTH: 30
<212> TYPE: PRT
```

<213> ORGANISM: Lama glama

<400> SEQUENCE: 616

Glu Val Gln Leu Val Glu Ser Gly Gly Gly Leu Val Gln Ala Gly Asp
1 5 10 15

Ser Leu Arg Leu Ser Cys Ala Ala Ser Gly Arg Thr Phe Ser
20 25 30

<210> SEQ ID NO 617
<211> LENGTH: 30
<212> TYPE: PRT
<213> ORGANISM: Lama glama

<400> SEQUENCE: 617

Glu Val Gln Leu Val Glu Ser Gly Gly Gly Leu Val Gln Pro Gly Asp
1 5 10 15

Ser Leu Lys Leu Ser Cys Val Ala Ser Gly Arg Thr Ser Ser
20 25 30

<210> SEQ ID NO 618
<211> LENGTH: 30
<212> TYPE: PRT
<213> ORGANISM: Lama glama

<400> SEQUENCE: 618

Glu Val Gln Leu Val Glu Ser Gly Gly Gly Leu Val Gln Pro Gly Asp
1 5 10 15

Ser Leu Lys Leu Ser Cys Val Ala Ser Gly Arg Thr Phe Ser
20 25 30

<210> SEQ ID NO 619
<211> LENGTH: 30
<212> TYPE: PRT
<213> ORGANISM: Lama glama

<400> SEQUENCE: 619

Glu Val Gln Leu Val Glu Ser Gly Gly Gly Leu Val Gln Pro Gly Asp
1 5 10 15

Ser Leu Lys Leu Ser Cys Ala Phe Ser Gly Arg Thr Phe Ser
20 25 30

<210> SEQ ID NO 620
<211> LENGTH: 30
<212> TYPE: PRT
<213> ORGANISM: Lama glama

<400> SEQUENCE: 620

Glu Val Gln Leu Val Glu Ser Gly Gly Gly Leu Val Gln Thr Gly Asp
1 5 10 15

Ser Leu Arg Leu Ser Cys Val Ala Ser Gly Arg Thr Phe Ser
20 25 30

<210> SEQ ID NO 621
<211> LENGTH: 30
<212> TYPE: PRT
<213> ORGANISM: Lama glama

<400> SEQUENCE: 621

Glu Val Gln Leu Val Glu Ser Gly Gly Gly Leu Val Gln Pro Gly Asp
1 5 10 15

Ser Leu Lys Leu Ser Cys Ala Phe Ser Gly Arg Thr Phe Gly
20 25 30

<210> SEQ ID NO 622
<211> LENGTH: 30
<212> TYPE: PRT
<213> ORGANISM: Lama glama

<400> SEQUENCE: 622

Glu Val Gln Leu Val Glu Ser Gly Gly Gly Leu Val Gln Thr Gly Asp
1               5                   10                  15

Ser Leu Arg Leu Ser Cys Glu Val Ser Gly Arg Thr Phe Ser
            20                  25                  30

<210> SEQ ID NO 623
<211> LENGTH: 30
<212> TYPE: PRT
<213> ORGANISM: Lama glama

<400> SEQUENCE: 623

Glu Val Gln Leu Val Glu Ser Gly Gly Gly Leu Val Gln Pro Gly Asp
1               5                   10                  15

Ser Leu Arg Leu Ser Cys Ala Phe Ser Gly Arg Thr Phe Ser
            20                  25                  30

<210> SEQ ID NO 624
<211> LENGTH: 30
<212> TYPE: PRT
<213> ORGANISM: Lama glama

<400> SEQUENCE: 624

Glu Val Gln Leu Val Glu Ser Glu Gly Gly Leu Val Gln Pro Gly Asp
1               5                   10                  15

Ser Leu Lys Leu Ser Cys Val Ala Ser Gly Arg Thr Ser Ser
            20                  25                  30

<210> SEQ ID NO 625
<211> LENGTH: 30
<212> TYPE: PRT
<213> ORGANISM: Lama glama

<400> SEQUENCE: 625

Glu Met Gln Leu Val Glu Ser Gly Gly Gly Leu Val Gln Pro Gly Asp
1               5                   10                  15

Ser Leu Lys Leu Ser Cys Ala Phe Ser Gly Arg Thr Phe Ser
            20                  25                  30

<210> SEQ ID NO 626
<211> LENGTH: 30
<212> TYPE: PRT
<213> ORGANISM: Lama glama

<400> SEQUENCE: 626

Glu Val Gln Leu Val Glu Ser Gly Gly Gly Leu Val Gln Thr Gly Asp
1               5                   10                  15

Ser Leu Arg Leu Ser Cys Ala Ala Ser Gly Arg Thr Phe Ser
            20                  25                  30

<210> SEQ ID NO 627
<211> LENGTH: 30
<212> TYPE: PRT
<213> ORGANISM: Lama glama

<400> SEQUENCE: 627

Glu Val Gln Leu Val Glu Ser Gly Gly Gly Leu Val Gln Pro Gly Asp
1 5 10 15

Ser Leu Lys Leu Ser Cys Ile Ala Ser Gly Arg Thr Ser Ser
20 25 30

<210> SEQ ID NO 628
<211> LENGTH: 30
<212> TYPE: PRT
<213> ORGANISM: Lama glama

<400> SEQUENCE: 628

Glu Val Gln Leu Val Glu Ser Gly Gly Gly Leu Val Gln Thr Gly Asp
1 5 10 15

Ser Leu Arg Leu Ser Cys Ala Ala Ser Gly Gly Thr Phe Ser
20 25 30

<210> SEQ ID NO 629
<211> LENGTH: 30
<212> TYPE: PRT
<213> ORGANISM: Lama glama

<400> SEQUENCE: 629

Glu Val Gln Leu Val Glu Ser Gly Gly Gly Leu Val Gln Pro Gly Asp
1 5 10 15

Pro Leu Lys Leu Ser Cys Ala Phe Ser Gly Arg Thr Phe Ser
20 25 30

<210> SEQ ID NO 630
<211> LENGTH: 30
<212> TYPE: PRT
<213> ORGANISM: Lama glama

<400> SEQUENCE: 630

Glu Val Pro Leu Val Glu Ser Gly Gly Gly Leu Val Gln Ala Gly Asp
1 5 10 15

Ser Leu Arg Leu Ser Cys Ala Ala Ser Gly Arg Thr Phe Ser
20 25 30

<210> SEQ ID NO 631
<211> LENGTH: 30
<212> TYPE: PRT
<213> ORGANISM: Lama glama

<400> SEQUENCE: 631

Glu Val Gln Leu Met Glu Ser Gly Gly Gly Leu Val Gln Pro Gly Asp
1 5 10 15

Ser Leu Lys Leu Ser Cys Ala Phe Ser Gly Arg Thr Phe Ser
20 25 30

<210> SEQ ID NO 632
<211> LENGTH: 30
<212> TYPE: PRT
<213> ORGANISM: Lama glama

<400> SEQUENCE: 632

Glu Val Gln Leu Val Glu Ser Gly Gly Gly Leu Val Gln Pro Gly Gly
1 5 10 15

Ser Leu Arg Leu Ser Cys Ala Phe Ser Gly Arg Thr Phe Ser
20 25 30

<210> SEQ ID NO 633
<211> LENGTH: 30

<212> TYPE: PRT
<213> ORGANISM: Lama glama

<400> SEQUENCE: 633

Glu Val Gln Leu Val Glu Ser Gly Gly Gly Leu Val Gln Ala Gly Gly
1 5 10 15

Ser Leu Arg Leu Ser Cys Ala Phe Ser Gly Arg Thr Phe Ser
20 25 30

<210> SEQ ID NO 634
<211> LENGTH: 30
<212> TYPE: PRT
<213> ORGANISM: Lama glama

<400> SEQUENCE: 634

Glu Val Gln Leu Val Glu Ser Gly Gly Asp Leu Val Gln Pro Gly Asp
1 5 10 15

Ser Leu Lys Leu Ser Cys Ala Ala Ser Gly Arg Thr Phe Ser
20 25 30

<210> SEQ ID NO 635
<211> LENGTH: 30
<212> TYPE: PRT
<213> ORGANISM: Lama glama

<400> SEQUENCE: 635

Glu Val Gln Leu Val Glu Ser Glu Gly Gly Leu Val Gln Ala Gly Asp
1 5 10 15

Ser Leu Arg Leu Ser Cys Ala Ala Ser Gly Arg Thr Phe Ser
20 25 30

<210> SEQ ID NO 636
<211> LENGTH: 14
<212> TYPE: PRT
<213> ORGANISM: Lama glama

<400> SEQUENCE: 636

Trp Phe Arg Gln Ala Gln Gly Lys Glu Arg Glu Phe Val Val
1 5 10

<210> SEQ ID NO 637
<211> LENGTH: 14
<212> TYPE: PRT
<213> ORGANISM: Lama glama

<400> SEQUENCE: 637

Trp Phe Arg Gln Ala Gln Gly Gln Glu Arg Glu Phe Val Val
1 5 10

<210> SEQ ID NO 638
<211> LENGTH: 32
<212> TYPE: PRT
<213> ORGANISM: Lama glama

<400> SEQUENCE: 638

Arg Phe Thr Ile Ser Arg Asp Asn Thr Lys Asn Thr Val Tyr Leu Gln
1 5 10 15

Thr Pro Ser Leu Lys Pro Glu Asp Thr Ala Asp Tyr Tyr Cys Ala Ala
20 25 30

<210> SEQ ID NO 639
<211> LENGTH: 32
<212> TYPE: PRT

<213> ORGANISM: Lama glama

<400> SEQUENCE: 639

Arg Phe Thr Ile Ser Arg Asp Asn Thr Lys Asn Thr Val Tyr Leu Gln
1 5 10 15

Thr Pro Ser Leu Lys Pro Glu Asp Thr Ala Val Tyr Tyr Cys Ala Ala
20 25 30

<210> SEQ ID NO 640
<211> LENGTH: 32
<212> TYPE: PRT
<213> ORGANISM: Lama glama

<400> SEQUENCE: 640

Arg Phe Thr Ile Ser Arg Asp Asn Thr Lys Asn Thr Val Tyr Leu Gln
1 5 10 15

Ile Asn Ser Leu Lys Pro Glu Asp Thr Ala Val Tyr Tyr Cys Ala Ala
20 25 30

<210> SEQ ID NO 641
<211> LENGTH: 32
<212> TYPE: PRT
<213> ORGANISM: Lama glama

<400> SEQUENCE: 641

Arg Phe Thr Ile Ser Arg Asp Asn Ser Lys Asn Thr Val Tyr Leu Gln
1 5 10 15

Thr Pro Ser Leu Lys Pro Glu Asp Thr Ala Val Tyr Tyr Cys Ala Ala
20 25 30

<210> SEQ ID NO 642
<211> LENGTH: 32
<212> TYPE: PRT
<213> ORGANISM: Lama glama

<400> SEQUENCE: 642

Arg Phe Thr Ile Ser Lys Asp Asn Ala Lys Asn Thr Val Tyr Leu Gln
1 5 10 15

Ile Asn Ser Leu Lys Pro Glu Asp Thr Ala Val Tyr Tyr Cys Ala Ser
20 25 30

<210> SEQ ID NO 643
<211> LENGTH: 32
<212> TYPE: PRT
<213> ORGANISM: Lama glama

<400> SEQUENCE: 643

Arg Phe Thr Ile Ser Arg Asp Asn Thr Lys Asn Thr Val Tyr Leu Gln
1 5 10 15

Ile Asn Ser Leu Lys Pro Lys Asp Thr Ala Val Tyr Tyr Cys Ala Ala
20 25 30

<210> SEQ ID NO 644
<211> LENGTH: 32
<212> TYPE: PRT
<213> ORGANISM: Lama glama

<400> SEQUENCE: 644

Arg Phe Thr Ile Ser Arg Asp Asn Thr Gln Asn Thr Val Tyr Leu Gln
1 5 10 15

Ile Asn Ser Leu Lys Pro Glu Asp Thr Ala Val Tyr Tyr Cys Ala Ala
20 25 30

<210> SEQ ID NO 645
<211> LENGTH: 32
<212> TYPE: PRT
<213> ORGANISM: Lama glama

<400> SEQUENCE: 645

Arg Phe Thr Ile Ser Arg Asp Asn Thr Lys Asn Thr Val Tyr Leu Gln
1 5 10 15

Thr Pro Ser Leu Lys Pro Glu Gly Thr Ala Val Tyr Tyr Cys Ala Ala
20 25 30

<210> SEQ ID NO 646
<211> LENGTH: 32
<212> TYPE: PRT
<213> ORGANISM: Lama glama

<400> SEQUENCE: 646

Arg Phe Thr Ile Ser Arg Asp Asn Thr Lys Asn Ala Val Tyr Leu Gln
1 5 10 15

Thr Pro Ser Leu Lys Pro Glu Asp Thr Ala Asp Tyr Tyr Cys Ala Ala
20 25 30

<210> SEQ ID NO 647
<211> LENGTH: 32
<212> TYPE: PRT
<213> ORGANISM: Lama glama

<400> SEQUENCE: 647

Arg Phe Thr Ile Ser Arg Glu Asn Thr Lys Asn Thr Val Tyr Leu Gln
1 5 10 15

Thr Pro Ser Leu Lys Pro Glu Asp Thr Ala Val Tyr Tyr Cys Ala Ala
20 25 30

<210> SEQ ID NO 648
<211> LENGTH: 32
<212> TYPE: PRT
<213> ORGANISM: Lama glama

<400> SEQUENCE: 648

Arg Phe Thr Ile Ser Arg Asp Asn Thr Lys Asn Thr Val Tyr Leu Gln
1 5 10 15

Met Pro Ser Leu Lys Pro Glu Asp Thr Ala Asp Tyr Tyr Cys Ala Ala
20 25 30

<210> SEQ ID NO 649
<211> LENGTH: 32
<212> TYPE: PRT
<213> ORGANISM: Lama glama

<400> SEQUENCE: 649

Arg Phe Thr Ile Ser Arg Asp Asn Thr Lys Asn Thr Val Tyr Leu Gln
1 5 10 15

Thr Pro Ser Leu Lys Pro Glu Asp Ala Ala Asp Tyr Tyr Cys Ala Ala
20 25 30

<210> SEQ ID NO 650
<211> LENGTH: 32
<212> TYPE: PRT
<213> ORGANISM: Lama glama

<400> SEQUENCE: 650

```
Arg Phe Thr Ile Ser Arg Asp Asn Thr Arg Asn Thr Val Tyr Leu Gln
1               5                   10                  15

Thr Pro Ser Leu Lys Pro Glu Asp Thr Ala Asp Tyr Tyr Cys Ala Ala
            20                  25                  30


<210> SEQ ID NO 651
<211> LENGTH: 32
<212> TYPE: PRT
<213> ORGANISM: Lama glama

<400> SEQUENCE: 651

Arg Phe Thr Ile Ser Arg Asp Asn Thr Lys Asp Thr Val Tyr Leu Gln
1               5                   10                  15

Thr Pro Ser Leu Lys Pro Glu Asp Thr Ala Val Tyr Tyr Cys Ala Ala
            20                  25                  30


<210> SEQ ID NO 652
<211> LENGTH: 11
<212> TYPE: PRT
<213> ORGANISM: Lama glama

<400> SEQUENCE: 652

Trp Gly Gln Gly Thr Arg Val Thr Val Ser Ser
1               5                   10


<210> SEQ ID NO 653
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 653

Glu Val Gln Leu Val Glu Ser Gly Gly Gly Leu Val Gln Thr Gly Gly
1               5                   10                  15

Ser Leu Arg Leu Ser Cys Glu Ala Ser Gly Arg Thr Phe Ser
            20                  25                  30


<210> SEQ ID NO 654
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 654

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30


<210> SEQ ID NO 655
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 655

Glu Val Gln Leu Val Glu Ser Gly Gly Gly Leu Val Gln Pro Gly Gly
1               5                   10                  15
```

Ser Leu Arg Leu Ser Cys Glu Ala Ser Gly Arg Thr Phe Ser
20 25 30

<210> SEQ ID NO 656
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 656

Glu Val Gln Leu Val Glu Ser Gly Gly Gly Leu Val Gln Thr Gly Gly
1 5 10 15

Ser Leu Arg Leu Ser Cys Glu Val Ser Gly Arg Thr Phe Ser
20 25 30

<210> SEQ ID NO 657
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 657

Glu Val Gln Leu Val Glu Ser Gly Gly Gly Leu Val Gln Pro Gly Asp
1 5 10 15

Ser Leu Arg Leu Ser Cys Glu Val Ser Gly Arg Thr Phe Ser
20 25 30

<210> SEQ ID NO 658
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 658

Glu Val Gln Leu Val Glu Ser Gly Gly Gly Leu Val Gln Thr Gly Asp
1 5 10 15

Ser Leu Arg Leu Ser Cys Ala Val Ser Gly Arg Thr Phe Ser
20 25 30

<210> SEQ ID NO 659
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 659

Trp Phe Arg Gln Ala Pro Gly Lys Glu Arg Glu Phe Val Val
1 5 10

<210> SEQ ID NO 660
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 660

```
Arg Phe Thr Ile Ser Arg Asp Asn Ala Lys Asn Thr Val Tyr Leu Gln
1               5                   10                  15

Ile Asn Ser Leu Arg Pro Glu Asp Thr Ala Val Tyr Tyr Cys Ala Ser
            20                  25                  30


<210> SEQ ID NO 661
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 661

Arg Phe Thr Ile Ser Arg Asp Asn Ala Lys Asn Thr Val Tyr Leu Gln
1               5                   10                  15

Met Asn Ser Leu Arg Pro Glu Asp Thr Ala Val Tyr Tyr Cys Ala Ser
            20                  25                  30


<210> SEQ ID NO 662
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 662

Arg Phe Thr Ile Ser Lys Asp Asn Ala Lys Asn Thr Val Tyr Leu Gln
1               5                   10                  15

Ile Asn Ser Leu Arg Pro Glu Asp Thr Ala Val Tyr Tyr Cys Ala Ser
            20                  25                  30


<210> SEQ ID NO 663
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 663

Arg Phe Thr Ile Ser Lys Asp Asn Ala Lys Asn Thr Val Tyr Leu Gln
1               5                   10                  15

Met Asn Ser Leu Arg Pro Glu Asp Thr Ala Val Tyr Tyr Cys Ala Ser
            20                  25                  30


<210> SEQ ID NO 664
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Trp Gly Gln Gly Thr Leu Val Thr Val Ser Ser
1               5                   10


<210> SEQ ID NO 665
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 665

Trp Gly Gln Gly Thr Gln Val Thr Val Ser Ser
1 5 10

<210> SEQ ID NO 666
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 666

Asp Val Gln Leu Val Glu Ser Gly Gly Gly Leu Val Gln Pro Gly Gly
1 5 10 15

Ser Leu Arg Leu Ser Cys Ala Ala Ser Gly Arg Thr Phe Ser
20 25 30

<210> SEQ ID NO 667
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 667

Glu Val Gln Leu Val Glu Ser Gly Gly Gly Leu Val Gln Pro Gly Gly
1 5 10 15

Ser Leu Arg Leu Ser Cys Ala Ala Ser Gly Ile Arg Phe Met
20 25 30

<210> SEQ ID NO 668
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 668

Glu Val Gln Leu Val Glu Ser Gly Gly Gly Leu Val Gln Pro Gly Gly
1 5 10 15

Ser Leu Arg Leu Ser Cys Val Ala Ser Gly Ile Arg Phe Ile
20 25 30

<210> SEQ ID NO 669
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 669

Trp Tyr Arg Gln Ala Pro Gly Lys Gln Arg Glu Leu Val Ala
1 5 10

<210> SEQ ID NO 670
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 670

Trp Tyr Arg Gln Ala Pro Gly Lys His Arg Glu Leu Val Ala
1 5 10

<210> SEQ ID NO 671
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 671

Arg Phe Thr Ile Ser Arg Asp Asn Ser Lys Asn Thr Val Tyr Leu Gln
1 5 10 15

Met Asn Ser Leu Arg Ala Glu Asp Thr Ala Val Tyr Tyr Cys Asn Thr
20 25 30

<210> SEQ ID NO 672
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 672

Arg Phe Thr Ile Ser Arg Asp Asn Ser Lys Asn Thr Val Tyr Leu Gln
1 5 10 15

Met Asn Ser Leu Lys Ala Glu Asp Thr Ala Val Tyr Tyr Cys Asn Thr
20 25 30

<210> SEQ ID NO 673
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 673

Trp Gly Ala Gly Thr Gln Val Thr Val Ser Ser
1 5 10

<210> SEQ ID NO 674
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 674

Glu Val Gln Leu Val Glu Ser Gly Gly Gly Leu Val Gln Pro Gly Gly
1 5 10 15

Ser Leu Arg Leu Ser Cys Ala Ala Ser Gly Ile Arg Phe Ile
20 25 30

<210> SEQ ID NO 675
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 675

Trp Tyr Arg Gln Ala Pro Gly Lys Gln Arg Glu Leu Val Ala
1               5                   10

<210> SEQ ID NO 676
<211> LENGTH: 14
<212> TYPE: PRT
<213> ORGANISM: Lama glama

<400> SEQUENCE: 676

Trp Phe Arg Gln Ala Ala Gly Lys Glu Arg Glu Gly Val Ser
1               5                   10

<210> SEQ ID NO 677
<211> LENGTH: 32
<212> TYPE: PRT
<213> ORGANISM: Lama glama

<400> SEQUENCE: 677

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 678
<211> LENGTH: 30
<212> TYPE: PRT
<213> ORGANISM: Lama glama

<400> SEQUENCE: 678

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Leu Asp
            20                  25                  30

<210> SEQ ID NO 679
<211> LENGTH: 14
<212> TYPE: PRT
<213> ORGANISM: Lama glama

<400> SEQUENCE: 679

Trp Phe Arg Gln Val Pro Gly Lys Glu Arg Glu Gly Val Ser
1               5                   10

<210> SEQ ID NO 680
<211> LENGTH: 32
<212> TYPE: PRT
<213> ORGANISM: Lama glama

<400> SEQUENCE: 680

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Thr
            20                  25                  30

<210> SEQ ID NO 681
<211> LENGTH: 30
<212> TYPE: PRT
<213> ORGANISM: Lama glama

<400> SEQUENCE: 681

Glu Val Gln Leu Val Glu Ser Gly Gly Gly Leu Val Gln Ala Gly Gly 1 5 10 15

Ser Leu Arg Leu Ser Cys Ala Ala Ser Gly Phe Thr Leu Asp
20 25 30

<210> SEQ ID NO 682
<211> LENGTH: 14
<212> TYPE: PRT
<213> ORGANISM: Lama glama

<400> SEQUENCE: 682

Trp Phe Arg Gln Ala Pro Gly Lys Glu Arg Glu Gly Val Ser
1 5 10

<210> SEQ ID NO 683
<211> LENGTH: 32
<212> TYPE: PRT
<213> ORGANISM: Lama glama

<400> SEQUENCE: 683

Arg Phe Thr Ile Ser Ser Asp Asn Asp Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 684
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 684

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Asp
20 25 30

<210> SEQ ID NO 685
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 685

Arg Phe Thr Ile Ser Ser Asp Asn Ser Lys Asn Thr Val Tyr Leu Gln
1 5 10 15

Met Asn Ser Leu Arg Pro Glu Asp Thr Ala Val Tyr Tyr Cys Ala Ala
20 25 30

<210> SEQ ID NO 686
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 686

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asp 20 25 30

<210> SEQ ID NO 687
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 687

Arg Phe Thr Ile Ser Arg Asp Asn Ser Lys Asn Thr Val Tyr Leu Gln
1 5 10 15

Met Asn Ser Leu Arg Pro Glu Asp Thr Ala Val Tyr Tyr Cys Ala Thr
20 25 30

<210> SEQ ID NO 688
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 688

Glu Val Gln Leu Val Glu Ser Gly Gly Gly Leu Val Gln Pro Gly Gly
1 5 10 15

Ser Leu Arg Leu Ser Cys Ala Val Ser Gly Ile Thr Leu Asp
20 25 30

<210> SEQ ID NO 689
<211> LENGTH: 30
<212> TYPE: PRT
<213> ORGANISM: Lama glama

<400> SEQUENCE: 689

Glu Val Gln Leu Val Glu Ser Gly Gly Gly Leu Val Gln Ala Gly Gly
1 5 10 15

Ser Leu Arg Leu Ser Cys Ala Ala Ser Gly Phe Thr Phe Asp
20 25 30

<210> SEQ ID NO 690
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 690

Glu Val Gln Leu Val Glu Ser Gly Gly Gly Leu Val Gln Thr Gly Asp
1 5 10 15

Ser Leu Arg Leu Ser Cys Glu Val Ser Gly Arg Thr Phe Ser
20 25 30

<210> SEQ ID NO 691
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 691

Trp Phe Arg Gln Ala Gln Gly Lys Glu Arg Glu Phe Val Val

-continued

```
1               5                   10


<210> SEQ ID NO 692
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 692

Arg Phe Thr Ile Ser Lys Asp Asn Ala Lys Asn Thr Val Tyr Leu Gln
1               5                   10                  15

Ile Asn Ser Leu Lys Pro Glu Asp Thr Ala Val Tyr Tyr Cys Ala Ser
            20                  25                  30


<210> SEQ ID NO 693
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 693

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Leu Asp
            20                  25                  30


<210> SEQ ID NO 694
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694

Trp Phe Arg Gln Ala Pro Gly Lys Glu Arg Glu Gly Val Ser
1               5                   10
```